United States Patent
Kalish et al.

(10) Patent No.: US 9,682,938 B2
(45) Date of Patent: Jun. 20, 2017

(54) PYRAZOLONE DERIVATIVES AS NITROXYL DONORS

(71) Applicants: Cardioxyl Pharmaceuticals, Inc., Chapel Hill, NC (US); The Johns Hopkins University, Baltimore, MD (US)

(72) Inventors: Vincent Jacob Kalish, Annapolis, MD (US); Frederick Arthur Brookfield, Abingdon (GB); Stephen Martin Courtney, Abingdon (GB); Lisa Marie Frost, Abingdon (GB); John P. Toscano, Glen Arm, MD (US); Daryl A. Guthrie, Baltimore, MD (US); Carl Leslie North, Abingdon (GB)

(73) Assignees: Cardioxyl Pharmaceuticals, Inc., Chapel Hill, NC (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/722,141

(22) Filed: May 26, 2015

(65) Prior Publication Data
US 2015/0344437 A1 Dec. 3, 2015

Related U.S. Application Data

(60) Provisional application No. 62/144,312, filed on Apr. 7, 2015, provisional application No. 62/003,428, filed on May 27, 2014.

(51) Int. Cl.
| | |
|---|---|
| *C07D 231/46* | (2006.01) |
| *C07D 231/56* | (2006.01) |
| *C07D 401/04* | (2006.01) |
| *C07D 405/04* | (2006.01) |
| *C07D 413/04* | (2006.01) |
| *C07D 491/048* | (2006.01) |
| *C07D 491/052* | (2006.01) |
| *A61K 31/4152* | (2006.01) |
| *A61P 9/00* | (2006.01) |
| *C07D 403/04* | (2006.01) |
| *C07D 401/10* | (2006.01) |
| *C07D 409/04* | (2006.01) |
| *C07D 491/044* | (2006.01) |

(52) U.S. Cl.
CPC ......... *C07D 231/46* (2013.01); *C07D 231/56* (2013.01); *C07D 401/04* (2013.01); *C07D 401/10* (2013.01); *C07D 403/04* (2013.01); *C07D 405/04* (2013.01); *C07D 409/04* (2013.01); *C07D 413/04* (2013.01); *C07D 491/044* (2013.01); *C07D 491/048* (2013.01); *C07D 491/052* (2013.01)

(58) Field of Classification Search
CPC .. C07D 403/04; C07D 231/46; C07D 231/56; C07D 401/04; C07D 401/10; C07D 491/052; C07D 409/04; C07D 413/04; C07D 491/44; C07D 491/48; C07D 405/04

See application file for complete search history.

(56) References Cited

U.S. PATENT DOCUMENTS

| | | |
|---|---|---|
| 3,751,255 A | 8/1973 | Wilson et al. |
| 4,369,174 A | 1/1983 | Nagai et al. |
| 4,539,321 A | 9/1985 | Campbell |
| 4,663,351 A | 5/1987 | Diamond |
| 4,798,824 A | 1/1989 | Belzer et al. |
| 4,842,866 A | 6/1989 | Horder et al. |
| 5,217,720 A | 6/1993 | Sekigawa et al. |
| 6,525,081 B1 | 2/2003 | Matsumoto et al. |
| 6,569,457 B2 | 5/2003 | Ullah et al. |
| 6,638,534 B1 | 10/2003 | Ishibashi et al. |
| 6,936,639 B2 | 8/2005 | Wink et al. |
| 7,696,373 B2 | 4/2010 | King |
| 7,863,262 B2 | 1/2011 | Wink et al. |
| 7,989,652 B2 | 8/2011 | King |
| 8,030,356 B2 | 10/2011 | Toscano et al. |
| 8,227,639 B2 | 7/2012 | Toscano et al. |
| 8,268,890 B2 | 9/2012 | Wink et al. |
| 8,269,034 B2 | 9/2012 | King |
| 8,318,705 B2 | 11/2012 | Frost et al. |
| 8,569,536 B2 | 10/2013 | King |

(Continued)

FOREIGN PATENT DOCUMENTS

| | | |
|---|---|---|
| CN | 101472576 | 7/2009 |
| CN | 102076342 | 5/2011 |

(Continued)

OTHER PUBLICATIONS

Metwally A. "Reactions of 4-isonitroso-3-methyl-2-pyrazolin-5-one derivatives" Indian J. Chem. Sect. B 1985, 24B, 870-872.*
Guthrie et al. ""Catch-and-Release" of HNO with Pyrazolones" J. Org. Chem. 2015, 80, 1338-1348.*
International Search Report and Written Opinion dated Sep. 18, 2015 in International Patent Application No. PCT/US2015/032496.
Guthrie, D.A. et al., "Development of N-Substituted Hydroxylamines as Efficient Nitroxyl (HNO) Donors", In the Journal of the American Chemical Society, vol. 134, No. 4, Jan. 9, 2012, pp. 1962-1965.
Guthrie, D.A. et al., "'Catch-and-Release' of HNO with Pyrazolones", In the Journal of Organic Chemistry, vol. 80, No. 3, Jan. 16, 2015, pp. 1338-1348.

(Continued)

*Primary Examiner* — Michael Barker
*Assistant Examiner* — Amanda L Aguirre
(74) *Attorney, Agent, or Firm* — Byrne Poh LLP; Nina R. Horan

(57) ABSTRACT

The disclosed subject matter provides pyrazolone derivative compounds, pharmaceutical compositions comprising such compounds, kits comprising such compounds, and methods of using such compounds or pharmaceutical compositions. In particular, the disclosed subject matter provides methods of using such compounds or pharmaceutical compositions for treating heart failure.

48 Claims, No Drawings

(56) References Cited

U.S. PATENT DOCUMENTS

| | | | |
|---|---|---|---|
| 8,674,132 | B2 | 3/2014 | Toscano et al. |
| 8,791,134 | B2 | 7/2014 | Frost et al. |
| RE45,314 | E | 12/2014 | Toscano et al. |
| 8,987,326 | B2 | 3/2015 | Kalish et al. |
| 9,018,411 | B2 | 4/2015 | Toscano et al. |
| 9,115,064 | B2 | 8/2015 | Toscano et al. |
| 9,156,804 | B2 | 10/2015 | Kalish et al. |
| 9,181,213 | B2 | 11/2015 | Toscano et al. |
| 9,221,780 | B2 | 12/2015 | Toscano et al. |
| 2004/0038947 | A1 | 2/2004 | Wink et al. |
| 2005/0153966 | A1 | 7/2005 | Gangloff et al. |
| 2005/0192254 | A1 | 9/2005 | Wink et al. |
| 2009/0163487 | A1 | 6/2009 | Toscano et al. |
| 2009/0186045 | A1 | 7/2009 | Ray et al. |
| 2009/0281067 | A1 | 11/2009 | Toscano et al. |
| 2009/0298795 | A1 | 12/2009 | Paolocci et al. |
| 2011/0081427 | A1 | 4/2011 | Wink et al. |
| 2011/0136827 | A1 | 6/2011 | Toscano et al. |
| 2011/0144067 | A1 | 6/2011 | Toscano et al. |
| 2011/0160200 | A1 | 6/2011 | Mazhari et al. |
| 2011/0306614 | A1 | 12/2011 | Toscano et al. |
| 2012/0201907 | A1 | 8/2012 | Wink et al. |
| 2014/0194416 | A1 | 7/2014 | Toscano et al. |
| 2014/0235636 | A1 | 8/2014 | Toscano et al. |
| 2014/0275134 | A1 | 9/2014 | Toscano et al. |
| 2014/0336137 | A1 | 11/2014 | Frost et al. |
| 2014/0336396 | A1 | 11/2014 | Toscano et al. |
| 2015/0004259 | A1 | 1/2015 | Wink et al. |
| 2015/0141378 | A1 | 5/2015 | Toscano et al. |
| 2015/0197502 | A1 | 7/2015 | Toscano et al. |
| 2015/0291519 | A1 | 10/2015 | Toscano et al. |
| 2015/0336880 | A1 | 11/2015 | Toscano et al. |
| 2015/0344437 | A1 | 12/2015 | Kalish et al. |
| 2015/0366977 | A1 | 12/2015 | Kalish et al. |
| 2016/0002156 | A1 | 1/2016 | Toscano et al. |
| 2016/0031807 | A1 | 2/2016 | Kalish et al. |
| 2016/0046569 | A1 | 2/2016 | Kalish et al. |
| 2016/0046570 | A1 | 2/2016 | Toscano et al. |
| 2016/0052862 | A1 | 2/2016 | Frost et al. |
| 2016/0060229 | A1 | 3/2016 | Toscano et al. |
| 2016/0081951 | A1 | 3/2016 | Mazhari et al. |
| 2016/0115148 | A1 | 4/2016 | Toscano et al. |
| 2016/0166604 | A1 | 6/2016 | Paolocci et al. |

FOREIGN PATENT DOCUMENTS

| | | |
|---|---|---|
| JP | 2011-523404 | 8/2011 |
| WO | WO/01/010827 | 2/2001 |
| WO | WO/02/100810 | 12/2002 |
| WO | WO/2005/074598 | 8/2005 |
| WO | WO/2006/086188 | 8/2006 |
| WO | WO/2007/002444 | 1/2007 |
| WO | WO/2007/109175 | 9/2007 |
| WO | WO/2007/120839 | 10/2007 |
| WO | WO/2009/042970 | 4/2009 |
| WO | WO/2009/137717 | 11/2009 |
| WO | WO/2011/063339 | 5/2011 |
| WO | WO/2011/063400 | 5/2011 |
| WO | WO/2011/071947 | 6/2011 |
| WO | WO/2011/071951 | 6/2011 |
| WO | WO/2013/059194 | 4/2013 |
| WO | WO2013/059194 A1 * | 4/2013 |
| WO | WO/2014/070919 | 5/2014 |
| WO | WO/2014/113696 | 7/2014 |
| WO | WO/2014/113700 | 7/2014 |
| WO | WO/2015/109210 | 7/2015 |
| WO | WO/2015/183838 | 12/2015 |
| WO | WO/2015/183839 | 12/2015 |

OTHER PUBLICATIONS

U.S. Appl. No. 15/133,781, filed Apr. 20, 2016.
U.S. Appl. No. 14/043,345, filed Oct. 1, 2013.
Paolocci, N. et al., "The Pharmacology of Nitroxyl (HNO) and its Therapeutic Potential: Not Just the Janus Fance of NO", In Pharmacology Therapeutics, vol. 113, No. 2, Feb. 2007, pp. 442-458.
Badesch, D.B. et al., "Diagnosis and Assessment of Pulmonary Arterial Hypertension", In the Journal of the American College of Cardiology, vol. 54, No. 1, suppl. S, Jun. 2009, pp. S55-S66.
Reisz, J.A. et al., "Reductive Phosphine-Mediated Ligation of Nitroxyl (HNO)", In Organic Letters, vol. 11, No. 13, Jul. 2009, pp. 2719-2721.
Reisz, J.A. et al., "Rapid and Selective Nitroxyl (HNO) Trapping by Phosphines: Kinetics and New Aqueous Ligations for HNO Detection and Quantitation", In the Journal of the American Chemical Society, vol. 133, No. 30, Aug. 2011, pp. 11675-11685.
Bazylinski, D.A. et al., "Metmyoglobin and Methemoglobin as Efficient Traps for Nitrosyl Hydride (Nitroxyl) in Neutral Aqueous Solution", In the Journal of the American Chemical Society, vol. 107, No. 26, Dec. 1985, pp. 7982-7986.
Saigal, N. et al., "Microcrystalline Cellulose as a Versatile Excipient in Drug Research", In the Journal of Young Pharmacists, vol. 1, No. 1, Mar. 2009, pp. 6-12.
Ingall, T.J., "Preventing Ischemic Stroke", In Postgraduate Medicine, vol. 107, No. 6, Nov./Dec. 2000, pp. 34-50.
Slotwiner-Nie, P.K. and Brandt, L.J., "Infectious Diarrhea in the Elderly", In Gastroenterology Clinics of North America, vol. 30, No. 3, Sep. 2001, pp. 625-635.
Fukuto, J.M. et al., "The Physiological Chemistry and Biological Activity of Nitroxyl (HNO): The Neglected, Misunderstood, and Enigmatic Nitrogen Oxide", In Chemical Research in Toxicology, vol. 18, No. 5, May 2005, pp. 790-801.
Scozzafava et al., "Carbonic Anhydrase and Matrix Metalloproteinase Inhibitors: Sulfonylated Amino Acid Hydroxamates with MMP Inhibitory Properties Act as Efficient Inhibitors of CA Isozymes I, II, and IV, and N-Hydroxysulfonamides Inhibit Both Zinc Enzymes", In J. Med. Chem., vol. 43, No. 20, Oct. 2000, pp. 3677-3687.
Armstrong, A. et al., "Oxaziridine-Mediated Amination of Primary Amines: Scope and Application to a One-Pot Pyrazole Synthesis", In Organic Letters, vol. 7, No. 4, Jan. 2005, pp. 713-716.
Mincione, F. et al., "Carbonic Anhydrase Inhibitors: Inhibition of Isozymes I, II and IV with N-Hydroxysulfonamides—A Novel Class of Intraocular Pressure Lowering Agents", In Journal of Enzyme Inhibition and Medicinal Chemistry, vol. 13, No. 4, Jan. 1998, pp. 267-284.
Guthrie, D.A. et al., "Curtailing the Hydroxylaminobarbituric Acid-Hydantoin Rearrangement to Favor HNO Generation", In the Journal of Organic Chemistry, vol. 80, No. 3, Jan. 13, 2015, pp. 1349-1356.
International Search Report and Written Opinion dated Sep. 30, 2015 in International Patent Application No. PCT/US2015/032493.
Notice of Allowance dated Jun. 7, 2016 in U.S. Appl. No. 14/926,607.
Tate et al., "Preparation of 5-Substituted Benzylbarburituric Acid and Investigation of the Effects of the Benzyl and Substituted Benzyl Groups on the Acidity of Barituric Acid", In the Journal of Heterocyclic Chemistry, Jan. 1986, pp. 9-11.
Andrei, D. et al., "Dual Mechanisms of HNO Generation by a Nitroxyl Prodrug of the Diazeniumdiolate (NONOate) Class", In the Journal of the American Chemical Society, vol. 132, No. 46, Nov. 24, 2010, pp. 16526-16532.
Bodor, N. and Buchwald, P., "Soft Drugs", In Retrometabolic Drug Design and Targeting, John Wiley & Sons, Oct. 2012, pp. 1-21.
Bonner, F.T. and Ko, Y., "Kinetic, Isotopic, and Nitrogen-15 NMR Study of N-Hydroxybenzenesulfonamide Decomposition: an Nitrosyl Hydride (HNO) Source Reaction", In Inorganic Chemistry, vol. 31, No. 12, Jun. 1, 1992, pp. 2514-2519.
Choe, C.U. et al., "Nitroxyl in the Central Nervous System", In Antioxidants & Redox Signaling, vol. 14, No. 9, May 1, 2011, pp. 1699-1711.
Cline, M.R. and Toscano, J.P., "Detection of Nitroxyl (HNO) by a Prefluorescent Probe", In the Journal of Physical Organic Chemistry, vol. 24, No. 10, Oct. 2011, pp. 993-998.
Cline, M.R. et al., "Oxidation of N-Hydroxy-I-Arginine by Hypochlorous Acid to Form Nitroxyl (HNO)", In the Journal of Inorganic Biochemistry, vol. 118, Jan. 2013, pp. 148-154.

(56) References Cited

OTHER PUBLICATIONS

Cline, M.R., "Detection of Nitroxyl (HNO) by Membrane Inlet Mass Spectrometry", In Free Radical Biology & Medicine, vol. 50, No. 10, May 2011, pp. 1274-1279.

Cohen, A.D. et al., "Direct Observation of an Acyl Nitroso Species in Solution by Time-Resolved IR Spectrocopy", In the Journal of the American Chemical Society, vol. 125, No. 6, Jan. 16, 2003, pp. 1444-1445.

Corrie, J.E.T. et al., "Reactions of Transient C-Nitrosocarbonyl Compounds with Dienes, Mono-Olefins, and Nucleophiles", In the Journal of the Chemical Society, Perkin Transactions 1, Jan. 1985, pp. 883-886.

Evans, A.S. and Toscano, J.P., "The Chemistry of NO- and HNO-Producing Diazeniumdiolates", In PATAI's Chemistry of Functional Groups, John Wiley & Sons, Ltd., Nov. 2010, pp. 1-16.

Evans, A.S. et al., "Photogeneration and Reactivity of Acyl Nitroso Compounds", In Canadian Journal of Chemistry, vol. 89, No. 2, Feb. 2011, pp. 130-138.

Flores-Santana, W. et al., "The Specificity of Nitroxyl Chemistry Is Unique Among Nitrogen Oxides in Biological Systems", In Antioxidants & Redox Signaling, vol. 14, No. 9, May 1, 2011, pp. 1659-1674.

Freelisch, M., "Nitroxyl gets to the Heart of the Matter", In Proceedings of the National Academy of Sciences, vol. 100, No. 9, Apr. 2003, pp. 4978-4980.

Froehlich, J.P. et al., "Phospholamban Thiols Play a Central Role in Activation of the Cardiac Muscle Sarcoplasmic Reticulum Calcium Pump by Nitroxyl", In Biochemistry, vol. 47, No. 50, Dec. 16, 2008, pp. 13150-13152.

Gladwin, M.T. et al., "Nitrite as a Vascular Endocrine Nitric Oxide Reservoir that Contributes to Hypoxic Signaling, Cytoprotection, and Vasodilation", In the American Journal of Physiology Heart and Circulatory Physiology, vol. 291, No. 5, Nov. 2006, pp. H2026-H2035.

Gladwin, M.T. et al., "The Emerging Biology of the Nitrite Anion", In Nature Chemical Biology, vol. 1, No. 6, Nov. 2005, pp. 308-314.

Higashi, Y. et al., "Edaravone (3-methyl-1-phenyl-2-pyrazolin-5-one), a Novel Free Radical Scavenger, for Treatment of Cardiovascular Diseases", In Recent Patents on Cardiovascular Drug Discovery, vol. 1, No. 1, Jan. 2006, pp. 85-93.

Hughes, M.N. and Cammack, R., "Synthesis, Chemistry, and Applications of Nitroxyl Ion Releasers Sodium Trioxodinitrate or Angeli's Salt and Piloty's Acid", In Methods in Enzymology, vol. 301, Feb. 1999, pp. 279-287.

International Preliminary Report on Patentability dated May 1, 2014 in International Patent Application No. PCT/US2012/060425.

Keceli, G. and Toscano, J.P., "Reactivity of Nitroxyl-Derived Sulfinamides", In Biochemistry, vol. 51, No. 20, May 2012, pp. 4206-4216.

Keceli, G. et al., "NMR Detection and Study of Hydrolysis of HNO-Derived Sulfinamides", In Biochemistry, vol. 52, No. 42, Oct. 2013, pp. 7387-7396.

Kemp-Harper, B.K., "Nitroxyl (HNO): A Novel Redox Signaling Molecule", In Andioxidants & Redox Signaling, vol. 14, No. 9, May 1, 2011, pp. 1609-1613.

Miranda, K.M. et al., "Comparison of the NO and HNO Donating Properties of Diazeniumdiolates: Primary Amine Adducts Release HNO in Vivo", In the Journal of Medicinal Chemistry, vol. 48, No. 26, Dec. 29, 2005, pp. 8220-8228.

Miranda, K.M. et al., "Donors of HNO", In Current Topics in Medicinal Chemistry, vol. 5, No. 7, Jan. 2005, pp. 649-664.

Office Action dated Jan. 23, 2015 in Chinese Application No. 201280051009.4.

Office Action dated Mar. 12, 2014 in Australian Patent Application No. 2013201929.

Paolocci, N. et al., "Nitroxyl Anion Exerts Redox-Sensitive Positive Cardiac Inotropy in Vivo by Calcitonin Gene-Related Peptide Signaling", In Proceedings of the National Academy of Sciences, vol. 98, No. 18, Aug. 28, 2001, pp. 10463-10468.

Paolocci, N. et al., "Positive Inotropic and Lusitropic Effects of HNO/NO- in Failing Hearts: Independence from β-Adrenergic Signaling", In Proceedings of the National Academy Sciences, vol. 100, No. 9, Apr. 29 2003, pp. 5537-5542.

Porcheddu, A. et al., "A Straightforward Route to Piloty's Acid Derivatives: A Class of Potential Nitroxyl-Generating Prodrugs", In Synlett, vol. 2009, No. 13, Aug. 2009, pp. 2149-2153.

Rehse, K. and Hahrouri, T., "New NO Donors with Antithrombotic and Vasodilating Activities, part 25. Hydroxylamine Derivatives", In Archiv der Pharmazie, vol. 331, No. 11, Nov. 1998, pp. 365-367.

Sabbah, H.N. et al., "Nitroxyl (HNO) a Novel Approach for the Acute Treatment of Heart Failure", In Circulation: Heart Failure, vol. 6, No. 6, Nov. 2013, pp. 1250-1258.

Salmon, D.J. et al., "HNO and NO Release from a Primary Amine-Based Diazeniumdiolate as a Function of pH", In Inorganic Chemistry, vol. 50. No. 8, Apr. 18, 2011, pp. 3262-3270.

Sha, X. et al., "Hydrolysis of Acyloxy Nitroso Compounds Yields Nitroxyl (HNO)", In the Journal of the American Chemical Society, vol. 128, No. 30, Jul. 2006, pp. 9687-9692.

Shoman, M.E. et al., "Acyloxy Nitroso Compounds as Nitroxyl (HNO) Donors: Kinetics, Reactions with Thiols, and Vasodilation Properties", In the Journal of Medicinal Chemistry, vol. 54, No. 4, Feb. 24, 2011, pp. 1059-1070.

Sutton, A.D. et al., "Optimization of HNO Production from N,O-Bis-Acylated Hydroxylamine Derivatives", In Organic Letters, vol. 14, No. 2, Jan. 20, 2012, pp. 472-475.

Tocchetti, C.G. et al., "Nitroxyl Improves Cellular Heart Function by Directly Enhancing Cardiac Sarcoplasmic Reticulum Ca2+ Cycling", In Circulation Research, vol. 100, No. 1, Jan. 5, 2007, pp. 96-104.

Tocchetti, C.G. et al., "Playing with Cardiac "Redox Switches": The "HNO Way" to Modulate Cardiac Function", In Antioxidants & Redox Signaling, vol. 14, No. 9, May 1, 2011, pp. 1687-1698.

Watanabe, K. et al. "Structure—Activity Relationship of 3-Methyl-1-Phenyl-2-Pyrazolin-5-One (Edaravone)", In Redox Report, vol. 8, No. 3, Jun. 1, 2003, pp. 151-155.

Watanabe, T. et al., "The Novel Antioxidant Edaravone: From Bench to Bedside", In Cardiovascular Therapeutics, vol. 26, No. 2, Jun. 2008, pp. 101-114.

Xu, Y. et al., "Production of Nitroxyl (HNO) at Biologically Relevant Temperatures from the Retro-Diels—Alder Reaction of N-Hydroxyurea-Derived Acyl Nitroso-9,10-Dimethylanthracene Cycloadducts", In Tetrahedron Letters, vol. 41, No. 22, Jun. 8, 2000, pp. 4265-4269.

Zamora, R. et al., "Oxidative Release of Nitric Oxide Accounts for Guanylyl Cyclase Stimulating, Vasodilator and Anti-Platelet Activity of Piloty's Acid: a Comparison with Angeli's Salt", In Biochemistry Journal, vol. 312, No. 2, Dec. 1995, pp. 333-339.

Office Action dated Jun. 9, 2015 in European Patent Application No. 12781538.9.

Inernational Search Report and Written Opinion dated May 1, 2014 in International Patent Application No. PCT/US2012/060425.

Notice of Allowance dated Jul. 6, 2015 in U.S. Appl. No. 14/352,399.

Office Action dated May 16, 2016 in Australian Patent Application No. 2015246114.

Office Action dated May 23, 2016 in Japanese Patent Application No. 2014-537151.

Office Action dated May 27, 2016 in European Patent Application No. 12781538.9.

Office Action dated Nov. 17, 2015 in Israel Patent Application No. 232101.

Office Action dated Nov. 27, 2015 in Chinese Patent Application No. 201280051009.4.

Crawford, J.H. et al., "Hypoxia, Red Blood Cells, and Nitrite Regulate NO-Dependent Hypoxic Vasodilation", In Blood, vol. 107, No. 2, Jan. 2006, pp. 566-574.

Gao, W.D. et al., "Myofilament Ca2+ Sensitivity in Intact Versus Skinned Rat Ventricular Muscle", In Circulation Research, vol. 74, No. 3, Mar. 1994, pp. 408-415.

Gao, W.D. et al., "Relationship Between Intracellular Calcium and Contractile Force in Stunned Mocardium: Direct Evidence for Decreased Myofilament CA2+ Responsiveness and Altered Dia-

(56) References Cited

OTHER PUBLICATIONS stolic Function in Intact Ventricular Muscle", In Circulation Research, vol. 76, No. 6, Jun. 1995, pp. 1036-1048.
Hare, J.M. et al., "Pertussis Toxin-Sensitive G Proteins Influence Nitric Oxide Synthase III Activity and Protein Levels in Rat Heart", In the Journal of Clinical Investigations, vol. 101, No. 6, Mar. 1998, pp. 1424-1431.
Katori, T. et al., "Calcitonin Gene-Related Peptide in Vivo Positive Inotropy is Attributable to Regional Sympatho-Stimulation and is Blunted in Congestive Heart Failure", In Circulation Research, vol. 96, No. 2, Feb. 2005, pp. 234-243.
Ma, X.L. et al., "Opposite Effects of Nitric Oxide and Nitroxyl on Postischemic Myocardial Injury", In Proceedings of the National Academy of Sciences of the United States of America, vol. 96, No. 25, Dec. 1999, pp. 14617-14622.
Norris, A.J. et al., "Nitroxyl Inhibits Breast Tumor Growth and Angiogenesis", In the International Journal of Cancer, vol. 122, No. 8, Apr. 2008, pp. 1905-1910.
Nutaitis, C.F. et al., "Reduction of Isopropylidene Acylmalonates, 5-Acylbarbituric Acids, and 3-Acyl-4-Hydroxycoumarins to the Corresponding Alkyl Derivatives by Sodium Cyanoborohydride-Acetic Acid", In the Journal of Organic Chemistry, vol. 45, No. 23, Nov. 1980, pp. 4606-4608.
Paolocci, N. et al., "cGMP-Independent Inotropic Effects of Nitric Oxide and Peroxynitrite Donors: Potential Role for Nitrosylation", In the American Journal of Physiology, Heart and Circulatory Physiology, vol. 279, No. 4, Oct. 2000, pp. H1982-H1988.
Raillard, S.P. et al., "Preparation and Improved Stability of N-Boc-α-Amino-5-Acyl Meldrum's Acids, a Versatile Class of Building Blocks for Combinatorial Chemistry", In the Journal of Combinatorial Chemistry, vol. 4, No. 5, Sep. 2002, pp. 470-474.
Rastaldo, R. et al., "Cytochrome P-450 Metabolite of Arachidonic Acid Mediates Bradykinin-Induced Negative Inotropic Effect", In the American Journal of Physiology Heart and Circulatory Physiology, vol. 280, No. 6, Jun. 2001, pp. H2823-H2832.
Simonneau, G. et al., "Updated Clinical Classification of Pulmonary Hypertension", In the Journal of the American College of Cardiology, vol. 54, No. 1s1, Jun. 2009, pp. S43-S54.
Stoyanovsky, D.A. et al., "Effects of pH on the Cytotoxicity of Sodium Trioxodinitrate (Angeli's Salt)", In the Journal of Medicinal Chemistry, vol. 47, No. 1, Dec. 2003, pp. 210-217.
Thevis, M. et al., "High Speed Determination of Beta-Receptor Blocking Agents in Human Urine by Liquied Chromatography/Tandem Mass Spectrometry", In Biomedical Chromatography, vol. 15, No. 6, Oct. 2001, pp. 393-402.
Yranzo, G.I. et al., "Flash Vacuum Pyrolysis of 2-Alkoxyiminated alkyl α-pyrone and 1,3-diazine Derivatives", In Journal of Analytical and Applied Pyrolysis, vol. 46, No. 2, Aug. 1998, pp. 101-112.
Timoshinina, L.G. and Vvedenskii, V.M., "Reaction of Dialuric Acid with Hydrazine Derivatives", In Chemistry of Heterocyclic Compounds, vol. 9, No. 2, Feb. 1973, pp. 247-249.

* cited by examiner

PYRAZOLONE DERIVATIVES AS NITROXYL DONORS

1. BACKGROUND

Nitroxyl (HNO) has been shown to have positive cardiovascular effects in in vitro and in vivo models of failing hearts. However, at physiological pH, nitroxyl dimerizes to hyponitrous acid, which subsequently dehydrates to nitrous oxide. Owing to this metastability, nitroxyl for therapeutic use is typically generated in situ from donor compounds. A variety of compounds capable of donating nitroxyl have been described and proposed for use in treating disorders known or suspected to be responsive to nitroxyl. See, e.g., U.S. Pat. Nos. 6,936,639, 7,696,373, 8,030,356, 8,268,890, 8,227,639, and 8,318,705, U.S. pre-grant publication nos. 2009/0281067, 2009/0298795, 2011/0136827, and 2011/0144067, PCT international publication no. WO 2013/059194, and Paolocci et al., Pharmacol. Therapeutics 113: 442-458 (2007). Although compounds in these references are disclosed to be capable of donating nitroxyl, they differ in various physicochemical properties and there remains a need to identify nitroxyl donors that have physicochemical properties best suited for treating specific clinical conditions via specific routes of administration.

Additionally, while nitroxyl donors for parenteral (e.g., intravenous) administration are currently being developed for clinical use, non-ideal solid state stability of the nitroxyl donors has impeded the development of oral dosage forms.

Accordingly, there is a need to provide nitroxyl donating compounds and compositions that are useful for the treatment of heart failure and that have a suitable safety profile. Moreover, there exists a need to provide nitroxyl donors that have increased solid state stability and, thus, are more amenable for oral administration.

Citation of any reference in Section 1 of this application is not to be construed as an admission that such reference is prior art to the present application.

2. SUMMARY OF THE DISCLOSURE

The present disclosure relates to pyrazolone derivative compounds, pharmaceutical compositions comprising such compounds, kits comprising such compounds, and methods of using such compounds or pharmaceutical compositions.

In a particular embodiment, a pyrazolone derivative compound of the disclosure is compound of formula (Ia)

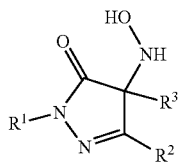

or a pharmaceutically acceptable salt thereof, wherein:

$R^1$ is $(C_1-C_6)$alkyl, unsubstituted (5- or 6-membered) heteroaryl or unsubstituted phenyl, wherein said alkyl is unsubstituted or substituted with $C(=O)OH$;

$R^2$ is phenyl wherein said phenyl is unsubstituted or substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, $-C(=O)OH$, $-C(=O)O(C_1-C_6)$alkyl, $-C(=O)NR^4R^5$, $-C(=O)-(C_5-C_7)$heterocycloalkyl, $(C_5-C_7)$heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, $-S(O)_2-NH_2$, $-S(O)_2-NR^6R^7$, $-S(O)_2$-phenyl, $-S(O)_2-(C_5-C_7)$heterocycloalkyl, $-S(=O)(=NR^8)(C_1-C_6)$alkyl, $-NR^4R^5$, N—$(C_1-C_6)$alkylaminosulfonyl, and N,N-di$(C_1-C_6)$alkylaminosulfonyl, wherein said $(C_5-C_7)$heterocycloalkyl is unsubstituted or substituted with 1 or 2 substituent(s) independently selected from halo or $(C_1-C_6)$alkyl;

$R^4$ and $R^6$ are independently H or $(C_1-C_6)$alkyl;

$R^5$ is H, $(C_1-C_6)$alkyl or $(C_1-C_6)$alkylsulfonyl, wherein said alkyl is unsubstituted or substituted with $C(=O)OH$ or wherein a methylene group of said alkyl is optionally replaced with an oxygen atom;

$R^7$ is H or $(C_1-C_6)$alkyl, wherein a methylene group of said alkyl is optionally replaced with an oxygen atom;

$R^8$ is H, $-(C=O)(C_1-C_6)$alkyl or $-(C=O)(C_1-C_4)$perhaloalkyl; and $R^3$ is $(C_1-C_6)$alkyl or $-C(=NOR^9)R^{10}$ wherein $R^9$ and $R^{10}$ are independently selected from $(C_1-C_6)$alkyl.

In another embodiment, a pyrazolone derivative compound of the disclosure is compound of formula (Ib)

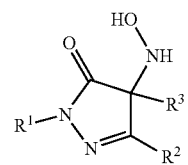

or a pharmaceutically acceptable salt thereof, wherein:

$R^1$ is $(C_1-C_6)$alkyl or unsubstituted phenyl;

$R^2$ is $(C_1-C_6)$alkyl, $(C_1-C_4)$haloalkyl, or $(C_1-C_4)$perhaloalkyl;

$R^3$ is (5- or 6-membered)heteroaryl or phenyl wherein said heteroaryl and phenyl are unsubstituted or substituted with 1, 2, 3, 4, or 5 substituent(s) independently selected from halo, $(C_1-C_6)$alkyl, $(C_1-C_6)$alkoxy, phenyl, $-C(=O)NR^4R^5$, $(C_1-C_6)$alkylsulfinyl, $(C_1-C_6)$alkylsulfonyl, and N,N-di$(C_1-C_6)$alkylaminosulfonyl; and $R^4$ and $R^5$ are independently H or $(C_1-C_6)$alkyl.

In another embodiment, a pyrazolone derivative compound of the disclosure is compound of formula (Ic)

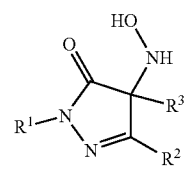

or a pharmaceutically acceptable salt thereof, wherein:

$R^1$ is $(C_1-C_6)$alkyl or phenyl, wherein said phenyl is unsubstituted or substituted with 1, 2, or 3 substituent(s) independently selected from halo;

$R^2$ is $(C_2-C_6)$alkyl, $(C_1-C_6)$alkoxy, phenylsulfanyl, phenylsulfonyl, phenylsulfinyl or $(C_3-C_6)$cycloalkyl; and $R^3$ is $(C_1-C_6)$alkyl, $-C(=NOR^9)R^{10}$ wherein $R^9$ and $R^{10}$ are independently selected from $(C_1-C_6)$alkyl.

In another embodiment, a pyrazolone derivative compound of the disclosure is compound of formula (Id)

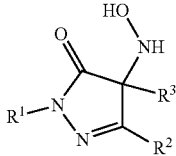
(Id)

or a pharmaceutically acceptable salt thereof, wherein:

$R^1$ is $(C_1-C_6)$alkyl;

$R^2$ is $(C_1-C_6)$alkyl or $(C_1-C_6)$alkoxy; and $R^3$ is —C(=NOR$^9$)R$^{10}$ wherein R$^9$ is phenyl, $(C_1-C_6)$ alkyl substituted with phenyl or $(C_2-C_6)$alkyl and wherein said phenyl is unsubstituted or independently substituted with 1 or 2 halo(s); and R$^{10}$ is $(C_1-C_6)$alkyl.

In another embodiment, a pyrazolone derivative compound of the disclosure is compound of formula (Ie)

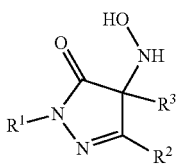
(Ie)

or a pharmaceutically acceptable salt thereof, wherein:

$R^1$ is phenyl substituted with 1, 2, or 3 substituent(s) independently selected from $(C_1-C_6)$alkylsulfonyl;

$R^2$ is $(C_1-C_6)$alkyl; and $R^3$ is $(C_1-C_6)$alkyl.

In another embodiment, a pyrazolone derivative compound of the disclosure is compound of formula (If)

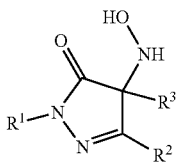
(If)

or a pharmaceutically acceptable salt thereof, wherein:

$R^1$ is phenyl substituted with 1, 2, 3, 4, or 5 substituent(s) independently selected from halo, $(C_1-C_6)$alkoxy, $(C_1-C_6)$alkylsulfinyl, and $(C_1-C_6)$alkylsulfonyl;

$R^2$ is phenyl wherein said phenyl is unsubstituted or substituted with 1, 2, 3, 4, or 5 substituent(s) independently selected from halo, $(C_1-C_6)$alkoxy, $(C_1-C_6)$alkylsulfinyl, and $(C_1-C_6)$alkylsulfonyl; and $R^3$ is $(C_1-C_6)$alkyl or —C(=NOR$^9$)R$^{10}$ wherein R$^9$ and R$^{10}$ are independently selected from $(C_1-C_6)$alkyl.

In another embodiment, a pyrazolone derivative compound of the disclosure is compound of formula (Ig)

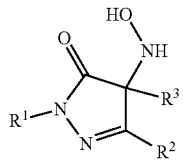
(Ig)

or a pharmaceutically acceptable salt thereof, wherein:

$R^1$ is H;

$R^2$ is $(C_1-C_6)$alkyl, phenyl or (5- or 6-membered)heteroaryl, wherein said phenyl and said heteroaryl are unsubstituted or substituted with 1, 2, 3, 4, or 5 substituent(s) independently selected from halo, cyano, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O$(C_1-C_6)$alkyl, —C(=O)NR$^4$R$^5$, —C(=O)—$(C_5-C_7)$heterocycloalkyl, $(C_5-C_7)$heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$NHOH, —S(O)$_2$—NR$^6$R$^7$, —S(O)$_2$-phenyl, —S(O)$_2$—$(C_5-C_7)$heterocycloalkyl, —S(=O)(=NR$^8$)$(C_1-C_6)$alkyl, —NR$^4$R$^5$, N—$(C_1-C_6)$alkylaminosulfonyl, and N,N-di$(C_1-C_6)$alkylaminosulfonyl, wherein said $(C_5-C_7)$heterocycloalkyl is unsubstituted or substituted with 1 or 2 substituent(s) independently selected from halo or $(C_1-C_6)$alkyl;

$R^4$ and $R^6$ are independently H or $(C_1-C_6)$alkyl;

$R^5$ is H, $(C_1-C_6)$alkyl or $(C_1-C_6)$alkylsulfonyl, wherein said alkyl is unsubstituted or substituted with C(=O)OH or wherein a methylene group of said alkyl is optionally replaced with an oxygen atom;

$R^7$ is H or $(C_1-C_6)$alkyl, wherein a methylene group of said alkyl is optionally replaced with an oxygen atom;

$R^8$ is H, —(C=O)$(C_1-C_6)$alkyl or —(C=O)$(C_1-C_4)$perhaloalkyl;

$R^3$ is (5- or 6-membered)heteroaryl, $(C_6-C_{10})$aryl, phenyl or —C(=NOR$^9$)R$^{10}$, wherein R$^9$ is $(C_1-C_6)$alkyl, phenyl or $(C_1-C_6)$alkyl substituted with phenyl and R$^{10}$ is $(C_1-C_6)$ alkyl, wherein said heteroaryl, aryl and phenyl are unsubstituted or substituted with 1, 2, 3, 4, or 5 substituent(s) independently selected from halo, cyano, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O$(C_1-C_6)$alkyl, —C(=O)NR$^4$R$^5$, —C(=O)—$(C_5-C_7)$heterocycloalkyl, $(C_5-C_7)$heterocycloalkyl, $(C_6-C_{10})$aryl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$—$(C_5-C_7)$heterocycloalkyl, —S(=O)(=NR$^8$)$(C_1-C_6)$alkyl, —NR$^4$R$^5$, N—$(C_1-C_6)$alkylaminosulfonyl, and N,N-di$(C_1-C_6)$alkylaminosulfonyl, wherein said $(C_5-C_7)$ heterocycloalkyl is unsubstituted or substituted with 1 or 2 substituent(s) independently selected from halo or $(C_1-C_6)$ alkyl; or $R^2$ and $R^3$ are taken together with the carbon atoms to which they are attached to form a $(C_3-C_6)$cycloalkyl.

In another embodiment, a pyrazolone derivative compound of the disclosure is compound of formula (Ih)

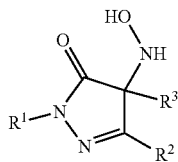

(Ih)

or a pharmaceutically acceptable salt thereof, wherein:

$R^1$ is H;

$R^2$ is $(C_1-C_6)$alkyl, phenyl or (5- or 6-membered)heteroaryl, wherein said alkyl is substituted with 1, 2 or 3 substituent(s) independently selected from $(C_1-C_6)$alkoxy, —C(=O)OH, or —C(=O)O$(C_1-C_6)$alkyl and said phenyl and said heteroaryl are unsubstituted or substituted with 1, 2, 3, 4, or 5 substituent(s) independently selected from $(C_1-C_6)$alkylsulfanyl, $(C_1-C_6)$alkylsulfinyl, $(C_1-C_6)$alkylsulfonyl, —S(O)$_2$—NH$_2$, —S(O)$_2$NHOH, —S(O)$_2$N(($C_1-C_6$)alkyl)(O($C_1-C_6$)alkyl)) or N,N-di($C_1-C_6$)alkylaminosulfonyl; and $R^3$ is $(C_1-C_6)$alkyl.

In another embodiment, a pyrazolone derivative compound of the disclosure is compound of formula (Ii)

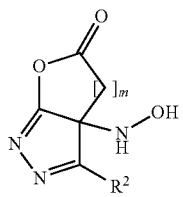

(Ii)

or a pharmaceutically acceptable salt thereof, wherein:

$R^2$ is $(C_1-C_6)$alkyl or phenyl, wherein said phenyl is unsubstituted or substituted with 1, 2, 3, 4, or 5 substituent(s) independently selected from halo, cyano, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O$(C_1-C_6)$alkyl, —C(=O)NR$^4$R$^5$, —C(=O)—$(C_5-C_7)$heterocycloalkyl, $(C_5-C_7)$heterocycloalkyl, $(C_6-C_{10})$aryl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$—$(C_5-C_7)$heterocycloalkyl, —S(=O)(=NR$^8$)$(C_1-C_6)$alkyl, —NR$^4$R$^5$, N—$(C_1-C_6)$alkylaminosulfonyl, and N,N-di($C_1-C_6$)alkylaminosulfonyl, wherein said $(C_5-C_7)$heterocycloalkyl is unsubstituted or substituted with 1 or 2 substituent(s) independently selected from halo or $(C_1-C_6)$alkyl; and m is 1, 2 or 3.

In another embodiment, a pyrazolone derivative compound of the disclosure is compound of formula (IIa) or formula (IIb):

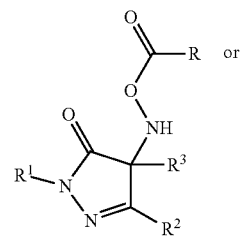

(IIa)

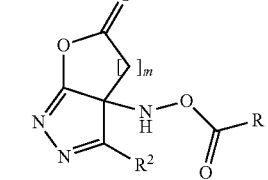

(IIb)

or a pharmaceutically acceptable salt thereof, wherein:

$R^1$, $R^2$, $R^3$ and m together are as defined herein for each of compounds of formulae (Ia), (Ib), (Ic), (Id), (Ie), (If), (Ig), (Ih) and (Ii); and R is hydrogen, —$(C_1-C_6)$alkyl, —$(C_2-C_4)$alkenyl, phenyl, benzyl, cyclopentyl, cyclohexyl, —$(C_5-C_7)$heterocycloalkyl, benzyloxy, —O—$(C_1-C_6)$alkyl, —NH$_2$, —NH—$(C_1-C_4)$alkyl, or —N(($C_1-C_4$)alkyl)$_2$, wherein said —$(C_1-C_6)$alkyl, —$(C_2-C_4)$alkenyl, phenyl, benzyl, cyclopentyl, cyclohexyl, —$(C_5-C_7)$heterocycloalkyl, benzyloxy, —O—$(C_1-C_6)$alkyl, —NH—$(C_1-C_4)$alkyl, or —N(($C_1-C_4$)alkyl)$_2$ can be unsubstituted or substituted with 1, 2 or 3 substituents selected from halo, —$(C_1-C_6)$alkyl, —$(C_2-C_4)$alkenyl, —$(C_2-C_3)$alkynyl, -(5- or 6-membered)heteroaryl, —O—$(C_1-C_6)$alkyl, —S—$(C_1-C_6)$alkyl, —C(halo)$_3$, —CH(halo)$_2$, —CH$_2$(halo), —CN, —NO$_2$, —NH$_2$, —NH—$(C_1-C_4)$alkyl, —N(—$(C_1-C_4)$alkyl)$_2$, —C(O)$(C_1-C_4)$alkyl, —C(O)O$(C_1-C_4)$alkyl, —OC(O)$(C_1-C_4)$alkyl, —OC(O)NH$_2$, —S(O)$(C_1-C_4)$alkyl, or —S(O)$_2$$(C_1-C_4)$alkyl.

3. DETAILED DESCRIPTION

The invention includes the following:

(1) A compound of formula (Ia)

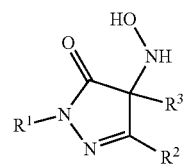

(Ia)

or a pharmaceutically acceptable salt thereof, wherein:

$R^1$ is $(C_1-C_6)$alkyl, unsubstituted (5- or 6-membered) heteroaryl or unsubstituted phenyl, wherein said alkyl is unsubstituted or substituted with C(=O)OH;

$R^2$ is phenyl wherein said phenyl is unsubstituted or substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O$(C_1-C_6)$alkyl, —C(=O)NR$^4$R$^5$, —C(=O)—$(C_5-C_7)$heterocycloalkyl, $(C_5-C_7)$heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, (C₁-C₆)alkylsulfonyl, (C₃-C₆)cycloalkylsulfonyl, (C₁-C₄)haloalkylsulfinyl, (C₁-C₄)haloalkylsulfonyl, (C₁-C₄) perhaloalkylsulfinyl, (C₁-C₄)perhaloalkylsulfonyl, —S(O)₂—NH₂, —S(O)₂—NR⁶R⁷, —S(O)₂-phenyl, —S(O)₂—(C₅-C₇)heterocycloalkyl, —S(=O)(=NR⁸)(C₁-C₆)alkyl, —NR⁴R⁵, N—(C₁-C₆)alkylaminosulfonyl, and N,N-di(C₁-C₆)alkylaminosulfonyl, wherein said (C₅-C₇) heterocycloalkyl is unsubstituted or substituted with 1 or 2 substituent(s) independently selected from halo or (C₁-C₆) alkyl;

R⁴ and R⁶ are independently H or (C₁-C₆)alkyl;

R⁵ is H, (C₁-C₆)alkyl or (C₁-C₆)alkylsulfonyl, wherein said alkyl is unsubstituted or substituted with C(=O)OH or wherein a methylene group of said alkyl is optionally replaced with an oxygen atom;

R⁷ is H or (C₁-C₆)alkyl, wherein a methylene group of said alkyl is optionally replaced with an oxygen atom;

R⁸ is H, —C(=O)(C₁-C₆)alkyl or —C(=O)(C₁-C₄)perhaloalkyl; and

R³ is (C₁-C₆)alkyl or —C(=NOR⁹)R¹⁰ wherein R⁹ and R¹⁰ are independently selected from (C₁-C₆)alkyl.

(2) The compound of the above (1), wherein:

R¹ is (C₁-C₆)alkyl or unsubstituted phenyl;

R² is phenyl wherein said phenyl is unsubstituted or substituted with 1, 2, 3, 4, or 5 substituent(s) independently selected from halo, (C₁-C₆)alkyl, (C₁-C₄)haloalkyl, (C₁-C₄) perhaloalkyl, (C₁-C₆)alkoxy, (C₁-C₄)haloalkoxy, (C₁-C₄) perhaloalkoxy, (C₁-C₆)alkylsulfanyl, (C₁-C₄)haloalkylsulfanyl, (C₁-C₄)perhaloalkylsulfanyl, (C₁-C₆)alkylsulfinyl, (C₁-C₆)alkylsulfonyl, (C₃-C₆)cycloalkylsulfonyl, (C₁-C₄) haloalkylsulfinyl, (C₁-C₄)haloalkylsulfonyl, (C₁-C₄) perhaloalkylsulfinyl, (C₁-C₄)perhaloalkylsulfonyl, —S(O)₂—NH₂, N—(C₁-C₆)alkylaminosulfonyl, and N,N-di(C₁-C₆)alkylaminosulfonyl; and R³ is (C₁-C₆)alkyl or —C(=NOR⁹)R¹⁰ wherein R⁹ and R¹⁰ are independently selected from (C₁-C₆)alkyl.

(3) The compound of the above (1) or (2), wherein R¹ is (C₁-C₆)alkyl.

(4) The compound of the above (1) or (2), wherein R¹ is unsubstituted phenyl.

(5) The compound of any one of the above (1)-(4), wherein R² is unsubstituted phenyl.

(6) The compound of any one of the above (1)-(4), wherein R² is phenyl substituted with 1, 2, or 3 substituent(s) independently selected from halo, (C₁-C₆)alkyl, (C₁-C₄) perhaloalkyl, (C₁-C₆)alkoxy, (C₁-C₄)haloalkoxy, (C₁-C₄) perhaloalkoxy, —C(=O)OH, —C(=O)O(C₁-C₆)alkyl, —C(=O)NR⁴R⁵, —C(=O)—(C₅-C₇)heterocycloalkyl, (C₅-C₇)heterocycloalkyl, (C₁-C₆)alkylsulfanyl, (C₁-C₆) alkylsulfinyl, (C₁-C₆)alkylsulfonyl, (C₁-C₄)haloalkylsulfinyl, (C₁-C₄)haloalkylsulfonyl, (C₁-C₄)perhaloalkylsulfinyl, (C₁-C₄)perhaloalkylsulfonyl, —S(O)₂—NR⁶R⁷, —S(O)₂-phenyl, —S(O)₂—(C₅-C₇)heterocycloalkyl, —S(=O)(=NR⁸)(C₁-C₆)alkyl, —NR⁴R⁵, and N,N-di (C₁-C₆)alkylaminosulfonyl, wherein said (C₅-C₇)heterocycloalkyl is unsubstituted or substituted with 1 or 2 substituent(s) independently selected from halo or (C₁-C₆)alkyl.

(7) The compound of any one of the above (1)-(6), wherein R³ is (C₁-C₆)alkyl.

(8) The compound of any one of the above (1)-(6), wherein R³ is —C(=NOR⁹)R¹⁰.

(9) The compound of any one of the above (1)-(6), wherein, R³ is —C(=NOR⁹)R¹⁰ wherein each of R⁴ and R⁵ is methyl.

(10) A compound of formula (Ib)

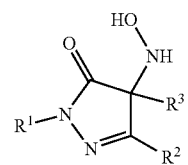

(Ib)

or a pharmaceutically acceptable salt thereof, wherein:

R¹ is (C₁-C₆)alkyl or unsubstituted phenyl;

R² is (C₁-C₆)alkyl, (C₁-C₄)haloalkyl, or (C₁-C₄)perhaloalkyl;

R³ is (5- or 6-membered)heteroaryl or phenyl wherein said heteroaryl and phenyl are unsubstituted or substituted with 1, 2, 3, 4, or 5 substituent(s) independently selected from halo, (C₁-C₆)alkyl, (C₁-C₆)alkoxy, phenyl, —C(=O) NR⁴R⁵, (C₁-C₆)alkylsulfinyl, (C₁-C₆)alkylsulfonyl, and N,N-di(C₁-C₆)alkylaminosulfonyl; and R⁴ and R⁵ are independently H or (C₁-C₆)alkyl.

(11) The compound of the above (10), wherein:

R¹ is (C₁-C₆)alkyl or unsubstituted phenyl;

R² is (C₁-C₆)alkyl, (C₁-C₄)haloalkyl, or (C₁-C₄)perhaloalkyl; and

R³ is phenyl wherein said phenyl is unsubstituted or substituted with 1, 2, 3, 4, or 5 substituent(s) independently selected from halo, (C₁-C₆)alkoxy, (C₁-C₆)alkylsulfinyl and (C₁-C₆)alkylsulfonyl.

(12) The compound of the above (10), wherein R¹ is (C₁-C₆)alkyl.

(13) The compound of the above (10), wherein R¹ is unsubstituted phenyl.

(14) The compound of any one of the above (10)-(13), wherein R² is methyl.

(15) The compound of any one of the above (10)-(14), wherein R³ is unsubstituted phenyl.

(16) The compound of any one of the above (10)-(14), wherein R³ is phenyl substituted with halo.

(17) The compound of any one of the above (10)-(14), wherein R³ is phenyl substituted (C₁-C₆)alkylsulfonyl.

(18) A compound of formula (Ic)

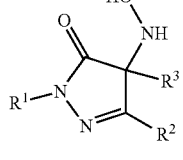

(Ic)

or a pharmaceutically acceptable salt thereof, wherein:

R¹ is (C₁-C₆)alkyl or phenyl, wherein said phenyl is unsubstituted or substituted with 1, 2, or 3 substituent(s) independently selected from halo;

R² is (C₂-C₆)alkyl, (C₁-C₆)alkoxy, phenylsulfanyl, phenylsulfonyl, phenylsulfinyl or (C₃-C₆)cycloalkyl; and R³ is (C₁-C₆)alkyl, —C(=NOR⁹)R¹⁰ wherein R⁹ and R¹⁰ are independently selected from (C₁-C₆)alkyl.

(19) The compound of the above (18), wherein:

R¹ is (C₁-C₆)alkyl or phenyl, wherein said phenyl is unsubstituted or substituted with 1, 2, or 3 substituent(s) independently selected from halo;

R² is (C₂-C₆)alkyl or (C₃-C₆)cycloalkyl; and

R³ is —C(=NOR⁹)R¹⁰ wherein R⁹ and R¹⁰ are independently selected from (C₁-C₆)alkyl.

(20) The compound of the above (18), wherein $R^1$ is $(C_1-C_6)$alkyl.
(21) The compound of the above (18), wherein $R^1$ is unsubstituted phenyl.
(22) The compound of the above (18), wherein $R^1$ is phenyl substituted with 1, 2, or 3 substituent(s) independently selected from halo.
(23) The compound of any one of the above (18)-(22), wherein $R^2$ is propyl, butyl or cyclopropyl.
(24) The compound of any one of the above (18)-(23), wherein $R^3$ is —C(=NOR$^9$)R$^{10}$ wherein each of $R^9$ and $R^{10}$ is methyl.
(25) A compound of formula (Id)

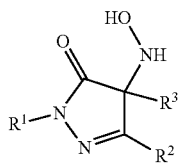

or a pharmaceutically acceptable salt thereof, wherein:
$R^1$ is $(C_1-C_6)$alkyl;
$R^2$ is $(C_1-C_6)$alkyl or $(C_1-C_6)$alkoxy; and
$R^3$ is —C(=NOR$^9$)R$^{10}$ wherein $R^9$ is phenyl, $(C_1-C_6)$alkyl substituted with phenyl or $(C_2-C_6)$alkyl and wherein said phenyl is unsubstituted or independently substituted with 1 or 2 halo(s); and $R^{10}$ is $(C_1-C_6)$alkyl.
(26) The compound of the above (25), wherein $R^1$ is methyl.
(27) The compound of the above (25) or (26), wherein $R^2$ is $(C_1-C_6)$alkyl.
(28) The compound of the above (25) or (26), wherein $R^2$ is $(C_1-C_6)$alkoxy.
(29) The compound of any one of the above (25)-(28), wherein $R^9$ is phenyl.
(30) The compound of any one of the above (25)-(28), wherein $R^9$ is benzyl.
(31) The compound of any one of the above (25)-(28), wherein $R^9$ is $(C_2-C_6)$alkyl.
(32) The compound of any one of the above (25)-(31), wherein $R^{10}$ is methyl.
(33) A compound of formula (Ie)

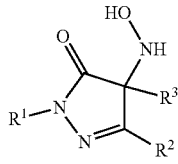

or a pharmaceutically acceptable salt thereof, wherein:
$R^1$ is phenyl substituted with 1, 2, or 3 substituent(s) independently selected from $(C_1-C_6)$alkylsulfonyl;
$R^2$ is $(C_1-C_6)$alkyl; and
$R^3$ is $(C_1-C_6)$alkyl.
(34) The compound of the above (33), wherein $R^1$ is phenyl monosubstituted with $(C_1-C_6)$alkylsulfonyl.
(35) The compound of the above (33) or (34), wherein $R^2$ is methyl.
(36) The compound of any one of the above (33)-(35), wherein $R^3$ is methyl.

(37) A compound of formula (If)

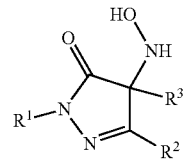

or a pharmaceutically acceptable salt thereof, wherein:
$R^1$ is phenyl substituted with 1, 2, 3, 4, or 5 substituent(s) independently selected from halo, $(C_1-C_6)$alkoxy, $(C_1-C_6)$alkylsulfinyl, and $(C_1-C_6)$alkylsulfonyl;
$R^2$ is phenyl wherein said phenyl is unsubstituted or substituted with 1, 2, 3, 4, or 5 substituent(s) independently selected from halo, $(C_1-C_6)$alkoxy, $(C_1-C_6)$alkylsulfinyl, and $(C_1-C_6)$alkylsulfonyl; and
$R^3$ is $(C_1-C_6)$alkyl or —C(=NOR$^9$)R$^{10}$ wherein $R^9$ and $R^{10}$ are independently selected from $(C_1-C_6)$alkyl.
(38) The compound of the above (37), wherein $R^1$ is phenyl monosubstituted with halo.
(39) The compound of the above (37) or (38), wherein $R^2$ is unsubstituted phenyl or phenyl monosubstituted with halo.
(40) The compound of any one of the above (37)-(39), wherein $R^3$ is $(C_1-C_4)$alkyl.
(41) The compound of any one of the above (37)-(40), wherein $R^3$ is methyl.
(42) The compound of any one of the above (37)-(41), wherein said halo is chloro or bromo.
(43) A compound of formula (Ig)

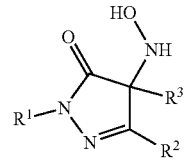

or a pharmaceutically acceptable salt thereof, wherein:
$R^1$ is H;
$R^2$ is $(C_1-C_6)$alkyl, phenyl or (5- or 6-membered)heteroaryl, wherein said phenyl and said heteroaryl are unsubstituted or substituted with 1, 2, 3, 4, or 5 substituent(s) independently selected from halo, cyano, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O(C$_1$-C$_6$)alkyl, —C(=O)NR$^4$R$^5$, —C(=O)—(C$_5$-C$_7$)heterocycloalkyl, (C$_5$-C$_7$)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$NHOH, —S(O)$_2$—NR$^6$R$^7$, —S(O)$_2$-phenyl, —S(O)$_2$—(C$_5$-C$_7$)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl, wherein said (C$_5$-C$_7$)heterocycloalkyl is unsubstituted or substituted with 1 or 2 substituent(s) independently selected from halo or $(C_1-C_6)$alkyl;
$R^4$ and $R^6$ are independently H or $(C_1-C_6)$alkyl;
$R^5$ is H, $(C_1-C_6)$alkyl or $(C_1-C_6)$alkylsulfonyl, wherein said alkyl is unsubstituted or substituted with C(=O)OH or wherein a methylene group of said alkyl is optionally replaced with an oxygen atom;

$R^7$ is H or $(C_1$-$C_6)$alkyl, wherein a methylene group of said alkyl is optionally replaced with an oxygen atom;

$R^8$ is H, —(C=O)($C_1$-$C_6$)alkyl or —(C=O)($C_1$-$C_4$)perhaloalkyl;

$R^3$ is (5- or 6-membered)heteroaryl, ($C_6$-$C_{10}$)aryl, phenyl or —C(=NOR$^9$)R$^{10}$, wherein R$^9$ is ($C_1$-$C_6$)alkyl, phenyl or ($C_1$-$C_6$)alkyl substituted with phenyl and R$^{10}$ is ($C_1$-$C_6$)alkyl, wherein said heteroaryl, aryl and phenyl are unsubstituted or substituted with 1, 2, 3, 4, or 5 substituent(s) independently selected from halo, cyano, ($C_1$-$C_6$)alkyl, ($C_1$-$C_4$)haloalkyl, ($C_1$-$C_4$)perhaloalkyl, ($C_1$-$C_6$)alkoxy, ($C_1$-$C_4$)haloalkoxy, ($C_1$-$C_4$)perhaloalkoxy, —C(=O)OH, —C(=O)O($C_1$-$C_6$)alkyl, —C(=O)NR$^4$R$^5$, —C(=O)—($C_5$-$C_7$)heterocycloalkyl, ($C_5$-$C_7$)heterocycloalkyl, ($C_6$-$C_{10}$)aryl, ($C_1$-$C_6$)alkylsulfanyl, ($C_1$-$C_4$)haloalkylsulfanyl, ($C_1$-$C_4$)perhaloalkylsulfanyl, ($C_1$-$C_6$)alkylsulfinyl, ($C_1$-$C_6$)alkylsulfonyl, ($C_3$-$C_6$)cycloalkylsulfonyl, ($C_1$-$C_4$)haloalkylsulfinyl, ($C_1$-$C_4$)haloalkylsulfonyl, ($C_1$-$C_4$)perhaloalkylsulfinyl, ($C_1$-$C_4$)perhaloalkylsulfonyl, —S(O)$_2$—NH$_2$, —S(O)$_2$—NR$^6$R$^7$, —S(O)$_2$-phenyl, —S(O)$_2$—($C_5$-$C_7$)heterocycloalkyl, —S(=O)(=NR$^8$)($C_1$-$C_6$)alkyl, —NR$^4$R$^5$, N—($C_1$-$C_6$)alkylaminosulfonyl, and N,N-di($C_1$-$C_6$)alkylaminosulfonyl, wherein said ($C_5$-$C_7$) heterocycloalkyl is unsubstituted or substituted with 1 or 2 substituent(s) independently selected from halo or ($C_1$-$C_6$)alkyl; or $R^2$ and $R^3$ are taken together with the carbon atoms to which they are attached to form a ($C_3$-$C_6$)cycloalkyl.

(44) The compound of the above (43), wherein
 $R^1$ is H;
 $R^2$ is ($C_1$-$C_6$)alkyl; and
 $R^3$ is —C(=NOR$^9$)R$^{10}$ wherein R$^9$ and R$^{10}$ are independently selected from ($C_1$-$C_6$)alkyl.

(45) The compound of the above (43) or (44), wherein $R^2$ is methyl.

(46) The compound of the above (43)-(45), wherein $R^3$ is —C(=NOR$^9$)R$^{10}$ wherein each of R$^9$ and R$^{10}$ is methyl.

(47) A compound of formula (Ih)

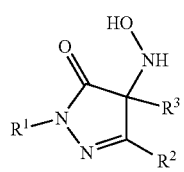

(Ih)

or a pharmaceutically acceptable salt thereof, wherein:
 $R^1$ is H;
 $R^2$ is ($C_1$-$C_6$)alkyl, phenyl or (5- or 6-membered)heteroaryl, wherein said alkyl is substituted with 1, 2 or 3 substituent(s) independently selected from ($C_1$-$C_6$)alkoxy, —C(=O)OH, or —C(=O)O($C_1$-$C_6$)alkyl and said phenyl and said heteroaryl are unsubstituted or substituted with 1, 2, 3, 4, or 5 substituent(s) independently selected from ($C_1$-$C_6$)alkylsulfanyl, ($C_1$-$C_6$)alkylsulfinyl, ($C_1$-$C_6$)alkylsulfonyl, —S(O)$_2$—NH$_2$, —S(O)$_2$NHOH, —S(O)$_2$N(($C_1$-$C_6$)alkyl)(O($C_1$-$C_6$)alkyl)) or N,N-di($C_1$-$C_6$)alkylaminosulfonyl; and
 $R^3$ is ($C_1$-$C_6$)alkyl.

(48) The compound of the above (47), wherein $R^2$ is phenyl substituted with 1, 2, 3, 4, or 5 substituent(s) independently selected from ($C_1$-$C_6$)alkylsulfonyl or N,N-di($C_1$-$C_6$)alkylaminosulfonyl.

(49) The compound of the above (47) or (48), wherein $R^3$ is methyl.

(50) A compound of formula (Ii)

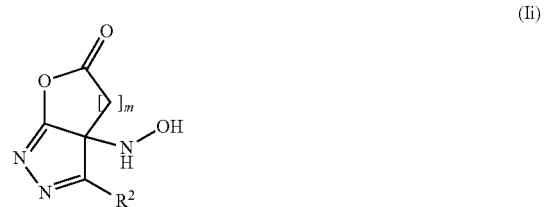

(Ii)

or a pharmaceutically acceptable salt thereof, wherein:
 $R^2$ is ($C_1$-$C_6$)alkyl or phenyl, wherein said phenyl is unsubstituted or substituted with 1, 2, 3, 4, or 5 substituent(s) independently selected from halo, cyano, ($C_1$-$C_6$)alkyl, ($C_1$-$C_4$)haloalkyl, ($C_1$-$C_4$)perhaloalkyl, ($C_1$-$C_6$)alkoxy, ($C_1$-$C_4$)haloalkoxy, ($C_1$-$C_4$)perhaloalkoxy, —C(=O)OH, —C(=O)O($C_1$-$C_6$)alkyl, —C(=O)NR$^4$R$^5$, —C(=O)—($C_5$-$C_7$)heterocycloalkyl, ($C_5$-$C_7$)heterocycloalkyl, ($C_6$-$C_{10}$)aryl, ($C_1$-$C_6$)alkylsulfanyl, ($C_1$-$C_4$)haloalkylsulfanyl, ($C_1$-$C_4$)perhaloalkylsulfanyl, ($C_1$-$C_6$)alkylsulfinyl, ($C_1$-$C_6$)alkylsulfonyl, ($C_3$-$C_6$)cycloalkylsulfonyl, ($C_1$-$C_4$)haloalkylsulfinyl, ($C_1$-$C_4$)haloalkylsulfonyl, ($C_1$-$C_4$)perhaloalkylsulfinyl, ($C_1$-$C_4$)perhaloalkylsulfonyl, —S(O)$_2$—NH$_2$, —S(O)$_2$—NR$^6$R$^7$, —S(O)$_2$-phenyl, —S(O)$_2$—($C_5$-$C_7$)heterocycloalkyl, —S(=O)(=NR$^8$)($C_1$-$C_6$)alkyl, —NR$^4$R$^5$, N—($C_1$-$C_6$)alkylaminosulfonyl, and N,N-di($C_1$-$C_6$)alkylaminosulfonyl, wherein said ($C_5$-$C_7$) heterocycloalkyl is unsubstituted or substituted with 1 or 2 substituent(s) independently selected from halo or ($C_1$-$C_6$)alkyl; and m is 1, 2 or 3.

(51) The compound of the above (50), wherein m is 1.

(52) The compound of the above (50), wherein m is 2.

(53) The compound of the above (50), wherein m is 3.

(54) The compound of any of the above (50)-(53), wherein $R^2$ is ($C_1$-$C_6$)alkyl.

(55) The compound of any of the above (50)-(53), wherein $R^2$ is unsubstituted phenyl.

(56) The compound of any of the above (50)-(53), wherein $R^2$ is phenyl monosubstituted with a substituent selected from halo, cyano, ($C_1$-$C_6$)alkyl, ($C_1$-$C_4$)haloalkyl, ($C_1$-$C_4$)perhaloalkyl, ($C_1$-$C_6$)alkoxy, ($C_1$-$C_4$)haloalkoxy, ($C_1$-$C_4$)perhaloalkoxy, —C(=O)OH, —C(=O)O($C_1$-$C_6$)alkyl, —C(=O)NR$^4$R$^5$, —C(=O)—($C_5$-$C_7$)heterocycloalkyl, ($C_5$-$C_7$)heterocycloalkyl, ($C_6$-$C_{10}$)aryl, ($C_1$-$C_6$)alkylsulfanyl, ($C_1$-$C_4$)haloalkylsulfanyl, ($C_1$-$C_4$)perhaloalkylsulfanyl, ($C_1$-$C_6$)alkylsulfinyl, ($C_1$-$C_6$)alkylsulfonyl, ($C_3$-$C_6$)cycloalkylsulfonyl, ($C_1$-$C_4$)haloalkylsulfinyl, ($C_1$-$C_4$)haloalkylsulfonyl, ($C_1$-$C_4$)perhaloalkylsulfinyl, ($C_1$-$C_4$)perhaloalkylsulfonyl, —S(O)$_2$—NH$_2$, —S(O)$_2$—NR$^6$R$^7$, —S(O)$_2$-phenyl, —S(O)$_2$—($C_5$-$C_7$)heterocycloalkyl, —S(=O)(=NR$^8$) ($C_1$-$C_6$)alkyl, —NR$^4$R$^5$, N—($C_1$-$C_6$)alkylaminosulfonyl, and N,N-di($C_1$-$C_6$)alkylaminosulfonyl, wherein said ($C_5$-$C_7$)heterocycloalkyl is unsubstituted or substituted with 1 or 2 substituent(s) independently selected from halo or ($C_1$-$C_6$)alkyl.

(57) A compound of formula (IIa) or formula (IIb):

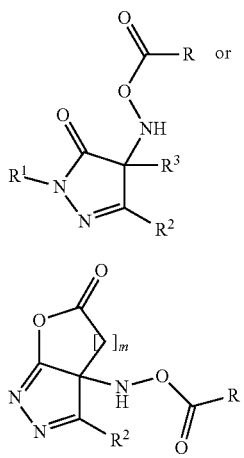

or a pharmaceutically acceptable salt thereof, wherein:
$R^1$, $R^2$, $R^3$ and m together are as defined for each of compounds of formulae (Ia), (Ib), (Ic), (Id), (Ie), (If), (Ig), (Ih) and (Ii) in the above (1)-(56); and R is hydrogen, —($C_1$-$C_6$)alkyl, —($C_2$-$C_4$)alkenyl, phenyl, benzyl, cyclopentyl, cyclohexyl, —($C_5$-$C_7$)heterocycloalkyl, benzyloxy, —O—($C_1$-$C_6$)alkyl, —$NH_2$, —NH—($C_1$-$C_4$)alkyl, or —N(($C_1$-$C_4$)alkyl)$_2$, wherein said —($C_1$-$C_6$)alkyl, —($C_2$-$C_4$)alkenyl, phenyl, benzyl, cyclopentyl, cyclohexyl, —($C_5$-$C_7$)heterocycloalkyl, benzyloxy, —O—($C_1$-$C_6$)alkyl, —NH—($C_1$-$C_4$)alkyl, or —N(($C_1$-$C_4$)alkyl)$_2$ can be unsubstituted or substituted with 1, 2 or 3 substituents selected from halo, —($C_1$-$C_6$)alkyl, —($C_2$-$C_4$)alkenyl, —($C_2$-$C_3$)alkynyl, -(5- or 6-membered)heteroaryl, —O—($C_1$-$C_6$)alkyl, —S—($C_1$-$C_6$)alkyl, —C(halo)$_3$, —CH(halo)$_2$, —$CH_2$(halo), —CN, —$NO_2$, —$NH_2$, —NH—($C_1$-$C_4$)alkyl, —N(—($C_1$-$C_4$)alkyl)$_2$, —C(O)($C_1$-$C_4$)alkyl, —C(O)O($C_1$-$C_4$)alkyl, —OC(O)($C_1$-$C_4$)alkyl, —OC(O)$NH_2$, —S(O)($C_1$-$C_4$)alkyl, or —S(O)$_2$($C_1$-$C_4$)alkyl.

(58) The compound of the above (57), wherein R is methyl, ethyl, benzyl, or phenyl.

(59) The compound of the above (57), wherein R is methyl.

(60) A compound selected from:
5-(4-chlorophenyl)-4-(hydroxyamino)-2,4-dimethyl-2,4-dihydro-3H-pyrazol-3-one,
5-(2-chlorophenyl)-4-(hydroxyamino)-2,4-dimethyl-2,4-dihydro-3H-pyrazol-3-one,
5-(2-fluorophenyl)-4-(hydroxyamino)-2,4-dimethyl-2,4-dihydro-3H-pyrazol-3-one,
4-(hydroxyamino)-2,4-dimethyl-5-(4-(trifluoromethyl)phenyl)-2,4-dihydro-3H-pyrazol-3-one,
5-(4-fluorophenyl)-4-(hydroxyamino)-2,4-dimethyl-2,4-dihydro-3H-pyrazol-3-one,
4-(hydroxyamino)-2,5-dimethyl-4-phenyl-2,4-dihydro-3H-pyrazol-3-one,
5-(3,5-dimethylphenyl)-4-(hydroxyamino)-2,4-dimethyl-2,4-dihydro-3H-pyrazol-3-one,
5-(2-chlorophenyl)-4-(hydroxyamino)-2-iso-propyl-4-methyl-2,4-dihydro-3H-pyrazol-3-one,
5-(3,5-dichlorophenyl)-4-(hydroxyamino)-2,4-dimethyl-2,4-dihydro-3H-pyrazol-3-one,
5-(tert-butyl)-4-(hydroxyamino)-4-(1-(methoxyimino)ethyl)-2-methyl-2,4-dihydro-3H-pyrazol-3-one,
4-(hydroxyamino)-2,4-dimethyl-5-(4-(methylsulfinyl)phenyl)-2,4-dihydro-3H-pyrazol-3-one,
5-(2-chloro-4-fluorophenyl)-4-(hydroxyamino)-2,4-dimethyl-2,4-dihydro-3H-pyrazol-3-one,
4-(hydroxyamino)-4-(1-(methoxyimino)ethyl)-5-methyl-2,4-dihydro-3H-pyrazol-3-one,
4-(hydroxyamino)-2,4-dimethyl-5-(4-(methylsulfonyl)phenyl)-2,4-dihydro-3H-pyrazol-3-one,
4-(hydroxyamino)-2,4-dimethyl-5-phenyl-2,4-dihydro-3H-pyrazol-3-one,
4-(hydroxyamino)-5-iso-propyl-4-(1-(methoxyimino)ethyl)-2-phenyl-2,4-dihydro-3H-pyrazol-3-one,
2-(4-bromophenyl)-4-(hydroxyamino)-5-iso-propyl-4-(1-(methoxyimino)ethyl)-2,4-dihydro-3H-pyrazol-3-one,
5-(tert-butyl)-4-(hydroxyamino)-4-(1-(methoxyimino)ethyl)-2-phenyl-2,4-dihydro-3H-pyrazol-3-one,
5-(3-fluoro-4-methoxyphenyl)-4-(hydroxyamino)-2,4-dimethyl-2,4-dihydro-3H-pyrazol-3-one,
5-cyclopropyl-4-(hydroxyamino)-4-(1-(methoxyimino)ethyl)-2-methyl-2,4-dihydro-3H-pyrazol-3-one,
4-(hydroxyamino)-2,4-dimethyl-5-(2-(methylsulfinyl)phenyl)-2,4-dihydro-3H-pyrazol-3-one,
4-(hydroxyamino)-2,4-dimethyl-5-(3-(trifluoromethyl)phenyl)-2,4-dihydro-3H-pyrazol-3-one,
5-(tert-butyl)-4-(hydroxyamino)-4-methyl-2-phenyl-2,4-dihydro-3H-pyrazol-3-one,
4-(hydroxyamino)-5-methyl-2,4-diphenyl-2,4-dihydro-3H-pyrazol-3-one,
4-(hydroxyamino)-4-methyl-2,5-diphenyl-2,4-dihydro-3H-pyrazol-3-one,
5-(2-fluorophenyl)-4-(hydroxyamino)-2-iso-propyl-4-methyl-2,4-dihydro-3H-pyrazol-3-one,
4-(4-fluorophenyl)-4-(hydroxyamino)-2,5-dimethyl-2,4-dihydro-3H-pyrazol-3-one,
5-(tert-butyl)-4-(hydroxyamino)-2-iso-propyl-4-(1-(methoxyimino)ethyl)-2,4-dihydro-3H-pyrazol-3-one,
5-(2-fluorophenyl)-4-(hydroxyamino)-4-methyl-2-phenyl-2,4-dihydro-3H-pyrazol-3-one,
4-(hydroxyamino)-1-isopropyl-3-methyl-4-phenyl-1H-pyrazol-5(4H)-one,
4-ethyl-5-(2-fluorophenyl)-4-(hydroxyamino)-2-methyl-2,4-dihydro-3H-pyrazol-3-one,
4-(hydroxyamino)-2-iso-propyl-4-methyl-5-(4-(methylsulfonyl)phenyl)-2,4-dihydro-3H-pyrazol-3-one,
4-(hydroxyamino)-4,5-dimethyl-2-(4-(methylsulfonyl)phenyl)-2,4-dihydro-3H-pyrazol-3-one,
4-(hydroxyamino)-2,4-dimethyl-5-(4-((trifluoromethyl)sulfonyl)phenyl)-2,4-dihydro-3H-pyrazol-3-one,
4-(hydroxyamino)-2,4-dimethyl-5-(4-((trifluoromethyl)sulfinyl)phenyl)-2,4-dihydro-3H-pyrazol-3-one,
4-(hydroxyamino)-2,4-dimethyl-5-(4-(methylthio)phenyl)-2,4-dihydro-3H-pyrazol-3-one,
4-(hydroxyamino)-2,5-dimethyl-4-(4-(methylsulfonyl)phenyl)-2,4-dihydro-3H-pyrazol-3-one,
5-(3-fluoro-4-(methylsulfinyl)phenyl)-4-(hydroxyamino)-2,4-dimethyl-2,4-dihydro-3H-pyrazol-3-one,
4-(hydroxyamino)-2,4-dimethyl-5-(3-methyl-4-(methylsulfinyl)phenyl)-2,4-dihydro-3H-pyrazol-3-one,
5-(3-fluoro-4-(methylsulfonyl)phenyl)-4-(hydroxyamino)-2,4-dimethyl-2,4-dihydro-3H-pyrazol-3-one,
4-(hydroxyamino)-2,4-dimethyl-5-(3-methyl-4-(methylsulfonyl)phenyl)-2,4-dihydro-3H-pyrazol-3-one,
4-(hydroxyamino)-4-(1-(methoxyimino)ethyl)-2-methyl-5-(4-(methylsulfonyl)-phenyl)-2,4-dihydro-3H-pyrazol-3-one,
4-(hydroxyamino)-4-(4-methoxyphenyl)-1,3-dimethyl-1H-pyrazol-5(4H)-one,
1-(4-bromophenyl)-3-(2-chlorophenyl)-4-(hydroxyamino)-4-methyl-1H-pyrazol-5(4H)-one, 5-(3,5-difluoro-4-(methylsulfonyl)phenyl)-4-(hydroxyamino)-2,4-dimethyl-2,4-dihydro-3H-pyrazol-3-one,
4-(hydroxyamino)-4-(1-(methoxyimino)ethyl)-2-methyl-5-phenyl-2,4-dihydro-3H-pyrazol-3-one,
1-(4-bromophenyl)-4-(hydroxyamino)-3-methyl-4-phenyl-1H-pyrazol-5(4H)-one,
4-(hydroxyamino)-2,4-dimethyl-5-(3-(methylsulfonyl)phenyl)-2,4-dihydro-3H-pyrazol-3-one,
4-(4-(hydroxyamino)-1,4-dimethyl-5-oxo-4,5-dihydro-1H-pyrazol-3-yl)-N,N-dimethylbenzenesulfonamide,
1-(4-bromophenyl)-4-(hydroxyamino)-4-methyl-3-phenyl-1H-pyrazol-5(4H)-one,
4-(hydroxyamino)-1,4-dimethyl-3-(o-tolyl)-1H-pyrazol-5(4H)-one,
4-(hydroxyamino)-4-(1-(methoxyimino)ethyl)-1-methyl-3-(4-(trifluoromethyl)phenyl)-1H-pyrazol-5(4H)-one,
4-(hydroxyamino)-3-(4-methoxyphenyl)-1,4-dimethyl-1H-pyrazol-5(4H)-one,
3-(3-chlorophenyl)-4-(hydroxyamino)-1,4-dimethyl-1H-pyrazol-5(4H)-one,
4-(hydroxyamino)-3-(2-methoxyphenyl)-1,4-dimethyl-1H-pyrazol-5(4H)-one,
4-(hydroxyamino)-1,4-dimethyl-3-(2-(trifluoromethoxy)phenyl)-1H-pyrazol-5(4H)-one,
3-(2,3-dichlorophenyl)-4-(hydroxyamino)-1,4-dimethyl-1H-pyrazol-5(4H)-one,
3-(2,4-dichlorophenyl)-4-(hydroxyamino)-1,4-dimethyl-1H-pyrazol-5(4H)-one,
4-(hydroxyamino)-1,4-dimethyl-3-(4-(trifluoromethoxy)phenyl)-1H-pyrazol-5(4H)-one,
4-(hydroxyamino)-1,4-dimethyl-3-(2-(trifluoromethyl)phenyl)-1H-pyrazol-5(4H)-one,
4-(hydroxyamino)-4-methyl-1-phenyl-3-(trifluoromethyl)-1H-pyrazol-5(4H)-one,
3-(2-ethoxy-4-fluorophenyl)-4-(hydroxyamino)-1,4-dimethyl-1H-pyrazol-5(4H)-one,
4-(hydroxyamino)-3-isopropyl-4-(1-(methoxyimino)ethyl)-1-methyl-1H-pyrazol-5(4H)-one,
3-(4-fluorophenyl)-4-(hydroxyamino)-4-(1-(methoxyimino)ethyl)-1-methyl-1H-pyrazol-5(4H)-one,
4-(hydroxyamino)-1,3-dimethyl-4-(4-(methylsulfinyl)phenyl)-1H-pyrazol-5(4H)-one,
4-(4-chlorophenyl)-4-(hydroxyamino)-1,3-dimethyl-1H-pyrazol-5(4H)-one,
4-(hydroxyamino)-1,4-dimethyl-3-(4-((trifluoromethyl)thio)phenyl)-1H-pyrazol-5(4H)-one,
4-(3-bromo-4-methoxyphenyl)-4-(hydroxyamino)-1,3-dimethyl-1H-pyrazol-5(4H)-one,
3-(3,5-bis(trifluoromethyl)phenyl)-4-(hydroxyamino)-1,4-dimethyl-1H-pyrazol-5(4H)-one,
3-(3-Chloro-4-methanesulfonylphenyl)-4-(hydroxyamino)-1,4-dimethyl-4,5-dihydro-1H-pyrazol-5-one,
methyl 4-[4-(hydroxyamino)-1,4 dimethyl-5-oxo-4,5-dihydro-1H-pyrazol-3-yl]benzoate,
2,2,2-trifluoro-N-({4-[4-(hydroxyamino)-1,4-dimethyl-5-oxo-4,5-dihydro-1H-pyrazol-3-yl]phenyl}(methyl)oxo-λ⁶-sulfanylidene)acetamide,
4-(3,4-dimethoxyphenyl)-4-(hydroxyamino)-1,3-dimethyl-4,5-dihydro-1H-pyrazol-5-one,
4-[4-(hydroxyamino)-1,4-dimethyl-5-oxo-4,5-dihydro-1H-pyrazol-3-yl]benzoic acid,
4-(hydroxyamino)-3-{4-[imino(methyl)oxo-λ⁶-sulfanyl]phenyl}-1,4-dimethyl-4,5-dihydro-1H-pyrazol-5-one,
4-(hydroxyamino)-4-(4-methoxy-3-methylphenyl)-1,3-dimethyl-4,5-dihydro-1H-pyrazol-5-one,
4-(hydroxyamino)-3-(4-methanesulfonyl-3-methoxyphenyl)-1,4-dimethyl-4,5-dihydro-1H-pyrazol-5-one,
4-(hydroxyamino)-1,4-dimethyl-3-[4-(propane-2-sulfonyl)phenyl]-4,5-dihydro-1H-pyrazol-5-one,
4-(hydroxyamino)-3-(4-methanesulfonyl-3,5-dimethylphenyl)-1,4-dimethyl-4,5-dihydro-1H-pyrazol-5-one,
4-(hydroxyamino)-1,4-dimethyl-3-[4-(morpholine-4-sulfonyl)phenyl]-4,5-dihydro-1H-pyrazol-5-one,
4-(hydroxyamino)-1,4-dimethyl-3-[4-(morpholine-4-carbonyl)phenyl]-4,5-dihydro-1H-pyrazol-5-one,
4-(hydroxyamino)-3-[4-methanesulfonyl-3-(morpholin-4-yl)phenyl]-1,4-dimethyl-4,5-dihydro-1H-pyrazol-5-one,
4-(hydroxyamino)-3-{4-methanesulfonyl-3-[(2-methoxyethyl)(methyl)amino]phenyl}-1,4-dimethyl-4,5-dihydro-1H-pyrazol-5-one,
4-[4-(hydroxyamino)-1,4-dimethyl-5-oxo-4,5-dihydro-1H-pyrazol-3-yl]-N,N-dimethylbenzamide,
3-[4-(4,4-difluoropiperidine-1-carbonyl)phenyl]-4-(hydroxyamino)-1,4-dimethyl-4,5-dihydro-1H-pyrazol-5-one,
3-[4-(ethanesulfonyl)phenyl]-4-(hydroxyamino)-1,4-dimethyl-4,5-dihydro-1H-pyrazol-5-one,
3-[3-(dimethylamino)-4-methanesulfonylphenyl]-4-(hydroxyamino)-1,4-dimethyl-4,5-dihydro-1H-pyrazol-5-one,
4-(hydroxyamino)-3-[4-methanesulfonyl-3-(4-methylpiperazin-1-yl)phenyl]-1,4-dimethyl-4,5-dihydro-1H-pyrazol-5-one,
3-[4-(benzenesulfonyl)phenyl]-4-(hydroxyamino)-1,4-dimethyl-4,5-dihydro-1H-pyrazol-5-one,
4-[4-(hydroxyamino)-1,4-dimethyl-5-oxo-4,5-dihydro-1H-pyrazol-3-yl]-N-(2-methoxyethyl)-N-methylbenzene-1-sulfonamide,
3-(4-tert-butylphenyl)-4-(hydroxyamino)-1,4-dimethyl-4,5-dihydro-1H-pyrazol-5-one,
4-[4-(hydroxyamino)-1,4-dimethyl-5-oxo-4,5-dihydro-1H-pyrazol-3-yl]benzamide,
4-(hydroxyamino)-3-[4-methanesulfonyl-3-(piperazin-1-yl)phenyl]-1,4-dimethyl-4,5-dihydro-1H-pyrazol-5-one,
2-({4-[4-(hydroxyamino)-1,4-dimethyl-5-oxo-4,5-dihydro-1H-pyrazol-3-yl]phenyl}formamido)propanoic acid,
2-({4-[4-(hydroxyamino)-1,4-dimethyl-5-oxo-4,5-dihydro-1H-pyrazol-3-yl]phenyl}formamido)acetic acid,
4-(3-fluorophenyl)-4-(hydroxyamino)-1,3-dimethyl-4,5-dihydro-1H-pyrazol-5-one,
4-(hydroxyamino)-3-[4-methanesulfonyl-3-(trifluoromethyl)phenyl]-1,4-dimethyl-4,5-dihydro-1H-pyrazol-5-one,
4-(hydroxyamino)-1,3-dimethyl-4-(3-methylphenyl)-4,5-dihydro-1H-pyrazol-5-one,
4-(3-chlorophenyl)-4-(hydroxyamino)-1,3-dimethyl-4,5-dihydro-1H-pyrazol-5-one,
4-(hydroxyamino)-4-(3-methoxyphenyl)-1,3-dimethyl-4,5-dihydro-1H-pyrazol-5-one,
4-[4-(hydroxyamino)-1,4-dimethyl-5-oxo-4,5-dihydro-1H-pyrazol-3-yl]-N-methanesulfonylbenzamide,
4-(hydroxyamino)-1,3-dimethyl-4-[1-(phenoxyimino)ethyl]-4,5-dihydro-1H-pyrazol-5-one,
4-(hydroxyamino)-1,3-dimethyl-4-[1-(benzyloxyimino)ethyl]-4,5-dihydro-1H-pyrazol-5-one,
3-(3,4-dimethanesulfonylphenyl)-4-(hydroxyamino)-1,4-dimethyl-4,5-dihydro-1H-pyrazol-5-one,
4-(hydroxyamino)-1,3-dimethyl-4-[1-[(2-methylpropoxy)imino]ethyl]-4,5-dihydro-1H-pyrazol-5-one,
4-[1-(ethoxyimino)ethyl]-4-(hydroxyamino)-1,3-dimethyl-4,5-dihydro-1H-pyrazol-5-one, 4-(hydroxyamino)-4-[1-(methoxyimino)ethyl]-3-(4-methoxyphenyl)-1-methyl-4,5-dihydro-1H-pyrazol-5-one,
3-(4-bromophenyl)-4-(hydroxyamino)-1,4-dimethyl-4,5-dihydro-1H-pyrazol-5-one,
4-(hydroxyamino)-1-methyl-3,4-diphenyl-4,5-dihydro-1H-pyrazol-5-one,
3-ethoxy-4-(hydroxyamino)-4-[1-(methoxyimino)ethyl]-1-phenyl-4,5-dihydro-1H-pyrazol-5-one,
1-(4-bromophenyl)-3-ethoxy-4-(hydroxyamino)-4-[1-(methoxyimino)ethyl]-4,5-dihydro-1H-pyrazol-5-one,
3-tert-butyl-4-[1-(ethoxyimino)ethyl]-4-(hydroxyamino)-1-methyl-4,5-dihydro-1H-pyrazol-5-one,
3-tert-butyl-4-(hydroxyamino)-1-methyl-4-phenyl-4,5-dihydro-1H-pyrazol-5-one,
3-{4-[(4,4-difluoropiperidin-1-yl)sulfonyl]phenyl}-4-(hydroxyamino)-1,4-dimethyl-4,5-dihydro-1H-pyrazol-5-one,
4-[1-[(benzyloxy)imino]ethyl]-3-tert-butyl-4-(hydroxyamino)-1-methyl-4,5-dihydro-1H-pyrazol-5-one,
4-(hydroxyamino)-3-methoxy-4-[1-(methoxyimino)ethyl]-1-phenyl-4,5-dihydro-1H-pyrazol-5-one,
4-[1-[(tert-butoxy)imino]ethyl]-3-tert-butyl-4-(hydroxyamino)-1-methyl-4,5-dihydro-1H-pyrazol-5-one,
4-[1-[(4-bromophenoxy)imino]ethyl]-3-tert-butyl-4-(hydroxyamino)-1-methyl-4,5-dihydro-1H-pyrazol-5-one,
3-tert-butyl-4-(hydroxyamino)-1-methyl-4-[1-(phenoxyimino)ethyl]-4,5-dihydro-1H-pyrazol-5-one,
4-(hydroxyamino)-3-{4-[imino(oxo)propan-2-yl-$\lambda^6$-sulfanyl]phenyl}-1,4-dimethyl-4,5-dihydro-1H-pyrazol-5-one,
4-[4-(hydroxyamino)-4-[1-(methoxyimino)ethyl]-1-methyl-5-oxo-4,5-dihydro-1H-pyrazol-3-yl]-N,N-dimethylbenzene-1-sulfonamide,
4-[3-tert-butyl-4-(hydroxyamino)-1-methyl-5-oxo-4,5-dihydro-1H-pyrazol-4-yl]-N,N-dimethylbenzene-1-sulfonamide,
4-[4-(hydroxyamino)-4-[1-(methoxyimino)ethyl]-1-methyl-5-oxo-4,5-dihydro-1H-pyrazol-3-yl]-N,N-dimethylbenzamide,
4-[3-tert-butyl-4-(hydroxyamino)-1-methyl-5-oxo-4,5-dihydro-1H-pyrazol-4-yl]-N,N-dimethylbenzamide,
4-[1-[(benzyloxy)imino]ethyl]-3-ethoxy-4-(hydroxyamino)-1-methyl-4,5-dihydro-1H-pyrazol-5-one,
3-ethoxy-4-(hydroxyamino)-4-[1-(methoxyimino)ethyl]-1-methyl-4,5-dihydro-1H-pyrazol-5-one,
3-ethoxy-4-(hydroxyamino)-4-methyl-1-phenyl-4,5-dihydro-1H-pyrazol-5-one,
4-(hydroxyamino)-4-[1 (methoxyimino)ethyl]-1-phenyl-3-(phenylsulfanyl)-4,5-dihydro-1H-pyrazol-5-one,
3-(benzenesulfonyl)-4-(hydroxyamino)-4-[1-(methoxyimino)ethyl]-1-phenyl-4,5-dihydro-1H-pyrazol-5-one pyrazol-5-one,
3-(benzenesulfinyl)-4-(hydroxyamino)4-[1-(methoxyimino)ethyl]-1-phenyl-4,5-dihydro H-pyrazol-5-one,
3-tert-Butyl-4-(hydroxyamino)-4-[1-(methoxyimino)ethyl]-4,5-dihydro-1H-pyrazol-5-one,
4-(Hydroxyamino)-1,3-dimethyl-4-(5-phenyl-1,2,4-oxadiazol-3-yl)-4,5-dihydro-1H-pyrazol-5-one,
4-(hydroxyamino)-3-(4-methanesulfonylphenyl)-4-methyl-4,5-dihydro-1H-pyrazol-5-one,
3-tert-Butyl-4-[1-(ethoxyimino)ethyl]-4-(hydroxyamino)-4,5-dihydro-1H-pyrazol-5-one,
4-[4-(Hydroxyamino)-4-methyl-5-oxo-4,5-dihydro-1H-pyrazol-3-yl]-N,N-dimethylbenzene-1-sulfonamide,
4-(Hydroxyamino)-3-(4-methanesulfonylphenyl)-4-methyl-1-phenyl-4,5-dihydro-1H-pyrazol-5-one,
4-(Hydroxyamino)-3-methyl-4-phenyl-4,5-dihydro-1H-pyrazol-5-one,
4-(Hydroxyamino)-3-(4-methanesulfonylphenyl)-4-methyl-1-(pyrazin-2-yl)-4,5-dihydro-1H-pyrazol-5-one,
[3-(4-Methanesulfonylphenyl)-1,4-dimethyl-5-oxo-4,5-dihydro-1H-pyrazol-4-yl]amino acetate,
(1,4-Dimethyl-5-oxo-3-phenyl-4,5-dihydro-1H-pyrazol-4-yl)amino acetate,
4-[4-(Hydroxyamino)-4-methyl-5-oxo-4,5-dihydro-1H-pyrazol-3-yl]-N-methoxy-N-methylbenzene-1-sulfonamide,
ethyl 3-[4-(hydroxyamino)-3-methyl-5-oxo-4,5-dihydro-1H-pyrazol-4-yl]propanoate,
3a-(hydroxyamino)-3-methyl-3aH,4H,5H,6H-pyrano[2,3-c]pyrazol-6-one,
3a-(Hydroxyamino)-3,3a,4,5,6,7-hexahydro-2H-indazol-3-one,
2-(4-(hydroxyamino)-4-methyl-3-(4-(methylsulfonyl)phenyl)-5-oxo-4,5-dihydro-1H-pyrazol-1-yl)acetic acid,
4-(hydroxyamino)-4-methyl-3-(pyridin-4-yl)-1H-pyrazol-5(4H)-one,
4-(4-(hydroxyamino)-4-methyl-5-oxo-4,5-dihydro-1H-pyrazol-3-yl)pyridine 1-oxide,
4-(hydroxyamino)-4-methyl-3-(thiophen-2-yl)-1H-pyrazol-5(4H)-one,
N-hydroxy-5-(4-(hydroxyamino)-4-methyl-5-oxo-4,5-dihydro-1H-pyrazol-3-yl)thiophene-2-sulfonamide,
3-(furan-2-yl)-4-(hydroxyamino)-4-methyl-1H-pyrazol-5(4H)-one, and
N-hydroxy-5-(4-(hydroxyamino)-4-methyl-5-oxo-4,5-dihydro-1H-pyrazol-3-yl)furan-2-sulfonamide,
3a-(hydroxyamino)-3-phenyl-4,5-dihydropyrano[2,3-c]pyrazol-6(3 aH)-one,
3a-(hydroxyamino)-3-methyl-5,6-dihydro-3aH-oxepino[2,3-c]pyrazol-7(4H)-one,
3a-(hydroxyamino)-3-methyl-3aH-furo[2,3-c]pyrazol-5(4H)-one, and
3a-(hydroxyamino)-3-phenyl-3aH-furo[2,3-c]pyrazol-5(4H)-one.
(61) The compound of the above (60), which is 5-(4-chlorophenyl)-4-(hydroxyamino)-2,4-dimethyl-2,4-dihydro-3H-pyrazol-3-one.
(62) The compound of the above (60), which is 4-(hydroxyamino)-2,4-dimethyl-5-(4-(methylsulfonyl)phenyl)-2,4-dihydro-3H-pyrazol-3-one.
(63) The compound of the above (60), which is 5-(2-fluorophenyl)-4-(hydroxyamino)-2,4-dimethyl-2,4-dihydro-3H-pyrazol-3-one.
(64) The compound of the above (60), which is 4-(hydroxyamino)-2,4-dimethyl-5-(4-(trifluoromethyl)phenyl)-2,4-dihydro-3H-pyrazol-3-one.
(65) The compound of the above (60), which is 4-(hydroxyamino)-2-iso-propyl-4-methyl-5-(4-(methylsulfonyl)phenyl)-2,4-dihydro-3H-pyrazol-3-one.
(66) The compound of the above (60), which is 5-(2-fluorophenyl)-4-(hydroxyamino)-2-iso-propyl-4-methyl-2,4-dihydro-3H-pyrazol-3-one.
(67) The compound of the above (60), which is ethyl 3-[4-(hydroxyamino)-3-methyl-5-oxo-4,5-dihydro-1H-pyrazol-4-yl]propanoate.
(68) The compound of the above (60), which is 3a-(hydroxyamino)-3-methyl-3aH,4H,5H,6H-pyrano[2,3-c]pyrazol-6-one.
(69) The compound of the above (60), which is 3a-(Hydroxyamino)-3,3a,4,5,6,7-hexahydro-2H-indazol-3-one.

(70) A pharmaceutical composition comprising the compound of any one of the above (1)-(69) and at least one pharmaceutically acceptable excipient.

(71) The pharmaceutical composition of the above (70), wherein the pharmaceutical composition is suitable for oral administration.

(72) The pharmaceutical composition of the above (70) or (71), wherein the pharmaceutical composition is formulated for administration in solid form.

(73) The pharmaceutical composition of any one of the above (70)-(72), wherein the at least one pharmaceutically acceptable excipient is selected from lactose, microcrystalline cellulose, croscarmellose, or any mixture thereof.

(74) A method of treating a cardiovascular disease, comprising administering an effective amount of the compound of any one of the above (1)-(69) or the pharmaceutical composition of any one of the above (70)-(73) to a patient in need thereof.

(75) The method of the above (74), wherein the cardiovascular disease is heart failure.

(76) The method of the above (74), wherein the cardiovascular disease is acute decompensated heart failure.

(77) The method of any one of the above (74)-(76), wherein the compound or the pharmaceutical composition is administered orally.

(78) Use of the compound of any one of the above (1)-(69) or the pharmaceutical composition of any one of the above (70)-(73) for the manufacture of a medicament useful for treating a cardiovascular disease.

(79) Use of the compound of any one of the above (1)-(69) or the pharmaceutical composition of any one of the above (70)-(73) for the manufacture of a medicament useful for treating heart failure.

(80) Use of the compound of any one of the above (1)-(69) or the pharmaceutical composition of any one of the above (70)-(73) for the manufacture of a medicament useful for treating acute decompensated heart failure.

(81) The use of any one of the above (78)-(80), wherein the compound or the pharmaceutical composition is administered orally.

(82) The compound of any one of the above (1)-(69) or the pharmaceutical composition of any one of the above (70)-(73) for use in the treatment of a cardiovascular disease.

(83) The compound of any one of the above (1)-(69) or the pharmaceutical composition of any one of the above (70)-(73) for use in the treatment of heart failure.

(84) The compound of any one of the above (1)-(69) or the pharmaceutical composition of any one of the above (70)-(73) for use in the treatment of acute decompensated heart failure.

3.1 Definitions

Unless clearly indicated otherwise, the following terms as used herein have the meanings indicated below.

A "pharmaceutically acceptable salt" refers to a salt of any therapeutic agent disclosed herein, which salt can include any of a variety of organic and inorganic counter ions known in the art and which salt is pharmaceutically acceptable. When the therapeutic agent contains an acidic functionality, various exemplary embodiments of counter ions are sodium, potassium, calcium, magnesium, ammonium, tetraalkylammonium, and the like. When the therapeutic agent contains a basic functionality, a pharmaceutically acceptable salt can include as a counter ion, by way of example, an organic or inorganic acid, such as hydrochloride, hydrobromide, tartrate, mesylate, acetate, maleate, oxalate, and the like. Illustrative salts include, but are not limited to, sulfate, citrate, acetate, chloride, bromide, iodide, nitrate, bisulfate, phosphate, acid phosphate, lactate, salicylate, acid citrate, tartrate, oleate, tannate, pantothenate, bitartrate, ascorbate, succinate, maleate, besylate, fumarate, gluconate, glucaronate, saccharate, formate, benzoate, glutamate, methanesulfonate, ethanesulfonate, benzenesulfonate, and p-toluenesulfonate salts. Accordingly, a salt can be prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl-N-ethylamine; diethylamine; triethylamine; mono-, bis-, or tris-(2-hydroxy-lower-alkyl amines), such as mono-, bis-, or tris-(2-hydroxyethyl)amine, 2-hydroxy-tert-butylamine, or tris-(hydroxymethyl)methylamine, N,N-di-lower-alkyl-N-(hydroxy-lower-alkyl)-amines, such as N,N-dimethyl-N-(2-hydroxyethyl)amine, or tri-(2-hydroxyethyl)amine; N-methyl-D-glucamine; and amino acids such as arginine, lysine, and the like. A salt can also be prepared from a compound of any one of the formulae disclosed herein having a basic functional group, such as an amino functional group, and a pharmaceutically acceptable inorganic or organic acid. Suitable acids include hydrogen sulfate, citric acid, acetic acid, hydrochloric acid (HCl), hydrogen bromide (HBr), hydrogen iodide (HI), nitric acid, phosphoric acid, lactic acid, salicylic acid, tartaric acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

"Pharmaceutically acceptable excipient" refers to any substance, not itself a therapeutic agent, used as a carrier, diluent, adjuvant, binder, and/or vehicle for delivery of a therapeutic agent to a patient, or added to a pharmaceutical composition to improve its handling or storage properties or to permit or facilitate formation of a compound or pharmaceutical composition into a unit dosage form for administration. Pharmaceutically acceptable excipients are known in the pharmaceutical arts and are disclosed, for example, in Gennaro, Ed., *Remington: The Science and Practice of Pharmacy*, 20$^{th}$ Ed. (Lippincott Williams & Wilkins, Baltimore, Md., 2000) and *Handbook of Pharmaceutical Excipients*, American Pharmaceutical Association, Washington, D.C., (e.g., 1$^{st}$, 2$^{nd}$ and 3$^{rd}$ Eds., 1986, 1994 and 2000, respectively). As will be known to those in the art, pharmaceutically acceptable excipients can provide a variety of functions and can be described as wetting agents, buffering agents, suspending agents, lubricating agents, emulsifiers, disintegrants, absorbents, preservatives, surfactants, colorants, flavorants, and sweeteners. Examples of pharmaceutically acceptable excipients include without limitation: (1) sugars, such as lactose, glucose and sucrose, (2) starches, such as corn starch and potato starch, (3) cellulose and its derivatives, such as sodium carboxymethyl cellulose, ethyl cellulose, cellulose acetate, hydroxypropylmethylcellulose, hydroxypropylcellulose, microcrystalline cellulose, and croscarmellose, such as or croscarmellose sodium, (4) powdered tragacanth, (5) malt, (6) gelatin, (7) talc, (8) excipients, such as cocoa butter and suppository waxes, (9) oils, such as peanut oil, cottonseed oil, safflower oil, sesame oil, olive oil, corn oil and soybean oil, (10) glycols, such as propylene glycol, (11) polyols, such as glycerin, sorbitol, mannitol and polyethylene glycol, (12) esters, such as ethyl oleate and ethyl laurate, (13) agar, (14) buffering agents, such as magnesium hydroxide and aluminum hydroxide, (15) alginic acid, (16) pyrogen-free water, (17) isotonic saline, (18) Ringer's solution, (19) ethyl alcohol, (20) pH buffered solutions, (21) polyesters, polycarbonates and/or polyanhydrides, and (22) other non-toxic compatible substances employed in pharmaceutical formulations.

"Unit dosage form" refers to a physically discrete unit suitable as a unitary dosage for a human or an animal. Each unit dosage form can contain a predetermined amount of a therapeutic agent calculated to produce a desired effect.

Unless clearly indicated otherwise, a "patient" refers to an animal, such as a mammal, including but not limited to a human. Hence, the methods disclosed herein can be useful in human therapy and veterinary applications. In particular embodiments, the patient is a mammal. In certain embodiments, the patient is a human.

"Effective amount" refers to such amount of a therapeutic agent or a pharmaceutically acceptable salt thereof, which in combination with its parameters of efficacy and potential for toxicity, as well as based on the knowledge of the practicing specialist, should be effective in a given therapeutic form. As is understood in the art, an effective amount can be administered in one or more doses.

"Treatment", "treating" and the like is an approach for obtaining a beneficial or desired result, including clinical results. For purposes of this disclosure, beneficial or desired results include but are not limited to inhibiting and/or suppressing the onset and/or development of a condition or reducing the severity of such condition, such as reducing the number and/or severity of symptoms associated with the condition, increasing the quality of life of those suffering from the condition, decreasing the dose of other medications required to treat the condition, enhancing the effect of another medication a patient is taking for the condition, and/or prolonging survival of patients having the condition.

"Prevent", "preventing" and the like refers to reducing the probability of developing a condition in a patient who does not have, but is at risk of developing a condition. A patient "at risk" may or may not have a detectable condition, and may or may not have displayed a detectable condition prior to the treatment methods disclosed herein. "At risk" denotes that a patient has one or more so-called risk factors, which are measurable parameters that correlate with development of a condition and are known in the art. A patient having one or more of these risk factors has a higher probability of developing the condition than a patient without such risk factor(s).

"Positive inotrope" refers to an agent that causes an increase in myocardial contractile function. Exemplary positive inotropes are a beta-adrenergic receptor agonist, an inhibitor of phosphodiesterase activity, and calcium-sensitizers. Beta-adrenergic receptor agonists include, among others, dopamine, dobutamine, terbutaline, and isoproterenol. Analogs and derivatives of such compounds are also included within positive inotropes. For example, U.S. Pat. No. 4,663,351 discloses a dobutamine prodrug that can be administered orally.

A condition that is "responsive to nitroxyl therapy" includes any condition in which administration of a compound that donates an effective amount of nitroxyl under physiological conditions treats and/or prevents the condition, as those terms are defined herein. A condition whose symptoms are suppressed or diminished upon administration of nitroxyl donor is a condition responsive to nitroxyl therapy.

"Pulmonary hypertension" or "PH" refers to a condition in which the pulmonary arterial pressure is elevated. The current hemodynamic definition of PH is a mean pulmonary arterial pressure ("MPAP") at rest of greater than or equal to 25 mmHg. Badesch et al., *J. Amer. Coll. Cardiol.* 54(Suppl.): S55-S66 (2009).

"N/A" means not assessed.

"$(C_1-C_6)$alkyl" refers to saturated linear and branched hydrocarbon structures having 1, 2, 3, 4, 5, or 6 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of $(C_1-C_6)$alkyl groups include methyl, ethyl, n-propyl, iso-propyl, n-butyl, tert-butyl, n-hexyl, and the like.

"$(C_2-C_6)$alkyl" refers to saturated linear and branched hydrocarbon structures having 2, 3, 4, 5, or 6 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of $(C_2-C_6)$alkyl groups include ethyl, n-propyl, iso-propyl, n-butyl, tert-butyl, n-hexyl, and the like.

"$(C_1-C_4)$alkyl" refers to saturated linear and branched hydrocarbon structures having 1, 2, 3, or 4 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of $(C_1-C_4)$alkyl groups include methyl, ethyl, n-propyl, iso-propyl, n-butyl, tert-butyl, and the like.

"$(C_2-C_4)$alkenyl" refers to a straight-chain or branched unsaturated hydrocarbon radical having 2, 3, or 4 carbon atoms and a double bond in any position, e.g., ethenyl, 1-propenyl, 2-propenyl (allyl), 1-butenyl, 2-butenyl, 3-butenyl, 1-methylethenyl, 1-methyl-1-propenyl, 2-methyl-2-propenyl, 2-methyl-1-propenyl, 1-methyl-2-propenyl, and the like.

"$(C_3-C_6)$cycloalkyl" refers to a saturated cyclic hydrocarbon containing 3, 4, 5, or 6 ring carbon atoms. Examples of $(C_3-C_6)$cycloalkyl groups include cyclopropyl, cyclobutyl, cyclopentyl, cyclohexyl, and the like.

"$(C_1-C_4)$perhaloalkyl" refers to a $(C_1-C_4)$alkyl group wherein every hydrogen atom is replaced by halo, each halo being independently selected. Examples of $(C_1-C_4)$perhaloalkyl groups include —$CF_3$, —$CCl_3$, —$CF_2CF_3$, —$CCl_2CF_3$, —$CClFCClF_2$, —$CF(CF_3)_2$, —$CBr(CF_3)$ ($CFCl_2$), and the like.

"$(C_1-C_4)$haloalkyl" refers to a $(C_1-C_4)$alkyl group wherein at least one hydrogen atom is replaced by halo but wherein the $(C_1-C_4)$haloalkyl contains few halos than a $(C_1-C_4)$perhaloalkyl having the same number of carbon atoms as the $(C_1-C_4)$haloalkyl. Each halo of a $(C_1-C_4)$ haloalkyl is independently selected. Examples of $(C_1-C_4)$ haloalkyl groups include —$CHF_2$, —$CH_2F$, —$CHFCl$, —$CH_2CF_3$, —$CHClCHF_2$, —$CHFCHClF$, —$CH(CF_3)_2$, —$CH(CF_3)(CH_3)$, —$CBr(CHF_2)(CHCl_2)$, and the like.

"$(C_1-C_6)$alkoxy" refers to —O—$(C_1-C_6)$alkyl. Examples of $(C_1-C_6)$alkoxy groups include methoxy, ethoxy, propoxy, n-propoxy, iso-propoxy, butoxy, n-butoxy, sec-butoxy, tert-butoxy, pentoxy, hexyloxy, and the like.

"$(C_1$-$C_4)$alkoxy" refers to —O—$(C_1$-$C_4)$alkyl. Examples of $(C_1$-$C_4)$alkoxy groups include methoxy, ethoxy, propoxy, n-propoxy, iso-propoxy, butoxy, n-butoxy, sec-butoxy, tert-butoxy, and the like.

"$(C_1$-$C_4)$haloalkoxy" refers to —O—$(C_1$-$C_4)$haloalkyl. Examples of $(C_1$-$C_4)$haloalkoxy groups include —OCHF$_2$, —OCH$_2$F, —OCHFCl, —OCH$_2$CF$_3$, —OCHClCHF$_2$, —OCHFCHClF, —OCH(CF$_3$)$_2$, —OCH(CF$_3$)(CH$_3$), —OCBr(CHF$_2$)(CHCl$_2$), and the like.

"$(C_1$-$C_4)$perhaloalkoxy" refers to —O—$(C_1$-$C_4)$perhaloalkyl. Examples of $(C_1$-$C_4)$perhaloalkoxy groups include —OCF$_3$, —OCCl$_3$, —OCF$_2$CF$_3$, —OCCl$_2$CF$_3$, —OCClFCClF$_2$, —OCF(CF$_3$)$_2$, —OCBr(CF$_3$)(CFCl$_2$), and the like.

"$(C_1$-$C_6)$alkylsulfanyl" refers to —S—$(C_1$-$C_6)$alkyl. Examples of $(C_1$-$C_6)$alkylsulfanyl groups include methylsulfanyl, ethylsulfanyl, propylsulfanyl, n-propylsulfanyl, iso-propylsulfanyl, butylsulfanyl, n-butylsulfanyl, sec-butylsulfanyl, tert-butylsulfanyl, pentylsulfanyl, hexylsulfanyl, and the like.

"$(C_1$-$C_4)$haloalkylsulfanyl" refers to —S—$(C_1$-$C_4)$haloalkyl. Examples of $(C_1$-$C_4)$haloalkylsulfanyl groups include —SCHF$_2$, —SCH$_2$F, —SCHFCl, —SCH$_2$CF$_3$, —SCHClCHF$_2$, —SCHFCHClF, —SCH(CF$_3$)$_2$, —SCH(CF$_3$)(CH$_3$), —SCBr(CHF$_2$)(CHCl$_2$), and the like.

"$(C_1$-$C_4)$perhaloalkylsulfanyl" refers to —S—$(C_1$-$C_4)$perhaloalkyl. Examples of $(C_1$-$C_4)$perhaloalkylsulfanyl groups include —SCF$_3$, —SCCl$_3$, —SCF$_2$CF$_3$, —SCCl$_2$CF$_3$, —SCClFCClF$_2$, —SCF(CF$_3$)$_2$, —SCBr(CF$_3$)(CFCl$_2$), and the like.

"$(C_1$-$C_6)$alkylsulfinyl" refers to —S(O)—$(C_1$-$C_6)$alkyl. Examples of $(C_1$-$C_6)$alkylsulfinyl groups include methylsulfinyl, ethylsulfinyl, propylsulfinyl, n-propylsulfinyl, iso-propylsulfinyl, butylsulfinyl, n-butylsulfinyl, sec-butylsulfinyl, tert-butylsulfinyl, pentylsulfinyl, hexylsulfinyl, and the like.

"$(C_1$-$C_6)$alkylsulfonyl" refers to —S(O)$_2$—$(C_1$-$C_6)$alkyl. Examples of $(C_1$-$C_6)$alkylsulfonyl groups include methylsulfonyl, ethylsulfonyl, propylsulfonyl, n-propylsulfonyl, iso-propylsulfonyl, butylsulfonyl, n-butylsulfonyl, sec-butylsulfonyl, tert-butylsulfonyl, pentylsulfonyl, hexylsulfonyl, and the like.

"$(C_3$-$C_6)$cycloalkylsulfonyl" refers to —S(O)$_2$—$(C_3$-$C_6)$cycloalkyl. Examples of $(C_3$-$C_6)$cycloalkylsulfonyl groups include —S(O)$_2$-cyclopropyl, —S(O)$_2$-cyclobutyl, —S(O)$_2$-cyclopentyl, —S(O)$_2$-cyclohexyl, and the like.

"$(C_1$-$C_4)$perhaloalkylsulfinyl" refers to —S(O)—$(C_1$-$C_4)$perhaloalkyl. Examples of $(C_1$-$C_4)$perhaloalkylsulfinyl groups include —S(O)—CF$_3$, —S(O)—CCl$_3$, —S(O)—CF$_2$CF$_3$, —S(O)—CCl$_2$CF$_3$, —S(O)—CClFCClF$_2$, —S(O)—CClFCClF$_2$, —S(O)—CClFCClF$_2$, —S(O)—CF(CF$_3$)$_2$, —S(O)—CBr(CF$_3$)(CFCl$_2$), and the like.

"$(C_1$-$C_4)$perhaloalkylsulfonyl" refers to —S(O)$_2$—$(C_1$-$C_4)$perhaloalkyl. Examples of $(C_1$-$C_4)$perhaloalkylsulfonyl groups include —S(O)$_2$—CF$_3$, —S(O)$_2$—CCl$_3$, —S(O)$_2$—CF$_2$CF$_3$, —S(O)$_2$—CCl$_2$CF$_3$, —S(O)$_2$—CClFCClF$_2$, —S(O)$_2$—CClFCClF$_2$, —S(O)$_2$—CClFCClF$_2$, —S(O)$_2$—CF(CF$_3$)$_2$, —S(O)$_2$—CBr(CF$_3$)(CFCl$_2$), and the like.

"$(C_1$-$C_4)$haloalkylsulfinyl" refers to —S(O)—$(C_1$-$C_4)$haloalkyl. Examples of $(C_1$-$C_4)$haloalkylsulfinyl groups include —S(O)—CHF$_2$, —S(O)—CH$_2$F, —S(O)—CHFCl, —S(O)—CH$_2$CF$_3$, —S(O)—CHClCHF$_2$, —S(O)—CHFCHClF, —S(O)—CH(CF$_3$)$_2$, —S(O)—CH(CF$_3$)(CH$_3$), —S(O)—CBr(CHF$_2$)(CHCl$_2$), and the like.

"$(C_1$-$C_4)$haloalkylsulfonyl" refers to —S(O)$_2$—$(C_1$-$C_4)$haloalkyl. Examples of $(C_1$-$C_4)$haloalkylsulfonyl groups include —S(O)$_2$—CHF$_2$, —S(O)$_2$—CH$_2$F, —S(O)$_2$—CHFCl, —S(O)$_2$—CH$_2$CF$_3$, —S(O)$_2$—CHClCHF$_2$, —S(O)$_2$—CHFCHClF, —S(O)$_2$—CH(CF$_3$)$_2$, —S(O)$_2$—CH(CF$_3$)(CH$_3$), —S(O)$_2$—CBr(CHF$_2$)(CHCl$_2$), and the like.

"N—$(C_1$-$C_6)$alkylaminosulfonyl" refers to —S(O)$_2$—NH—$(C_1$-$C_6)$alkyl. Examples of N—$(C_1$-$C_6)$alkylaminosulfonyl groups include —S(O)$_2$—NH-methyl, —S(O)$_2$—NH-ethyl, —S(O)$_2$—NH-n-propyl, —S(O)$_2$—NH-iso-propyl, —S(O)$_2$—NH-n-butyl, —S(O)$_2$—NH-sec-butyl, —S(O)$_2$—NH-iso-butyl, —S(O)$_2$—NH-tert-butyl, —S(O)$_2$—NH-n-hexyl, and the like.

"N,N-di$(C_1$-$C_6)$alkylaminosulfonyl" refers to —S(O)$_2$—N—(($C_1$-$C_6)$alkyl)$_2$ wherein each $(C_1$-$C_6)$alkyl is independently selected. Examples of N,N-di$(C_1$-$C_6)$alkylaminosulfonyl groups include —S(O)$_2$—N(methyl)$_2$, —S(O)$_2$—N(methyl)(ethyl), —S(O)$_2$—N(ethyl)$_2$, —S(O)$_2$—N(methyl)(n-propyl), —S(O)$_2$—N(ethyl)(iso-propyl), —S(O)$_2$—N(methyl)(n-butyl), —S(O)$_2$—N(ethyl)(sec-butyl), —S(O)$_2$—N(iso-propyl)(iso-butyl), —S(O)$_2$—N(tert-butyl)$_2$, —S(O)$_2$—N(methyl)(n-hexyl), and the like.

"$(C_5$-$C_7)$heterocycloalkyl" refers to a 5-, 6-, or 7-membered, saturated or partially unsaturated, monocyclic-heterocycle containing 1, 2, 3, or 4 ring heteroatoms each independently selected from nitrogen, oxygen, and sulfur, wherein said nitrogen and sulfur heteroatoms may optionally be oxidized and the nitrogen heteroatom may optionally be quaternized. A heterocycloalkyl group can be attached to the parent structure through a carbon or a heteroatom. Examples of $(C_5$-$C_7)$heterocycloalkyl groups include pyrrolidinyl, piperidinyl, piperazinyl, tetrahydro-oxazinyl, tetrahydrofuranyl, thiolanyl, dithiolanyl, pyrrolinyl, pyrazolinyl, pyrazolidinyl, imidazolinyl, imidazolidinyl, tetrahydrofuranone, γ-butyrolactone, 2H-pyranyl, 4H-pyranyl, dioxolanyl, tetrahydropyranyl, dioxanyl, dihydrothiophenyl, morpholinyl, thiomorpholinyl, oxazinyl, tetrahydro-oxazinyl, 1,2,3-triazinanyl, and the like.

"(5- or 6-membered)heteroaryl" refers to a monocyclic aromatic heterocycle ring of 5 or 6 members, i.e., a monocyclic aromatic ring comprising at least one ring heteroatom, e.g., 1, 2, 3, or 4 ring heteroatoms, each independently selected from nitrogen, oxygen, and sulfur. When the (5- or 6-membered)heteroaryl comprises a nitrogen or sulfur atom(s), the nitrogen atom or sulfur atom(s) are optionally oxidized to form the N-oxide or S-oxide(s). A (5- or 6-membered)heteroaryl group can be attached to the parent structure through a carbon or heteroatom. Examples of (5- or 6-membered)heteroaryls include pyridyl, pyrrolyl, pyrazolyl, furyl, imidazolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, thiophenyl, and the like.

"$(C_6$-$C_{10})$aryl" refers to a monovalent aromatic hydrocarbon group which may be monocyclic, bicyclic or tricyclic, wherein at least one ring in the system is aromatic and wherein each ring in the system contains 3, 4, 5, 6 or 7 ring members. Examples of $(C_6$-$C_{10})$aryl groups include without limitation phenyl, naphthyl, indanyl, indenyl and tetralinyl. In some embodiments, the aryl is phenyl.

Unless clearly indicated otherwise, each substituent of a "substituted phenyl", "phenyl substituted with 1, 2, or 3 independently selected substituent(s)", "monosubstituted phenyl", "disubstituted phenyl", "trisubstituted phenyl", and the like is independently selected from halo, $(C_1$-$C_6)$alkyl, ($C_1$-$C_4$)haloalkyl, ($C_1$-$C_4$)perhaloalkyl, ($C_1$-$C_6$)alkoxy, ($C_1$-$C_4$)haloalkoxy, ($C_1$-$C_4$)perhaloalkoxy, C(=O)OH, C(=O)O($C_1$-$C_6$)alkyl, C(=O)NR$^4$R$^5$, C(=O)—($C_5$-$C_7$)heterocycloalkyl, ($C_5$-$C_7$)heterocycloalkyl, ($C_1$-$C_6$)alkylsulfanyl, ($C_1$-$C_6$)alkylsulfinyl, ($C_1$-$C_6$)alkylsulfonyl, ($C_1$-$C_4$)haloalkylsulfinyl, ($C_1$-$C_4$)haloalkylsulfonyl, ($C_1$-$C_4$)perhaloalkylsulfinyl, ($C_1$-$C_4$)perhaloalkylsulfonyl, —S(O)$_2$—NH$_2$, S(O)$_2$—NR$^6$R$^7$, S(O)$_2$-phenyl, S(O)$_2$—($C_5$-$C_7$)heterocycloalkyl, S(=O)(=NR$^8$)($C_1$-$C_6$)alkyl, NR$^4$R$^5$, N—($C_1$-$C_6$)alkylaminosulfonyl, and N,N-di($C_1$-$C_6$)alkylaminosulfonyl, wherein said ($C_5$-$C_7$)heterocycloalkyl is unsubstituted or substituted with 1 or 2 substituent(s) independently selected from halo or ($C_1$-$C_6$)alkyl.

"Halo" or "halogen" refers to fluoro (—F), chloro (—Cl), bromo (—Br) and iodo (—I).

A compound of the disclosure can contain one, two, or more asymmetric centers and thus can give rise to enantiomers, diastereomers, and other stereoisomeric forms. The disclosure encompasses compounds with all such possible forms, as well as their racemic and resolved forms or any mixture thereof, unless specifically otherwise indicated. When a compound of the disclosure contains an olefinic double bond, a C=N double bond, or any other center of geometric asymmetry, it is intended to include all "geometric isomers", e.g., both Z and E geometric isomers, unless specifically otherwise indicated. All "tautomers", e.g., amine-imine, enamine-enimine, enamine-imine, urea-isourea, ketone-enol, amide-imidic acid, lactam-lactim, are intended to be encompassed by the disclosure as well unless specifically otherwise indicated.

3.2 Compounds of the Disclosure

One aspect of the disclosure provides a compound of formula (Ia)

(Ia)

or a pharmaceutically acceptable salt thereof, wherein:

R$^1$ is ($C_1$-$C_6$)alkyl, unsubstituted (5- or 6-membered) heteroaryl or unsubstituted phenyl, wherein said alkyl is unsubstituted or substituted with C(=O)OH;

R$^2$ is phenyl wherein said phenyl is unsubstituted or substituted with 1, 2, 3, 4, or 5 substituent(s) independently selected from halo, ($C_1$-$C_6$)alkyl, ($C_1$-$C_4$)haloalkyl, ($C_1$-$C_4$)perhaloalkyl, ($C_1$-$C_6$)alkoxy, ($C_1$-$C_4$)haloalkoxy, ($C_1$-$C_4$)perhaloalkoxy, —C(=O)OH, —C(=O)O($C_1$-$C_6$)alkyl, —C(=O)NR$^4$R$^5$, —C(=O)—($C_5$-$C_7$)heterocycloalkyl, ($C_5$-$C_7$)heterocycloalkyl, ($C_1$-$C_6$)alkylsulfanyl, ($C_1$-$C_4$)haloalkylsulfanyl, ($C_1$-$C_4$)perhaloalkylsulfanyl, ($C_1$-$C_6$)alkylsulfinyl, ($C_1$-$C_6$)alkylsulfonyl, ($C_3$-$C_6$)cycloalkylsulfonyl, ($C_1$-$C_4$)haloalkylsulfinyl, ($C_1$-$C_4$)haloalkylsulfonyl, ($C_1$-$C_4$)perhaloalkylsulfinyl, ($C_1$-$C_4$)perhaloalkylsulfonyl, —S(O)$_2$—NH$_2$, —S(O)$_2$—NR$^6$R$^7$, —S(O)$_2$-phenyl, —S(O)$_2$—($C_5$-$C_7$)heterocycloalkyl, —S(=O)(=NR$^8$)($C_1$-$C_6$)alkyl, —NR$^4$R$^5$, N—($C_1$-$C_6$)alkylaminosulfonyl, and N,N-di($C_1$-$C_6$)alkylaminosulfonyl, wherein said ($C_5$-$C_7$)heterocycloalkyl is unsubstituted or substituted with 1 or 2 substituent(s) independently selected from halo or ($C_1$-$C_6$)alkyl;

R$^4$ and R$^6$ are independently H or ($C_1$-$C_6$)alkyl;

R$^5$ is H, ($C_1$-$C_6$)alkyl or ($C_1$-$C_6$)alkylsulfonyl, wherein said alkyl is unsubstituted or substituted with C(=O)OH or wherein a methylene group of said alkyl is optionally replaced with an oxygen atom;

R$^7$ is H or ($C_1$-$C_6$)alkyl, wherein a methylene group of said alkyl is optionally replaced with an oxygen atom;

R$^8$ is H, —(C=O)($C_1$-$C_6$)alkyl or —(C=O)($C_1$-$C_4$)perhaloalkyl; and

R$^3$ is ($C_1$-$C_6$)alkyl or —C(=NOR$^9$)R$^{10}$ wherein R$^9$ and R$^{10}$ are independently selected from ($C_1$-$C_6$)alkyl.

In one embodiment, R$^1$ is unsubstituted (5- or 6-membered)heteroaryl, unsubstituted phenyl, methyl, ethyl, iso-propyl, tert-butyl or methylcarboxylic acid. In one embodiment, R$^1$ is unsubstituted (5- or 6-membered)heteroaryl, unsubstituted phenyl, methyl, ethyl, iso-propyl or tert-butyl. In another embodiment, R$^1$ is unsubstituted (5- or 6-membered)heteroaryl, unsubstituted phenyl, methyl, ethyl, or iso-propyl. In another embodiment, R$^1$ is unsubstituted (5- or 6-membered)heteroaryl, unsubstituted phenyl, methyl, ethyl, or tert-butyl. In one embodiment, R$^1$ is unsubstituted (5- or 6-membered)heteroaryl, unsubstituted phenyl, methyl, ethyl or methylcarboxylic acid. In another embodiment, R$^1$ is unsubstituted (5- or 6-membered)heteroaryl, unsubstituted phenyl, methyl, iso-propyl, or tert-butyl. In one embodiment, R$^1$ is unsubstituted (5- or 6-membered) heteroaryl, unsubstituted phenyl, methyl, iso-propyl, or methylcarboxylic acid. In one embodiment, R$^1$ is unsubstituted (5- or 6-membered)heteroaryl, unsubstituted phenyl, methyl, tert-butyl or methylcarboxylic acid. In another embodiment, R$^1$ is unsubstituted (5- or 6-membered)heteroaryl, unsubstituted phenyl, ethyl, iso-propyl, or tert-butyl. In one embodiment, R$^1$ is unsubstituted (5- or 6-membered) heteroaryl, unsubstituted phenyl, ethyl, iso-propyl or methylcarboxylic acid. In one embodiment, R$^1$ is unsubstituted (5- or 6-membered)heteroaryl, unsubstituted phenyl, ethyl, tert-butyl or methylcarboxylic acid. In another embodiment, R$^1$ is unsubstituted (5- or 6-membered)heteroaryl, unsubstituted phenyl, methyl, or ethyl. In another embodiment, R$^1$ is unsubstituted (5- or 6-membered)heteroaryl, unsubstituted phenyl, methyl, or iso-propyl. In another embodiment, R$^1$ is unsubstituted (5- or 6-membered)heteroaryl, unsubstituted phenyl, methyl, or tert-butyl. In one embodiment, R$^1$ is unsubstituted (5- or 6-membered)heteroaryl, unsubstituted phenyl, methyl or methylcarboxylic acid. In another embodiment, R$^1$ is unsubstituted (5- or 6-membered)heteroaryl, unsubstituted phenyl, ethyl, or iso-propyl. In another embodiment, R$^1$ is unsubstituted (5- or 6-membered)heteroaryl, unsubstituted phenyl, ethyl, or tert-butyl. In one embodiment, R$^1$ is unsubstituted (5- or 6-membered) heteroaryl, unsubstituted phenyl, ethyl or methylcarboxylic acid. In another embodiment, R$^1$ is unsubstituted (5- or 6-membered)heteroaryl, unsubstituted phenyl, iso-propyl, or tert-butyl. In one embodiment, R$^1$ is unsubstituted (5- or 6-membered)heteroaryl, unsubstituted phenyl, iso-propyl or methylcarboxylic acid. In one embodiment, R$^1$ is unsubstituted (5- or 6-membered)heteroaryl, unsubstituted phenyl, tert-butyl or methylcarboxylic acid. In another embodiment, R$^1$ is unsubstituted (5- or 6-membered)heteroaryl, unsubstituted phenyl or methyl. In another embodiment, R$^1$ is unsubstituted (5- or 6-membered)heteroaryl, unsubstituted phenyl or ethyl. In another embodiment, R$^1$ is unsubstituted (5- or 6-membered)heteroaryl, unsubstituted phenyl or iso-propyl. In another embodiment, R$^1$ is unsubstituted (5- or 6-membered)heteroaryl, unsubstituted phenyl or tert-butyl. In one embodiment, R$^1$ is unsubstituted (5- or 6-membered) heteroaryl, unsubstituted phenyl, or methylcarboxylic acid.

In another embodiment, $R^1$ is unsubstituted phenyl. In another embodiment, $R^1$ is unsubstituted (5- or 6-membered)heteroaryl.

In another embodiment, $R^1$ is methyl, ethyl, iso-propyl, tert-butyl or methylcarboxylic acid. In another embodiment, $R^1$ is methyl, ethyl, or iso-propyl. In another embodiment, $R^1$ is methyl, ethyl, or tert-butyl. In another embodiment, $R^1$ is methyl, ethyl or methylcarboxylic acid. In another embodiment, $R^1$ is methyl, iso-propyl, or tert-butyl. In another embodiment, $R^1$ is methyl, iso-propyl, or methylcarboxylic acid. In another embodiment, $R^1$ is methyl, tert-butyl or methylcarboxylic acid. In another embodiment, $R^1$ is ethyl, iso-propyl, or tert-butyl. In another embodiment, $R^1$ is ethyl, iso-propyl or methylcarboxylic acid. In another embodiment, $R^1$ is ethyl, tert-butyl or methylcarboxylic acid. In another embodiment, $R^1$ is methyl or ethyl. In another embodiment, $R^1$ is methyl or iso-propyl. In another embodiment, $R^1$ is methyl or tert-butyl. In another embodiment, $R^1$ is methyl or methylcarboxylic acid. In another embodiment, $R^1$ is ethyl or iso-propyl. In another embodiment, $R^1$ is ethyl or tert-butyl. In another embodiment, $R^1$ is ethyl or methylcarboxylic acid. In another embodiment, $R^1$ is iso-propyl or tert-butyl. In another embodiment, $R^1$ is iso-propyl or methylcarboxylic acid. In another embodiment, $R^1$ is tert-butyl or methylcarboxylic acid. In another embodiment, $R^1$ is methyl. In another embodiment, $R^1$ is ethyl. In another embodiment, $R^1$ is propyl. In another embodiment, $R^1$ is iso-propyl. In another embodiment, $R^1$ is butyl. In another embodiment, $R^1$ is tert-butyl. In one embodiment, $R^1$ is methylcarboxylic acid.

In another embodiment, $R^2$ is phenyl substituted with 1, 2, or 3 independently selected substituent(s), at least one of which is halo. In another embodiment, $R^2$ is phenyl substituted with 1, 2, or 3 independently selected substituent(s), at least one of which is chloro. In another embodiment, $R^2$ is phenyl substituted with 1, 2, or 3 independently selected substituent(s), at least one of which is fluoro. In another embodiment, $R^2$ is phenyl substituted with 1, 2, or 3 independently selected substituent(s), at least one of which is $(C_1-C_6)$alkyl. In another embodiment, $R^2$ is phenyl substituted with 1, 2, or 3 independently selected substituent(s), at least one of which is methyl. In another embodiment, $R^2$ is phenyl substituted with 1, 2, or 3 independently selected substituent(s), at least one of which is $(C_1-C_4)$haloalkyl. In another embodiment, $R^2$ is phenyl substituted with 1, 2, or 3 independently selected substituent(s), at least one of which is $(C_1-C_4)$perhaloalkyl. In another embodiment, $R^2$ is phenyl substituted with 1, 2, or 3 independently selected substituent(s), at least one of which is perfluoromethyl. In another embodiment, $R^2$ is phenyl substituted with 1, 2, or 3 independently selected substituent(s), at least one of which is $(C_1-C_6)$alkoxy. In another embodiment, $R^2$ is phenyl substituted with 1, 2, or 3 independently selected substituent(s), at least one of which is methoxy. In another embodiment, $R^2$ is phenyl substituted with 1, 2, or 3 independently selected substituent(s), at least one of which is $(C_1-C_4)$perhaloalkoxy. In another embodiment, $R^2$ is phenyl substituted with 1, 2, or 3 independently selected substituent(s), at least one of which is $(C_1-C_4)$perfluoroalkoxy.

In another embodiment, $R^2$ is phenyl substituted with 1, 2, or 3 independently selected substituent(s), at least one of which is —C(=O)OH. In another embodiment, $R^2$ is phenyl substituted with 1, 2, or 3 independently selected substituent(s), at least one of which is —C(=O)O($C_1$-$C_6$)alkyl. In another embodiment, $R^2$ is phenyl substituted with 1, 2, or 3 independently selected substituent(s), at least one of which is —C(=O)OCH$_3$. In another embodiment, $R^2$ is phenyl substituted with 1, 2, or 3 independently selected substituent(s), at least one of which is —C(=O)NR$^4$R$^5$. In another embodiment, $R^2$ is phenyl substituted with 1, 2, or 3 independently selected substituent(s), at least one of which is —C(=O)N(CH$_3$)$_2$. In another embodiment, $R^2$ is phenyl substituted with 1, 2, or 3 independently selected substituent(s), at least one of which is —C(=O)NH$_2$. In another embodiment, $R^2$ is phenyl substituted with 1, 2, or 3 independently selected substituent(s), at least one of which is —C(=O)NH($C_1$-$C_6$)alkyl, wherein said alkyl is substituted with COOH. In another embodiment, $R^2$ is phenyl substituted with 1, 2, or 3 independently selected substituent(s), at least one of which is —C(=O)NH—($C_1$-$C_6$)alkylsulfonyl.

In another embodiment, $R^2$ is phenyl substituted with 1, 2, or 3 independently selected substituent(s), at least one of which is —C(=O)—($C_5$-$C_7$)heterocycloalkyl. In another embodiment, $R^2$ is phenyl substituted with 1, 2, or 3 independently selected substituent(s), at least one of which is —C(=O)-morpholinyl, —C(=O)-piperidinyl or —C(=O)-piperazinyl. In another embodiment, $R^2$ is phenyl substituted with 1, 2, or 3 independently selected substituent(s), at least one of which is —C(=O)-morpholinyl. In another embodiment, $R^2$ is phenyl substituted with 1, 2, or 3 independently selected substituent(s), at least one of which is —C(=O)-piperidinyl. In another embodiment, $R^2$ is phenyl substituted with 1, 2, or 3 independently selected substituent(s), at least one of which is —C(=O)-piperazinyl.

In another embodiment, $R^2$ is phenyl substituted with 1, 2, or 3 independently selected substituent(s), at least one of which is ($C_5$-$C_7$)heterocycloalkyl. In another embodiment, $R^2$ is phenyl substituted with 1, 2, or 3 independently selected substituent(s), at least one of which is morpholinyl, piperidinyl or piperazinyl. In another embodiment, $R^2$ is phenyl substituted with 1, 2, or 3 independently selected substituent(s), at least one of which is morpholinyl. In another embodiment, $R^2$ is phenyl substituted with 1, 2, or 3 independently selected substituent(s), at least one of which is piperidinyl. In another embodiment, $R^2$ is phenyl substituted with 1, 2, or 3 independently selected substituent(s), at least one of which is piperazinyl.

In another embodiment, $R^2$ is phenyl substituted with 1, 2, or 3 independently selected substituent(s), at least one of which is ($C_1$-$C_6$)alkylsulfanyl. In another embodiment, $R^2$ is phenyl substituted with 1, 2, or 3 independently selected substituent(s), at least one of which is methylsulfanyl. In another embodiment, $R^2$ is phenyl substituted with 1, 2, or 3 independently selected substituent(s), at least one of which is ($C_1$-$C_4$)perhaloalkylsulfanyl. In another embodiment, $R^2$ is phenyl substituted with 1, 2, or 3 independently selected substituent(s), at least one of which is trifluoromethylsulfanyl. In another embodiment, $R^2$ is phenyl substituted with 1, 2, or 3 independently selected substituent(s), at least one of which is ($C_1$-$C_6$)alkylsulfinyl. In another embodiment, $R^2$ is phenyl substituted with 1, 2, or 3 independently selected substituent(s), at least one of which is methylsulfinyl. In another embodiment, $R^2$ is phenyl substituted with 1, 2, or 3 independently selected substituent(s), at least one of which is ($C_1$-$C_6$)alkylsulfonyl. In another embodiment, $R^2$ is phenyl substituted with 1, 2, or 3 independently selected substituent(s), at least one of which is methylsulfonyl. In another embodiment, $R^2$ is phenyl substituted with 1, 2, or 3 independently selected substituent(s), at least one of which is ($C_3$-$C_6$)cycloalkylsulfonyl. In another embodiment, $R^2$ is phenyl substituted with 1, 2, or 3 independently selected substituent(s), at least one of which is cyclopropylsulfonyl.

In another embodiment, $R^2$ is phenyl substituted with 1, 2, or 3 independently selected substituent(s), at least one of which is $(C_1-C_4)$haloalkylsulfinyl. In another embodiment, $R^2$ is phenyl substituted with 1, 2, or 3 independently selected substituent(s), at least one of which is $(C_1-C_4)$haloalkylsulfonyl. In another embodiment, $R^2$ is phenyl substituted with 1, 2, or 3 independently selected substituent(s), at least one of which is $(C_1-C_4)$perhaloalkylsulfinyl. In another embodiment, $R^2$ is phenyl substituted with 1, 2, or 3 independently selected substituent(s), at least one of which is perhalomethylsulfinyl. In another embodiment, $R^2$ is phenyl substituted with 1, 2, or 3 independently selected substituent(s), at least one of which is perfluoromethylsulfinyl. In another embodiment, $R^2$ is phenyl substituted with 1, 2, or 3 independently selected substituent(s), at least one of which is $(C_1-C_4)$perhaloalkylsulfonyl. In another embodiment, $R^2$ is phenyl substituted with 1, 2, or 3 independently selected substituent(s), at least one of which is perhalomethylsulfonyl. In another embodiment, $R^2$ is phenyl substituted with 1, 2, or 3 independently selected substituent(s), at least one of which is perfluoromethylsulfonyl.

In another embodiment, $R^2$ is phenyl substituted with 1, 2, or 3 independently selected substituent(s), at least one of which is —S(O)$_2$—NR$^6$R$^7$. In another embodiment, $R^2$ is phenyl substituted with 1, 2, or 3 independently selected substituent(s), at least one of which is —S(O)$_2$—N(CH$_3$)(CH$_2$CH$_2$OCH$_3$), —S(O)$_2$—NH(CH$_2$CH$_2$OCH$_3$), —S(O)$_2$—N(CH$_3$)$_2$ or —S(O)$_2$—NH(CH$_3$).

In another embodiment, $R^2$ is phenyl substituted with 1, 2, or 3 independently selected substituent(s), at least one of which is —S(O)$_2$-phenyl. In another embodiment, $R^2$ is phenyl substituted with 1, 2, or 3 independently selected substituent(s), at least one of which is —S(O)$_2$—(C$_5$-C$_7$)heterocycloalkyl. In another embodiment, $R^2$ is phenyl substituted with 1, 2, or 3 independently selected substituent(s), at least one of which is —S(O)$_2$-morpholinyl, —S(O)$_2$-piperidinyl or —S(O)$_2$-piperazinyl. In another embodiment, $R^2$ is phenyl substituted with 1, 2, or 3 independently selected substituent(s), at least one of which is —S(O)$_2$-morpholinyl. In another embodiment, $R^2$ is phenyl substituted with 1, 2, or 3 independently selected substituent(s), at least one of which is —S(O)$_2$-piperidinyl. In another embodiment, $R^2$ is phenyl substituted with 1, 2, or 3 independently selected substituent(s), at least one of which is —S(O)$_2$-piperazinyl.

In another embodiment, $R^2$ is phenyl substituted with 1, 2, or 3 independently selected substituent(s), at least one of which is —S(=O)(=NR$^8$)(C$_1$-C$_6$)alkyl. In another embodiment, $R^2$ is phenyl substituted with 1, 2, or 3 independently selected substituent(s), at least one of which is —S(=O)(=NR$^8$)(CH$_3$). In another embodiment, $R^2$ is phenyl substituted with 1, 2, or 3 independently selected substituent(s), at least one of which is —S(=O)(=NH)(C$_1$-C$_6$)alkyl or —S(=O)(=NC(=O)CF$_3$)(C$_1$-C$_6$)alkyl. In another embodiment, $R^2$ is phenyl substituted with 1, 2, or 3 independently selected substituent(s), at least one of which is —S(=O)(=NH)(CH$_3$) or —S(=O)(=NC(=O)CF$_3$)(CH$_3$).

In another embodiment, $R^2$ is phenyl substituted with 1, 2, or 3 independently selected substituent(s), at least one of which is N,N-di(C$_1$-C$_6$)alkylaminosulfonyl. In another embodiment, $R^2$ is phenyl substituted with 1, 2, or 3 independently selected substituent(s), at least one of which is N,N-dimethylaminosulfonyl.

In another embodiment, $R^2$ is phenyl wherein the phenyl is unsubstituted or substituted with 1, 2, or 3 substituent(s) independently selected from halo, (C$_1$-C$_6$)alkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)—(C$_5$-C$_7$)heterocycloalkyl, (C$_5$-C$_7$)heterocycloalkyl, (C$_1$-C$_6$)alkylsulfanyl, (C$_1$-C$_4$)perhaloalkylsulfanyl, (C$_1$-C$_6$)alkylsulfinyl, (C$_1$-C$_6$)alkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$—(C$_5$-C$_7$)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl. In another embodiment, $R^2$ is phenyl wherein the phenyl is unsubstituted or substituted with 1, 2, or 3 substituent(s) independently selected from halo, (C$_1$-C$_6$)alkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)—(C$_5$-C$_7$)heterocycloalkyl, (C$_5$-C$_7$)heterocycloalkyl, (C$_1$-C$_6$)alkylsulfanyl, (C$_1$-C$_4$)perhaloalkylsulfanyl, (C$_1$-C$_6$)alkylsulfinyl, (C$_1$-C$_6$)alkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NR$^6$R$^7$, —S(O)$_2$-phenyl, —S(O)$_2$—(C$_5$-C$_7$)heterocycloalkyl, —S(=O)(=NR$^8$)(C$_1$-C$_6$)alkyl, —NR$^4$R$^5$, and N,N-di(C$_1$-C$_6$)alkylaminosulfonyl. In another embodiment, $R^2$ is phenyl wherein the phenyl is unsubstituted or substituted with 1, 2, or 3 substituent(s) independently selected from chloro, fluoro, bromo, trifluoromethyl, methyl, butyl, methylsulfanyl, methylsulfinyl, methylsulfonyl, ethylsulfonyl, propylsulfonyl, phenylsulfonyl, methylsulfonylcarbamyl, methoxy, carboxyl, methylsulfonylcarbamyl, formamidopropanoic acid, formamidoacetic acid, methoxycarbonyl, morpholinylcarbonyl, 4,4-difluoropiperidinylcarbonyl, trifluoromethoxy, trifluoromethylsulfinyl, trifluoromethylsulfonyl, trifluoromethylsulfanyl, morpholinylsulfonyl, 4,4-difluoropiperidinylsulfonyl, N,N-dimethylcarbamyl, (methyl)oxo-λ$^6$-sulfanylidene-2,2,2-trifluoroacetamide, methylsulfonimidoyl, isopropylsulfonimidoyl, (methoxyethyl)methylamino, (methoxyethyl)-N-methylaminosulfonyl, dimethylcarbamyl, carbamyl, and N,N-dimethylaminosulfonyl. In another embodiment, $R^2$ is phenyl wherein the phenyl is unsubstituted or substituted with 1, 2, or 3 substituent(s) independently selected from 2-chloro, 3-chloro, 4-chloro, 5-chloro, 2-fluoro, 3-fluoro, 4-fluoro, 5-fluoro, 2-bromo, 3-bromo, 4-bromo, 5-bromo, 2-trifluoromethyl, 3-trifluoromethyl, 4-trifluoromethyl, 2-methyl, 3-methyl, 4-methyl, 5-methyl, 2-butyl, 3-butyl, 4-butyl, 5-butyl, 4-methylsulfanyl, 2-methylsulfinyl, 4-methylsulfinyl, 3-methylsulfonyl, 4-methylsulfonyl, 4-ethylsulfonyl, 4-propylsulfonyl, 2-methoxy, 4-methoxy, 2-trifluoromethoxy, 4-trifluoromethoxy, 4-carboxyl, 4-methylsulfonylcarbamyl, 4-formamidopropanoic acid, 4-formamidoacetic acid, 4-methoxycarbonyl, 4-morpholinylcarbonyl, 4-(4,4-difluoropiperidinylcarbonyl), 4-isopropylsulfonyl, 4-trifluoromethylsulfanyl, 4-trifluoromethylsulfinyl, 4-trifluoromethylsulfonyl, 4-phenylsulfonyl, 4-morpholinylsulfonyl, 4-(4,4-difluoropiperidinyl)sulfonyl, 4-dimethylcarbamyl, 4-(methyl)oxo-λ$^6$-sulfanylidene-2,2,2-trifluoroacetamide, 4-methylsulfonimidoyl, 4-isopropylsulfonimidoyl, 4-(methoxyethyl)-N-methylaminosulfonyl, 4-carbamyl, and 4-N,N-dimethylaminosulfonyl.

In another embodiment, $R^2$ is monosubstituted phenyl substituted with halo, (C$_1$-C$_6$)alkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)—(C$_5$-C$_7$)heterocycloalkyl, (C$_1$-C$_6$)alkylsulfanyl, (C$_1$-C$_4$)perhaloalkylsulfanyl, (C$_1$-C$_6$)alkylsulfinyl, (C$_1$-C$_6$)alkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$—(C$_5$-C$_7$)heterocycloalkyl, —S(=O)(=NR$^8$)(C$_1$-C$_6$)alkyl, N—(C$_1$-C$_6$)alkylaminosulfonyl, or N,N-di(C$_1$-C$_6$)alkylaminosulfonyl. In another embodiment, R$^2$ is monosubstituted phenyl substituted with halo, (C$_1$-C$_6$) alkyl, (C$_1$-C$_4$)haloalkyl, (C$_1$-C$_4$)perhaloalkyl, (C$_1$-C$_6$) alkoxy, (C$_1$-C$_4$)perhaloalkoxy, —C(=O)OH, —C(=O)O(C$_1$-C$_6$)alkyl, —C(=O)NR$^4$R$^5$, —C(=O)—(C$_5$-C$_7$) heterocycloalkyl, (C$_5$-C$_7$)heterocycloalkyl, (C$_1$-C$_6$) alkylsulfanyl, (C$_1$-C$_4$)perhaloalkylsulfanyl, (C$_1$-C$_6$) alkylsulfinyl, (C$_1$-C$_6$)alkylsulfonyl, (C$_1$-C$_4$) haloalkylsulfinyl, (C$_1$-C$_4$)haloalkylsulfonyl, (C$_1$-C$_4$) perhaloalkylsulfinyl, (C$_1$-C$_4$)perhaloalkylsulfonyl, —S(O)$_2$—NR$^6$R$^7$, —S(O)$_2$-phenyl, —S(O)$_2$—(C$_5$-C$_7$)heterocycloalkyl, —S(=O)(=NR$^8$)(C$_1$-C$_6$)alkyl, —NR$^4$R$^5$, or N,N-di(C$_1$-C$_6$)alkylaminosulfonyl. In another embodiment, R$^2$ is monosubstituted phenyl substituted with chloro, fluoro, bromo, methyl, butyl, trifluoromethyl, methoxy, trifluoromethoxy, morpholinyl, piperazinyl, methylpiperazinyl, carboxyl, methylsulfonylcarbamyl, formamidopropanoic acid, formamidoacetic acid, methoxycarbonyl, morpholinylcarbonyl, 4,4-difluoropiperidinylcarbonyl, methylsulfanyl, methylsulfinyl, methylsulfonyl, ethylsulfonyl, propylsulfonyl, trifluoromethylsulfanyl, trifluoromethylsulfinyl, trifluoromethylsulfonyl, phenylsulfonyl, morpholinylsulfonyl, 4,4-difluoropiperidinylsulfonyl, dimethylcarbamyl, (methyl)oxo-λ$^6$-sulfanylidene-2,2,2-trifluoroacetamide, methylsulfonimidoyl, isopropylsulfonimidoyl, (methoxyethyl)-N-methyl-aminosulfonyl, carbamyl, methoxyethyl (methyl)amino and dimethylamino or N,N-dimethylaminosulfonyl. In another embodiment, R$^2$ is monosubstituted phenyl substituted with 2-chloro, 3-chloro, 4-chloro, 5-chloro, 2-fluoro, 3-fluoro, 4-fluoro, 5-fluoro, 4-bromo, 2-methyl, 3-methyl, 4-methyl, 5-methyl, 4-butyl, 4-t-butyl, 2-trifluoromethyl, 3-trifluoromethyl, 4-trifluoromethyl, 5-trifluoromethyl, 2-methoxy, 3-methoxy, 4-methoxy, 2-trifluoromethoxy, 4-trifluoromethoxy, 3-morpholin-4-yl, 3-(piperazin-1-yl), 3-(4-methylpiperazin-1-yl), 4-carboxyl, 4-methylsulfonylcarbamyl, 4-formamidopropanoic acid, 4-formamidoacetic acid, 4-methoxycarbonyl, 4-morpholinylcarbonyl, 4-(4,4-difluoropiperidinylcarbonyl), 4-methylsulfanyl, 2-methylsulfinyl, 4-methylsulfinyl, 3-methylsulfonyl, 4-methylsulfonyl, 4-ethylsulfonyl, 4-propylsulfonyl, 4-isopropylsulfonyl, 4-trifluoromethylsulfanyl, 4-trifluoromethylsulfinyl, 4-trifluoromethylsulfonyl, 4-phenylsulfonyl, 4-morpholinylsulfonyl, 4-(4,4-difluoropiperidinyl)sulfonyl, 4-dimethylcarbamyl, 4-(methyl)oxo-λ$^6$-sulfanylidene-2,2,2-trifluoroacetamide, 4-methylsulfonimidoyl, 4-isopropylsulfonimidoyl, 4-(methoxyethyl)-N-methyl-aminosulfonyl, 4-carbamyl, 4-methoxyethyl(methyl)amino, 3-dimethylamino or 4-N,N-dimethylaminosulfonyl.

In another embodiment, R$^2$ is disubstituted phenyl, each substituent being independently selected from halo, (C$_1$-C$_6$) alkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)—(C$_5$-C$_7$) heterocycloalkyl, (C$_5$-C$_7$)heterocycloalkyl, (C$_1$-C$_6$) alkylsulfanyl, (C$_1$-C$_4$)perhaloalkylsulfanyl, (C$_1$-C$_6$) alkylsulfinyl, (C$_1$-C$_6$)alkylsulfonyl, (C$_1$-C$_4$) haloalkylsulfinyl, (C$_1$-C$_4$)haloalkylsulfonyl, (C$_1$-C$_4$) perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$—(C$_5$-C$_7$)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl. In another embodiment, R$^2$ is disubstituted phenyl, each substituent being independently selected from halo, (C$_1$-C$_6$)alkyl, (C$_1$-C$_4$)perhaloalkyl, (C$_1$-C$_6$)alkoxy, (C$_5$-C$_7$)heterocycloalkyl, (C$_1$-C$_6$) alkylsulfinyl, (C$_1$-C$_6$)alkylsulfonyl and —NR$^4$R$^5$. In another embodiment, R$^2$ is disubstituted phenyl, each substituent being independently selected from chloro, fluoro, methyl, trifluoromethyl, methoxy, morpholinyl, piperazinyl, methylpiperazinyl, methylsulfinyl, methylsulfonyl, methoxyethyl (methyl)amino and dimethylamino. In another embodiment, R$^2$ is disubstituted phenyl, each substituent being independently selected from 2-chloro, 3-chloro, 4-chloro, 5-chloro, 3-fluoro, 4-fluoro, 5-fluoro, 3-methyl, 5-methyl, 3-trifluoromethyl, 5-trifluoromethyl, 2-methoxy, 3-methoxy, 4-methoxy, 3-morpholin-4-yl, 3-(piperazin-1-yl), 3-(4-methylpiperazin-1-yl), 4-methylsulfinyl, 3-methylsulfonyl, 4-methylsulfonyl, 4-methoxyethyl(methyl)amino and 3-dimethylamino.

In another embodiment, R$^2$ is trisubstituted phenyl, each substituent being independently selected from halo, (C$_1$-C$_6$) alkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)—(C$_5$-C$_7$) heterocycloalkyl, (C$_5$-C$_7$)heterocycloalkyl, (C$_1$-C$_6$) alkylsulfanyl, (C$_1$-C$_4$)perhaloalkylsulfanyl, (C$_1$-C$_6$) alkylsulfinyl, (C$_1$-C$_6$)alkylsulfonyl, (C$_1$-C$_4$) haloalkylsulfinyl, (C$_1$-C$_4$)haloalkylsulfonyl, (C$_1$-C$_4$) perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$—(C$_5$-C$_7$)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl. In another embodiment, R$^2$ is trisubstituted phenyl, each substituent being independently selected from halo, (C$_1$-C$_6$)alkyl, and (C$_1$-C$_6$)alkylsulfonyl. In another embodiment, R$^2$ is trisubstituted phenyl, each substituent being independently selected from fluoro, methyl and methylsulfonyl.

In another embodiment, R$^2$ is selected from unsubstituted phenyl, 4-chlorophenyl, 2-chlorophenyl, 3-chlorophenyl, 2,3-dichlorophenyl, 2,4-dichlorophenyl, 3,5-dichlorophenyl, 2-fluorophenyl, 4-fluorophenyl, 4-bromophenyl, 2-chloro-4-fluorophenyl, 2-methylphenyl, 4-butylphenyl, 4-t-butylphenyl, 3,5-dimethylphenyl, 4-methoxyphenyl, 2-methoxyphenyl, 2-trifluoromethoxyphenyl, 4-trifluoromethoxyphenyl, 4-methoxycarbonylphenyl, 4-carboxyl, 4-carbamylphenyl, 4-phenyl(formamido)propanoic acid, 4-phenyl(formamido)acetic acid, 4-N,N-dimethylcarbamylphenyl, 4-cyclopropylsulfonylphenyl, 4-phenylsulfonyl, 4-(4-4-difluoropiperidin-1-yl)sulfonylphenyl, 4-(isopropylsulfonimidoyl)phenyl, 4-morpholine-4-sulfonylphenyl, 4-morpholine-4-carbonylphenyl, 4-(4,4-difluoropiperidine-1-carbonyl)phenyl, 3-morpholinyl-4-methylsulfonylphenyl, 3-(methoxyethyl)methylamino-4-methylsulfonylphenyl, 3,5-difluoro-4-methylsulfonylphenyl, 2-ethoxy-4-fluorophenyl, 3-fluoro-4-methoxyphenyl, 2-trifluoromethylphenyl, 3-trifluoromethylphenyl, 4-trifluoromethylphenyl, 3,5-bis(trifluoromethyl)phenyl, 3-methylsulfonylphenyl, 4-methylsulfanylphenyl, 4-trifluoromethylsulfanylphenyl, 2-methylsulfinylphenyl, 4-methylsulfinylphenyl, 3-fluoro-4-methylsulfinylphenyl, 3-methyl-4-methylsulfinylphenyl, 4-methylsulfonylphenyl, 4-ethylsulfonylphenyl, 4-isopropylsulfonylphenyl, 4-morpholine-4-methylsulfonylphenyl, 3-(4-methylpiperazin-1-yl)-4-methylsulfonylphenyl, 3-piperazin-1-yl-4-methylsulfonylphenyl, 3-methoxy-4-methylsulfonylphenyl, 3-trifluoromethyl-4-methylsulfonylphenyl, 3-fluoro-4-methylsulfonylphenyl, 3-chloro-4-methylsulfonylphenyl, 3-methyl-4-methylsulfonylphenyl, 3,4-dimethylsulfonylphenyl, 3,5-dimethyl-4-methylsulfonylphenyl, 3-(dimethylamino)-4-methylsulfonylphenyl, 4-trifluoromethylsulfinylphenyl, 4-trifluoromethylsulfonylphenyl, 4-phenyl(methyl)oxo-$\lambda^6$-sulfanylidene-2,2,2-trifluoroacetamide, 4-methylsulfonimidoylphenyl, 4-isopropylsulfonimidoylphenyl, and 4-N,N-dimethylaminosulfonylphenyl. In another embodiment, $R^2$ is unsubstituted phenyl. In another embodiment, $R^2$ is 4-chlorophenyl. In another embodiment, $R^2$ is 2-chlorophenyl. In another embodiment, $R^2$ is 3-chlorophenyl. In another embodiment, $R^2$ is 2,3-dichlorophenyl. In another embodiment, $R^2$ is 2,4-dichlorophenyl. In another embodiment, $R^2$ is 3,5-dichlorophenyl. In another embodiment, $R^2$ is 2-fluorophenyl. In another embodiment, $R^2$ is 4-fluorophenyl. In another embodiment, $R^2$ is 4-bromophenyl. In another embodiment, $R^2$ is 2-chloro-4-fluorophenyl. In another embodiment, $R^2$ is 2-methylphenyl. In another embodiment, $R^2$ is 4-butylphenyl. In another embodiment, $R^2$ is 4-t-butylphenyl. In another embodiment, $R^2$ is 3,5-dimethylphenyl. In another embodiment, $R^2$ is 4-methoxyphenyl. In another embodiment, $R^2$ is 2-methoxyphenyl. In another embodiment, $R^2$ is 2-trifluoromethoxyphenyl. In another embodiment, $R^2$ is 4-trifluoromethoxyphenyl. In another embodiment, $R^2$ is 4-methoxycarbonylphenyl. In another embodiment, $R^2$ is 4-carboxyphenyl. In another embodiment, $R^2$ is 4-carbamylphenyl. In another embodiment, $R^2$ is 4-phenyl(formamido)propanoic acid. In another embodiment, $R^2$ is 4-phenyl(formamido)acetic acid. In another embodiment, $R^2$ is 4-N,N-dimethylcarbamylphenyl. In another embodiment, $R^2$ is 4-cyclopropylsulfonylphenyl. In another embodiment, $R^2$ is 4-phenylsulfonyl. In another embodiment, $R^2$ is 4-(4,4-difluoropiperidin-1-yl)sulfonylphenyl. In another embodiment, $R^2$ is 4-(isopropylsulfonimidoyl)phenyl. In another embodiment, $R^2$ is 4-morpholine-4-sulfonylphenyl. In another embodiment, $R^2$ is 4-morpholine-4-carbonylphenyl. In another embodiment, $R^2$ is 4-(4,4-difluoropiperidine-1-carbonyl)phenyl. In another embodiment, $R^2$ is 3-morpholinyl-4-methylsulfonylphenyl. In another embodiment, $R^2$ is 3-(methoxyethyl)methylamino-4-methylsulfonylphenyl. In another embodiment, $R^2$ is 3,5-difluoro-4-methylsulfonylphenyl. In another embodiment, $R^2$ is 3,5-difluoro-4-methylsulfonylphenyl. In another embodiment, $R^2$ is 2-ethoxy-4-fluorophenyl. In another embodiment, $R^2$ is 3-fluoro-4-methoxyphenyl. In another embodiment, $R^2$ is 2-trifluoromethylphenyl. In another embodiment, $R^2$ is 3-trifluoromethylphenyl. In another embodiment, $R^2$ is 4-trifluoromethylphenyl. In another embodiment, $R^2$ is 3,5-bis(trifluoromethyl)phenyl. In another embodiment, $R^2$ is 3-methylsulfonylphenyl. In another embodiment, $R^2$ is 4-methylsulfanylphenyl. In another embodiment, $R^2$ is 4-trifluoromethylsulfanylphenyl. In another embodiment, $R^2$ is 2-methylsulfinylphenyl. In another embodiment, $R^2$ is 4-methylsulfinylphenyl. In another embodiment, $R^2$ is 3-fluoro-4-methylsulfinylphenyl. In another embodiment, $R^2$ is 3-methyl-4-methylsulfinylphenyl. In another embodiment, $R^2$ is 4-methylsulfonylphenyl. In another embodiment, $R^2$ is 4-ethylsulfonylphenyl. In another embodiment, $R^2$ is 4-isopropylsulfonylphenyl. In another embodiment, $R^2$ is 4-morpholine-4-methylsulfonylphenyl. In another embodiment, $R^2$ is 3-(4-methylpiperazin-1-yl)-4-methylsulfonylphenyl. In another embodiment, $R^2$ is 3-piperazin-1-yl-4-methylsulfonylphenyl. In another embodiment, $R^2$ is 3-methoxy-4-methylsulfonylphenyl. In another embodiment, $R^2$ is 3-trifluoromethyl-4-methylsulfonylphenyl. In another embodiment, $R^2$ is 3-fluoro-4-methylsulfonylphenyl. In another embodiment, $R^2$ is 3-chloro-4-methylsulfonylphenyl. In another embodiment, $R^2$ is 3-methyl-4-methylsulfonylphenyl. In another embodiment, $R^2$ is 3,5-dimethyl-4-methylsulfonylphenyl. In another embodiment, $R^2$ is 3-(dimethylamino)-4-methylsulfonylphenyl. In another embodiment, $R^2$ is 4-trifluoromethylsulfinylphenyl. In another embodiment, $R^2$ is 4-trifluoromethylsulfonylphenyl. In another embodiment, $R^2$ is 4-phenyl(methyl)oxo-$\lambda^6$-sulfanylidene-2,2,2-trifluoroacetamide. In another embodiment, $R^2$ is 4-methylsulfonimidoylphenyl. In another embodiment, $R^2$ is 4-isopropylsulfonimidoylphenyl. In another embodiment, $R^2$ is 4-N,N-dimethylaminosulfonylphenyl.

In another embodiment, $R^3$ is $(C_1-C_6)$alkyl. In another embodiment, $R^3$ is —C(=NOR$^9$)R$^{10}$. In another embodiment, $R^3$ is methyl, ethyl or —C(=NOR$^9$)R$^{10}$ wherein at least one of R$^9$ and R$^{10}$ is methyl. In another embodiment, $R^3$ is methyl, ethyl or —C(=NOR$^9$)R$^{10}$ wherein each of R$^9$ and R$^{10}$ is methyl. In another embodiment, $R^3$ is methyl, ethyl or —C(=NOR$^9$)R$^{10}$ wherein one of R$^9$ and R$^{10}$ is methyl and the other is ethyl. In another embodiment, $R^3$ is methyl. In another embodiment, $R^3$ is ethyl. In another embodiment, $R^3$ is —C(=NOR$^9$)R$^{10}$ wherein at least one of R$^9$ and R$^{10}$ is methyl. In another embodiment, $R^3$ is —C(=NOR$^9$)R$^{10}$ wherein each of R$^9$ and R$^{10}$ is methyl. In another embodiment, $R^3$ is —C(=NOR$^9$)R$^{10}$ wherein one of R$^9$ and R$^{10}$ is methyl and the other is ethyl.

In another embodiment, $R^1$ is methyl and $R^2$ is unsubstituted phenyl. In another embodiment, $R^1$ is ethyl and $R^2$ is unsubstituted phenyl. In another embodiment, $R^1$ is iso-propyl and $R^2$ is unsubstituted phenyl. In another embodiment, $R^1$ is tert-butyl and $R^2$ is unsubstituted phenyl. In one embodiment, $R^1$ is methylcarboxylic acid and $R^2$ is unsubstituted phenyl. In another embodiment, $R^1$ is unsubstituted phenyl and $R^2$ is unsubstituted phenyl. In another embodiment, $R^1$ is unsubstituted (5- or 6-membered)heteroaryl and $R^2$ is unsubstituted phenyl. In another embodiment, $R^1$ is methyl and $R^2$ is monosubstituted phenyl, e.g., selected from among the monosubstituted $R^2$ phenyl groups disclosed above in connection with the compounds of formula (Ia). In another embodiment, $R^1$ is ethyl and $R^2$ is monosubstituted phenyl, e.g., selected from among the monosubstituted $R^2$ phenyl groups disclosed above in connection with the compounds of formula (Ia). In another embodiment, $R^1$ is iso-propyl and $R^2$ is monosubstituted phenyl, e.g., selected from among the monosubstituted $R^2$ phenyl groups disclosed above in connection with the compounds of formula (Ia). In another embodiment, $R^1$ is tert-butyl and $R^2$ is monosubstituted phenyl, e.g., selected from among the monosubstituted $R^2$ phenyl groups disclosed above in connection with the compounds of formula (Ia). In one embodiment, $R^1$ is methylcarboxylic acid and $R^2$ is monosubstituted phenyl, e.g., selected from among the monosubstituted $R^2$ phenyl groups disclosed above in connection with the compounds of formula (Ia). In another embodiment, $R^1$ is unsubstituted phenyl and $R^2$ is monosubstituted phenyl, e.g., selected from among the monosubstituted $R^2$ phenyl groups disclosed above in connection with the compounds of formula (Ia). In another embodiment, $R^1$ is unsubstituted (5- or 6-membered)heteroaryl and $R^2$ is monosubstituted phenyl, e.g., selected from among the monosubstituted $R^2$ phenyl groups disclosed above in connection with the compounds of formula (Ia). In another embodiment, $R^1$ is methyl and $R^2$ is disubstituted phenyl, e.g., selected from among the disubstituted $R^2$ phenyl groups disclosed above in connection with the compounds of formula (Ia). In another embodiment, $R^1$ is ethyl and $R^2$ is disubstituted phenyl, e.g., selected from among the disubstituted $R^2$ phenyl groups disclosed above in connection with the compounds of formula (Ia). In another embodiment, $R^1$ is iso-propyl and $R^2$ is disubstituted phenyl, e.g., selected from among the disubstituted $R^2$ phenyl groups disclosed above in connection with the compounds of formula (Ia). In another embodiment, $R^1$ is tert-butyl and $R^2$ is disubstituted phenyl, e.g., selected from among the disubstituted $R^2$ phenyl groups disclosed above in connection with the compounds of formula (Ia). In one embodiment, $R^1$ is methylcarboxylic acid and $R^2$ is disubstituted phenyl, e.g., selected from among the disubstituted $R^2$ phenyl groups disclosed above in connection with the compounds of formula (Ia). In another embodiment, $R^1$ is unsubstituted phenyl and $R^2$ is disubstituted phenyl, e.g., selected from among the disubstituted $R^2$ phenyl groups disclosed above in connection with the compounds of formula (Ia). In another embodiment, $R^1$ is unsubstituted (5- or 6-membered)heteroaryl and $R^2$ is disubstituted phenyl, e.g., selected from among the disubstituted $R^2$ phenyl groups disclosed above in connection with the compounds of formula (Ia). In another embodiment, $R^1$ is methyl and $R^2$ is trisubstituted phenyl, e.g., selected from among the trisubstituted $R^2$ phenyl groups disclosed above in connection with the compounds of formula (Ia). In another embodiment, $R^1$ is ethyl and $R^2$ is trisubstituted phenyl, e.g., selected from among the trisubstituted $R^2$ phenyl groups disclosed above in connection with the compounds of formula (Ia). In another embodiment, $R^1$ is iso-propyl and $R^2$ is trisubstituted phenyl, e.g., selected from among the trisubstituted $R^2$ phenyl groups disclosed above in connection with the compounds of formula (Ia). In another embodiment, $R^1$ is tert-butyl and $R^2$ is trisubstituted phenyl, e.g., selected from among the trisubstituted $R^2$ phenyl groups disclosed above in connection with the compounds of formula (Ia). In one embodiment, $R^1$ is methylcarboxylic acid and $R^2$ is trisubstituted phenyl, e.g., selected from among the trisubstituted $R^2$ phenyl groups disclosed above in connection with the compounds of formula (Ia). In another embodiment, $R^1$ is unsubstituted phenyl and $R^2$ is trisubstituted phenyl, e.g., selected from among the trisubstituted $R^2$ phenyl groups disclosed above in connection with the compounds of formula (Ia). In another embodiment, $R^1$ is unsubstituted (5- or 6-membered)heteroaryl and $R^2$ is trisubstituted phenyl, e.g., selected from among the trisubstituted $R^2$ phenyl groups disclosed above in connection with the compounds of formula (Ia).

In another embodiment, $R^1$ is methyl and $R^3$ is methyl. In another embodiment, $R^1$ is methyl and $R^3$ is ethyl. In another embodiment, $R^1$ is ethyl and $R^3$ is methyl. In another embodiment, $R^1$ is ethyl and $R^3$ is ethyl. In another embodiment, $R^1$ is iso-propyl and $R^3$ is methyl. In another embodiment, $R^1$ is iso-propyl and $R^3$ is ethyl. In another embodiment, $R^1$ is methyl and $R^3$ is iso-propyl. In another embodiment, $R^1$ is ethyl and $R^3$ is iso-propyl. In another embodiment, $R^1$ is iso-propyl and $R^3$ is iso-propyl. In one embodiment, $R^1$ is methylcarboxylic acid and $R^3$ is methyl. In one embodiment, $R^1$ is methylcarboxylic acid and $R^3$ is ethyl. In one embodiment, $R^1$ is methylcarboxylic acid and $R^3$ is iso-propyl. In another embodiment, $R^1$ is unsubstituted phenyl and $R^3$ is methyl. In another embodiment, $R^1$ is unsubstituted phenyl and $R^3$ is ethyl. In another embodiment, $R^1$ is unsubstituted phenyl and $R^3$ is iso-propyl. In another embodiment, $R^1$ is unsubstituted (5- or 6-membered)heteroaryl and $R^3$ is methyl. In another embodiment, $R^1$ is unsubstituted (5- or 6-membered)heteroaryl and $R^3$ is ethyl. In another embodiment, $R^1$ is unsubstituted (5- or 6-membered)heteroaryl and $R^3$ is iso-propyl. In another embodiment, $R^1$ is methyl and $R^3$ is —C(=NOR$^9$)R$^{10}$. In another embodiment, $R^1$ is methyl and $R^3$ is —C(=NOR$^9$)R$^{10}$ wherein at least one of $R^9$ and $R^{10}$ is methyl. In another embodiment, $R^1$ is methyl and $R^3$ is —C(=NOR$^9$)R$^{10}$ wherein each of $R^9$ and $R^{10}$ is methyl. In another embodiment, $R^1$ is methyl and $R^3$ is —C(=NOR$^9$)R$^{10}$ wherein one of $R^9$ and $R^{10}$ is methyl and the other is ethyl. In another embodiment, $R^1$ is ethyl and $R^3$ is —C(=NOR$^9$)R$^{10}$. In another embodiment, $R^1$ is ethyl and $R^3$ is —C(=NOR$^9$)R$^{10}$ wherein at least one of $R^9$ and $R^{10}$ is methyl. In another embodiment, $R^1$ is ethyl and $R^3$ is —C(=NOR$^9$)R$^{10}$ wherein each of $R^9$ and $R^{10}$ is methyl. In another embodiment, $R^1$ is ethyl and $R^3$ is —C(=NOR$^9$)R$^{10}$ wherein one of $R^9$ and $R^{10}$ is methyl and the other is ethyl. In another embodiment, $R^1$ is iso-propyl and $R^3$ is —C(=NOR$^9$)R$^{10}$. In another embodiment, $R^1$ is iso-propyl and $R^3$ is —C(=NOR$^9$)R$^{10}$ wherein at least one of $R^9$ and $R^{10}$ is methyl. In another embodiment, $R^1$ is iso-propyl and $R^3$ is —C(=NOR$^9$)R$^{10}$ wherein each of $R^9$ and $R^{10}$ is methyl. In another embodiment, $R^1$ is iso-propyl and $R^3$ is —C(=NOR$^9$)R$^{10}$ wherein one of $R^9$ and $R^{10}$ is methyl and the other is ethyl. In another embodiment, $R^1$ is unsubstituted phenyl and $R^3$ is —C(=NOR$^9$)R$^{10}$. In another embodiment, $R^1$ is unsubstituted phenyl and $R^3$ is —C(=NOR$^9$)R$^{10}$ wherein at least one of $R^9$ and $R^{10}$ is methyl. In another embodiment, $R^1$ is unsubstituted phenyl and $R^3$ is —C(=NOR$^9$)R$^{10}$ wherein each of $R^9$ and $R^{10}$ is methyl. In another embodiment, $R^1$ is unsubstituted phenyl and $R^3$ is —C(=NOR$^9$)R$^{10}$ wherein one of $R^9$ and $R^{10}$ is methyl and the other is ethyl. In another embodiment, $R^1$ is unsubstituted (5- or 6-membered)heteroaryl and $R^3$ is —C(=NOR$^9$)R$^{10}$ wherein at least one of $R^9$ and $R^{10}$ is methyl. In another embodiment, $R^1$ is unsubstituted (5- or 6-membered)heteroaryl and $R^3$ is —C(=NOR$^9$)R$^{10}$ wherein each of $R^9$ and $R^{10}$ is methyl. In another embodiment, $R^1$ is unsubstituted (5- or 6-membered)heteroaryl and $R^3$ is —C(=NOR$^9$)R$^{10}$ wherein one of $R^9$ and $R^{10}$ is methyl and the other is ethyl.

In another embodiment, $R^2$ is unsubstituted phenyl and $R^3$ is methyl. In another embodiment, $R^2$ is unsubstituted phenyl and $R^3$ is ethyl. In another embodiment, $R^2$ is unsubstituted phenyl and $R^3$ is iso-propyl. In another embodiment, $R^2$ is unsubstituted phenyl and $R^3$ is tert-butyl. In another embodiment, $R^2$ is unsubstituted phenyl and $R^3$ is —C(=NOR$^9$)R$^{10}$. In another embodiment, $R^2$ is unsubstituted phenyl and $R^3$ is —C(=NOR$^9$)R$^{10}$ wherein at least one of $R^9$ and $R^{10}$ is methyl. In another embodiment, $R^2$ is unsubstituted phenyl and $R^3$ is —C(=NOR$^9$)R$^{10}$ wherein each of $R^9$ and $R^{10}$ is methyl. In another embodiment, $R^2$ is unsubstituted phenyl and $R^3$ is —C(=NOR$^9$)R$^{10}$ wherein one of $R^9$ and $R^{10}$ is methyl and the other is ethyl.

In another embodiment, $R^2$ is monosubstituted phenyl, e.g., selected from among the monosubstituted $R^2$ phenyl groups disclosed above in connection with the compounds of formula (Ia), and $R^3$ is methyl. In another embodiment, $R^2$ is monosubstituted phenyl, e.g., selected from among the monosubstituted $R^2$ phenyl groups disclosed above in connection with the compounds of formula (Ia), and $R^3$ is ethyl. In another embodiment, $R^2$ is monosubstituted phenyl, e.g., selected from among the monosubstituted $R^2$ phenyl groups disclosed above in connection with the compounds of formula (Ia), and $R^3$ is iso-propyl. In another embodiment, $R^2$ is monosubstituted phenyl, e.g., selected from among the monosubstituted $R^2$ phenyl groups disclosed above in connection with the compounds of formula (Ia), and $R^3$ is tert-butyl. In another embodiment, $R^2$ is monosubstituted phenyl, e.g., selected from among the monosubstituted $R^2$ phenyl groups disclosed above in connection with the compounds of formula (Ia), and $R^3$ is —C(=NOR$^9$)R$^{10}$. In another embodiment, $R^2$ is monosubstituted phenyl, e.g., selected from among the monosubstituted $R^2$ phenyl groups disclosed above in connection with the compounds of formula (Ia), and R³ is —C(=NOR⁹)R¹⁰ wherein at least one of R⁹ and R¹⁰ is methyl. In another embodiment, R² is monosubstituted phenyl, e.g., selected from among the monosubstituted R² phenyl groups disclosed above in connection with the compounds of formula (Ia), and R³ is —C(=NOR⁹)R¹⁰ wherein each of R⁹ and R¹⁰ is methyl. In another embodiment, R² is monosubstituted phenyl, e.g., selected from among the monosubstituted R² phenyl groups disclosed above in connection with the compounds of formula (Ia), and R³ is —C(=NOR⁹)R¹⁰ wherein one of R⁹ and R¹⁰ is methyl and the other is ethyl.

In another embodiment, R² is disubstituted phenyl, e.g., selected from among the disubstituted R² phenyl groups disclosed above in connection with the compounds of formula (Ia), and R³ is methyl. In another embodiment, R² is disubstituted phenyl, e.g., selected from among the disubstituted R² phenyl groups disclosed above in connection with the compounds of formula (Ia), and R³ is ethyl. In another embodiment, R² is disubstituted phenyl, e.g., selected from among the disubstituted R² phenyl groups disclosed above in connection with the compounds of formula (Ia), and R³ is iso-propyl. In another embodiment, R² is disubstituted phenyl, e.g., selected from among the disubstituted R² phenyl groups disclosed above in connection with the compounds of formula (Ia), and R³ is tert-butyl. In another embodiment, R² is disubstituted phenyl, e.g., selected from among the disubstituted R² phenyl groups disclosed above in connection with the compounds of formula (Ia), and R³ is —C(=NOR⁹)R¹⁰. In another embodiment, R² is disubstituted phenyl, e.g., selected from among the disubstituted R² phenyl groups disclosed above in connection with the compounds of formula (Ia), and R³ is —C(=NOR⁹)R¹⁰ wherein at least one of R⁹ and R¹⁰ is methyl. In another embodiment, R² is disubstituted phenyl, e.g., selected from among the disubstituted R² phenyl groups disclosed above in connection with the compounds of formula (Ia), and R³ is —C(=NOR⁹)R¹⁰ wherein each of R⁹ and R¹⁰ is methyl. In another embodiment, R² is disubstituted phenyl, e.g., selected from among the disubstituted R² phenyl groups disclosed above in connection with the compounds of formula (Ia), and R³ is —C(=NOR⁹)R¹⁰ wherein one of R⁹ and R¹⁰ is methyl and the other is ethyl.

In another embodiment, R² is trisubstituted phenyl, e.g., selected from among the trisubstituted R² phenyl groups disclosed above in connection with the compounds of formula (Ia), and R³ is methyl. In another embodiment, R² is trisubstituted phenyl, e.g., selected from among the trisubstituted R² phenyl groups disclosed above in connection with the compounds of formula (Ia), and R³ is ethyl. In another embodiment, R² is trisubstituted phenyl, e.g., selected from among the trisubstituted R² phenyl groups disclosed above in connection with the compounds of formula (Ia), and R³ is iso-propyl. In another embodiment, R² is trisubstituted phenyl, e.g., selected from among the trisubstituted R² phenyl groups disclosed above in connection with the compounds of formula (Ia), and R³ is tert-butyl. In another embodiment, R² is trisubstituted phenyl, e.g., selected from among the trisubstituted R² phenyl groups disclosed above in connection with the compounds of formula (Ia), and R³ is —C(=NOR⁹)R¹⁰. In another embodiment, R² is trisubstituted phenyl, e.g., selected from among the trisubstituted R² phenyl groups disclosed above in connection with the compounds of formula (Ia), and R³ is —C(=NOR⁹)R¹⁰ wherein at least one of R⁹ and R¹⁰ is methyl. In another embodiment, R² is trisubstituted phenyl, e.g., selected from among the trisubstituted R² phenyl groups disclosed above in connection with the compounds of formula (Ia), and R³ is —C(=NOR⁹)R¹⁰ wherein each of R⁹ and R¹⁰ is methyl. In another embodiment, R² is trisubstituted phenyl, e.g., selected from among the trisubstituted R² phenyl groups disclosed above in connection with the compounds of formula (Ia), and R³ is —C(=NOR⁹)R¹⁰ wherein one of R⁹ and R¹⁰ is methyl and the other is ethyl.

Another aspect of the disclosure provides a compound of formula (Ib)

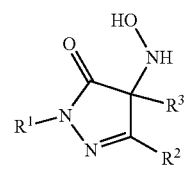

(Ib)

or a pharmaceutically acceptable salt thereof, wherein:

$R^1$ is $(C_1-C_6)$alkyl or unsubstituted phenyl;

$R^2$ is $(C_1-C_6)$alkyl, $(C_1-C_4)$haloalkyl, or $(C_1-C_4)$perhaloalkyl;

$R^3$ is (5- or 6-membered)heteroaryl or phenyl wherein said heteroaryl and phenyl are unsubstituted or substituted with 1, 2, 3, 4, or 5 substituent(s) independently selected from halo, $(C_1-C_6)$alkyl, $(C_1-C_6)$alkoxy, phenyl, —C(=O)NR⁴R⁵, $(C_1-C_6)$alkylsulfinyl, $(C_1-C_6)$alkylsulfonyl, and N,N-di$(C_1-C_6)$alkylaminosulfonyl; and $R^4$ and $R^5$ are independently H or $(C_1-C_6)$alkyl.

In one embodiment, R¹ is unsubstituted phenyl, methyl, ethyl, iso-propyl, or tert-butyl. In another embodiment, R¹ is unsubstituted phenyl, methyl, ethyl, or iso-propyl. In another embodiment, R¹ is unsubstituted phenyl, methyl, ethyl, or tert-butyl. In another embodiment, R¹ is unsubstituted phenyl, methyl, iso-propyl, or tert-butyl. In another embodiment, R¹ is unsubstituted phenyl, ethyl, iso-propyl, or tert-butyl. In another embodiment, R¹ is unsubstituted phenyl, methyl, or ethyl. In another embodiment, R¹ is unsubstituted phenyl, methyl, or iso-propyl. In another embodiment, R¹ is unsubstituted phenyl, methyl, or tert-butyl. In another embodiment, R¹ is unsubstituted phenyl, ethyl, or iso-propyl. In another embodiment, R¹ is unsubstituted phenyl, ethyl, or tert-butyl. In another embodiment, R¹ is unsubstituted phenyl, iso-propyl, or tert-butyl. In another embodiment, R¹ is unsubstituted phenyl or methyl. In another embodiment, R¹ is unsubstituted phenyl or ethyl. In another embodiment, R¹ is unsubstituted phenyl or iso-propyl. In another embodiment, R¹ is unsubstituted phenyl or tert-butyl. In another embodiment, R¹ is unsubstituted phenyl.

In another embodiment, R¹ is methyl, ethyl, iso-propyl, or tert-butyl. In another embodiment, R¹ is methyl, ethyl, or iso-propyl. In another embodiment, R¹ is methyl, ethyl, or tert-butyl. In another embodiment, R¹ is methyl, iso-propyl, or tert-butyl. In another embodiment, R¹ is ethyl, iso-propyl, or tert-butyl. In another embodiment, R¹ is methyl or ethyl. In another embodiment, R¹ is methyl or iso-propyl. In another embodiment, R¹ is methyl or tert-butyl. In another embodiment, R¹ is ethyl or iso-propyl. In another embodiment, R¹ is ethyl or tert-butyl. In another embodiment, R¹ is iso-propyl or tert-butyl. In another embodiment, R¹ is methyl. In another embodiment, R¹ is ethyl. In another embodiment, R¹ is propyl. In another embodiment, R¹ is iso-propyl. In another embodiment, R¹ is butyl. In another embodiment, R¹ is tert-butyl.

In one embodiment, $R^2$ is methyl, trifluoromethyl, ethyl, iso-propyl, or tert-butyl. In another embodiment, $R^2$ is methyl, trifluoromethyl, ethyl, or iso-propyl. In another embodiment, $R^2$ is methyl, trifluoromethyl, ethyl, or tert-butyl. In another embodiment, $R^2$ is methyl, trifluoromethyl, iso-propyl, or tert-butyl. In another embodiment, $R^2$ is trifluoromethyl, ethyl, iso-propyl, or tert-butyl. In another embodiment, $R^2$ is methyl, trifluoromethyl, or ethyl. In another embodiment, $R^2$ is methyl, trifluoromethyl, or iso-propyl. In another embodiment, $R^2$ is methyl, trifluoromethyl, or tert-butyl. In another embodiment, $R^2$ is trifluoromethyl, ethyl or iso-propyl. In another embodiment, $R^2$ is trifluoromethyl, ethyl or tert-butyl. In another embodiment, $R^2$ is iso-propyl or tert-butyl.

In another embodiment, $R^2$ is methyl, ethyl, iso-propyl, or tert-butyl. In another embodiment, $R^2$ is methyl, ethyl, or iso-propyl. In another embodiment, $R^2$ is methyl, ethyl, or tert-butyl. In another embodiment, $R^2$ is methyl, iso-propyl, or tert-butyl. In another embodiment, $R^2$ is ethyl, iso-propyl, or tert-butyl. In another embodiment, $R^2$ is methyl or ethyl. In another embodiment, $R^2$ is methyl or iso-propyl. In another embodiment, $R^2$ is methyl or tert-butyl. In another embodiment, $R^2$ is ethyl or iso-propyl. In another embodiment, $R^2$ is ethyl or tert-butyl. In another embodiment, $R^2$ is iso-propyl or tert-butyl. In one embodiment, $R^2$ is trifluoromethyl, ethyl, iso-propyl, or tert-butyl. In another embodiment, $R^2$ is trifluoromethyl, ethyl, or iso-propyl. In another embodiment, $R^2$ is trifluoromethyl, ethyl, or tert-butyl. In another embodiment, $R^2$ is trifluoromethyl, iso-propyl, or tert-butyl. In another embodiment, $R^2$ is trifluoromethyl, ethyl, iso-propyl, or tert-butyl. In another embodiment, $R^2$ is trifluoromethyl or ethyl. In another embodiment, $R^2$ is trifluoromethyl or iso-propyl. In another embodiment, $R^2$ is trifluoromethyl or tert-butyl. In another embodiment, $R^2$ is methyl. In another embodiment, $R^2$ is trifluoromethyl. In another embodiment, $R^2$ is ethyl. In another embodiment, $R^2$ is propyl. In another embodiment, $R^2$ is iso-propyl. In another embodiment, $R^2$ is butyl. In another embodiment, $R^2$ is tert-butyl.

In one embodiment, $R^3$ is (5- or 6-membered)heteroaryl wherein the heteroaryl is unsubstituted or substituted with 1, 2 or 3 substituent(s) independently selected from halo, $(C_1\text{-}C_6)$alkyl, $(C_1\text{-}C_6)$alkoxy, phenyl, —C(=O)NR$^4$R$^5$, $(C_1\text{-}C_6)$alkylsulfinyl, $(C_1\text{-}C_6)$alkylsulfonyl, and N,N-di($C_1$-$C_6$)alkylaminosulfonyl. In one embodiment, $R^3$ is (5- or 6-membered)heteroaryl wherein the heteroaryl is unsubstituted or substituted with 1, 2 or 3 substituent(s) independently selected from halo, $(C_1\text{-}C_6)$alkyl, or $(C_1\text{-}C_6)$alkoxy. In one embodiment, $R^3$ is (5- or 6-membered)heteroaryl wherein the heteroaryl is unsubstituted or substituted with 1, 2 or 3 substituent(s) independently selected from halo, $(C_1\text{-}C_6)$alkyl, or phenyl. In one embodiment, $R^3$ is (5- or 6-membered)heteroaryl wherein the heteroaryl is unsubstituted or substituted with 1, 2 or 3 substituent(s) independently selected from halo, $(C_1\text{-}C_6)$alkyl, or —C(=O)NR$^4$R$^5$. In one embodiment, $R^3$ is (5- or 6-membered) heteroaryl wherein the heteroaryl is unsubstituted or substituted with 1, 2 or 3 substituent(s) independently selected from halo, $(C_1\text{-}C_6)$alkyl, or $(C_1\text{-}C_6)$alkylsulfinyl. In one embodiment, $R^3$ is (5- or 6-membered)heteroaryl wherein the heteroaryl is unsubstituted or substituted with 1, 2 or 3 substituent(s) independently selected from halo, $(C_1\text{-}C_6)$alkyl, or $(C_1\text{-}C_6)$alkylsulfonyl. In one embodiment, $R^3$ is (5- or 6-membered)heteroaryl wherein the heteroaryl is unsubstituted or substituted with 1, 2 or 3 substituent(s) independently selected from halo, $(C_1\text{-}C_6)$alkyl, or N,N-di$(C_1\text{-}C_6)$alkylaminosulfonyl. In one embodiment, $R^3$ is (5- or 6-membered)heteroaryl wherein the heteroaryl is unsubstituted or substituted with 1, 2 or 3 substituent(s) independently selected from $(C_1\text{-}C_6)$alkyl, $(C_1\text{-}C_6)$alkoxy or phenyl. In one embodiment, $R^3$ is (5- or 6-membered)heteroaryl wherein the heteroaryl is unsubstituted or substituted with 1, 2 or 3 substituent(s) independently selected from $(C_1\text{-}C_6)$alkyl, $(C_1\text{-}C_6)$alkoxy or —C(=O)NR$^4$R$^5$. In one embodiment, $R^3$ is (5- or 6-membered)heteroaryl wherein the heteroaryl is unsubstituted or substituted with 1, 2 or 3 substituent(s) independently selected from $(C_1\text{-}C_6)$alkyl, $(C_1\text{-}C_6)$alkoxy or $(C_1\text{-}C_6)$alkylsulfinyl. In one embodiment, $R^3$ is (5- or 6-membered)heteroaryl wherein the heteroaryl is unsubstituted or substituted with 1, 2 or 3 substituent(s) independently selected from $(C_1\text{-}C_6)$alkyl, $(C_1\text{-}C_6)$alkoxy or $(C_1\text{-}C_6)$alkylsulfonyl. In one embodiment, $R^3$ is (5- or 6-membered)heteroaryl wherein the heteroaryl is unsubstituted or substituted with 1, 2 or 3 substituent(s) independently selected from $(C_1\text{-}C_6)$alkyl, $(C_1\text{-}C_6)$alkoxy or N,N-di$(C_1\text{-}C_6)$alkylaminosulfonyl. In one embodiment, $R^3$ is (5- or 6-membered)heteroaryl wherein the heteroaryl is unsubstituted or substituted with 1, 2 or 3 substituent(s) independently selected from $(C_1\text{-}C_6)$alkoxy, phenyl or —C(=O)NR$^4$R$^5$. In one embodiment, $R^3$ is (5- or 6-membered) heteroaryl wherein the heteroaryl is unsubstituted or substituted with 1, 2 or 3 substituent(s) independently selected from $(C_1\text{-}C_6)$alkoxy, phenyl or $(C_1\text{-}C_6)$alkylsulfinyl. In one embodiment, $R^3$ is (5- or 6-membered)heteroaryl wherein the heteroaryl is unsubstituted or substituted with 1, 2 or 3 substituent(s) independently selected from $(C_1\text{-}C_6)$alkoxy, phenyl or $(C_1\text{-}C_6)$alkylsulfonyl. In one embodiment, $R^3$ is (5- or 6-membered)heteroaryl wherein the heteroaryl is unsubstituted or substituted with 1, 2 or 3 substituent(s) independently selected from $(C_1\text{-}C_6)$alkoxy, phenyl or N,N-di$(C_1\text{-}C_6)$alkylaminosulfonyl. In one embodiment, $R^3$ is (5- or 6-membered)heteroaryl wherein the heteroaryl is unsubstituted or substituted with 1, 2 or 3 substituent(s) independently selected from phenyl, —C(=O)NR$^4$R$^5$ or $(C_1\text{-}C_6)$alkylsulfinyl. In one embodiment, $R^3$ is (5- or 6-membered) heteroaryl wherein the heteroaryl is unsubstituted or substituted with 1, 2 or 3 substituent(s) independently selected from phenyl, —C(=O)NR$^4$R$^5$ or $(C_1\text{-}C_6)$alkylsulfonyl. In one embodiment, $R^3$ is (5- or 6-membered)heteroaryl wherein the heteroaryl is unsubstituted or substituted with 1, 2 or 3 substituent(s) independently selected from phenyl, —C(=O)NR$^4$R$^5$ or N,N-di$(C_1\text{-}C_6)$alkylaminosulfonyl. In one embodiment, $R^3$ is (5- or 6-membered)heteroaryl wherein the heteroaryl is unsubstituted or substituted with 1, 2 or 3 substituent(s) independently selected from —C(=O)NR$^4$R$^5$, $(C_1\text{-}C_6)$alkylsulfinyl or $(C_1\text{-}C_6)$alkylsulfonyl. In one embodiment, $R^3$ is (5- or 6-membered)heteroaryl wherein the heteroaryl is unsubstituted or substituted with 1, 2 or 3 substituent(s) independently selected from —C(=O)NR$^4$R$^5$, $(C_1\text{-}C_6)$alkylsulfinyl or (N,N-di$(C_1\text{-}C_6)$alkylaminosulfonyl. In one embodiment, $R^3$ is (5- or 6-membered) heteroaryl wherein the heteroaryl is unsubstituted or substituted with 1, 2 or 3 substituent(s) independently selected from $(C_1\text{-}C_6)$alkylsulfinyl, $(C_1\text{-}C_6)$alkylsulfonyl or N,N-di$(C_1\text{-}C_6)$alkylaminosulfonyl.

In another embodiment, $R^3$ is (5- or 6-membered)heteroaryl wherein the heteroaryl is unsubstituted or substituted with 1, 2, or 3 substituent(s) independently selected from fluoro, bromo, methoxy, phenyl, methylsulfinyl, methylsulfonyl, dimethylaminosulfonyl and dimethylcarbamyl. In another embodiment, $R^3$ is (5- or 6-membered)heteroaryl wherein the heteroaryl is unsubstituted or substituted with 1, 2, or 3 substituent(s) independently selected from fluoro, phenyl, methylsulfinyl, and methylsulfonyl.

In one embodiment, $R^3$ is (5- or 6-membered)heteroaryl wherein the heteroaryl is monosubstituted with a substituent selected from fluoro, bromo, methoxy, phenyl, methylsulfinyl, methylsulfonyl, dimethylaminosulfonyl and dimethylcarbamyl. In another embodiment, $R^3$ is (5- or 6-membered) heteroaryl wherein the heteroaryl is monosubstituted with a substituent selected from fluoro, phenyl, methylsulfinyl, and methylsulfonyl.

In one embodiment, $R^3$ is (5- or 6-membered)heteroaryl wherein the heteroaryl is disubstituted with substituents independently selected from fluoro, bromo, methoxy, phenyl, methylsulfinyl, methylsulfonyl, dimethylaminosulfonyl and dimethylcarbamyl. In another embodiment, $R^3$ is (5- or 6-membered)heteroaryl wherein the heteroaryl is disubstituted with substituents independently selected from fluoro, phenyl, methylsulfinyl, and methylsulfonyl.

In one embodiment, $R^3$ is (5- or 6-membered)heteroaryl wherein the heteroaryl is trisubstituted with substituents independently selected from fluoro, bromo, methoxy, phenyl, methylsulfinyl, methylsulfonyl, dimethylaminosulfonyl and dimethylcarbamyl. In another embodiment, $R^3$ is (5- or 6-membered)heteroaryl wherein the heteroaryl is trisubstituted with substituents independently selected from a substituent selected from fluoro, phenyl, methylsulfinyl, and methylsulfonyl.

In one embodiment, $R^3$ is phenyl wherein the phenyl is unsubstituted or substituted with 1, 2, or 3 substituent(s) independently selected from halo, $(C_1-C_6)$alkoxy, —C(=O)NR$^4$R$^5$, $(C_1-C_6)$alkylsulfinyl, $(C_1-C_6)$alkylsulfonyl and N,N-di$(C_1-C_6)$alkylaminosulfonyl. In one embodiment, $R^3$ is phenyl wherein the phenyl is unsubstituted or substituted with 1, 2, or 3 substituent(s) independently selected from halo, $(C_1-C_6)$alkoxy, and $(C_1-C_6)$alkylsulfinyl. In one embodiment, $R^3$ is phenyl wherein the phenyl is unsubstituted or substituted with 1, 2, or 3 substituent(s) independently selected from halo, $(C_1-C_6)$alkoxy, and $(C_1-C_6)$alkylsulfonyl. In one embodiment, $R^3$ is phenyl wherein the phenyl is unsubstituted or substituted with 1, 2, or 3 substituent(s) independently selected from $(C_1-C_6)$alkoxy, $(C_1-C_6)$alkylsulfinyl, and $(C_1-C_6)$alkylsulfonyl. In another embodiment, $R^3$ is phenyl wherein the phenyl is unsubstituted or substituted with 1, 2, or 3 substituent(s) independently selected from halo, $(C_1-C_6)$alkoxy, and —C(=O)NR$^4$R$^5$. In another embodiment, $R^3$ is phenyl wherein the phenyl is unsubstituted or substituted with 1, 2, or 3 substituent(s) independently selected from halo, $(C_1-C_6)$alkoxy, and $(C_1-C_6)$alkylsulfonyl. In another embodiment, $R^3$ is phenyl wherein the phenyl is unsubstituted or substituted with 1, 2, or 3 substituent(s) independently selected from halo, $(C_1-C_6)$alkoxy, and N,N-di$(C_1-C_6)$alkylaminosulfonyl. In another embodiment, $R^3$ is phenyl wherein the phenyl is unsubstituted or substituted with 1, 2, or 3 substituent(s) independently selected from $(C_1-C_6)$alkoxy, —C(=O)NR$^4$R$^5$, and $(C_1-C_6)$alkylsulfinyl. In another embodiment, $R^3$ is phenyl wherein the phenyl is unsubstituted or substituted with 1, 2, or 3 substituent(s) independently selected from $(C_1-C_6)$alkoxy, —C(=O)NR$^4$R$^5$ and $(C_1-C_6)$alkylsulfonyl. In another embodiment, $R^3$ is phenyl wherein the phenyl is unsubstituted or substituted with 1, 2, or 3 substituent(s) independently selected from $(C_1-C_6)$alkoxy, —C(=O)NR$^4$R$^5$ and N,N-di$(C_1-C_6)$alkylaminosulfonyl. In another embodiment, $R^3$ is phenyl wherein the phenyl is unsubstituted or substituted with 1, 2, or 3 substituent(s) independently selected from —C(=O)NR$^4$R$^5$, $(C_1-C_6)$alkylsulfinyl and $(C_1-C_6)$alkylsulfonyl. In another embodiment, $R^3$ is phenyl wherein the phenyl is unsubstituted or substituted with 1, 2, or 3 substituent(s) independently selected from —C(=O)NR$^4$R$^5$, $(C_1-C_6)$alkylsulfinyl and N,N-di$(C_1-C_6)$alkylaminosulfonyl. In another embodiment, $R^3$ is phenyl wherein the phenyl is unsubstituted or substituted with 1, 2, or 3 substituent(s) independently selected from $(C_1-C_6)$alkylsulfinyl, $(C_1-C_6)$alkylsulfonyl and N,N-di$(C_1-C_6)$alkylaminosulfonyl.

In another embodiment, $R^3$ is phenyl wherein the phenyl is unsubstituted or substituted with 1, 2, or 3 substituent(s) independently selected from halo and $(C_1-C_6)$alkylsulfinyl. In one embodiment, $R^3$ is phenyl wherein the phenyl is unsubstituted or substituted with 1, 2, or 3 substituent(s) independently selected from halo and $(C_1-C_6)$alkylsulfonyl. In one embodiment, $R^3$ is phenyl wherein the phenyl is unsubstituted or substituted with 1, 2, or 3 substituent(s) independently selected from halo and —C(=O)NR$^4$R$^5$. In one embodiment, $R^3$ is phenyl wherein the phenyl is unsubstituted or substituted with 1, 2, or 3 substituent(s) independently selected from halo and N,N-di$(C_1-C_6)$alkylaminosulfonyl. In one embodiment, $R^3$ is phenyl wherein the phenyl is unsubstituted or substituted with 1, 2, or 3 substituent(s) independently selected from $(C_1-C_6)$alkylsulfinyl and $(C_1-C_6)$alkylsulfonyl. In one embodiment, $R^3$ is phenyl wherein the phenyl is unsubstituted or substituted with 1, 2, or 3 substituent(s) independently selected from $(C_1-C_6)$alkylsulfinyl and —C(=O)NR$^4$R$^5$. In one embodiment, $R^3$ is phenyl wherein the phenyl is unsubstituted or substituted with 1, 2, or 3 substituent(s) independently selected from $(C_1-C_6)$alkylsulfinyl and N,N-di$(C_1-C_6)$alkylaminosulfonyl. In one embodiment, $R^3$ is phenyl wherein the phenyl is unsubstituted or substituted with 1, 2, or 3 substituent(s) independently selected from $(C_1-C_6)$alkylsulfonyl and —C(=O)NR$^4$R$^5$. In one embodiment, $R^3$ is phenyl wherein the phenyl is unsubstituted or substituted with 1, 2, or 3 substituent(s) independently selected from $(C_1-C_6)$alkylsulfonyl and N,N-di$(C_1-C_6)$alkylaminosulfonyl. In one embodiment, $R^3$ is phenyl wherein the phenyl is unsubstituted or substituted with 1, 2, or 3 substituent(s) independently selected from —C(=O)NR$^4$R$^5$ and N,N-di$(C_1-C_6)$alkylaminosulfonyl.

In another embodiment, $R^3$ is phenyl wherein the phenyl is unsubstituted or substituted with 1, 2, or 3 substituent(s) independently selected from fluoro, bromo, methoxy, methylsulfinyl, methylsulfonyl, dimethylaminosulfonyl and dimethylcarbamyl. In another embodiment, $R^3$ is phenyl wherein the phenyl is unsubstituted or substituted with 1, 2, or 3 substituent(s) independently selected from fluoro, methylsulfinyl, and methylsulfonyl.

In another embodiment, $R^3$ is phenyl wherein the phenyl is unsubstituted or substituted with 1 or 2 substituent(s), each substituent being independently selected from halo, $(C_1-C_6)$alkylsulfinyl, and $(C_1-C_6)$alkylsulfonyl. In another embodiment, $R^3$ is phenyl wherein the phenyl is unsubstituted or substituted with 1 or 2 substituent(s), each substituent being independently selected from $(C_1-C_6)$alkoxy, $(C_1-C_6)$alkylsulfinyl, and $(C_1-C_6)$alkylsulfonyl. In another embodiment, $R^3$ is phenyl wherein the phenyl is unsubstituted or substituted with 1 or 2 substituent(s), each substituent being independently selected from halo, $(C_1-C_6)$alkoxy, and $(C_1-C_6)$alkylsulfonyl. In another embodiment, $R^3$ is phenyl wherein the phenyl is unsubstituted or substituted with 1 or 2 substituent(s), each substituent being independently selected from halo, $(C_1-C_6)$alkylsulfinyl, and $(C_1-C_6)$alkoxy. In another embodiment, $R^3$ is phenyl wherein the phenyl is unsubstituted or substituted with 1 or 2 substituent(s), each substituent being independently selected from halo, $(C_1-C_6)$alkoxy, and —C(=O)NR$^4$R$^5$. In another embodiment, $R^3$ is phenyl wherein the phenyl is unsubstituted or substituted with 1 or 2 substituent(s), each substituent being independently selected from halo, $(C_1-C_6)$alkoxy, and $(C_1-C_6)$alkylsulfonyl. In another embodiment, $R^3$ is phenyl wherein the phenyl is unsubstituted or substituted with 1 or 2 substituent(s), each substituent being independently selected from halo, $(C_1-C_6)$alkoxy, and N,N-di$(C_1-C_6)$alkylaminosulfonyl. In another embodiment, $R^3$ is phenyl wherein the phenyl is unsubstituted or substituted with 1 or 2 substituent(s), each substituent being independently selected from $(C_1-C_6)$alkoxy, —C(=O)NR$^4$R$^5$, and $(C_1-C_6)$alkylsulfinyl. In another embodiment, $R^3$ is phenyl wherein the phenyl is unsubstituted or substituted with 1 or 2 substituent(s), each substituent being independently selected from $(C_1-C_6)$alkoxy, —C(=O)NR$^4$R$^5$ and $(C_1-C_6)$alkylsulfonyl. In another embodiment, $R^3$ is phenyl wherein the phenyl is unsubstituted or substituted with 1 or 2 substituent(s), each substituent being independently selected from $(C_1-C_6)$alkoxy, —C(=O)NR$^4$R$^5$ and N,N-di$(C_1-C_6)$alkylaminosulfonyl. In another embodiment, $R^3$ is phenyl wherein the phenyl is unsubstituted or substituted with 1 or 2 substituent(s), each substituent being independently selected from —C(=O)NR$^4$R$^5$, $(C_1-C_6)$alkylsulfinyl and $(C_1-C_6)$alkylsulfonyl. In another embodiment, $R^3$ is phenyl wherein the phenyl is unsubstituted or substituted with 1 or 2 substituent(s), each substituent being independently selected from —C(=O)NR$^4$R$^5$, $(C_1-C_6)$alkylsulfinyl and N,N-di$(C_1-C_6)$alkylaminosulfonyl. In another embodiment, $R^3$ is phenyl wherein the phenyl is unsubstituted or substituted with 1 or 2 substituent(s), each substituent being independently selected from $(C_1-C_6)$alkylsulfinyl, $(C_1-C_6)$alkylsulfonyl and N,N-di$(C_1-C_6)$alkylaminosulfonyl.

In another embodiment, $R^3$ is phenyl wherein the phenyl is unsubstituted or substituted with 1 or 2 substituent(s), each substituent being independently selected from fluoro, bromo, methoxy, methylsulfinyl, methylsulfonyl, dimethylaminosulfonyl and dimethylcarbamyl. In another embodiment, $R^3$ is phenyl wherein the phenyl is unsubstituted or substituted with 1 or 2 substituent(s), each substituent being independently selected from fluoro, methylsulfinyl, and methylsulfonyl.

In another embodiment, $R^3$ is phenyl wherein the phenyl is unsubstituted or monosubstituted with halo, $(C_1-C_6)$alkoxy, —C(=O)NR$^4$R$^5$, $(C_1-C_6)$alkylsulfinyl, $(C_1-C_6)$alkylsulfonyl and N,N-di$(C_1-C_6)$alkylaminosulfonyl. In another embodiment, $R^3$ is phenyl wherein the phenyl is unsubstituted or monosubstituted with $(C_1-C_6)$alkoxy, $(C_1-C_6)$alkylsulfinyl, or $(C_1-C_6)$alkylsulfonyl. In another embodiment, $R^3$ is phenyl wherein the phenyl is unsubstituted or monosubstituted with halo, $(C_1-C_6)$alkoxy, or $(C_1-C_6)$alkylsulfonyl. In another embodiment, $R^3$ is phenyl wherein the phenyl is unsubstituted or monosubstituted with halo, $(C_1-C_6)$alkylsulfinyl, or $(C_1-C_6)$alkylsulfinyl. In another embodiment, $R^3$ is phenyl wherein the phenyl is unsubstituted or monosubstituted with halo, $(C_1-C_6)$alkoxy, or $(C_1-C_6)$alkylsulfonyl. In another embodiment, $R^3$ is phenyl wherein the phenyl is unsubstituted or monosubstituted with halo, $(C_1-C_6)$alkoxy, and —C(=O)NR$^4$R$^5$. In another embodiment, $R^3$ is phenyl wherein the phenyl is unsubstituted or monosubstituted with halo, $(C_1-C_6)$alkoxy, and $(C_1-C_6)$alkylsulfonyl. In another embodiment, $R^3$ is phenyl wherein the phenyl is unsubstituted or monosubstituted with halo, $(C_1-C_6)$alkoxy, and N,N-di$(C_1-C_6)$alkylaminosulfonyl. In another embodiment, $R^3$ is phenyl wherein the phenyl is unsubstituted or monosubstituted with $(C_1-C_6)$alkoxy, —C(=O)NR$^4$R$^5$, and $(C_1-C_6)$alkylsulfinyl. In another embodiment, $R^3$ is phenyl wherein the phenyl is unsubstituted or monosubstituted with $(C_1-C_6)$alkoxy, —C(=O) NR$^4$R$^5$ and $(C_1-C_6)$alkylsulfonyl. In another embodiment, $R^3$ is phenyl wherein the phenyl is unsubstituted or monosubstituted with $(C_1-C_6)$alkoxy, —C(=O)NR$^4$R$^5$ and N,N-di$(C_1-C_6)$alkylaminosulfonyl. In another embodiment, $R^3$ is phenyl wherein the phenyl is unsubstituted or monosubstituted with —C(=O)NR$^4$R$^5$, $(C_1-C_6)$alkylsulfinyl and $(C_1-C_6)$alkylsulfonyl. In another embodiment, $R^3$ is phenyl wherein the phenyl is unsubstituted or monosubstituted with —C(=O)NR$^4$R$^5$, $(C_1-C_6)$alkylsulfinyl and N,N-di$(C_1-C_6)$alkylaminosulfonyl. In another embodiment, $R^3$ is phenyl wherein the phenyl is unsubstituted or monosubstituted with $(C_1-C_6)$alkylsulfinyl, $(C_1-C_6)$alkylsulfonyl and N,N-di$(C_1-C_6)$alkylaminosulfonyl.

In another embodiment, $R^3$ is phenyl wherein the phenyl is unsubstituted or monosubstituted with fluoro, bromo, methoxy, methylsulfinyl, methylsulfonyl, dimethylaminosulfonyl or dimethylcarbamyl. In another embodiment, $R^3$ is phenyl wherein the phenyl is unsubstituted or monosubstituted with fluoro, methylsulfinyl, or methylsulfonyl. In another embodiment, $R^3$ is unsubstituted phenyl, fluorophenyl, bromophenyl, methoxyphenyl, methylsulfinylphenyl, methylsulfonylphenyl, dimethylaminosulfonylphenyl or dimethylcarbamylphenyl. In another embodiment, $R^3$ is unsubstituted phenyl, fluorophenyl, methylsulfinylphenyl, or methylsulfonylphenyl. In another embodiment, $R^3$ is unsubstituted phenyl, 4-fluorophenyl, 4-bromophenyl, 4-methoxyphenyl, 4-methylsulfinylphenyl, 4-methylsulfonylphenyl, 4-dimethylaminosulfonylphenyl or 4-dimethylcarbamylphenyl. In another embodiment, $R^3$ is unsubstituted phenyl, 4-fluorophenyl, 4-methylsulfinylphenyl, or 4-methylsulfonylphenyl.

In another embodiment, $R^3$ is unsubstituted phenyl.

In another embodiment, $R^3$ is phenyl monosubstituted with $(C_1-C_6)$alkylsulfonyl. In another embodiment, $R^3$ is iso-propylsulfonylphenyl. In another embodiment, $R^3$ is ethylsulfonylphenyl. In another embodiment, $R^3$ is methylsulfonylphenyl. In another embodiment, $R^3$ is 4-$(C_1-C_6)$alkylsulfonylphenyl. In another embodiment, $R^3$ is 4-iso-propylsulfonylphenyl. In another embodiment, $R^3$ is 4-ethylsulfonylphenyl. In another embodiment, $R^3$ is 4-methylsulfonylphenyl.

In another embodiment, $R^3$ is phenyl monosubstituted with $(C_1-C_6)$alkylsulfinyl. In another embodiment, $R^3$ is iso-propylsulfinylphenyl. In another embodiment, $R^3$ is ethylsulfinylphenyl. In another embodiment, $R^3$ is methylsulfinylphenyl. In another embodiment, $R^3$ is 4-$(C_1-C_6)$alkylsulfinylphenyl. In another embodiment, $R^3$ is 4-iso-propylsulfinylphenyl. In another embodiment, $R^3$ is 4-ethylsulfinylphenyl. In another embodiment, $R^3$ is 4-methylsulfinylphenyl.

In another embodiment, $R^3$ is phenyl monosubstituted with $(C_1-C_6)$alkoxy. In another embodiment, $R^3$ is phenyl monosubstituted with $(C_1-C_4)$alkoxy. In another embodiment, $R^3$ is iso-propoxyphenyl. In another embodiment, $R^3$ is ethoxyphenyl. In another embodiment, $R^3$ is methoxyphenyl. In another embodiment, $R^3$ is 4-$(C_1-C_6)$alkoxyphenyl. In another embodiment, $R^3$ is 4-iso-propoxyphenyl. In another embodiment, $R^3$ is 4-ethoxyphenyl. In another embodiment, $R^3$ is 4-methoxyphenyl.

In another embodiment, $R^3$ is phenyl monosubstituted with —C(=O)NR$^4$R$^5$. In another embodiment, $R^3$ is phenyl monosubstituted with —C(=O)NR$^4$R$^5$ and at least one of $R^4$ and $R^5$ is $(C_1-C_6)$alkyl. In another embodiment, $R^3$ is phenyl monosubstituted with —C(=O)NR$^4$R$^5$ and both of $R^4$ and $R^5$ are $(C_1-C_6)$alkyl. In another embodiment, $R^3$ is phenyl monosubstituted with —C(=O)NR$^4$R$^5$ and at least one of $R^4$ and $R^5$ is methyl. In another embodiment, $R^3$ is phenyl monosubstituted with —C(=O)NR$^4$R$^5$ and both of R$^4$ and R$^5$ are methyl. In another embodiment, R$^3$ is phenyl monosubstituted with —C(=O)NR$^4$R$^5$ and at least one of R$^4$ and R$^5$ is H. In another embodiment, R$^3$ is phenyl monosubstituted with —C(=O)NR$^4$R$^5$ and both of R$^4$ and R$^5$ are H. In another embodiment, R$^3$ is dimethylcarbamylphenyl. In another embodiment, R$^3$ is methylcarbamylphenyl. In another embodiment, R$^3$ is carbamylphenyl. In another embodiment, R$^3$ is 4-C(=O)NR$^4$R$^5$phenyl. In another embodiment, R$^3$ is 4-dimethylcarbamylphenyl. In another embodiment, R$^3$ is 4-methylcarbamylphenyl. In another embodiment, R$^3$ is 4-carbamylphenyl.

In another embodiment, R$^3$ is phenyl monosubstituted with N,N-di(C$_1$-C$_6$)alkylaminosulfonyl. In another embodiment, R$^3$ is phenyl monosubstituted with N,N-di(C$_1$-C$_4$)alkylaminosulfonyl. In another embodiment, R$^3$ is dimethylaminosulfonylphenyl. In another embodiment, R$^3$ is diethylaminosulfonylphenyl. In another embodiment, R$^3$ is dipropylaminosulfonylphenyl. In another embodiment, R$^3$ is 4-dimethylaminosulfonylphenyl. In another embodiment, R$^3$ is 4-diethylaminosulfonylphenyl. In another embodiment, R$^3$ is dipropylaminosulfonylphenyl.

In another embodiment, R$^3$ is phenyl, wherein the phenyl is unsubstituted or substituted with 1 or 2 substituent(s), each substituent being independently selected from halo and (C$_1$-C$_6$)alkoxy. In another embodiment, R$^3$ is phenyl, wherein the phenyl is monosubstituted with halo and also monosubstituted with (C$_1$-C$_6$)alkoxy. In another embodiment, R$^3$ is phenyl, wherein the phenyl is unsubstituted or substituted with 1 or 2 substituent(s), each substituent being independently selected from halo and (C$_1$-C$_4$)alkoxy. In another embodiment, R$^3$ is phenyl, wherein the phenyl is disubstituted—monosubstituted with halo and also monosubstituted with (C$_1$-C$_4$)alkoxy. In another embodiment, R$^3$ is phenyl, wherein the phenyl is disubstituted with each substituent independently selected from fluoro, chloro, bromo, methoxy, and ethoxy. In another embodiment, R$^3$ is phenyl, wherein the phenyl is monosubstituted with a substituent selected from fluoro, chloro, bromo, methoxy, and ethoxy.

In another embodiment, R$^3$ is phenyl, wherein the phenyl is unsubstituted or substituted with 1 or 2 substituent(s), each substituent being independently selected from halo. In another embodiment, R$^3$ is phenyl, wherein the phenyl is unsubstituted or monosubstituted or disubstituted with halo. In another embodiment, R$^3$ is phenyl, wherein the phenyl is unsubstituted or monosubstituted or disubstituted with fluoro. In another embodiment, R$^3$ is phenyl, wherein the phenyl is unsubstituted or monosubstituted or disubstituted with chloro. In another embodiment, R$^3$ is phenyl, wherein the phenyl is unsubstituted or monosubstituted or disubstituted with bromo. In another embodiment, R$^3$ is unsubstituted phenyl. In another embodiment, R$^3$ is phenyl monosubstituted with halo. In another embodiment, R$^3$ is fluorophenyl. In another embodiment, R$^3$ is 4-fluorophenyl. In another embodiment, R$^3$ is 2-fluorophenyl. In another embodiment, R$^3$ is chlorophenyl. In another embodiment, R$^3$ is 4-chlorophenyl. In another embodiment, R$^3$ is 2-chlorophenyl. In another embodiment, R$^3$ is bromophenyl. In another embodiment, R$^3$ is 4-bromophenyl. In another embodiment, R$^3$ is 2-bromophenyl. In another embodiment, R$^3$ is phenyl monosubstituted with (C$_1$-C$_6$)alkoxy. In another embodiment, R$^3$ is phenyl monosubstituted with (C$_1$-C$_4$)alkoxy. In another embodiment, R$^3$ is iso-propoxyphenyl. In another embodiment, R$^3$ is methoxyphenyl. In another embodiment, R$^3$ is 4-(C$_1$-C$_6$)alkoxyphenyl. In another embodiment, R$^3$ is 4-(C$_1$-C$_4$)alkoxyphenyl. In another embodiment, R$^3$ is 4-iso-propoxyphenyl. In another embodiment, R$^3$ is 4-ethoxyphenyl. In another embodiment, R$^3$ is 4-methoxyphenyl.

In another embodiment, R$^1$ is methyl and R$^2$ is methyl. In another embodiment, R$^1$ is methyl and R$^2$ is ethyl. In another embodiment, R$^1$ is ethyl and R$^2$ is methyl. In another embodiment, R$^1$ is ethyl and R$^2$ is ethyl. In another embodiment, R$^1$ is iso-propyl and R$^2$ is methyl. In another embodiment, R$^1$ is iso-propyl and R$^2$ is ethyl. In another embodiment, R$^1$ is methyl and R$^2$ is iso-propyl. In another embodiment, R$^1$ is ethyl and R$^2$ is iso-propyl. In another embodiment, R$^1$ is iso-propyl and R$^2$ is iso-propyl. In another embodiment, R$^1$ is tert-butyl and R$^2$ is methyl. In another embodiment, R$^1$ is tert-butyl and R$^2$ is ethyl. In another embodiment, R$^1$ is methyl and R$^2$ is tert-butyl. In another embodiment, R$^1$ is ethyl and R$^2$ is tert-butyl. In another embodiment, R$^1$ is tert-butyl and R$^2$ is tert-butyl. In another embodiment, R$^1$ is unsubstituted phenyl and R$^2$ is methyl. In another embodiment, R$^1$ is unsubstituted phenyl and R$^2$ is ethyl. In another embodiment, R$^1$ is unsubstituted phenyl and R$^2$ is iso-propyl. In another embodiment, R$^1$ is unsubstituted phenyl and R$^2$ is tert-butyl.

In another embodiment, R$^1$ is methyl and R$^3$ is unsubstituted phenyl. In another embodiment, R$^1$ is ethyl and R$^3$ is unsubstituted phenyl. In another embodiment, R$^1$ is iso-propyl and R$^3$ is unsubstituted phenyl. In another embodiment, R$^1$ is unsubstituted phenyl and R$^3$ is unsubstituted phenyl. In another embodiment, R$^1$ is methyl and R$^3$ is monosubstituted phenyl, e.g., selected from among the monosubstituted R$^3$ phenyl groups disclosed above in connection with the compounds of formula (Ib). In another embodiment, R$^1$ is ethyl and R$^3$ is, e.g., selected from among the monosubstituted R$^3$ phenyl groups disclosed above in connection with the compounds of formula (Ib). In another embodiment, R$^1$ is iso-propyl and R$^3$ is, e.g., selected from among the monosubstituted R$^3$ phenyl groups disclosed above in connection with the compounds of formula (Ib). In another embodiment, R$^1$ is unsubstituted phenyl and R$^3$ is, e.g., selected from among the monosubstituted R$^3$ phenyl groups disclosed above in connection with the compounds of formula (Ib).

In another embodiment, R$^1$ is methyl and R$^3$ is unsubstituted (5- or 6-membered)heteroaryl. In another embodiment, R$^1$ is ethyl and R$^3$ is unsubstituted (5- or 6-membered)heteroaryl. In another embodiment, R$^1$ is iso-propyl and R$^3$ is unsubstituted (5- or 6-membered)heteroaryl. In another embodiment, R$^1$ is unsubstituted phenyl and R$^3$ is unsubstituted (5- or 6-membered)heteroaryl. In another embodiment, R$^1$ is methyl and R$^3$ is monosubstituted (5- or 6-membered) heteroaryl, e.g., selected from among the monosubstituted R$^3$ heteroaryl groups disclosed above in connection with the compounds of formula (Ib). In another embodiment, R$^1$ is ethyl and R$^3$ is monosubstituted (5- or 6-membered)heteroaryl, e.g., selected from among the monosubstituted R$^3$ heteroaryl groups disclosed above in connection with the compounds of formula (Ib). In another embodiment, R$^1$ is iso-propyl and R$^3$ is monosubstituted (5- or 6-membered) heteroaryl, e.g., selected from among the monosubstituted R$^3$ heteroaryl groups disclosed above in connection with the compounds of formula (Ib). In another embodiment, R$^1$ is unsubstituted phenyl and R$^3$ is monosubstituted (5- or 6-membered)heteroaryl, e.g., selected from among the monosubstituted R$^3$ heteroaryl groups disclosed above in connection with the compounds of formula (Ib).

In another embodiment, R$^2$ is methyl and R$^3$ is unsubstituted phenyl. In another embodiment, R$^2$ is ethyl and R$^3$ is unsubstituted phenyl. In another embodiment, $R^2$ is iso-propyl and $R^3$ is unsubstituted phenyl. In another embodiment, $R^2$ is tert-butyl and $R^3$ is unsubstituted phenyl. In another embodiment, $R^2$ is methyl and $R^3$ is monosubstituted phenyl, e.g., selected from among the monosubstituted $R^3$ phenyl groups disclosed above in connection with the compounds of formula (Ib). In another embodiment, $R^2$ is ethyl and $R^3$ is monosubstituted phenyl, e.g., selected from among the monosubstituted $R^3$ phenyl groups disclosed above in connection with the compounds of formula (Ib). In another embodiment, $R^2$ is iso-propyl and $R^3$ is monosubstituted phenyl, e.g., selected from among the monosubstituted $R^3$ phenyl groups disclosed above in connection with the compounds of formula (Ib). In another embodiment, $R^2$ is tert-butyl and $R^3$ is monosubstituted phenyl, e.g., selected from among the monosubstituted $R^3$ phenyl groups disclosed above in connection with the compounds of formula (Ib).

In another embodiment, $R^2$ is methyl and $R^3$ is unsubstituted (5- or 6-membered)heteroaryl. In another embodiment, $R^2$ is ethyl and $R^3$ is unsubstituted (5- or 6-membered)heteroaryl. In another embodiment, $R^2$ is iso-propyl and $R^3$ is unsubstituted (5- or 6-membered)heteroaryl. In another embodiment, $R^2$ is tert-butyl and $R^3$ is unsubstituted (5- or 6-membered)heteroaryl. In another embodiment, $R^2$ is methyl and $R^3$ is monosubstituted ((5- or 6-membered)heteroaryl, e.g., selected from among the monosubstituted $R^3$ heteroaryl groups disclosed above in connection with the compounds of formula (Ib). In another embodiment, $R^2$ is ethyl and $R^3$ is monosubstituted (5- or 6-membered)heteroaryl, e.g., selected from among the monosubstituted $R^3$ heteroaryl groups disclosed above in connection with the compounds of formula (Ib). In another embodiment, $R^2$ is iso-propyl and $R^3$ is monosubstituted (5- or 6-membered) heteroaryl, e.g., selected from among the monosubstituted $R^3$ heteroaryl groups disclosed above in connection with the compounds of formula (Ib). In another embodiment, $R^2$ is tert-butyl and $R^3$ is monosubstituted (5- or 6-membered) heteroaryl, e.g., selected from among the monosubstituted $R^3$ heteroaryl groups disclosed above in connection with the compounds of formula (Ib).

Another aspect of the disclosure provides a compound of formula (Ic)

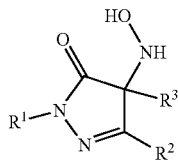

(Ic)

or a pharmaceutically acceptable salt thereof, wherein:
$R^1$ is $(C_1-C_6)$alkyl or phenyl, wherein said phenyl is unsubstituted or substituted with 1, 2, 3, 4, or 5 substituent(s) independently selected from halo;
$R^2$ is $(C_2-C_6)$alkyl, $(C_1-C_6)$alkoxy, phenylsulfanyl, phenylsulfonyl, phenylsulfinyl or $(C_3-C_6)$cycloalkyl; and
$R^3$ is $(C_1-C_6)$alkyl, —C(=NOR$^9$)R$^{10}$ wherein R$^9$ and R$^{10}$ are independently selected from $(C_1-C_6)$alkyl.

In one embodiment, $R^1$ is $(C_1-C_6)$alkyl or phenyl, wherein the phenyl is unsubstituted or substituted with 1, 2, or 3 substituent(s) independently selected from halo. In another embodiment, $R^1$ is $(C_1-C_6)$alkyl or phenyl, wherein the phenyl is unsubstituted or substituted with 1 or 2 substituent (s), each substituent being independently selected from halo. In another embodiment, $R^1$ is $(C_1-C_6)$alkyl or phenyl, wherein the phenyl is unsubstituted or monosubstituted or disubstituted with halo. In another embodiment, $R^1$ is $(C_1-C_6)$alkyl or phenyl, wherein the phenyl is unsubstituted or monosubstituted or disubstituted with fluoro. In another embodiment, $R^1$ is $(C_1-C_6)$alkyl or phenyl, wherein the phenyl is unsubstituted or monosubstituted or disubstituted with chloro. In another embodiment, $R^1$ is $(C_1-C_6)$alkyl or phenyl, wherein the phenyl is unsubstituted or monosubstituted or disubstituted with bromo. In another embodiment, $R^1$ is unsubstituted phenyl. In another embodiment, $R^1$ is phenyl monosubstituted with halo. In another embodiment, $R^1$ is fluorophenyl. In another embodiment, $R^1$ is 4-fluorophenyl. In another embodiment, $R^1$ is 2-fluorophenyl. In another embodiment, $R^1$ is chlorophenyl. In another embodiment, $R^1$ is 4-chlorophenyl. In another embodiment, $R^1$ is 2-chlorophenyl. In another embodiment, $R^1$ is bromophenyl. In another embodiment, $R^1$ is 4-bromophenyl. In another embodiment, $R^1$ is 2-bromophenyl. In another embodiment, $R^1$ is $(C_1-C_6)$alkyl. In one embodiment, $R^1$ is methyl, ethyl, iso-propyl, or tert-butyl. In another embodiment, $R^1$ is methyl, ethyl, or iso-propyl. In another embodiment, $R^1$ is methyl, ethyl, or tert-butyl. In another embodiment, $R^1$ is methyl, iso-propyl, or tert-butyl. In another embodiment, $R^1$ is ethyl, iso-propyl, or tert-butyl. In another embodiment, $R^1$ is methyl or ethyl. In another embodiment, $R^1$ is methyl or iso-propyl. In another embodiment, $R^1$ is methyl or tert-butyl. In another embodiment, $R^1$ is ethyl or iso-propyl. In another embodiment, $R^1$ is ethyl or tert-butyl. In another embodiment, $R^1$ is iso-propyl or tert-butyl. In another embodiment, $R^1$ is methyl. In another embodiment, $R^1$ is ethyl. In another embodiment, $R^1$ is iso-propyl. In another embodiment, $R^1$ is tert-butyl.

In one embodiment, $R^2$ is $(C_2-C_6)$alkyl. In another embodiment, $R^2$ is ethyl, propyl, or butyl. In another embodiment, $R^2$ is propyl or butyl. In another embodiment, $R^2$ is iso-propyl or tert-butyl. In another embodiment, $R^2$ is propyl. In another embodiment, $R^2$ is iso-propyl. In another embodiment, $R^2$ is butyl. In another embodiment, $R^2$ is tert-butyl. In another embodiment, $R^2$ is $(C_3-C_6)$cycloalkyl. In another embodiment, $R^2$ is cyclopropyl, cyclobutyl, cyclopentyl or cyclohexyl. In another embodiment, $R^2$ is cyclopropyl or cyclobutyl. In another embodiment, $R^2$ is cyclopropyl or cyclopentyl. In another embodiment, $R^2$ is cyclopropyl or cyclohexyl. In another embodiment, $R^2$ is cyclobutyl or cyclopentyl. In another embodiment, $R^2$ is cyclobutyl or cyclohexyl. In another embodiment, $R^2$ is cyclopentyl or cyclohexyl. In another embodiment, $R^2$ is cyclopropyl. In another embodiment, $R^2$ is cyclobutyl. In another embodiment, $R^2$ is cyclopentyl. In another embodiment, $R^2$ is cyclohexyl. In another embodiment, $R^2$ is propyl, butyl or cyclopropyl. In another embodiment, $R^2$ is iso-propyl, tert-butyl or cyclopropyl. In one embodiment, $R^2$ is $(C_1-C_6)$alkoxy. In another embodiment, $R^2$ is methoxy, ethoxy or propoxy. In another embodiment, $R^2$ is methoxy or ethoxy. In another embodiment, $R^2$ is methoxy. In another embodiment, $R^2$ is ethoxy. In one embodiment, $R^2$ is phenylsulfanyl, phenylsulfonyl or phenylsulfinyl. In another embodiment, $R^2$ is phenylsulfanyl. In another embodiment, $R^2$ is phenylsulfonyl. In another embodiment, $R^2$ is phenylsulfinyl. In another embodiment, $R^2$ is propyl, butyl, is methoxy, ethoxy, propoxy, cyclopropyl, phenylsulfanyl, phenylsulfonyl or phenylsulfinyl.

In one embodiment, $R^3$ is —C(=NOR$^9$)R$^{10}$ wherein at least one of $R^9$ and $R^{10}$ is methyl. In another embodiment, $R^3$ is —C(=NOR$^9$)R$^{10}$ wherein each of $R^9$ and $R^{10}$ is methyl. In another embodiment, $R^3$ is —C(=NOR$^9$)R$^{10}$ wherein one of $R^9$ and $R^{10}$ is methyl and the other is ethyl. In another embodiment, $R^3$ is —C(=NOR$^9$)R$^{10}$ wherein one of $R^9$ and $R^{10}$ is methyl and the other is tert-butyl.

In another embodiment, $R^3$ is $(C_1-C_6)$alkyl. In one embodiment, $R^3$ is methyl, ethyl, iso-propyl, or tert-butyl. In another embodiment, $R^3$ is methyl, ethyl, or iso-propyl. In another embodiment, $R^3$ is methyl, ethyl, or tert-butyl. In another embodiment, $R^3$ is methyl, iso-propyl, or tert-butyl. In another embodiment, $R^3$ is ethyl, iso-propyl, or tert-butyl. In another embodiment, $R^3$ is methyl or ethyl. In another embodiment, $R^3$ is methyl or iso-propyl. In another embodiment, $R^3$ is methyl or tert-butyl. In another embodiment, $R^3$ is ethyl or iso-propyl. In another embodiment, $R^3$ is ethyl or tert-butyl. In another embodiment, $R^3$ is iso-propyl or tert-butyl. In another embodiment, $R^3$ is methyl. In another embodiment, $R^3$ is ethyl. In another embodiment, $R^3$ is iso-propyl. In another embodiment, $R^3$ is tert-butyl.

In another embodiment, $R^1$ is methyl and $R^2$ is ethyl. In another embodiment, $R^1$ is ethyl and $R^2$ is ethyl. In another embodiment, $R^1$ is iso-propyl and $R^2$ is ethyl. In another embodiment, $R^1$ is methyl and $R^2$ is iso-propyl. In another embodiment, $R^1$ is ethyl and $R^2$ is iso-propyl. In another embodiment, $R^1$ is iso-propyl and $R^2$ is iso-propyl. In another embodiment, $R^1$ is tert-butyl and $R^2$ is ethyl. In another embodiment, $R^1$ is methyl and $R^2$ is tert-butyl. In another embodiment, $R^1$ is ethyl and $R^2$ is tert-butyl. In another embodiment, $R^1$ is tert-butyl and $R^2$ is tert-butyl. In another embodiment, $R^1$ is unsubstituted phenyl and $R^2$ is ethyl. In another embodiment, $R^1$ is unsubstituted phenyl and $R^2$ is iso-propyl. In another embodiment, $R^1$ is unsubstituted phenyl and $R^2$ is tert-butyl. In another embodiment, $R^1$ is monosubstituted phenyl, e.g., selected from among the monosubstituted $R^1$ phenyl groups disclosed above in connection with the compounds of formula (Ic), and $R^2$ is ethyl. In another embodiment, $R^1$ is monosubstituted phenyl, e.g., selected from among the monosubstituted $R^1$ phenyl groups disclosed above in connection with the compounds of formula (Ic), and $R^2$ is iso-propyl. In another embodiment, $R^1$ is monosubstituted phenyl, e.g., selected from among the monosubstituted $R^1$ phenyl groups disclosed above in connection with the compounds of formula (Ic), and $R^2$ is tert-butyl. In another embodiment, $R^1$ is methyl and $R^2$ is $(C_3-C_6)$cycloalkyl. In another embodiment, $R^1$ is ethyl and $R^2$ is $(C_3-C_6)$cycloalkyl. In another embodiment, $R^1$ is iso-propyl and $R^2$ is $(C_3-C_6)$cycloalkyl. In another embodiment, $R^1$ is tert-butyl and $R^2$ is $(C_3-C_6)$cycloalkyl. In another embodiment, $R^1$ is unsubstituted phenyl and $R^2$ is $(C_3-C_6)$cycloalkyl. In another embodiment, $R^1$ is monosubstituted phenyl, e.g., selected from among the monosubstituted $R^1$ phenyl groups disclosed above in connection with the compounds of formula (Ic), and $R^2$ is $(C_3-C_6)$cycloalkyl. In another embodiment, $R^1$ is methyl and $R^2$ is methoxy. In another embodiment, $R^1$ is ethyl and $R^2$ is methoxy. In another embodiment, $R^1$ is iso-propyl and $R^2$ is methoxy. In another embodiment, $R^1$ is tert-butyl and $R^2$ is methoxy. In another embodiment, $R^1$ is unsubstituted phenyl and $R^2$ is methoxy. In another embodiment, $R^1$ is methyl and $R^2$ is ethoxy. In another embodiment, $R^1$ is ethyl and $R^2$ is ethoxy. In another embodiment, $R^1$ is iso-propyl and $R^2$ is methoxy. In another embodiment, $R^1$ is tert-butyl and $R^2$ is ethoxy. In another embodiment, $R^1$ is unsubstituted phenyl and $R^2$ is ethoxy. In another embodiment, $R^1$ is methyl and $R^2$ is propoxy. In another embodiment, $R^1$ is ethyl and $R^2$ is propoxy. In another embodiment, $R^1$ is iso-propyl and $R^2$ is propoxy. In another embodiment, $R^1$ is tert-butyl and $R^2$ is propoxy. In another embodiment, $R^1$ is unsubstituted phenyl and $R^2$ is propoxy. In another embodiment, $R^1$ is methyl and $R^2$ is tert-butoxy. In another embodiment, $R^1$ is ethyl and $R^2$ is tert-butoxy. In another embodiment, $R^1$ is iso-propyl and $R^2$ is tert-butoxy. In another embodiment, $R^1$ is tert-butyl and $R^2$ is tert-butoxy. In another embodiment, $R^1$ is unsubstituted phenyl and $R^2$ is tert-butoxy.

In another embodiment, $R^1$ is methyl and $R^3$ is —C(=NOR$^9$)R$^{10}$ wherein at least one of $R^9$ and $R^{10}$ is methyl. In another embodiment, $R^1$ is ethyl and $R^3$ is —C(=NOR$^9$)R$^{10}$ wherein at least one of $R^9$ and $R^{10}$ is methyl. In another embodiment, $R^1$ is iso-propyl and $R^3$ is —C(=NOR$^9$)R$^{10}$ wherein at least one of $R^9$ and $R^{10}$ is methyl. In another embodiment, $R^1$ is unsubstituted phenyl and $R^3$ is —C(=NOR$^9$)R$^{10}$ wherein at least one of $R^9$ and $R^{10}$ is methyl. In another embodiment, $R^1$ is monosubstituted phenyl, e.g., selected from among the monosubstituted $R^1$ phenyl groups disclosed above in connection with the compounds of formula (Ic), and $R^3$ is —C(=NOR$^9$)R$^{10}$ wherein at least one of $R^9$ and $R^{10}$ is methyl. In another embodiment, $R^1$ is methyl and $R^3$ is —C(=NOR$^9$)R$^{10}$ wherein each of $R^9$ and $R^{10}$ is methyl. In another embodiment, $R^1$ is methyl and $R^3$ is —C(=NOR$^9$)R$^{10}$ wherein one of $R^9$ and $R^{10}$ is methyl and the other is ethyl. In another embodiment, $R^1$ is methyl and $R^3$ is —C(=NOR$^9$)R$^{10}$ wherein one of $R^9$ and $R^{10}$ is methyl and the other is tert-butyl. In another embodiment, $R^1$ is ethyl and $R^3$—C(=NOR$^9$)R$^{10}$ wherein each of $R^9$ and $R^{10}$ is methyl. In another embodiment, $R^1$ is ethyl and $R^3$ is —C(=NOR$^9$)R$^{10}$ wherein one of $R^9$ and $R^{10}$ is methyl and the other is ethyl. In another embodiment, $R^1$ is ethyl and $R^3$ is —C(=NOR$^9$)R$^{10}$ wherein one of $R^9$ and $R^{10}$ is methyl and the other is tert-butyl. In another embodiment, $R^1$ is iso-propyl and $R^3$ is —C(=NOR$^9$)R$^{10}$ wherein each of $R^9$ and $R^{10}$ is methyl. In another embodiment, $R^1$ is iso-propyl and $R^3$ is —C(=NOR$^9$)R$^{10}$ wherein one of $R^9$ and $R^{10}$ is methyl and the other is ethyl. In another embodiment, $R^1$ is iso-propyl and $R^3$ is —C(=NOR$^9$)R$^{10}$ wherein one of $R^9$ and $R^{10}$ is methyl and the other is tert-butyl. In another embodiment, $R^1$ is unsubstituted phenyl and $R^3$ is —C(=NOR$^9$)R$^{10}$ wherein each of $R^9$ and $R^{10}$ is methyl. In another embodiment, $R^1$ is unsubstituted phenyl and $R^3$ is —C(=NOR$^9$)R$^{10}$ wherein one of $R^9$ and $R^{10}$ is methyl and the other is ethyl. In another embodiment, $R^1$ is unsubstituted phenyl and $R^3$ is —C(=NOR$^9$)R$^{10}$ wherein one of $R^9$ and $R^{10}$ is methyl and the other is tert-butyl. In another embodiment, $R^1$ is monosubstituted phenyl, e.g., selected from among the monosubstituted $R^1$ phenyl groups disclosed above in connection with the compounds of formula (Ic), and $R^3$ is —C(=NOR$^9$)R$^{10}$ wherein each of $R^9$ and $R^{10}$ is methyl. In another embodiment, R is monosubstituted phenyl, e.g., selected from among the monosubstituted $R^1$ phenyl groups disclosed above in connection with the compounds of formula (Ic), and $R^3$ is —C(=NOR$^9$)R$^{10}$ wherein one of $R^9$ and $R^{10}$ is methyl and the other is ethyl. In another embodiment, $R^1$ is monosubstituted phenyl, e.g., selected from among the monosubstituted $R^1$ phenyl groups disclosed above in connection with the compounds of formula (Ic), and $R^3$ is —C(=NOR$^9$)R$^{10}$ wherein one of $R^9$ and $R^{10}$ is methyl and the other is tert-butyl.

In another embodiment, $R^1$ is methyl and $R^3$ is methyl. In another embodiment, $R^1$ is ethyl and $R^3$ is methyl. In another embodiment, $R^1$ is iso-propyl and $R^3$ is methyl. In another embodiment, $R^1$ is unsubstituted phenyl and $R^3$ is methyl. In another embodiment, $R^1$ is monosubstituted phenyl, e.g., selected from among the monosubstituted $R^1$ phenyl groups disclosed above in connection with the compounds of formula (Ic), and $R^3$ is methyl. In another embodiment, $R^1$ is methyl and $R^3$ is ethyl. In another embodiment, $R^1$ is ethyl and $R^3$ is ethyl. In another embodiment, $R^1$ is iso-propyl and $R^3$ is ethyl. In another embodiment, $R^1$ is unsubstituted phenyl and $R^3$ is ethyl. In another embodiment, $R^1$ is monosubstituted phenyl, e.g., selected from among the monosubstituted $R^1$ phenyl groups disclosed above in connection with the compounds of formula (Ic), and $R^3$ is ethyl. In another embodiment, $R^1$ is methyl and $R^3$ is propyl. In another embodiment, $R^1$ is ethyl and $R^3$ is propyl. In another embodiment, R is iso-propyl and $R^3$ is propyl. In another embodiment, $R^1$ is unsubstituted phenyl and $R^3$ is propyl. In another embodiment, $R^1$ is monosubstituted phenyl, e.g., selected from among the monosubstituted $R^1$ phenyl groups disclosed above in connection with the compounds of formula (Ic), and $R^3$ is propyl. In another embodiment, $R^1$ is methyl and $R^3$ is butyl. In another embodiment, $R^1$ is ethyl and $R^3$ is butyl. In another embodiment, $R^1$ is iso-propyl and $R^3$ is butyl. In another embodiment, $R^1$ is unsubstituted phenyl and $R^3$ is butyl. In another embodiment, $R^1$ is monosubstituted phenyl, e.g., selected from among the monosubstituted $R^1$ phenyl groups disclosed above in connection with the compounds of formula (Ic), and $R^3$ is butyl.

In another embodiment, $R^2$ is ethyl and $R^3$ is —C(=NOR$^9$)R$^{10}$ wherein at least one of $R^9$ and $R^{10}$ is methyl. In another embodiment, $R^2$ is iso-propyl and $R^3$ is —C(=NOR$^9$)R$^{10}$ wherein at least one of $R^9$ and $R^{10}$ is methyl. In another embodiment, $R^2$ is tert-butyl and $R^3$ is —C(=NOR$^9$)R$^{10}$ wherein at least one of $R^9$ and $R^{10}$ is methyl. In another embodiment, $R^2$ is $(C_3-C_6)$cycloalkyl and $R^3$ is —C(=NOR$^9$)R$^{10}$ wherein at least one of $R^9$ and $R^{10}$ is methyl. In another embodiment, $R^2$ is cyclopropyl and $R^3$ is —C(=NOR$^9$)R$^{10}$ wherein at least one of $R^9$ and $R^{10}$ is methyl. In another embodiment, $R^2$ is cyclobutyl and $R^3$ is —C(=NOR$^9$)R$^{10}$ wherein at least one of $R^9$ and $R^{10}$ is methyl. In another embodiment, $R^2$ is cyclopentyl and $R^3$ is —C(=NOR$^9$)R$^{10}$ wherein at least one of $R^9$ and $R^{10}$ is methyl. In another embodiment, $R^2$ is cyclohexyl and $R^3$ is —C(=NOR$^9$)R$^{10}$ wherein at least one of $R^9$ and $R^{10}$ is methyl. In another embodiment, $R^2$ is methoxy and $R^3$ is —C(=NOR$^9$)R$^{10}$ wherein at least one of $R^9$ and $R^{10}$ is methyl. In another embodiment, $R^2$ is ethoxy and $R^3$ is —C(=NOR$^9$)R$^{10}$ wherein at least one of $R^9$ and $R^{10}$ is methyl. In another embodiment, $R^2$ is propoxy and $R^3$ is —C(=NOR$^9$)R$^{10}$ wherein at least one of $R^9$ and $R^{10}$ is methyl. In another embodiment, $R^2$ is ethyl and $R^3$ is —C(=NOR$^9$)R$^{10}$ wherein each of $R^9$ and $R^{10}$ is methyl. In another embodiment, $R^2$ is ethyl and $R^3$ is —C(=NOR$^9$)R$^{10}$ wherein one of $R^9$ and $R^{10}$ is methyl and the other is ethyl. In another embodiment, $R^2$ is ethyl and $R^3$ is —C(=NOR$^9$)R$^{10}$ wherein one of $R^9$ and $R^{10}$ is methyl and the other is tert-butyl. In another embodiment, $R^2$ is iso-propyl and $R^3$ is —C(=NOR$^9$)R$^{10}$ wherein each of $R^9$ and $R^{10}$ is methyl. In another embodiment, $R^2$ is iso-propyl and $R^3$ is —C(=NOR$^9$)R$^{10}$ wherein one of $R^9$ and $R^{10}$ is methyl and the other is ethyl. In another embodiment, $R^2$ is iso-propyl and $R^3$ is —C(=NOR$^9$)R$^{10}$ wherein one of $R^9$ and $R^{10}$ is methyl and the other is tert-butyl. In another embodiment, $R^2$ is tert-butyl and $R^3$ is —C(=NOR$^9$)R$^{10}$ wherein each of $R^9$ and $R^{10}$ is methyl. In another embodiment, $R^2$ is tert-butyl and $R^3$ is —C(=NOR$^9$)R$^{10}$ wherein one of $R^9$ and $R^{10}$ is methyl and the other is ethyl. In another embodiment, $R^2$ is tert-butyl and $R^3$ is —C(=NOR$^9$)R$^{10}$ wherein one of $R^9$ and $R^{10}$ is methyl and the other is tert-butyl.

In another embodiment, $R^2$ is $(C_3-C_6)$cycloalkyl and $R^3$ is —C(=NOR$^9$)R$^{10}$ wherein each of $R^9$ and $R^{10}$ is methyl. In another embodiment, $R^2$ is $(C_3-C_6)$cycloalkyl and $R^3$ is —C(=NOR$^9$)R$^{10}$ wherein one of $R^9$ and $R^{10}$ is methyl and the other is ethyl. In another embodiment, $R^2$ is $(C_3-C_6)$cycloalkyl and $R^3$ is —C(=NOR$^9$)R$^{10}$ wherein one of $R^9$ and $R^{10}$ is methyl and the other is tert-butyl. In another embodiment, $R^2$ is cyclopropyl and $R^3$ is —C(=NOR$^9$)R$^{10}$ wherein each of $R^9$ and $R^{10}$ is methyl. In another embodiment, $R^2$ is cyclopropyl and $R^3$ is —C(=NOR$^9$)R$^{10}$ wherein one of $R^9$ and $R^{10}$ is methyl and the other is ethyl. In another embodiment, $R^2$ is cyclopropyl and $R^3$ is —C(=NOR$^9$)R$^{10}$ wherein one of $R^9$ and $R^{10}$ is methyl and the other is tert-butyl. In another embodiment, $R^2$ is cyclobutyl and $R^3$ is —C(=NOR$^9$)R$^{10}$ wherein each of $R^9$ and $R^{10}$ is methyl. In another embodiment, $R^2$ is cyclobutyl and $R^3$ is —C(=NOR$^9$)R$^{10}$ wherein one of $R^9$ and $R^{10}$ is methyl and the other is ethyl. In another embodiment, $R^2$ is cyclobutyl and $R^3$ is —C(=NOR$^9$)R$^{10}$ wherein one of $R^9$ and $R^{10}$ is methyl and the other is tert-butyl. In another embodiment, $R^2$ is cyclopentyl and $R^3$ is —C(=NOR$^9$)R$^{10}$ wherein each of $R^9$ and $R^{10}$ is methyl. In another embodiment, $R^2$ is cyclopentyl and $R^3$ is —C(=NOR$^9$)R$^{10}$ wherein one of $R^9$ and $R^{10}$ is methyl and the other is ethyl. In another embodiment, $R^2$ is cyclopentyl and $R^3$ is —C(=NOR$^9$)R$^{10}$ wherein one of $R^9$ and $R^{10}$ is methyl and the other is tert-butyl. In another embodiment, $R^2$ is cyclohexyl and $R^3$ is —C(=NOR$^9$)R$^{10}$ wherein each of $R^9$ and $R^{10}$ is methyl. In another embodiment, $R^2$ is cyclohexyl and $R^3$ is —C(=NOR$^9$)R$^{10}$ wherein one of $R^9$ and $R^{10}$ is methyl and the other is ethyl. In another embodiment, $R^2$ is cyclohexyl and $R^3$ is —C(=NOR$^9$)R$^{10}$ wherein one of $R^9$ and $R^{10}$ is methyl and the other is tert-butyl. In another embodiment, $R^2$ is methoxy and $R^3$ is —C(=NOR$^9$)R$^{10}$ wherein each of $R^9$ and $R^{10}$ is methyl. In another embodiment, $R^2$ is methoxy and $R^3$ is —C(=NOR$^9$)R$^{10}$ wherein one of $R^9$ and $R^{10}$ is methyl and the other is ethyl. In another embodiment, $R^2$ is methoxy and $R^3$ is —C(=NOR$^9$)R$^{10}$ wherein one of $R^9$ and $R^{10}$ is methyl and the other is tert-butyl. In another embodiment, $R^2$ is ethoxy and $R^3$ is —C(=NOR$^9$)R$^{10}$ wherein each of $R^9$ and $R^{10}$ is methyl. In another embodiment, $R^2$ is ethoxy and $R^3$ is —C(=NOR$^9$)R$^{10}$ wherein one of $R^9$ and $R^{10}$ is methyl and the other is ethyl. In another embodiment, $R^2$ is ethoxy and $R^3$ is —C(=NOR$^9$)R$^{10}$ wherein one of $R^9$ and $R^{10}$ is methyl and the other is tert-butyl. In another embodiment, $R^2$ is propoxy and $R^3$ is —C(=NOR$^9$)R$^{10}$ wherein each of $R^9$ and $R^{10}$ is methyl. In another embodiment, $R^2$ is propoxy and $R^3$ is —C(=NOR$^9$)R$^{10}$ wherein one of $R^9$ and $R^{10}$ is methyl and the other is ethyl. In another embodiment, $R^2$ is propoxy and $R^3$ is —C(=NOR$^9$)R$^{10}$ wherein one of $R^9$ and $R^{10}$ is methyl and the other is tert-butyl.

In another embodiment, $R^2$ is methyl and $R^3$ is methyl. In another embodiment, $R^2$ is ethyl and $R^3$ is methyl. In another embodiment, $R^2$ is iso-propyl and $R^3$ is methyl. In another embodiment, $R^2$ is tert-butyl and $R^3$ is methyl. In another embodiment, $R^2$ is $(C_3-C_6)$cycloalkyl and $R^3$ is methyl. In another embodiment, $R^2$ is cyclopropyl and $R^3$ is methyl. In another embodiment, $R^2$ is cyclobutyl and $R^3$ is methyl. In another embodiment, $R^2$ is cyclopentyl and $R^3$ is methyl. In another embodiment, $R^2$ is cyclohexyl and $R^3$ is methyl. In another embodiment, $R^2$ is methoxy and $R^3$ is methyl. In another embodiment, $R^2$ is ethoxy and $R^3$ is methyl. In another embodiment, $R^2$ is propoxy and $R^3$ is methyl. In another embodiment, $R^2$ is methyl and $R^3$ is ethyl. In another embodiment, $R^2$ is ethyl and $R^3$ is ethyl. In another embodiment, $R^2$ is iso-propyl and $R^3$ is ethyl. In another embodiment, $R^2$ is tert-butyl and $R^3$ is ethyl. In another embodiment, $R^2$ is $(C_3-C_6)$cycloalkyl and $R^3$ is ethyl. In another embodiment, $R^2$ is cyclopropyl and $R^3$ is ethyl. In another embodiment, $R^2$ is cyclobutyl and $R^3$ is ethyl. In another embodiment, $R^2$ is cyclopentyl and $R^3$ is ethyl. In another embodiment, $R^2$ is cyclohexyl and $R^3$ is ethyl. In another embodiment, $R^2$ is methoxy and $R^3$ is ethyl. In another embodiment, $R^2$ is ethoxy and $R^3$ is ethyl. In another embodiment, $R^2$ is propoxy and $R^3$ is ethyl. In another embodiment, $R^2$ is methyl and $R^3$ is ethyl. In another embodiment, $R^2$ is ethyl and $R^3$ is propyl. In another embodiment, $R^2$ is iso-propyl and $R^3$ is propyl. In another embodiment, $R^2$ is tert-butyl and $R^3$ is propyl. In another embodiment, $R^2$ is $(C_3-C_6)$cycloalkyl and $R^3$ is propyl. In another embodiment, $R^2$ is cyclopropyl and $R^3$ is propyl. In another embodiment, $R^2$ is cyclobutyl and $R^3$ is propyl. In another embodiment, $R^2$ is cyclopentyl and $R^3$ is propyl. In another embodiment, $R^2$ is cyclohexyl and $R^3$ is propyl. In another embodiment, $R^2$ is methoxy and $R^3$ is propyl. In another embodiment, $R^2$ is ethoxy and $R^3$ is propyl. In another embodiment, $R^2$ is propoxy and $R^3$ is propyl. In another embodiment, $R^2$ is methyl and $R^3$ is butyl. In another embodiment, $R^2$ is ethyl and $R^3$ is butyl. In another embodiment, $R^2$ is iso-propyl and $R^3$ is butyl. In another embodiment, $R^2$ is tert-butyl and $R^3$ is butyl. In another embodiment, $R^2$ is $(C_3-C_6)$cycloalkyl and $R^3$ is butyl. In another embodiment, $R^2$ is cyclopropyl and $R^3$ is butyl. In another embodiment, $R^2$ is cyclobutyl and $R^3$ is butyl. In another embodiment, $R^2$ is cyclopentyl and $R^3$ is butyl. In another embodiment, $R^2$ is cyclohexyl and $R^3$ is butyl. In another embodiment, $R^2$ is methoxy and $R^3$ is butyl. In another embodiment, $R^2$ is ethoxy and $R^3$ is butyl. In another embodiment, $R^2$ is propoxy and $R^3$ is butyl.

In another embodiment, a pyrazolone derivative compound of the disclosure is compound of formula (Id)

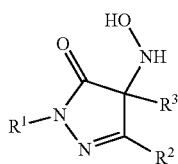

(Id)

or a pharmaceutically acceptable salt thereof, wherein:
$R^1$ is $(C_1-C_6)$alkyl;
$R^2$ is $(C_1-C_6)$alkyl or $(C_1-C_6)$alkoxy; and
$R^3$ is $-C(=NOR^9)R^{10}$ wherein $R^9$ is phenyl, $(C_1-C_6)$alkyl substituted with phenyl or $(C_2-C_6)$alkyl and wherein said phenyl is unsubstituted or independently substituted with 1 or 2 halo(s); and $R^{10}$ is $(C_1-C_6)$alkyl.

In one embodiment, $R^1$ is methyl, ethyl, propyl, or butyl. In another embodiment, $R^1$ is methyl, ethyl, or propyl. In another embodiment, $R^1$ is methyl, ethyl, or butyl. In another embodiment, $R^1$ is methyl, propyl, or butyl. In another embodiment, $R^1$ is ethyl, propyl, or butyl. In another embodiment, $R^1$ is methyl or ethyl. In another embodiment, $R^1$ is methyl or propyl. In another embodiment, $R^1$ is methyl or butyl. In another embodiment, $R^1$ is ethyl or propyl. In another embodiment, $R^1$ is ethyl or butyl. In another embodiment, $R^1$ is propyl or butyl. In another embodiment, $R^1$ is methyl. In another embodiment, $R^1$ is ethyl. In another embodiment, $R^1$ is propyl. In another embodiment, $R^1$ is iso-propyl. In another embodiment, $R^1$ is butyl. In another embodiment, $R^1$ is tert-butyl.

In one embodiment, $R^2$ is $(C_1-C_6)$alkyl. In another embodiment, $R^2$ is methyl, ethyl, propyl, or butyl. In another embodiment, $R^2$ is methyl, propyl or butyl. In another embodiment, $R^2$ is methyl, iso-propyl or tert-butyl. In one embodiment, $R^2$ is $(C_1-C_6)$alkoxy. In another embodiment, $R^2$ is methoxy, ethoxy or propoxy. In another embodiment, $R^2$ is methoxy or ethoxy. In another embodiment, $R^2$ is methoxy. In another embodiment, $R^2$ is ethoxy.

In one embodiment, $R^3$ is $-C(=NOR^9)R^{10}$ wherein $R^9$ is phenyl and $R^{10}$ is $(C_1-C_6)$alkyl. In another embodiment, $R^3$ is $-C(=NOR^9)R^{10}$ wherein $R^9$ is phenyl and $R^{10}$ is $(C_1-C_4)$alkyl. In another embodiment, $R^3$ is $-C(=NOR^9)R^{10}$ wherein $R^9$ is phenyl and $R^{10}$ is methyl, ethyl or propyl. In another embodiment, $R^3$ is $-C(=NOR^9)R^{10}$ wherein $R^9$ is phenyl and $R^{10}$ is methyl or ethyl. In another embodiment, $R^3$ is $-C(=NOR^9)R^{10}$ wherein $R^9$ is phenyl and $R^{10}$ is methyl. In another embodiment, $R^3$ is $-C(=NOR^9)R^{10}$ wherein $R^9$ is phenyl and $R^{10}$ is ethyl.

In one embodiment, $R^3$ is $-C(=NOR^9)R^{10}$ wherein $R^9$ is $(C_1-C_6)$alkyl substituted with phenyl and $R^{10}$ is $(C_1-C_6)$alkyl. In another embodiment, $R^3$ is $-C(=NOR^9)R^{10}$ wherein $R^9$ is $(C_1-C_6)$alkyl substituted with phenyl and $R^{10}$ is $(C_1-C_4)$alkyl. In another embodiment, $R^3$ is $-C(=NOR^9)R^{10}$ wherein $R^9$ is $(C_1-C_6)$alkyl substituted with phenyl and $R^{10}$ is methyl, ethyl or propyl. In another embodiment, $R^3$ is $-C(=NOR^9)R^{10}$ wherein $R^9$ is $(C_1-C_6)$alkyl substituted with phenyl and $R^{10}$ is methyl or ethyl. In another embodiment, $R^3$ is $-C(=NOR^9)R^{10}$ wherein $R^9$ is $(C_1-C_6)$alkyl substituted with phenyl and $R^{10}$ is methyl. In another embodiment, $R^3$ is $-C(=NOR^9)R^{10}$ wherein $R^9$ is phenyl and $R^{10}$ is ethyl.

In one embodiment, $R^3$ is $-C(=NOR^9)R^{10}$ wherein $R^9$ is $(C_1-C_4)$alkyl substituted with phenyl and $R^{10}$ is $(C_1-C_6)$alkyl. In one embodiment, $R^3$ is $-C(=NOR^9)R^{10}$ wherein $R^9$ is $(C_1)$alkyl substituted with phenyl and $R^{10}$ is $(C_1-C_6)$alkyl. In one embodiment, $R^3$ is $-C(=NOR^9)R^{10}$ wherein $R^9$ is $(C_2)$alkyl substituted with phenyl and $R^{10}$ is $(C_1-C_6)$alkyl. In one embodiment, $R^3$ is $-C(=NOR^9)R^{10}$ wherein $R^9$ is $(C_1-C_4)$alkyl substituted with phenyl and $R^{10}$ is $(C_1-C_4)$alkyl. In one embodiment, $R^3$ is $-C(=NOR^9)R^{10}$ wherein $R^9$ is $(C_1)$alkyl substituted with phenyl and $R^{10}$ is $(C_1-C_4)$alkyl. In one embodiment, $R^3$ is $-C(=NOR^9)R^{10}$ wherein $R^9$ is $(C_2)$alkyl substituted with phenyl and $R^{10}$ is $(C_1-C_4)$alkyl. In one embodiment, $R^3$ is $-C(=NOR^9)R^{10}$ wherein $R^9$ is $(C_1-C_4)$alkyl substituted with phenyl and $R^{10}$ is methyl, ethyl or propyl. In one embodiment, $R^3$ is $-C(=NOR^9)R^{10}$ wherein $R^9$ is $(C_1)$alkyl substituted with phenyl and $R^{10}$ is methyl, ethyl or propyl. In one embodiment, $R^3$ is $-C(=NOR^9)R^{10}$ wherein $R^9$ is $(C_2)$alkyl substituted with phenyl and $R^{10}$ is methyl, ethyl or propyl. In one embodiment, $R^3$ is $-C(=NOR^9)R^{10}$ wherein $R^9$ is $(C_1-C_4)$alkyl substituted with phenyl and $R^{10}$ is methyl or ethyl. In one embodiment, $R^3$ is $-C(=NOR^9)R^{10}$ wherein $R^9$ is $(C_1)$alkyl substituted with phenyl and $R^{10}$ is methyl or ethyl. In one embodiment, $R^3$ is $-C(=NOR^9)R^{10}$ wherein $R^9$ is $(C_2)$alkyl substituted with phenyl and $R^{10}$ is methyl or ethyl. In one embodiment, $R^3$ is $-C(=NOR^9)R^{10}$ wherein $R^9$ is $(C_1-C_4)$alkyl substituted with phenyl and $R^{10}$ is methyl. In one embodiment, $R^3$ is $-C(=NOR^9)R^{10}$ wherein $R^9$ is $(C_1)$alkyl substituted with phenyl and $R^{10}$ is methyl. In one embodiment, $R^3$ is $-C(=NOR^9)R^{10}$ wherein $R^9$ is $(C_2)$alkyl substituted with phenyl and $R^{10}$ is methyl. In one embodiment, $R^3$ is $-C(=NOR^9)R^{10}$ wherein $R^9$ is $(C_1-C_4)$alkyl substituted with phenyl and $R^{10}$ is ethyl. In one embodiment, $R^3$ is $-C(=NOR^9)R^{10}$ wherein $R^9$ is $(C_1)$alkyl substituted with phenyl and $R^{10}$ is ethyl. In one embodiment, $R^3$ is $-C(=NOR^9)R^{10}$ wherein $R^9$ is $(C_2)$alkyl substituted with phenyl and $R^{10}$ is ethyl.

In one embodiment, $R^3$ is $-C(=NOR^9)R^{10}$ wherein $R^9$ is $(C_2-C_6)$alkyl and $R^{10}$ is $(C_1-C_6)$alkyl. In another embodiment, $R^3$ is $-C(=NOR^9)R^{10}$ wherein $R^9$ is $(C_2-C_6)$alkyl and $R^{10}$ is $(C_1$-$C_4)$alkyl. In another embodiment, $R^3$ is —C(=NOR$^9$)R$^{10}$ wherein R$^9$ is $(C_2$-$C_6)$alkyl and R$^{10}$ is methyl, ethyl or propyl. In another embodiment, $R^3$ is —C(=NOR$^9$)R$^{10}$ wherein R$^9$ is $(C_2$-$C_6)$alkyl and R$^{10}$ is methyl or ethyl. In another embodiment, $R^3$ is —C(=NOR$^9$)R$^{10}$ wherein R$^9$ is $(C_2$-$C_6)$alkyl and R$^{10}$ is methyl. In another embodiment, $R^3$ is —C(=NOR$^9$)R$^{10}$ wherein R$^9$ is $(C_2$-$C_6)$alkyl and R$^{10}$ is ethyl.

In one embodiment, $R^3$ is —C(=NOR$^9$)R$^{10}$ wherein R$^9$ is ethyl, propyl or butyl and R$^{10}$ is $(C_1$-$C_6)$alkyl. In another embodiment, $R^3$ is —C(=NOR$^9$)R$^{10}$ wherein R$^9$ is ethyl, propyl or butyl and R$^{10}$ is $(C_1$-$C_4)$alkyl. In another embodiment, $R^3$ is —C(=NOR$^9$)R$^{10}$ wherein R$^9$ is ethyl, propyl or butyl and R$^{10}$ is methyl, ethyl or propyl. In another embodiment, $R^3$ is —C(=NOR$^9$)R$^{10}$ wherein R$^9$ is ethyl, propyl or butyl and R$^{10}$ is methyl or ethyl. In another embodiment, $R^3$ is —C(=NOR$^9$)R$^{10}$ wherein R$^9$ is ethyl, propyl or butyl and R$^{10}$ is methyl. In another embodiment, $R^3$ is —C(=NOR$^9$)R$^{10}$ wherein R$^9$ is ethyl, propyl or butyl and R$^{10}$ is ethyl. In one embodiment, $R^3$ is —C(=NOR$^9$)R$^{10}$ wherein R$^9$ is ethyl and R$^{10}$ is $(C_1$-$C_6)$alkyl. In another embodiment, $R^3$ is —C(=NOR$^9$)R$^{10}$ wherein R$^9$ is ethyl and R$^{10}$ is $(C_1$-$C_4)$alkyl. In another embodiment, $R^3$ is —C(=NOR$^9$)R$^{10}$ wherein R$^9$ is ethyl and R$^{10}$ is methyl, ethyl or propyl. In another embodiment, $R^3$ is —C(=NOR$^9$)R$^{10}$ wherein R$^9$ is ethyl and R$^{10}$ is methyl or ethyl. In another embodiment, $R^3$ is —C(=NOR$^9$)R$^{10}$ wherein R$^9$ is ethyl and R$^{10}$ is methyl. In another embodiment, $R^3$ is —C(=NOR$^9$)R$^{10}$ wherein R$^9$ is ethyl and R$^{10}$ is ethyl. In one embodiment, $R^3$ is —C(=NOR$^9$)R$^{10}$ wherein R$^9$ is propyl and R$^{10}$ is $(C_1$-$C_6)$alkyl. In another embodiment, $R^3$ is —C(=NOR$^9$)R$^{10}$ wherein R$^9$ is propyl and R$^{10}$ is $(C_1$-$C_4)$alkyl. In another embodiment, $R^3$ is —C(=NOR$^9$)R$^{10}$ wherein R$^9$ is propyl and R$^{10}$ is methyl, ethyl or propyl. In another embodiment, $R^3$ is —C(=NOR$^9$)R$^{10}$ wherein R$^9$ is propyl and R$^{10}$ is methyl or ethyl. In another embodiment, $R^3$ is —C(=NOR$^9$)R$^{10}$ wherein R$^9$ is propyl and R$^{10}$ is methyl. In another embodiment, $R^3$ is —C(=NOR$^9$)R$^{10}$ wherein R$^9$ is propyl and R$^{10}$ is ethyl. In one embodiment, $R^3$ is —C(=NOR$^9$)R$^{10}$ wherein R$^9$ is butyl and R$^{10}$ is $(C_1$-$C_6)$alkyl. In another embodiment, $R^3$ is —C(=NOR$^9$)R$^{10}$ wherein R$^9$ is butyl and R$^{10}$ is $(C_1$-$C_4)$alkyl. In another embodiment, $R^3$ is —C(=NOR$^9$)R$^{10}$ wherein R$^9$ is butyl and R$^{10}$ is methyl, ethyl or propyl. In another embodiment, $R^3$ is —C(=NOR$^9$)R$^{10}$ wherein R$^9$ is butyl and R$^{10}$ is methyl or ethyl. In another embodiment, $R^3$ is —C(=NOR$^9$)R$^{10}$ wherein R$^9$ is butyl and R$^{10}$ is methyl. In another embodiment, $R^3$ is —C(=NOR$^9$)R$^{10}$ wherein R$^9$ is butyl and R$^{10}$ is ethyl. In one embodiment, $R^3$ is —C(=NOR$^9$)R$^{10}$ wherein R$^9$ is tert-butyl and R$^{10}$ is $(C_1$-$C_6)$alkyl. In another embodiment, $R^3$ is —C(=NOR$^9$)R$^{10}$ wherein R$^9$ is tert-butyl and R$^{10}$ is $(C_1$-$C_4)$alkyl. In another embodiment, $R^3$ is —C(=NOR$^9$)R$^{10}$ wherein R$^9$ is tert-butyl and R$^{10}$ is methyl, ethyl or propyl. In another embodiment, $R^3$ is —C(=NOR$^9$)R$^{10}$ wherein R$^9$ is tert-butyl and R$^{10}$ is methyl or ethyl. In another embodiment, $R^3$ is —C(=NOR$^9$)R$^{10}$ wherein R$^9$ is tert-butyl and R$^{10}$ is methyl. In another embodiment, $R^3$ is —C(=NOR$^9$)R$^{10}$ wherein R$^9$ is tert-butyl and R$^{10}$ is ethyl. In one embodiment, $R^3$ is —C(=NOR$^9$)R$^{10}$ wherein R$^9$ is iso-butyl and R$^{10}$ is $(C_1$-$C_6)$alkyl. In another embodiment, $R^3$ is —C(=NOR$^9$)R$^{10}$ wherein R$^9$ is iso-butyl and R$^{10}$ is $(C_1$-$C_4)$alkyl. In another embodiment, $R^3$ is —C(=NOR$^9$)R$^{10}$ wherein R$^9$ is iso-butyl and R$^{10}$ is methyl, ethyl or propyl. In another embodiment, $R^3$ is —C(=NOR$^9$)R$^{10}$ wherein R$^9$ is iso-butyl and R$^{10}$ is methyl or ethyl. In another embodiment, $R^3$ is —C(=NOR$^9$)R$^{10}$ wherein R$^9$ is iso-butyl and R$^1$ is methyl. In another embodiment, $R^3$ is —C(=NOR$^9$)R$^{10}$ wherein R$^9$ is iso-butyl and R$^{10}$ is ethyl.

In another embodiment, $R^1$ is methyl and $R^2$ is methyl. In another embodiment, $R^1$ is ethyl and $R^2$ is methyl. In another embodiment, $R^1$ is iso-propyl and $R^2$ is methyl. In another embodiment, $R^1$ is tert-butyl and $R^2$ is methyl. In another embodiment, $R^1$ is methyl and $R^2$ is ethyl. In another embodiment, $R^1$ is ethyl and $R^2$ is ethyl. In another embodiment, $R^1$ is iso-propyl and $R^2$ is ethyl. In another embodiment, $R^1$ is methyl and $R^2$ is iso-propyl. In another embodiment, $R^1$ is ethyl and $R^2$ is iso-propyl. In another embodiment, $R^1$ is iso-propyl and $R^2$ is iso-propyl. In another embodiment, $R^1$ is tert-butyl and $R^2$ is ethyl. In another embodiment, $R^1$ is methyl and $R^2$ is tert-butyl. In another embodiment, $R^1$ is ethyl and $R^2$ is tert-butyl. In another embodiment, $R^1$ is tert-butyl and $R^2$ is tert-butyl. In another embodiment, $R^1$ is methyl and $R^2$ is methoxy. In another embodiment, $R^1$ is ethyl and $R^2$ is methoxy. In another embodiment, $R^1$ is iso-propyl and $R^2$ is methoxy. In another embodiment, $R^1$ is tert-butyl and $R^2$ is methoxy. In another embodiment, $R^1$ is methyl and $R^2$ is ethoxy. In another embodiment, $R^1$ is ethyl and $R^2$ is ethoxy. In another embodiment, $R^1$ is iso-propyl and $R^2$ is methoxy. In another embodiment, $R^1$ is tert-butyl and $R^2$ is ethoxy. In another embodiment, $R^1$ is methyl and $R^2$ is propoxy. In another embodiment, $R^1$ is ethyl and $R^2$ is propoxy. In another embodiment, $R^1$ is iso-propyl and $R^2$ is propoxy. In another embodiment, $R^1$ is tert-butyl and $R^2$ is propoxy. In another embodiment, $R^1$ is methyl and $R^2$ is tert-butoxy. In another embodiment, $R^1$ is ethyl and $R^2$ is tert-butoxy. In another embodiment, $R^1$ is iso-propyl and $R^2$ is tert-butoxy. In another embodiment, $R^1$ is tert-butyl and $R^2$ is tert-butoxy.

In another embodiment, $R^1$ is methyl and $R^3$ is —C(=NOR$^9$)R$^{10}$ wherein R$^9$ is phenyl and R$^{10}$ is methyl, ethyl or propyl. In another embodiment, $R^1$ is methyl and $R^3$ is —C(=NOR$^9$)R$^{10}$ wherein R$^9$ is phenyl and R$^{10}$ is methyl or ethyl. In another embodiment, $R^1$ is methyl and $R^3$ is —C(=NOR$^9$)R$^{10}$ wherein R$^9$ is phenyl and R$^{10}$ is methyl. In another embodiment, $R^1$ is methyl and $R^3$ is —C(=NOR$^9$)R$^{10}$ wherein R$^9$ is phenyl and R$^{10}$ is ethyl.

In another embodiment, $R^1$ is methyl and $R^3$ is —C(=NOR$^9$)R$^{10}$ wherein R$^9$ is $(C_1$-$C_6)$alkyl substituted with phenyl and R$^{10}$ is methyl, ethyl or propyl. In another embodiment, $R^1$ is methyl and $R^3$ is —C(=NOR$^9$)R$^{10}$ wherein R$^9$ is $(C_1$-$C_6)$alkyl substituted with phenyl and R$^{10}$ is methyl or ethyl. In another embodiment, $R^1$ is methyl and $R^3$ is —C(=NOR$^9$)R$^{10}$ wherein R$^9$ is $(C_1$-$C_6)$alkyl substituted with phenyl and R$^{10}$ is methyl. In another embodiment, $R^1$ is methyl and $R^3$ is —C(=NOR$^9$)R$^{10}$ wherein R$^9$ is $(C_1$-$C_6)$alkyl substituted with phenyl and R$^{10}$ is ethyl. In another embodiment, $R^1$ is methyl and $R^3$ is —C(=NOR$^9$)R$^{10}$ wherein R$^9$ is $(C_1)$alkyl substituted with phenyl and R$^{10}$ is methyl, ethyl or propyl. In another embodiment, $R^1$ is methyl and $R^3$ is —C(=NOR$^9$)R$^{10}$ wherein R$^9$ is $(C_1)$alkyl substituted with phenyl and R$^{10}$ is methyl or ethyl. In another embodiment, $R^1$ is methyl and $R^3$ is —C(=NOR$^9$)R$^{10}$ wherein R$^9$ is $(C_1)$alkyl substituted with phenyl and R$^{10}$ is methyl. In another embodiment, $R^1$ is methyl and $R^3$ is —C(=NOR$^9$)R$^{10}$ wherein R$^9$ is $(C_1)$alkyl substituted with phenyl and R$^{10}$ is ethyl. In another embodiment, $R^1$ is methyl and $R^3$ is —C(=NOR$^9$)R$^{10}$ wherein R$^9$ is $(C_2)$alkyl substituted with phenyl and R$^{10}$ is methyl, ethyl or propyl. In another embodiment, $R^1$ is methyl and $R^3$ is —C(=NOR$^9$)R$^{10}$ wherein R$^9$ is $(C_2)$alkyl substituted with phenyl and R$^{10}$ is methyl or ethyl. In another embodiment, $R^1$ is methyl and $R^3$ is —C(=NOR$^9$)R$^{10}$ wherein R$^9$ is (C$_2$)alkyl substituted with phenyl and R$^{10}$ is methyl. In another embodiment, R$^1$ is methyl and R$^3$ is —C(=NOR$^9$)R$^{10}$ wherein R$^9$ is (C$_2$)alkyl substituted with phenyl and R$^{10}$ is ethyl.

In another embodiment, R$^1$ is methyl and R$^3$ is —C(=NOR$^9$)R$^{10}$ wherein R$^9$ is (C$_2$-C$_6$)alkyl and R$^{10}$ is methyl, ethyl or propyl. In another embodiment, R$^1$ is methyl and R$^3$ is —C(=NOR$^9$)R$^{10}$ wherein R$^9$ is (C$_2$-C$_6$)alkyl and R$^{10}$ is methyl or ethyl. In another embodiment, R$^1$ is methyl and R$^3$ is —C(=NOR$^9$)R$^{10}$ wherein R$^9$ is (C$_2$-C$_6$)alkyl and R$^{10}$ is methyl. In another embodiment, R$^1$ is methyl and R$^3$ is —C(=NOR$^9$)R$^{10}$ wherein R$^9$ is (C$_2$-C$_6$)alkyl and R$^{10}$ is ethyl. In another embodiment, R$^1$ is methyl and R$^3$ is —C(=NOR$^9$)R$^{10}$ wherein R$^9$ is ethyl and R$^{10}$ is methyl, ethyl or propyl. In another embodiment, R$^1$ is methyl and R$^3$ is —C(=NOR$^9$)R$^{10}$ wherein R$^9$ is ethyl and R$^{10}$ is methyl or ethyl. In another embodiment, R$^1$ is methyl and R$^3$ is —C(=NOR$^9$)R$^{10}$ wherein R$^9$ is ethyl and R$^{10}$ is methyl. In another embodiment, R$^1$ is methyl and R$^3$ is —C(=NOR$^9$)R$^{10}$ wherein R$^9$ is ethyl and R$^{10}$ is ethyl. In another embodiment, R$^1$ is methyl and R$^3$ is —C(=NOR$^9$)R$^{10}$ wherein R$^9$ is ethyl and R$^{10}$ is methyl, ethyl or propyl. In another embodiment, R$^1$ is methyl and R$^3$ is —C(=NOR$^9$)R$^{10}$ wherein R$^9$ is propyl and R$^{10}$ is methyl or ethyl. In another embodiment, R$^1$ is methyl and R$^3$ is —C(=NOR$^9$)R$^{10}$ wherein R$^9$ is propyl and R$^{10}$ is methyl. In another embodiment, R$^1$ is methyl and R$^3$ is —C(=NOR$^9$)R$^{10}$ wherein R$^9$ is propyl and R$^{10}$ is ethyl. In another embodiment, R$^1$ is methyl and R$^3$ is —C(=NOR$^9$)R$^{10}$ wherein R$^9$ is tert-butyl and R$^{10}$ is methyl, ethyl or propyl. In another embodiment, R$^1$ is methyl and R$^3$ is —C(=NOR$^9$)R$^{10}$ wherein R$^9$ is tert-butyl and R$^{10}$ is methyl or ethyl. In another embodiment, R$^1$ is methyl and R$^3$ is —C(=NOR$^9$)R$^{10}$ wherein R$^9$ is tert-butyl and R$^{10}$ is methyl. In another embodiment, R$^1$ is methyl and R$^3$ is —C(=NOR$^9$)R$^{10}$ wherein R$^9$ is tert-butyl and R$^{10}$ is ethyl.

In another embodiment, R$^1$ is ethyl and R$^3$ is —C(=NOR$^9$)R$^{10}$ wherein R$^9$ is phenyl and R$^{10}$ is methyl, ethyl or propyl. In another embodiment, R$^1$ is ethyl and R$^3$ is —C(=NOR$^9$)R$^{10}$ wherein R$^9$ is phenyl and R$^{10}$ is methyl or ethyl. In another embodiment, R$^1$ is ethyl and R$^3$ is —C(=NOR$^9$)R$^{10}$ wherein R$^9$ is phenyl and R$^{10}$ is methyl. In another embodiment, R$^1$ is ethyl and R$^3$ is —C(=NOR$^9$)R$^{10}$ wherein R$^9$ is phenyl and R$^{10}$ is ethyl.

In another embodiment, R$^1$ is ethyl and R$^3$ is —C(=NOR$^9$)R$^{10}$ wherein R$^9$ is (C$_1$-C$_6$)alkyl substituted with phenyl and R$^{10}$ is methyl, ethyl or propyl. In another embodiment, R$^1$ is ethyl and R$^3$ is —C(=NOR$^9$)R$^{10}$ wherein R$^9$ is (C$_1$-C$_6$)alkyl substituted with phenyl and R$^{10}$ is methyl or ethyl. In another embodiment, R$^1$ is ethyl and R$^3$ is —C(=NOR$^9$)R$^{10}$ wherein R$^9$ is (C$_1$-C$_6$)alkyl substituted with phenyl and R$^{10}$ is methyl. In another embodiment, R$^1$ is ethyl and R$^3$ is —C(=NOR$^9$)R$^{10}$ wherein R$^9$ is (C$_1$-C$_6$)alkyl substituted with phenyl and R$^{10}$ is ethyl. In another embodiment, R$^1$ is ethyl and R$^3$ is —C(=NOR$^9$)R$^{10}$ wherein R$^9$ is (C$_1$)alkyl substituted with phenyl and R$^{10}$ is methyl, ethyl or propyl. In another embodiment, R$^1$ is ethyl and R$^3$ is —C(=NOR$^9$)R$^{10}$ wherein R$^9$ is (C$_1$)alkyl substituted with phenyl and R$^{10}$ is methyl or ethyl. In another embodiment, R$^1$ is ethyl and R$^3$ is —C(=NOR$^9$)R$^{10}$ wherein R$^9$ is (C$_1$)alkyl substituted with phenyl and R$^{10}$ is methyl. In another embodiment, R$^1$ is ethyl and R$^3$ is —C(=NOR$^9$)R$^{10}$ wherein R$^9$ is (C$_1$)alkyl substituted with phenyl and R$^{10}$ is ethyl. In another embodiment, R$^1$ is ethyl and R$^3$ is —C(=NOR$^9$)R$^{10}$ wherein R$^9$ is (C$_2$)alkyl substituted with phenyl and R$^{10}$ is methyl, ethyl or propyl. In another embodiment, R$^1$ is ethyl and R$^3$ is —C(=NOR$^9$)R$^{10}$ wherein R$^9$ is (C$_2$)alkyl substituted with phenyl and R$^{10}$ is methyl or ethyl. In another embodiment, R$^1$ is ethyl and R$^3$ is —C(=NOR$^9$)R$^{10}$ wherein R$^9$ is (C$_2$)alkyl substituted with phenyl and R$^{10}$ is methyl. In another embodiment, R$^1$ is ethyl and R$^3$ is —C(=NOR$^9$)R$^{10}$ wherein R$^9$ is (C$_2$)alkyl substituted with phenyl and R$^{10}$ is ethyl.

In another embodiment, R$^1$ is ethyl and R$^3$ is —C(=NOR$^9$)R$^{10}$ wherein R$^9$ is (C$_2$-C$_6$)alkyl and R$^{10}$ is methyl, ethyl or propyl. In another embodiment, R$^1$ is ethyl and R$^3$ is —C(=NOR$^9$)R$^{10}$ wherein R$^9$ is (C$_2$-C$_6$)alkyl and R$^{10}$ is methyl or ethyl. In another embodiment, R$^1$ is ethyl and R$^3$ is —C(=NOR$^9$)R$^{10}$ wherein R$^9$ is (C$_2$-C$_6$)alkyl and R$^{10}$ is methyl. In another embodiment, R$^1$ is ethyl and R$^3$ is —C(=NOR$^9$)R$^{10}$ wherein R$^9$ is (C$_2$-C$_6$)alkyl and R$^{10}$ is ethyl. In another embodiment, R$^1$ is ethyl and R$^3$ is —C(=NOR$^9$)R$^{10}$ wherein R$^9$ is ethyl and R$^{10}$ is methyl, ethyl or propyl. In another embodiment, R$^1$ is ethyl and R$^3$ is —C(=NOR$^9$)R$^{10}$ wherein R$^9$ is ethyl and R$^{10}$ is methyl or ethyl. In another embodiment, R$^1$ is ethyl and R$^3$ is —C(=NOR$^9$)R$^{10}$ wherein R$^9$ is ethyl and R$^{10}$ is methyl. In another embodiment, R$^1$ is ethyl and R$^3$ is —C(=NOR$^9$)R$^{10}$ wherein R$^9$ is ethyl and R$^{10}$ is ethyl. In another embodiment, R$^1$ is ethyl and R$^3$ is —C(=NOR$^9$)R$^{10}$ wherein R$^9$ is propyl and R$^{10}$ is methyl, ethyl or propyl. In another embodiment, R$^1$ is ethyl and R$^3$ is —C(=NOR$^9$)R$^{10}$ wherein R$^9$ is propyl and R$^{10}$ is methyl or ethyl. In another embodiment, R$^1$ is ethyl and R$^3$ is —C(=NOR$^9$)R$^{10}$ wherein R$^9$ is propyl and R$^{10}$ is methyl. In another embodiment, R$^1$ is ethyl and R$^3$ is —C(=NOR$^9$)R$^{10}$ wherein R$^9$ is propyl and R$^{10}$ is ethyl. In another embodiment, R$^1$ is ethyl and R$^3$ is —C(=NOR$^9$)R$^{10}$ wherein R$^9$ is tert-butyl and R$^{10}$ is methyl, ethyl or propyl. In another embodiment, R$^1$ is ethyl and R$^3$ is —C(=NOR$^9$)R$^{10}$ wherein R$^9$ is tert-butyl and R$^{10}$ is methyl or ethyl. In another embodiment, R$^1$ is ethyl and R$^3$ is —C(=NOR$^9$)R$^{10}$ wherein R$^9$ is tert-butyl and R$^{10}$ is methyl. In another embodiment, R$^1$ is ethyl and R$^3$ is —C(=NOR$^9$)R$^{10}$ wherein R$^9$ is tert-butyl and R$^{10}$ is ethyl.

In another embodiment, R$^1$ is iso-propyl and R$^3$ is —C(=NOR$^9$)R$^{10}$ wherein R$^9$ is phenyl and R$^{10}$ is methyl, ethyl or propyl. In another embodiment, R$^1$ is iso-propyl and R$^3$ is —C(=NOR$^9$)R$^{10}$ wherein R$^9$ is phenyl and R$^{10}$ is methyl or ethyl. In another embodiment, R$^1$ is iso-propyl and R$^3$ is —C(=NOR$^9$)R$^{10}$ wherein R$^9$ is phenyl and R$^{10}$ is methyl. In another embodiment, R$^1$ is iso-propyl and R$^3$ is —C(=NOR$^9$)R$^{10}$ wherein R$^9$ is phenyl and R$^{10}$ is ethyl.

In another embodiment, R$^1$ is iso-propyl and R$^3$ is —C(=NOR$^9$)R$^{10}$ wherein R$^9$ is (C$_1$-C$_6$)alkyl substituted with phenyl and R$^{10}$ is methyl, ethyl or propyl. In another embodiment, R$^1$ is iso-propyl and R$^3$ is —C(=NOR$^9$)R$^{10}$ wherein R$^9$ is (C$_1$-C$_6$)alkyl substituted with phenyl and R$^{10}$ is methyl or ethyl. In another embodiment, R$^1$ is iso-propyl and R$^3$ is —C(=NOR$^9$)R$^{10}$ wherein R$^9$ is (C$_1$-C$_6$)alkyl substituted with phenyl and R$^{10}$ is methyl. In another embodiment, R$^1$ is iso-propyl and R$^3$ is —C(=NOR$^9$)R$^{10}$ wherein R$^9$ is (C$_1$-C$_6$)alkyl substituted with phenyl and R$^{10}$ is ethyl. In another embodiment, R$^1$ is iso-propyl and R$^3$ is —C(=NOR$^9$)R$^{10}$ wherein R$^9$ is (C$_1$)alkyl substituted with phenyl and R$^{10}$ is methyl, ethyl or propyl. In another embodiment, R$^1$ is iso-propyl and R$^3$ is —C(=NOR$^9$)R$^{10}$ wherein R$^9$ is (C$_1$)alkyl substituted with phenyl and R$^{10}$ is methyl or ethyl. In another embodiment, R$^1$ is iso-propyl and R$^3$ is —C(=NOR$^9$)R$^{10}$ wherein R$^9$ is (C$_1$)alkyl substituted with phenyl and R$^{10}$ is methyl. In another embodiment, R$^1$ is iso-propyl and R$^3$ is —C(=NOR$^9$)R$^{10}$ wherein R$^9$ is (C$_1$)alkyl substituted with phenyl and R$^{10}$ is ethyl. In another embodiment, R$^1$ is iso-propyl and R$^3$ is —C(=NOR$^9$)R$^{10}$ wherein R$^9$ is (C$_2$)alkyl substituted with phenyl and R$^{10}$ is methyl, ethyl or propyl. In another embodiment, $R^1$ is iso-propyl and $R^3$ is —C(=NOR$^9$)R$^{10}$ wherein $R^9$ is (C$_2$)alkyl substituted with phenyl and $R^{10}$ is methyl or ethyl. In another embodiment, $R^1$ is iso-propyl and $R^3$ is —C(=NOR$^9$)R$^{10}$ wherein $R^9$ is (C$_2$)alkyl substituted with phenyl and $R^{10}$ is methyl. In another embodiment, $R^1$ is iso-propyl and $R^3$ is —C(=NOR$^9$)R$^{10}$ wherein $R^9$ is (C$_2$) alkyl substituted with phenyl and $R^{10}$ is ethyl.

In another embodiment, $R^1$ is iso-propyl and $R^3$ is —C(=NOR$^9$)R$^{10}$ wherein $R^9$ is (C$_2$-C$_6$)alkyl and $R^{10}$ is methyl, ethyl or propyl. In another embodiment, $R^1$ is iso-propyl and $R^3$ is —C(=NOR$^9$)R$^{10}$ wherein $R^9$ is (C$_2$-C$_6$)alkyl and $R^{10}$ is methyl or ethyl. In another embodiment, $R^1$ is iso-propyl and $R^3$ is —C(=NOR$^9$)R$^{10}$ wherein $R^9$ is (C$_2$-C$_6$)alkyl and $R^{10}$ is methyl. In another embodiment, $R^1$ is iso-propyl and $R^3$ is —C(=NOR$^9$)R$^{10}$ wherein $R^9$ is (C$_2$-C$_6$)alkyl and $R^{10}$ is ethyl. In another embodiment, $R^1$ is iso-propyl and $R^3$ is —C(=NOR$^9$)R$^{10}$ wherein $R^9$ is ethyl and $R^{10}$ is methyl, ethyl or propyl. In another embodiment, $R^1$ is iso-propyl and $R^3$ is —C(=NOR$^9$)R$^{10}$ wherein $R^9$ is ethyl and $R^{10}$ is methyl or ethyl. In another embodiment, $R^1$ is ethyl and $R^3$ is —C(=NOR$^9$)R$^{10}$ wherein $R^9$ is ethyl and $R^{10}$ is methyl. In another embodiment, $R^1$ is iso-propyl and $R^3$ is —C(=NOR$^9$)R$^{10}$ wherein $R^9$ is ethyl and $R^{10}$ is ethyl. In another embodiment, $R^1$ is iso-propyl and $R^3$ is —C(=NOR$^9$)R$^{10}$ wherein $R^9$ is propyl and $R^{10}$ is methyl, ethyl or propyl. In another embodiment, $R^1$ is iso-propyl and $R^3$ is —C(=NOR$^9$)R$^{10}$ wherein $R^9$ is propyl and $R^{10}$ is methyl or ethyl. In another embodiment, $R^1$ is iso-propyl and $R^3$ is —C(=NOR$^9$)R$^{10}$ wherein $R^9$ is propyl and $R^{10}$ is methyl. In another embodiment, $R^1$ is iso-propyl and $R^3$ is —C(=NOR$^9$)R$^{10}$ wherein $R^9$ is propyl and $R^{10}$ is ethyl. In another embodiment, $R^1$ is iso-propyl and $R^3$ is —C(=NOR$^9$)R$^{10}$ wherein $R^9$ is tert-butyl and $R^{10}$ is methyl, ethyl or propyl. In another embodiment, $R^1$ is iso-propyl and $R^3$ is —C(=NOR$^9$)R$^{10}$ wherein $R^9$ is tert-butyl and $R^{10}$ is methyl or ethyl. In another embodiment, $R^1$ is iso-propyl and $R^3$ is —C(=NOR$^9$)R$^{10}$ wherein $R^9$ is tert-butyl and $R^{10}$ is methyl. In another embodiment, $R^1$ is iso-propyl and $R^3$ is —C(=NOR$^9$)R$^{10}$ wherein $R^9$ is tert-butyl and $R^{10}$ is ethyl.

In another embodiment, $R^2$ is methyl and $R^3$ is —C(=NOR$^9$)R$^{10}$ wherein $R^9$ is phenyl and $R^{10}$ is methyl, ethyl or propyl. In another embodiment, $R^2$ is methyl and $R^3$ is —C(=NOR$^9$)R$^{10}$ wherein $R^9$ is phenyl and $R^{10}$ is methyl or ethyl. In another embodiment, $R^2$ is methyl and $R^3$ is —C(=NOR$^9$)R$^{10}$ wherein $R^9$ is phenyl and $R^{10}$ is methyl. In another embodiment, $R^2$ is methyl and $R^3$ is —C(=NOR$^9$)R$^{10}$ wherein $R^9$ is phenyl and $R^{10}$ is ethyl.

In another embodiment, $R^2$ is methyl and $R^3$ is —C(=NOR$^9$)R$^{10}$ wherein $R^9$ is (C$_1$-C$_6$)alkyl substituted with phenyl and $R^{10}$ is methyl, ethyl or propyl. In another embodiment, $R^2$ is methyl and $R^3$ is —C(=NOR$^9$)R$^{10}$ wherein $R^9$ is (C$_1$-C$_6$)alkyl substituted with phenyl and $R^{10}$ is methyl or ethyl. In another embodiment, $R^2$ is methyl and $R^3$ is —C(=NOR$^9$)R$^{10}$ wherein $R^9$ is (C$_1$-C$_6$)alkyl substituted with phenyl and $R^{10}$ is methyl. In another embodiment, $R^2$ is methyl and $R^3$ is —C(=NOR$^9$)R$^{10}$ wherein $R^9$ is (C$_1$-C$_6$)alkyl substituted with phenyl and $R^{10}$ is ethyl. In another embodiment, $R^2$ is methyl and $R^3$ is —C(=NOR$^9$) R$^{10}$ wherein $R^9$ is (C$_1$)alkyl substituted with phenyl and $R^{10}$ is methyl, ethyl or propyl. In another embodiment, $R^2$ is methyl and $R^3$ is —C(=NOR$^9$)R$^{10}$ wherein $R^9$ is (C$_1$)alkyl substituted with phenyl and $R^{10}$ is methyl or ethyl. In another embodiment, $R^2$ is methyl and $R^3$ is —C(=NOR$^9$) R$^{10}$ wherein $R^9$ is (C$_1$)alkyl substituted with phenyl and $R^{10}$ is methyl. In another embodiment, $R^2$ is methyl and $R^3$ is —C(=NOR$^9$)R$^{10}$ wherein $R^9$ is (C$_1$)alkyl substituted with phenyl and $R^{10}$ is ethyl. In another embodiment, $R^2$ is methyl and $R^3$ is —C(=NOR$^9$)R$^{10}$ wherein $R^9$ is (C$_2$)alkyl substituted with phenyl and $R^{10}$ is methyl, ethyl or propyl. In another embodiment, $R^2$ is methyl and $R^3$ is —C(=NOR$^9$)R$^{10}$ wherein $R^9$ is (C$_2$)alkyl substituted with phenyl and $R^{10}$ is methyl or ethyl. In another embodiment, $R^2$ is methyl and $R^3$ is —C(=NOR$^9$)R$^{10}$ wherein $R^9$ is (C$_2$)alkyl substituted with phenyl and $R^{10}$ is methyl. In another embodiment, $R^2$ is methyl and $R^3$ is —C(=NOR$^9$) R$^{10}$ wherein $R^9$ is (C$_2$)alkyl substituted with phenyl and $R^{10}$ is ethyl.

In another embodiment, $R^2$ is methyl and $R^3$ is —C(=NOR$^9$)R$^{10}$ wherein $R^9$ is (C$_2$-C$_6$)alkyl and $R^{10}$ is methyl, ethyl or propyl. In another embodiment, $R^2$ is methyl and $R^3$ is —C(=NOR$^9$)R$^{10}$ wherein $R^9$ is (C$_2$-C$_6$) alkyl and $R^{10}$ is methyl or ethyl. In another embodiment, $R^2$ is methyl and $R^3$ is —C(=NOR$^9$)R$^{10}$ wherein $R^9$ is (C$_2$-C$_6$)alkyl and $R^{10}$ is methyl. In another embodiment, $R^2$ is methyl and $R^3$ is —C(=NOR$^9$)R$^{10}$ wherein $R^9$ is (C$_2$-C$_6$) alkyl and $R^{10}$ is ethyl. In another embodiment, $R^2$ is methyl and $R^3$ is —C(=NOR$^9$)R$^{10}$ wherein $R^9$ is ethyl and $R^{10}$ is methyl, ethyl or propyl. In another embodiment, $R^2$ is methyl and $R^3$ is —C(=NOR$^9$)R$^{10}$ wherein $R^9$ is ethyl and $R^{10}$ is methyl or ethyl. In another embodiment, $R^2$ is methyl and $R^3$ is —C(=NOR$^9$)R$^{10}$ wherein $R^9$ is ethyl and $R^{10}$ is methyl. In another embodiment, $R^2$ is methyl and $R^3$ is —C(=NOR$^9$)R$^{10}$ wherein $R^9$ is ethyl and $R^{10}$ is ethyl. In another embodiment, $R^2$ is methyl and $R^3$ is —C(=NOR$^9$) R$^{10}$ wherein $R^9$ is propyl and $R^{10}$ is methyl, ethyl or propyl. In another embodiment, $R^2$ is methyl and $R^3$ is —C(=NOR$^9$)R$^{10}$ wherein $R^9$ is propyl and $R^{10}$ is methyl or ethyl. In another embodiment, $R^2$ is methyl and $R^3$ is —C(=NOR$^9$)R$^{10}$ wherein $R^9$ is propyl and $R^{10}$ is methyl. In another embodiment, $R^2$ is methyl and $R^3$ is —C(=NOR$^9$) R$^{10}$ wherein $R^9$ is propyl and $R^{10}$ is ethyl. In another embodiment, $R^2$ is methyl and $R^3$ is —C(=NOR$^9$)R$^{10}$ wherein $R^9$ is tert-butyl and $R^{10}$ is methyl, ethyl or propyl. In another embodiment, $R^2$ is methyl and $R^3$ is —C(=NOR$^9$)R$^{10}$ wherein $R^9$ is tert-butyl and $R^{10}$ is methyl or ethyl. In another embodiment, $R^2$ is methyl and $R^3$ is —C(=NOR$^9$)R$^{10}$ wherein $R^9$ is tert-butyl and $R^{10}$ is methyl. In another embodiment, $R^2$ is methyl and $R^3$ is —C(=NOR$^9$)R$^{10}$ wherein $R^9$ is tert-butyl and $R^{10}$ is ethyl.

In another embodiment, $R^2$ is ethyl and $R^3$ is —C(=NOR$^9$)R$^{10}$ wherein $R^9$ is phenyl and $R^{10}$ is methyl, ethyl or propyl. In another embodiment, $R^2$ is ethyl and $R^3$ is —C(=NOR$^9$)R$^{10}$ wherein $R^9$ is phenyl and $R^{10}$ is methyl or ethyl. In another embodiment, $R^2$ is ethyl and $R^3$ is —C(=NOR$^9$)R$^{10}$ wherein $R^9$ is phenyl and $R^{10}$ is methyl. In another embodiment, $R^2$ is ethyl and $R^3$ is —C(=NOR$^9$) R$^{10}$ wherein $R^9$ is phenyl and $R^{10}$ is ethyl.

In another embodiment, $R^2$ is ethyl and $R^3$ is —C(=NOR$^9$)R$^{10}$ wherein $R^9$ is (C$_1$-C$_6$)alkyl substituted with phenyl and $R^{10}$ is methyl, ethyl or propyl. In another embodiment, $R^2$ is ethyl and $R^3$ is —C(=NOR$^9$)R$^{10}$ wherein $R^9$ is (C$_1$-C$_6$)alkyl substituted with phenyl and $R^{10}$ is methyl or ethyl. In another embodiment, $R^2$ is ethyl and $R^3$ is —C(=NOR$^9$)R$^{10}$ wherein $R^9$ is (C$_1$-C$_6$)alkyl substituted with phenyl and $R^{10}$ is methyl. In another embodiment, $R^2$ is ethyl and $R^3$ is —C(=NOR$^9$)R$^{10}$ wherein $R^9$ is (C$_1$-C$_6$)alkyl substituted with phenyl and $R^{10}$ is ethyl. In another embodiment, $R^2$ is ethyl and $R^3$ is —C(=NOR$^9$)R$^{10}$ wherein $R^9$ is (C$_1$)alkyl substituted with phenyl and $R^{10}$ is methyl, ethyl or propyl. In another embodiment, $R^2$ is ethyl and $R^3$ is —C(=NOR$^9$)R$^{10}$ wherein $R^9$ is (C$_1$)alkyl substituted with phenyl and $R^{10}$ is methyl or ethyl. In another embodiment, $R^2$ is ethyl and $R^3$ is —C(=NOR$^9$)R$^{10}$ wherein $R^9$ is $(C_1)$alkyl substituted with phenyl and $R^{10}$ is methyl. In another embodiment, $R^2$ is ethyl and $R^3$ is —C(=NOR$^9$)R$^{10}$ wherein $R^9$ is $(C_1)$alkyl substituted with phenyl and $R^{10}$ is ethyl. In another embodiment, $R^2$ is ethyl and $R^3$ is —C(=NOR$^9$)R$^{10}$ wherein $R^9$ is $(C_2)$alkyl substituted with phenyl and $R^{10}$ is methyl, ethyl or propyl. In another embodiment, $R^2$ is ethyl and $R^3$ is —C(=NOR$^9$)R$^{10}$ wherein $R^9$ is $(C_2)$alkyl substituted with phenyl and $R^{10}$ is methyl or ethyl. In another embodiment, $R^2$ is ethyl and $R^3$ is —C(=NOR$^9$)R$^{10}$ wherein $R^9$ is $(C_2)$alkyl substituted with phenyl and $R^{10}$ is methyl. In another embodiment, $R^2$ is ethyl and $R^3$ is —C(=NOR$^9$)R$^{10}$ wherein $R^9$ is $(C_2)$alkyl substituted with phenyl and $R^{10}$ is ethyl.

In another embodiment, $R^2$ is ethyl and $R^3$ is —C(=NOR$^9$)R$^{10}$ wherein $R^9$ is $(C_2$-$C_6)$alkyl and $R^{10}$ is methyl, ethyl or propyl. In another embodiment, $R^2$ is ethyl and $R^3$ is —C(=NOR$^9$)R$^{10}$ wherein $R^9$ is $(C_2$-$C_6)$alkyl and $R^{10}$ is methyl or ethyl. In another embodiment, $R^2$ is ethyl and $R^3$ is —C(=NOR$^9$)R$^{10}$ wherein $R^9$ is $(C_2$-$C_6)$alkyl and $R^{10}$ is methyl. In another embodiment, $R^2$ is ethyl and $R^3$ is —C(=NOR$^9$)R$^{10}$ wherein $R^9$ is $(C_2$-$C_6)$alkyl and $R^{10}$ is ethyl. In another embodiment, $R^2$ is ethyl and $R^3$ is —C(=NOR$^9$)R$^{10}$ wherein $R^9$ is ethyl and $R^{10}$ is methyl, ethyl or propyl. In another embodiment, $R^2$ is ethyl and $R^3$ is —C(=NOR$^9$)R$^{10}$ wherein $R^9$ is ethyl and $R^{10}$ is methyl or ethyl. In another embodiment, $R^2$ is ethyl and $R^3$ is —C(=NOR$^9$)R$^{10}$ wherein $R^9$ is ethyl and $R^{10}$ is methyl. In another embodiment, $R^2$ is ethyl and $R^3$ is —C(=NOR$^9$)R$^{10}$ wherein $R^9$ is ethyl and $R^{10}$ is ethyl. In another embodiment, $R^2$ is ethyl and $R^3$ is —C(=NOR$^9$)R$^{10}$ wherein $R^9$ is propyl and $R^{10}$ is methyl, ethyl or propyl. In another embodiment, $R^2$ is ethyl and $R^3$ is —C(=NOR$^9$)R$^{10}$ wherein $R^9$ is propyl and $R^{10}$ is methyl or ethyl. In another embodiment, $R^2$ is ethyl and $R^3$ is —C(=NOR$^9$)R$^{10}$ wherein $R^9$ is propyl and $R^{10}$ is methyl. In another embodiment, $R^2$ is ethyl and $R^3$ is —C(=NOR$^9$)R$^{10}$ wherein $R^9$ is propyl and $R^{10}$ is ethyl. In another embodiment, $R^2$ is ethyl and $R^3$ is —C(=NOR$^9$)R$^{10}$ wherein $R^9$ is tert-butyl and $R^{10}$ is methyl, ethyl or propyl. In another embodiment, $R^2$ is ethyl and $R^3$ is —C(=NOR$^9$)R$^{10}$ wherein $R^9$ is tert-butyl and $R^{10}$ is methyl or ethyl. In another embodiment, $R^2$ is ethyl and $R^3$ is —C(=NOR$^9$)R$^{10}$ wherein $R^9$ is tert-butyl and $R^{10}$ is methyl. In another embodiment, $R^2$ is ethyl and $R^3$ is —C(=NOR$^9$)R$^{10}$ wherein $R^9$ is tert-butyl and $R^{10}$ is ethyl.

In another embodiment, $R^2$ is iso-propyl and $R^3$ is —C(=NOR$^9$)R$^{10}$ wherein $R^9$ is phenyl and $R^{10}$ is methyl, ethyl or propyl. In another embodiment, $R^2$ is iso-propyl and $R^3$ is —C(=NOR$^9$)R$^{10}$ wherein $R^9$ is phenyl and $R^{10}$ is methyl or ethyl. In another embodiment, $R^2$ is iso-propyl and $R^3$ is —C(=NOR$^9$)R$^{10}$ wherein $R^9$ is phenyl and $R^{10}$ is methyl. In another embodiment, $R^2$ is iso-propyl and $R^3$ is —C(=NOR$^9$)R$^{10}$ wherein $R^9$ is phenyl and $R^{10}$ is ethyl.

In another embodiment, $R^2$ is iso-propyl and $R^3$ is —C(=NOR$^9$)R$^{10}$ wherein $R^9$ is $(C_1$-$C_6)$alkyl substituted with phenyl and $R^{10}$ is methyl, ethyl or propyl. In another embodiment, $R^2$ is iso-propyl and $R^3$ is —C(=NOR$^9$)R$^{10}$ wherein $R^9$ is $(C_1$-$C_6)$alkyl substituted with phenyl and $R^{10}$ is methyl or ethyl. In another embodiment, $R^2$ is iso-propyl and $R^3$ is —C(=NOR$^9$)R$^{10}$ wherein $R^9$ is $(C_1$-$C_6)$alkyl substituted with phenyl and $R^{10}$ is methyl. In another embodiment, $R^2$ is iso-propyl and $R^3$ is —C(=NOR$^9$)R$^{10}$ wherein $R^9$ is $(C_1$-$C_6)$alkyl substituted with phenyl and $R^{10}$ is ethyl. In another embodiment, $R^2$ is iso-propyl and $R^3$ is —C(=NOR$^9$)R$^{10}$ wherein $R^9$ is $(C_1)$alkyl substituted with phenyl and $R^{10}$ is methyl, ethyl or propyl. In another embodiment, $R^2$ is iso-propyl and $R^3$ is —C(=NOR$^9$)R$^{10}$ wherein $R^9$ is $(C_1)$alkyl substituted with phenyl and $R^{10}$ is methyl or ethyl. In another embodiment, $R^2$ is iso-propyl and $R^3$ is —C(=NOR$^9$)R$^{10}$ wherein $R^9$ is $(C_1)$alkyl substituted with phenyl and $R^{10}$ is methyl. In another embodiment, $R^2$ is iso-propyl and $R^3$ is —C(=NOR$^9$)R$^{10}$ wherein $R^9$ is $(C_1)$alkyl substituted with phenyl and $R^{10}$ is ethyl. In another embodiment, $R^2$ is iso-propyl and $R^3$ is —C(=NOR$^9$)R$^{10}$ wherein $R^9$ is $(C_2)$alkyl substituted with phenyl and $R^{10}$ is methyl, ethyl or propyl. In another embodiment, $R^2$ is iso-propyl and $R^3$ is —C(=NOR$^9$)R$^{10}$ wherein $R^9$ is $(C_2)$ alkyl substituted with phenyl and $R^{10}$ is methyl or ethyl. In another embodiment, $R^2$ is iso-propyl and $R^3$ is —C(=NOR$^9$)R$^{10}$ wherein $R^9$ is $(C_2)$alkyl substituted with phenyl and $R^{10}$ is methyl. In another embodiment, $R^2$ is iso-propyl and $R^3$ is —C(=NOR$^9$)R$^{10}$ wherein $R^9$ is $(C_2)$ alkyl substituted with phenyl and $R^{10}$ is ethyl.

In another embodiment, $R^2$ is iso-propyl and $R^3$ is —C(=NOR$^9$)R$^{10}$ wherein $R^9$ is $(C_2$-$C_6)$alkyl and $R^{10}$ is methyl, ethyl or propyl. In another embodiment, $R^2$ is iso-propyl and $R^3$ is —C(=NOR$^9$)R$^{10}$ wherein $R^9$ is $(C_2$-$C_6)$alkyl and $R^{10}$ is methyl or ethyl. In another embodiment, $R^2$ is iso-propyl and $R^3$ is —C(=NOR$^9$)R$^{10}$ wherein $R^9$ is $(C_2$-$C_6)$alkyl and $R^{10}$ is methyl. In another embodiment, $R^2$ is iso-propyl and $R^3$ is —C(=NOR$^9$)R$^{10}$ wherein $R^9$ is $(C_2$-$C_6)$alkyl and $R^{10}$ is ethyl. In another embodiment, $R^2$ is iso-propyl and $R^3$ is —C(=NOR$^9$)R$^{10}$ wherein $R^9$ is ethyl and $R^{10}$ is methyl, ethyl or propyl. In another embodiment, $R^2$ is iso-propyl and $R^3$ is —C(=NOR$^9$)R$^{10}$ wherein $R^9$ is ethyl and $R^{10}$ is methyl or ethyl. In another embodiment, $R^2$ is iso-propyl and $R^3$ is —C(=NOR$^9$)R$^{10}$ wherein $R^9$ is ethyl and $R^{10}$ is methyl. In another embodiment, $R^2$ is iso-propyl and $R^3$ is —C(=NOR$^9$)R$^{10}$ wherein $R^9$ is ethyl and $R^{10}$ is ethyl. In another embodiment, $R^2$ is iso-propyl and $R^3$ is —C(=NOR$^9$)R$^{10}$ wherein $R^9$ is propyl and $R^{10}$ is methyl, ethyl or propyl. In another embodiment, $R^2$ is iso-propyl and $R^3$ is —C(=NOR$^9$)R$^{10}$ wherein $R^9$ is propyl and $R^{10}$ is methyl or ethyl. In another embodiment, $R^2$ is iso-propyl and $R^3$ is —C(=NOR$^9$)R$^{10}$ wherein $R^9$ is propyl and $R^{10}$ is methyl. In another embodiment, $R^2$ is iso-propyl and $R^3$ is —C(=NOR$^9$)R$^{10}$ wherein $R^9$ is propyl and $R^{10}$ is ethyl. In another embodiment, $R^2$ is iso-propyl and $R^3$ is —C(=NOR$^9$)R$^{10}$ wherein $R^9$ is tert-butyl and $R^{10}$ is methyl, ethyl or propyl. In another embodiment, $R^2$ is iso-propyl and $R^3$ is —C(=NOR$^9$)R$^{10}$ wherein $R^9$ is tert-butyl and $R^{10}$ is methyl or ethyl. In another embodiment, $R^2$ is iso-propyl and $R^3$ is —C(=NOR$^9$)R$^{10}$ wherein $R^9$ is tert-butyl and $R^{10}$ is methyl. In another embodiment, $R^2$ is iso-propyl and $R^3$ is —C(=NOR$^9$)R$^{10}$ wherein $R^9$ is tert-butyl and $R^{10}$ is ethyl.

In another embodiment, $R^2$ is tert-butyl and $R^3$ is —C(=NOR$^9$)R$^{10}$ wherein $R^9$ is phenyl and $R^{10}$ is methyl, ethyl or propyl. In another embodiment, $R^2$ is tert-butyl and $R^3$ is —C(=NOR$^9$)R$^{10}$ wherein $R^9$ is phenyl and $R^{10}$ is methyl or ethyl. In another embodiment, $R^2$ is tert-butyl and $R^3$ is —C(=NOR$^9$)R$^{10}$ wherein $R^9$ is phenyl and $R^{10}$ is methyl. In another embodiment, $R^2$ is tert-butyl and $R^3$ is —C(=NOR$^9$)R$^{10}$ wherein $R^9$ is phenyl and $R^{10}$ is ethyl.

In another embodiment, $R^2$ is tert-butyl and $R^3$ is —C(=NOR$^9$)R$^{10}$ wherein $R^9$ is $(C_1$-$C_6)$alkyl substituted with phenyl and $R^{10}$ is methyl, ethyl or propyl. In another embodiment, $R^2$ is tert-butyl and $R^3$ is —C(=NOR$^9$)R$^{10}$ wherein $R^9$ is $(C_1$-$C_6)$alkyl substituted with phenyl and $R^{10}$ is methyl or ethyl. In another embodiment, $R^2$ is tert-butyl and $R^3$ is —C(=NOR$^9$)R$^{10}$ wherein $R^9$ is $(C_1$-$C_6)$alkyl substituted with phenyl and $R^{10}$ is methyl. In another embodiment, $R^2$ is tert-butyl and $R^3$ is —C(=NOR$^9$)R$^{10}$ wherein $R^9$ is $(C_1$-$C_6)$alkyl substituted with phenyl and $R^{10}$ is ethyl. In another embodiment, $R^2$ is tert-butyl and $R^3$ is —C(=NOR$^9$)R$^{10}$ wherein $R^9$ is $(C_1)$alkyl substituted with phenyl and $R^{10}$ is methyl, ethyl or propyl. In another embodiment, $R^2$ is tert-butyl and $R^3$ is —C(=NOR$^9$)R$^{10}$ wherein $R^9$ is (C$_1$)alkyl substituted with phenyl and $R^{10}$ is methyl or ethyl. In another embodiment, $R^2$ is tert-butyl and $R^3$ is —C(=NOR$^9$)R$^{10}$ wherein $R^9$ is (C$_1$)alkyl substituted with phenyl and $R^{10}$ is methyl. In another embodiment, $R^2$ is tert-butyl and $R^3$ is —C(=NOR$^9$)R$^{10}$ wherein $R^9$ is (C$_1$)alkyl substituted with phenyl and $R^{10}$ is ethyl. In another embodiment, $R^2$ is tert-butyl and $R^3$ is —C(=NOR$^9$)R$^{10}$ wherein $R^9$ is (C$_2$)alkyl substituted with phenyl and $R^{10}$ is methyl, ethyl or propyl. In another embodiment, $R^2$ is tert-butyl and $R^3$ is —C(=NOR$^9$)R$^{10}$ wherein $R^9$ is (C$_2$)alkyl substituted with phenyl and $R^{10}$ is methyl or ethyl. In another embodiment, $R^2$ is tert-butyl and $R^3$ is —C(=NOR$^9$)R$^{10}$ wherein $R^9$ is (C$_2$)alkyl substituted with phenyl and $R^{10}$ is methyl. In another embodiment, $R^2$ is tert-butyl and $R^3$ is —C(=NOR$^9$)R$^{10}$ wherein $R^9$ is (C$_2$)alkyl substituted with phenyl and $R^{10}$ is ethyl.

In another embodiment, $R^2$ is tert-butyl and $R^3$ is —C(=NOR$^9$)R$^{10}$ wherein $R^9$ is (C$_2$-C$_6$)alkyl and $R^{10}$ is methyl, ethyl or propyl. In another embodiment, $R^2$ is tert-butyl and $R^3$ is —C(=NOR$^9$)R$^{10}$ wherein $R^9$ is (C$_2$-C$_6$)alkyl and $R^{10}$ is methyl or ethyl. In another embodiment, $R^2$ is tert-butyl and $R^3$ is —C(=NOR$^9$)R$^{10}$ wherein $R^9$ is (C$_2$-C$_6$)alkyl and $R^{10}$ is methyl. In another embodiment, $R^2$ is tert-butyl and $R^3$ is —C(=NOR$^9$)R$^{10}$ wherein $R^9$ is (C$_2$-C$_6$)alkyl and $R^{10}$ is ethyl. In another embodiment, $R^2$ is tert-butyl and $R^3$ is —C(=NOR$^9$)R$^{10}$ wherein $R^9$ is ethyl and $R^{10}$ is methyl, ethyl or propyl. In another embodiment, $R^2$ is tert-butyl and $R^3$ is —C(=NOR$^9$)R$^{10}$ wherein $R^9$ is ethyl and $R^{10}$ is methyl or ethyl. In another embodiment, $R^2$ is tert-butyl and $R^3$ is —C(=NOR$^9$)R$^{10}$ wherein $R^9$ is ethyl and $R^{10}$ is methyl. In another embodiment, $R^2$ is tert-butyl and $R^3$ is —C(=NOR$^9$)R$^{10}$ wherein $R^9$ is ethyl and $R^{10}$ is ethyl. In another embodiment, $R^2$ is tert-butyl and $R^3$ is —C(=NOR$^9$)R$^{10}$ wherein $R^9$ is propyl and $R^{10}$ is methyl, ethyl or propyl. In another embodiment, $R^2$ is tert-butyl and $R^3$ is —C(=NOR$^9$)R$^{10}$ wherein $R^9$ is propyl and $R^{10}$ is methyl or ethyl. In another embodiment, $R^2$ is tert-butyl and $R^3$ is —C(=NOR$^9$)R$^{10}$ wherein $R^9$ is propyl and $R^{10}$ is methyl. In another embodiment, $R^2$ is tert-butyl and $R^3$ is —C(=NOR$^9$)R$^{10}$ wherein $R^9$ is propyl and $R^{10}$ is ethyl. In another embodiment, $R^2$ is tert-butyl and $R^3$ is —C(=NOR$^9$)R$^{10}$ wherein $R^9$ is tert-butyl and $R^{10}$ is methyl, ethyl or propyl. In another embodiment, $R^2$ is tert-butyl and $R^3$ is —C(=NOR$^9$)R$^{10}$ wherein $R^9$ is tert-butyl and $R^{10}$ is methyl or ethyl. In another embodiment, $R^2$ is tert-butyl and $R^3$ is —C(=NOR$^9$)R$^{10}$ wherein $R^9$ is tert-butyl and $R^{10}$ is methyl. In another embodiment, $R^2$ is tert-butyl and $R^3$ is —C(=NOR$^9$)R$^{10}$ wherein $R^9$ is tert-butyl and $R^{10}$ is ethyl.

In another embodiment, $R^2$ is methoxy and $R^3$ is —C(=NOR$^9$)R$^{10}$ wherein $R^9$ is phenyl and $R^{10}$ is methyl, ethyl or propyl. In another embodiment, $R^2$ is methoxy and $R^3$ is —C(=NOR$^9$)R$^{10}$ wherein $R^9$ is phenyl and $R^{10}$ is methyl or ethyl. In another embodiment, $R^2$ is methoxy and $R^3$ is —C(=NOR$^9$)R$^{10}$ wherein $R^9$ is phenyl and $R^{10}$ is methyl. In another embodiment, $R^2$ is methoxy and $R^3$ is —C(=NOR$^9$)R$^{10}$ wherein $R^9$ is phenyl and $R^{10}$ is ethyl.

In another embodiment, $R^2$ is methoxy and $R^3$ is —C(=NOR$^9$)R$^{10}$ wherein $R^9$ is (C$_1$-C$_6$)alkyl substituted with phenyl and $R^{10}$ is methyl, ethyl or propyl. In another embodiment, $R^2$ is methoxy and $R^3$ is —C(=NOR$^9$)R$^{10}$ wherein $R^9$ is (C$_1$-C$_6$)alkyl substituted with phenyl and $R^{10}$ is methyl or ethyl. In another embodiment, $R^2$ is methoxy and $R^3$ is —C(=NOR$^9$)R$^{10}$ wherein $R^9$ is (C$_1$-C$_6$)alkyl substituted with phenyl and $R^{10}$ is methyl. In another embodiment, $R^2$ is methoxy and $R^3$ is —C(=NOR$^9$)R$^{10}$ wherein $R^9$ is (C$_1$-C$_6$)alkyl substituted with phenyl and $R^{10}$ is ethyl. In another embodiment, $R^2$ is methoxy and $R^3$ is —C(=NOR$^9$)R$^{10}$ wherein $R^9$ is (C$_1$)alkyl substituted with phenyl and $R^{10}$ is methyl, ethyl or propyl. In another embodiment, $R^2$ is methoxy and $R^3$ is —C(=NOR$^9$)R$^{10}$ wherein $R^9$ is (C$_1$)alkyl substituted with phenyl and $R^{10}$ is methyl or ethyl. In another embodiment, $R^2$ is methoxy and $R^3$ is —C(=NOR$^9$)R$^{10}$ wherein $R^9$ is (C$_1$)alkyl substituted with phenyl and $R^{10}$ is methyl. In another embodiment, $R^2$ is methoxy and $R^3$ is —C(=NOR$^9$)R$^{10}$ wherein $R^9$ is (C$_1$)alkyl substituted with phenyl and $R^{10}$ is ethyl. In another embodiment, $R^2$ is methoxy and $R^3$ is —C(=NOR$^9$)R$^{10}$ wherein $R^9$ is (C$_2$)alkyl substituted with phenyl and $R^{10}$ is methyl, ethyl or propyl. In another embodiment, $R^2$ is methoxy and $R^3$ is —C(=NOR$^9$)R$^{10}$ wherein $R^9$ is (C$_2$)alkyl substituted with phenyl and $R^{10}$ is methyl or ethyl. In another embodiment, $R^2$ is methoxy and $R^3$ is —C(=NOR$^9$)R$^{10}$ wherein $R^9$ is (C$_2$)alkyl substituted with phenyl and $R^{10}$ is methyl. In another embodiment, $R^2$ is methoxy and $R^3$ is —C(=NOR$^9$)R$^{10}$ wherein $R^9$ is (C$_2$)alkyl substituted with phenyl and $R^{10}$ is ethyl.

In another embodiment, $R^2$ is methoxy and $R^3$ is —C(=NOR$^9$)R$^{10}$ wherein $R^9$ is (C$_2$-C$_6$)alkyl and $R^{10}$ is methyl, ethyl or propyl. In another embodiment, $R^2$ is methoxy and $R^3$ is —C(=NOR$^9$)R$^{10}$ wherein $R^9$ is (C$_2$-C$_6$)alkyl and $R^{10}$ is methyl or ethyl. In another embodiment, $R^2$ is methoxy and $R^3$ is —C(=NOR$^9$)R$^{10}$ wherein $R^9$ is (C$_2$-C$_6$)alkyl and $R^{10}$ is methyl. In another embodiment, $R^2$ is methoxy and $R^3$ is —C(=NOR$^9$)R$^{10}$ wherein $R^9$ is (C$_2$-C$_6$)alkyl and $R^{10}$ is ethyl. In another embodiment, $R^2$ is methoxy and $R^3$ is —C(=NOR$^9$)R$^{10}$ wherein $R^9$ is ethyl and $R^{10}$ is methyl, ethyl or propyl. In another embodiment, $R^2$ is methoxy and $R^3$ is —C(=NOR$^9$)R$^{10}$ wherein $R^9$ is ethyl and $R^{10}$ is methyl or ethyl. In another embodiment, $R^2$ is methoxy and $R^3$ is —C(=NOR$^9$)R$^{10}$ wherein $R^9$ is ethyl and $R^{10}$ is methyl. In another embodiment, $R^2$ is methoxy and $R^3$ is —C(=NOR$^9$)R$^{10}$ wherein $R^9$ is ethyl and $R^{10}$ is ethyl. In another embodiment, $R^2$ is methoxy and $R^3$ is —C(=NOR$^9$)R$^{10}$ wherein $R^9$ is propyl and $R^{10}$ is methyl, ethyl or propyl. In another embodiment, $R^2$ is methoxy and $R^3$ is —C(=NOR$^9$)R$^{10}$ wherein $R^9$ is propyl and $R^{10}$ is methyl or ethyl. In another embodiment, $R^2$ is methoxy and $R^3$ is —C(=NOR$^9$)R$^{10}$ wherein $R^9$ is propyl and $R^{10}$ is methyl. In another embodiment, $R^2$ is methoxy and $R^3$ is —C(=NOR$^9$)R$^{10}$ wherein $R^9$ is propyl and $R^{10}$ is ethyl. In another embodiment, $R^2$ is methoxy and $R^3$ is —C(=NOR$^9$)R$^{10}$ wherein $R^9$ is tert-butyl and $R^{10}$ is methyl, ethyl or propyl. In another embodiment, $R^2$ is methoxy and $R^3$ is —C(=NOR$^9$)R$^{10}$ wherein $R^9$ is tert-butyl and $R^{10}$ is methyl or ethyl. In another embodiment, $R^2$ is methoxy and $R^3$ is —C(=NOR$^9$)R$^{10}$ wherein $R^9$ is tert-butyl and $R^{10}$ is methyl. In another embodiment, $R^2$ is methoxy and $R^3$ is —C(=NOR$^9$)R$^{10}$ wherein $R^9$ is tert-butyl and $R^{10}$ is ethyl.

In another embodiment, $R^2$ is ethoxy and $R^3$ is —C(=NOR$^9$)R$^{10}$ wherein $R^9$ is phenyl and $R^{10}$ is methyl, ethyl or propyl. In another embodiment, $R^2$ is ethoxy and $R^3$ is —C(=NOR$^9$)R$^{10}$ wherein $R^9$ is phenyl and $R^{10}$ is methyl or ethyl. In another embodiment, $R^2$ is ethoxy and $R^3$ is —C(=NOR$^9$)R$^{10}$ wherein $R^9$ is phenyl and $R^{10}$ is methyl. In another embodiment, $R^2$ is ethoxy and $R^3$ is —C(=NOR$^9$)R$^{10}$ wherein $R^9$ is phenyl and $R^{10}$ is ethyl.

In another embodiment, $R^2$ is ethoxy and $R^3$ is —C(=NOR$^9$)R$^{10}$ wherein $R^9$ is (C$_1$-C$_6$)alkyl substituted with phenyl and $R^{10}$ is methyl, ethyl or propyl. In another embodiment, $R^2$ is ethoxy and $R^3$ is —C(=NOR$^9$)R$^{10}$ wherein $R^9$ is (C$_1$-C$_6$)alkyl substituted with phenyl and $R^{10}$ is methyl or ethyl. In another embodiment, $R^2$ is ethoxy and $R^3$ is —C(=NOR$^9$)R$^{10}$ wherein R$^9$ is (C$_1$-C$_6$)alkyl substituted with phenyl and R$^{10}$ is methyl. In another embodiment, R$^2$ is ethoxy and R$^3$ is —C(=NOR$^9$)R$^{10}$ wherein R$^9$ is (C$_1$-C$_6$)alkyl substituted with phenyl and R$^{10}$ is ethyl. In another embodiment, R$^2$ is ethoxy and R$^3$ is —C(=NOR$^9$)R$^{10}$ wherein R$^9$ is (C$_1$)alkyl substituted with phenyl and R$^{10}$ is methyl, ethyl or propyl. In another embodiment, R$^2$ is ethoxy and R$^3$ is —C(=NOR$^9$)R$^{10}$ wherein R$^9$ is (C$_1$)alkyl substituted with phenyl and R$^{10}$ is methyl or ethyl. In another embodiment, R$^2$ is ethoxy and R$^3$ is —C(=NOR$^9$)R$^{10}$ wherein R$^9$ is (C$_1$)alkyl substituted with phenyl and R$^{10}$ is methyl. In another embodiment, R$^2$ is ethoxy and R$^3$ is —C(=NOR$^9$)R$^{10}$ wherein R$^9$ is (C$_1$)alkyl substituted with phenyl and R$^{10}$ is ethyl. In another embodiment, R$^2$ is ethoxy and R$^3$ is —C(=NOR$^9$)R$^{10}$ wherein R$^9$ is (C$_2$)alkyl substituted with phenyl and R$^{10}$ is methyl, ethyl or propyl. In another embodiment, R$^2$ is ethoxy and R$^3$ is —C(=NOR$^9$)R$^{10}$ wherein R$^9$ is (C$_2$)alkyl substituted with phenyl and R$^{10}$ is methyl or ethyl. In another embodiment, R$^2$ is ethoxy and R$^3$ is —C(=NOR$^9$)R$^{10}$ wherein R$^9$ is (C$_2$)alkyl substituted with phenyl and R$^{10}$ is methyl. In another embodiment, R$^2$ is ethoxy and R$^3$ is —C(=NOR$^9$)R$^{10}$ wherein R$^9$ is (C$_2$)alkyl substituted with phenyl and R$^{10}$ is ethyl.

In another embodiment, R$^2$ is ethoxy and R$^3$ is —C(=NOR$^9$)R$^{10}$ wherein R$^9$ is (C$_2$-C$_6$)alkyl and R$^{10}$ is methyl, ethyl or propyl. In another embodiment, R$^2$ is ethoxy and R$^3$ is —C(=NOR$^9$)R$^{10}$ wherein R$^9$ is (C$_2$-C$_6$)alkyl and R$^{10}$ is methyl or ethyl. In another embodiment, R$^2$ is ethoxy and R$^3$ is —C(=NOR$^9$)R$^{10}$ wherein R$^9$ is (C$_2$-C$_6$)alkyl and R$^{10}$ is methyl. In another embodiment, R$^2$ is ethoxy and R$^3$ is —C(=NOR$^9$)R$^{10}$ wherein R$^9$ is (C$_2$-C$_6$)alkyl and R$^{10}$ is ethyl. In another embodiment, R$^2$ is ethoxy and R$^3$ is —C(=NOR$^9$)R$^{10}$ wherein R$^9$ is ethyl and R$^{10}$ is methyl, ethyl or propyl. In another embodiment, R$^2$ is ethoxy and R$^3$ is —C(=NOR$^9$)R$^{10}$ wherein R$^9$ is ethyl and R$^{10}$ is methyl or ethyl. In another embodiment, R$^2$ is ethoxy and R$^3$ is —C(=NOR$^9$)R$^{10}$ wherein R$^9$ is ethyl and R$^{10}$ is methyl. In another embodiment, R$^2$ is ethoxy and R$^3$ is —C(=NOR$^9$)R$^{10}$ wherein R$^9$ is ethyl and R$^{10}$ is ethyl. In another embodiment, R$^2$ is ethoxy and R$^3$ is —C(=NOR$^9$)R$^{10}$ wherein R$^9$ is propyl and R$^{10}$ is methyl, ethyl or propyl. In another embodiment, R$^2$ is ethoxy and R$^3$ is —C(=NOR$^9$)R$^{10}$ wherein R$^9$ is propyl and R$^{10}$ is methyl or ethyl. In another embodiment, R$^2$ is ethoxy and R$^3$ is —C(=NOR$^9$)R$^{10}$ wherein R$^9$ is propyl and R$^{10}$ is methyl. In another embodiment, R$^2$ is ethoxy and R$^3$ is —C(=NOR$^9$)R$^{10}$ wherein R$^9$ is propyl and R$^{10}$ is ethyl. In another embodiment, R$^2$ is ethoxy and R$^3$ is —C(=NOR$^9$)R$^{10}$ wherein R$^9$ is tert-butyl and R$^{10}$ is methyl, ethyl or propyl. In another embodiment, R$^2$ is ethoxy and R$^3$ is —C(=NOR$^9$)R$^{10}$ wherein R$^9$ is tert-butyl and R$^{10}$ is methyl or ethyl. In another embodiment, R$^2$ is ethoxy and R$^3$ is —C(=NOR$^9$)R$^{10}$ wherein R$^9$ is tert-butyl and R$^{10}$ is methyl. In another embodiment, R$^2$ is ethoxy and R$^3$ is —C(=NOR$^9$)R$^{10}$ wherein R$^9$ is tert-butyl and R$^{10}$ is ethyl.

In another embodiment, R$^2$ is propoxy and R$^3$ is —C(=NOR$^9$)R$^{10}$ wherein R$^9$ is phenyl and R$^{10}$ is methyl, ethyl or propyl. In another embodiment, R$^2$ is propoxy and R$^3$ is —C(=NOR$^9$)R$^{10}$ wherein R$^9$ is phenyl and R$^{10}$ is methyl or ethyl. In another embodiment, R$^2$ is propoxy and R$^3$ is —C(=NOR$^9$)R$^{10}$ wherein R$^9$ is phenyl and R$^{10}$ is methyl. In another embodiment, R$^2$ is propoxy and R$^3$ is —C(=NOR$^9$)R$^{10}$ wherein R$^9$ is phenyl and R$^{10}$ is ethyl.

In another embodiment, R$^2$ is propoxy and R$^3$ is —C(=NOR$^9$)R$^{10}$ wherein R$^9$ is (C$_1$-C$_6$)alkyl substituted with phenyl and R$^{10}$ is methyl, ethyl or propyl. In another embodiment, R$^2$ is propoxy and R$^3$ is —C(=NOR$^9$)R$^{10}$ wherein R$^9$ is (C$_1$-C$_6$)alkyl substituted with phenyl and R$^{10}$ is methyl or ethyl. In another embodiment, R$^2$ is propoxy and R$^3$ is —C(=NOR$^9$)R$^{10}$ wherein R$^9$ is (C$_1$-C$_6$)alkyl substituted with phenyl and R$^{10}$ is methyl. In another embodiment, R$^2$ is propoxy and R$^3$ is —C(=NOR$^9$)R$^{10}$ wherein R$^9$ is (C$_1$-C$_6$)alkyl substituted with phenyl and R$^{10}$ is ethyl. In another embodiment, R$^2$ is propoxy and R$^3$ is —C(=NOR$^9$)R$^{10}$ wherein R$^9$ is (C$_1$)alkyl substituted with phenyl and R$^{10}$ is methyl, ethyl or propyl. In another embodiment, R$^2$ is propoxy and R$^3$ is —C(=NOR$^9$)R$^{10}$ wherein R$^9$ is (C$_1$)alkyl substituted with phenyl and R$^{10}$ is methyl or ethyl. In another embodiment, R$^2$ is propoxy and R$^3$ is —C(=NOR$^9$)R$^{10}$ wherein R$^9$ is (C$_1$)alkyl substituted with phenyl and R$^{10}$ is methyl. In another embodiment, R$^2$ is propoxy and R$^3$ is —C(=NOR$^9$)R$^{10}$ wherein R$^9$ is (C$_1$)alkyl substituted with phenyl and R$^{10}$ is ethyl. In another embodiment, R$^2$ is propoxy and R$^3$ is —C(=NOR$^9$)R$^{10}$ wherein R$^9$ is (C$_2$)alkyl substituted with phenyl and R$^{10}$ is methyl, ethyl or propyl. In another embodiment, R$^2$ is propoxy and R$^3$ is —C(=NOR$^9$)R$^{10}$ wherein R$^9$ is (C$_2$)alkyl substituted with phenyl and R$^{10}$ is methyl or ethyl. In another embodiment, R$^2$ is propoxy and R$^3$ is —C(=NOR$^9$)R$^{10}$ wherein R$^9$ is (C$_2$)alkyl substituted with phenyl and R$^{10}$ is methyl. In another embodiment, R$^2$ is propoxy and R$^3$ is —C(=NOR$^9$)R$^{10}$ wherein R$^9$ is (C$_2$)alkyl substituted with phenyl and R$^{10}$ is ethyl.

In another embodiment, R$^2$ is propoxy and R$^3$ is —C(=NOR$^9$)R$^{10}$ wherein R$^9$ is (C$_2$-C$_6$)alkyl and R$^{10}$ is methyl, ethyl or propyl. In another embodiment, R$^2$ is propoxy and R$^3$ is —C(=NOR$^9$)R$^{10}$ wherein R$^9$ is (C$_2$-C$_6$)alkyl and R$^{10}$ is methyl or ethyl. In another embodiment, R$^2$ is propoxy and R$^3$ is —C(=NOR$^9$)R wherein R$^9$ is (C$_2$-C$_6$)alkyl and R$^{10}$ is methyl. In another embodiment, R$^2$ is propoxy and R$^3$ is —C(=NOR$^9$)R$^{10}$ wherein R$^9$ is (C$_2$-C$_6$)alkyl and R is ethyl. In another embodiment, R$^2$ is propoxy and R$^3$ is —C(=NOR$^9$)R$^{10}$ wherein R$^9$ is ethyl and R$^{10}$ is methyl, ethyl or propyl. In another embodiment, R$^2$ is propoxy and R$^3$ is —C(=NOR$^9$)R$^{10}$ wherein R$^9$ is ethyl and R$^{10}$ is methyl or ethyl. In another embodiment, R$^2$ is propoxy and R$^3$ is —C(=NOR$^9$)R$^{10}$ wherein R$^9$ is ethyl and R$^{10}$ is methyl. In another embodiment, R$^2$ is propoxy and R$^3$ is —C(=NOR$^9$)R$^{10}$ wherein R$^9$ is ethyl and R$^{10}$ is ethyl. In another embodiment, R$^2$ is propoxy and R$^3$ is —C(=NOR$^9$)R$^{10}$ wherein R$^9$ is propyl and R$^{10}$ is methyl, ethyl or propyl. In another embodiment, R$^2$ is propoxy and R$^3$ is —C(=NOR$^9$)R$^{10}$ wherein R$^9$ is propyl and R$^{10}$ is methyl or ethyl. In another embodiment, R$^2$ is propoxy and R$^3$ is —C(=NOR$^9$)R$^{10}$ wherein R$^9$ is propyl and R$^{10}$ is methyl. In another embodiment, R$^2$ is propoxy and R$^3$ is —C(=NOR$^9$)R$^{10}$ wherein R$^9$ is propyl and R$^{10}$ is ethyl. In another embodiment, R$^2$ is propoxy and R$^3$ is —C(=NOR$^9$)R$^{10}$ wherein R$^9$ is tert-butyl and R$^{10}$ is methyl, ethyl or propyl. In another embodiment, R$^2$ is propoxy and R$^3$ is —C(=NOR$^9$)R$^{10}$ wherein R$^9$ is tert-butyl and R$^{10}$ is methyl or ethyl. In another embodiment, R$^2$ is propoxy and R$^3$ is —C(=NOR$^9$)R$^{10}$ wherein R$^9$ is tert-butyl and R$^{10}$ is methyl. In another embodiment, R$^2$ is propoxy and R$^3$ is —C(=NOR$^9$)R$^{10}$ wherein R$^9$ is tert-butyl and R$^{10}$ is ethyl.

Another aspect of the disclosure provides a compound of formula (Ie)

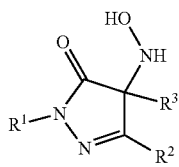

(Ie)

or a pharmaceutically acceptable salt thereof, wherein:

$R^1$ is phenyl substituted with 1, 2, or 3 substituent(s) independently selected from $(C_1-C_6)$alkylsulfonyl;

$R^2$ is $(C_1-C_6)$alkyl; and $R^3$ is $(C_1-C_6)$alkyl.

In one embodiment, $R^1$ is phenyl substituted with 1, 2, or 3 substituent(s) independently selected from $(C_1-C_6)$alkylsulfonyl. In another embodiment, $R^1$ is phenyl substituted with 1 or 2 substituent(s), each substituent being independently selected from $(C_1-C_6)$alkylsulfonyl.

In another embodiment, $R^1$ is phenyl disubstituted with $(C_1-C_6)$alkylsulfonyl. In another embodiment, $R^1$ is di(iso-propylsulfonyl)phenyl. In another embodiment, $R^1$ is di(ethylsulfonyl)phenyl. In another embodiment, $R^1$ is di(methylsulfonyl)phenyl. In another embodiment, $R^1$ is 3,4-di(($C_1$-$C_6$)alkylsulfonyl)phenyl. In another embodiment, $R^1$ is 3,4-di(iso-propylsulfonyl)phenyl. In another embodiment, $R^1$ is 3,4-di(ethylsulfonyl)phenyl. In another embodiment, $R^1$ is 3,4-di(methylsulfonyl)phenyl. In another embodiment, $R^1$ is 2,4-di(($C_1$-$C_6$)alkylsulfonyl)phenyl. In another embodiment, $R^1$ is 2,4-di(iso-propylsulfonyl)phenyl. In another embodiment, $R^1$ is 2,4-di(ethylsulfonyl)phenyl. In another embodiment, $R^1$ is 2,4-di(methylsulfonyl)phenyl. In another embodiment, $R^1$ is 2,5-di(($C_1$-$C_6$)alkylsulfonyl)phenyl. In another embodiment, $R^1$ is 2,5-di(iso-propylsulfonyl)phenyl. In another embodiment, $R^1$ is 2,5-di(ethylsulfonyl)phenyl. In another embodiment, $R^1$ is 2,5-di(methylsulfonyl)phenyl. In another embodiment, $R^1$ is 2,3-di(($C_1$-$C_6$)alkylsulfonyl)phenyl. In another embodiment, $R^1$ is 2,3-di(iso-propylsulfonyl)phenyl. In another embodiment, $R^1$ is 2,3-di(ethylsulfonyl)phenyl. In another embodiment, $R^1$ is 2,3-di(methylsulfonyl)phenyl. In another embodiment, $R^1$ is 2,6-di(($C_1$-$C_6$)alkylsulfonyl)phenyl. In another embodiment, $R^1$ is 2,6-di(iso-propylsulfonyl)phenyl. In another embodiment, $R^1$ is 2,6-di(ethylsulfonyl)phenyl. In another embodiment, $R^1$ is 2,6-di(methylsulfonyl)phenyl. In another embodiment, $R^1$ is 3,5-di(($C_1$-$C_6$)alkylsulfonyl)phenyl. In another embodiment, $R^1$ is 3,5-di(iso-propylsulfonyl)phenyl. In another embodiment, $R^1$ is 3,5-di(ethylsulfonyl)phenyl. In another embodiment, $R^1$ is 3,5-di(methylsulfonyl)phenyl. In another embodiment, $R^1$ is 3,6-di(($C_1$-$C_6$)alkylsulfonyl)phenyl. In another embodiment, $R^1$ is 3,6-di(iso-propylsulfonyl)phenyl. In another embodiment, $R^1$ is 3,6-di(ethylsulfonyl)phenyl. In another embodiment, $R^1$ is 3,6-di(methylsulfonyl)phenyl.

In another embodiment, $R^1$ is phenyl monosubstituted with $(C_1-C_6)$alkylsulfonyl. In another embodiment, $R^1$ is iso-propylsulfonylphenyl. In another embodiment, $R^1$ is ethylsulfonylphenyl. In another embodiment, $R^1$ is methylsulfonylphenyl. In another embodiment, $R^1$ is 4-$(C_1-C_6)$alkylsulfonylphenyl. In another embodiment, $R^1$ is 4-iso-propylsulfonylphenyl. In another embodiment, $R^1$ is 4-ethylsulfonylphenyl. In another embodiment, $R^1$ is 4-methylsulfonylphenyl. In another embodiment, $R^1$ is 3-$(C_1-C_6)$alkylsulfonylphenyl. In another embodiment, $R^1$ is 3-iso-propylsulfonylphenyl. In another embodiment, $R^1$ is 3-ethylsulfonylphenyl. In another embodiment, $R^1$ is 3-methylsulfonylphenyl. In another embodiment, $R^1$ is 2-$(C_1-C_6)$alkylsulfonylphenyl. In another embodiment, $R^1$ is 2-iso-propylsulfonylphenyl. In another embodiment, $R^1$ is 2-ethylsulfonylphenyl. In another embodiment, $R^1$ is 2-methylsulfonylphenyl.

In one embodiment, $R^2$ is methyl, ethyl, iso-propyl, or tert-butyl. In another embodiment, $R^2$ is methyl, ethyl, or iso-propyl. In another embodiment, $R^2$ is methyl, ethyl, or tert-butyl. In another embodiment, $R^2$ is methyl, iso-propyl, or tert-butyl. In another embodiment, $R^2$ is ethyl, iso-propyl, or tert-butyl. In another embodiment, $R^2$ is methyl or ethyl. In another embodiment, $R^2$ is methyl or iso-propyl. In another embodiment, $R^2$ is methyl or tert-butyl. In another embodiment, $R^2$ is ethyl or iso-propyl. In another embodiment, $R^2$ is ethyl or tert-butyl. In another embodiment, $R^2$ is iso-propyl or tert-butyl. In another embodiment, $R^2$ is methyl. In another embodiment, $R^2$ is ethyl. In another embodiment, $R^2$ is iso-propyl. In another embodiment, $R^2$ is tert-butyl.

In one embodiment, $R^3$ is methyl, ethyl, iso-propyl, or tert-butyl. In another embodiment, $R^3$ is methyl, ethyl, or iso-propyl. In another embodiment, $R^3$ is methyl, ethyl, or tert-butyl. In another embodiment, $R^3$ is methyl, iso-propyl, or tert-butyl. In another embodiment, $R^3$ is ethyl, iso-propyl, or tert-butyl. In another embodiment, $R^3$ is methyl or ethyl. In another embodiment, $R^3$ is methyl or iso-propyl. In another embodiment, $R^3$ is methyl or tert-butyl. In another embodiment, $R^3$ is ethyl or iso-propyl. In another embodiment, $R^3$ is ethyl or tert-butyl. In another embodiment, $R^3$ is iso-propyl or tert-butyl. In another embodiment, $R^3$ is methyl. In another embodiment, $R^3$ is ethyl. In another embodiment, $R^3$ is iso-propyl. In another embodiment, $R^3$ is tert-butyl.

In another embodiment, $R^1$ is monosubstituted phenyl, e.g., selected from among the monosubstituted $R^1$ phenyl groups disclosed above in connection with the compounds of formula (Ie), and $R^2$ is methyl. In another embodiment, $R^1$ is monosubstituted phenyl, e.g., selected from among the monosubstituted $R^1$ phenyl groups disclosed above in connection with the compounds of formula (Ie), and $R^2$ is ethyl. In another embodiment, $R^1$ is monosubstituted phenyl, e.g., selected from among the monosubstituted $R^1$ phenyl groups disclosed above in connection with the compounds of formula (Ie), and $R^2$ is iso-propyl. In another embodiment, $R^1$ is monosubstituted phenyl, e.g., selected from among the monosubstituted $R^1$ phenyl groups disclosed above in connection with the compounds of formula (Ie), and $R^2$ is tert-butyl. In another embodiment, $R^1$ is disubstituted phenyl, e.g., selected from among the disubstituted $R^1$ phenyl groups disclosed above in connection with the compounds of formula (Ie), and $R^2$ is methyl. In another embodiment, $R^1$ is disubstituted phenyl, e.g., selected from among the disubstituted $R^1$ phenyl groups disclosed above in connection with the compounds of formula (Ie), and $R^2$ is ethyl. In another embodiment, $R^1$ is disubstituted phenyl, e.g., selected from among the disubstituted $R^1$ phenyl groups disclosed above in connection with the compounds of formula (Ie), and $R^2$ is iso-propyl. In another embodiment, $R^1$ is disubstituted phenyl, e.g., selected from among the disubstituted $R^1$ phenyl groups disclosed above in connection with the compounds of formula (Ie), and $R^2$ is tert-butyl.

In another embodiment, $R^1$ is monosubstituted phenyl, e.g., selected from among the monosubstituted $R^1$ phenyl groups disclosed above in connection with the compounds of formula (Ie), and $R^3$ is methyl. In another embodiment, $R^1$ is monosubstituted phenyl, e.g., selected from among the monosubstituted $R^1$ phenyl groups disclosed above in connection with the compounds of formula (Ie), and $R^3$ is ethyl. In another embodiment, $R^1$ is monosubstituted phenyl, e.g., selected from among the monosubstituted $R^1$ phenyl groups disclosed above in connection with the compounds of formula (Ie), and $R^3$ is iso-propyl. In another embodiment, $R^1$ is monosubstituted phenyl, e.g., selected from among the monosubstituted $R^1$ phenyl groups disclosed above in connection with the compounds of formula (Ie), and $R^3$ is tert-butyl. In another embodiment, $R^1$ is disubstituted phenyl, e.g., selected from among the disubstituted $R^1$ phenyl groups disclosed above in connection with the compounds of formula (Ie), and $R^3$ is methyl. In another embodiment, $R^1$ is disubstituted phenyl, e.g., selected from among the disubstituted $R^1$ phenyl groups disclosed above in connection with the compounds of formula (Ie), and $R^3$ is ethyl. In another embodiment, $R^1$ is disubstituted phenyl, e.g., selected from among the disubstituted $R^1$ phenyl groups disclosed above in connection with the compounds of formula (Ie), and $R^3$ is iso-propyl. In another embodiment, $R^1$ is disubstituted phenyl, e.g., selected from among the disubstituted $R^1$ phenyl groups disclosed above in connection with the compounds of formula (Ie), and $R^3$ is tert-butyl.

In another embodiment, $R^2$ is methyl and $R^3$ is methyl. In another embodiment, $R^2$ is methyl and $R^3$ is ethyl. In another embodiment, $R^2$ is ethyl and $R^3$ is methyl. In another embodiment, $R^2$ is ethyl and $R^3$ is ethyl. In another embodiment, $R^2$ is iso-propyl and $R^3$ is methyl. In another embodiment, $R^2$ is iso-propyl and $R^3$ is ethyl. In another embodiment, $R^2$ is methyl and $R^3$ is iso-propyl. In another embodiment, $R^2$ is ethyl and $R^3$ is iso-propyl. In another embodiment, $R^2$ is iso-propyl and $R^3$ is iso-propyl. In another embodiment, $R^2$ is tert-butyl and $R^3$ is methyl. In another embodiment, $R^2$ is tert-butyl and $R^3$ is ethyl. In another embodiment, $R^2$ is methyl and $R^3$ is tert-butyl. In another embodiment, $R^2$ is ethyl and $R^3$ is tert-butyl. In another embodiment, $R^2$ is tert-butyl and $R^3$ is tert-butyl.

Another aspect of the disclosure provides a compound of formula (If)

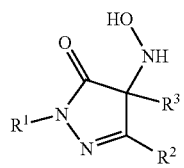

(If)

or a pharmaceutically acceptable salt thereof, wherein:

$R^1$ is phenyl substituted with 1, 2, 3, 4, or 5 substituent(s) independently selected from halo, $(C_1-C_6)$alkoxy, $(C_1-C_6)$alkylsulfinyl, and $(C_1-C_6)$alkylsulfonyl;

$R^2$ is phenyl wherein said phenyl is unsubstituted or substituted with 1, 2, 3, 4, or 5 substituent(s) independently selected from halo, $(C_1-C_6)$alkoxy, $(C_1-C_6)$alkylsulfinyl, and $(C_1-C_6)$alkylsulfonyl; and $R^3$ is $(C_1-C_6)$alkyl or —C(=NOR$^9$)R$^{10}$ wherein R$^9$ and R$^{10}$ are independently selected from $(C_1-C_6)$alkyl.

In one embodiment, $R^1$ is phenyl wherein the phenyl is substituted with 1, 2, or 3 substituent(s) independently selected from halo, $(C_1-C_6)$alkoxy, and $(C_1-C_6)$alkylsulfinyl. In one embodiment, $R^1$ is phenyl wherein the phenyl is substituted with 1, 2, or 3 substituent(s) independently selected from halo, $(C_1-C_6)$alkoxy, and $(C_1-C_6)$alkylsulfonyl. In one embodiment, $R^1$ is phenyl wherein the phenyl is substituted with 1, 2, or 3 substituent(s) independently selected from $(C_1-C_6)$alkoxy, $(C_1-C_6)$alkylsulfinyl, and $(C_1-C_6)$alkylsulfonyl. In another embodiment, $R^1$ is phenyl wherein the phenyl is substituted with 1, 2, or 3 substituent(s) independently selected from halo and $(C_1-C_6)$alkylsulfinyl. In one embodiment, $R^1$ is phenyl wherein the phenyl is substituted with 1, 2, or 3 substituent(s) independently selected from halo and $(C_1-C_6)$alkylsulfonyl. In one embodiment, $R^1$ is phenyl wherein the phenyl is substituted with 1, 2, or 3 substituent(s) independently selected from $(C_1-C_6)$alkylsulfinyl and $(C_1-C_6)$alkylsulfonyl. In another embodiment, $R^1$ is phenyl wherein the phenyl is substituted with 1, 2, or 3 substituent(s) independently selected from fluoro, bromo, methoxy, methylsulfinyl, and methylsulfonyl. In another embodiment, $R^1$ is phenyl wherein the phenyl is substituted with 1, 2, or 3 substituent(s) independently selected from bromo, methylsulfinyl, and methylsulfonyl.

In another embodiment, $R^1$ is phenyl wherein the phenyl is substituted with 1 or 2 substituent(s), each substituent being independently selected from halo, $(C_1-C_6)$alkylsulfinyl, and $(C_1-C_6)$alkylsulfonyl. In another embodiment, $R^1$ is phenyl wherein the phenyl is substituted with 1 or 2 substituent(s), each substituent being independently selected from $(C_1-C_6)$alkoxy, $(C_1-C_6)$alkylsulfinyl, and $(C_1-C_6)$alkylsulfonyl. In another embodiment, $R^1$ is phenyl wherein the phenyl is substituted with 1 or 2 substituent(s), each substituent being independently selected from halo, $(C_1-C_6)$alkoxy, and $(C_1-C_6)$alkylsulfonyl. In another embodiment, $R^1$ is phenyl wherein the phenyl is substituted with 1 or 2 substituent(s), each substituent being independently selected from halo, $(C_1-C_6)$alkylsulfinyl, and $(C_1-C_6)$alkoxy. In another embodiment, $R^1$ is phenyl wherein the phenyl is substituted with 1 or 2 substituent(s), each substituent being independently selected from fluoro, bromo, methoxy, methylsulfinyl, and methylsulfonyl. In another embodiment, $R^1$ is phenyl wherein the phenyl is substituted with 1 or 2 substituent(s), each substituent being independently selected from bromo, methylsulfinyl, and methylsulfonyl.

In another embodiment, $R^1$ is phenyl wherein the phenyl is monosubstituted with halo, $(C_1-C_6)$alkoxy, $(C_1-C_6)$alkylsulfinyl, or $(C_1-C_6)$alkylsulfonyl. In another embodiment, $R^1$ is phenyl wherein the phenyl is monosubstituted with $(C_1-C_6)$alkoxy, $(C_1-C_6)$alkylsulfinyl, or $(C_1-C_6)$alkylsulfonyl. In another embodiment, $R^1$ is phenyl wherein the phenyl is monosubstituted with halo, $(C_1-C_6)$alkoxy, or $(C_1-C_6)$alkylsulfonyl. In another embodiment, $R^1$ is phenyl wherein the phenyl is monosubstituted with halo, $(C_1-C_6)$alkylsulfinyl, or $(C_1-C_6)$alkylsulfinyl. In another embodiment, $R^1$ is phenyl wherein the phenyl is monosubstituted with halo, $(C_1-C_6)$alkoxy, or $(C_1-C_6)$alkylsulfonyl. In another embodiment, $R^1$ is phenyl wherein the phenyl is monosubstituted with fluoro, bromo, methoxy, methylsulfinyl, or methylsulfonyl. In another embodiment, $R^1$ is phenyl wherein the phenyl is monosubstituted with bromo, methylsulfinyl, or methylsulfonyl. In another embodiment, $R^1$ is fluorophenyl, bromophenyl, methoxyphenyl, methylsulfinylphenyl, or methylsulfonylphenyl. In another embodiment, $R^1$ is fluorophenyl, bromophenyl, methylsulfinylphenyl, or methylsulfonylphenyl. In another embodiment, $R^1$ is 4-fluorophenyl, 4-bromophenyl, 4-methoxyphenyl, 4-methylsulfinylphenyl, or 4-methylsulfonylphenyl. In another embodiment, $R^1$ is 4-bromophenyl, 4-methylsulfinylphenyl, or 4-methylsulfonylphenyl.

In another embodiment, $R^1$ is phenyl monosubstituted with $(C_1-C_6)$alkylsulfonyl. In another embodiment, $R^1$ is iso-propylsulfonylphenyl. In another embodiment, $R^1$ is ethylsulfonylphenyl. In another embodiment, $R^1$ is methylsulfonylphenyl. In another embodiment, $R^1$ is 4-$(C_1-C_6)$ alkylsulfonylphenyl. In another embodiment, $R^1$ is 4-iso-propylsulfonylphenyl. In another embodiment, $R^1$ is 4-ethylsulfonylphenyl. In another embodiment, $R^1$ is 4-methylsulfonylphenyl.

In another embodiment, $R^1$ is phenyl monosubstituted with $(C_1-C_6)$alkylsulfinyl. In another embodiment, $R^1$ is iso-propylsulfinylphenyl. In another embodiment, $R^1$ is ethylsulfinylphenyl. In another embodiment, $R^1$ is methylsulfinylphenyl. In another embodiment, $R^1$ is 4-$(C_1-C_6)$alkylsulfinylphenyl. In another embodiment, $R^1$ is 4-iso-propylsulfinylphenyl. In another embodiment, $R^1$ is 4-ethylsulfinylphenyl. In another embodiment, $R^1$ is 4-methylsulfinylphenyl.

In another embodiment, $R^1$ is phenyl monosubstituted with $(C_1-C_6)$alkoxy. In another embodiment, $R^1$ is phenyl monosubstituted with $(C_1-C_4)$alkoxy. In another embodiment, $R^1$ is iso-propoxyphenyl. In another embodiment, $R^1$ is ethoxyphenyl. In another embodiment, $R^1$ is methoxyphenyl. In another embodiment, $R^1$ is 4-$(C_1-C_6)$alkoxyphenyl. In another embodiment, $R^1$ is 4-iso-propoxyphenyl. In another embodiment, $R^1$ is 4-ethoxyphenyl. In another embodiment, $R^1$ is 4-methoxyphenyl.

In another embodiment, $R^1$ is phenyl, wherein the phenyl is substituted with 1 or 2 substituent(s), each substituent being independently selected from halo and $(C_1-C_6)$alkoxy. In another embodiment, $R^1$ is phenyl, wherein the phenyl is monosubstituted with halo and also monosubstituted with $(C_1-C_6)$alkoxy. In another embodiment, $R^1$ is phenyl, wherein the phenyl is substituted with 1 or 2 substituent(s), each substituent being independently selected from halo and $(C_1-C_4)$alkoxy. In another embodiment, $R^1$ is phenyl, wherein the phenyl is disubstituted—monosubstituted with halo and also monosubstituted with $(C_1-C_4)$alkoxy. In another embodiment, $R^1$ is phenyl, wherein the phenyl is disubstituted with each substituent independently selected from fluoro, chloro, bromo, methoxy, and ethoxy. In another embodiment, $R^1$ is phenyl, wherein the phenyl is monosubstituted with a substituent selected from fluoro, chloro, bromo, methoxy, and ethoxy.

In another embodiment, $R^1$ is phenyl, wherein the phenyl is monosubstituted or disubstituted with halo. In another embodiment, $R^1$ is phenyl, wherein the phenyl is monosubstituted or disubstituted with fluoro. In another embodiment, $R^1$ is phenyl, wherein the phenyl is monosubstituted or disubstituted with chloro. In another embodiment, $R^1$ is phenyl, wherein the phenyl is monosubstituted or disubstituted with bromo. In another embodiment, $R^1$ is phenyl monosubstituted with halo. In another embodiment, $R^1$ is fluorophenyl. In another embodiment, $R^1$ is 4-fluorophenyl. In another embodiment, $R^1$ is 2-fluorophenyl. In another embodiment, $R^1$ is chlorophenyl. In another embodiment, $R^1$ is 4-chlorophenyl. In another embodiment, $R^1$ is 2-chlorophenyl. In another embodiment, $R^1$ is bromophenyl. In another embodiment, $R^1$ is 4-bromophenyl. In another embodiment, $R^1$ is 2-bromophenyl. In another embodiment, $R^1$ is phenyl monosubstituted with $(C_1-C_6)$alkoxy. In another embodiment, $R^1$ is phenyl monosubstituted with $(C_1-C_4)$alkoxy. In another embodiment, $R^1$ is iso-propoxyphenyl. In another embodiment, $R^1$ is ethoxyphenyl. In another embodiment, $R^1$ is methoxyphenyl. In another embodiment, $R^1$ is 4-$(C_1-C_6)$alkoxyphenyl. In another embodiment, $R^1$ is 4-$(C_1-C_4)$alkoxyphenyl. In another embodiment, $R^1$ is 4-iso-propoxyphenyl. In another embodiment, $R^1$ is 4-ethoxyphenyl. In another embodiment, $R^1$ is 4-methoxyphenyl.

In one embodiment, $R^2$ is unsubstituted phenyl. In another embodiment, $R^2$ is phenyl wherein the phenyl is unsubstituted or substituted with 1, 2, or 3 substituent(s) independently selected from halo, $(C_1-C_6)$alkoxy, and $(C_1-C_6)$alkylsulfinyl. In one embodiment, $R^2$ is phenyl wherein the phenyl is unsubstituted or substituted with 1, 2, or 3 substituent(s) independently selected from halo, $(C_1-C_6)$alkoxy, and $(C_1-C_6)$alkylsulfonyl. In one embodiment, $R^2$ is phenyl wherein the phenyl is unsubstituted or substituted with 1, 2, or 3 substituent(s) independently selected from $(C_1-C_6)$alkoxy, $(C_1-C_6)$alkylsulfinyl, and $(C_1-C_6)$alkylsulfonyl. In another embodiment, $R^2$ is phenyl wherein the phenyl is unsubstituted or substituted with 1, 2, or 3 substituent(s) independently selected from halo and $(C_1-C_6)$alkylsulfinyl. In one embodiment, $R^2$ is phenyl wherein the phenyl is unsubstituted or substituted with 1, 2, or 3 substituent(s) independently selected from halo and $(C_1-C_6)$alkylsulfonyl. In one embodiment, $R^2$ is phenyl wherein the phenyl is unsubstituted or substituted with 1, 2, or 3 substituent(s) independently selected from $(C_1-C_6)$alkylsulfinyl and $(C_1-C_6)$alkylsulfonyl. In another embodiment, $R^2$ is phenyl wherein the phenyl is unsubstituted or substituted with 1, 2, or 3 substituent(s) independently selected from fluoro, bromo, methoxy, methylsulfinyl, and methylsulfonyl. In another embodiment, $R^2$ is phenyl wherein the phenyl is unsubstituted or substituted with 1, 2, or 3 substituent(s) independently selected from fluoro, methylsulfinyl, and methylsulfonyl.

In another embodiment, $R^2$ is phenyl wherein the phenyl is unsubstituted or substituted with 1 or 2 substituent(s), each substituent being independently selected from halo, $(C_1-C_6)$alkylsulfinyl, and $(C_1-C_6)$alkylsulfonyl. In another embodiment, $R^2$ is phenyl wherein the phenyl is unsubstituted or substituted with 1 or 2 substituent(s), each substituent being independently selected from $(C_1-C_6)$alkoxy, $(C_1-C_6)$alkylsulfinyl, and $(C_1-C_6)$alkylsulfonyl. In another embodiment, $R^2$ is phenyl wherein the phenyl is unsubstituted or substituted with 1 or 2 substituent(s), each substituent being independently selected from halo, $(C_1-C_6)$alkoxy, and $(C_1-C_6)$alkylsulfonyl. In another embodiment, $R^2$ is phenyl wherein the phenyl is unsubstituted or substituted with 1 or 2 substituent(s), each substituent being independently selected from halo, $(C_1-C_6)$alkylsulfinyl, and $(C_1-C_6)$alkoxy. In another embodiment, $R^2$ is phenyl wherein the phenyl is unsubstituted or substituted with 1 or 2 substituent(s), each substituent being independently selected from fluoro, bromo, methoxy, methylsulfinyl, and methylsulfonyl. In another embodiment, $R^2$ is phenyl wherein the phenyl is unsubstituted or substituted with 1 or 2 substituent(s), each substituent being independently selected from fluoro, methylsulfinyl, and methylsulfonyl.

In another embodiment, $R^2$ is phenyl wherein the phenyl is unsubstituted or monosubstituted with halo, $(C_1-C_6)$alkoxy, $(C_1-C_6)$alkylsulfinyl, or $(C_1-C_6)$alkylsulfonyl. In another embodiment, $R^2$ is phenyl wherein the phenyl is unsubstituted or monosubstituted with $(C_1-C_6)$alkoxy, $(C_1-C_6)$alkylsulfinyl, or $(C_1-C_6)$alkylsulfonyl. In another embodiment, $R^2$ is phenyl wherein the phenyl is unsubstituted or monosubstituted with halo, $(C_1-C_6)$alkoxy, or $(C_1-C_6)$alkylsulfonyl. In another embodiment, $R^2$ is phenyl wherein the phenyl is unsubstituted or monosubstituted with halo, $(C_1-C_6)$alkylsulfinyl, or $(C_1-C_6)$alkylsulfinyl. In another embodiment, $R^2$ is phenyl wherein the phenyl is unsubstituted or monosubstituted with halo, $(C_1-C_6)$alkylsulfinyl, or $(C_1-C_6)$alkylsulfonyl. In another embodiment, $R^2$ is phenyl wherein the phenyl is unsubstituted or monosubstituted with fluoro, bromo, methoxy, methylsulfinyl, or methylsulfonyl. In another embodiment, $R^2$ is phenyl wherein the phenyl is unsubstituted or monosubstituted with chloro, methylsulfinyl, or methylsulfonyl. In another embodiment, $R^2$ is unsubstituted phenyl, chlorophenyl, bromophenyl, methoxyphenyl, methylsulfinylphenyl, or methylsulfonylphenyl. In another embodiment, $R^2$ is unsubstituted phenyl, chlorophenyl, methylsulfinylphenyl, or methylsulfonylphenyl. In another embodiment, $R^2$ is unsubstituted phenyl, 4-chlorophenyl, 4-bromophenyl, 4-methoxyphenyl, 4-methylsulfinylphenyl, or 4-methylsulfonylphenyl. In another embodiment, $R^2$ is unsubstituted phenyl, 4-chlorophenyl, 4-methylsulfinylphenyl, or 4-methylsulfonylphenyl.

In another embodiment, $R^2$ is phenyl monosubstituted with $(C_1-C_6)$alkylsulfonyl. In another embodiment, $R^2$ is iso-propylsulfonylphenyl. In another embodiment, $R^2$ is ethylsulfonylphenyl. In another embodiment, $R^2$ is methylsulfonylphenyl. In another embodiment, $R^2$ is 4-$(C_1-C_6)$alkylsulfonylphenyl. In another embodiment, $R^2$ is 4-iso-propylsulfonylphenyl. In another embodiment, $R^2$ is 4-ethylsulfonylphenyl. In another embodiment, $R^2$ is 4-methylsulfonylphenyl.

In another embodiment, $R^2$ is phenyl monosubstituted with $(C_1-C_6)$alkylsulfinyl. In another embodiment, $R^2$ is iso-propylsulfinylphenyl. In another embodiment, $R^2$ is ethylsulfinylphenyl. In another embodiment, $R^2$ is methylsulfinylphenyl. In another embodiment, $R^2$ is 4-$(C_1-C_6)$alkylsulfinylphenyl. In another embodiment, $R^2$ is 4-iso-propylsulfinylphenyl. In another embodiment, $R^2$ is 4-ethylsulfinylphenyl. In another embodiment, $R^2$ is 4-methylsulfinylphenyl.

In another embodiment, $R^2$ is phenyl monosubstituted with $(C_1-C_6)$alkoxy. In another embodiment, $R^2$ is phenyl monosubstituted with $(C_1-C_4)$alkoxy. In another embodiment, $R^2$ is iso-propoxyphenyl. In another embodiment, $R^2$ is ethoxyphenyl. In another embodiment, $R^2$ is methoxyphenyl. In another embodiment, $R^2$ is 4-$(C_1-C_6)$alkoxyphenyl. In another embodiment, $R^2$ is 4-iso-propoxyphenyl. In another embodiment, $R^2$ is 4-ethoxyphenyl. In another embodiment, $R^2$ is 4-methoxyphenyl.

In another embodiment, $R^2$ is phenyl, wherein the phenyl is unsubstituted or substituted with 1 or 2 substituent(s), each substituent being independently selected from halo and $(C_1-C_6)$alkoxy. In another embodiment, $R^2$ is phenyl, wherein the phenyl is monosubstituted with halo and also monosubstituted with $(C_1-C_6)$alkoxy. In another embodiment, $R^2$ is phenyl, wherein the phenyl is unsubstituted or substituted with 1 or 2 substituent(s), each substituent being independently selected from halo and $(C_1-C_4)$alkoxy. In another embodiment, $R^2$ is phenyl, wherein the phenyl is disubstituted—monosubstituted with halo and also monosubstituted with $(C_1-C_4)$alkoxy. In another embodiment, $R^2$ is phenyl, wherein the phenyl is disubstituted with each substituent independently selected from fluoro, chloro, bromo, methoxy, and ethoxy. In another embodiment, $R^2$ is phenyl, wherein the phenyl is monosubstituted with a substituent selected from fluoro, chloro, bromo, methoxy, and ethoxy.

In another embodiment, $R^2$ is phenyl, wherein the phenyl is unsubstituted or monosubstituted or disubstituted with halo. In another embodiment, $R^2$ is phenyl, wherein the phenyl is unsubstituted or monosubstituted or disubstituted with fluoro. In another embodiment, $R^2$ is phenyl, wherein the phenyl is unsubstituted or monosubstituted or disubstituted with chloro. In another embodiment, $R^2$ is phenyl, wherein the phenyl is unsubstituted or monosubstituted or disubstituted with bromo. In another embodiment, $R^2$ is unsubstituted phenyl. In another embodiment, $R^2$ is phenyl monosubstituted with halo. In another embodiment, $R^2$ is fluorophenyl. In another embodiment, $R^2$ is 4-fluorophenyl. In another embodiment, $R^2$ is 2-fluorophenyl. In another embodiment, $R^2$ is chlorophenyl. In another embodiment, $R^2$ is 4-chlorophenyl. In another embodiment, $R^2$ is 2-chlorophenyl. In another embodiment, $R^2$ is bromophenyl. In another embodiment, $R^2$ is 4-bromophenyl. In another embodiment, $R^2$ is 2-bromophenyl. In another embodiment, $R^2$ is phenyl monosubstituted with $(C_1-C_6)$alkoxy. In another embodiment, $R^2$ is phenyl monosubstituted with $(C_1-C_4)$alkoxy. In another embodiment, $R^2$ is iso-propoxyphenyl. In another embodiment, $R^2$ is ethoxyphenyl. In another embodiment, $R^2$ is methoxyphenyl. In another embodiment, $R^2$ is 4-$(C_1-C_6)$alkoxyphenyl. In another embodiment, $R^2$ is 4-$(C_1-C_4)$alkoxyphenyl. In another embodiment, $R^2$ is 4-iso-propoxyphenyl. In another embodiment, $R^2$ is 4-ethoxyphenyl. In another embodiment, $R^2$ is 4-methoxyphenyl.

In another embodiment, $R^3$ is $(C_1-C_6)$alkyl. In another embodiment, $R^3$ is $—C(=NOR^9)R^{10}$. In another embodiment, $R^3$ is methyl or $—C(=NOR^9)R^{10}$ wherein at least one of $R^9$ and $R^{10}$ is methyl. In another embodiment, $R^3$ is methyl or $—C(=NOR^9)R^{10}$ wherein each of $R^9$ and $R^{10}$ is methyl. In another embodiment, $R^3$ is methyl or $—C(=NOR^9)R^{10}$ wherein one of $R^9$ and $R^{10}$ is methyl and the other is ethyl. In another embodiment, $R^3$ is methyl. In another embodiment, $R^3$ is $—C(=NOR^9)R^{10}$ wherein at least one of $R^9$ and $R^{10}$ is methyl. In another embodiment, $R^3$ is $—C(=NOR^9)R^{10}$ wherein each of $R^9$ and $R^{10}$ is methyl. In another embodiment, $R^3$ is $—C(=NOR^9)R^{10}$ wherein one of $R^9$ and $R^{10}$ is methyl and the other is ethyl.

In another embodiment, $R^1$ is monosubstituted phenyl, e.g., selected from among the monosubstituted $R^1$ phenyl groups disclosed above in connection with the compounds of formula (If), and $R^2$ is unsubstituted phenyl. In another embodiment, $R^1$ and $R^2$ are each monosubstituted phenyl, e.g., each is independently selected from among the monosubstituted $R^1$ phenyl groups and the monosubstituted $R^2$ phenyl groups disclosed above in connection with the compounds of formula (If). In another embodiment, $R^1$ is phenyl monosubstituted with halo and $R^2$ is unsubstituted phenyl. In another embodiment, $R^1$ and $R^2$ are each independently selected from phenyl monosubstituted with halo. In another embodiment, $R^1$ is phenyl monosubstituted with bromo and $R^2$ is unsubstituted phenyl. In another embodiment, $R^1$ and $R^2$ are each phenyl monosubstituted with halo wherein each halo is independently selected from fluoro, chloro, and bromo. In another embodiment, $R^1$ and $R^2$ are each phenyl monosubstituted with halo wherein each halo is independently selected from fluoro and chloro. In another embodiment, $R^1$ and $R^2$ are each phenyl monosubstituted with halo wherein each halo is independently selected from fluoro and bromo. In another embodiment, $R^1$ and $R^2$ are each phenyl monosubstituted with halo wherein each halo is independently selected from chloro and bromo. In another embodiment, $R^1$ and $R^2$ are each phenyl monosubstituted with halo wherein one halo is fluoro and the other halo is chloro. In another embodiment, $R^1$ and $R^2$ are each phenyl monosubstituted with halo wherein one halo is fluoro and the other halo is bromo. In another embodiment, $R^1$ and $R^2$ are each phenyl monosubstituted with halo wherein one halo is chloro and the other halo is bromo.

In another embodiment, $R^1$ is monosubstituted phenyl, e.g., selected from among the monosubstituted $R^1$ phenyl groups disclosed above in connection with the compounds of formula (If), and $R^3$ is methyl. In another embodiment, $R^1$ is monosubstituted phenyl, e.g., selected from among the monosubstituted $R^1$ phenyl groups disclosed above in connection with the compounds of formula (If), and $R^3$ is ethyl.

In another embodiment, $R^1$ is monosubstituted phenyl, e.g., selected from among the monosubstituted $R^1$ phenyl groups disclosed above in connection with the compounds of formula (If), and $R^3$ is iso-propyl. In another embodiment, $R^1$ is monosubstituted phenyl, e.g., selected from among the monosubstituted $R^1$ phenyl groups disclosed above in connection with the compounds of formula (If), and $R^3$ is tert-butyl. In another embodiment, $R^1$ is disubstituted phenyl, e.g., selected from among the disubstituted $R^1$ phenyl groups disclosed above in connection with the compounds of formula (If), and $R^3$ is methyl. In another embodiment, $R^1$ is disubstituted phenyl, e.g., selected from among the disubstituted $R^1$ phenyl groups disclosed above in connection with the compounds of formula (If), and $R^3$ is ethyl. In another embodiment, $R^1$ is disubstituted phenyl, e.g., selected from among the disubstituted $R^1$ phenyl groups disclosed above in connection with the compounds of formula (If), and $R^3$ is iso-propyl. In another embodiment, $R^1$ is disubstituted phenyl, e.g., selected from among the disubstituted $R^1$ phenyl groups disclosed above in connection with the compounds of formula (If), and $R^3$ is tert-butyl. In another embodiment, $R^1$ is monosubstituted phenyl, e.g., selected from among the monosubstituted $R^1$ phenyl groups disclosed above in connection with the compounds of formula (If), and $R^3$ is —C(=NOR$^9$)R$^{10}$ wherein each of $R^9$ and $R^{10}$ is methyl. In another embodiment, $R^1$ is monosubstituted phenyl, e.g., selected from among the monosubstituted $R^1$ phenyl groups disclosed above in connection with the compounds of formula (If), and $R^3$ is —C(=NOR$^9$)R$^{10}$ wherein one of $R^9$ and $R^{10}$ is methyl and the other is ethyl.

In another embodiment, $R^2$ is unsubstituted phenyl and $R^3$ is methyl. In another embodiment, $R^2$ is monosubstituted phenyl, e.g., selected from among the monosubstituted $R^2$ phenyl groups disclosed above in connection with the compounds of formula (If), and $R^3$ is methyl. In another embodiment, $R^2$ is unsubstituted phenyl and $R^3$ is ethyl. In another embodiment, $R^2$ is monosubstituted phenyl, e.g., selected from among the monosubstituted $R^2$ phenyl groups disclosed above in connection with the compounds of formula (If), and $R^3$ is ethyl. In another embodiment, $R^2$ is unsubstituted phenyl and $R^3$ is iso-propyl. In another embodiment, $R^2$ is monosubstituted phenyl, e.g., selected from among the monosubstituted $R^2$ phenyl groups disclosed above in connection with the compounds of formula (If), and $R^3$ is iso-propyl. In another embodiment, $R^2$ is unsubstituted phenyl and $R^3$ is tert-butyl. In another embodiment, $R^2$ is monosubstituted phenyl, e.g., selected from among the monosubstituted $R^2$ phenyl groups disclosed above in connection with the compounds of formula (If), and $R^3$ is tert-butyl. In another embodiment, $R^2$ is disubstituted phenyl, e.g., selected from among the disubstituted $R^2$ phenyl groups disclosed above in connection with the compounds of formula (If), and $R^3$ is methyl. In another embodiment, $R^2$ is disubstituted phenyl, e.g., selected from among the disubstituted $R^2$ phenyl groups disclosed above in connection with the compounds of formula (If), and $R^3$ is ethyl. In another embodiment, $R^2$ is disubstituted phenyl, e.g., selected from among the disubstituted $R^2$ phenyl groups disclosed above in connection with the compounds of formula (If), and $R^3$ is iso-propyl. In another embodiment, $R^2$ is disubstituted phenyl, e.g., selected from among the disubstituted $R^2$ phenyl groups disclosed above in connection with the compounds of formula (If), and $R^3$ is tert-butyl. In another embodiment, $R^2$ is unsubstituted phenyl and $R^3$ is —C(=NOR$^9$)R$^{10}$ wherein each of $R^9$ and $R^{10}$ is methyl. In another embodiment, $R^2$ is unsubstituted phenyl and $R^3$ is —C(=NOR$^9$)R$^{10}$ wherein one of $R^9$ and $R^{10}$ is methyl and the other is ethyl. In another embodiment, $R^2$ is monosubstituted phenyl, e.g., selected from among the monosubstituted $R^2$ phenyl groups disclosed above in connection with the compounds of formula (If), and $R^3$ is —C(=NOR$^9$)R$^{10}$ wherein each of $R^9$ and $R^{10}$ is methyl. In another embodiment, $R^2$ is monosubstituted phenyl, e.g., selected from among the monosubstituted $R^2$ phenyl groups disclosed above in connection with the compounds of formula (If), and $R^3$ is —C(=NOR$^9$)R$^{10}$ wherein one of $R^9$ and $R^{10}$ is methyl and the other is ethyl.

Another aspect of the disclosure provides a compound of formula (Ig)

(Ig)

or a pharmaceutically acceptable salt thereof, wherein:

$R^1$ is H;

$R^2$ is $(C_1-C_6)$alkyl, phenyl or (5- or 6-membered)heteroaryl, wherein said phenyl and said heteroaryl are unsubstituted or substituted with 1, 2, 3, 4, or 5 substituent(s) independently selected from halo, cyano, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O(C$_1$-C$_6$)alkyl, —C(=O)NR$^4$R$^5$, —C(=O)—(C$_5$-C$_7$)heterocycloalkyl, (C$_5$-C$_7$)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$NHOH, —S(O)$_2$—NR$^6$R$^7$, —S(O)$_2$-phenyl, —S(O)$_2$—(C$_5$-C$_7$)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl, wherein said (C$_5$-C$_7$)heterocycloalkyl is unsubstituted or substituted with 1 or 2 substituent(s) independently selected from halo or (C$_1$-C$_6$)alkyl;

$R^4$ and $R^6$ are independently H or (C$_1$-C$_6$)alkyl;

$R^5$ is H, (C$_1$-C$_6$)alkyl or (C$_1$-C$_6$)alkylsulfonyl, wherein said alkyl is unsubstituted or substituted with C(=O)OH or wherein a methylene group of said alkyl is optionally replaced with an oxygen atom;

$R^7$ is H or (C$_1$-C$_6$)alkyl, wherein a methylene group of said alkyl is optionally replaced with an oxygen atom;

$R^8$ is H, —(C=O)(C$_1$-C$_6$)alkyl or —(C=O)(C$_1$-C$_4$)perhaloalkyl;

$R^3$ is (5- or 6-membered)heteroaryl, (C$_6$-C$_{10}$)aryl, phenyl or —C(=NOR$^9$)R$^{10}$, wherein R$^9$ is (C$_1$-C$_6$)alkyl, phenyl or (C$_1$-C$_6$)alkyl substituted with phenyl and R$^{10}$ is (C$_1$-C$_6$)alkyl, wherein said heteroaryl, aryl and phenyl are unsubstituted or substituted with 1, 2, 3, 4, or 5 substituent(s) independently selected from halo, cyano, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)—(C$_5$-C$_7$)heterocycloalkyl, (C$_5$-C$_7$)heterocycloalkyl, (C$_6$-C$_{10}$)aryl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)

perhaloalkylsulfinyl, $(C_1-C_4)$perhaloalkylsulfonyl, $-S(O)_2-NH_2$, $-S(O)_2NHOH$, $-S(O)_2-NR^6R^7$, $-S(O)_2$-phenyl, $-S(O)_2-(C_5-C_7)$heterocycloalkyl, $-S(=O)(=NR^8)(C_1-C_6)$alkyl, $-NR^4R^5$, $N-(C_1-C_6)$alkylaminosulfonyl, and N,N-di$(C_1-C_6)$alkylaminosulfonyl, wherein said $(C_5-C_7)$heterocycloalkyl is unsubstituted or substituted with 1 or 2 substituent(s) independently selected from halo or $(C_1-C_6)$alkyl; or $R^2$ and $R^3$ are taken together with the carbon atoms to which they are attached to form a $(C_3-C_6)$cycloalkyl.

In one embodiment, $R^2$ is methyl, ethyl, iso-propyl, or tert-butyl. In another embodiment, $R^2$ is methyl, ethyl, or iso-propyl. In another embodiment, $R^2$ is methyl, ethyl, or tert-butyl. In another embodiment, $R^2$ is methyl, iso-propyl, or tert-butyl. In another embodiment, $R^2$ is ethyl, iso-propyl, or tert-butyl. In another embodiment, $R^2$ is methyl or ethyl. In another embodiment, $R^2$ is methyl or iso-propyl. In another embodiment, $R^2$ is methyl or tert-butyl. In another embodiment, $R^2$ is ethyl or iso-propyl. In another embodiment, $R^2$ is ethyl or tert-butyl. In another embodiment, $R^2$ is iso-propyl or tert-butyl. In another embodiment, $R^2$ is methyl. In another embodiment, $R^2$ is ethyl. In another embodiment, $R^2$ is iso-propyl. In another embodiment, $R^2$ is tert-butyl.

In another embodiment, $R^2$ is phenyl substituted with 1, 2, or 3 independently selected substituent(s), at least one of which is halo. In another embodiment, $R^2$ is phenyl substituted with 1, 2, or 3 independently selected substituent(s), at least one of which is chloro. In another embodiment, $R^2$ is phenyl substituted with 1, 2, or 3 independently selected substituent(s), at least one of which is fluoro. In another embodiment, $R^2$ is phenyl substituted with 1, 2, or 3 independently selected substituent(s), at least one of which is $(C_1-C_6)$alkyl. In another embodiment, $R^2$ is phenyl substituted with 1, 2, or 3 independently selected substituent(s), at least one of which is methyl. In another embodiment, $R^2$ is phenyl substituted with 1, 2, or 3 independently selected substituent(s), at least one of which is $(C_1-C_4)$haloalkyl. In another embodiment, $R^2$ is phenyl substituted with 1, 2, or 3 independently selected substituent(s), at least one of which is $(C_1-C_4)$perhaloalkyl. In another embodiment, $R^2$ is phenyl substituted with 1, 2, or 3 independently selected substituent(s), at least one of which is perfluoromethyl. In another embodiment, $R^2$ is phenyl substituted with 1, 2, or 3 independently selected substituent(s), at least one of which is $(C_1-C_6)$alkoxy. In another embodiment, $R^2$ is phenyl substituted with 1, 2, or 3 independently selected substituent(s), at least one of which is methoxy. In another embodiment, $R^2$ is phenyl substituted with 1, 2, or 3 independently selected substituent(s), at least one of which is $(C_1-C_4)$perhaloalkoxy. In another embodiment, $R^2$ is phenyl substituted with 1, 2, or 3 independently selected substituent(s), at least one of which is $(C_1-C_4)$perfluoroalkoxy.

In another embodiment, $R^2$ is phenyl substituted with 1, 2, or 3 independently selected substituent(s), at least one of which is $-C(=O)OH$. In another embodiment, $R^2$ is phenyl substituted with 1, 2, or 3 independently selected substituent(s), at least one of which is $-C(=O)O(C_1-C_6)$alkyl. In another embodiment, $R^2$ is phenyl substituted with 1, 2, or 3 independently selected substituent(s), at least one of which is $-C(=O)OCH_3$. In another embodiment, $R^2$ is phenyl substituted with 1, 2, or 3 independently selected substituent(s), at least one of which is $-C(=O)NR^4R^5$. In another embodiment, $R^2$ is phenyl substituted with 1, 2, or 3 independently selected substituent(s), at least one of which is $-C(=O)N(CH_3)_2$. In another embodiment, $R^2$ is phenyl substituted with 1, 2, or 3 independently selected substituent(s), at least one of which is $-C(=O)NH_2$. In another embodiment, $R^2$ is phenyl substituted with 1, 2, or 3 independently selected substituent(s), at least one of which is $-C(=O)NH(C_1-C_6)$alkyl, wherein said alkyl is substituted with COOH. In another embodiment, $R^2$ is phenyl substituted with 1, 2, or 3 independently selected substituent(s), at least one of which is $-C(=O)NH-(C_1-C_6)$alkylsulfonyl.

In another embodiment, $R^2$ is phenyl substituted with 1, 2, or 3 independently selected substituent(s), at least one of which is $-C(=O)-(C_5-C_7)$heterocycloalkyl. In another embodiment, $R^2$ is phenyl substituted with 1, 2, or 3 independently selected substituent(s), at least one of which is $-C(=O)$-morpholinyl, $-C(=O)$-piperidinyl or $-C(=O)$-piperazinyl. In another embodiment, $R^2$ is phenyl substituted with 1, 2, or 3 independently selected substituent(s), at least one of which is $-C(=O)$-morpholinyl. In another embodiment, $R^2$ is phenyl substituted with 1, 2, or 3 independently selected substituent(s), at least one of which is $-C(=O)$-piperidinyl. In another embodiment, $R^2$ is phenyl substituted with 1, 2, or 3 independently selected substituent(s), at least one of which is $-C(=O)$-piperazinyl.

In another embodiment, $R^2$ is phenyl substituted with 1, 2, or 3 independently selected substituent(s), at least one of which is $(C_5-C_7)$heterocycloalkyl. In another embodiment, $R^2$ is phenyl substituted with 1, 2, or 3 independently selected substituent(s), at least one of which is morpholinyl, piperidinyl or piperazinyl. In another embodiment, $R^2$ is phenyl substituted with 1, 2, or 3 independently selected substituent(s), at least one of which is morpholinyl. In another embodiment, $R^2$ is phenyl substituted with 1, 2, or 3 independently selected substituent(s), at least one of which is piperidinyl. In another embodiment, $R^2$ is phenyl substituted with 1, 2, or 3 independently selected substituent(s), at least one of which is piperazinyl.

In another embodiment, $R^2$ is phenyl substituted with 1, 2, or 3 independently selected substituent(s), at least one of which is $(C_1-C_6)$alkylsulfanyl. In another embodiment, $R^2$ is phenyl substituted with 1, 2, or 3 independently selected substituent(s), at least one of which is methylsulfanyl. In another embodiment, $R^2$ is phenyl substituted with 1, 2, or 3 independently selected substituent(s), at least one of which is $(C_1-C_4)$perhaloalkylsulfanyl. In another embodiment, $R^2$ is phenyl substituted with 1, 2, or 3 independently selected substituent(s), at least one of which is trifluoromethylsulfanyl. In another embodiment, $R^2$ is phenyl substituted with 1, 2, or 3 independently selected substituent(s), at least one of which is $(C_1-C_6)$alkylsulfinyl. In another embodiment, $R^2$ is phenyl substituted with 1, 2, or 3 independently selected substituent(s), at least one of which is methylsulfinyl. In another embodiment, $R^2$ is phenyl substituted with 1, 2, or 3 independently selected substituent(s), at least one of which is $(C_1-C_6)$alkylsulfonyl. In another embodiment, $R^2$ is phenyl substituted with 1, 2, or 3 independently selected substituent(s), at least one of which is methylsulfonyl. In another embodiment, $R^2$ is phenyl substituted with 1, 2, or 3 independently selected substituent(s), at least one of which is $(C_3-C_6)$cycloalkylsulfonyl. In another embodiment, $R^2$ is phenyl substituted with 1, 2, or 3 independently selected substituent(s), at least one of which is cyclopropylsulfonyl.

In another embodiment, $R^2$ is phenyl substituted with 1, 2, or 3 independently selected substituent(s), at least one of which is $(C_1-C_4)$haloalkylsulfinyl. In another embodiment, $R^2$ is phenyl substituted with 1, 2, or 3 independently selected substituent(s), at least one of which is $(C_1-C_4)$ haloalkylsulfonyl. In another embodiment, $R^2$ is phenyl substituted with 1, 2, or 3 independently selected substituent(s), at least one of which is ($C_1$-$C_4$)perhaloalkylsulfinyl. In another embodiment, $R^2$ is phenyl substituted with 1, 2, or 3 independently selected substituent(s), at least one of which is perhalomethylsulfinyl. In another embodiment, $R^2$ is phenyl substituted with 1, 2, or 3 independently selected substituent(s), at least one of which is perfluoromethylsulfinyl. In another embodiment, $R^2$ is phenyl substituted with 1, 2, or 3 independently selected substituent(s), at least one of which is ($C_1$-$C_4$)perhaloalkylsulfonyl. In another embodiment, $R^2$ is phenyl substituted with 1, 2, or 3 independently selected substituent(s), at least one of which is perhalomethylsulfonyl. In another embodiment, $R^2$ is phenyl substituted with 1, 2, or 3 independently selected substituent(s), at least one of which is perfluoromethylsulfonyl.

In another embodiment, $R^2$ is phenyl substituted with 1, 2, or 3 independently selected substituent(s), at least one of which is —S(O)$_2$—NR$^6$R$^7$. In another embodiment, $R^2$ is phenyl substituted with 1, 2, or 3 independently selected substituent(s), at least one of which is —S(O)$_2$—N(CH$_3$)(CH$_2$CH$_2$OCH$_3$), —S(O)$_2$—NH(CH$_2$CH$_2$OCH$_3$), —S(O)$_2$—N(CH$_3$)$_2$ or —S(O)$_2$—NH(CH$_3$).

In another embodiment, $R^2$ is phenyl substituted with 1, 2, or 3 independently selected substituent(s), at least one of which is —S(O)$_2$-phenyl. In another embodiment, $R^2$ is phenyl substituted with 1, 2, or 3 independently selected substituent(s), at least one of which is —S(O)$_2$—($C_5$-$C_7$)heterocycloalkyl. In another embodiment, $R^2$ is phenyl substituted with 1, 2, or 3 independently selected substituent(s), at least one of which is —S(O)$_2$-morpholinyl, —S(O)$_2$-piperidinyl or —S(O)$_2$-piperazinyl. In another embodiment, $R^2$ is phenyl substituted with 1, 2, or 3 independently selected substituent(s), at least one of which is —S(O)$_2$-morpholinyl. In another embodiment, $R^2$ is phenyl substituted with 1, 2, or 3 independently selected substituent(s), at least one of which is —S(O)$_2$-piperidinyl. In another embodiment, $R^2$ is phenyl substituted with 1, 2, or 3 independently selected substituent(s), at least one of which is —S(O)$_2$-piperazinyl.

In another embodiment, $R^2$ is phenyl substituted with 1, 2, or 3 independently selected substituent(s), at least one of which is —S(=O)(=NR$^8$)($C_1$-$C_6$)alkyl. In another embodiment, $R^2$ is phenyl substituted with 1, 2, or 3 independently selected substituent(s), at least one of which is —S(=O)(=NR$^8$)(CH$_3$). In another embodiment, $R^2$ is phenyl substituted with 1, 2, or 3 independently selected substituent(s), at least one of which is —S(=O)(=NH)($C_1$-$C_6$)alkyl or —S(=O)(=NC(=O)CF$_3$)($C_1$-$C_6$)alkyl. In another embodiment, $R^2$ is phenyl substituted with 1, 2, or 3 independently selected substituent(s), at least one of which is —S(=O)(=NH)(CH$_3$) or —S(=O)(=NC(=O)CF$_3$)(CH$_3$).

In another embodiment, $R^2$ is phenyl substituted with 1, 2, or 3 independently selected substituent(s), at least one of which is N,N-di($C_1$-$C_6$)alkylaminosulfonyl. In another embodiment, $R^2$ is phenyl substituted with 1, 2, or 3 independently selected substituent(s), at least one of which is N,N-dimethylaminosulfonyl.

In another embodiment, $R^2$ is phenyl wherein the phenyl is unsubstituted or substituted with 1, 2, or 3 substituent(s) independently selected from halo, ($C_1$-$C_6$)alkyl, ($C_1$-$C_4$)perhaloalkyl, ($C_1$-$C_6$)alkoxy, ($C_1$-$C_4$)haloalkoxy, ($C_1$-$C_4$)perhaloalkoxy, —C(=O)OH, —C(=O)O($C_1$-$C_6$)alkyl, —C(=O)NR$^4$R$^5$, —C(=O)—($C_5$-$C_7$)heterocycloalkyl, ($C_5$-$C_7$)heterocycloalkyl, ($C_1$-$C_6$)alkylsulfanyl, ($C_1$-$C_4$)perhaloalkylsulfanyl, ($C_1$-$C_6$)alkylsulfinyl, ($C_1$-$C_6$)alkylsulfonyl, ($C_1$-$C_4$)haloalkylsulfinyl, ($C_1$-$C_4$)haloalkylsulfonyl, ($C_1$-$C_4$)perhaloalkylsulfinyl, ($C_1$-$C_4$)perhaloalkylsulfonyl, —S(O)$_2$—NH$_2$, —S(O)$_2$—NR$^6$R$^7$, —S(O)$_2$-phenyl, —S(O)$_2$—($C_5$-$C_7$)heterocycloalkyl, —S(=O)(=NR$^8$)($C_1$-$C_6$)alkyl, —NR$^4$R$^5$, N—($C_1$-$C_6$)alkylaminosulfonyl, and N,N-di($C_1$-$C_6$)alkylaminosulfonyl. In another embodiment, $R^2$ is phenyl wherein the phenyl is unsubstituted or substituted with 1, 2, or 3 substituent(s) independently selected from halo, ($C_1$-$C_6$)alkyl, ($C_1$-$C_4$)perhaloalkyl, ($C_1$-$C_6$)alkoxy, ($C_1$-$C_4$)haloalkoxy, ($C_1$-$C_4$)perhaloalkoxy, —C(=O)OH, —C(=O)O($C_1$-$C_6$)alkyl, —C(=O)NR$^4$R$^5$, —C(=O)—($C_5$-$C_7$)heterocycloalkyl, ($C_5$-$C_7$)heterocycloalkyl, ($C_1$-$C_6$)alkylsulfanyl, ($C_1$-$C_4$)perhaloalkylsulfanyl, ($C_1$-$C_6$)alkylsulfinyl, ($C_1$-$C_6$)alkylsulfonyl, ($C_1$-$C_4$)haloalkylsulfinyl, ($C_1$-$C_4$)haloalkylsulfonyl, ($C_1$-$C_4$)perhaloalkylsulfinyl, ($C_1$-$C_4$)perhaloalkylsulfonyl, —S(O)$_2$—NR$^6$R$^7$, —S(O)$_2$-phenyl, —S(O)$_2$—($C_5$-$C_7$)heterocycloalkyl, —S(=O)(=NR$^8$)($C_1$-$C_6$)alkyl, —NR$^4$R$^5$, and N,N-di($C_1$-$C_6$)alkylaminosulfonyl. In another embodiment, $R^2$ is phenyl wherein the phenyl is unsubstituted or substituted with 1, 2, or 3 substituent(s) independently selected from chloro, fluoro, bromo, trifluoromethyl, methyl, butyl, methylsulfanyl, methylsulfinyl, methylsulfonyl, ethylsulfonyl, propylsulfonyl, phenylsulfonyl, methylsulfonylcarbamyl, methoxy, carboxyl, methylsulfonylcarbamyl, formamidopropanoic acid, formamidoacetic acid, methoxycarbonyl, morpholinylcarbonyl, 4,4-difluoropiperidinylcarbonyl, trifluoromethoxy, trifluoromethylsulfinyl, trifluoromethylsulfonyl, trifluoromethylsulfanyl, morpholinylsulfonyl, 4,4-difluoropiperidinylsulfonyl, N,N-dimethylcarbamyl, (methyl)oxo-λ$^6$-sulfanylidene-2,2,2-trifluoroacetamide, methylsulfonimidoyl, isopropylsulfonimidoyl, (methoxyethyl)methylamino, (methoxyethyl)-N-methylaminosulfonyl, dimethylcarbamyl, carbamyl, and N,N-dimethylaminosulfonyl. In another embodiment, $R^2$ is phenyl wherein the phenyl is unsubstituted or substituted with 1, 2, or 3 substituent(s) independently selected from 2-chloro, 3-chloro, 4-chloro, 5-chloro, 2-fluoro, 3-fluoro, 4-fluoro, 5-fluoro, 2-bromo, 3-bromo, 4-bromo, 5-bromo, 2-trifluoromethyl, 3-trifluoromethyl, 4-trifluoromethyl, 2-methyl, 3-methyl, 4-methyl, 5-methyl, 2-butyl, 3-butyl, 4-butyl, 5-butyl, 4-methylsulfanyl, 2-methylsulfinyl, 4-methylsulfinyl, 3-methylsulfonyl, 4-methylsulfonyl, 4-ethylsulfonyl, 4-propylsulfonyl, 2-methoxy, 4-methoxy, 2-trifluoromethoxy, 4-trifluoromethoxy, 4-carboxyl, 4-methylsulfonylcarbamyl, 4-formamidopropanoic acid, 4-formamidoacetic acid, 4-methoxycarbonyl, 4-morpholinylcarbonyl, 4-(4,4-difluoropiperidinylcarbonyl), 4-isopropylsulfonyl, 4-trifluoromethylsulfanyl, 4-trifluoromethylsulfinyl, 4-trifluoromethylsulfonyl, 4-phenylsulfonyl, 4-morpholinylsulfonyl, 4-(4,4-difluoropiperidinyl)sulfonyl, 4-dimethylcarbamyl, 4-(methyl)oxo-λ$^6$-sulfanylidene-2,2,2-trifluoroacetamide, 4-methylsulfonimidoyl, 4-isopropylsulfonimidoyl, 4-(methoxyethyl)-N-methylaminosulfonyl, 4-carbamyl, and 4-N,N-dimethylaminosulfonyl.

In another embodiment, $R^2$ is monosubstituted phenyl substituted with halo, ($C_1$-$C_6$)alkyl, ($C_1$-$C_4$)perhaloalkyl, ($C_1$-$C_6$)alkoxy, ($C_1$-$C_4$)haloalkoxy, ($C_1$-$C_4$)perhaloalkoxy, —C(=O)OH, —C(=O)O($C_1$-$C_6$)alkyl, —C(=O)NR$^4$R$^5$, —C(=O)—($C_5$-$C_7$)heterocycloalkyl, ($C_1$-$C_6$)alkylsulfanyl, ($C_1$-$C_4$)perhaloalkylsulfanyl, ($C_1$-$C_6$)alkylsulfinyl, ($C_1$-$C_6$)alkylsulfonyl, ($C_1$-$C_4$)haloalkylsulfinyl, ($C_1$-$C_4$)haloalkylsulfonyl, ($C_1$-$C_4$)perhaloalkylsulfinyl, ($C_1$-$C_4$)perhaloalkylsulfonyl, —S(O)$_2$—NH$_2$, —S(O)$_2$—NR$^6$R$^7$, —S(O)$_2$-phenyl, —S(O)$_2$—($C_5$-$C_7$)heterocycloalkyl, —S(=O)

(=NR$^8$)(C$_1$-C$_6$)alkyl, N—(C$_1$-C$_6$)alkylaminosulfonyl, or N,N-di(C$_1$-C$_6$)alkylaminosulfonyl. In another embodiment, R$^2$ is monosubstituted phenyl substituted with halo, (C$_1$-C$_6$) alkyl, (C$_1$-C$_4$)haloalkyl, (C$_1$-C$_4$)perhaloalkyl, (C$_1$-C$_6$) alkoxy, (C$_1$-C$_4$)perhaloalkoxy, —C(=O)OH, —C(=O)O (C$_1$-C$_6$)alkyl, —C(=O)NR$^4$R$^5$, —C(=O)—(C$_5$-C$_7$) heterocycloalkyl, (C$_5$-C$_7$)heterocycloalkyl, (C$_1$-C$_6$) alkylsulfanyl, (C$_1$-C$_4$)perhaloalkylsulfanyl, (C$_1$-C$_6$) alkylsulfinyl, (C$_1$-C$_6$)alkylsulfonyl, (C$_1$-C$_4$) haloalkylsulfinyl, (C$_1$-C$_4$)haloalkylsulfonyl, (C$_1$-C$_4$) perhaloalkylsulfinyl, (C$_1$-C$_4$)perhaloalkylsulfonyl, —S(O)$_2$—NR$^6$R$^7$, —S(O)$_2$-phenyl, —S(O)$_2$—(C$_5$-C$_7$)heterocycloalkyl, —S(=O)(=NR$^8$)(C$_1$-C$_6$)alkyl, —NR$^4$R$^5$, or N,N-di(C$_1$-C$_6$)alkylaminosulfonyl. In another embodiment, R$^2$ is monosubstituted phenyl substituted with chloro, fluoro, bromo, methyl, butyl, trifluoromethyl, methoxy, trifluoromethoxy, morpholinyl, piperazinyl, methylpiperazinyl, carboxyl, methylsulfonylcarbamyl, formamidopropanoic acid, formamidoacetic acid, methoxycarbonyl, morpholinylcarbonyl, 4,4-difluoropiperidinylcarbonyl, methylsulfanyl, methylsulfinyl, methylsulfonyl, ethylsulfonyl, propylsulfonyl, trifluoromethylsulfanyl, trifluoromethylsulfinyl, trifluoromethylsulfonyl, phenylsulfonyl, morpholinylsulfonyl, 4,4-difluoropiperidinylsulfonyl, dimethylcarbamyl, (methyl)oxo-λ$^6$-sulfanylidene-2,2,2-trifluoroacetamide, methylsulfonimidoyl, isopropylsulfonimidoyl, (methoxyethyl)-N-methyl-aminosulfonyl, carbamyl, methoxyethyl (methyl)amino and dimethylamino or N,N-dimethylaminosulfonyl. In another embodiment, R$^2$ is monosubstituted phenyl substituted with 2-chloro, 3-chloro, 4-chloro, 5-chloro, 2-fluoro, 3-fluoro, 4-fluoro, 5-fluoro, 4-bromo, 2-methyl, 3-methyl, 4-methyl, 5-methyl, 4-butyl, 4-t-butyl, 2-trifluoromethyl, 3-trifluoromethyl, 4-trifluoromethyl, 5-trifluoromethyl, 2-methoxy, 3-methoxy, 4-methoxy, 2-trifluoromethoxy, 4-trifluoromethoxy, 3-morpholin-4-yl, 3-(piperazin-1-yl), 3-(4-methylpiperazin-1-yl), 4-carboxyl, 4-methylsulfonylcarbamyl, 4-formamidopropanoic acid, 4-formamidoacetic acid, 4-methoxycarbonyl, 4-morpholinylcarbonyl, 4-(4,4-difluoropiperidinylcarbonyl), 4-methylsulfanyl, 2-methylsulfinyl, 4-methylsulfinyl, 3-methylsulfonyl, 4-methylsulfonyl, 4-ethylsulfonyl, 4-propylsulfonyl, 4-isopropylsulfonyl, 4-trifluoromethylsulfanyl, 4-trifluoromethylsulfinyl, 4-trifluoromethylsulfonyl, 4-phenylsulfonyl, 4-morpholinylsulfonyl, 4-(4,4-difluoropiperidinyl)sulfonyl, 4-dimethylcarbamyl, 4-(methyl)oxo-λ$^6$-sulfanylidene-2,2,2-trifluoroacetamide, 4-methylsulfonimidoyl, 4-isopropylsulfonimidoyl, 4-(methoxyethyl)-N-methyl-aminosulfonyl, 4-carbamyl, 4-methoxyethyl(methyl)amino, 3-dimethylamino or 4-N,N-dimethylaminosulfonyl.

In another embodiment, R$^2$ is disubstituted phenyl, each substituent being independently selected from halo, (C$_1$-C$_6$) alkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O (C$_1$-C$_6$)alkyl, —C(=O)NR$^4$R$^5$, —C(=O)—(C$_5$-C$_7$) heterocycloalkyl, (C$_5$-C$_7$)heterocycloalkyl, (C$_1$-C$_6$) alkylsulfanyl, (C$_1$-C$_4$)perhaloalkylsulfanyl, (C$_1$-C$_6$) alkylsulfinyl, (C$_1$-C$_6$)alkylsulfonyl, (C$_1$-C$_4$) haloalkylsulfinyl, (C$_1$-C$_4$)haloalkylsulfonyl, (C$_1$-C$_4$) perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$—(C$_5$-C$_7$)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl. In another embodiment, R$^2$ is disubstituted phenyl, each substituent being independently selected from halo, (C$_1$-C$_6$)alkyl, (C$_1$-C$_4$)perhaloalkyl, (C$_1$-C$_6$)alkoxy, (C$_5$-C$_7$)heterocycloalkyl, (C$_1$-C$_6$) alkylsulfinyl, (C$_1$-C$_6$)alkylsulfonyl and —NR$^4$R$^5$. In another embodiment, R$^2$ is disubstituted phenyl, each substituent being independently selected from chloro, fluoro, methyl, trifluoromethyl, methoxy, morpholinyl, piperazinyl, methylpiperazinyl, methylsulfinyl, methylsulfonyl, methoxyethyl (methyl)amino and dimethylamino. In another embodiment, R$^2$ is disubstituted phenyl, each substituent being independently selected from 2-chloro, 3-chloro, 4-chloro, 5-chloro, 3-fluoro, 4-fluoro, 5-fluoro, 3-methyl, 5-methyl, 3-trifluoromethyl, 5-trifluoromethyl, 2-methoxy, 3-methoxy, 4-methoxy, 3-morpholin-4-yl, 3-(piperazin-1-yl), 3-(4-methylpiperazin-1-yl), 4-methylsulfinyl, 3-methylsulfonyl, 4-methylsulfonyl, 4-methoxyethyl(methyl)amino and 3-dimethylamino.

In another embodiment, R$^2$ is trisubstituted phenyl, each substituent being independently selected from halo, (C$_1$-C$_6$) alkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O (C$_1$-C$_6$)alkyl, —C(=O)NR$^4$R$^5$, —C(=O)—(C$_5$-C$_7$) heterocycloalkyl, (C$_5$-C$_7$)heterocycloalkyl, (C$_1$-C$_6$) alkylsulfanyl, (C$_1$-C$_4$)perhaloalkylsulfanyl, (C$_1$-C$_6$) alkylsulfinyl, (C$_1$-C$_6$)alkylsulfonyl, (C$_1$-C$_4$) haloalkylsulfinyl, (C$_1$-C$_4$)haloalkylsulfonyl, (C$_1$-C$_4$) perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$—(C$_5$-C$_7$)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl. In another embodiment, R$^2$ is trisubstituted phenyl, each substituent being independently selected from halo, (C$_1$-C$_6$)alkyl, and (C$_1$-C$_6$)alkylsulfonyl. In another embodiment, R$^2$ is trisubstituted phenyl, each substituent being independently selected from fluoro, methyl and methylsulfonyl.

In another embodiment, R$^2$ is selected from unsubstituted phenyl, 4-chlorophenyl, 2-chlorophenyl, 3-chlorophenyl, 2,3-dichlorophenyl, 2,4-dichlorophenyl, 3,5-dichlorophenyl, 2-fluorophenyl, 4-fluorophenyl, 4-bromophenyl, 2-chloro-4-fluorophenyl, 2-methylphenyl, 4-butylphenyl, 4-t-butylphenyl, 3,5-dimethylphenyl, 4-methoxyphenyl, 2-methoxyphenyl, 2-trifluoromethoxyphenyl, 4-trifluoromethoxyphenyl, 4-methoxycarbonylphenyl, 4-carboxylphenyl, 4-carbamylphenyl, 4-phenyl(formamido)propanoic acid, 4-phenyl(formamido)acetic acid, 4-N,N-dimethylcarbamylphenyl, 4-cyclopropylsulfonylphenyl, 4-phenylsulfonyl, 4-(4-4-difluoropiperidin-1-yl)sulfonylphenyl, 4-(isopropylsulfonimidoyl)phenyl, 4-morpholine-4-sulfonylphenyl, 4-morpholine-4-carbonylphenyl, 4-(4,4-difluoropiperidine-1-carbonyl)phenyl, 3-morpholinyl-4-methylsulfonylphenyl, 3-(methoxyethyl)methylamino-4-methylsulfonylphenyl, 3,5-difluoro-4-methylsulfonylphenyl, 2-ethoxy-4-fluorophenyl, 3-fluoro-4-methoxyphenyl, 2-trifluoromethylphenyl, 3-trifluoromethylphenyl, 4-trifluoromethylphenyl, 3,5-bis (trifluoromethyl)phenyl, 3-methylsulfonylphenyl, 4-methylsulfanylphenyl, 4-trifluoromethylsulfanylphenyl, 2-methylsulfinylphenyl, 4-methylsulfinylphenyl, 3-fluoro-4-methylsulfinylphenyl, 3-methyl-4-methylsulfinylphenyl, 4-methylsulfonylphenyl, 4-ethylsulfonylphenyl, 4-isopropylsulfonylphenyl, 4-morpholine-4-methylsulfonylphenyl, 3-(4-methylpiperazin-1-yl)-4-methylsulfonylphenyl, 3-piperazin-1-yl-4-methylsulfonylphenyl, 3-methoxy-4-methylsulfonylphenyl, 3-trifluoromethyl-4-methylsulfonylphenyl, 3-fluoro-4-methylsulfonylphenyl, 3-chloro-4-methylsulfonylphenyl, 3-methyl-4-methylsulfonylphenyl, 3,4-dimethylsulfonylphenyl, 3,5-dimethyl-4-methylsulfonylphenyl, 3-(dimethylamino)-4-methylsulfonylphenyl, 4-trifluoromethylsulfinylphenyl, 4-trifluoromethylsulfonylphenyl, 4-phenyl(methyl)oxo-$\lambda^6$-sulfanylidene-2,2,2-trifluoroacetamide, 4-methylsulfonimidoylphenyl, 4-isopropylsulfonimidoylphenyl, and 4-N,N-dimethylaminosulfonylphenyl. In another embodiment, $R^2$ is unsubstituted phenyl. In another embodiment, $R^2$ is 4-chlorophenyl. In another embodiment, $R^2$ is 2-chlorophenyl. In another embodiment, $R^2$ is 3-chlorophenyl. In another embodiment, $R^2$ is 2,3-dichlorophenyl. In another embodiment, $R^2$ is 2,4-dichlorophenyl. In another embodiment, $R^2$ is 3,5-dichlorophenyl. In another embodiment, $R^2$ is 2-fluorophenyl. In another embodiment, $R^2$ is 4-fluorophenyl. In another embodiment, $R^2$ is 4-bromophenyl. In another embodiment, $R^2$ is 2-chloro-4-fluorophenyl. In another embodiment, $R^2$ is 2-methylphenyl. In another embodiment, $R^2$ is 4-butylphenyl. In another embodiment, $R^2$ is 4-t-butylphenyl. In another embodiment, $R^2$ is 3,5-dimethylphenyl. In another embodiment, $R^2$ is 4-methoxyphenyl. In another embodiment, $R^2$ is 2-methoxyphenyl. In another embodiment, $R^2$ is 2-trifluoromethoxyphenyl. In another embodiment, $R^2$ is 4-trifluoromethoxyphenyl. In another embodiment, $R^2$ is 4-methoxycarbonylphenyl. In another embodiment, $R^2$ is 4-carboxyphenyl. In another embodiment, $R^2$ is 4-carbamylphenyl. In another embodiment, $R^2$ is 4-phenyl(formamido)propanoic acid. In another embodiment, $R^2$ is 4-phenyl(formamido)acetic acid. In another embodiment, $R^2$ is 4-N,N-dimethylcarbamylphenyl. In another embodiment, $R^2$ is 4-cyclopropylsulfonylphenyl. In another embodiment, $R^2$ is 4-phenylsulfonyl. In another embodiment, $R^2$ is 4-(4,4-difluoropiperidin-1-yl)sulfonylphenyl. In another embodiment, $R^2$ is 4-(isopropylsulfonimidoyl)phenyl. In another embodiment, $R^2$ is 4-morpholine-4-sulfonylphenyl. In another embodiment, $R^2$ is 4-morpholine-4-carbonylphenyl. In another embodiment, $R^2$ is 4-(4,4-difluoropiperidine-1-carbonyl)phenyl. In another embodiment, $R^2$ is 3-morpholinyl-4-methylsulfonylphenyl. In another embodiment, $R^2$ is 3-(methoxyethyl)methylamino-4-methylsulfonylphenyl. In another embodiment, $R^2$ is 3,5-difluoro-4-methylsulfonylphenyl. In another embodiment, $R^2$ is 3,5-difluoro-4-methylsulfonylphenyl. In another embodiment, $R^2$ is 2-ethoxy-4-fluorophenyl. In another embodiment, $R^2$ is 3-fluoro-4-methoxyphenyl. In another embodiment, $R^2$ is 2-trifluoromethylphenyl. In another embodiment, $R^2$ is 3-trifluoromethylphenyl. In another embodiment, $R^2$ is 4-trifluoromethylphenyl. In another embodiment, $R^2$ is 3,5-bis(trifluoromethyl)phenyl. In another embodiment, $R^2$ is 3-methylsulfonylphenyl. In another embodiment, $R^2$ is 4-methylsulfanylphenyl. In another embodiment, $R^2$ is 4-trifluoromethylsulfanylphenyl. In another embodiment, $R^2$ is 2-methylsulfinylphenyl. In another embodiment, $R^2$ is 4-methylsulfinylphenyl. In another embodiment, $R^2$ is 3-fluoro-4-methylsulfinylphenyl. In another embodiment, $R^2$ is 3-methyl,4-methylsulfinylphenyl. In another embodiment, $R^2$ is 4-methylsulfonylphenyl. In another embodiment, $R^2$ is 4-ethylsulfonylphenyl. In another embodiment, $R^2$ is 4-isopropylsulfonylphenyl. In another embodiment, $R^2$ is 4-morpholine-4-methylsulfonylphenyl. In another embodiment, $R^2$ is 3-(4-methylpiperazin-1-yl)-4-methylsulfonylphenyl. In another embodiment, $R^2$ is 3-piperazin-1-yl-4-methylsulfonylphenyl. In another embodiment, $R^2$ is 3-methoxy-4-methylsulfonylphenyl. In another embodiment, $R^2$ is 3-trifluoromethyl-4-methylsulfonylphenyl. In another embodiment, $R^2$ is 3-fluoro-4-methylsulfonylphenyl. In another embodiment, $R^2$ is 3-chloro-4-methylsulfonylphenyl. In another embodiment, $R^2$ is 3-methyl-4-methylsulfonylphenyl. In another embodiment, $R^2$ is 3,5-dimethyl-4-methylsulfonylphenyl. In another embodiment, $R^2$ is 3-(dimethylamino)-4-methylsulfonylphenyl. In another embodiment, $R^2$ is 4-trifluoromethylsulfinylphenyl. In another embodiment, $R^2$ is 4-trifluoromethylsulfonylphenyl. In another embodiment, $R^2$ is 4-phenyl(methyl)oxo-$\lambda^6$-sulfanylidene-2,2,2-trifluoroacetamide. In another embodiment, $R^2$ is 4-methylsulfonimidoylphenyl. In another embodiment, $R^2$ is 4-isopropylsulfonimidoylphenyl. In another embodiment, $R^2$ is 4-N,N-dimethylaminosulfonylphenyl.

In another embodiment, $R^2$ is (5- or 6-membered)heteroaryl, wherein said heteroaryl is unsubstituted or substituted with 1, 2, 3, 4, or 5 substituent(s) independently selected from halo, cyano, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O($C_1-C_6$)alkyl, —C(=O)NR$^4$R$^5$, —C(=O)—($C_5-C_7$)heterocycloalkyl, $(C_5-C_7)$heterocycloalkyl, $(C_6-C_{10})$aryl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$NHOH, —S(O)$_2$—NR$^6$R$^7$, —S(O)$_2$-phenyl, —S(O)$_2$—($C_5-C_7$)heterocycloalkyl, —S(=O)(=NR$^8$)($C_1-C_6$)alkyl, —NR$^4$R$^5$, N—($C_1-C_6$)alkylaminosulfonyl, and N,N-di($C_1-C_6$)alkylaminosulfonyl, wherein said $(C_5-C_7)$heterocycloalkyl is unsubstituted or substituted with 1 or 2 substituent(s) independently selected from halo or $(C_1-C_6)$alkyl. In one embodiment, $R^2$ is unsubstituted (5- or 6-membered)heteroaryl. In one embodiment, $R^2$ is thienyl. In another embodiment, $R^2$ is pyridyl. In another embodiment, $R^2$ is pyridyl-N-oxide. In another embodiment, $R^2$ is furyl.

In one embodiment, $R^3$ is (5- or 6-membered)heteroaryl, wherein said heteroaryl is unsubstituted or substituted with 1, 2, 3, 4, or 5 substituent(s) independently selected from halo, cyano, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O($C_1-C_6$)alkyl, —C(=O)NR$^4$R$^5$, —C(=O)—($C_5-C_7$)heterocycloalkyl, $(C_5-C_7)$heterocycloalkyl, $(C_6-C_{10})$aryl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$NHOH, —S(O)$_2$—NR$^6$R$^7$, —S(O)$_2$-phenyl, —S(O)$_2$—($C_5-C_7$)heterocycloalkyl, —S(=O)(=NR$^8$)($C_1-C_6$)alkyl, —NR$^4$R$^5$, N—($C_1-C_6$)alkylaminosulfonyl, and N,N-di($C_1-C_6$)alkylaminosulfonyl, wherein said $(C_5-C_7)$heterocycloalkyl is unsubstituted or substituted with 1 or 2 substituent(s) independently selected from halo or $(C_1-C_6)$alkyl. In one embodiment, $R^3$ is unsubstituted (5- or 6-membered)heteroaryl. In one embodiment, $R^2$ is thienyl. In another embodiment, $R^2$ is pyridyl. In another embodiment, $R^2$ is pyridyl-N-oxide. In another embodiment, $R^2$ is furyl.

In another embodiment, $R^3$ is $(C_6-C_{10})$aryl, wherein said aryl is unsubstituted or substituted with 1, 2, 3, 4, or 5 substituent(s) independently selected from halo, cyano, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O($C_1-C_6$)alkyl, —C(=O)NR$^4$R$^5$, —C(=O)—($C_5-C_7$)heterocycloalkyl, $(C_5-C_7)$heterocycloalkyl, $(C_6-C_{10})$aryl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$—(C$_5$-C$_7$)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl, wherein said (C$_5$-C$_7$)heterocycloalkyl is unsubstituted or substituted with 1 or 2 substituent(s) independently selected from halo or (C$_1$-C$_6$)alkyl. In another embodiment, R$^3$ is phenyl, wherein said phenyl is unsubstituted or substituted with 1, 2, 3, 4, or 5 substituent(s) independently selected from halo, cyano, (C$_1$-C$_6$)alkyl, (C$_1$-C$_4$)haloalkyl, (C$_1$-C$_4$)perhaloalkyl, (C$_1$-C$_6$) alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)—(C$_5$-C$_7$)heterocycloalkyl, (C$_5$-C$_7$)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$) alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$—(C$_5$-C$_7$)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl, wherein said (C$_5$-C$_7$)heterocycloalkyl is unsubstituted or substituted with 1 or 2 substituent(s) independently selected from halo or (C$_1$-C$_6$)alkyl. In one embodiment, R$^3$ is unsubstituted phenyl.

In one embodiment, R$^3$ is —C(=NOR$^9$)R$^{10}$ wherein R$^9$ is phenyl and R$^{10}$ is (C$_1$-C$_6$)alkyl. In another embodiment, R$^3$ is —C(=NOR$^9$)R$^{10}$ wherein R$^9$ is phenyl and R$^{10}$ is (C$_1$-C$_4$)alkyl. In another embodiment, R$^3$ is —C(=NOR$^9$)R$^{10}$ wherein R$^9$ is phenyl and R$^{10}$ is methyl, ethyl or propyl. In another embodiment, R$^3$ is —C(=NOR$^9$)R$^{10}$ wherein R$^9$ is phenyl and R$^{10}$ is methyl or ethyl. In another embodiment, R$^3$ is —C(=NOR$^9$)R$^{10}$ wherein R$^9$ is phenyl and R$^{10}$ is methyl. In another embodiment, R$^3$ is —C(=NOR$^9$)R$^{10}$ wherein R$^9$ is phenyl and R$^{10}$ is ethyl.

In one embodiment, R$^3$ is —C(=NOR$^9$)R$^{10}$ wherein R$^9$ is (C$_1$-C$_6$)alkyl substituted with phenyl and R$^{10}$ is (C$_1$-C$_6$) alkyl. In another embodiment, R$^3$ is —C(=NOR$^9$)R$^{10}$ wherein R$^9$ is (C$_1$-C$_6$)alkyl substituted with phenyl and R$^{10}$ is (C$_1$-C$_4$)alkyl. In another embodiment, R$^3$ is —C(=NOR$^9$)R$^{10}$ wherein R$^9$ is (C$_1$-C$_6$)alkyl substituted with phenyl and R$^{10}$ is methyl, ethyl or propyl. In another embodiment, R$^3$ is —C(=NOR$^9$)R$^{10}$ wherein R$^9$ is (C$_1$-C$_6$) alkyl substituted with phenyl and R$^{10}$ is methyl or ethyl. In another embodiment, R$^3$ is —C(=NOR$^9$)R$^{10}$ wherein R$^9$ is (C$_1$-C$_6$)alkyl substituted with phenyl and R$^{10}$ is methyl. In another embodiment, R$^3$ is —C(=NOR$^9$)R$^{10}$ wherein R$^9$ is phenyl and R$^{10}$ is ethyl.

In one embodiment, R$^3$ is —C(=NOR$^9$)R$^{10}$ wherein R$^9$ is (C$_1$-C$_4$)alkyl substituted with phenyl and R$^{10}$ is (C$_1$-C$_6$) alkyl. In one embodiment, R$^3$ is —C(=NOR$^9$)R$^{10}$ wherein R$^9$ is (C$_1$)alkyl substituted with phenyl and R$^{10}$ is (C$_1$-C$_6$) alkyl. In one embodiment, R$^3$ is —C(=NOR$^9$)R$^{10}$ wherein R$^9$ is (C$_2$)alkyl substituted with phenyl and R$^{10}$ is (C$_1$-C$_6$) alkyl. In one embodiment, R$^3$ is —C(=NOR$^9$)R$^{10}$ wherein R$^9$ is (C$_1$-C$_4$)alkyl substituted with phenyl and R$^{10}$ is (C$_1$-C$_4$)alkyl. In one embodiment, R$^3$ is —C(=NOR$^9$)R$^{10}$ wherein R$^9$ is (C$_1$)alkyl substituted with phenyl and R$^{10}$ is (C$_1$-C$_4$)alkyl. In one embodiment, R$^3$ is —C(=NOR$^9$)R$^{10}$ wherein R$^9$ is (C$_2$)alkyl substituted with phenyl and R$^{10}$ is (C$_1$-C$_4$)alkyl. In one embodiment, R$^3$ is —C(=NOR$^9$)R$^{10}$ wherein R$^9$ is (C$_1$-C$_4$)alkyl substituted with phenyl and R$^{10}$ is methyl, ethyl or propyl. In one embodiment, R$^3$ is —C(=NOR$^9$)R$^{10}$ wherein R$^9$ is (C$_1$)alkyl substituted with phenyl and R$^{10}$ is methyl, ethyl or propyl. In one embodiment, R$^3$ is —C(=NOR$^9$)R$^{10}$ wherein R$^9$ is (C$_2$)alkyl substituted with phenyl and R$^{10}$ is methyl, ethyl or propyl. In one embodiment, R$^3$ is —C(=NOR$^9$)R$^{10}$ wherein R$^9$ is (C$_1$-C$_4$)alkyl substituted with phenyl and R$^{10}$ is methyl or ethyl. In one embodiment, R$^3$ is —C(=NOR$^9$)R$^{10}$ wherein R$^9$ is (C$_1$)alkyl substituted with phenyl and R$^{10}$ is methyl or ethyl. In one embodiment, R$^3$ is —C(=NOR$^9$)R$^{10}$ wherein R$^9$ is (C$_2$)alkyl substituted with phenyl and R$^{10}$ is methyl or ethyl. In one embodiment, R$^3$ is —C(=NOR$^9$)R$^{10}$ wherein R$^9$ is (C$_1$-C$_4$)alkyl substituted with phenyl and R$^{10}$ is methyl. In one embodiment, R$^3$ is —C(=NOR$^9$)R$^{10}$ wherein R$^9$ is (C$_1$)alkyl substituted with phenyl and R$^{10}$ is methyl. In one embodiment, R$^3$ is —C(=NOR$^9$)R$^{10}$ wherein R$^9$ is (C$_2$) alkyl substituted with phenyl and R$^{10}$ is methyl. In one embodiment, R$^3$ is —C(=NOR$^9$)R$^{10}$ wherein R$^9$ is (C$_1$-C$_4$) alkyl substituted with phenyl and R$^{10}$ is ethyl. In one embodiment, R$^3$ is —C(=NOR$^9$)R$^{10}$ wherein R$^9$ is (C$_1$) alkyl substituted with phenyl and R is ethyl. In one embodiment, R$^3$ is —C(=NOR$^9$)R wherein R$^9$ is (C$_2$)alkyl substituted with phenyl and R$^{10}$ is ethyl.

In another embodiment, R$^3$ is —C(=NOR$^9$)R$^{10}$ wherein R$^9$ is (C$_1$-C$_6$)alkyl and R$^{10}$ is (C$_1$-C$_6$)alkyl. In another embodiment, R$^3$ is —C(=NOR$^9$)R$^{10}$ wherein R$^9$ is (C$_1$-C$_6$) alkyl and R is (C$_1$-C$_4$)alkyl. In another embodiment, R$^3$ is —C(=NOR$^9$)R$^{10}$ wherein R$^9$ is (C$_1$-C$_6$)alkyl and R$^{10}$ is methyl, ethyl or propyl. In another embodiment, R$^3$ is —C(=NOR$^9$)R$^{10}$ wherein R$^9$ is (C$_1$-C$_6$)alkyl and R is methyl or ethyl. In another embodiment, R$^3$ is —C(=NOR$^9$)R$^{10}$ wherein R$^9$ is (C$_1$-C$_6$)alkyl and R$^{10}$ is methyl. In another embodiment, R$^3$ is —C(=NOR$^9$)R$^{10}$ wherein R$^9$ is (C$_1$-C$_6$)alkyl and R$^{10}$ is ethyl.

In another embodiment, R$^3$ is —C(=NOR$^9$)R$^{10}$ wherein R$^9$ is methyl, ethyl, propyl or butyl and R$^{10}$ is (C$_1$-C$_6$)alkyl. In another embodiment, R$^3$ is —C(=NOR$^9$)R$^{10}$ wherein R$^9$ is methyl, ethyl, propyl or butyl and R$^{10}$ is (C$_1$-C$_4$)alkyl. In another embodiment, R$^3$ is —C(=NOR$^9$)R$^{10}$ wherein R$^9$ is methyl, ethyl, propyl or butyl and R$^{10}$ is methyl, ethyl or propyl. In another embodiment, R$^3$ is —C(=NOR$^9$)R$^{10}$ wherein R$^9$ is methyl, ethyl, propyl or butyl and R$^{10}$ is methyl or ethyl. In another embodiment, R$^3$ is —C(=NOR$^9$)R$^{10}$ wherein R$^9$ is methyl, ethyl, propyl or butyl and R$^{10}$ is methyl. In another embodiment, R$^3$ is —C(=NOR$^9$)R$^{10}$ wherein R$^9$ is methyl, ethyl, propyl or butyl and R$^{10}$ is ethyl. In one embodiment, R$^3$ is —C(=NOR$^9$)R$^{10}$ wherein R$^9$ is methyl and R$^{10}$ is (C$_1$-C$_6$) alkyl. In another embodiment, R$^3$ is —C(=NOR$^9$)R$^{10}$ wherein R$^9$ is methyl and R$^1$ is (C$_1$-C$_4$)alkyl. In another embodiment, R$^3$ is —C(=NOR$^9$)R$^{10}$ wherein R$^9$ is methyl and R$^{10}$ is methyl, ethyl or propyl. In another embodiment, R$^3$ is —C(=NOR$^9$)R$^{10}$ wherein R$^9$ is methyl and R$^{10}$ is methyl or ethyl. In another embodiment, R$^3$ is —C(=NOR$^9$)R$^{10}$ wherein R$^9$ is methyl and R$^{10}$ is methyl. In another embodiment, R$^3$ is —C(=NOR$^9$)R$^{10}$ wherein R$^9$ is methyl and R$^{10}$ is ethyl. In one embodiment, R$^3$ is —C(=NOR$^9$)R$^{10}$ wherein R$^9$ is ethyl and R$^{10}$ is (C$_1$-C$_6$) alkyl. In another embodiment, R$^3$ is —C(=NOR$^9$)R$^{10}$ wherein R$^9$ is ethyl and R$^{10}$ is (C$_1$-C$_4$)alkyl. In another embodiment, R$^3$ is —C(=NOR$^9$)R$^{10}$ wherein R$^9$ is ethyl and R$^{10}$ is methyl, ethyl or propyl. In another embodiment, R$^3$ is —C(=NOR$^9$)R$^{10}$ wherein R$^9$ is ethyl and R$^{10}$ is methyl or ethyl. In another embodiment, R$^3$ is —C(=NOR$^9$)R$^{10}$ wherein R$^9$ is ethyl and R$^{10}$ is methyl. In another embodiment, R$^3$ is —C(=NOR$^9$)R$^{10}$ wherein R$^9$ is ethyl and R$^{10}$ is ethyl. In one embodiment, R$^3$ is —C(=NOR$^9$)R$^{10}$ wherein R$^9$ is propyl and R$^{10}$ is (C$_1$-C$_6$) alkyl. In another embodiment, R$^3$ is —C(=NOR$^9$)R$^{10}$ wherein R$^9$ is propyl and R$^{10}$ is (C$_1$-C$_4$)alkyl. In another embodiment, R$^3$ is —C(=NOR$^9$)R$^{10}$ wherein R$^9$ is propyl and R$^{10}$ is methyl, ethyl or propyl. In another embodiment, $R^3$ is —C(=NOR$^9$)R$^{10}$ wherein R$^9$ is propyl and R$^{10}$ is methyl or ethyl. In another embodiment, R$^3$ is —C(=NOR$^9$)R$^{10}$ wherein R$^9$ is propyl and R$^{10}$ is methyl. In another embodiment, R$^3$ is —C(=NOR$^9$)R$^{10}$ wherein R$^9$ is propyl and R$^{10}$ is ethyl. In one embodiment, R$^3$ is —C(=NOR$^9$)R$^{10}$ wherein R$^9$ is butyl and R$^{10}$ is (C$_1$-C$_6$)alkyl. In another embodiment, R$^3$ is —C(=NOR$^9$)R$^{10}$ wherein R$^9$ is butyl and R$^{10}$ is (C$_1$-C$_4$)alkyl. In another embodiment, R$^3$ is —C(=NOR$^9$)R$^{10}$ wherein R$^9$ is butyl and R$^{10}$ is methyl, ethyl or propyl. In another embodiment, R$^3$ is —C(=NOR$^9$)R$^{10}$ wherein R$^9$ is butyl and R$^{10}$ is methyl or ethyl. In another embodiment, R$^3$ is —C(=NOR$^9$)R$^{10}$ wherein R$^9$ is butyl and R$^{10}$ is methyl. In another embodiment, R$^3$ is —C(=NOR$^9$)R$^{10}$ wherein R$^9$ is butyl and R$^{10}$ is ethyl. In one embodiment, R$^3$ is —C(=NOR$^9$)R$^{10}$ wherein R$^9$ is tert-butyl and R$^{10}$ is (C$_1$-C$_6$)alkyl. In another embodiment, R$^3$ is —C(=NOR$^9$)R$^{10}$ wherein R$^9$ is tert-butyl and R$^{10}$ is (C$_1$-C$_4$)alkyl. In another embodiment, R$^3$ is —C(=NOR$^9$)R$^{10}$ wherein R$^9$ is tert-butyl and R$^1$ is methyl, ethyl or propyl. In another embodiment, R$^3$ is —C(=NOR$^9$)R$^{10}$ wherein R$^9$ is tert-butyl and R$^1$ is methyl or ethyl. In another embodiment, R$^3$ is —C(=NOR$^9$)R$^{10}$ wherein R$^9$ is tert-butyl and R$^{10}$ is methyl. In another embodiment, R$^3$ is —C(=NOR$^9$)R$^{10}$ wherein R$^9$ is tert-butyl and R$^{10}$ is ethyl. In one embodiment, R$^3$ is —C(=NOR$^9$)R$^{10}$ wherein R$^9$ is iso-butyl and R$^{10}$ is (C$_1$-C$_6$)alkyl. In another embodiment, R$^3$ is —C(=NOR$^9$)R$^{10}$ wherein R$^9$ is iso-butyl and R$^{10}$ is (C$_1$-C$_4$)alkyl. In another embodiment, R$^3$ is —C(=NOR$^9$)R$^{10}$ wherein R$^9$ is iso-butyl and R$^{10}$ is methyl, ethyl or propyl. In another embodiment, R$^3$ is —C(=NOR$^9$)R$^{10}$ wherein R$^9$ is iso-butyl and R$^{10}$ is methyl or ethyl. In another embodiment, R$^3$ is —C(=NOR$^9$)R$^{10}$ wherein R$^9$ is iso-butyl and R$^{10}$ is methyl. In another embodiment, R$^3$ is —C(=NOR$^9$)R$^{10}$ wherein R$^9$ is iso-butyl and R$^{10}$ is ethyl.

In another embodiment, R$^3$ is —C(=NOR$^9$)R$^{10}$ wherein at least one of R$^9$ and R$^{10}$ is methyl. In another embodiment, R$^3$ is —C(=NOR$^9$)R$^{10}$ wherein each of R$^9$ and R$^{10}$ is methyl. In another embodiment, R$^3$ is —C(=NOR$^9$)R$^{10}$ wherein one of R$^9$ and R$^{10}$ is methyl and the other is ethyl.

In another embodiment, R$^2$ is methyl and R$^3$ is —C(=NOR$^9$)R$^{10}$ wherein at least one of R$^9$ and R$^{10}$ is methyl. In another embodiment, R$^2$ is ethyl and R$^3$ is —C(=NOR$^9$)R$^{10}$ wherein at least one of R$^9$ and R$^{10}$ is methyl. In another embodiment, R$^2$ is iso-propyl and R$^3$ is —C(=NOR$^9$)R$^{10}$ wherein at least one of R$^9$ and R$^{10}$ is methyl. In another embodiment, R$^2$ is tert-butyl and R$^3$ is —C(=NOR$^9$)R$^{10}$ wherein at least one of R$^9$ and R$^{10}$ is methyl. In another embodiment, R$^2$ is (5- or 6-membered)heteroaryl and R$^3$ is —C(=NOR$^9$)R$^{10}$ wherein at least one of R$^9$ and R$^{10}$ is methyl. In another embodiment, R$^2$ is methyl and R$^3$ is —C(=NOR$^9$)R$^{10}$ wherein each of R$^9$ and R$^{10}$ is methyl. In another embodiment, R$^2$ is methyl and R$^3$ is —C(=NOR$^9$)R$^{10}$ wherein one of R$^9$ and R$^{10}$ is methyl and the other is ethyl. In another embodiment, R$^2$ is ethyl and R$^3$ is —C(=NOR$^9$)R$^{10}$ wherein each of R$^9$ and R$^{10}$ is methyl. In another embodiment, R$^2$ is ethyl and R$^3$ is —C(=NOR$^9$)R$^{10}$ wherein one of R$^9$ and R$^{10}$ is methyl and the other is ethyl. In another embodiment, R$^2$ is iso-propyl and R$^3$ is —C(=NOR$^9$)R$^{10}$ wherein each of R$^9$ and R$^{10}$ is methyl. In another embodiment, R$^2$ is iso-propyl and R$^3$ is —C(=NOR$^9$)R$^{10}$ wherein one of R$^9$ and R$^{10}$ is methyl and the other is ethyl. In another embodiment, R$^2$ is tert-butyl and R$^3$ is —C(=NOR$^9$)R$^{10}$ wherein each of R$^9$ and R$^{10}$ is methyl. In another embodiment, R$^2$ is tert-butyl and R$^3$ is —C(=NOR$^9$)R$^{10}$ wherein one of R$^9$ and R$^{10}$ is methyl and the other is ethyl. In another embodiment, R$^2$ is (5- or 6-membered)heteroaryl and R$^3$ is —C(=NOR$^9$)R$^{10}$ wherein each of R$^9$ and R$^{10}$ is methyl. In another embodiment, R$^2$ is (5- or 6-membered)heteroaryl and R$^3$ is —C(=NOR$^9$)R$^{10}$ wherein one of R$^9$ and R$^{10}$ is methyl and the other is ethyl. In various embodiments in which R$^2$ is (5- or 6-membered)heteroaryl, said (5- or 6-membered)heteroaryl is unsubstituted in one embodiment and, in additional embodiments, is substituted with 1, 2, 3, 4, or 5 substituent(s) independently selected from halo, cyano, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)—(C$_5$-C$_7$)heterocycloalkyl, (C$_5$-C$_7$)heterocycloalkyl, (C$_6$-C$_{10}$)aryl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$NHOH, —S(O)$_2$—NR$^6$R$^7$, —S(O)$_2$-phenyl, —S(O)$_2$—(C$_5$-C$_7$)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl, wherein said (C$_5$-C$_7$)heterocycloalkyl is unsubstituted or substituted with 1 or 2 substituent(s) independently selected from halo or (C$_1$-C$_6$)alkyl.

In another embodiment, R$^2$ is methyl and R$^3$ is (5- or 6-membered)heteroaryl, wherein said heteroaryl is unsubstituted or substituted with 1, 2, 3, 4, or 5 substituent(s) independently selected from halo, cyano, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)—(C$_5$-C$_7$)heterocycloalkyl, (C$_5$-C$_7$)heterocycloalkyl, (C$_6$-C$_{10}$)aryl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$—(C$_5$-C$_7$)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl, wherein said (C$_5$-C$_7$)heterocycloalkyl is unsubstituted or substituted with 1 or 2 substituent(s) independently selected from halo or (C$_1$-C$_6$)alkyl. In another embodiment, R$^2$ is methyl and R$^3$ is (5- or 6-membered)heteroaryl, wherein said heteroaryl is unsubstituted. In another embodiment, R$^2$ is methyl and R$^3$ is (5- or 6-membered)heteroaryl, wherein said heteroaryl is substituted with 1, 2 or 3 substituent(s) independently selected from halo, cyano, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)—(C$_5$-C$_7$)heterocycloalkyl, (C$_5$-C$_7$)heterocycloalkyl, (C$_6$-C$_{10}$)aryl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$—(C$_5$-C$_7$)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl, wherein said (C$_5$-C$_7$)heterocycloalkyl is unsubstituted or substituted with 1 or 2 substituent(s) independently selected from halo or (C$_1$-C$_6$)alkyl. In another embodiment, R$^2$ is methyl and R$^3$ is (5- or 6-membered)heteroaryl, wherein said heteroaryl is substituted with 1, 2 or 3 substituent(s)

independently selected from halo, cyano, $(C_1$-$C_6)$alkyl, $(C_1$-$C_4)$haloalkyl, $(C_1$-$C_4)$perhaloalkyl, $(C_1$-$C_6)$alkoxy, $(C_1$-$C_4)$haloalkoxy, $(C_1$-$C_4)$perhaloalkoxy or $(C_6)$aryl.

In another embodiment, $R^2$ is methyl and $R^3$ is $(C_6$-$C_{10})$aryl, wherein said aryl is unsubstituted or substituted with 1, 2, 3, 4, or 5 substituent(s) independently selected from halo, cyano, $(C_1$-$C_6)$alkyl, $(C_1$-$C_4)$haloalkyl, $(C_1$-$C_4)$perhaloalkyl, $(C_1$-$C_6)$alkoxy, $(C_1$-$C_4)$haloalkoxy, $(C_1$-$C_4)$perhaloalkoxy, —C(=O)OH, —C(=O)O$(C_1$-$C_6)$alkyl, —C(=O)NR$^4$R$^5$, —C(=O)—$(C_5$-$C_7)$heterocycloalkyl, $(C_5$-$C_7)$heterocycloalkyl, $(C_6$-$C_{10})$aryl, $(C_1$-$C_6)$alkylsulfanyl, $(C_1$-$C_4)$haloalkylsulfanyl, $(C_1$-$C_4)$perhaloalkylsulfanyl, $(C_1$-$C_6)$alkylsulfinyl, $(C_1$-$C_6)$alkylsulfonyl, $(C_3$-$C_6)$cycloalkylsulfonyl, $(C_1$-$C_4)$haloalkylsulfinyl, $(C_1$-$C_4)$haloalkylsulfonyl, $(C_1$-$C_4)$perhaloalkylsulfinyl, $(C_1$-$C_4)$perhaloalkylsulfonyl, —S(O)$_2$—NH$_2$, —S(O)$_2$—NR$^6$R$^7$, —S(O)$_2$-phenyl, —S(O)$_2$—$(C_5$-$C_7)$heterocycloalkyl, —S(=O)(=NR$^8$)$(C_1$-$C_6)$alkyl, —NR$^4$R$^5$, N—$(C_1$-$C_6)$alkylaminosulfonyl, and N,N-di$(C_1$-$C_6)$alkylaminosulfonyl, wherein said $(C_5$-$C_7)$heterocycloalkyl is unsubstituted or substituted with 1 or 2 substituent(s) independently selected from halo or $(C_1$-$C_6)$alkyl. In another embodiment, $R^2$ is methyl and $R^3$ is $(C_6$-$C_{10})$aryl, wherein said aryl is unsubstituted. In another embodiment, $R^2$ is methyl and $R^3$ is $(C_6$-$C_{10})$aryl, wherein said aryl is substituted with 1, 2 or 3 substituent(s) independently selected from halo, cyano, $(C_1$-$C_6)$alkyl, $(C_1$-$C_4)$haloalkyl, $(C_1$-$C_4)$perhaloalkyl, $(C_1$-$C_6)$alkoxy, $(C_1$-$C_4)$haloalkoxy, $(C_1$-$C_4)$perhaloalkoxy, —C(=O)OH, —C(=O)O$(C_1$-$C_6)$alkyl, —C(=O)NR$^4$R$^5$, —C(=O)—$(C_5$-$C_7)$heterocycloalkyl, $(C_5$-$C_7)$heterocycloalkyl, $(C_6$-$C_{10})$aryl, $(C_1$-$C_6)$alkylsulfanyl, $(C_1$-$C_4)$haloalkylsulfanyl, $(C_1$-$C_4)$perhaloalkylsulfanyl, $(C_1$-$C_6)$alkylsulfinyl, $(C_1$-$C_6)$alkylsulfonyl, $(C_3$-$C_6)$cycloalkylsulfonyl, $(C_1$-$C_4)$haloalkylsulfinyl, $(C_1$-$C_4)$haloalkylsulfonyl, $(C_1$-$C_4)$perhaloalkylsulfinyl, $(C_1$-$C_4)$perhaloalkylsulfonyl, —S(O)$_2$—NH$_2$, —S(O)$_2$—NR$^6$R$^7$, —S(O)$_2$-phenyl, —S(O)$_2$—$(C_5$-$C_7)$heterocycloalkyl, —S(=O)(=NR$^8$)$(C_1$-$C_6)$alkyl, —NR$^4$R$^5$, N—$(C_1$-$C_6)$alkylaminosulfonyl, and N,N-di$(C_1$-$C_6)$alkylaminosulfonyl, wherein said $(C_5$-$C_7)$heterocycloalkyl is unsubstituted or substituted with 1 or 2 substituent(s) independently selected from halo or $(C_1$-$C_6)$alkyl. In another embodiment, $R^2$ is methyl and $R^3$ is $(C_6$-$C_{10})$aryl, wherein said aryl is substituted with 1, 2 or 3 substituent(s) independently selected from halo, cyano, $(C_1$-$C_6)$alkyl, $(C_1$-$C_4)$haloalkyl, $(C_1$-$C_4)$perhaloalkyl, $(C_1$-$C_6)$alkoxy, $(C_1$-$C_4)$haloalkoxy, $(C_1$-$C_4)$perhaloalkoxy.

In another embodiment, $R^2$ is methyl and $R^3$ is phenyl, wherein said phenyl is unsubstituted or substituted with 1, 2, 3, 4, or 5 substituent(s) independently selected from halo, cyano, $(C_1$-$C_6)$alkyl, $(C_1$-$C_4)$haloalkyl, $(C_1$-$C_4)$perhaloalkyl, $(C_1$-$C_6)$alkoxy, $(C_1$-$C_4)$haloalkoxy, $(C_1$-$C_4)$perhaloalkoxy, —C(=O)OH, —C(=O)O$(C_1$-$C_6)$alkyl, —C(=O)NR$^4$R$^5$, —C(=O)—$(C_5$-$C_7)$heterocycloalkyl, $(C_5$-$C_7)$heterocycloalkyl, $(C_6$-$C_{10})$aryl, $(C_1$-$C_6)$alkylsulfanyl, $(C_1$-$C_4)$haloalkylsulfanyl, $(C_1$-$C_4)$perhaloalkylsulfanyl, $(C_1$-$C_6)$alkylsulfinyl, $(C_1$-$C_6)$alkylsulfonyl, $(C_3$-$C_6)$cycloalkylsulfonyl, $(C_1$-$C_4)$haloalkylsulfinyl, $(C_1$-$C_4)$haloalkylsulfonyl, $(C_1$-$C_4)$perhaloalkylsulfinyl, $(C_1$-$C_4)$perhaloalkylsulfonyl, —S(O)$_2$—NH$_2$, —S(O)$_2$—NR$^6$R$^7$, —S(O)$_2$-phenyl, —S(O)$_2$—$(C_5$-$C_7)$heterocycloalkyl, —S(=O)(=NR$^8$)$(C_1$-$C_6)$alkyl, —NR$^4$R$^5$, N—$(C_1$-$C_6)$alkylaminosulfonyl, and N,N-di$(C_1$-$C_6)$alkylaminosulfonyl, wherein said $(C_5$-$C_7)$heterocycloalkyl is unsubstituted or substituted with 1 or 2 substituent(s) independently selected from halo or $(C_1$-$C_6)$alkyl. In another embodiment, $R^2$ is methyl and $R^3$ is phenyl, wherein said phenyl is unsubstituted. In another embodiment, $R^2$ is methyl and $R^3$ is phenyl, wherein said phenyl is substituted with 1, 2 or 3 substituent(s) independently selected from halo, cyano, $(C_1$-$C_6)$alkyl, $(C_1$-$C_4)$haloalkyl, $(C_1$-$C_4)$perhaloalkyl, $(C_1$-$C_6)$alkoxy, $(C_1$-$C_4)$haloalkoxy, $(C_1$-$C_4)$perhaloalkoxy, —C(=O)OH, —C(=O)O$(C_1$-$C_6)$alkyl, —C(=O)NR$^4$R$^5$, —C(=O)—$(C_5$-$C_7)$heterocycloalkyl, $(C_5$-$C_7)$heterocycloalkyl, $(C_6$-$C_{10})$aryl, $(C_1$-$C_6)$alkylsulfanyl, $(C_1$-$C_4)$haloalkylsulfanyl, $(C_1$-$C_4)$perhaloalkylsulfanyl, $(C_1$-$C_6)$alkylsulfinyl, $(C_1$-$C_6)$alkylsulfonyl, $(C_3$-$C_6)$cycloalkylsulfonyl, $(C_1$-$C_4)$haloalkylsulfinyl, $(C_1$-$C_4)$haloalkylsulfonyl, $(C_1$-$C_4)$perhaloalkylsulfinyl, $(C_1$-$C_4)$perhaloalkylsulfonyl, —S(O)$_2$—NH$_2$, —S(O)$_2$—NR$^6$R$^7$, —S(O)$_2$-phenyl, —S(O)$_2$—$(C_5$-$C_7)$heterocycloalkyl, —S(=O)(=NR$^8$)$(C_1$-$C_6)$alkyl, —NR$^4$R$^5$, N—$(C_1$-$C_6)$alkylaminosulfonyl, and N,N-di$(C_1$-$C_6)$alkylaminosulfonyl, wherein said $(C_5$-$C_7)$heterocycloalkyl is unsubstituted or substituted with 1 or 2 substituent(s) independently selected from halo or $(C_1$-$C_6)$alkyl. In another embodiment, $R^2$ is methyl and $R^3$ is phenyl, wherein said phenyl is substituted with 1, 2 or 3 substituent(s) independently selected from halo, cyano, $(C_1$-$C_6)$alkyl, $(C_1$-$C_4)$haloalkyl, $(C_1$-$C_4)$perhaloalkyl, $(C_1$-$C_6)$alkoxy, $(C_1$-$C_4)$haloalkoxy, $(C_1$-$C_4)$perhaloalkoxy.

In another embodiment, $R^2$ is methyl and $R^3$ is —C(=NOR$^9$)R$^{10}$, wherein R$^9$ is phenyl and R$^{10}$ is $(C_1$-$C_6)$alkyl. In another embodiment, $R^2$ is methyl and $R^3$ is —C(=NOR$^9$)R$^{10}$, wherein R$^9$ is phenyl and R$^{10}$ is methyl. In another embodiment, $R^2$ is methyl and $R^3$ is —C(=NOR$^9$)R$^{10}$, wherein R$^9$ is phenyl and R$^{10}$ is ethyl. In another embodiment, $R^2$ is methyl and $R^3$ is —C(=NOR$^9$)R$^{10}$, wherein R$^9$ is phenyl and R$^{10}$ is propyl. In another embodiment, $R^2$ is methyl and $R^3$ is —C(=NOR$^9$)R$^{10}$, wherein R$^9$ is phenyl and R$^{10}$ is butyl.

In another embodiment, $R^2$ is methyl and $R^3$ is —C(=NOR$^9$)R$^{10}$, wherein R$^9$ is $(C_1$-$C_6)$alkyl substituted with phenyl and R$^{10}$ is $(C_1$-$C_6)$alkyl. In another embodiment, $R^2$ is methyl and $R^3$ is —C(=NOR$^9$)R$^{10}$, wherein R$^9$ is $(C_1$-$C_4)$alkyl substituted with phenyl and R$^{10}$ is $(C_1$-$C_4)$alkyl. In another embodiment, $R^2$ is methyl and $R^3$ is —C(=NOR$^9$)R$^{10}$, wherein R$^9$ is $(C_1)$alkyl substituted with phenyl and R$^{10}$ is methyl, ethyl or propyl. In another embodiment, $R^2$ is methyl and $R^3$ is —C(=NOR$^9$)R$^{10}$, wherein R$^9$ is $(C_2)$alkyl substituted with phenyl and R$^{10}$ is methyl, ethyl or propyl. In another embodiment, $R^2$ is methyl and $R^3$ is —C(=NOR$^9$)R$^{10}$, wherein R$^9$ is $(C_1)$alkyl substituted with phenyl and R$^{10}$ is methyl. In another embodiment, $R^2$ is methyl and $R^3$ is —C(=NOR$^9$)R$^{10}$, wherein R$^9$ is $(C_2)$alkyl substituted with phenyl and R$^{10}$ is methyl. In another embodiment, $R^2$ is methyl and $R^3$ is —C(=NOR$^9$)R$^{10}$, wherein R$^9$ is $(C_1)$alkyl substituted with phenyl and R$^{10}$ is ethyl. In another embodiment, $R^2$ is methyl and $R^3$ is —C(=NOR$^9$)R$^{10}$, wherein R$^9$ is $(C_2)$alkyl substituted with phenyl and R$^{10}$ is ethyl. In another embodiment, $R^2$ is methyl and $R^3$ is —C(=NOR$^9$)R$^{10}$, wherein R$^9$ is $(C_1)$alkyl substituted with phenyl and R$^{10}$ is propyl. In another embodiment, $R^2$ is methyl and $R^3$ is —C(=NOR$^9$)R$^{10}$, wherein R$^9$ is $(C_2)$alkyl substituted with phenyl and R$^{10}$ is propyl.

In another embodiment, $R^2$ and $R^3$ are taken together with the carbon atoms to which they are attached to form a $(C_3$-$C_6)$cycloalkyl. In one embodiment, $R^2$ and $R^3$ are taken together with the carbon atoms to which they are attached to form a cyclopropyl ring. In one embodiment, $R^2$ and $R^3$ are taken together with the carbon atoms to which they are attached to form a cyclobutyl ring. In one embodiment, $R^2$ and $R^3$ are taken together with the carbon atoms to which they are attached to form a cyclopentyl ring. In one embodiment, $R^2$ and $R^3$ are taken together with the carbon atoms to which they are attached to form a cyclohexyl ring.

In another embodiment, a pyrazolone derivative compound of the disclosure is compound of formula (Ih)

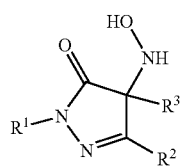

(Ih)

or a pharmaceutically acceptable salt thereof, wherein:

$R^1$ is H;

$R^2$ is $(C_1-C_6)$alkyl, phenyl or (5- or 6-membered)heteroaryl, wherein said alkyl is substituted with 1, 2 or 3 substituent(s) independently selected from $(C_1-C_6)$alkoxy, —C(═O)OH, or —C(═O)O$(C_1-C_6)$alkyl and said phenyl and said heteroaryl are unsubstituted or substituted with 1, 2, 3, 4, or 5 substituent(s) independently selected from $(C_1-C_6)$alkylsulfanyl, $(C_1-C_6)$alkylsulfinyl, $(C_1-C_6)$alkylsulfonyl, —S(O)$_2$—NH$_2$, —S(O)$_2$N(($C_1-C_6$)alkyl)(O($C_1-C_6$ alkyl)), S(O)$_2$NHOH or N,N-di$(C_1-C_6)$alkylaminosulfonyl; and $R^3$ is $(C_1-C_6)$alkyl.

In one embodiment, $R^2$ is $(C_1-C_6)$alkyl substituted with 1, 2 or 3 substituent(s) independently selected from $(C_1-C_6)$alkoxy, —C(═O)OH, or —C(═O)O$(C_1-C_6)$alkyl. In another embodiment, $R^2$ is $(C_1-C_6)$alkyl substituted with 1, 2 or 3 substituent(s), at least one of which is $(C_1-C_6)$alkoxy. In another embodiment, $R^2$ is $(C_1-C_6)$alkyl substituted with 1, 2 or 3 substituent(s), at least one of which is —C(═O)OH. In another embodiment, $R^2$ is $(C_1-C_6)$alkyl substituted with 1, 2 or 3 substituent(s), at least one of which is —C(═O)O$(C_1-C_6)$alkyl.

In one embodiment, $R^2$ is $(C_1-C_4)$alkyl substituted with 1 or 2 substituent(s) independently selected from $(C_1-C_6)$alkoxy, —C(═O)OH, or —C(═O)O$(C_1-C_6)$alkyl. In another embodiment, $R^2$ is $(C_1-C_4)$alkyl substituted with 1 or 2 substituent(s), at least one of which is $(C_1-C_6)$alkoxy. In another embodiment, $R^2$ is $(C_1-C_4)$alkyl substituted with 1 or 2 substituent(s), at least one of which is —C(═O)OH. In another embodiment, $R^2$ is $(C_1-C_4)$alkyl substituted with 1 or 2 substituent(s), at least one of which is —C(═O)O$(C_1-C_6)$alkyl.

In one embodiment, $R^2$ is $(C_1)$alkyl substituted with 1 or 2 substituent(s) independently selected from $(C_1-C_6)$alkoxy, —C(═O)OH, or —C(═O)O$(C_1-C_6)$alkyl. In another embodiment, $R^2$ is $(C_1)$alkyl substituted with 1 or 2 substituent(s), at least one of which is $(C_1-C_6)$alkoxy. In another embodiment, $R^2$ is $(C_1)$alkyl substituted with 1 or 2 substituent(s), at least one of which is methoxy. In another embodiment, $R^2$ is $(C_1)$alkyl substituted with 1 or 2 substituent(s), at least one of which is ethoxy. In another embodiment, $R^2$ is $(C_1)$alkyl substituted with 1 or 2 substituent(s), at least one of which is —C(═O)OH. In another embodiment, $R^2$ is $(C_1)$alkyl substituted with 1 or 2 substituent(s), at least one of which is —C(═O)O$(C_1-C_6)$alkyl. In another embodiment, $R^2$ is $(C_1)$alkyl substituted with 1 or 2 substituent(s), at least one of which is —C(═O)O$(C_1)$alkyl. In another embodiment, $R^2$ is $(C_1)$alkyl substituted with 1 or 2 substituent(s), at least one of which is —C(═O)O$(C_2)$alkyl.

In one embodiment, $R^2$ is $(C_2)$alkyl substituted with 1 or 2 substituent(s) independently selected from $(C_1-C_6)$alkoxy, —C(═O)OH, or —C(═O)O$(C_1-C_6)$alkyl. In another embodiment, $R^2$ is $(C_2)$alkyl substituted with 1 or 2 substituent(s), at least one of which is $(C_1-C_6)$alkoxy. In another embodiment, $R^2$ is $(C_2)$alkyl substituted with 1 or 2 substituent(s), at least one of which is methoxy. In another embodiment, $R^2$ is $(C_2)$alkyl substituted with 1 or 2 substituent(s), at least one of which is ethoxy. In another embodiment, $R^2$ is $(C_2)$alkyl substituted with 1 or 2 substituent(s), at least one of which is —C(═O)OH. In another embodiment, $R^2$ is $(C_2)$alkyl substituted with 1 or 2 substituent(s), at least one of which is —C(═O)O$(C_1-C_6)$alkyl. In another embodiment, $R^2$ is $(C_2)$alkyl substituted with 1 or 2 substituent(s), at least one of which is —C(═O)O$(C_1)$alkyl. In another embodiment, $R^2$ is $(C_2)$alkyl substituted with 1 or 2 substituent(s), at least one of which is —C(═O)O$(C_2)$alkyl.

In one embodiment, $R^2$ is $(C_1)$alkyl monosubstituted with $(C_1-C_6)$alkoxy, —C(═O)OH, or —C(═O)O$(C_1-C_6)$alkyl. In another embodiment, $R^2$ is $(C_1)$alkyl monosubstituted with $(C_1-C_6)$alkoxy. In another embodiment, $R^2$ is $(C_1)$alkyl substituted with 1 or 2 substituent(s) monosubstituted with methoxy. In another embodiment, $R^2$ is $(C_1)$alkyl monosubstituted with ethoxy. In another embodiment, $R^2$ is $(C_1)$alkyl monosubstituted with —C(═O)OH. In another embodiment, $R^2$ is $(C_1)$alkyl monosubstituted with —C(═O)O$(C_1-C_6)$alkyl. In another embodiment, $R^2$ is $(C_1)$alkyl monosubstituted with —C(═O)O$(C_1)$alkyl. In another embodiment, $R^2$ is $(C_1)$alkyl monosubstituted with —C(═O)O$(C_2)$alkyl.

In one embodiment, $R^2$ is $(C_2)$alkyl monosubstituted with $(C_1-C_6)$alkoxy, —C(═O)OH, or —C(═O)O$(C_1-C_6)$alkyl. In another embodiment, $R^2$ is $(C_2)$alkyl monosubstituted with $(C_1-C_6)$alkoxy. In another embodiment, $R^2$ is $(C_2)$alkyl substituted with 1 or 2 substituent(s) monosubstituted with methoxy. In another embodiment, $R^2$ is $(C_2)$alkyl monosubstituted with ethoxy. In another embodiment, $R^2$ is $(C_2)$alkyl monosubstituted with —C(═O)OH. In another embodiment, $R^2$ is $(C_2)$alkyl monosubstituted with —C(═O)O$(C_1-C_6)$alkyl. In another embodiment, $R^2$ is $(C_2)$alkyl monosubstituted with —C(═O)O$(C_1)$alkyl. In another embodiment, $R^2$ is $(C_2)$alkyl monosubstituted with —C(═O)O$(C_2)$alkyl.

In one embodiment, $R^2$ is unsubstituted phenyl. In another embodiment, $R^2$ is phenyl substituted with 1, 2, or 3 independently selected substituent(s), at least one of which is $(C_1-C_6)$alkylsulfanyl. In another embodiment, $R^2$ is phenyl substituted with 1, 2, or 3 independently selected substituent(s), at least one of which is methylsulfanyl. In another embodiment, $R^2$ is phenyl substituted with 1, 2, or 3 independently selected substituent(s), at least one of which is $(C_1-C_6)$alkylsulfinyl. In another embodiment, $R^2$ is phenyl substituted with 1, 2, or 3 independently selected substituent(s), at least one of which is methylsulfinyl. In another embodiment, $R^2$ is phenyl substituted with 1, 2, or 3 independently selected substituent(s), at least one of which is $(C_1-C_6)$alkylsulfonyl. In another embodiment, $R^2$ is phenyl substituted with 1, 2, or 3 independently selected substituent(s), at least one of which is methylsulfonyl. In another embodiment, $R^2$ is phenyl substituted with 1, 2, or 3 independently selected substituent(s), at least one of which is —S(O)$_2$N(($C_1-C_6$)alkyl)(O($C_1-C_6$)alkyl)). In another embodiment, $R^2$ is phenyl substituted with 1, 2, or 3 independently selected substituent(s), at least one of which is N-methoxy-N-methylaminosulfonyl. In another embodiment, $R^2$ is phenyl substituted with 1, 2, or 3 independently selected substituent(s), at least one of which is N,N-di$(C_1-C_6)$alkylaminosulfonyl. In another embodiment, $R^2$ is phenyl substituted with 1, 2, or 3 independently selected substituent(s), at least one of which is N,N-dimethylaminosulfonyl.

In another embodiment, $R^2$ is monosubstituted phenyl substituted with $(C_1-C_6)$alkylsulfanyl, $(C_1-C_6)$alkylsulfinyl, $(C_1-C_6)$alkylsulfonyl, —S(O)$_2$—NH$_2$, S(O)$_2$N(($C_1-C_6$)alkyl)(O($C_1-C_6$)alkyl)) or N,N-di($C_1-C_6$)alkylaminosulfonyl. In one embodiment, $R^2$ is monosubstituted phenyl substituted with $(C_1-C_6)$alkylsulfonyl, S(O)$_2$N(($C_1-C_6$)alkyl)(O($C_1-C_6$)alkyl)) or N,N-di($C_1-C_6$)alkylaminosulfonyl. In one embodiment, $R^2$ is monosubstituted phenyl substituted with $(C_1-C_6)$alkylsulfonyl. In one embodiment, $R^2$ is monosubstituted phenyl substituted with —S(O)$_2$N(($C_1-C_6$)alkyl)(O($C_1-C_6$)alkyl)). In one embodiment, $R^2$ is monosubstituted phenyl substituted with N,N-di($C_1-C_6$)alkylaminosulfonyl. In one embodiment, $R^2$ is monosubstituted phenyl substituted with methylsulfonyl. In one embodiment, $R^2$ is monosubstituted phenyl substituted with N-methoxy-N-methylaminosulfonyl. In one embodiment, $R^2$ is monosubstituted phenyl substituted with N,N-dimethylaminosulfonyl. In one embodiment, $R^2$ is 4-methylsulfonyl phenyl. In another embodiment, $R^2$ is 4-N,N-dimethylaminosulfonyl phenyl. In one embodiment, $R^2$ is 4-N-methoxy-N-methylaminosulfonyl phenyl.

In another embodiment, $R^2$ is (5- or 6-membered)heteroaryl. The heteroaryl is unsubstituted in one embodiment, monosubstituted in another embodiment, disubstituted in an additional embodiment, or trisubstituted in a further embodiment, wherein the substituent(s) are selected from among the substituents disclosed above in connection with the compounds of formula (Ih). In one embodiment, $R^2$ is thienyl. In another embodiment, $R^2$ is thienyl substituted with —S(O)$_2$NHOH. In another embodiment, $R^2$ is pyridyl. In another embodiment, $R^2$ is pyridyl-N-oxide. In another embodiment, $R^2$ is furyl. In another embodiment, $R^2$ is furyl substituted with —S(O)$_2$NHOH.

In one embodiment, $R^3$ is methyl, ethyl, iso-propyl, or tert-butyl. In another embodiment, $R^3$ is methyl, ethyl, or iso-propyl. In another embodiment, $R^3$ is methyl, ethyl, or tert-butyl. In another embodiment, $R^3$ is methyl, iso-propyl, or tert-butyl. In another embodiment, $R^3$ is ethyl, iso-propyl, or tert-butyl. In another embodiment, $R^3$ is methyl or ethyl. In another embodiment, $R^3$ is methyl or iso-propyl. In another embodiment, $R^3$ is methyl or tert-butyl. In another embodiment, $R^3$ is ethyl or iso-propyl. In another embodiment, $R^3$ is ethyl or tert-butyl. In another embodiment, $R^3$ is iso-propyl or tert-butyl. In another embodiment, $R^3$ is methyl. In another embodiment, $R^3$ is ethyl. In another embodiment, $R^3$ is iso-propyl. In another embodiment, $R^3$ is tert-butyl.

In one embodiment, $R^2$ is $(C_1-C_6)$alkyl substituted with 1, 2 or 3 substituent(s) independently selected from $(C_1-C_6)$alkoxy, —C(=O)OH, or —C(=O)O($C_1-C_6$)alkyl and $R^3$ is methyl. In another embodiment, $R^2$ is $(C_1-C_6)$alkyl substituted with 1, 2 or 3 substituent(s), at least one of which is $(C_1-C_6)$alkoxy and $R^3$ is methyl. In another embodiment, $R^2$ is $(C_1-C_6)$alkyl substituted with 1, 2 or 3 substituent(s), at least one of which is methoxy and $R^3$ is methyl. In another embodiment, $R^2$ is $(C_1-C_6)$alkyl substituted with 1, 2 or 3 substituent(s), at least one of which is ethoxy and $R^3$ is methyl. In another embodiment, $R^2$ is $(C_1-C_4)$alkyl substituted with 1 or 2 substituent(s), at least one of which is methoxy and $R^3$ is methyl. In another embodiment, $R^2$ is $(C_1-C_4)$alkyl substituted with 1 or 2 substituent(s), at least one of which is ethoxy and $R^3$ is methyl. In another embodiment, $R^2$ is $(C_1-C_6)$alkyl substituted with 1 or 2 substituent(s), at least one of which is —C(=O)OH and $R^3$ is methyl. In another embodiment, $R^2$ is $(C_1-C_4)$alkyl substituted with 1 or 2 substituent(s), at least one of which is —C(=O)OH and $R^3$ is methyl. In another embodiment, $R^2$ is $(C_1-C_6)$alkyl substituted with 1, 2 or 3 substituent(s), at least one of which is —C(=O)O($C_1-C_6$)alkyl and $R^3$ is methyl. In another embodiment, $R^2$ is $(C_1-C_6)$alkyl substituted with 1, 2 or 3 substituent(s), at least one of which is —C(=O)O($C_1$)alkyl and $R^3$ is methyl. In another embodiment, $R^2$ is $(C_1-C_6)$alkyl substituted with 1, 2 or 3 substituent(s), at least one of which is —C(=O)O($C_2$)alkyl and $R^3$ is methyl. In another embodiment, $R^2$ is $(C_1-C_4)$alkyl substituted with 1 or 2 substituent(s), at least one of which is —C(=O)O($C_1-C_6$)alkyl and $R^3$ is methyl. In another embodiment, $R^2$ is $(C_1-C_4)$alkyl substituted with 1 or 2 substituent(s), at least one of which is —C(=O)O($C_1$)alkyl and $R^3$ is methyl. In another embodiment, $R^2$ is $(C_1-C_4)$alkyl substituted with 1 or 2 substituent(s), at least one of which is —C(=O)O($C_2$)alkyl and $R^3$ is methyl.

In one embodiment, $R^2$ is unsubstituted phenyl and $R^3$ is methyl. In another embodiment, $R^2$ is unsubstituted phenyl and $R^3$ is ethyl. In one embodiment, $R^2$ is unsubstituted phenyl and $R^3$ is iso-propyl. In another embodiment, $R^2$ is unsubstituted phenyl and $R^3$ is tert-butyl. In one embodiment, $R^2$ is monosubstituted phenyl substituted with $(C_1-C_6)$alkylsulfonyl and $R^3$ is methyl. In another embodiment, $R^2$ is monosubstituted phenyl substituted with $(C_1-C_6)$alkylsulfonyl and $R^3$ is ethyl. In one embodiment, $R^2$ is monosubstituted phenyl substituted with $(C_1-C_6)$alkylsulfonyl and $R^3$ is iso-propyl. In one embodiment, $R^2$ is monosubstituted phenyl substituted with $(C_1-C_6)$alkylsulfonyl and $R^3$ is tert-butyl. In one embodiment, $R^2$ is monosubstituted phenyl substituted with —S(O)$_2$N(($C_1-C_6$)alkyl)(O($C_1-C_6$)alkyl)) and $R^3$ is methyl. In one embodiment, $R^2$ is monosubstituted phenyl substituted with —S(O)$_2$N(($C_1-C_6$)alkyl)(O($C_1-C_6$)alkyl)) and $R^3$ is ethyl. In one embodiment, $R^2$ is monosubstituted phenyl substituted with —S(O)$_2$N(($C_1-C_6$)alkyl)(O($C_1-C_6$)alkyl)) and $R^3$ is iso-propyl. In one embodiment, $R^2$ is monosubstituted phenyl substituted with —S(O)$_2$N(($C_1-C_6$)alkyl)(O($C_1-C_6$)alkyl)) and $R^3$ is tert-butyl. In one embodiment, $R^2$ is monosubstituted phenyl substituted with N,N-di($C_1-C_6$)alkylaminosulfonyl and $R^3$ is methyl. In another embodiment, $R^2$ is monosubstituted phenyl substituted with N,N-di($C_1-C_6$)alkylaminosulfonyl and $R^3$ is ethyl. In one embodiment, $R^2$ is monosubstituted phenyl substituted with N,N-di($C_1-C_6$)alkylaminosulfonyl and $R^3$ is iso-propyl. In one embodiment, $R^2$ is monosubstituted phenyl substituted with (N,N-di($C_1-C_6$)alkylaminosulfonyl and $R^3$ is tert-butyl.

In one embodiment, $R^2$ is monosubstituted phenyl substituted with methylsulfonyl and $R^3$ is methyl. In another embodiment, $R^2$ is monosubstituted phenyl substituted with methylsulfonyl and $R^3$ is ethyl. In one embodiment, $R^2$ is monosubstituted phenyl substituted with methylsulfonyl and $R^3$ is iso-propyl. In one embodiment, $R^2$ is monosubstituted phenyl substituted with methylsulfonyl and $R^3$ is tert-butyl. In one embodiment, $R^2$ is monosubstituted phenyl substituted with N-methoxy-N-methylaminosulfonyl and $R^3$ is methyl. In one embodiment, $R^2$ is monosubstituted phenyl substituted with N-methoxy-N-methylaminosulfonyl and $R^3$ is ethyl. In one embodiment, $R^2$ is monosubstituted phenyl substituted with N-methoxy-N-methylaminosulfonyl and $R^3$ is iso-propyl. In one embodiment, $R^2$ is monosubstituted phenyl substituted with N-methoxy-N-methylaminosulfonyl and $R^3$ is tert-butyl. In one embodiment, $R^2$ is monosubstituted phenyl substituted with N,N-dimethylaminosulfonyl and $R^3$ is methyl. In another embodiment, $R^2$ is monosubstituted phenyl substituted with N,N-dimethylaminosulfonyl and $R^3$ is ethyl. In one embodiment, $R^2$ is monosubstituted phenyl substituted with N,N-dimethylaminosulfonyl and $R^3$ is iso-propyl. In one embodiment, $R^2$ is monosubstituted phenyl substituted with N,N-dimethylaminosulfonyl and $R^3$ is tert-butyl.

In another embodiment, $R^2$ is (5- or 6-membered)heteroaryl and $R^3$ is methyl. In another embodiment, $R^2$ is (5- or 6-membered)heteroaryl and $R^3$ is ethyl. In another embodiment, $R^2$ is (5- or 6-membered)heteroaryl and $R^3$ is iso-propyl. In another embodiment, $R^2$ is (5- or 6-membered)heteroaryl and $R^3$ is tert-butyl. In each of the embodiments in this paragraph, the heteroaryl is unsubstituted in one embodiment, monosubstituted in another embodiment, disubstituted in an additional embodiment, or trisubstituted in a further embodiment, wherein the substituent(s) are selected from among the substituents disclosed above in connection with the compounds of formula (Ih). In one embodiment, $R^2$ is thienyl. In another embodiment, $R^2$ is thienyl substituted with —$S(O)_2NHOH$. In another embodiment, $R^2$ is pyridyl. In another embodiment, $R^2$ is pyridyl-N-oxide. In another embodiment, $R^2$ is furyl. In another embodiment, $R^2$ is furyl substituted with —$S(O)_2NHOH$.

In another embodiment, a pyrazolone derivative compound of the disclosure is compound of formula (Ii)

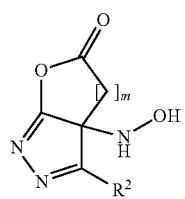

(Ii)

or a pharmaceutically acceptable salt thereof, wherein:
$R^2$ is $(C_1-C_6)$alkyl or phenyl, wherein said phenyl is unsubstituted or substituted with 1, 2, 3, 4, or 5 substituent(s) independently selected from halo, cyano, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —$C(=O)OH$, —$C(=O)O(C_1-C_6)$alkyl, —$C(=O)NR^4R^5$, —$C(=O)$—$(C_5-C_7)$heterocycloalkyl, $(C_5-C_7)$heterocycloalkyl, $(C_6-C_{10})$aryl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —$S(O)_2$—$NH_2$, —$S(O)_2$—$NR^6R^7$, —$S(O)_2$-phenyl, —$S(O)_2$—$(C_5-C_7)$heterocycloalkyl, —$S(=O)(=NR^8)(C_1-C_6)$alkyl, —$NR^4R^5$, N—$(C_1-C_6)$alkylaminosulfonyl, and N,N-di$(C_1-C_6)$alkylaminosulfonyl, wherein said $(C_5-C_7)$heterocycloalkyl is unsubstituted or substituted with 1 or 2 substituent(s) independently selected from halo or $(C_1-C_6)$alkyl; and
m is 1, 2 or 3.

In one embodiment, m is 1. In another embodiment, m is 2. In another embodiment, m is 3.

In another embodiment, $R^2$ is methyl, ethyl, iso-propyl, or tert-butyl. In another embodiment, $R^2$ is methyl, ethyl, or iso-propyl. In another embodiment, $R^2$ is methyl, ethyl, or tert-butyl. In another embodiment, $R^2$ is methyl, iso-propyl, or tert-butyl. In another embodiment, $R^2$ is ethyl, iso-propyl, or tert-butyl. In another embodiment, $R^2$ is methyl or ethyl. In another embodiment, $R^2$ is methyl or iso-propyl. In another embodiment, $R^2$ is methyl or tert-butyl. In another embodiment, $R^2$ is ethyl or iso-propyl. In another embodiment, $R^2$ is ethyl or tert-butyl. In another embodiment, $R^2$ is iso-propyl or tert-butyl. In another embodiment, $R^2$ is methyl. In another embodiment, $R^2$ is ethyl. In another embodiment, $R^2$ is propyl. In another embodiment, $R^2$ is iso-propyl. In another embodiment, $R^2$ is butyl. In another embodiment, $R^2$ is tert-butyl.

In one embodiment, $R^2$ is unsubstituted phenyl. In another embodiment, $R^2$ is phenyl substituted with 1, 2, or 3 independently selected substituent(s), at least one of which is halo. In another embodiment, $R^2$ is phenyl substituted with 1, 2, or 3 independently selected substituent(s), at least one of which is chloro. In another embodiment, $R^2$ is phenyl substituted with 1, 2, or 3 independently selected substituent(s), at least one of which is fluoro. In another embodiment, $R^2$ is phenyl substituted with 1, 2, or 3 independently selected substituent(s), at least one of which is $(C_1-C_6)$alkyl. In another embodiment, $R^2$ is phenyl substituted with 1, 2, or 3 independently selected substituent(s), at least one of which is methyl. In another embodiment, $R^2$ is phenyl substituted with 1, 2, or 3 independently selected substituent(s), at least one of which is $(C_1-C_4)$haloalkyl. In another embodiment, $R^2$ is phenyl substituted with 1, 2, or 3 independently selected substituent(s), at least one of which is $(C_1-C_4)$perhaloalkyl. In another embodiment, $R^2$ is phenyl substituted with 1, 2, or 3 independently selected substituent(s), at least one of which is perfluoromethyl. In another embodiment, $R^2$ is phenyl substituted with 1, 2, or 3 independently selected substituent(s), at least one of which is $(C_1-C_6)$alkoxy. In another embodiment, $R^2$ is phenyl substituted with 1, 2, or 3 independently selected substituent(s), at least one of which is methoxy. In another embodiment, $R^2$ is phenyl substituted with 1, 2, or 3 independently selected substituent(s), at least one of which is $(C_1-C_4)$perhaloalkoxy. In another embodiment, $R^2$ is phenyl substituted with 1, 2, or 3 independently selected substituent(s), at least one of which is $(C_1-C_4)$perfluoroalkoxy.

In another embodiment, $R^2$ is phenyl substituted with 1, 2, or 3 independently selected substituent(s), at least one of which is —$C(=O)OH$. In another embodiment, $R^2$ is phenyl substituted with 1, 2, or 3 independently selected substituent(s), at least one of which is —$C(=O)O(C_1-C_6)$alkyl. In another embodiment, $R^2$ is phenyl substituted with 1, 2, or 3 independently selected substituent(s), at least one of which is —$C(=O)OCH_3$. In another embodiment, $R^2$ is phenyl substituted with 1, 2, or 3 independently selected substituent(s), at least one of which is —$C(=O)NR^4R^5$. In another embodiment, $R^2$ is phenyl substituted with 1, 2, or 3 independently selected substituent(s), at least one of which is —$C(=O)N(CH_3)_2$. In another embodiment, $R^2$ is phenyl substituted with 1, 2, or 3 independently selected substituent(s), at least one of which is —$C(=O)NH_2$. In another embodiment, $R^2$ is phenyl substituted with 1, 2, or 3 independently selected substituent(s), at least one of which is —$C(=O)NH(C_1-C_6)$alkyl, wherein said alkyl is substituted with COOH. In another embodiment, $R^2$ is phenyl substituted with 1, 2, or 3 independently selected substituent(s), at least one of which is —$C(=O)NH$—$(C_1-C_6)$alkylsulfonyl.

In another embodiment, $R^2$ is phenyl substituted with 1, 2, or 3 independently selected substituent(s), at least one of which is —$C(=O)$—$(C_5-C_7)$heterocycloalkyl. In another embodiment, $R^2$ is phenyl substituted with 1, 2, or 3 independently selected substituent(s), at least one of which is —$C(=O)$-morpholinyl, —$C(=O)$-piperidinyl or —$C(=O)$-piperazinyl. In another embodiment, $R^2$ is phenyl substituted with 1, 2, or 3 independently selected substituent(s), at least one of which is —C(=O)-morpholinyl. In another embodiment, $R^2$ is phenyl substituted with 1, 2, or 3 independently selected substituent(s), at least one of which is —C(=O)-piperidinyl. In another embodiment, $R^2$ is phenyl substituted with 1, 2, or 3 independently selected substituent(s), at least one of which is —C(=O)-piperazinyl.

In another embodiment, $R^2$ is phenyl substituted with 1, 2, or 3 independently selected substituent(s), at least one of which is $(C_5-C_7)$heterocycloalkyl. In another embodiment, $R^2$ is phenyl substituted with 1, 2, or 3 independently selected substituent(s), at least one of which is morpholinyl, piperidinyl or piperazinyl. In another embodiment, $R^2$ is phenyl substituted with 1, 2, or 3 independently selected substituent(s), at least one of which is morpholinyl. In another embodiment, $R^2$ is phenyl substituted with 1, 2, or 3 independently selected substituent(s), at least one of which is piperidinyl. In another embodiment, $R^2$ is phenyl substituted with 1, 2, or 3 independently selected substituent(s), at least one of which is piperazinyl.

In another embodiment, $R^2$ is phenyl substituted with 1, 2, or 3 independently selected substituent(s), at least one of which is $(C_1-C_6)$alkylsulfanyl. In another embodiment, $R^2$ is phenyl substituted with 1, 2, or 3 independently selected substituent(s), at least one of which is methylsulfanyl. In another embodiment, $R^2$ is phenyl substituted with 1, 2, or 3 independently selected substituent(s), at least one of which is $(C_1-C_4)$perhaloalkylsulfanyl. In another embodiment, $R^2$ is phenyl substituted with 1, 2, or 3 independently selected substituent(s), at least one of which is trifluoromethylsulfanyl. In another embodiment, $R^2$ is phenyl substituted with 1, 2, or 3 independently selected substituent(s), at least one of which is $(C_1-C_6)$alkylsulfinyl. In another embodiment, $R^2$ is phenyl substituted with 1, 2, or 3 independently selected substituent(s), at least one of which is methylsulfinyl. In another embodiment, $R^2$ is phenyl substituted with 1, 2, or 3 independently selected substituent(s), at least one of which is $(C_1-C_6)$alkylsulfonyl. In another embodiment, $R^2$ is phenyl substituted with 1, 2, or 3 independently selected substituent(s), at least one of which is methylsulfonyl. In another embodiment, $R^2$ is phenyl substituted with 1, 2, or 3 independently selected substituent(s), at least one of which is $(C_3-C_6)$cycloalkylsulfonyl. In another embodiment, $R^2$ is phenyl substituted with 1, 2, or 3 independently selected substituent(s), at least one of which is cyclopropylsulfonyl.

In another embodiment, $R^2$ is phenyl substituted with 1, 2, or 3 independently selected substituent(s), at least one of which is $(C_1-C_4)$haloalkylsulfinyl. In another embodiment, $R^2$ is phenyl substituted with 1, 2, or 3 independently selected substituent(s), at least one of which is $(C_1-C_4)$haloalkylsulfonyl. In another embodiment, $R^2$ is phenyl substituted with 1, 2, or 3 independently selected substituent(s), at least one of which is $(C_1-C_4)$perhaloalkylsulfinyl. In another embodiment, $R^2$ is phenyl substituted with 1, 2, or 3 independently selected substituent(s), at least one of which is perhalomethylsulfinyl. In another embodiment, $R^2$ is phenyl substituted with 1, 2, or 3 independently selected substituent(s), at least one of which is perfluoromethylsulfinyl. In another embodiment, $R^2$ is phenyl substituted with 1, 2, or 3 independently selected substituent(s), at least one of which is $(C_1-C_4)$perhaloalkylsulfonyl. In another embodiment, $R^2$ is phenyl substituted with 1, 2, or 3 independently selected substituent(s), at least one of which is perhalomethylsulfonyl. In another embodiment, $R^2$ is phenyl substituted with 1, 2, or 3 independently selected substituent(s), at least one of which is perfluoromethylsulfonyl.

In another embodiment, $R^2$ is phenyl substituted with 1, 2, or 3 independently selected substituent(s), at least one of which is —S(O)$_2$—NR$^6$R$^7$. In another embodiment, $R^2$ is phenyl substituted with 1, 2, or 3 independently selected substituent(s), at least one of which is —S(O)$_2$—N(CH$_3$)(CH$_2$CH$_2$OCH$_3$), —S(O)$_2$—NH(CH$_2$CH$_2$OCH$_3$), —S(O)$_2$—N(CH$_3$)$_2$ or —S(O)$_2$—NH(CH$_3$).

In another embodiment, $R^2$ is phenyl substituted with 1, 2, or 3 independently selected substituent(s), at least one of which is —S(O)$_2$-phenyl. In another embodiment, $R^2$ is phenyl substituted with 1, 2, or 3 independently selected substituent(s), at least one of which is —S(O)$_2$—$(C_5-C_7)$heterocycloalkyl. In another embodiment, $R^2$ is phenyl substituted with 1, 2, or 3 independently selected substituent(s), at least one of which is —S(O)$_2$-morpholinyl, —S(O)$_2$-piperidinyl or —S(O)$_2$-piperazinyl. In another embodiment, $R^2$ is phenyl substituted with 1, 2, or 3 independently selected substituent(s), at least one of which is —S(O)$_2$-morpholinyl. In another embodiment, $R^2$ is phenyl substituted with 1, 2, or 3 independently selected substituent(s), at least one of which is —S(O)$_2$-piperidinyl. In another embodiment, $R^2$ is phenyl substituted with 1, 2, or 3 independently selected substituent(s), at least one of which is —S(O)$_2$-piperazinyl.

In another embodiment, $R^2$ is phenyl substituted with 1, 2, or 3 independently selected substituent(s), at least one of which is —S(=O)(=NR$^8$)(C$_1$-C$_6$)alkyl. In another embodiment, $R^2$ is phenyl substituted with 1, 2, or 3 independently selected substituent(s), at least one of which is —S(=O)(=NR$^8$)(CH$_3$). In another embodiment, $R^2$ is phenyl substituted with 1, 2, or 3 independently selected substituent(s), at least one of which is —S(=O)(=NH)(C$_1$-C$_6$)alkyl or —S(=O)(=NC(=O)CF$_3$)(C$_1$-C$_6$)alkyl. In another embodiment, $R^2$ is phenyl substituted with 1, 2, or 3 independently selected substituent(s), at least one of which is —S(=O)(=NH)(CH$_3$) or —S(=O)(=NC(=O)CF$_3$)(CH$_3$).

In another embodiment, $R^2$ is phenyl substituted with 1, 2, or 3 independently selected substituent(s), at least one of which is N,N-di(C$_1$-C$_6$)alkylaminosulfonyl. In another embodiment, $R^2$ is phenyl substituted with 1, 2, or 3 independently selected substituent(s), at least one of which is N,N-dimethylaminosulfonyl.

In another embodiment, $R^2$ is phenyl wherein the phenyl is unsubstituted or substituted with 1, 2, or 3 substituent(s) independently selected from halo, (C$_1$-C$_6$)alkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)—(C$_5$-C$_7$)heterocycloalkyl, (C$_5$-C$_7$)heterocycloalkyl, (C$_1$-C$_6$)alkylsulfanyl, (C$_1$-C$_4$)perhaloalkylsulfanyl, (C$_1$-C$_6$)alkylsulfinyl, (C$_1$-C$_6$)alkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$—(C$_5$-C$_7$)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl. In another embodiment, $R^2$ is phenyl wherein the phenyl is unsubstituted or substituted with 1, 2, or 3 substituent(s) independently selected from halo, (C$_1$-C$_6$)alkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)—(C$_5$-C$_7$)heterocycloalkyl, (C$_5$-C$_7$)heterocycloalkyl, (C$_1$-C$_6$)alkylsulfanyl, (C$_1$-C$_4$)perhaloalkylsulfanyl, $(C_1-C_6)$alkylsulfinyl, $(C_1-C_6)$alkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NR$^6$R$^7$, —S(O)$_2$-phenyl, —S(O)$_2$—(C$_5$-C$_7$)heterocycloalkyl, —S(=O)(=NR$^8$)(C$_1$-C$_6$)alkyl, —NR$^4$R$^5$, and N,N-di(C$_1$-C$_6$)alkylaminosulfonyl. In another embodiment, R$^2$ is phenyl wherein the phenyl is unsubstituted or substituted with 1, 2, or 3 substituent(s) independently selected from chloro, fluoro, bromo, trifluoromethyl, methyl, butyl, methylsulfanyl, methylsulfinyl, methylsulfonyl, ethylsulfonyl, propylsulfonyl, phenylsulfonyl, methylsulfonylcarbamyl, methoxy, carboxyl, methylsulfonylcarbamyl, formamidopropanoic acid, formamidoacetic acid, methoxycarbonyl, morpholinylcarbonyl, 4,4-difluoropiperidinylcarbonyl, trifluoromethoxy, trifluoromethylsulfinyl, trifluoromethylsulfonyl, trifluoromethylsulfanyl, morpholinylsulfonyl, 4,4-difluoropiperidinylsulfonyl, N,N-dimethylcarbamyl, (methyl)oxo-λ$^6$-sulfanylidene-2,2,2-trifluoroacetamide, methylsulfonimidoyl, isopropylsulfonimidoyl, (methoxyethyl)methylamino, (methoxyethyl)-N-methyl-aminosulfonyl, dimethylcarbamyl, carbamyl, and N,N-dimethylaminosulfonyl. In another embodiment, R$^2$ is phenyl wherein the phenyl is unsubstituted or substituted with 1, 2, or 3 substituent(s) independently selected from 2-chloro, 3-chloro, 4-chloro, 5-chloro, 2-fluoro, 3-fluoro, 4-fluoro, 5-fluoro, 2-bromo, 3-bromo, 4-bromo, 5-bromo, 2-trifluoromethyl, 3-trifluoromethyl, 4-trifluoromethyl, 2-methyl, 3-methyl, 4-methyl, 5-methyl, 2-butyl, 3-butyl, 4-butyl, 5-butyl, 4-methylsulfanyl, 2-methylsulfinyl, 4-methylsulfinyl, 3-methylsulfonyl, 4-methylsulfonyl, 4-ethylsulfonyl, 4-propylsulfonyl, 2-methoxy, 4-methoxy, 2-trifluoromethoxy, 4-trifluoromethoxy, 4-carboxyl, 4-methylsulfonylcarbamyl, 4-formamidopropanoic acid, 4-formamidoacetic acid, 4-methoxycarbonyl, 4-morpholinylcarbonyl, 4-(4,4-difluoropiperidinylcarbonyl), 4-isopropylsulfonyl, 4-trifluoromethylsulfanyl, 4-trifluoromethylsulfinyl, 4-trifluoromethylsulfonyl, 4-phenylsulfonyl, 4-morpholinylsulfonyl, 4-(4,4-difluoropiperidinyl)sulfonyl, 4-dimethylcarbamyl, 4-(methyl)oxo-λ$^6$-sulfanylidene-2,2,2-trifluoroacetamide, 4-methylsulfonimidoyl, 4-isopropylsulfonimidoyl, 4-(methoxyethyl)-N-methyl-aminosulfonyl, 4-carbamyl, and 4-N,N-dimethylaminosulfonyl.

In another embodiment, R$^2$ is monosubstituted phenyl substituted with halo, $(C_1-C_6)$alkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O(C$_1$-C$_6$)alkyl, —C(=O)NR$^4$R$^5$, —C(=O)—(C$_5$-C$_7$)heterocycloalkyl, $(C_1-C_6)$alkylsulfanyl, $(C_1-C_4)$perhaloalkylsulfanyl, $(C_1-C_6)$alkylsulfinyl, $(C_1-C_6)$alkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$—(C$_5$-C$_7$)heterocycloalkyl, —S(=O)(=NR$^8$)(C$_1$-C$_6$)alkyl, N—(C$_1$-C$_6$)alkylaminosulfonyl, or N,N-di(C$_1$-C$_6$)alkylaminosulfonyl. In another embodiment, R$^2$ is monosubstituted phenyl substituted with chloro, fluoro, bromo, methyl, butyl, trifluoromethyl, methoxy, trifluoromethoxy, morpholinyl, piperazinyl, methylpiperazinyl, carboxyl, methylsulfonylcarbamyl, formamidopropanoic acid, formamidoacetic acid, methoxycarbonyl, morpholinylcarbonyl, 4,4-difluoropiperidinylcarbonyl, methylsulfanyl, methylsulfinyl, methylsulfonyl, ethylsulfonyl, propylsulfonyl, trifluoromethylsulfanyl, trifluoromethylsulfinyl, trifluoromethylsulfonyl, phenylsulfonyl, morpholinylsulfonyl, 4,4-difluoropiperidinylsulfonyl, dimethylcarbamyl, (methyl)oxo-λ$^6$-sulfanylidene-2,2,2-trifluoroacetamide, methylsulfonimidoyl, isopropylsulfonimidoyl, (methoxyethyl)-N-methyl-aminosulfonyl, carbamyl, methoxyethyl(methyl)amino and dimethylamino or N,N-dimethylaminosulfonyl. In another embodiment, R$^2$ is monosubstituted phenyl substituted with 2-chloro, 3-chloro, 4-chloro, 5-chloro, 2-fluoro, 3-fluoro, 4-fluoro, 5-fluoro, 4-bromo, 2-methyl, 3-methyl, 4-methyl, 5-methyl, 4-butyl, 4-t-butyl, 2-trifluoromethyl, 3-trifluoromethyl, 4-trifluoromethyl, 5-trifluoromethyl, 2-methoxy, 3-methoxy, 4-methoxy, 2-trifluoromethoxy, 4-trifluoromethoxy, 3-morpholin-4-yl, 3-(piperazin-1-yl), 3-(4-methylpiperazin-1-yl), 4-carboxyl, 4-methylsulfonylcarbamyl, 4-formamidopropanoic acid, 4-formamidoacetic acid, 4-methoxycarbonyl, 4-morpholinylcarbonyl, 4-(4,4-difluoropiperidinylcarbonyl), 4-methylsulfanyl, 2-methylsulfinyl, 4-methylsulfinyl, 3-methylsulfonyl, 4-methylsulfonyl, 4-ethylsulfonyl, 4-propylsulfonyl, 4-isopropylsulfonyl, 4-trifluoromethylsulfanyl, 4-trifluoromethylsulfinyl, 4-trifluoromethylsulfonyl, 4-phenylsulfonyl, 4-morpholinylsulfonyl, 4-(4,4-difluoropiperidinyl)sulfonyl, 4-dimethylcarbamyl, 4-(methyl)oxo-λ$^6$-sulfanylidene-2,2,2-trifluoroacetamide, 4-methylsulfonimidoyl, 4-isopropylsulfonimidoyl, 4-(methoxyethyl)-N-methyl-aminosulfonyl, 4-carbamyl, 4-methoxyethyl(methyl)amino, 3-dimethylamino or 4-N,N-dimethylaminosulfonyl.

In another embodiment, R$^2$ is disubstituted phenyl, each substituent being independently selected from halo, $(C_1-C_6)$alkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O(C$_1$-C$_6$)alkyl, —C(=O)NR$^4$R$^5$, —C(=O)—(C$_5$-C$_7$)heterocycloalkyl, $(C_5-C_7)$heterocycloalkyl, $(C_1-C_6)$alkylsulfanyl, $(C_1-C_4)$perhaloalkylsulfanyl, $(C_1-C_6)$alkylsulfinyl, $(C_1-C_6)$alkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$—(C$_5$-C$_7$)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl. In another embodiment, R$^2$ is disubstituted phenyl, each substituent being independently selected from halo, $(C_1-C_6)$alkyl, $(C_1-C_4)$perhaloalkyl, $(C_1-C_6)$alkoxy, $(C_5-C_7)$heterocycloalkyl, $(C_1-C_6)$alkylsulfinyl, $(C_1-C_6)$alkylsulfonyl and —NR$^4$R$^5$. In another embodiment, R$^2$ is disubstituted phenyl, each substituent being independently selected from chloro, fluoro, methyl, trifluoromethyl, methoxy, morpholinyl, piperazinyl, methylpiperazinyl, methylsulfinyl, methylsulfonyl, methoxyethyl(methyl)amino and dimethylamino. In another embodiment, R$^2$ is disubstituted phenyl, each substituent being independently selected from 2-chloro, 3-chloro, 4-chloro, 5-chloro, 3-fluoro, 4-fluoro, 5-fluoro, 3-methyl, 5-methyl, 3-trifluoromethyl, 5-trifluoromethyl, 2-methoxy, 3-methoxy, 4-methoxy, 3-morpholin-4-yl, 3-(piperazin-1-yl), 3-(4-methylpiperazin-1-yl), 4-methylsulfinyl, 3-methylsulfonyl, 4-methylsulfonyl, 4-methoxyethyl(methyl)amino and 3-dimethylamino.

In another embodiment, $R^2$ is trisubstituted phenyl, each substituent being independently selected from halo, $(C_1-C_6)$alkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O$(C_1-C_6)$alkyl, —C(=O)NR$^4$R$^5$, —C(=O)—$(C_5-C_7)$heterocycloalkyl, $(C_5-C_7)$heterocycloalkyl, $(C_1-C_6)$alkylsulfanyl, $(C_1-C_4)$perhaloalkylsulfanyl, $(C_1-C_6)$alkylsulfinyl, $(C_1-C_6)$alkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$—$(C_5-C_7)$heterocycloalkyl, —S(=O)(=NR$^8$)$(C_1-C_6)$alkyl, —NR$^4$R$^5$, N—$(C_1-C_6)$alkylaminosulfonyl, and N,N-di$(C_1-C_6)$alkylaminosulfonyl. In another embodiment, $R^2$ is trisubstituted phenyl, each substituent being independently selected from halo, $(C_1-C_6)$alkyl, and $(C_1-C_6)$alkylsulfonyl. In another embodiment, $R^2$ is trisubstituted phenyl, each substituent being independently selected from fluoro, methyl and methylsulfonyl.

In another embodiment, $R^2$ is selected from unsubstituted phenyl, 4-chlorophenyl, 2-chlorophenyl, 3-chlorophenyl, 2,3-dichlorophenyl, 2,4-dichlorophenyl, 3,5-dichlorophenyl, 2-fluorophenyl, 4-fluorophenyl, 4-bromophenyl, 2-chloro-4-fluorophenyl, 2-methylphenyl, 4-butylphenyl, 4-t-butylphenyl, 3,5-dimethylphenyl, 4-methoxyphenyl, 2-methoxyphenyl, 2-trifluoromethoxyphenyl, 4-trifluoromethoxyphenyl, 4-methoxycarbonylphenyl, 4-carboxyl, 4-carbamylphenyl, 4-phenyl(formamido)propanoic acid, 4-phenyl(formamido)acetic acid, 4-N,N-dimethylcarbamylphenyl, 4-cyclopropylsulfonylphenyl, 4-phenylsulfonyl, 4-(4-4-difluoropiperidin-1-yl)sulfonylphenyl, 4-(isopropylsulfonimidoyl)phenyl, 4-morpholine-4-sulfonylphenyl, 4-morpholine-4-carbonylphenyl, 4-(4,4-difluoropiperidine-1-carbonyl)phenyl, 3-morpholinyl-4-methylsulfonylphenyl, 3-(methoxyethyl)methylamino-4-methylsulfonylphenyl, 3,5-difluoro-4-methylsulfonylphenyl, 2-ethoxy-4-fluorophenyl, 3-fluoro-4-methoxyphenyl, 2-trifluoromethylphenyl, 3-trifluoromethylphenyl, 4-trifluoromethylphenyl, 3,5-bis(trifluoromethyl)phenyl, 3-methylsulfonylphenyl, 4-methylsulfanylphenyl, 4-trifluoromethylsulfanylphenyl, 2-methylsulfinylphenyl, 4-methylsulfinylphenyl, 3-fluoro-4-methylsulfinylphenyl, 3-methyl-4-methylsulfinylphenyl, 4-methylsulfonylphenyl, 4-ethylsulfonylphenyl, 4-isopropylsulfonylphenyl, 4-morpholine-4-methylsulfonylphenyl, 3-(4-methylpiperazin-1-yl)-4-methylsulfonylphenyl, 3-piperazin-1-yl-4-methylsulfonylphenyl, 3-methoxy-4-methylsulfonylphenyl, 3-trifluoromethyl-4-methylsulfonylphenyl, 3-fluoro-4-methylsulfonylphenyl, 3-chloro-4-methylsulfonylphenyl, 3-methyl-4-methylsulfonylphenyl, 3,4-dimethylsulfonylphenyl, 3,5-dimethyl-4-methylsulfonylphenyl, 3-(dimethylamino)-4-methylsulfonylphenyl, 4-trifluoromethylsulfinylphenyl, 4-trifluoromethylsulfonylphenyl, 4-phenyl(methyl)oxo-$\lambda^6$-sulfanylidene-2,2,2-trifluoroacetamide, 4-methylsulfonimidoylphenyl, 4-isopropylsulfonimidoylphenyl, and 4-N,N-dimethylaminosulfonylphenyl. In another embodiment, $R^2$ is unsubstituted phenyl. In another embodiment, $R^2$ is 4-chlorophenyl. In another embodiment, $R^2$ is 2-chlorophenyl. In another embodiment, $R^2$ is 3-chlorophenyl. In another embodiment, $R^2$ is 2,3-dichlorophenyl. In another embodiment, $R^2$ is 2,4-dichlorophenyl. In another embodiment, $R^2$ is 3,5-dichlorophenyl. In another embodiment, $R^2$ is 2-fluorophenyl. In another embodiment, $R^2$ is 4-fluorophenyl. In another embodiment, $R^2$ is 4-bromophenyl. In another embodiment, $R^2$ is 2-chloro-4-fluorophenyl. In another embodiment, $R^2$ is 2-methylphenyl. In another embodiment, $R^2$ is 4-butylphenyl. In another embodiment, $R^2$ is 4-t-butylphenyl. In another embodiment, $R^2$ is 3,5-dimethylphenyl. In another embodiment, $R^2$ is 4-methoxyphenyl. In another embodiment, $R^2$ is 2-methoxyphenyl. In another embodiment, $R^2$ is 2-trifluoromethoxyphenyl. In another embodiment, $R^2$ is 4-trifluoromethoxyphenyl. In another embodiment, $R^2$ is 4-methoxycarbonylphenyl. In another embodiment, $R^2$ is 4-carboxylphenyl. In another embodiment, $R^2$ is 4-carbamylphenyl. In another embodiment, $R^2$ is 4-phenyl(formamido)propanoic acid. In another embodiment, $R^2$ is 4-phenyl(formamido)acetic acid. In another embodiment, $R^2$ is 4-N,N-dimethylcarbamylphenyl. In another embodiment, $R^2$ is 4-cyclopropylsulfonylphenyl. In another embodiment, $R^2$ is 4-phenylsulfonyl. In another embodiment, $R^2$ is 4-(4,4-difluoropiperidin-1-yl)sulfonylphenyl. In another embodiment, $R^2$ is 4-(isopropylsulfonimidoyl)phenyl. In another embodiment, $R^2$ is 4-morpholine-4-sulfonylphenyl. In another embodiment, $R^2$ is 4-morpholine-4-carbonylphenyl. In another embodiment, $R^2$ is 4-(4,4-difluoropiperidine-1-carbonyl)phenyl. In another embodiment, $R^2$ is 3-morpholinyl-4-methylsulfonylphenyl. In another embodiment, $R^2$ is 3-(methoxyethyl)methylamino-4-methylsulfonylphenyl. In another embodiment, $R^2$ is 3,5-difluoro-4-methylsulfonylphenyl. In another embodiment, $R^2$ is 3,5-difluoro-4-methylsulfonylphenyl. In another embodiment, $R^2$ is 2-ethoxy-4-fluorophenyl. In another embodiment, $R^2$ is 3-fluoro-4-methoxyphenyl. In another embodiment, $R^2$ is 2-trifluoromethylphenyl. In another embodiment, $R^2$ is 3-trifluoromethylphenyl. In another embodiment, $R^2$ is 4-trifluoromethylphenyl. In another embodiment, $R^2$ is 3,5-bis(trifluoromethyl)phenyl. In another embodiment, $R^2$ is 3-methylsulfonylphenyl. In another embodiment, $R^2$ is 4-methylsulfanylphenyl. In another embodiment, $R^2$ is 4-trifluoromethylsulfanylphenyl. In another embodiment, $R^2$ is 2-methylsulfinylphenyl. In another embodiment, $R^2$ is 4-methylsulfinylphenyl. In another embodiment, $R^2$ is 3-fluoro-4-methylsulfinylphenyl. In another embodiment, $R^2$ is 3-methyl-4-methylsulfinylphenyl. In another embodiment, $R^2$ is 4-methylsulfonylphenyl. In another embodiment, $R^2$ is 4-ethylsulfonylphenyl. In another embodiment, $R^2$ is 4-isopropylsulfonylphenyl. In another embodiment, $R^2$ is 4-morpholine-4-methylsulfonylphenyl. In another embodiment, $R^2$ is 3-(4-methylpiperazin-1-yl)-4-methylsulfonylphenyl. In another embodiment, $R^2$ is 3-piperazin-1-yl-4-methylsulfonylphenyl. In another embodiment, $R^2$ is 3-methoxy-4-methylsulfonylphenyl. In another embodiment, $R^2$ is 3-trifluoromethyl-4-methylsulfonylphenyl. In another embodiment, $R^2$ is 3-fluoro-4-methylsulfonylphenyl. In another embodiment, $R^2$ is 3-chloro-4-methylsulfonylphenyl. In another embodiment, $R^2$ is 3-methyl-4-methylsulfonylphenyl. In another embodiment, $R^2$ is 3,5-dimethyl-4-methylsulfonylphenyl. In another embodiment, $R^2$ is 3-(dimethylamino)-4-methylsulfonylphenyl. In another embodiment, $R^2$ is 4-trifluoromethylsulfinylphenyl. In another embodiment, $R^2$ is 4-trifluoromethylsulfonylphenyl. In another embodiment, $R^2$ is 4-phenyl(methyl)oxo-$\lambda^6$-sulfanylidene-2,2,2-trifluoroacetamide. In another embodiment, $R^2$ is 4-methylsulfonimidoylphenyl. In another embodiment, $R^2$ is 4-isopropylsulfonimidoylphenyl. In another embodiment, $R^2$ is 4-N,N-dimethylaminosulfonylphenyl.

In another embodiment, m is 1 and $R^2$ is unsubstituted phenyl. In another embodiment, m is 2 and $R^2$ is unsubstituted phenyl. In another embodiment, m is 3 and $R^2$ is unsubstituted phenyl. In another embodiment, m is 1 and $R^2$ is monosubstituted phenyl, e.g., selected from among the monosubstituted $R^2$ phenyl groups disclosed above in connection with the compounds of formula (Ii). In another embodiment, m is 2 and $R^2$ is monosubstituted phenyl, e.g., selected from among the monosubstituted $R^2$ phenyl groups disclosed above in connection with the compounds of formula (Ii). In another embodiment, m is 3 and $R^2$ is monosubstituted phenyl, e.g., selected from among the monosubstituted $R^2$ phenyl groups disclosed above in connection with the compounds of formula (Ii). In another embodiment, m is 1 and $R^2$ is disubstituted phenyl, e.g., selected from among the disubstituted $R^2$ phenyl groups disclosed above in connection with the compounds of formula (Ii). In another embodiment, m is 2 and $R^2$ is disubstituted phenyl, e.g., selected from among the disubstituted $R^2$ phenyl groups disclosed above in connection with the compounds of formula (Ii). In another embodiment, m is 3 and $R^2$ is disubstituted phenyl, e.g., selected from among the disubstituted $R^2$ phenyl groups disclosed above in connection with the compounds of formula (Ii). In another embodiment, m is 1 and $R^2$ is trisubstituted phenyl, e.g., selected from among the trisubstituted $R^2$ phenyl groups disclosed above in connection with the compounds of formula (Ii). In another embodiment, m is 2 and $R^2$ is trisubstituted phenyl, e.g., selected from among the trisubstituted $R^2$ phenyl groups disclosed above in connection with the compounds of formula (Ii). In another embodiment, $R^1$ is m is 3 and $R^2$ is trisubstituted phenyl, e.g., selected from among the trisubstituted $R^2$ phenyl groups disclosed above in connection with the compounds of formula (Ii).

In another embodiment, m is 1 and $R^2$ is methyl. In another embodiment, m is 1 and $R^2$ is ethyl. In another embodiment, m is 1 and $R^2$ is propyl. In another embodiment, m is 1 and $R^2$ is iso-propyl. In another embodiment, m is 1 and $R^2$ is butyl. In another embodiment, m is 1 and $R^2$ is tert-butyl. In another embodiment, m is 2 and $R^2$ is methyl. In another embodiment, m is 2 and $R^2$ is ethyl. In another embodiment, m is 2 and $R^2$ is propyl. In another embodiment, m is 2 and $R^2$ is iso-propyl. In another embodiment, m is 2 and $R^2$ is butyl. In another embodiment, m is 2 and $R^2$ is tert-butyl. In another embodiment, m is 3 and $R^2$ is methyl. In another embodiment, m is 3 and $R^2$ is ethyl. In another embodiment, m is 3 and $R^2$ is propyl. In another embodiment, m is 3 and $R^2$ is iso-propyl. In another embodiment, m is 3 and $R^2$ is butyl. In another embodiment, m is 3 and $R^2$ is tert-butyl.

In addition to the compounds of formulae (Ia)-(Ii), the present disclosure provides prodrugs thereof. In particular, the present disclosure provides a compound of formula (IIa) or formula (IIb):

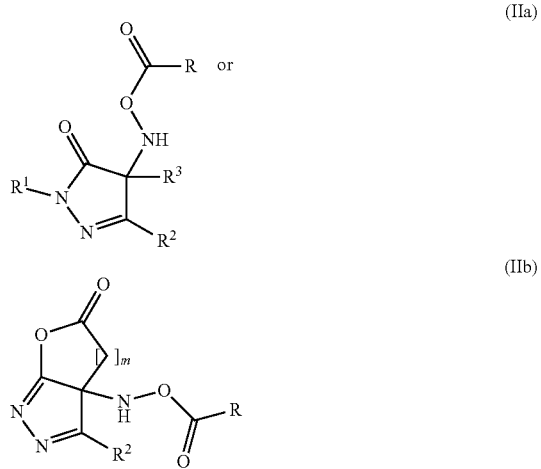

or a pharmaceutically acceptable salt thereof, wherein:

$R^1$, $R^2$, $R^3$ and m together are as defined herein for each of compounds of formulae (Ia), (Ib), (Ic), (Id), (Ie), (If), (Ig), (Ih) and (Ii); and R is hydrogen, —$(C_1$-$C_6)$alkyl, —$(C_2$-$C_4)$alkenyl, phenyl, benzyl, cyclopentyl, cyclohexyl, —$(C_5$-$C_7)$heterocycloalkyl, benzyloxy, —O—$(C_1$-$C_6)$alkyl, —$NH_2$, —NH—$(C_1$-$C_4)$alkyl, or —N$((C_1$-$C_4)$alkyl$)_2$, wherein said —$(C_1$-$C_6)$alkyl, —$(C_2$-$C_4)$alkenyl, phenyl, benzyl, cyclopentyl, cyclohexyl, —$(C_5$-$C_7)$heterocycloalkyl, benzyloxy, —O—$(C_1$-$C_6)$alkyl, —NH—$(C_1$-$C_4)$alkyl, or —N$((C_1$-$C_4)$alkyl$)_2$ can be unsubstituted or substituted with 1, 2 or 3 substituents selected from halo, —$(C_1$-$C_6)$alkyl, —$(C_2$-$C_4)$alkenyl, —$(C_2$-$C_3)$alkynyl, -(5- or 6-membered)heteroaryl, —O—$(C_1$-$C_6)$alkyl, —S—$(C_1$-$C_6)$alkyl, —C(halo)$_3$, —CH(halo)$_2$, —$CH_2$(halo), —CN, —$NO_2$, —$NH_2$, —NH—$(C_1$-$C_4)$alkyl, —N(—$(C_1$-$C_4)$alkyl$)_2$, —C(O)$(C_1$-$C_4)$alkyl, —C(O)O$(C_1$-$C_4)$alkyl, —OC(O)$(C_1$-$C_4)$alkyl, —OC(O)$NH_2$, —S(O)$(C_1$-$C_4)$alkyl, or —S(O)$_2$$(C_1$-$C_4)$alkyl.

In particular embodiments, R is methyl, ethyl, benzyl, or phenyl. In particular embodiments, R is methyl or ethyl. In particular embodiments, R is methyl. In particular embodiments, R is ethyl. In particular embodiments, R is benzyl or phenyl. In particular embodiments, R is benzyl. In particular embodiments, R is phenyl. In other embodiments, R is —$NH_2$. In each of the above embodiments in this paragraph, R is unsubstituted in one embodiment, monosubstituted in another embodiment, disubstituted with two independently selected substituents in an additional embodiment, or trisubstituted with three independently selected substituents in a further embodiment. In various embodiments of each of the above embodiments in this paragraph, the substituent is -halo, —$NH_2$, —$NHCH_3$, —$CF_3$ or —$OCH_3$ or the substituents are independently selected from -halo, —$NH_2$, —$NHCH_3$, —$CF_3$ or —$OCH_3$.

In one embodiment, the compound is a compound of formula (IIa). In each of the embodiments in this paragraph, the compound is a compound of formula (IIa). In particular embodiments, $R^1$, $R^2$ and $R^3$ together are as defined herein compound of formula (Ia). In other embodiments, $R^1$, $R^2$ and $R^3$ together are as defined herein compound of formula (Ib). In other embodiments, $R^1$, $R^2$ and $R^3$ together are as defined herein compound of formula (Ic). In other embodiments, $R^1$, $R^2$ and $R^3$ together are as defined herein compound of formula (Id). In other embodiments, $R^1$, $R^2$ and $R^3$ together are as defined herein compound of formula (Ie). In other embodiments, $R^1$, $R^2$ and $R^3$ together are as defined herein compound of formula (If), In other embodiments, $R^1$, $R^2$ and $R^3$ together are as defined herein compound of formula (Ig). In other embodiments, $R^1$, $R^2$ and $R^3$ together are as defined herein compound of formula (Ih).

In one embodiment, the compound is a compound of formula (IIb). In another embodiment, the compound is a compound of formula (IIb) and m and $R^2$ together are as defined herein compound of formula (Ii).

In each of the embodiments in this paragraph, the compound is a compound of formula (IIa). In one embodiment, $R^1$, $R^2$ and $R^3$ together are as defined herein compound of formula (Ia) and R is methyl, ethyl, benzyl, or phenyl. In one embodiment, $R^1$, $R^2$ and $R^3$ together are as defined herein compound of formula (Ia) and R is methyl or ethyl. In one embodiment, $R^1$, $R^2$ and $R^3$ together are as defined herein compound of formula (Ia) and R is methyl. In one embodiment, $R^1$, $R^2$ and $R^3$ together are as defined herein compound of formula (Ia) and R is ethyl. In one embodiment, $R^1$, $R^2$ and $R^3$ together are as defined herein compound of formula (Ia) and R is benzyl or phenyl. In one embodiment, $R^1$, $R^2$ and $R^3$ together are as defined herein compound of formula (Ia) and R is benzyl. In one embodiment, $R^1$, $R^2$ and $R^3$ together are as defined herein compound of formula (Ia) and R is phenyl. In one embodiment, $R^1$, $R^2$ and $R^3$ together are as defined herein compound of formula (Ia) and R is —NH$_2$. In each of the above embodiments in this paragraph, R is unsubstituted in one embodiment, monosubstituted in another embodiment, disubstituted with two independently selected substitutents in an additional embodiment, or tri-substituted with three independently selected substitutents in a further embodiment. In various embodiments of each of the above embodiments in this paragraph, the substituent is -halo, —NH$_2$, —NHCH$_3$, —CF$_3$ or —OCH$_3$ or the substituents are independently selected from -halo, —NH$_2$, —NHCH$_3$, —CF$_3$ or —OCH$_3$.

In each of the embodiments in this paragraph, the compound is a compound of formula (IIa). In one embodiment, $R^1$, $R^2$ and $R^3$ together are as defined herein compound of formula (Ib) and R is methyl, ethyl, benzyl, or phenyl. In one embodiment, $R^1$, $R^2$ and $R^3$ together are as defined herein compound of formula (Ib) and R is methyl or ethyl. In one embodiment, $R^1$, $R^2$ and $R^3$ together are as defined herein compound of formula (Ib) and R is methyl. In one embodiment, $R^1$, $R^2$ and $R^3$ together are as defined herein compound of formula (Ib) and R is ethyl. In one embodiment, $R^1$, $R^2$ and $R^3$ together are as defined herein compound of formula (Ib) and R is benzyl or phenyl. In one embodiment, $R^1$, $R^2$ and $R^3$ together are as defined herein compound of formula (Ib) and R is benzyl. In one embodiment, $R^1$, $R^2$ and $R^3$ together are as defined herein compound of formula (Ib) and R is phenyl. In one embodiment, $R^1$, $R^2$ and $R^3$ together are as defined herein compound of formula (Ib) and R is —NH$_2$. In each of the above embodiments in this paragraph, R is unsubstituted in one embodiment, monosubstituted in another embodiment, disubstituted with two independently selected substitutents in an additional embodiment, or tri-substituted with three independently selected substitutents in a further embodiment. In various embodiments of each of the above embodiments in this paragraph, the substituent is -halo, —NH$_2$, —NHCH$_3$, —CF$_3$ or —OCH$_3$ or the substituents are independently selected from -halo, —NH$_2$, —NHCH$_3$, —CF$_3$ or —OCH$_3$.

In each of the embodiments in this paragraph, the compound is a compound of formula (IIa). In one embodiment, $R^1$, $R^2$ and $R^3$ together are as defined herein compound of formula (Ic) and R is methyl, ethyl, benzyl, or phenyl. In one embodiment, $R^1$, $R^2$ and $R^3$ together are as defined herein compound of formula (Ic) and R is methyl or ethyl. In one embodiment, $R^1$, $R^2$ and $R^3$ together are as defined herein compound of formula (Ic) and R is methyl. In one embodiment, $R^1$, $R^2$ and $R^3$ together are as defined herein compound of formula (Ic) and R is ethyl. In one embodiment, $R^1$, $R^2$ and $R^3$ together are as defined herein compound of formula (Ic) and R is benzyl or phenyl. In one embodiment, $R^1$, $R^2$ and $R^3$ together are as defined herein compound of formula (Ic) and R is benzyl. In one embodiment, $R^1$, $R^2$ and $R^3$ together are as defined herein compound of formula (Ic) and R is phenyl. In one embodiment, $R^1$, $R^2$ and $R^3$ together are as defined herein compound of formula (Ic) and R is —NH$_2$. In each of the above embodiments in this paragraph, R is unsubstituted in one embodiment, monosubstituted in another embodiment, disubstituted with two independently selected substitutents in an additional embodiment, or tri-substituted with three independently selected substitutents in a further embodiment. In various embodiments of each of the above embodiments in this paragraph, the substituent is -halo, —NH$_2$, —NHCH$_3$, —CF$_3$ or —OCH$_3$ or the substituents are independently selected from -halo, —NH$_2$, —NHCH$_3$, —CF$_3$ or —OCH$_3$.

In each of the embodiments in this paragraph, the compound is a compound of formula (IIa). In one embodiment, $R^1$, $R^2$ and $R^3$ together are as defined herein compound of formula (Id) and R is methyl, ethyl, benzyl, or phenyl. In one embodiment, $R^1$, $R^2$ and $R^3$ together are as defined herein compound of formula (Id) and R is methyl or ethyl. In one embodiment, $R^1$, $R^2$ and $R^3$ together are as defined herein compound of formula (Id) and R is methyl. In one embodiment, $R^1$, $R^2$ and $R^3$ together are as defined herein compound of formula (Id) and R is ethyl. In one embodiment, $R^1$, $R^2$ and $R^3$ together are as defined herein compound of formula (Id) and R is benzyl or phenyl. In one embodiment, $R^1$, $R^2$ and $R^3$ together are as defined herein compound of formula (Id) and R is benzyl. In one embodiment, $R^1$, $R^2$ and $R^3$ together are as defined herein compound of formula (Id) and R is phenyl. In one embodiment, $R^1$, $R^2$ and $R^3$ together are as defined herein compound of formula (Id) and R is —NH$_2$. In each of the above embodiments in this paragraph, R is unsubstituted in one embodiment, monosubstituted in another embodiment, disubstituted with two independently selected substitutents in an additional embodiment, or tri-substituted with three independently selected substitutents in a further embodiment. In various embodiments of each of the above embodiments in this paragraph, the substituent is -halo, —NH$_2$, —NHCH$_3$, —CF$_3$ or —OCH$_3$ or the substituents are independently selected from -halo, —NH$_2$, —NHCH$_3$, —CF$_3$ or —OCH$_3$.

In each of the embodiments in this paragraph, the compound is a compound of formula (IIa). In one embodiment, $R^1$, $R^2$ and $R^3$ together are as defined herein compound of formula (Ie) and R is methyl, ethyl, benzyl, or phenyl. In one embodiment, $R^1$, $R^2$ and $R^3$ together are as defined herein compound of formula (Ie) and R is methyl or ethyl. In one embodiment, $R^1$, $R^2$ and $R^3$ together are as defined herein compound of formula (Ie) and R is methyl. In one embodiment, $R^1$, $R^2$ and $R^3$ together are as defined herein compound of formula (Ie) and R is ethyl. In one embodiment, $R^1$, $R^2$ and $R^3$ together are as defined herein compound of formula (Ie) and R is benzyl or phenyl. In one embodiment, $R^1$, $R^2$ and $R^3$ together are as defined herein compound of formula (Ie) and R is benzyl. In one embodiment, $R^1$, $R^2$ and $R^3$ together are as defined herein compound of formula (Ie) and R is phenyl. In one embodiment, $R^1$, $R^2$ and $R^3$ together are as defined herein compound of formula (Ie) and R is —NH$_2$. In each of the above embodiments in this paragraph, R is unsubstituted in one embodiment, monosubstituted in another embodiment, disubstituted with two independently selected substitutents in an additional embodiment, or tri-substituted with three independently selected substitutents in a further embodiment. In various embodiments of each of the above embodiments in this paragraph, the substituent is -halo, —NH$_2$, —NHCH$_3$, —CF$_3$ or —OCH$_3$ or the substituents are independently selected from -halo, —NH$_2$, —NHCH$_3$, —CF$_3$ or —OCH$_3$.

In each of the embodiments in this paragraph, the compound is a compound of formula (IIa). In one embodiment, $R^1$, $R^2$ and $R^3$ together are as defined herein compound of formula (If) and R is methyl, ethyl, benzyl, or phenyl. In one embodiment, $R^1$, $R^2$ and $R^3$ together are as defined herein compound of formula (If) and R is methyl or ethyl. In one embodiment, $R^1$, $R^2$ and $R^3$ together are as defined herein compound of formula (If) and R is methyl. In one embodiment, $R^1$, $R^2$ and $R^3$ together are as defined herein compound of formula (If) and R is ethyl. In one embodiment, $R^1$, $R^2$ and $R^3$ together are as defined herein compound of formula (If) and R is benzyl or phenyl. In one embodiment, $R^1$, $R^2$ and $R^3$ together are as defined herein compound of formula (If) and R is benzyl. In one embodiment, $R^1$, $R^2$ and $R^3$ together are as defined herein compound of formula (If)

and R is phenyl. In one embodiment, $R^1$, $R^2$ and $R^3$ together are as defined herein compound of formula (If) and R is —$NH_2$. In each of the above embodiments in this paragraph, R is unsubstituted in one embodiment, monosubstituted in another embodiment, disubstituted with two independently selected substitutents in an additional embodiment, or trisubstituted with three independently selected substitutents in a further embodiment. In various embodiments of each of the above embodiments in this paragraph, the substituent is -halo, —$NH_2$, —$NHCH_3$, —$CF_3$ or —$OCH_3$ or the substituents are independently selected from -halo, —$NH_2$, —$NHCH_3$, —$CF_3$ or —$OCH_3$.

In each of the embodiments in this paragraph, the compound is a compound of formula (IIa). In one embodiment, $R^1$, $R^2$ and $R^3$ together are as defined herein compound of formula (Ig) and R is methyl, ethyl, benzyl, or phenyl. In one embodiment, $R^1$, $R^2$ and $R^3$ together are as defined herein compound of formula (Ig) and R is methyl or ethyl. In one embodiment, $R^1$, $R^2$ and $R^3$ together are as defined herein compound of formula (Ig) and R is methyl. In one embodiment, $R^1$, $R^2$ and $R^3$ together are as defined herein compound of formula (Ig) and R is ethyl. In one embodiment, $R^1$, $R^2$ and $R^3$ together are as defined herein compound of formula (Ig) and R is benzyl or phenyl. In one embodiment, $R^1$, $R^2$ and $R^3$ together are as defined herein compound of formula (Ig) and R is benzyl. In one embodiment, $R^1$, $R^2$ and $R^3$ together are as defined herein compound of formula (Ig) and R is phenyl. In one embodiment, $R^1$, $R^2$ and $R^3$ together are as defined herein compound of formula (Ig) and R is —$NH_2$. In each of the above embodiments in this paragraph, R is unsubstituted in one embodiment, monosubstituted in another embodiment, disubstituted with two independently selected substitutents in an additional embodiment, or trisubstituted with three independently selected substitutents in a further embodiment. In various embodiments of each of the above embodiments in this paragraph, the substituent is -halo, —$NH_2$, —$NHCH_3$, —$CF_3$ or —$OCH_3$ or the substituents are independently selected from -halo, —$NH_2$, —$NHCH_3$, —$CF_3$ or —$OCH_3$.

In each of the embodiments in this paragraph, the compound is a compound of formula (IIa). In one embodiment, $R^1$, $R^2$ and $R^3$ together are as defined herein compound of formula (Ih) and R is methyl, ethyl, benzyl, or phenyl. In one embodiment, $R^1$, $R^2$ and $R^3$ together are as defined herein compound of formula (Ih) and R is methyl or ethyl. In one embodiment, $R^1$, $R^2$ and $R^3$ together are as defined herein compound of formula (Ih) and R is methyl. In one embodiment, $R^1$, $R^2$ and $R^3$ together are as defined herein compound of formula (Ih) and R is ethyl. In one embodiment, $R^1$, $R^2$ and $R^3$ together are as defined herein compound of formula (Ih) and R is benzyl or phenyl. In one embodiment, $R^1$, $R^2$ and $R^3$ together are as defined herein compound of formula (Ih) and R is benzyl. In one embodiment, $R^1$, $R^2$ and $R^3$ together are as defined herein compound of formula (Ih) and R is phenyl. In one embodiment, $R^1$, $R^2$ and $R^3$ together are as defined herein compound of formula (Ih) and R is —$NH_2$. In each of the above embodiments in this paragraph, R is unsubstituted in one embodiment, monosubstituted in another embodiment, disubstituted with two independently selected substitutents in an additional embodiment, or trisubstituted with three independently selected substitutents in a further embodiment. In various embodiments of each of the above embodiments in this paragraph, the substituent is -halo, —$NH_2$, —$NHCH_3$, —$CF_3$ or —$OCH_3$ or the substituents are independently selected from -halo, —$NH_2$, —$NHCH_3$, —$CF_3$ or —$OCH_3$.

In each of the embodiments in this paragraph, the compound is a compound of formula (IIb). In one embodiment, m and $R^2$ together are as defined herein compound of formula (Ii) and R is methyl, ethyl, benzyl, or phenyl. In one embodiment, m and $R^2$ together are as defined herein compound of formula (Ii) and R is methyl or ethyl. In one embodiment, m and $R^2$ together are as defined herein compound of formula (Ii) and R is methyl. In one embodiment, m and $R^2$ together are as defined herein compound of formula (Ii) and R is ethyl. In one embodiment, m and $R^2$ together are as defined herein compound of formula (Ii) and R is benzyl or phenyl. In one embodiment, m and $R^2$ together are as defined herein compound of formula (Ii) and R is benzyl. In one embodiment, m and $R^2$ together are as defined herein compound of formula (Ii) and R is phenyl. In one embodiment, m and $R^2$ together are as defined herein compound of formula (Ii) and R is —$NH_2$. In each of the above embodiments in this paragraph, R is unsubstituted in one embodiment, monosubstituted in another embodiment, disubstituted with two independently selected substitutents in an additional embodiment, or trisubstituted with three independently selected substitutents in a further embodiment. In various embodiments of each of the above embodiments in this paragraph, the substituent is -halo, —$NH_2$, —$NHCH_3$, —$CF_3$ or —$OCH_3$ or the substituents are independently selected from -halo, —$NH_2$, —$NHCH_3$, —$CF_3$ or —$OCH_3$.

Table 1 provides representative compounds of the disclosure.

TABLE 1

Pyrazolone Derivative Compounds of the Disclosure

| Compound No. | Compound Structure | Compound Name |
| --- | --- | --- |
| 1 | 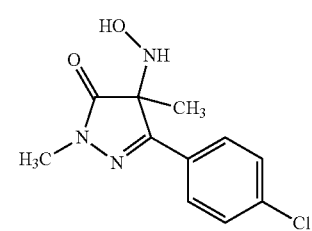 [SMILES: CN1N=C(c2ccc(Cl)cc2)C(C)(NO)C1=O] | 5-(4-chlorophenyl)-4-(hydroxyamino)-2,4-dimethyl-2,4-dihydro-3H-pyrazol-3-one |

TABLE 1-continued

Pyrazolone Derivative Compounds of the Disclosure

| Compound No. | Compound Structure | Compound Name |
|---|---|---|
| 2 | 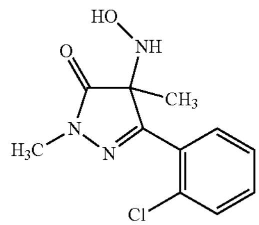 [SMILES: CN1N=C(c2ccccc2Cl)C(C)(NO)C1=O] | 5-(2-chlorophenyl)-4-(hydroxyamino)-2,4-dimethyl-2,4-ddihydro-3H-pyrazol-3-one |
| 3 | 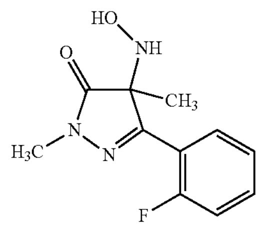 [SMILES: CN1N=C(c2ccccc2F)C(C)(NO)C1=O] | 5-(2-fluorophenyl)-4-(hydroxyamino)-2,4-dimethyl-2,4-dihydro-3H-pyrazol-3-one |
| 4 | 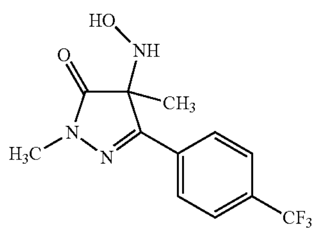 [SMILES: CN1N=C(c2ccc(C(F)(F)F)cc2)C(C)(NO)C1=O] | 4-(hydroxyamino)-2,4-dimethyl-5-(4-(trifluoromethyl)phenyl)-2,4-dihydro-3H-pyrazol-3-one |
| 5 | 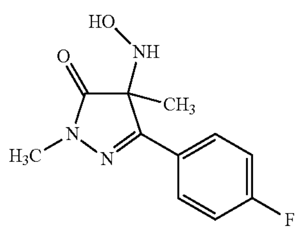 [SMILES: CN1N=C(c2ccc(F)cc2)C(C)(NO)C1=O] | 5-(4-fluorophenyl)-4-(hydroxyamino)-2,4-dimethyl-2,4-dihydro-3H-pyrazol-3-one |
| 6 | 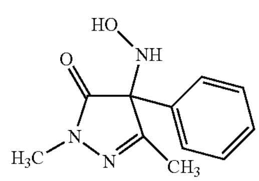 [SMILES: CC1=NN(C)C(=O)C1(NO)c1ccccc1] | 4-(hydroxyamino)-2,5-dimethyl-4-phenyl-2,4-dihydro-3H-pyrazol-3-one |
| 7 | 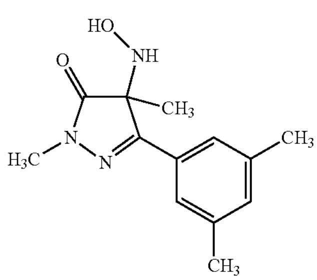 | 5-(3,5-dimethylphenyl)-4-(hydroxyamino)-2,4-dimethyl-2,4-dihydro-3H-pyrazol-3-one |

TABLE 1-continued

Pyrazolone Derivative Compounds of the Disclosure

| Compound No. | Compound Structure | Compound Name |
|---|---|---|
| 8 | 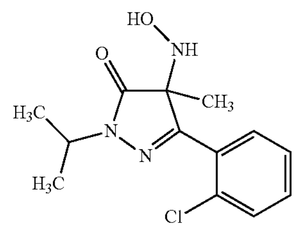 [SMILES: CC(C)N1N=C(c2ccccc2Cl)C(C)(NO)C1=O] | 5-(2-chlorophenyl)-4-(hydroxyamino)-2-iso-propyl-4-methyl-2,4-dihydro-3H-pyrazol-3-one |
| 9 | 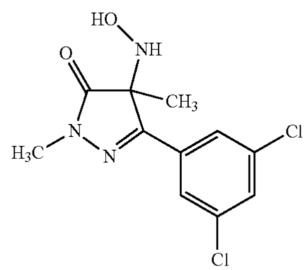 [SMILES: CN1N=C(c2cc(Cl)cc(Cl)c2)C(C)(NO)C1=O] | 5-(3,5-dichlorophenyl)-4-(hydroxyamino)-2,4-dimethyl-2,4-dihydro-3H-pyrazol-3-one |
| 10 | 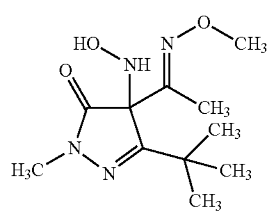 | 5-(tert-butyl)-4-(hydroxyamino)-4-(1-(methoxyimino)ethyl)-2-methyl-2,4-dihydro-3H-pyrazol-3-one |
| 11 | 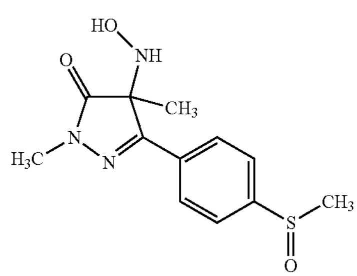 | 4-(hydroxyamino)-2,4-dimethyl-5-(4-(methylsulfinyl)phenyl)-2,4-dihydro-3H-pyrazol-3-one |
| 12 | 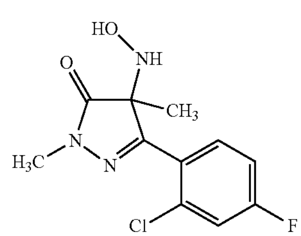 [SMILES: CN1N=C(c2ccc(F)cc2Cl)C(C)(NO)C1=O] | 5-(2-chloro-4-fluorophenyl)-4-(hydroxyamino)-2,4-dimethyl-2,4-dihydro-3H-pyrazol-3-one |
| 13 | 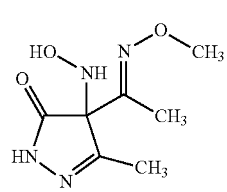 | 4-(hydroxyamino)-4-(1-(methoxyimino)ethyl)-5-methyl-2,4-dihydro-3H-pyrazol-3-one |

TABLE 1-continued

Pyrazolone Derivative Compounds of the Disclosure

| Compound No. | Compound Structure | Compound Name |
|---|---|---|
| 14 | 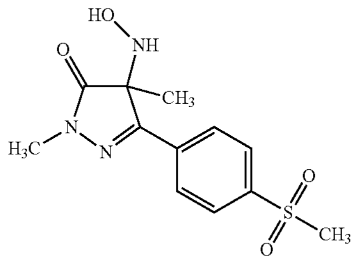 | 4-(hydroxyamino)-2,4-dimethyl-5-(4-(methylsulfonyl)phenyl)-2,4-dihydro-3H-pyrazol-3-one |
| 15 | 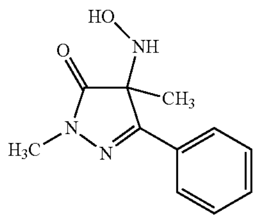 [SMILES: CN1N=C(c2ccccc2)C(C)(NO)C1=O] | 4-(hydroxyamino)-2,4-dimethyl-5-phenyl-2,4-dihydro-3H-pyrazol-3-one |
| 16 | 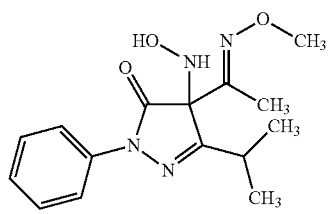 [SMILES: CO/N=C(\C)C1(NO)C(=O)N(c2ccccc2)N=C1C(C)C] | 4-(hydroxyamino)-5-iso-propyl-4-(1-(methoxyimino)ethyl)-2-phenyl-2,4-dihydro-3H-pyrazol-3-one |
| 17 | 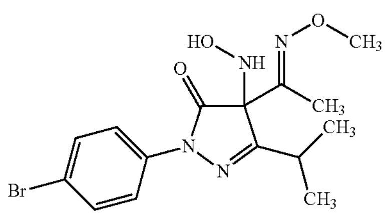 [SMILES: CO/N=C(\C)C1(NO)C(=O)N(c2ccc(Br)cc2)N=C1C(C)C] | 2-(4-bromophenyl)-4-(hydroxyamino)-5-iso-propyl-4-(1-(methoxyimino)ethyl)-2,4-dihydro-3H-pyrazol-3-one |
| 18 | 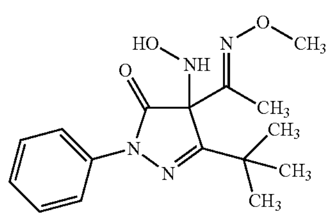 [SMILES: CO/N=C(\C)C1(NO)C(=O)N(c2ccccc2)N=C1C(C)(C)C] | 5-(tert-butyl)-4-(hydroxyamino)-4-(1-(methoxyimino)ethyl)-2-phenyl-2,4-dihydro-3H-pyrazol-3-one |
| 19 | 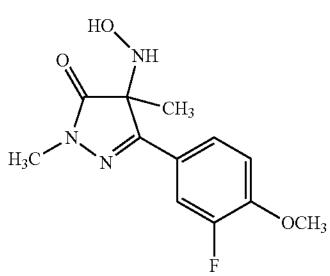 [SMILES: COc1ccc(C2=NN(C)C(=O)C2(C)NO)cc1F] | 5-(3-fluoro-4-methoxyphenyl)-4-(hydroxyamino)-2,4-dimethyl-2,4-dihydro-3H-pyrazol-3-one |
| 20 | 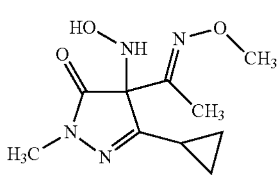 | 5-cyclopropyl-4-(hydroxyamino)-4-(1-(methoxyimino)ethyl)-2-methyl-2,4-dihydro-3H-pyrazol-3-one |

TABLE 1-continued

Pyrazolone Derivative Compounds of the Disclosure

| Compound No. | Compound Structure | Compound Name |
|---|---|---|
| 21 | 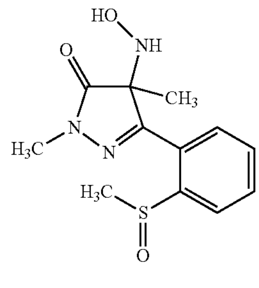 [SMILES: CN1N=C(c2ccccc2S(C)=O)C(C)(NO)C1=O] | 4-(hydroxyamino)-2,4-dimethyl-5-(2-(methylsulfinyl)phenyl)-2,4-dihydro-3H-pyrazol-3-one |
| 22 | 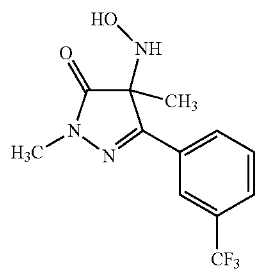 [SMILES: CN1N=C(c2cccc(C(F)(F)F)c2)C(C)(NO)C1=O] | 4-(hydroxyamino)-2,4-dimethyl-5-(3-(trifluoromethyl)phenyl)-2,4-dihydro-3H-pyrazol-3-one |
| 23 | 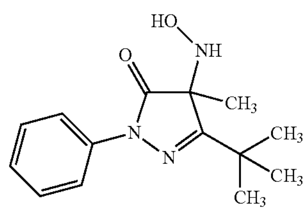 [SMILES: CC(C)(C)C1=NN(c2ccccc2)C(=O)C1(C)NO] | 5-(tert-butyl)-4-(hydroxyamino)-4-methyl-2-phenyl-2,4-dihydro-3H-pyrazol-3-one |
| 24 | 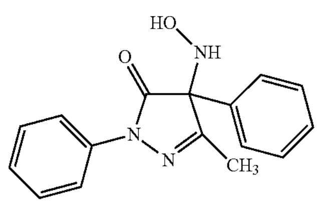 [SMILES: CC1=NN(c2ccccc2)C(=O)C1(NO)c1ccccc1] | 4-(hydroxyamino)-5-methyl-2,4-diphenyl-2,4-dihydro-3H-pyrazol-3-one |
| 25 | 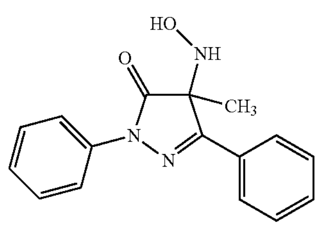 [SMILES: CC1(NO)C(=O)N(c2ccccc2)N=C1c1ccccc1] | 4-(hydroxyamino)-4-methyl-2,5-diphenyl-2,4-dihydro-3H-pyrazol-3-one |
| 26 | 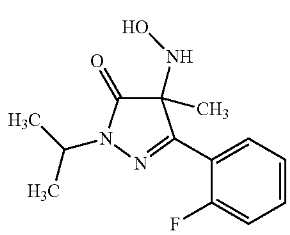 [SMILES: CC(C)N1N=C(c2ccccc2F)C(C)(NO)C1=O] | 5-(2-fluorophenyl)-4-(hydroxyamino)-2-iso-propyl-4-methyl-2,4-dihydro-3H-pyrazol-3-one |

TABLE 1-continued

Pyrazolone Derivative Compounds of the Disclosure

| Compound No. | Compound Structure | Compound Name |
|---|---|---|
| 27 | 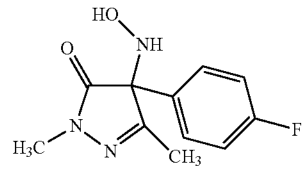 | 4-(4-fluorophenyl)-4-(hydroxyamino)-2,5-dimethyl-2,4-dihydro-3H-pyrazol-3-one |
| 28 | 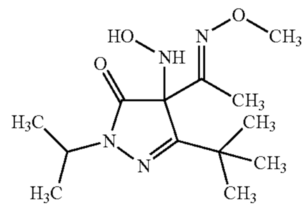 [SMILES: CO/N=C(\C)C1(NO)C(=O)N(C(C)C)N=C1C(C)(C)C] | 5-(tert-butyl)-4-(hydroxyamino)-2-iso-propyl-4-(1-(methoxyimino)ethyl)-2,4-dihydro-3H-pyrazol-3-one |
| 29 | 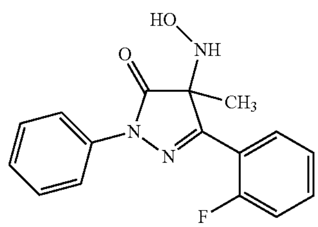 [SMILES: CC1(NO)C(=O)N(c2ccccc2)N=C1c1ccccc1F] | 5-(2-fluorophenyl)-4-(hydroxyamino)-4-methyl-2-phenyl-2,4-dihydro-3H-pyrazol-3-one |
| 30 | 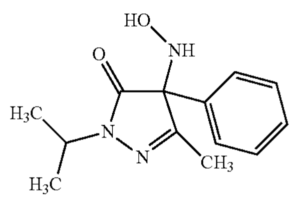 [SMILES: CC1=NN(C(C)C)C(=O)C1(NO)c1ccccc1] | 4-(hydroxyamino)-1-isopropyl-3-methyl-4-phenyl-1H-pyrazol-5(4H)-one |
| 31 | 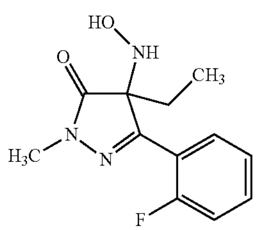 [SMILES: CCC1(NO)C(=O)N(C)N=C1c1ccccc1F] | 4-ethyl-5-(2-fluorophenyl)-4-(hydroxyamino)-2-methyl-2,4-dihydro-3H-pyrazol-3-one |
| 32 | 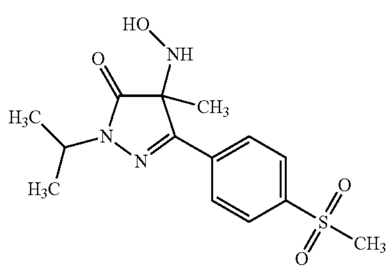 [SMILES: CC(C)N1N=C(c2ccc(S(C)(=O)=O)cc2)C(C)(NO)C1=O] | 4-(hydroxyamino)-2-iso-propyl-4-methyl-5-(4-(methylsulfonyl)phenyl)-2,4-dihydro-3H-pyrazol-3-one |
| 33 | 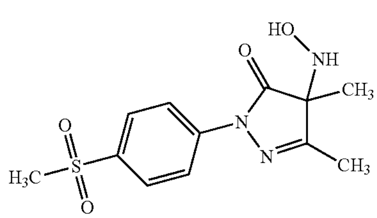 | 4-(hydroxyamino)-4,5-dimethyl-2-(4-(methylsulfonyl)phenyl)-2,4-dihydro-3H-pyrazol-3-one |

TABLE 1-continued

Pyrazolone Derivative Compounds of the Disclosure

| Compound No. | Compound Structure | Compound Name |
| --- | --- | --- |
| 34 | 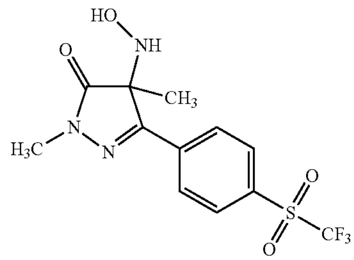 [SMILES: CN1N=C(c2ccc(S(=O)(=O)C(F)(F)F)cc2)C(C)(NO)C1=O] | 4-(hydroxyamino)-2,4-dimethyl-5-(4-((trifluoromethyl)sulfonyl)phenyl)-2,4-dihydro-3H-pyrazol-3-one |
| 35 | 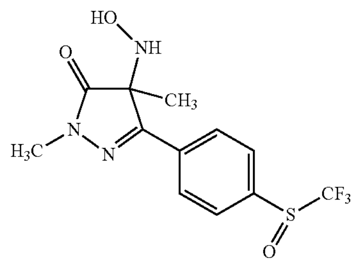 [SMILES: CN1N=C(c2ccc(S(=O)C(F)(F)F)cc2)C(C)(NO)C1=O] | 4-(hydroxyamino)-2,4-dimethyl-5-(4-((trifluoromethyl)sulfinyl)phenyl)-2,4-dihydro-3H-pyrazol-3-one |
| 36 | 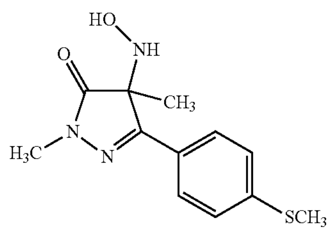 | 4-(hydroxyamino)-2,4-dimethyl-5-(4-(methylthio)phenyl)-2,4-dihydro-3H-pyrazol-3-one |
| 37 | 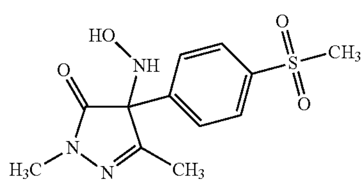 | 4-(hydroxyamino)-2,5-dimethyl-4-(4-(methylsulfonyl)phenyl)-2,4-dihydro-3H-pyrazol-3-one |
| 38 | 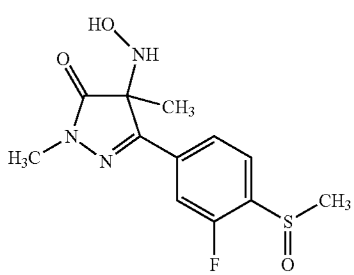 | 5-(3-fluoro-4-(methylsulfinyl)phenyl)-4-(hydroxyamino)-2,4-dimethyl-2,4-dihydro-3H-pyrazol-3-one |
| 39 | 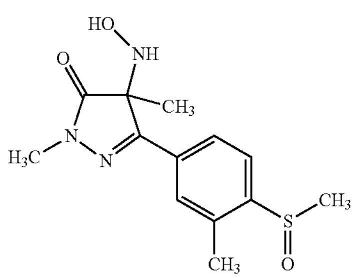 | 4-(hydroxyamino)-2,4-dimethyl-5-(3-methyl-4-(methylsulfinyl)phenyl)-2,4-dihydro-3H-pyrazol-3-one |

TABLE 1-continued

Pyrazolone Derivative Compounds of the Disclosure

| Compound No. | Compound Structure | Compound Name |
|---|---|---|
| 40 | 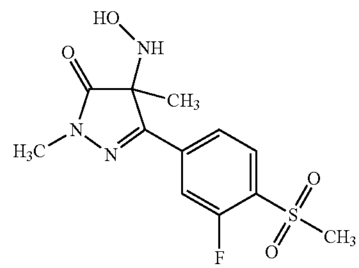 | 5-(3-fluoro-4-(methylsulfonyl)phenyl)-4-(hydroxyamino)-2,4-dimethyl-2,4-dihydro-3H-pyrazol-3-one |
| 41 | 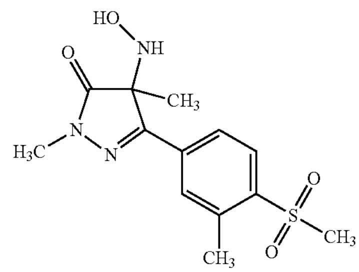 | 4-(hydroxyamino)-2,4-dimethyl-5-(3-methyl-4-(methylsulfonyl)phenyl)-2,4-dihydro-3H-pyrazol-3-one |
| 42 | 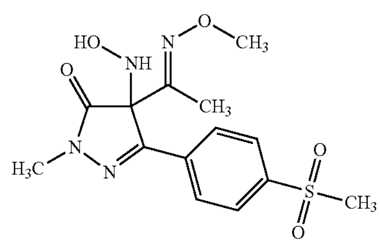 | 4-(hydroxyamino)-4-(1-(methoxyimino)ethyl)-2-methyl-5-(4-(methylsulfonyl)phenyl)-2,4-dihydro-3H-pyrazol-3-one |
| 43 | 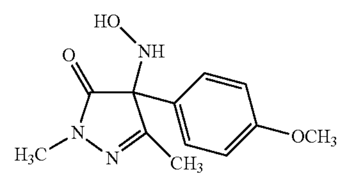 | 4-(hydroxyamino)-4-(4-methoxyphenyl)-1,3-dimethyl-1H-pyrazol-5(4H)-one |
| 44 | 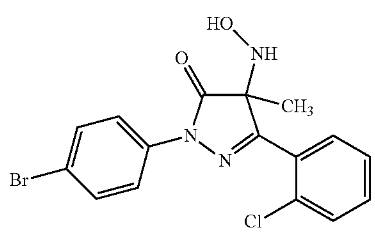 [SMILES: CC1(NO)C(=O)N(c2ccc(Br)cc2)N=C1c1ccccc1Cl] | 1-(4-bromophenyl)-3-(2-chlorophenyl)-4-(hydroxyamino)-4-methyl-1H-pyrazol-5(4H)-one |
| 45 | 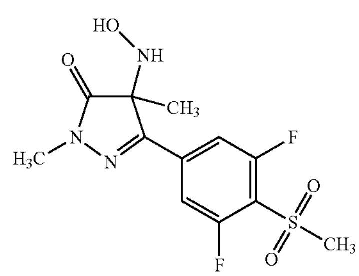 | 5-(3,5-difluoro-4-(methylsulfonyl)phenyl)-4-(hydroxyamino)-2,4-dimethyl-2,4-dihydro-3H-pyrazol-3-one |

TABLE 1-continued

Pyrazolone Derivative Compounds of the Disclosure

| Compound No. | Compound Structure | Compound Name |
| --- | --- | --- |
| 46 | 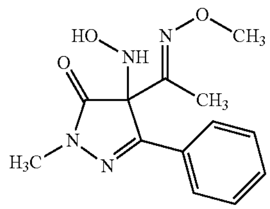 [SMILES: CO/N=C(\C)C1(NO)C(=O)N(C)N=C1c1ccccc1] | 4-(hydroxyamino)-4-(1-(methoxyimino)ethyl)-2-methyl-5-phenyl-2,4-dihydro-3H-pyrazol-3-one 46 |
| 47 | 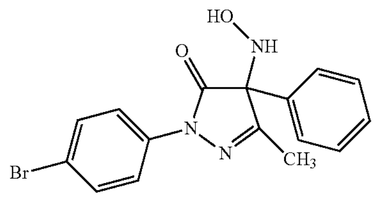 [SMILES: CC1=NN(c2ccc(Br)cc2)C(=O)C1(NO)c1ccccc1] | 1-(4-bromophenyl)-4-(hydroxyamino)-3-methyl-4-phenyl-1H-pyrazol-5(4H)-one |
| 48 | 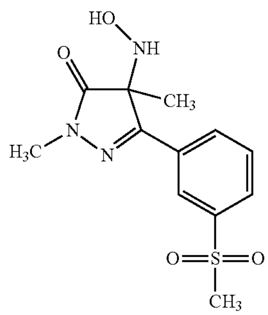 [SMILES: CN1N=C(c2cccc(S(C)(=O)=O)c2)C(C)(NO)C1=O] | 4-(hydroxyamino)-2,4-dimethyl-5-(3-(methylsulfonyl)phenyl)-2,4-dihydro-3H-pyrazol-3-one |
| 49 | 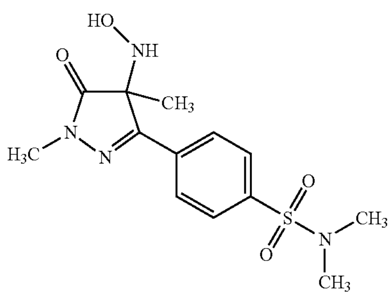 | 4-(4-(hydroxyamino)-1,4-dimethyl-5-oxo-4,5-dihydro-1H-pyrazol-3-yl)-N,N-dimethylbenzenesulfonamide |
| 50 | 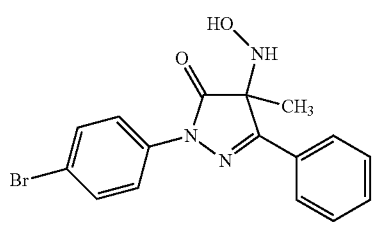 [SMILES: CC1(NO)C(=O)N(c2ccc(Br)cc2)N=C1c1ccccc1] | 1-(4-bromophenyl)-4-(hydroxyamino)-4-methyl-3-phenyl-1H-pyrazol-5(4H)-one |
| 51 | 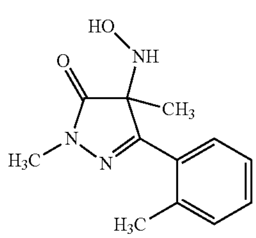 [SMILES: Cc1ccccc1C1=NN(C)C(=O)C1(C)NO] | 4-(hydroxyamino)-1,4-dimethyl-3-(o-tolyl)-1H-pyrazol-5(4H)-one |

TABLE 1-continued

Pyrazolone Derivative Compounds of the Disclosure

| Compound No. | Compound Structure | Compound Name |
|---|---|---|
| 52 | 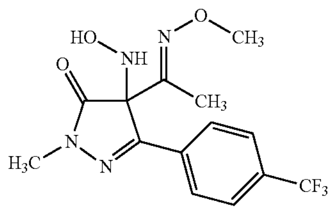 [SMILES: CO/N=C(\C)C1(NO)C(=O)N(C)N=C1c1ccc(C(F)(F)F)cc1] | 4-(hydroxyamino)-4-(1-(methoxyimino)ethyl)-1-methyl-3-(4-(trifluoromethyl)phenyl)-1H-pyrazol-5(4H)-one |
| 53 | 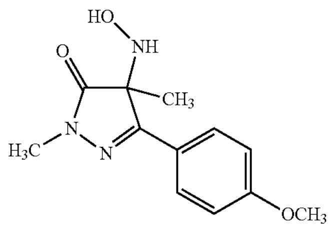 [SMILES: COc1ccc(C2=NN(C)C(=O)C2(C)NO)cc1] | 4-(hydroxyamino)-3-(4-methoxyphenyl)-1,4-dimethyl-1H-pyrazol-5(4H)-one |
| 54 | 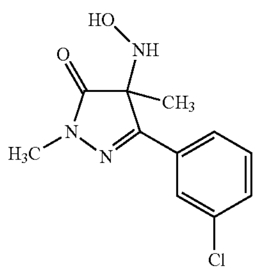 [SMILES: CN1N=C(c2cccc(Cl)c2)C(C)(NO)C1=O] | 3-(3-chlorophenyl)-4-(hydroxyamino)-1,4-dimethyl-1H-pyrazol-5(4H)-one |
| 55 | 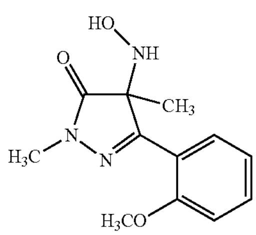 [SMILES: COc1ccccc1C1=NN(C)C(=O)C1(C)NO] | 4-(hydroxyamino)-3-(2-methoxyphenyl)-1,4-dimethyl-1H-pyrazol-5(4H)-one |
| 56 | 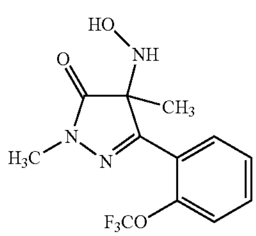 [SMILES: CN1N=C(c2ccccc2OC(F)(F)F)C(C)(NO)C1=O] | 4-(hydroxyamino)-1,4-dimethyl-3-(2-(trifluoromethoxy)phenyl)-1H-pyrazol-5(4H)-one |
| 57 | 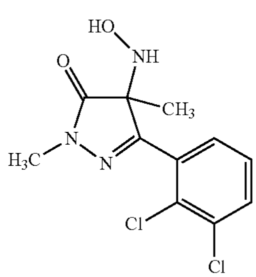 [SMILES: CN1N=C(c2cccc(Cl)c2Cl)C(C)(NO)C1=O] | 3-(2,3-dichlorophenyl)-4-(hydroxyamino)-1,4-dimethyl-1H-pyrazol-5(4H)-one |

TABLE 1-continued

Pyrazolone Derivative Compounds of the Disclosure

| Compound No. | Compound Structure | Compound Name |
| --- | --- | --- |
| 58 | 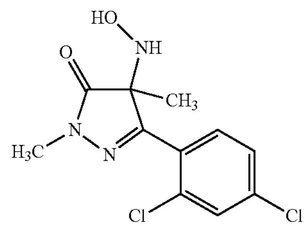 [SMILES: CN1N=C(c2ccc(Cl)cc2Cl)C(C)(NO)C1=O] | 3-(2,4-dichlorophenyl)-4-(hydroxyamino)-1,4-dimethyl-1H-pyrazol-5(4H)-one |
| 59 | 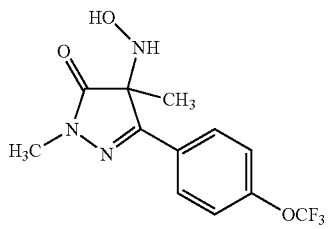 | 4-(hydroxyamino)-1,4-dimethyl-3-(4-(trifluoromethoxy)phenyl)-1-pyrazol-5(4H)-one |
| 60 | 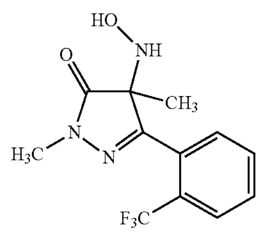 [SMILES: CN1N=C(c2ccccc2C(F)(F)F)C(C)(NO)C1=O] | 4-(hydroxyamino)-1,4-dimethyl-3-(2-(trifluoromethyl)phenyl)-1H-pyrazol-5(4H)-one |
| 61 | 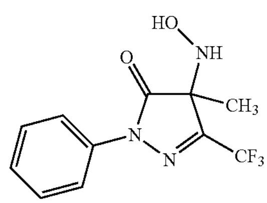 [SMILES: CC1(NO)C(=O)N(c2ccccc2)N=C1C(F)(F)F] | 4-(hydroxyamino)-4-methyl-1-phenyl-3-(trifluoromethyl)-1H-pyrazol-5(4H)-one |
| 62 | 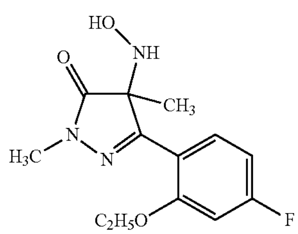 | 3-(2-ethoxy-4-fluorophenyl)-4-(hydroxyamino)-1,4-dimethyl-1H-pyrazol-5(4H)-one |
| 63 | 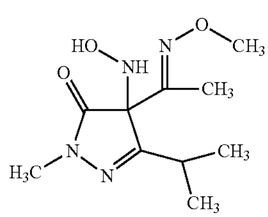 | 4-(hydroxyamino)-3-isopropyl-4-(1-(methoxyimino)ethyl)-1-methyl-1H-pyrazol-5(4H)-one |
| 64 | 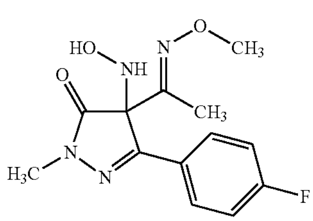 [SMILES: CO/N=C(\C)C1(NO)C(=O)N(C)N=C1c1ccc(F)cc1] | 3-(4-fluorophenyl)-4-(hydroxyamino)-4-(1-(methoxyimino)ethyl)-1-methyl-1H-pyrazol-5(4H)-one |

TABLE 1-continued

Pyrazolone Derivative Compounds of the Disclosure

| Compound No. | Compound Structure | Compound Name |
| --- | --- | --- |
| 65 | 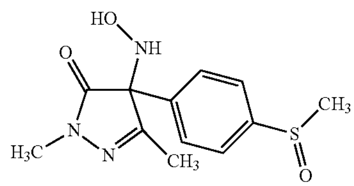 | 4-(hydroxyamino)-1,3-dimethyl-4-(4-(methylsulfinyl)phenyl)-1H-pyrazaol-5(4H)-one |
| 66 | 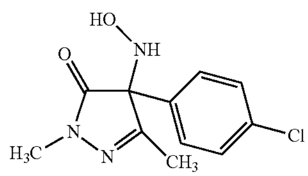 [SMILES: CC1=NN(C)C(=O)C1(NO)c1ccc(Cl)cc1] | 4-(4-chlorophenyl)-4-(hydroxyamino)-1,3-dimethyl-1H-pyrazol-5(4H)-one |
| 67 | 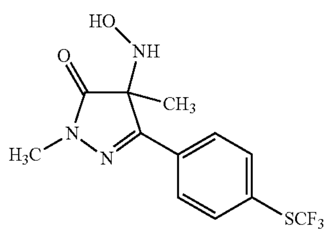 | 4-(hydroxyamino)-1,4-dimethyl-3-(4-((trifluoromethyl)thio)phenyl)-1H-pyrazol-5(4H)-one |
| 68 | 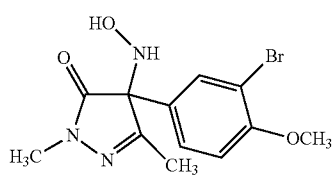 | 4-(3-bromo-4-methoxyphenyl)-4-(hydroxyamino)-1,3-dimethyl-1H-pyrazol-5(4H)-one |
| 69 | 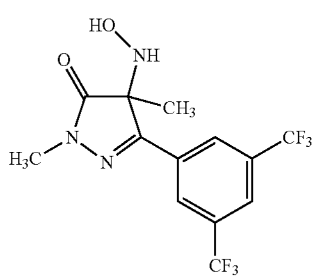 [SMILES: CN1N=C(c2cc(C(F)(F)F)cc(C(F)(F)F)c2)C(C)(NO)C1=O] | 3-(3,5-bis(trifluoromethyl)phenyl)-4-(hydroxyamino)-1,4-dimethyl-1H-pyrazol-5(4H)-one |
| 70 | 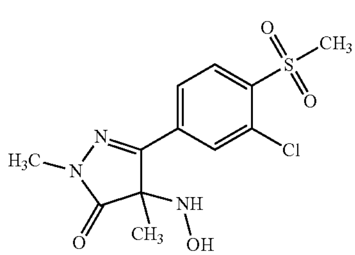 | 3-(3-Chloro-4-methanesulfonylphenyl)-4-(hydroxyamino)-1,4-dimethyl-4,5-dihydro-1H-pyrazol-5-one |

TABLE 1-continued

Pyrazolone Derivative Compounds of the Disclosure

| Compound No. | Compound Name |
|---|---|
| 71 | Methyl 4-[4-(hydroxyamino)-1,4 dimethyl-5-oxo-4,5-dihydro-1H-pyrazol-3-yl]benzoate |
| 72 | 2,2,2-Trifluoro-N-({4-[4-(hydroxyamino)-1,4-dimethyl-5-oxo-4,5-dihydro-1H-pyrazol-3-yl]phenyl}(methyl)oxo-$\lambda^6$-sulfanylidene)acetamide |
| 73 | 4-(3,4-Dimethoxyphenyl)-4-(hydroxyamino)-1,3-dimethyl-4,5-dihydro-1H-pyrazol-5-one |
| 74 | 4-[4-(Hydroxyamino)-1,4-dimethyl-5-oxo-4,5-dihydro-1H-pyrazol-3-yl]benzoic acid |
| 75 | 4-(Hydroxyamino)-3-{4-[imino(methyl)oxo-$\lambda^6$-sulfanyl]phenyl}-1,4-dimethyl-4,5-dihydro-1H-pyrazol-5-one |
| 76 | 4-(Hydroxyamino)-4-(4-methoxy-3-methylphenyl)-1,3-dimethyl-4,5-dihydro-1H-pyrazol-5-one |

TABLE 1-continued

Pyrazolone Derivative Compounds of the Disclosure

| Compound No. | Compound Structure | Compound Name |
|---|---|---|
| 77 | 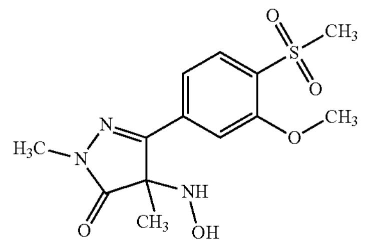 | 4-(Hydroxyamino)-3-(4-methanesulfonyl-3-methoxyphenyl)-1,4-dimethyl-4,5-dihydro-1H-pyrazol-5-one |
| 78 | 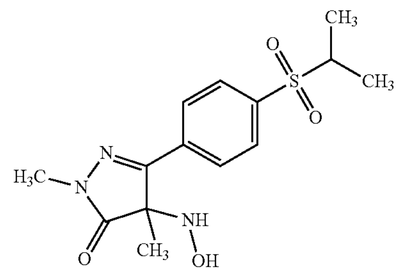 [SMILES: CC(C)S(=O)(=O)c1ccc(C2=NN(C)C(=O)C2(C)NO)cc1] | 4-(Hydroxyamino)-1,4-dimethyl-3-[4-(propane-2-sulfonyl)phenyl]-4,5-dihydro-1H-pyrazol-5-one |
| 79 | 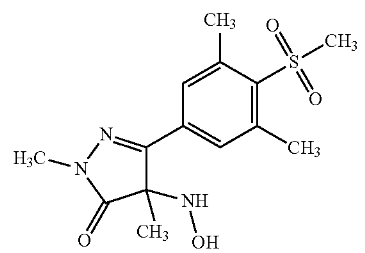 | 4-(Hydroxyamino)-3-(4-methanesulfonyl-3,5-dimethylphenyl)-1,4-dimethyl-4,5-dihydro-1H-pyrazol-5-one |
| 80 | 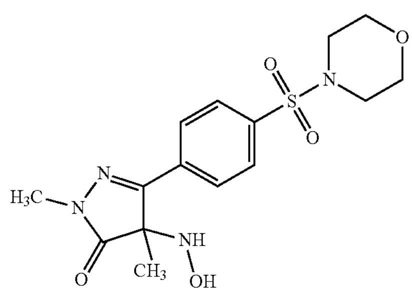 [SMILES: CN1N=C(c2ccc(S(=O)(=O)N3CCOCC3)cc2)C(C)(NO)C1=O] | 4-(Hydroxyamino)-1,4-dimethyl-3-[4-(morpholine-4-sulfonyl)phenyl]-4,5-dihydro-1H-pyrazol-5-one |
| 81 | 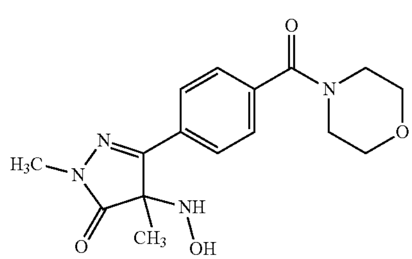 [SMILES: CN1N=C(c2ccc(C(=O)N3CCOCC3)cc2)C(C)(NO)C1=O] | 4-(Hydroxyamino)-1,4-dimethyl-3-[4-(morpholine-4-carbonyl)phenyl]-4,5-dihydro-1H-pyrazol-5-one |
| 82 | 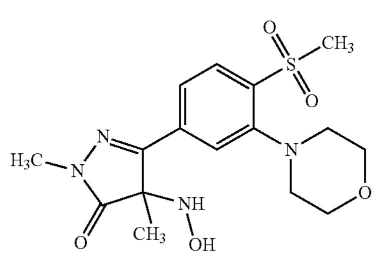 [SMILES: CN1N=C(c2ccc(S(C)(=O)=O)c(N3CCOCC3)c2)C(C)(NO)C1=O] | 4-(Hydroxyamino)-3-[4-methanesulfonyl-3-(morpholin-4-yl)phenyl]-1,4-dimethyl-4,5-dihydro-1H-pyrazol-5-one |

TABLE 1-continued

Pyrazolone Derivative Compounds of the Disclosure

| Compound No. | Compound Structure | Compound Name |
| --- | --- | --- |
| 83 | 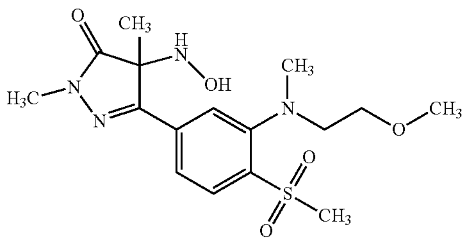 | 4-(Hydroxyamino)-3-{4-methanesulfonyl-3-[(2-methoxyethyl)(methyl)amino]phenyl}-1,4-dimethyl-4,5-dihydro-1H-pyrazol-5-one |
| 84 | 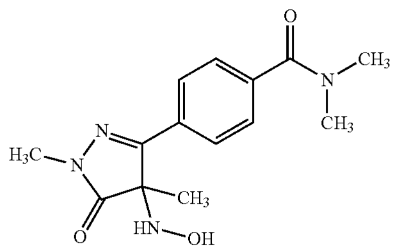 | 4-[4-(Hydroxyamino)-1,4-dimethyl-5-oxo-4,5-dihydro-1H-pyrazol-3-yl]-N,N-dimethylbenzamide |
| 85 | 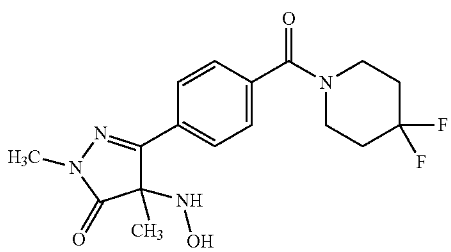 [SMILES: CN1N=C(c2ccc(C(=O)N3CCC(F)(F)CC3)cc2)C(C)(NO)C1=O] | 3-[4-(4,4-Difluoropiperidine-1-carbonyl)phenyl]-4-(hydroxyamino)-1,4-dimethyl-4,5-dihydro-1H-pyrazol-5-one |
| 86 | 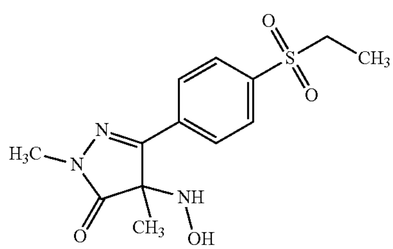 [SMILES: CCS(=O)(=O)c1ccc(C2=NN(C)C(=O)C2(C)NO)cc1] | 3-[4-(Ethanesulfonyl)phenyl]-4-(hydroxyamino)-1,4-dimethyl-4,5-dihydro-1H-pyrazol-5-one |
| 87 | 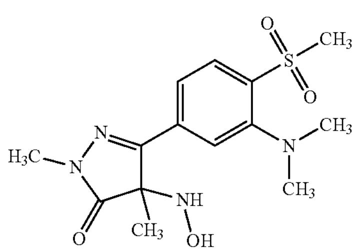 | 3-[3-(Dimethylamino)-4-methanesulfonylphenyl]-4-(hydroxyamino)-1,4-dimethyl-4,5-dihydro-1H-pyrazol-5-one |
| 88 | 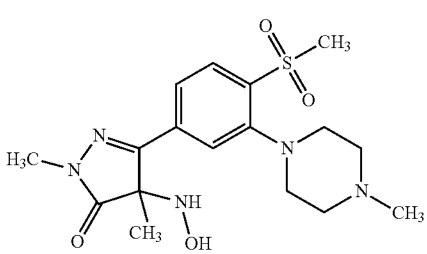 | 4-(Hydroxyamino)-3-[4-methanesulfonyl-3-(4-methylpiperazin-1-yl)phenyl]-1,4-dimethyl-4,5-dihydro-1H-pyrazol-5-one |

TABLE 1-continued

Pyrazolone Derivative Compounds of the Disclosure

| Compound No. | Compound Structure | Compound Name |
| --- | --- | --- |
| 89 | 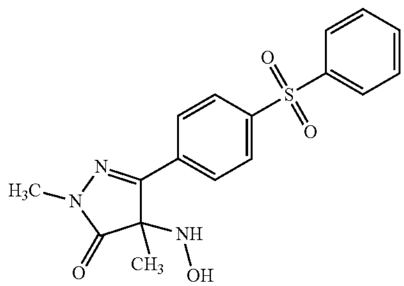 [SMILES: CN1N=C(c2ccc(S(=O)(=O)c3ccccc3)cc2)C(C)(NO)C1=O] | 3-[4-(Benzenesulfonyl)phenyl]-4-(hydroxyamino)-1,4-dimethyl-4,5-dihydro-1H-pyrazol-5-one |
| 90 | 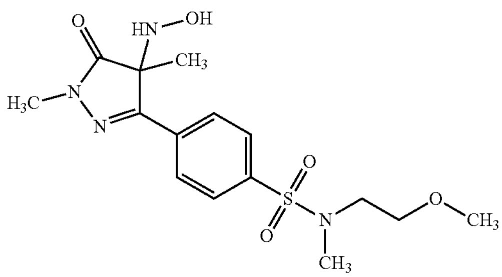 | 4-[4-(Hydroxyamino)-1,4-dimethyl-5-oxo-4,5-dihydro-1H-pyrazol-3-yl]-N-(2-methoxyethyl)-N-methylbenzene-1-sulfonamide |
| 91 | 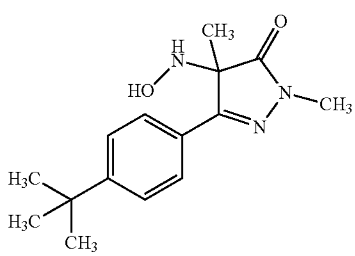 [SMILES: CN1N=C(c2ccc(C(C)(C)C)cc2)C(C)(NO)C1=O] | 3-(4-tert-Butylphenyl)-4-(hydroxyamino)-1,4-dimethyl-4,5-dihydro-1H-pyrazol-5-one |
| 92 | 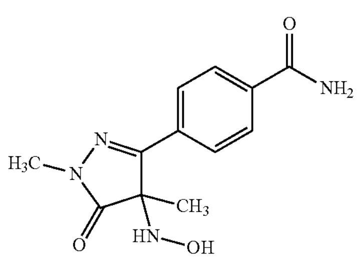 [SMILES: CN1N=C(c2ccc(C(N)=O)cc2)C(C)(NO)C1=O] | 4-[4-(Hydroxyamino)-1,4-dimethyl-5-oxo-4,5-dihydro-1H-pyrazol-3-yl]benzamide |
| 93 | 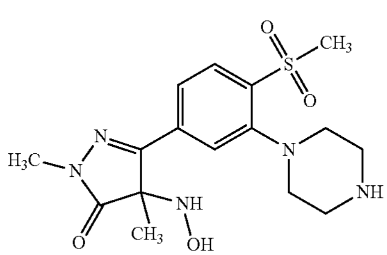 [SMILES: CN1N=C(c2ccc(S(C)(=O)=O)c(N3CCNCC3)c2)C(C)(NO)C1=O] | 4-(Hydroxyamino)-3-[4-methanesulfonyl-3-(piperazin-1-yl)phenyl]-1,4-dimethyl-4,5-dihydro-1H-pyrazol-5-one |

TABLE 1-continued

Pyrazolone Derivative Compounds of the Disclosure

| Compound No. | Compound Structure | Compound Name |
|---|---|---|
| 94 | 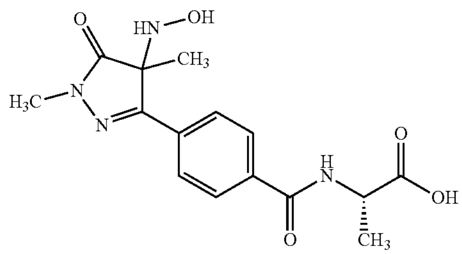 [SMILES: C[C@H](NC(=O)c1ccc(C2=NN(C)C(=O)C2(C)NO)cc1)C(=O)O] | 2-({2-[4-(Hydroxyamino)-1,4-dimethyl-5-oxo-4,5-dihydro-1H-pyrazol-3-yl]phenyl}formamido)propanoic acid |
| 95 | 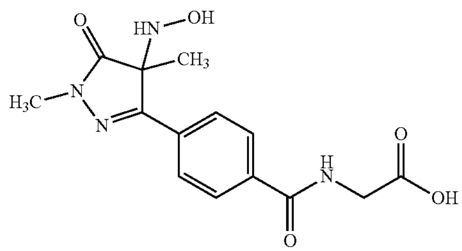 [SMILES: CN1N=C(c2ccc(C(=O)NCC(=O)O)cc2)C(C)(NO)C1=O] | 2-({4-[4-(Hydroxyamino)-1,4-dimethyl-5-oxo-4,5-dihydro-1H-pyrazol-3-yl]phenyl}formamido)acetic acid |
| 96 | 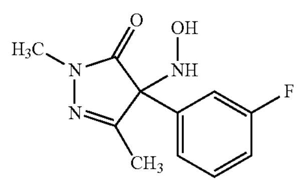 [SMILES: CC1=NN(C)C(=O)C1(NO)c1cccc(F)c1] | 4-(3-Fluorophenyl)-4-(hydroxyamino)-1,3-dimethyl-4,5-dihydro-1H-pyrazol-5-one |
| 97 | 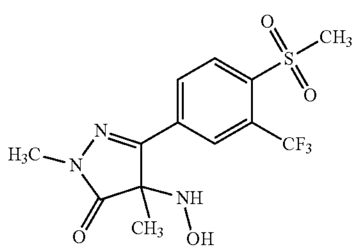 | 4-(Hydroxyamino)-3-[4-methanesulfonyl-3-(trifluoromethyl)phenyl]-1,4-dimethyl-4,5-dihydro-1H-pyrazol-5-one |
| 98 | 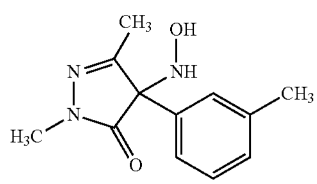 | 4-(Hydroxyamino)-1,3-dimethyl-4-(3-methylphenyl)-4,5-dihydro-1H-pyrazol-5-one |
| 99 | 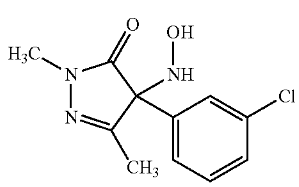 [SMILES: CC1=NN(C)C(=O)C1(NO)c1cccc(Cl)c1] | 4-(3-Chlorophenyl)-4-(hydroxyamino)-1,3-dimethyl-4,5-dihydro-1H-pyrazol-5-one |
| 100 | 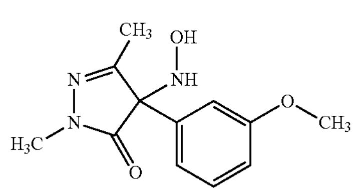 | 4-(Hydroxyamino)-4-(3-methoxyphenyl)-1,3-dimethyl-4,5-dihydro-1H-pyrazol-5-one |

TABLE 1-continued

Pyrazolone Derivative Compounds of the Disclosure

| Compound No. | Compound Structure | Compound Name |
| --- | --- | --- |
| 101 | 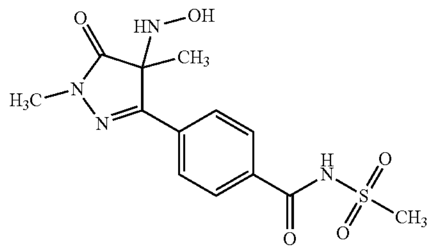 | 4-[4-(Hydroxyamino)-1,4-dimethyl-5-oxo-4,5-dihydro-1H-pyrazol-3-yl]-N-methanesulfonylbenzamide |
| 102 | 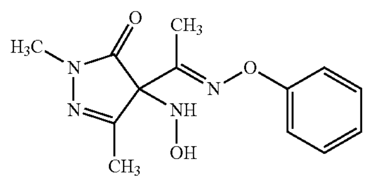 [SMILES: CC1=NN(C)C(=O)C1(NO)/C(C)=N/Oc1ccccc1] | 4-(Hydroxyamino)-1,3-dimethyl-4-[1-(phenoxyimino)ethyl]-4,5-dihydro-1H-pyrazol-5-one |
| 103 | 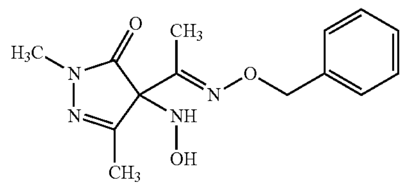 [SMILES: CC1=NN(C)C(=O)C1(NO)/C(C)=N/OCc1ccccc1] | 4-(Hydroxyamino)-1,3-dimethyl-4-[1-(benzyloxyimino)ethyl]-4,5-dihydro-1H-pyrazol-5-one |
| 104 | 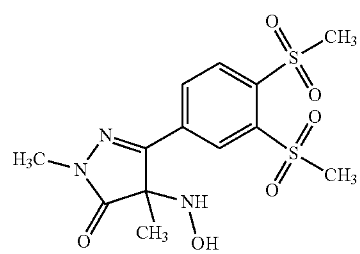 | 3-(3,4-Dimethanesulfonylphenyl)-4-(hydroxyamino)-1,4-dimethyl-4,5-dihydro-1H-pyrazol-5-one |
| 105 | 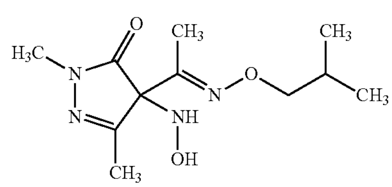 [SMILES: CC1=NN(C)C(=O)C1(NO)/C(C)=N/OCC(C)C] | 4-(Hydroxyamino)-1,3-dimethyl-4-[1-[(2-methylpropoxy)imino]ethyl]-4,5-dihydro-1H-pyrazol-5-one |
| 106 | 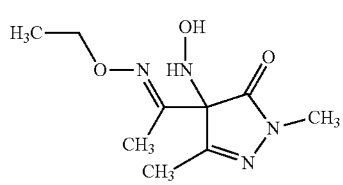 [SMILES: CCO/N=C(\C)C1(NO)C(=O)N(C)N=C1C] | 4-[1-(Ethoxyimino)ethyl]-4-(hydroxyamino)-1,3-dimethyl-4,5-dihydro-1H-pyrazol-5-one |
| 107 | 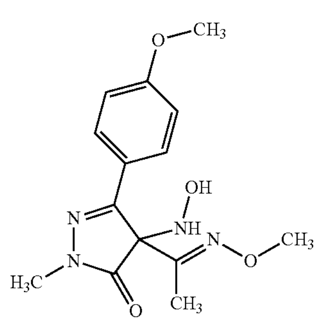 | 4-(Hydroxyamino)-4-[1-(methoxyimino)ethyl]-3-(4-methoxyphenyl)-1-methyl-4,5-dihydro-1H-pyrazol-5-one |

TABLE 1-continued

Pyrazolone Derivative Compounds of the Disclosure

| Compound No. | Compound Structure | Compound Name |
| --- | --- | --- |
| 108 | 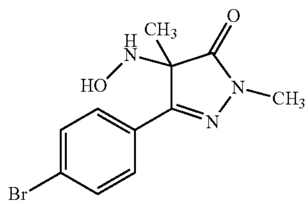 [SMILES: CN1N=C(c2ccc(Br)cc2)C(C)(NO)C1=O] | 3-(4-Bromophenyl)-4-(hydroxyamino)-1,4-dimethyl-4,5-dihydro-1H-pyrazol-5-one |
| 109 | 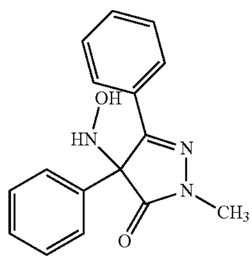 [SMILES: CN1N=C(c2ccccc2)C(NO)(c2ccccc2)C1=O] | 4-(Hydroxyamino)-1-methyl-3,4-diphenyl-4,5-dihydro-1H-pyrazol-5-one |
| 110 | 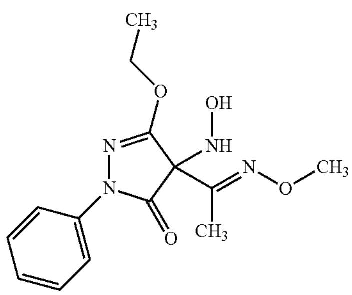 [SMILES: CCOC1=NN(c2ccccc2)C(=O)C1(NO)/C(C)=N/OC] | 3-Ethoxy-4-(hydroxyamino)-4-[1-(methoxyimino)ethyl]-1-phenyl-4,5-dihydro-1H-pyrazol-5-one |
| 111 | 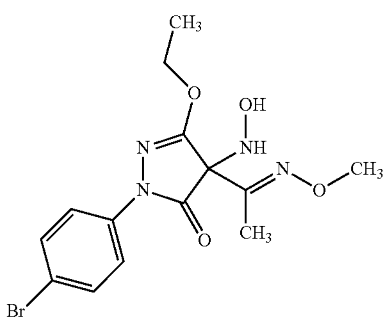 [SMILES: CCOC1=NN(c2ccc(Br)cc2)C(=O)C1(NO)/C(C)=N/OC] | 1-(4-Bromophenyl)-3-ethoxy-4-(hydroxyamino)-4-[1-(methoxyimino)ethyl]-4,5-dihydro-1H-pyrazol-5-one |
| 112 | 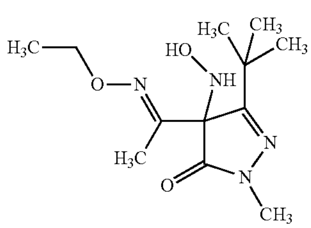 [SMILES: CCO/N=C(\C)C1(NO)C(=O)N(C)N=C1C(C)(C)C] | 3-tert-Butyl-4-[1-(ethoxyimino)ethyl]-4-(hydroxyamino)-1-methyl-4,5-dihydro-1H-pyrazol-5-one |
| 113 | 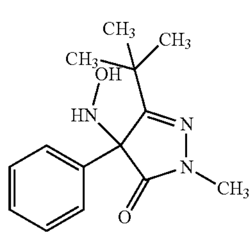 [SMILES: CN1N=C(C(C)(C)C)C(NO)(c2ccccc2)C1=O] | 3-tert-Butyl-4-(hydroxyamino)-1-methyl-4-phenyl-4,5-dihydro-1H-pyrazol-5-one |

TABLE 1-continued

Pyrazolone Derivative Compounds of the Disclosure

| Compound No. | Compound Structure | Compound Name |
| --- | --- | --- |
| 114 | 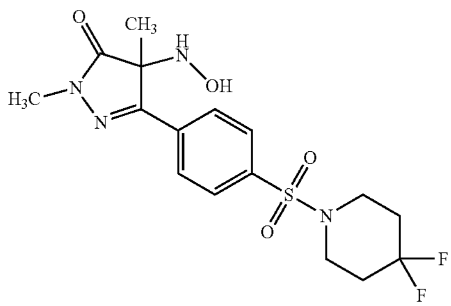 [SMILES: CN1N=C(c2ccc(S(=O)(=O)N3CCC(F)(F)CC3)cc2)C(C)(NO)C1=O] | 3-{4-[(4,4-Difluoropiperidin-1-yl)sulfonyl]phenyl}-4-(hydroxyamino)-1,4-dimethyl-4,5-dihydro-1H-pyrazol-5-one |
| 115 | 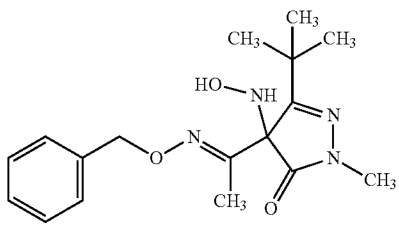 [SMILES: C/C(=N\OCc1ccccc1)C1(NO)C(=O)N(C)N=C1C(C)(C)C] | 4-[1-[(Benzyloxy)imino]ethyl]-3-tert-butyl-4-(hydroxyamino)-1-methyl-4,5-dihydro-1H-pyrazol-5-one |
| 116 | 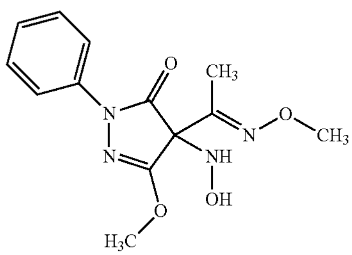 [SMILES: CO/N=C(\C)C1(NO)C(=O)N(c2ccccc2)N=C1OC] | 4-(Hydroxyamino)-3-methoxy-4-[1-(methoxyimino)ethyl]-1-phenyl-4,5-dihydro-1H-pyrazol-5-one |
| 117 | 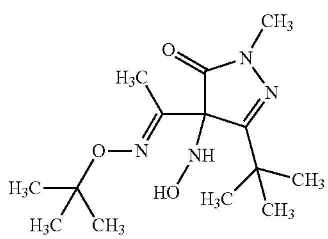 [SMILES: C/C(=N\OC(C)(C)C)C1(NO)C(=O)N(C)N=C1C(C)(C)C] | 4-[1-[(tert-Butoxy)imino]ethyl]-3-tert-butyl-4-(hydroxyamino)-1-methyl-4,5-dihydro-1H-pyrazol-5-one |
| 118 | 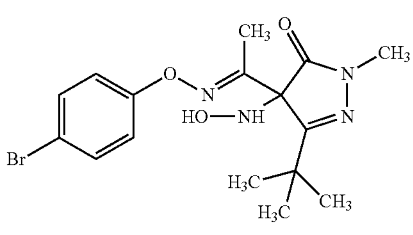 [SMILES: C/C(=N\Oc1ccc(Br)cc1)C1(NO)C(=O)N(C)N=C1C(C)(C)C] | 4-[1-[(4-Bromophenoxy)imino]ethyl]-3-tert-butyl-4-(hydroxyamino)-1-methyl-4,5-dihydro-1H-pyrazol-5-one |
| 119 | 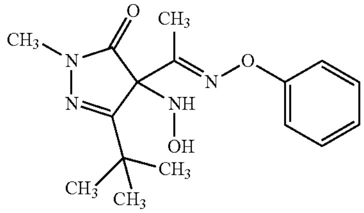 [SMILES: C/C(=N\Oc1ccccc1)C1(NO)C(=O)N(C)N=C1C(C)(C)C] | 3-tert-Butyl-4-(hydroxyamino)-1-methyl-4-[1-(phenoxyimino)ethyl]-4,5-dihydro-1H-pyrazol-5-one |

TABLE 1-continued

Pyrazolone Derivative Compounds of the Disclosure

| Compound No. | Compound Structure | Compound Name |
|---|---|---|
| 120 | 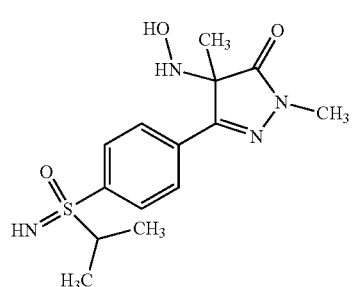 | 4-(Hydroxyamino)-3-{4-[imino(oxo)propan-2-yl-$\lambda^6$-sulfanyl]phenyl}-1,4-dimethyl-4,5-dihydro-1H-pyrazol-5-one |
| 121 | 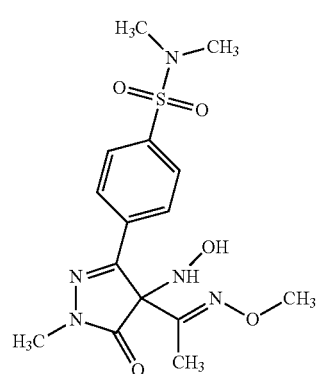 | 4-[4-(Hydroxyamino)-4-[1-(methoxyimino)ethyl]-1-methyl-5-oxo-4,5-dihydro-1H-pyrazol-3-yl]-N,N-dimethylbenzene-1-sulfonamide |
| 122 | 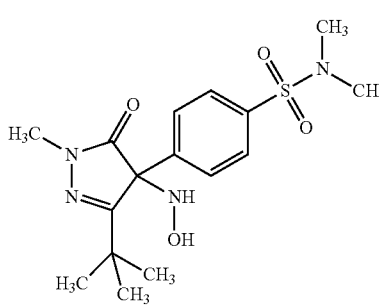 | 4-[3-tert-Butyl-4-(hydroxyamino)-1-methyl-5-oxo-4,5-dihydro-1H-pyrazol-4-yl]-N,N-dimethylbenzene-1-sulfonamide |
| 123 | 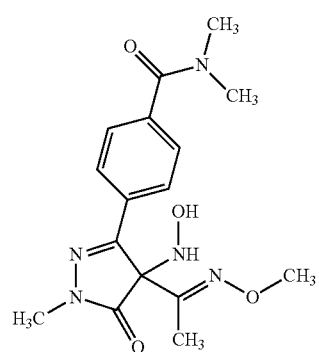 | 4-[4-(Hydroxyamino)-4-[1-(methoxyimino)ethyl]-1-methyl-5-oxo-4,5-dihydro-1H-pyrazol-3-yl]-N,N-dimethylbenzamide |

TABLE 1-continued

Pyrazolone Derivative Compounds of the Disclosure

| Compound No. | Compound Structure | Compound Name |
| --- | --- | --- |
| 124 | 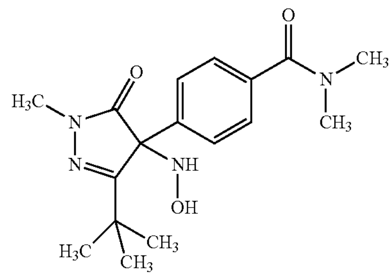 | 4-[3-tert-Butyl-4-(hydroxyamino)-1-methyl-5-oxo-4,5-dihydro-1H-pyrazol-4-yl]-N,N-dimethylbenzamide |
| 125 | 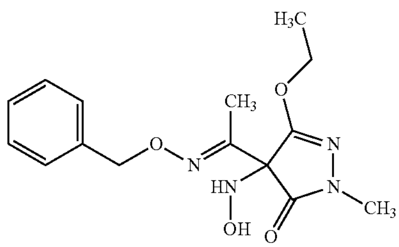 [SMILES: CCOC1=NN(C)C(=O)C1(NO)/C(C)=N/OCc1ccccc1] | 4-[1-[(Benzyloxy)imino]ethyl]-3-ethoxy-4-(hydroxyamino)-1-methyl-4,5-dihydro-1H-pyrazol-5-one |
| 126 | 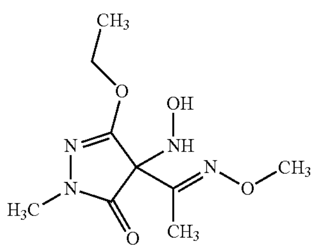 | 3-Ethoxy-4-(hydroxyamino)-4-[1-(methoxyimino)ethyl]-1-methyl-4,5-dihydro-1H-pyrazol-5-one |
| 127 | 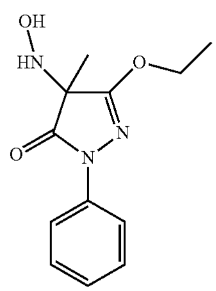 [SMILES: CCOC1=NN(c2ccccc2)C(=O)C1(C)NO] | 3-Ethoxy-4-(hydroxyamino)-4-methyl-1-phenyl-4,5-dihydro-1H-pyrazol-5-one |
| 128 | 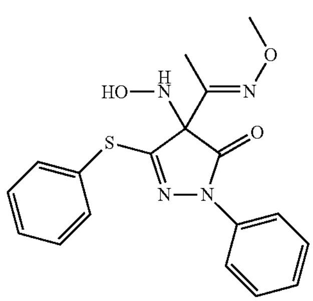 [SMILES: CO/N=C(\C)C1(NO)C(=O)N(c2ccccc2)N=C1Sc1ccccc1] | 4-(Hydroxyamino)-4-[1(methoxyimino)ethyl]-1-phenyl-3-(phenylsulfanyl)-4,5-dihydro-1H-pyrazol-5-one |

TABLE 1-continued

Pyrazolone Derivative Compounds of the Disclosure

| Compound No. | Compound Structure | Compound Name |
| --- | --- | --- |
| 129 | 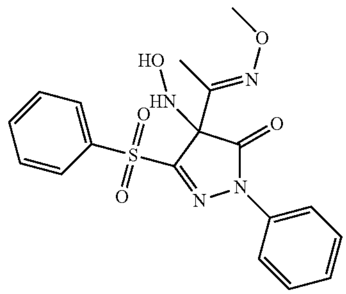 [SMILES: CO/N=C(\C)C1(NO)C(=O)N(c2ccccc2)N=C1S(=O)(=O)c1ccccc1] | 3-(Benzenesulfonyl)-4-(hydroxyamino)-4[1-(methoxyimino)ethyl]-1-phenyl-4,5-dihydro-1H-pyrazol-5-one pyrazol-5-one |
| 130 | 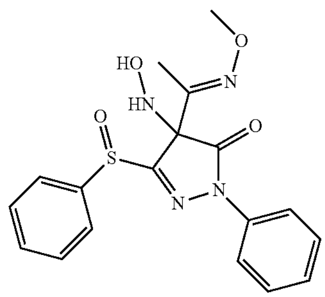 [SMILES: CO/N=C(\C)C1(NO)C(=O)N(c2ccccc2)N=C1S(=O)c1ccccc1] | 3-(Benzenesulfinyl)-4-(hydroxyamino)4[1-(methoxyimino)ethyl]-1-phenyl-4,5-dihydro1H-pyrazol-5-one |
| 131 | 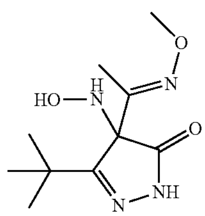 [SMILES: CO/N=C(\C)C1(NO)C(=O)NN=C1C(C)(C)C] | 3-tert-Butyl-4-(hydroxyamino)-4-[1-(methoxyimino)ethyl]-4,5-dihydro-1H-pyrazol-5-one |
| 132 | 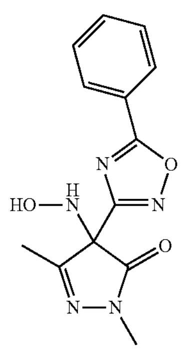 [SMILES: CC1=NN(C)C(=O)C1(NO)c1noc(-c2ccccc2)n1] | 4-(Hydroxyamino)-1,3-dimethyl-4-(5-phenyl-1,2,4-oxadiazol-3-yl)-4,5-dihydro-1H-pyrazol-5-one |
| 133 | 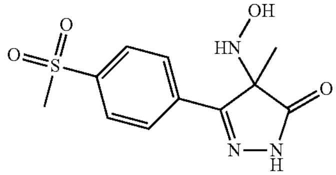 [SMILES: CC1(NO)C(=O)NN=C1c1ccc(S(C)(=O)=O)cc1] | 4-(Hydroxyamino)-3-(4-methanesulfonylphenyl)-4-methyl-4,5-dihydro-1H-pyrazol-5-one |
| 134 | 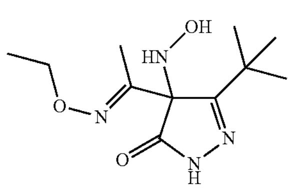 [SMILES: CCO/N=C(\C)C1(NO)C(=O)NN=C1C(C)(C)C] | 3-tert-Butyl-4-[1-(ethoxyimino)ethyl]-4-(hydroxyamino)-4,5-dihydro-1H-pyrazol-5-one |

TABLE 1-continued

Pyrazolone Derivative Compounds of the Disclosure

| Compound No. | Compound Structure | Compound Name |
|---|---|---|
| 135 | 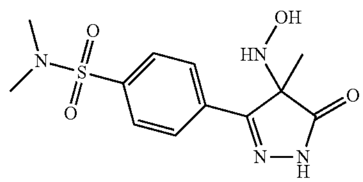 [SMILES: CN(C)S(=O)(=O)c1ccc(C2=NNC(=O)C2(C)NO)cc1] | 4-[4-(Hydroxyamino)-4-methyl-5-oxo-4,5-dihydro-1GH-pyrazol-3-yl]-N,N-dimethylbenzene-1-sulfonamide |
| 136 | 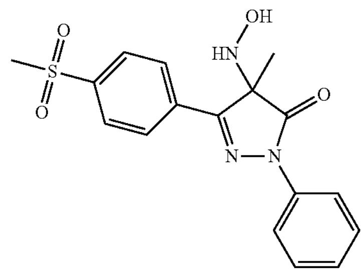 [SMILES: CC1(NO)C(=O)N(c2ccccc2)N=C1c1ccc(S(C)(=O)=O)cc1] | 4-(Hydroxyamino)-3-(4-methanesulfonylphenyl)-4-methyl-1-phenyl-4,5-dihydro-1H-pyrazol-5-one |
| 137 | 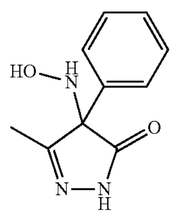 | 4-(Hydroxyamino)-3-methyl-4-phenyl-4,5-dihydro-1H-pyrazol-5-one |
| 138 | 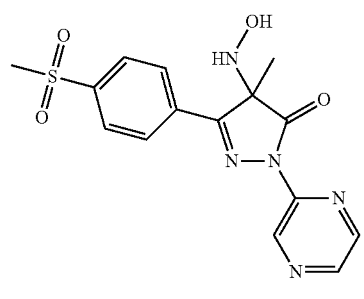 [SMILES: CC1(NO)C(=O)N(c2cnccn2)N=C1c1ccc(S(C)(=O)=O)cc1] | 4-(Hydroxyamino)-3-(4-methanesulfonylphenyl)-4-methyl-1-(pyrazin-2-yl)-4,5-dihydro-1H-pyrazol-5-one |
| 139 | 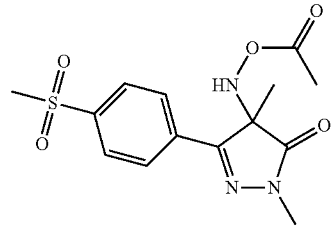 [SMILES: CC(=O)ONC1(C)C(=O)N(C)N=C1c1ccc(S(C)(=O)=O)cc1] | [3-(4-Methanesulfonylphenyl)-1,4-dimethyl-5-oxo-4,5-dihydro-1H-pyrazol-4-yl]amino acetate |
| 140 | 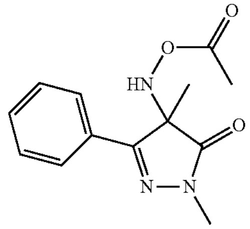 [SMILES: CC(=O)ONC1(C)C(=O)N(C)N=C1c1ccccc1] | (1,4-Dimethyl-5-oxo-3-phenyl-4,5-dihydro-1H-pyrazol-4-yl)amino acetate |

TABLE 1-continued

Pyrazolone Derivative Compounds of the Disclosure

| Compound No. | Compound Structure | Compound Name |
|---|---|---|
| 141 | 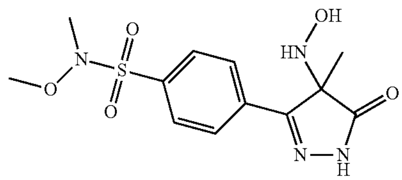 [SMILES: CON(C)S(=O)(=O)c1ccc(C2=NNC(=O)C2(C)NO)cc1] | 4-[4-(Hydroxyamino)-4-methyl-5-oxo-4,5-dihydro-1H-pyrazol-3-yl]-N-methoxy-N-methylbenzene-1-sulfonamide |
| 142 | 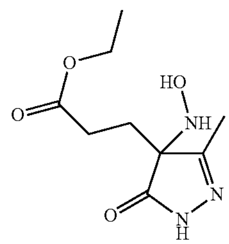 [SMILES: CCOC(=O)CCC1(NO)C(=O)NN=C1C] | ethyl 3-[4-(hydroxyamino)-3-methyl-5-oxo-4,5-dihydro-1H-pyrazol-4-yl]propanoate |
| 143 | 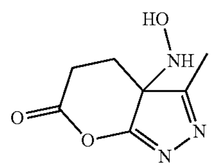 | 3a-(hydroxyamino)-3-methyl-3aH,4H,5H,6H-pyrano[2,3-c]pyrazol-6-one |
| 144 | 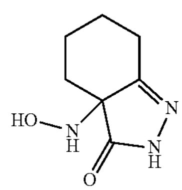 [SMILES: O=C1NN=C2CCCCC12NO] | 3a-(Hydroxyamino)-3,3a,4,5,6,7-hexahydro-2H-indazol-3-one |
| 145 | 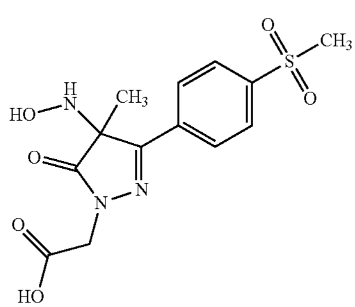 [SMILES: CC1(NO)C(=O)N(CC(=O)O)N=C1c1ccc(S(C)(=O)=O)cc1] | 2-(4-(hydroxyamino)-4-methyl-3-(4-(methylsulfonyl)phenyl)-5-oxo-4,5-dihydro-1H-pyrazol-1-yl)acetic acid |
| 146 | 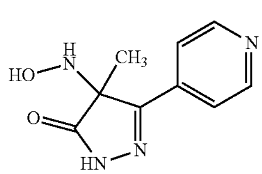 | 4-(hydroxyamino)-4-methyl-3-(pyridin-4-yl)-1H-pyrazol-5(4H)-one |
| 147 | 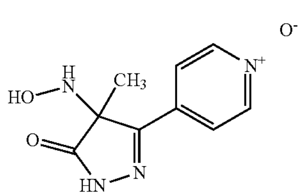 | 4-(4-(hydroxyamino)-4-methyl-5-oxo-4,5-dihydro-1H-pyrazol-3-yl)pyridine-1-oxide |

TABLE 1-continued

Pyrazolone Derivative Compounds of the Disclosure

| Compound No. | Compound Structure | Compound Name |
|---|---|---|
| 148 | 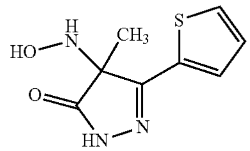 | 4-(hydroxyamino)-4-methyl-3-(thiophen-2-yl)-1H-pyrazol-5(4H)-one |
| 149 | 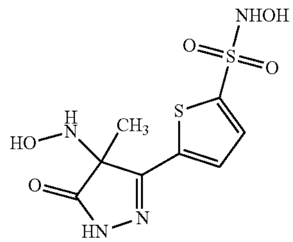 | N-hydroxy-5-(4-(hydroxyamino)-4-methyl-5-oxo-4,5-dihydro-1H-pyrazol-3-yl)thiophene-2-sulfonamide |
| 150 | 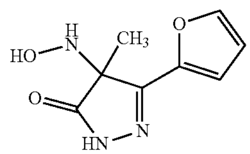 | 3-(furan-2-yl)-4-(hydroxyamino)-4-methyl-1H-pyrazol-5(4H)-one |
| 151 | 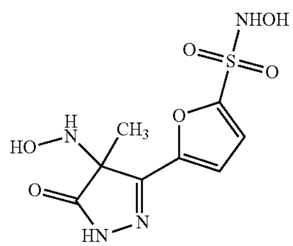 | N-hydroxy-5-(4-(hydroxyamino)-4-methyl-5-oxo-4,5-dihydro-1H-pyrazol-3-yl)furan-2-sulfonamide |
| 152 | 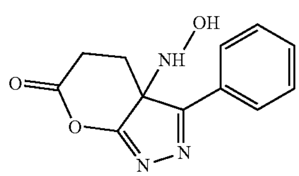 [SMILES: O=C1CCC2(NO)C(=NN=C2c2ccccc2)O1] | 3a-(hydroxyamino)-3-phenyl-4,5-dihydropyrano[2,3-c]pyrazol-6(3aH)-one |
| 153 | 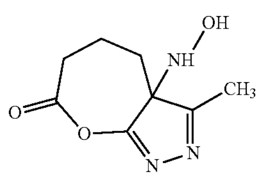 | 3a-(hydroxyamino)-3-methyl-5,6-dihydro-3aH-oxepino[2,3-c]pyrazol-7(4H)-one |
| 154 | 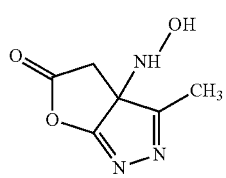 | 3a-(hydroxyamino)-3-methyl-3aH-furo[2,3-c]pyrazol-5(4H)-one |
| 155 | 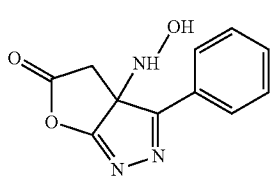 [SMILES: O=C1CC2(NO)C(=NN=C2c2ccccc2)O1] | 3a-(hydroxyamino)-3-phenyl-3aH-furo[2,3-c]pyrazol-5(4H)-one |

In particular embodiments, a compound from Table 1 is utilized as a pharmaceutically acceptable salt thereof.

In one embodiment, a compound of the disclosure is not 4-(hydroxyamino)-4-(1-(methoxyimino)ethyl)-3-methyl-1-phenyl-1H-pyrazol-5(4H)-one. In another embodiment, a compound of the disclosure is not 4-(hydroxyamino)-4-(1-(methoxyimino)ethyl)-1,3-dimethyl-1H-pyrazol-5(4H)-one. In another embodiment, a compound of the disclosure is not 4-(hydroxyamino)-3,4-dimethyl-1-phenyl-1H-pyrazol-5(4H)-one. In another embodiment, a compound of the disclosure is not 4-(hydroxyamino)-1,3,4-trimethyl-1H-pyrazol-5(4H)-one. In another embodiment, a compound of the disclosure is not 1-(4-chlorophenyl)-4-(hydroxyamino)-3,4-dimethyl-1H-pyrazol-5(4H)-one. In another embodiment, a compound of the disclosure is not 1-(2-chlorophenyl)-4-(hydroxyamino)-3,4-dimethyl-1H-pyrazol-5(4H)-one. In another embodiment, a compound of the disclosure is not 4-(hydroxyamino)-3,4-dimethyl-1H-pyrazol-5(4H)-one. In another embodiment, a compound of the disclosure is not 4-(hydroxyamino)-4-(1-(methoxyimino)ethyl)-3-methyl-1-phenyl-1H-pyrazol-5(4H)-one, 4-(hydroxyamino)-4-(1-(methoxyimino)ethyl)-1,3-dimethyl-1H-pyrazol-5(4H)-one, 4-(hydroxyamino)-3,4-dimethyl-1-phenyl-1H-pyrazol-5(4H)-one, 4-(hydroxyamino)-1,3,4-trimethyl-1H-pyrazol-5(4H)-one, 1-(4-chlorophenyl)-4-(hydroxyamino)-3,4-dimethyl-1H-pyrazol-5(4H)-one, 1-(2-chlorophenyl)-4-(hydroxyamino)-3,4-dimethyl-1H-pyrazol-5(4H)-one, or 4-(hydroxyamino)-3,4-dimethyl-1H-pyrazol-5(4H)-one.

Unexpectedly, it has been discovered that compounds falling within the scope of formulae (Ia) to (Ii) are sufficiently stable under solid state conditions and, thus, are amenable to oral administration (see, e.g., Example 148). Moreover, particular compounds falling within the scope of formulae (Ia) to (Ii) have a plasma half-life of greater than about 10 minutes, e.g., when measured in dog, rat and/or human plasma in the presence of an anticoagulant (e.g., heparin or sodium citrate) at pH 7.4, in accordance with the procedure described in Example 149. It has been discovered that such compounds have a favorable toxicological profile.

3.3 Measuring Nitroxyl Donating Ability

Compounds are easily tested for nitroxyl donation by routine experiments. Although it is typically impractical to directly measure whether nitroxyl is donated, several analytical approaches are accepted as suitable for determining whether a compound donates nitroxyl. For example, the compound of interest can be placed in solution, for example in phosphate buffered saline ("PBS") or in a phosphate buffered solution at a pH of about 7.4, in a sealed container. After sufficient time for disassociation has elapsed, such as from several minutes to several hours, the headspace gas is withdrawn and analyzed to determine its composition, such as by gas chromatography and/or mass spectrometry. If the gas $N_2O$ is formed (which occurs by HNO dimerization), the test is positive for nitroxyl donation and the compound is deemed to be a nitroxyl donor.

Alternatively, the compound of interest can be placed in a solution of tris(4,6-dimethyl-3-sulfanatophenyl)phosphine trisodium salt (TXPTS) in e.g., a phosphate buffered solution at a pH of about 7.4. The amount of nitroxyl released from the compound of interest can be detected by monitoring the formation of TXPTS aza-ylide by $^1$H NMR. See Reisz et al., *Org. Lett.* 11:2719-2721 (2009), Reisz et al., *J. Am. Chem. Soc.* 133:11675-11685 (2011) and Guthrie et al., *J. Org. Chem.* 80:1338-1348 (2015). Accordingly, if TXPTS aza-ylide is formed, the test is positive for nitroxyl donation.

If desired, nitroxyl donation also can be detected by exposing the test compound to metmyoglobin ("$Mb^{3+}$"). See Bazylinski et al., *J. Amer. Chem. Soc.* 107(26):7982-7986 (1985). Nitroxyl reacts with $Mb^{3+}$ to form a $Mb^{2+}$—NO complex, which can be detected by changes in the ultraviolet/visible spectrum or by electron paramagnetic resonance ("EPR"). The $Mb^{2+}$—NO complex has an EPR signal centered around a g-value of about 2. Nitric oxide, on the other hand, reacts with $Mb^{3+}$ to form an $Mb^{3+}$—NO complex that has a negligible, if any, EPR signal. Accordingly, if a compound reacts with $Mb^{3+}$ to form a complex detectable by common methods, such as ultraviolet/visible or EPR, then the test is positive for nitroxyl donation.

The level of nitroxyl donating ability can be expressed as a percentage of a compound's theoretical stoichiometric maximum. A compound that donates a "significant level of nitroxyl" means, in various embodiments, a compound that donates about 40% or more, about 50% or more, about 60% or more, about 70% or more, about 80% or more, about 90% or more, or about 95% or more of its theoretical maximum amount of nitroxyl. In particular embodiments, a compound donates from about 70% to about 90% of its theoretical maximum amount of nitroxyl. In particular embodiments, a compound donates from about 85% to about 95% of its theoretical maximum amount of nitroxyl. In particular embodiments, a compound donates from about 90% to about 95% of its theoretical maximum amount of nitroxyl. Compounds that donate less than about 40%, or less than about 50%, of their theoretical maximum amount of nitroxyl are still nitroxyl donors and can be used in the methods disclosed. A compound that donates less than about 50% of its theoretical amount of nitroxyl can be used in the methods disclosed, but may require higher dosing levels as compared to a compound that donates a higher level of nitroxyl.

Testing for nitroxyl donation can be performed at a physiologically relevant pH. In particular embodiments, a compound of the disclosure is capable of donating nitroxyl at physiological pH (i.e., a pH of about 7.4) and physiological temperature (i.e., a temperature of about 37° C.) (together, "physiological conditions"). In particular embodiments, a compound of the disclosure can donate about 40% or more of its theoretical maximum (i.e., 100%) amount of nitroxyl under physiological conditions. In particular embodiments, a compound of the disclosure can donate about 50% or more of its theoretical maximum amount of nitroxyl under physiological conditions. In particular embodiments, a compound of the disclosure can donate about 60% or more of its theoretical maximum amount of nitroxyl under physiological conditions. In particular embodiments, a compound of the disclosure can donate about 70% or more of its theoretical maximum amount of nitroxyl under physiological conditions. In particular embodiments, a compound of the disclosure can donate about 80% or more of its theoretical maximum amount of nitroxyl under physiological conditions. In particular embodiments, a compound of the disclosure can donate about 90% or more of its theoretical maximum amount of nitroxyl under physiological conditions.

It will be understood that a compound of the disclosure might also donate a limited amount of nitric oxide, so long as the amount of nitroxyl donation exceeds the amount of nitric oxide donation. In certain embodiments, a compound of the disclosure can donate about 25 mole % or less of nitric oxide under physiological conditions. In particular embodiments, a compound of the disclosure can donate about 20 mole % or less of nitric oxide under physiological conditions. In particular embodiments, a compound of the disclosure can donate about 15 mole % or less of nitric oxide under physiological conditions. In particular embodiments, a compound of the disclosure can donate about 10 mole % or less of nitric oxide under physiological conditions. In particular embodiments, a compound of the disclosure can donates about 5 mole % or less of nitric oxide under physiological conditions. In particular embodiments, a compound of the disclosure can donate about 2 mole % or less of nitric oxide under physiological conditions. In particular embodiments, a compound of the disclosure can donate an insignificant amount (e.g., about 1 mole % or less) of nitric oxide under physiological conditions.

3.4 Pharmaceutical Compositions

The disclosure also encompasses pharmaceutical compositions comprising at least one compound of formula (Ia), (Ib), (Ic), (Id), (Ie), (If), (Ig), (Ih), (Ii), (IIa) or (IIb) and at least one pharmaceutically acceptable excipient. Examples of pharmaceutically acceptable excipients include those described above, such as carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and any combination thereof. The selection and use of pharmaceutically acceptable excipients is taught, e.g., in Troy, Ed., *Remington: The Science and Practice of Pharmacy*, $21^{st}$ Ed. (Lippincott Williams & Wilkins, Baltimore, Md., 2005).

In one embodiment, the at least one pharmaceutically acceptable excipient is selected from lactose, microcrystalline cellulose, croscarmellose, or any mixture thereof. In another embodiment, the at least one pharmaceutically acceptable excipient is selected from lactose, microcrystalline cellulose, croscarmellose sodium, or any mixture thereof. Lactose, the naturally-occurring disaccharide of galactose and glucose, being available in a range of varieties, e.g., granulated, sieved, milled, spray dried, and anhydrous, is a well-accepted excipient for medical and pharmaceutical uses. Reilly, "Pharmaceutical Necessities," pp. 1015-1050 in *Remington: The Science and Practice of Pharmacy* (Gennaro, ed., $20^{th}$ ed., Lippincott, Williams & Wilkins, Baltimore, Md., 2000). Microcrystalline cellulose is disclosed to be a most resourceful excipient because of the profusion of grades available for different needs and its physical properties that support a variety of functional requirements, e.g., as a bulking agent, disintegrant, binder, lubricant, glidant, and/or stability enhancer. Baboota et al., "Microcrystalline cellulose as a versatile excipient in drug research," *J. Young Pharmacists* 1:6-12 (2009). Croscarmellose is an internally cross-linked carboxymethylcellulose; croscarmellose sodium is the sodium salt of an internally cross-linked, at least partially O-(carboxymethylated) cellulose. Either form of this excipient has reduced water solubility, attributed to the cross-linking, thus providing, inter alia, enhanced dissolution characteristics. Boylan et al., pp. 2623-2624 in *Encyclopedia of Pharmaceut. Technol.* ($1^{st}$ ed., Marcel Dekker, New York, 1988).

The pharmaceutical compositions can be formulated for administration in solid or liquid form, including those adapted for the following: (1) oral administration, for example, as drenches (for example, aqueous or non-aqueous solutions or suspensions), tablets (for example, those targeted for buccal, sublingual and systemic absorption), caplets, boluses, powders, granules, pastes for application to the tongue, hard gelatin capsules, soft gelatin capsules, mouth sprays, troches, lozenges, pellets, syrups, suspensions, elixirs, liquids, emulsions and microemulsions; or (2) parenteral administration by, for example, subcutaneous, intramuscular, intravenous or epidural injection as, for example, a sterile solution or suspension. The pharmaceutical compositions can be for immediate, sustained or controlled release.

In one particular embodiment, the pharmaceutical composition is formulated for intravenous administration. In another embodiment, the pharmaceutical composition is formulated for intravenous administration by continuous infusion.

In another embodiment, the pharmaceutical composition is formulated for oral administration. In another embodiment, the pharmaceutical composition is formulated for oral administration as a liquid dosage form. In another embodiment, the pharmaceutical composition is formulated for oral administration in solid dosage form. In particular embodiments where the pharmaceutical composition is formulated as an oral liquid or solid dosage form, polyethylene glycol, such as polyethylene glycol 300 ("PEG300"), polyethylene glycol 400 ("PEG400"), and mixtures thereof, can serve as an excipient.

The pharmaceutical composition can be prepared as any appropriate unit dosage form, such as capsule, sachet, tablet, powder, granule, solution, suspension in an aqueous liquid, suspension in a non-aqueous liquid, oil-in-water liquid emulsion, water-in-oil liquid emulsion, liposomes or bolus. In one embodiment, the pharmaceutical composition is formulated as a tablet. In another embodiment, the pharmaceutical composition is formulated as a capsule.

Tablets can be made by compression or molding, optionally with one or more accessory ingredients. Compressed tablets can be prepared by compressing in a suitable machine the therapeutic agent or agents in a free-flowing form such as a powder or granules, optionally mixed with a binder, lubricant, inert diluent, preservative, surface-active or dispersing agent. Molded tablets can be made by molding in a suitable machine a mixture of the powdered compound moistened with an inert liquid diluent. The tablets can be optionally coated or scored and can be formulated so as to provide slow or controlled release of the active ingredient therein. Methods of formulating such slow or controlled release compositions of pharmaceutically active ingredients, such as the therapeutic agents herein and other compounds known in the art, are known in the art and disclosed in issued U.S. patents, some of which include, but are not limited to, U.S. Pat. Nos. 4,369,174, 4,842,866, and the references cited therein. Coatings can be used for delivery of compounds to the intestine (see, e.g., U.S. Pat. Nos. 6,638,534, 5,217,720, 6,569,457, and the references cited therein). An artisan will recognize that in addition to tablets, other dosage forms can be formulated to provide slow or controlled release of the active ingredient. Such dosage forms include, but are not limited to, capsules, granulations and gel-caps.

Pharmaceutical compositions suitable for topical administration include, without limitation, lozenges comprising the ingredients in a flavored basis, such as sucrose, acacia and tragacanth; and pastilles comprising the active ingredient in a flavored basis or in an inert basis, such as gelatin and glycerin.

Various embodiments of pharmaceutical compositions suitable for parenteral administration include, without limitation, either aqueous sterile injection solutions or non-aqueous sterile injection solutions, each containing, for example, anti-oxidants, buffers, bacteriostats and solutes that render the formulation isotonic with the blood of the intended recipient; and aqueous sterile suspensions and non-aqueous sterile suspensions, each containing, for example, suspending agents and thickening agents. The formulations can be presented in unit-dose or multi-dose containers, for example, sealed ampules or vials, and can be stored in a freeze dried (lyophilized) condition requiring only the addition of a sterile liquid carrier, such as water, immediately prior to use.

Pharmaceutical compositions administered parenterally can be administered in an acidic, neutral or basic solution. In one embodiment, pharmaceutical compositions are formulated in an acidic solution having a pH of from about 4 to about 5, for instance, a pH of about 4, about 4.5, about 4.8, or about 5, including values there between. While a pH of about 4 has generally been considered optimal for formulating nitroxyl donating compositions to achieve adequate stability of the compound, it has been discovered that formulating under such acidic conditions can potentially cause or exacerbate venous irritation following parenteral administration. The amount of irritation can be attenuated by formulating the pharmaceutical compositions in less acidic or even neutral solutions. Accordingly, in particular embodiments, a pharmaceutical composition formulated for parenteral use at a pH of from about 5 to about 6.2 (e.g., pH of about 5, about 5.5, about 5.8, about 6, or about 6.2, including values there between).

3.5 Methods of Use

In one aspect, the disclosure provides a method of increasing in vivo nitroxyl levels, comprising administering to a patient in need thereof an effective amount of a compound or a pharmaceutical composition as disclosed herein. In various embodiments, the patient has, is suspected of having, or is at risk of having or developing a condition that is responsive to nitroxyl therapy.

In particular embodiments, the disclosure provides a method of treating, preventing or delaying the onset and/or development of a condition, comprising administering to a patient (including a patient identified as in need of such treatment, prevention or delay) an effective amount of a compound or a pharmaceutical composition as disclosed herein. Identifying a patient in need thereof can be in the judgment of a physician, clinical staff, emergency response personnel or other health care professional and can be subjective (e.g., opinion) or objective (e.g., measurable by a test or diagnostic method).

Particular conditions embraced by the methods disclosed herein include, without limitation, cardiovascular diseases, ischemia/reperfusion injury, and pulmonary hypertension.

3.5.1 Cardiovascular Diseases

In one embodiment, the disclosure provides a method of treating a cardiovascular disease, comprising administering an effective amount of a compound or a pharmaceutical composition as disclosed herein to a patient in need thereof.

Examples of cardiovascular diseases and symptoms that can usefully be treated with the compounds and compositions disclosed herein include cardiovascular diseases that are responsive to nitroxyl therapy, coronary obstructions, coronary artery disease ("CAD"), angina, heart attack, myocardial infarction, high blood pressure, ischemic cardiomyopathy and infarction, pulmonary congestion, pulmonary edema, cardiac fibrosis, valvular heart disease, pericardial disease, circulatory congestive states, peripheral edema, ascites, Chagas' disease, ventricular hypertrophy, heart valve disease, heart failure, diastolic heart failure, systolic heart failure, congestive heart failure, acute congestive heart failure, acute decompensated heart failure, and cardiac hypertrophy.

3.5.1.1 Heart Failure

The compounds and compositions of the disclosure can be used to treat patients suffering from heart failure. The heart failure can be of any type or form, including any of the heart failures disclosed herein. Nonlimiting examples of heart failure include early stage heart failure, Class I, II, III and IV heart failure, acute heart failure, congestive heart failure ("CHF") and acute CHF. In one embodiment, the compounds and compositions of the disclosure can be used to treat acute decompensated heart failure.

In embodiments where the compounds and pharmaceutical compositions of the disclosure are used to treat patients suffering from heart failure, another active agent that treats heart failure can also be administered. In one such embodiment, the compound or pharmaceutical composition of the disclosure can be administered in conjunction with a positive inotrope such as a beta-agonist. Examples of beta-agonists include, without limitation, dopamine, dobutamine, isoproterenol, analogs of such compounds and derivatives of such compounds. In another embodiment, the compound or pharmaceutical composition of the disclosure can be administered in conjunction with a beta-adrenergic receptor antagonist (also referred to herein as beta-antagonist or beta-blocker). Examples of beta-antagonists include, without limitation, propranolol, metoprolol, bisoprolol, bucindolol, and carvedilol.

Compounds of the disclosure compounds can be administered as pharmaceutical formulations to patients in need of modulating in vivo nitroxyl levels. For instance, a pharmaceutical formulation comprising a compound of the disclosure can be administered to a patient intravenously.

3.5.1.2 Ischemia/Reperfusion Injury

In another embodiment, the disclosed subject matter provides a method of treating, preventing or delaying the onset and/or development of ischemia/reperfusion injury, comprising administering an effective amount of a compound or pharmaceutical composition as disclosed herein to a subject in need thereof.

In a particular embodiment, the method is for preventing ischemia/reperfusion injury. In a particular embodiment, a compound or pharmaceutical composition of the disclosure is administered prior to the onset of ischemia. In a particular embodiment, a pharmaceutical composition of the disclosure is administered prior to procedures in which myocardial ischemia can occur, for example an angioplasty or surgery, such as a coronary artery bypass graft surgery. In a particular embodiment, a pharmaceutical composition of the disclosure is administered after ischemia but before reperfusion. In a particular embodiment, a pharmaceutical composition of the disclosure is administered after ischemia and reperfusion.

In another embodiment, a pharmaceutical composition of the disclosure can be administered to a patient who is at risk for an ischemic event. In a particular embodiment, a pharmaceutical composition of the disclosure is administered to a patient at risk for a future ischemic event, but who has no present evidence of ischemia. The determination of whether a patient is at risk for an ischemic event can be performed by any method known in the art, such as by examining the patient or the patient's medical history. In a particular embodiment, the patient has had a prior ischemic event. Thus, the patient can be at risk of a first or subsequent ischemic event. Examples of patients at risk for an ischemic event include patients with known hypercholesterolemia, EKG changes associated with ischemia (e.g., peaked or inverted T-waves or ST segment elevations or depression in an appropriate clinical context), abnormal EKG not associated with active ischemia, elevated CKMB, clinical evidence of ischemia (e.g., crushing sub-sternal chest pain or arm pain, shortness of breath and/or diaphoresis), prior history of myocardial infarction ("MI"), elevated serum cholesterol, sedentary lifestyle, angiographic evidence of partial coronary artery obstruction, echocardiographic evidence of myocardial damage, or any other evidence of a risk for a future ischemic event. Examples of ischemic events include, without limitation, MI and neurovascular ischemia, such as a cerebrovascular accident ("CVA").

In another embodiment, the subject of treatment is an organ that is to be transplanted. In a particular embodiment, a pharmaceutical composition of the disclosure can be administered prior to reperfusion of the organ in a transplant recipient. In a particular embodiment, a pharmaceutical composition of the disclosure can be administered prior to removal of the organ from the donor, for example through the perfusion cannulas used in the organ removal process. If the organ donor is a live donor, for example a kidney donor, the compounds or pharmaceutical compositions of the disclosure can be administered to the organ donor. In a particular embodiment, the compounds or pharmaceutical compositions of the disclosure are administered by storing the organ in a solution comprising the compound or pharmaceutical composition. For example, a compound or pharmaceutical composition of the disclosure can be included in the organ preservation solution, such as the University of Wisconsin "UW" solution, which is a solution comprising hydroxyethyl starch substantially free of ethylene glycol, ethylene chlorohydrin and acetone (see U.S. Pat. No. 4,798,824). In a particular embodiment, a pharmaceutical composition of the disclosure that is administered is such that ischemia/reperfusion injury to the tissues of the organ is reduced upon reperfusion in the recipient of transplanted organ. In a particular embodiment, the method reduces tissue necrosis (the size of infarct) in at-risk tissues.

Ischemia/reperfusion injury can damage tissues other than those of the myocardium and the disclosed subject matter embraces methods of treating or preventing such damage. In various embodiments, the ischemia/reperfusion injury is non-myocardial. In particular embodiments, the method reduces injury from ischemia/reperfusion in the tissue of the brain, liver, gut, kidney, bowel, or any part of the body other than the myocardium. In another embodiment, the patient is at risk for such injury. Selecting a person at risk for non-myocardial ischemia could include a determination of the indicators used to assess risk for myocardial ischemia. However, other factors can indicate a risk for ischemia/reperfusion in other tissues. For example, surgery patients often experience surgery related ischemia. Thus, patients scheduled for surgery could be considered at risk for an ischemic event. The following risk factors for stroke (or a subset of these risk factors) could demonstrate a patient's risk for ischemia of brain tissue: hypertension, cigarette smoking, carotid artery stenosis, physical inactivity, diabetes mellitus, hyperlipidemia, transient ischemic attack, atrial fibrillation, CAD, CHF, past MI, left ventricular dysfunction with mural thrombus, and mitral stenosis. Ingall, *Postgrad. Med.* 107(6):34-50 (2000). Further, complications of untreated infectious diarrhea in the elderly can include myocardial, renal, cerebrovascular and intestinal ischemia. Slotwiner-Nie et al., *Gastroenterol. Clin. N. Amer.* 30(3): 625-635 (2001). Alternatively, patients could be selected based on risk factors for ischemic bowel, kidney and/or liver disease. For example, treatment would be initiated in elderly patients at risk of hypotensive episodes (such as surgical blood loss). Thus, patients presenting with such an indication would be considered at risk for an ischemic event. In another embodiment, the patient has any one or more of the conditions listed herein, such as diabetes mellitus and hypertension. Other conditions that can result in ischemia, such as cerebral arteriovenous malformation, could demonstrate a patient's risk for an ischemic event.

3.5.2 Pulmonary Hypertension

In another embodiment, a compounds or pharmaceutical composition of the disclosure can be used to prevent or delay the onset and/or development of pulmonary hypertension. In one such embodiment, a compounds or pharmaceutical composition of the disclosure can be used to prevent or delay the onset and/or development of pulmonary arterial hypertension ("PAH").

In another embodiment, the disclosed subject matter provides a method of reducing mean pulmonary arterial pressure ("MPAP"), comprising administering an effective amount of a compound or a pharmaceutical composition disclosed herein to a patient in need thereof. In another embodiment, the MPAP is reduced by up to about 50%. In another embodiment, the MPAP is reduced by up to about 25%. In another embodiment, the MPAP is reduced by up to about 20%. In another embodiment, the MPAP is reduced by up to about 15%. In another embodiment, the MPAP is reduced by up to 10%. In another embodiment, the MPAP is reduced by up to about 5%. In another embodiment, the MPAP is reduced to be from about 12 mmHg to about 16 mmHg. In another embodiment, the MPAP is reduced to be about 15 mmHg.

3.6 Administration Modes, Regimens and Dose Levels

The compounds and pharmaceutical compositions of the disclosure can be administered via parenteral (e.g., subcutaneous, intramuscular, intravenous or intradermal) administration. In certain embodiments, the compound or pharmaceutical composition is administered by intravenous infusion. In other embodiments, the compounds and pharmaceutical compositions of the disclosure can be administered by oral administration.

When a pharmaceutical composition comprising a compound of the disclosure is administered, dosages are expressed based on the amount of active pharmaceutical ingredient, i.e., the amount of compound(s) of the disclosure present in the pharmaceutical composition.

In a variety of embodiments, including various oral administration embodiments, the compounds or pharmaceutical compositions of the disclosure are administered according to a weight-based daily dosing regimen, either as a single daily dose ("QD") or in multiple divided doses administered, e.g., twice a day ("BID"), 3 times a day ("TID"), or four times a day ("QID").

In certain embodiments, the compound or pharmaceutical composition of the disclosure is administered in a dose of at least about 0.5 mg/kg/d, at least about 0.75 mg/kg/d, at least about 1.0 mg/kg/d, at least about 1.5 mg/kg/d, at least about 2 mg/kg/d, at least about 2.5 mg/kg/d, at least about 3 mg/kg/d, at least about 4 mg/kg/d, at least about 5 mg/kg/d, at least about 7.5 mg/kg/d, at least about 10 mg/kg/d, at least about 12.5 mg/kg/d, at least about 15 mg/kg/d, at least about 17.5 mg/kg/d, at least about 20 mg/kg/d, at least about 25 mg/kg/d, at least about 30 mg/kg/d, at least about 35 mg/kg/d, at least about 40 mg/kg/d, at least about 45 mg/kg/d, at least about 50 mg/kg/d, at least about 60 mg/kg/d, at least about 70 mg/kg/d, at least about 80 mg/kg/d, at least about 90 mg/kg/d, or at least about 100 mg/kg/d.

In certain embodiments, the compound or pharmaceutical composition of the disclosure is administered at a dose of no more than about 100 mg/kg/d, no more than about 100 mg/kg/d, no more than about 90 mg/kg/d, no more than about 80 mg/kg/d, no more than about 80 mg/kg/d, no more than about 75 mg/kg/d, no more than about 70 mg/kg/d, no more than about 60 mg/kg/d, no more than about 50 mg/kg/d, no more than about 45 mg/kg/d, no more than about 40 mg/kg/d, no more than about 35 mg/kg/d, no more than about 30 mg/kg/d.

In a variety of embodiments, the dose is from about 0.001 mg/kg/d to about 10,000 mg/kg/d. In certain embodiments, the dose is from about 0.01 mg/kg/d to about 1,000 mg/kg/d. In certain embodiments, the dose is from about 0.01 mg/kg/d to about 100 mg/kg/d. In certain embodiments, the dose is from about 0.01 mg/kg/d to about 10 mg/kg/d. In certain embodiments, the dose is from about 0.1 mg/kg/d to about 1 mg/kg/d. In certain embodiments, the dose is less than about 1 g/kg/d.

In certain embodiments, a compound or pharmaceutical composition of the disclosure is administered in a dose range in which the low end of the range is any amount from about 0.1 mg/kg/day to about 90 mg/kg/day and the high end of the range is any amount from about 1 mg/kg/day to about 100 mg/kg/day (e.g., from about 0.5 mg/kg/day to about 2 mg/kg/day in one series of embodiments and from about 5 mg/kg/day to about 20 mg/kg/day in another series of embodiment).

In particular embodiments, the compound or pharmaceutical composition of the disclosure is administered in a dose range of about 3 to about 30 mg/kg, administered QD, BID, or TID.

In certain embodiments, compounds or pharmaceutical compositions of the disclosure are administered according to a flat (i.e., non-weight-based) dosing regimen, either QD or in multiple divided doses administered, e.g., BID, TID, or QID.

In various embodiments, the compound or pharmaceutical composition of the disclosure is administered at a dose of at least about 0.01 grams/day (g/d), at least about 0.05 g/d, at least about 0.1 g/d, at least about 0.5 g/d, at least about 1 g/d, at least about 1.5 g/d, at least about 2.0 g/d, at least about 2.5 g/d, at least about 3.0 g/d, or at least about 3.5 g/d.

In various embodiments, the compound or pharmaceutical composition of the disclosure is administered at a dose of no more than about 5 g/d, no more than about 4.5 g/d, no more than about 4 g/d, no more than about 3.5 g/d, no more than about 3 g/d, no more than about 2.5 g/d, or no more than about 2 g/d.

In certain embodiments, the compound or pharmaceutical composition of the disclosure is administered in a dose of about 0.01 grams per day to about 4.0 grams per day. In certain embodiments, a compound or pharmaceutical composition of the disclosure can be administered at a dose in which the low end of the range is any amount from about 0.1 mg/day to about 400 mg/day and the high end of the range is any amount from about 1 mg/day to about 4000 mg/day. In certain embodiments, the compound or pharmaceutical composition is administered in a dose of about 5 mg/day to about 100 mg/day. In various embodiments, the compound or pharmaceutical composition is administered at a dose of from about 150 mg/day to about 500 mg/day.

The dosing interval for parenteral or oral administration can be adjusted according to the needs of the patient. For longer intervals between administrations, extended release or depot formulations can be used.

For intravenous administration, the dose can usefully be expressed per unit time, either as a fixed amount per unit time or as a weight-based amount per unit time.

In various embodiments, a compound or pharmaceutical composition of the disclosure is administered intravenously in an amount of at least about 0.1 µg/kg/min, at least about 0.2 µg/kg/min, at least about 0.3 µg/kg/min, at least about 0.4 µg/kg/min, at least about 0.5 µg/kg/min, at least about 1 µg/kg/min, at least about 2.5 µg/kg/min, at least about 5 µg/kg/min, at least about 7.5 µg/kg/min, at least about 10 µg/kg/min, at least about 11 µg/kg/min, at least about 12 µg/kg/min, at least about 13 µg/kg/min, at least about 14 µg/kg/min, at least about 15 µg/kg/min, at least about 16 µg/kg/min, at least about 17 µg/kg/min, at least about 18 µg/kg/min, at least about 19 µg/kg/min, at least about 20 µg/kg/min, at least about 21 µg/kg/min, at least about 22 µg/kg/min, at least about 23 µg/kg/min, at least about 24 µg/kg/min, at least about 25 µg/kg/min, at least about 26 µg/kg/min, at least about 27 µg/kg/min, at least about 28 µg/kg/min, at least about 29 µg/kg/min, at least about 30 µg/kg/min, at least about 31 µg/kg/min, at least about 32 µg/kg/min, at least about 33 µg/kg/min, at least about 34 µg/kg/min, at least about 35 µg/kg/min, at least about 36 µg/kg/min, at least about 37 µg/kg/min, at least about 38 µg/kg/min, at least about 39 µg/kg/min, or at least about 40 µg/kg/min.

In various embodiments, the compound or pharmaceutical composition of the present disclosure is administered intravenously in an amount of no more than about 100 µg/kg/min, no more than about 90 µg/kg/min, no more than about 80 µg/kg/min, no more than about 70 µg/kg/min, no more than about 60 µg/kg/min, no more than about 50 µg/kg/min, no more than about 49 µg/kg/min, no more than about 48 µg/kg/min, no more than about 47 µg/kg/min, no more than about 46 µg/kg/min, no more than about 45 µg/kg/min, no more than about 44 µg/kg/min, no more than about 43 µg/kg/min, no more than about 42 µg/kg/min, no more than about 41 µg/kg/min, no more than about 40 µg/kg/min, no more than about 39 µg/kg/min, no more than about 38 µg/kg/min, no more than about 37 µg/kg/min, no more than about 36 µg/kg/min, no more than about 35 µg/kg/min, no more than about 34 µg/kg/min, no more than about 33 µg/kg/min, no more than about 32 µg/kg/min, no more than about 31 µg/kg/min, or no more than about 30 µg/kg/min.

In some embodiments, the compound or pharmaceutical composition of the present disclosure is administered intravenously in an amount ranging from about 0.1 µg/kg/min to about 100 µg/kg/min, about 1 µg/kg/min to about 100 µg/kg/min, about 2.5 µg/kg/min to about 100 µg/kg/min, about 5 µg/kg/min to about 100 µg/kg/min, about 10 µg/kg/min to about 100 µg/kg/min, about 1.0 µg/kg/min to about 80 µg/kg/min, from about 10.0 µg/kg/min to about 70 µg/kg/min, from about 20 µg/kg/min to about 60 µg/kg/min, from about 15 µg/kg/min to about 50 µg/kg/min, from about 0.01 µg/kg/min to about 1.0 µg/kg/min, from about 0.01 µg/kg/min to about 10 µg/kg/min, from about 0.1 µg/kg/min to about 1.0 µg/kg/min, from about 0.1 µg/kg/min to about 10 µg/kg/min, from about 1.0 µg/kg/min to about 5 µg/kg/min, from about 70 µg/kg/min to about 100 µg/kg/min, or from about 80 µg/kg/min to about 90 µg/kg/min.

In particular embodiments, the compound or pharmaceutical composition of the present disclosure is administered intravenously in an amount ranging from about 10 µg/kg/min to about 50 µg/kg/min, about 20 µg/kg/min to about 40 µg/kg/min, about 25 µg/kg/min to about 35 µg/kg/min, or about 30 µg/kg/min to about 40 µg/kg/min. In particular embodiments, a compound or pharmaceutical composition of the present disclosure is administered intravenously in an amount of from about 20 µg/kg/min to about 30 µg/kg/min.

A compound or pharmaceutical composition as disclosed herein can be administered prior to, at substantially the same time with, or after administration of an additional therapeutic agent. The administration regimen can include pretreatment and/or co-administration with the additional therapeutic agent. In such case, the compound or pharmaceutical composition and the additional therapeutic agent can be administered simultaneously, separately, or sequentially.

Examples of administration regimens include without limitation: administration of each compound, pharmaceutical composition or therapeutic agent in a sequential manner; and co-administration of each compound, pharmaceutical composition or therapeutic agent in a substantially simultaneous manner (e.g., as in a single unit dosage form) or in multiple, separate unit dosage forms for each compound, pharmaceutical composition or therapeutic agent.

It will be appreciated by those in the art that the "effective amount" or "dose" ("dose level") will depend on various factors such as the particular administration mode, administration regimen, compound, and pharmaceutical composition selected, as well as the particular condition and patient being treated. For example, the appropriate dose level can vary depending upon the activity, rate of excretion and potential for toxicity of the specific compound or pharmaceutical composition employed; the age, body weight, general health, gender and diet of the patient being treated; the frequency of administration; the other therapeutic agent(s) being co-administered; and the type and severity of the condition.

3.7 Kits Comprising the Compounds or Pharmaceutical Compositions

The disclosure provides kits comprising a compound or a pharmaceutical composition disclosed herein. In a particular embodiment, the kit comprises a compound or a pharmaceutical composition disclosed herein, each in dry form, and a pharmaceutically acceptable liquid diluent.

In particular embodiments, either a compound in dry form or a pharmaceutical composition in dry form contains about 2.0% or less water by weight, about 1.5% or less water by weight, about 1.0% or less water by weight, about 0.5% or less water by weight, about 0.3% or less water by weight, about 0.2% or less water by weight, about 0.1% or less water by weight, about 0.05% or less water by weight, about 0.03% or less water by weight, or about 0.01% or less water by weight.

Pharmaceutically acceptable liquid diluents are known in the art and include but are not limited to sterile water, saline solutions, aqueous dextrose, glycerol, glycerol solutions, and the like. Other examples of suitable liquid diluents are disclosed by Nairn, "Solutions, Emulsions, Suspensions and Extracts," pp. 721-752 in *Remington: The Science and Practice of Pharmacy*, 20th Ed. (Lippincott Williams & Wilkins, Baltimore, Md., 2000).

In one embodiment, the kit further comprises instructions for using the compound or pharmaceutical composition. The instructions can be in any appropriate form, such as written or electronic form. In another embodiment, the instructions can be written instructions. In another embodiment, the instructions are contained in an electronic storage medium (e.g., magnetic diskette or optical disk). In another embodiment, the instructions include information as to the compound or pharmaceutical composition and the manner of administering the compound or pharmaceutical composition to a patient. In another embodiment, the instructions relate to a method of use disclosed herein (e.g., treating, preventing and/or delaying onset and/or development of a condition selected from cardiovascular diseases, ischemia/reperfusion injury, pulmonary hypertension and other conditions responsive to nitroxyl therapy).

In another embodiment, the kit further comprises suitable packaging. Where the kit comprises more than one compound or pharmaceutical composition, the compounds or pharmaceutical compositions can be packaged patiently in separate containers, or combined in one container when cross-reactivity and shelf life permit.

Should there be doubt over the agreement of a depicted chemical structure and a chemical name, the chemical name governs.

4. EXAMPLES

The following examples are presented for illustrative purposes and should not serve to limit the scope of the disclosed subject matter.

4.1 Synthesis of Pyrazolone Derivative Compounds

The compounds disclosed herein can be made according to the methods disclosed below or by procedures known in the art. Starting materials for the reactions can be commercially available or can be prepared by known procedures or obvious modifications thereof. For example, some of the starting materials are available from commercial suppliers such as Sigma-Aldrich (St. Louis, Mo.). Others can be prepared by procedures or obvious modifications thereof disclosed in standard reference texts such as *March's Advanced Organic Chemistry* (John Wiley and Sons) and *Larock's Comprehensive Organic Transformations* (VCH Publishers).

The following "General Methods" were employed in specific steps of the compound syntheses disclosed in the Examples, which Examples appear after the General Methods. Throughout the General Methods, "R" represents the phenyl substituent or substituents that may be present on phenyl in a specific synthesis, "R'" is $(C_1\text{-}C_4)$alkyl, and "R''" is $(C_1\text{-}C_6)$alkyl, $(C_3\text{-}C_6)$cycloalkyl, $(C_1\text{-}C_4)$haloalkyl, $(C_1\text{-}C_4)$perhaloalkyl, $—NH_2$, $—N(H)—(C_1\text{-}C_6)$alkyl, or $—N—[(C_1\text{-}C_6)\text{alkyl}]_2$.

General Method 1: Beta-Ketoester Synthesis

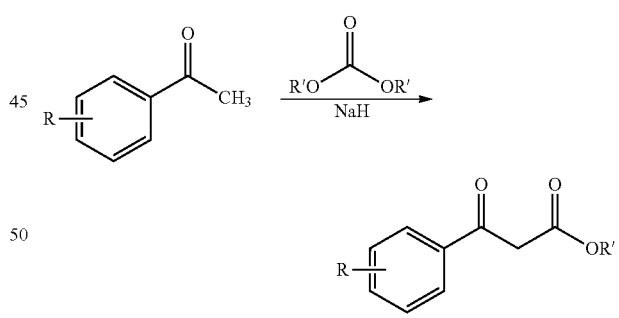

To a solution of an acetophenone (1 equiv) in THF (10 vol) was added a dialkyl carbonate (2 equiv) and NaH (60%, 2 equiv). The solution was heated to reflux for 17 hours, before cooling to 0° C. with the aid of an ice bath. The dark brown mixture was carefully acidified to pH 4 with 36% HCl and filtered to remove inorganic impurities. The filtrate was poured into a large amount of water (50 vol) and extracted with ethyl acetate (3×10 vol). The combined extracts were washed with brine (15 vol), dried over magnesium sulfate, filtered, and concentrated under reduced pressure. As required, the product was then purified via a standard method(s).

General Method 2: Pyrazolone Synthesis

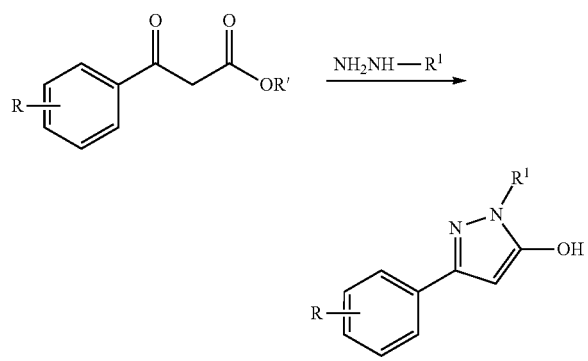

To a solution of the beta-ketoester from General Method 1 (1 equiv) in ethanol (5 vol) was added a ($C_1$-$C_6$)alkyl-, substituted phenyl-, or unsubstituted phenyl-hydrazine, such as methyl hydrazine, (1.1 equiv) with stirring. The reaction was heated to reflux until analysis showed substantially complete consumption of the starting material (about 3 hours). The reaction was allowed to cool to a temperature of about 25° C. and the solid that formed was collected by filtration, washed with cold ethanol (2 vol), and dried under reduced pressure. Alternatively, after concentration, the compound could be isolated by chromatography, e.g., by silica gel column chromatography.

General Method 3: Formylation by Process A

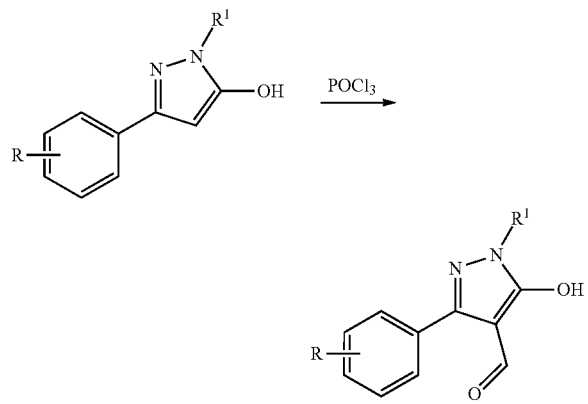

To a solution of the pyrazolone from General Method 2 (1 equiv) in dimethylformamide ("DMF", 2 vol) was added phosphorus oxychloride (0.7 equiv) and the reaction mixture was heated to 65° C. until substantially complete consumption of the starting material was determined by LC-MS. The mixture was diluted with water (5 vol) and allowed to stand at a temperature of about 25° C. until a solid precipitated (in about 12-72 hours). Filtration of the precipitate, followed by washing with water (until the solution was neutral in pH) provided the desired aldehyde which was dried at about 40° C. under reduced pressure.

General Method 4: Formylation by Process B

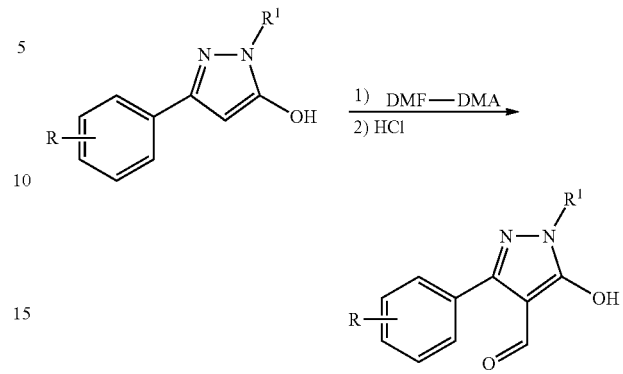

The pyrazolone from General Method 2 (1 equiv) was dissolved in 1,1-dimethoxy-N,N-dimethylmethanamine ("DMF-DMA") (6.5 equiv) and stirred at a temperature of about 25° C. until analysis showed substantially complete consumption of starting material (in about 1-4 hours), then the mixture was concentrated under reduced pressure. In the next step, the concentrate was treated with 6M HCl (10 vol) and stirred for 18 hours or until substantially complete consumption of the starting material was observed by LC-MS. The resulting solid was collected by filtration, washed with aliquots of water, then dried at about 40° C. under reduced pressure.

General Method 5: Reduction

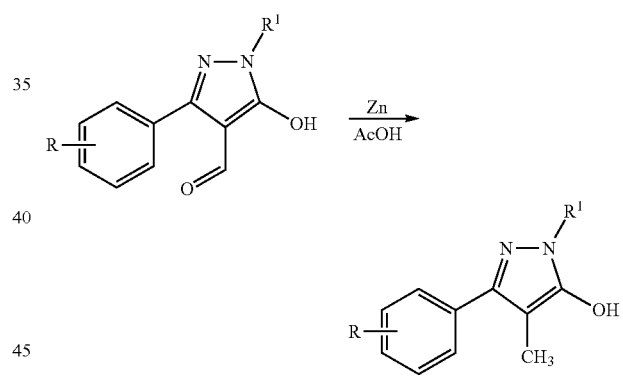

An acetic acid (8 vol) suspension of the formylated-pyrazolone from General Method 3 or 4 (1 equiv) and powdered zinc (10 equiv) was heated to about 65° C. for about 5.5 hours or until substantially complete consumption of the starting material was achieved, as determined by LC-MS. The zinc was removed by filtration and the solvent was removed under reduced pressure to provide the compound contaminated with acetic acid. Removal of the acetic acid was carried out by trituration with toluene, heptanes, and methanol.

General Method 6: Bromination by Process A

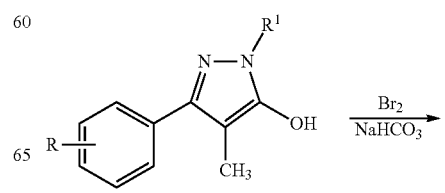

-continued

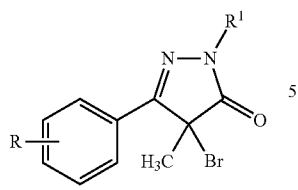

To a solution of the reduced pyrazolone from General Method 5 (1 equiv) in dichloromethane ("DCM"):water (1:1, 50 vol) was added sodium bicarbonate (1 equiv). The biphasic reaction mixture was vigorously stirred while bromine (1 equiv) was added dropwise. Stirring was continued for about 5 minutes before the reaction mixture was transferred to a separating funnel and shaken until a clear, colorless aqueous layer resulted. The organic layer was removed, dried over magnesium sulfate, filtered, and concentrated under reduced pressure to provide the brominated product.

General Method 7: Bromination by Process B

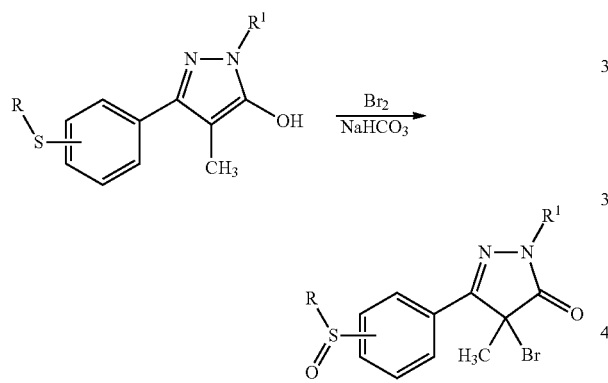

To a solution of the reduced pyrazolone from General Method 5 (1 equiv) in DCM:water (1:1, 50 vol) was added sodium bicarbonate (2 equiv). The biphasic reaction mixture was vigorously stirred while bromine (2 equiv) was added dropwise. Stirring was continued for about 5 minutes before the reaction mixture was transferred to a separating funnel and shaken until a clear, colorless aqueous layer resulted. The organic layer was removed, dried over magnesium sulfate, filtered and concentrated under reduced pressure to provide the brominated product.

General Method 8: Bromine Displacement

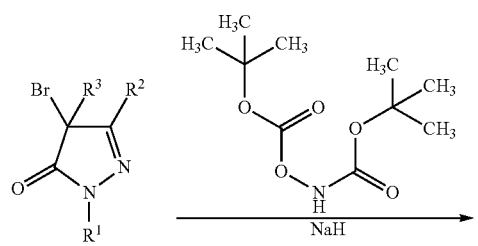

-continued

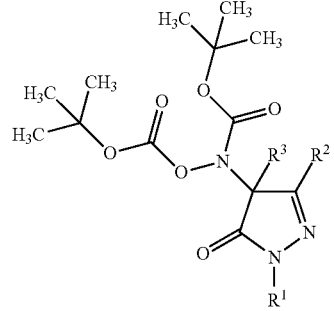

To a solution of N, O-di-BOC-hydroxylamine (1 equiv) in DMF (5 vol) was added sodium hydride (1.2 equiv, 60% dispersion). The reaction mixture was allowed to stand for about 1 hour after which time a brominated pyrazolone, e.g., the brominated pyrazolone synthesized in General Method 6 or 7, (1 equiv) was added as a solution in DMF (5 vol). Stirring was continued until substantially complete consumption of the bromide was achieved as determined by LC-MS (in about 1-24 hours). The mixture was diluted with diethyl ether (30 vol), washed with ammonium chloride (1×20 vol), washed with water (3×30 vol), and washed with brine (2×30 vol). The organic portion was dried over sodium sulfate, filtered, and concentrated under reduced pressure. As required, purification was carried out by silica gel column chromatography eluting with heptanes:ethyl acetate gradients.

General Method 9: Deprotection

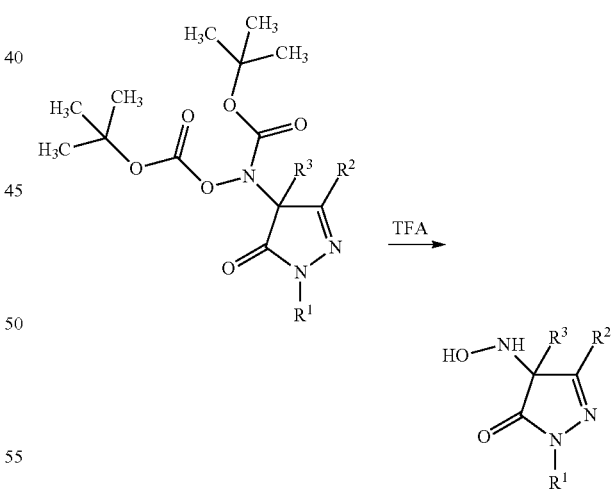

To a solution of the bis-BOC pyrazolone derivative from General Method 8 (1 equiv) in DCM (10 vol) was added trifluoroacetic acid ("TFA", 10 equiv). The reaction mixture was stirred at a temperature of about 25° C. until substantially complete consumption of the starting material was achieved as determined by LC-MS. The solvent was removed under reduced pressure and, as required, the product was purified by a standard method(s) including silica gel column chromatography or reverse phase HPLC.

General Method 10: Alkylsulfinyl Oxidation

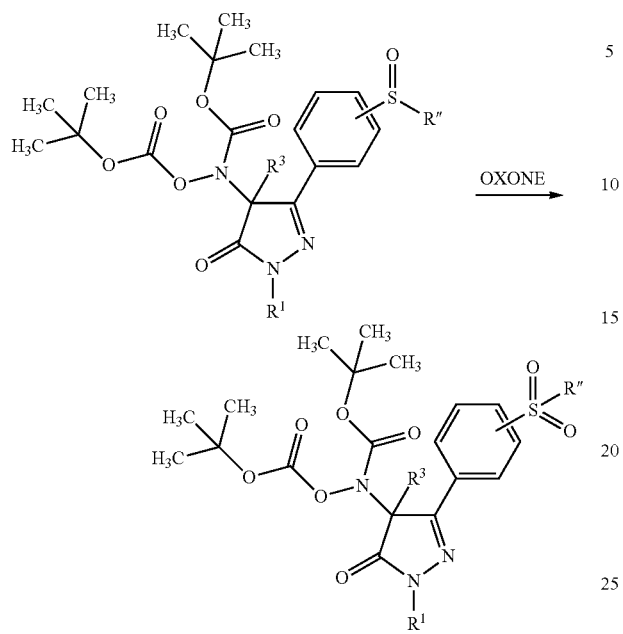

To a solution of a (C₁-C₆)alkylsulfinylphenyl-substituted bis-BOC pyrazolone derivative from General Method 8 (1 equiv) in dioxane:water (1:1, 10 vol) at a temperature of about 25° C. was added portionwise the potassium peroxymonosulfate compound OXONE (CAS Number 70693-62-8, 2 equiv). The reaction mixture was stirred at a temperature of about 25° C. for about 16 hours after which time the mixture was filtered and the filtrate was concentrated to remove the organic solvent. The organic solvent was extracted into ethyl acetate (2×10 vol), the organic portions were combined, washed with water (10 vol), washed with brine (10 vol), dried over magnesium sulfate, filtered, and the solvent was removed under reduced pressure to provide the product which, as required, was purified by a standard method(s).

General Method 11: Acetate Formation

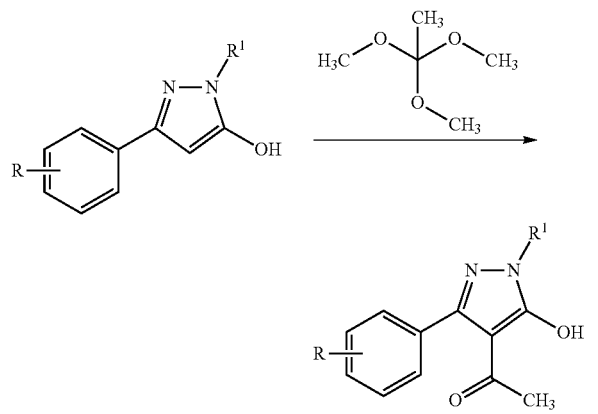

The synthesis was carried out according to the method disclosed in Janin et al., "Methyl orthocarboxylates as methylating agents of heterocycles," *Eur. J. Org. Chem.* 2002(11):1763-1769. A mixture of the pyrazolone from General Method 2 (1 equiv) and 1,1,1-trimethoxyethane (1.5 equiv) was refluxed for about 2 hours. The solution was concentrated under reduced pressure and the residue poured onto ice water. The resulting solid was filtered, washed with small amount of ice water (3 vol), and dried in an oven.

General Method 12: Oxime Formation

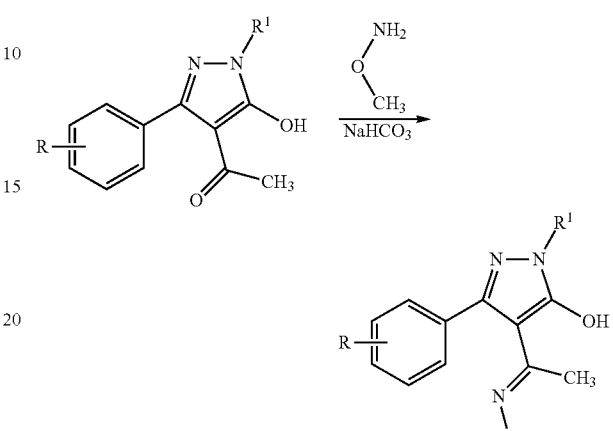

To a solution of the acetate from General Method 11 (1 equiv) in methanol (10 vol) was added O-methyl hydroxylamine HCl (1 equiv) and sodium bicarbonate (1 equiv). The reaction mixture was heated to reflux for about 1 hour (or until the reaction was substantially complete as determined by LC-MS) then allowed to cool to a temperature of about 25° C. The mixture was concentrated under reduced pressure, redissolved in DCM, filtered, and concentrated under reduced pressure. The product was either used directly in a subsequent step or chromatographed by column chromatography eluting with heptanes:ethyl acetate gradients before its use in a subsequent step.

General Method 13: Phenylbutanoate Synthesis

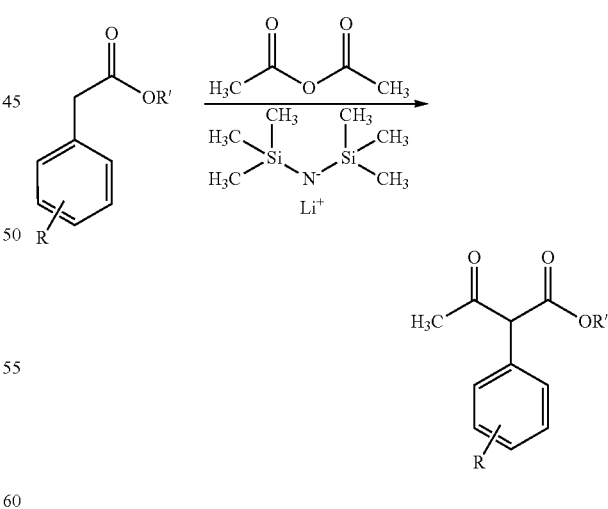

To a solution of an alkyl phenyl acetate (1 equiv) in THF (10 vol) in a flask at a temperature of about −78° C. (dry ice-acetone bath) was added 1M lithium 1,1,1,3,3,3-hexamethyldisilazan-2-ide in THF (2 equiv). The reaction mixture was stirred for about 20 minutes at about −78° C. Acetic anhydride (1 equiv) was added rapidly, the flask was removed from the dry ice-acetone bath and placed into an ice-water bath where it was allowed to warm to about 0° C., and stirred until substantially complete consumption of the starting material was achieved as determined by LC-MS. The mixture was quenched with ammonium chloride solution (10 vol) and the product was extracted into ethyl acetate (3×10 vol). The ethyl acetate layers were combined, dried over magnesium sulfate, filtered, and concentrated under reduced pressure to provide a product which was chromatographed by silica gel column chromatography eluting with 0-100% ethyl acetate:heptanes gradients.

General Method 14: Fluorine Displacement with Methyl Sulfide

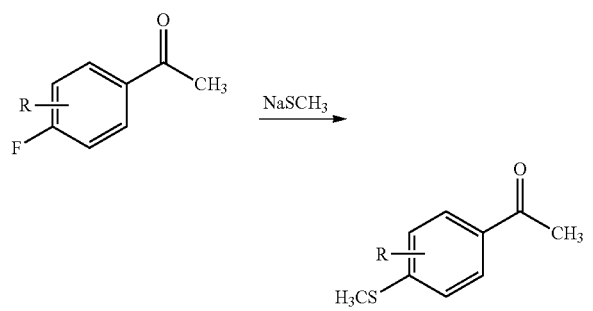

To a solution of a 4-fluoro acetophenone (1 equiv) in DMF (10 vol) at about 0° C. was added sodium thiomethoxide (1.1. equiv) and the reaction mixture stirred for about 40 minutes (or until substantially complete as determined by LC-MS). Water (25 vol) was added to the mixture and the product was extracted into diethyl ether (3×10 vol). The diethyl ether layers were combined, dried over magnesium sulfate, filtered, and concentrated under reduced pressure. The product was then used directly in a subsequent step or purified by a standard method(s) before its use in a subsequent step.

General Method 15: Amide Coupling

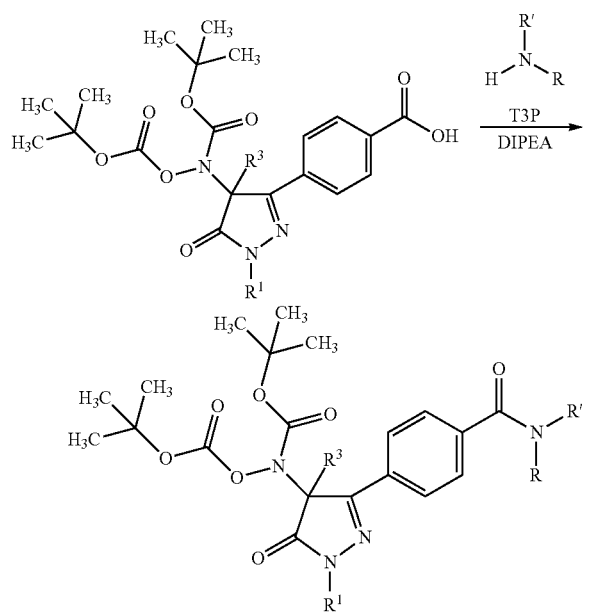

To a solution of a carboxylic acid (1 equiv) in THF (10 vol) was added an amine (1.1 equiv), diisopropylethylamine ("DIPEA"; 2.5 equiv) and propylphosphonic anhydride ("T3P") as a 50% solution in ethyl acetate (2 equiv). The reaction mixture was stirred at a temperature of about 25° C. until substantially complete as determined by LC-MS. Water (15 vol) was added and the product was extracted into ethyl acetate (2×10 vol). The combined organic layers were dried over magnesium sulfate, filtered and concentrated under reduced pressure to provide a product which was purified using standard methods.

General Method 16: Nucleophilic Aromatic Substitution

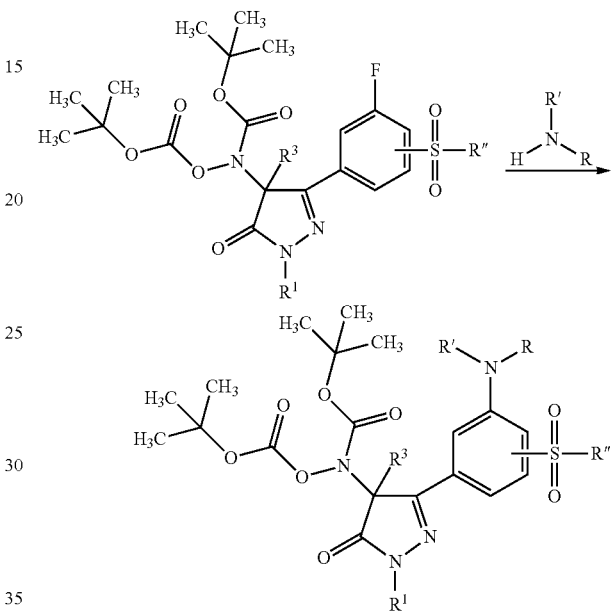

To a solution of a 3-fluoro-phenyl pyrazolone (1 equiv) in acetonitrile (6.7 vol) was added an amine and the reaction mixture was stirred at about 80° C. until substantially complete as determined by LC-MS (about 17 hours). The reaction mixture was cooled to a temperature of about 25° C. and ethyl acetate (33 vol) was added. The aqueous layer was isolated and re-extracted with further portions of ethyl acetate (3×33 vol). The combined organic layers were washed with water (2×33 vol), dried over magnesium sulfate, filtered and concentrated under reduced pressure to afford a product which was either used directly or purified using silica gel chromatography.

General Method 17: Nitroso Aldol

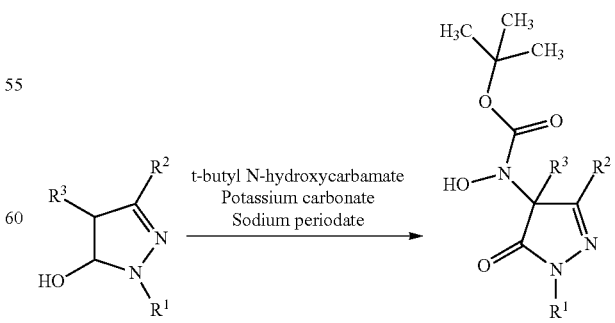

To a solution of a pyrazolone (1 equiv) in ethanol (28 vol) and water (28 vol) was added tert-butyl N-hydroxycarbamate (1.2 equiv) and potassium carbonate (0.35 equiv). Sodium periodate (1.2 equiv) was added and the reaction mixture was stirred at a temperature of about 25° C. for 30 minutes. Additional aliquots of tert-butyl N-hydroxycarbamate (1.2-3.6 equiv) and sodium periodate (1.2-3.6 equiv) were added at 30 minute intervals until reaction completion as determined by LC-MS. The white solid was removed by filtration and the resulting filtrate concentrated under reduced pressure. The product was then used directly or purified using standard methods.

Example 1

Compound 1 [5-(4-chlorophenyl)-4-(hydroxyamino)-2,4-dimethyl-2,4-dihydro-3H-pyrazol-3-one]

1.1 5-(4-Chlorophenyl)-2-methyl-2,3-dihydro-1H-pyrazol-3-one 5-(4-Chlorophenyl)-2-methyl-2,3-dihydro-1H-pyrazol-3-one was synthesized from methyl 3-(4-chlorophenyl)-3-oxopropanoate (15 g, 70.55 mmol) according to General Method 2 to provide the title compound as an off-white solid (12 g, 66% yield). $^1$H NMR (250 MHz, DMSO-$d_6$) δ ppm: 11.13 (s, 1H), 7.85-7.60 (m, 2H), 7.39 (d, J=8.5 Hz, 2H), 5.81 (s, 1H), 3.55 (s, 3H).

1.2 3-(4-Chlorophenyl)-5-hydroxy-1-methyl-1H-pyrazole-4-carbaldehyde 3-(4-Chlorophenyl)-5-hydroxy-1-methyl-1H-pyrazole-4-carbaldehyde was synthesized from 5-(4-chlorophenyl)-2-methyl-2,3-dihydro-1H-pyrazol-3-one (12 g, 57.51 mmol) according to General Method 4 to provide the title compound as an orange solid (11.5 g, 80% yield). $^1$H NMR (500 MHz, CDCl$_3$) δ ppm: 9.76 (s, 1H), 7.62 (d, J=8.4 Hz, 2H), 7.44 (d, J=8.4 Hz, 2H), 6.83 (s, 1H), 3.71 (s, 3H).

1.3 3-(4-Chlorophenyl)-1,4-dimethyl-1H-pyrazol-5-ol 3-(4-Chlorophenyl)-1,4-dimethyl-1H-pyrazol-5-ol was synthesized from 3-(4-chlorophenyl)-5-hydroxy-1-methyl-1H-pyrazole-4-carbaldehyde (11.0 g, 41.83 mmol) according to General Method 5 to provide the title compound as a brown solid which was used directly in the next step (>99.9% yield). LC-MS: $t_R$=1.58 min, [M+H]$^+$=223.

1.4 4-Bromo-3-(4-chlorophenyl)-1,4-dimethyl-4,5-dihydro-1H-pyrazol-5-one

4-Bromo-3-(4-chlorophenyl)-1,4-dimethyl-4,5-dihydro-1H-pyrazol-5-one was synthesized from 3-(4-chlorophenyl)-1,4-dimethyl-1H-pyrazol-5-ol (12.2 g, 43.28 mmol) according to General Method 6 to provide the title compound as a brown oil (14 g, 81% yield). LC-MS: $t_R$=2.14 min, [M+H]$^+$=302.8.

1.5 4-{[(tert-butoxy)carbonyl]({[(tert-butoxy)carbonyl]oxy})amino}-3-(4-chlorophenyl)-1,4-dimethyl-4,5-dihydro-1H-pyrazol-5-one 4-{[(tert-Butoxy)carbonyl]({[(tert-butoxy)carbonyl]oxy})amino}-3-(4-chlorophenyl)-1,4-dimethyl-4,5-dihydro-1H-pyrazol-5-one was synthesized from the corresponding bromide (14 g, 35.28 mmol) according to General Method 8 was chromatographed by silica gel column chromatography eluting with 20% ethyl acetate:heptanes to provide the title compound as a yellow solid (17.2 g, 75% yield). LC-MS: $t_R$=2.53 min, [M+Na]$^+$=476.01.

1.6 3-(4-Chlorophenyl)-4-(hydroxyamino)-1,4-dimethyl-4,5-dihydro-1H-pyrazol-5-one 3-(4-Chlorophenyl)-4-(hydroxyamino)-1,4-dimethyl-4,5-dihydro-1H-pyrazol-5-one was synthesized from 4-{[(tert-butoxy)carbonyl]({[(tert-butoxy)carbonyl]oxy})amino}-3-(4-chlorophenyl)-1,4-dimethyl-4,5-dihydro-1H-pyrazol-5-one (17.2 g, 26.52 mmol) according to General Method 9 and was chromatographed by silica gel column chromatography eluting with 30-70% ethyl acetate:heptanes to obtain a yellow solid which was washed with DCM:heptanes (1:5 vol:vol) to provide the title compound as an off-white solid (3.0 g, 42% yield). LC-MS: $t_R$=1.68 min, [M+H]$^+$=253.95. $^1$H NMR (500 MHz, DMSO-$d_6$) δ ppm: 8.06 (d, J=8.6 Hz, 2H), 7.66 (s, 1H), 7.53 (d, J=8.6 Hz, 2H), 6.53 (s, 1H), 3.30 (s, 3H), 1.20 (s, 3H).

Example 2

Compound 2 [5-(2-chlorophenyl)-4-(hydroxyamino)-2,4-dimethyl-2,4-dihydro-3H-pyrazol-3-one]

2.1 3-(2-Chlorophenyl)-1-methyl-4,5-dihydro-1H-pyrazol-5-one 3-(2-Chlorophenyl)-1-methyl-4,5-dihydro-1H-pyrazol-5-one was synthesized from methyl 3-(2-chlorophenyl)-3-oxopropanoate according to General Method 2. The filtrate recovered after filtration of the product was concentrated under reduced pressure until further precipitation occurred. This solid was isolated, washed with methanol and combined with the main batch. The process was repeated once more to provide the title compound as a white solid (10.82 g, 55% yield). LC-MS: $t_R$=1.48 min, [M+H]$^+$=209. $^1$H NMR (500 MHz, DMSO-$d_6$) δ ppm: 7.75 (dd, J=7.6, 1.9 Hz, 1H), 7.50-7.42 (m, 1H), 7.37-7.27 (m, 2H), 5.87 (s, 1H), 3.58 (s, 3H).

2.2 5-(2-Chlorophenyl)-2-methyl-3-oxo-2,3-dihydro-1H-pyrazole-4-carbaldehyde 5-(2-Chlorophenyl)-2-methyl-3-oxo-2,3-dihydro-1H-pyrazole-4-carbaldehyde was synthesized from 3-(2-chlorophenyl)-1-methyl-4,5-dihydro-1H-pyrazol-5-one according to General Method 3 (11.42 g, 83% yield). LC-MS: $t_R$=1.43 min, [M+H]$^+$=237/239. $^1$H NMR (500 MHz, DMSO-$d_6$) δ ppm: 9.53 (s, 1H), 7.52 (d, J=7.8 Hz, 1H), 7.47-7.41 (m, 1H), 7.38 (dd, J=6.5, 1.4 Hz, 2H), 3.60 (s, 3H).

2.3 3-(2-Chlorophenyl)-1,4-dimethyl-1H-pyrazol-5-ol 3-(2-Chlorophenyl)-1,4-dimethyl-1H-pyrazol-5-ol was synthesized from 5-(2-chlorophenyl)-2-methyl-3-oxo-2,3-dihydro-1H-pyrazole-4-carbaldehyde according to General Method 5 (12.4 g, 86% yield, containing 21.9% acetic acid). LC-MS: $t_R$=1.46 min, [M+H]$^+$=223/225. $^1$H NMR (500 MHz, DMSO-$d_6$) δ ppm: 7.49 (d, J=7.2 Hz, 1H), 7.41-7.27 (m, 3H), 3.52 (s, 3H), 1.72 (s, 3H).

2.4 4-Bromo-3-(2-chlorophenyl)-1,4-dimethyl-4,5-dihydro-1H-pyrazol-5-one

4-Bromo-3-(2-chlorophenyl)-1,4-dimethyl-4,5-dihydro-1H-pyrazol-5-one was synthesized from 3-(2-chlorophenyl)-1,4-dimethyl-1H-pyrazol-5-ol according to General Method 6, using 2.2 equiv of sodium bicarbonate (12.3 g, >99.9 yield). LC-MS: $t_R$=1.34 min, [M+H]$^+$=301/303.

2.5 4-{[(tert-Butoxy)carbonyl]({[(tert-butoxy)carbonyl]oxy})amino}-3-(2-chlorophenyl)-1,4-dimethyl-4,5-dihydro-1H-pyrazol-5-one 4-{[(tert-Butoxy)carbonyl]({[(tert-butoxy)carbonyl]oxy})amino}-3-(2-chlorophenyl)-1,4-dimethyl-4,5-dihydro-1H-pyrazol-5-one was synthesized from 4-bromo-3-(2-chlorophenyl)-1,4-dimethyl-4,5-dihydro-1H-pyrazol-5-one according to General Method 8 and was chromatographed by silica gel column chromatography eluting in 0-45% ethyl acetate:heptanes to provide the title compound as a yellow foam (8.2 g, 36% yield). LC-MS: $t_R$=2.32 min, [M+Na]$^+$=476/478.

2.6 3-(2-Chlorophenyl)-4-(hydroxyamino)-1,4-dimethyl-4,5-dihydro-1H-pyrazol-5-one 3-(2-Chlorophenyl)-4-(hydroxyamino)-1,4-dimethyl-4,5-dihydro-1H-pyrazol-5-one was synthesized from 4-{[(tert-butoxy)carbonyl]({[(tert-butoxy)carbonyl]oxy})amino}-3-(2-chlorophenyl)-1,4-dimethyl-4,5-dihydro-1H-pyrazol-5-one according to General Method 9 and was chromatographed by silica gel column chromatography eluting in 50% ethyl acetate:heptanes to provide the title compound as a pale yellow solid (3.17 g, 84% yield). LC-MS: $t_R$=1.51 min, [M+H]$^+$=254/256. $^1$H NMR (500 MHz, DMSO-d$_6$) δ ppm: 7.91 (dd, J=7.4, 2.0 Hz, 1H), 7.82 (s, 1H), 7.57 (dd, J=7.7, 1.5 Hz, 1H), 7.51-7.42 (m, 2H), 6.44 (s, 1H), 3.28 (s, 3H), 1.02 (s, 3H).

Example 3

Compound 3 [5-(2-fluorophenyl)-4-(hydroxyamino)-2,4-dimethyl-2,4-dihydro-3H-pyrazol-3-one]

3.1 5-(2-Fluorophenyl)-2-methyl-2,3-dihydro-1H-pyrrol-3-one 5-(2-Fluorophenyl)-2-methyl-2,3-dihydro-1H-pyrrol-3-one was synthesized from ethyl 3-(2-fluorophenyl)-3-oxopropanoate according to General Method 2. After stirring at 70° C. for 2 hours, the reaction mixture was concentrated under reduced pressure and the yellow solid obtained was slurried in DCM:heptanes (15 mL, 1:2 vol:vol). The solid was filtered, rinsed with heptanes (30 mL) and dried under reduced pressure to provide the title compound as an off-white solid (4.43 g, 85% yield). LC-MS: $t_R$=1.44 min, [M+H]$^+$=192. $^1$H NMR (500 MHz, DMSO-d$_6$) δ ppm: 7.87 (td, J=7.8, 1.6 Hz, 1H), 7.33-7.23 (m, 1H), 7.24-7.11 (m, 2H), 5.73 (d, J=4.3 Hz, 1H), 3.57 (s, 3H).

3.2 5-(2-Fluorophenyl)-2-methyl-3-oxo-2,3-dihydro-1H-pyrazole-4-carbaldehyde 5-(2-Fluorophenyl)-2-methyl-3-oxo-2,3-dihydro-1H-pyrazole-4-carbaldehyde was synthesized from 5-(2-fluorophenyl)-2-methyl-2,3-dihydro-1H-pyrrol-3-one according to General Method 3 (3.75 g, 81% yield). LC-MS: $t_R$=1.43 min, [M+H]$^+$=221. $^1$H NMR (250 MHz, DMSO-d$_6$) δ ppm: 9.59 (d, J=1.7 Hz, 1H), 7.54-7.39 (m, 2H), 7.35-7.17 (m, 2H), 3.61 (s, 3H).

3.3 3-(2-Fluorophenyl)-1,4-dimethyl-1H-pyrazol-5-ol 3-(2-Fluorophenyl)-1,4-dimethyl-1H-pyrazol-5-ol was synthesized from 5-(2-fluorophenyl)-2-methyl-3-oxo-2,3-dihydro-1H-pyrazole-4-carbaldehyde according to General Method 5 (3.66 g, 106% yield). LC-MS: $t_R$=1.44 min, [M+H]$^+$=207. $^1$H NMR (500 MHz, DMSO-d$_6$) δ ppm: 7.49-7.30 (m, 2H), 7.28-7.13 (m, 2H), 3.51 (s, 4H), 1.77 (s, 3H).

3.4 4-Bromo-3-(2-fluorophenyl)-1,4-dimethyl-4,5-dihydro-1H-pyrazol-5-one

4-Bromo-3-(2-fluorophenyl)-1,4-dimethyl-4,5-dihydro-1H-pyrazol-5-one was synthesized from 3-(2-fluorophenyl)-1,4-dimethyl-1H-pyrazol-5-ol according to General Method 6 and was used directly in the next step assuming 100% yield. LC-MS: $t_R$=1.99 min, [M+H]$^+$=285/287.

3.5 4-{[(tert-Butoxy)carbonyl]({[(tert-butoxy)carbonyl]oxy})amino}-3-(2-fluorophenyl)-1,4-dimethyl-4,5-dihydro-1H-pyrazol-5-one 4-{[(tert-Butoxy)carbonyl]({[(tert-butoxy)carbonyl]oxy})amino}-3-(2-fluorophenyl)-1,4-dimethyl-4,5-dihydro-1H-pyrazol-5-one was synthesized from 4-bromo-3-(2-fluorophenyl)-1,4-dimethyl-4,5-dihydro-1H-pyrazol-5-one according to General Method 8 and was chromatographed by silica gel column chromatography (ethyl acetate in heptanes) to provide the title compound as a yellow oil (2.78 g, 38% yield). LC-MS: $t_R$=2.37 min, [M+Na]$^+$=460.

3.6 3-(2-Fluorophenyl)-4-(hydroxyamino)-1,4-dimethyl-4,5-dihydro-1H-pyrazol-5-one 3-(2-Fluorophenyl)-4-(hydroxyamino)-1,4-dimethyl-4,5-dihydro-1H-pyrazol-5-one was synthesized from 4-{[(tert-butoxy)carbonyl]({[(tert-butoxy)carbonyl]oxy})amino}-3-(2-fluorophenyl)-1,4-dimethyl-4,5-dihydro-1H-pyrazol-5-one according to General Method 9. The residue was dissolved in DCM (40 mL) and washed with water (2×40 mL). The DCM layer was isolated, dried over magnesium sulfate, filtered and concentrated under reduced pressure to provide the title compound as a yellow solid (1.02 g, 68% yield). LC-MS: $t_R$=1.45 min, [M+H]$^+$=238. $^1$H NMR (500 MHz, DMSO-d$_6$) δ ppm: 8.18 (td, J=7.7, 1.6 Hz, 1H), 7.71 (d, J=2.4 Hz, 1H), 7.58-7.42 (m, 1H), 7.37-7.19 (m, 2H), 6.44 (d, J=2.4 Hz, 1H), 3.29 (s, 3H), 1.14 (s, 3H).

Example 4

Compound 4 [4-(hydroxyamino)-2,4-dimethyl-5-(4-(trifluoromethyl)phenyl)-2,4-dihydro-3H-pyrazol-3-one]

4.1 1-Methyl-3-[4-(trifluoromethyl)phenyl]-1H-pyrazol-5-ol

1-Methyl-3-[4-(trifluoromethyl)phenyl]-1H-pyrazol-5-ol was synthesized from 3-oxo-3-[4-(trifluoromethyl)phenyl]propanoate (5.79 g, 23.52 mmol) according to General Method 2 to provide the title compound as an off-white solid (5.3 g, 80% yield) LC-MS: $t_R$=1.19 min, [M+H]$^+$=242.95. $^1$H NMR (500 MHz, CDCl$_3$) δ ppm: 7.84-7.61 (m, 4H), 3.61 (s, 2H), 3.43 (s, 3H).

4.2 5-Hydroxy-1-methyl-3-[4-(trifluoromethyl)phenyl]-1H-pyrazole-4-carbaldehyde 5-Hydroxy-1-methyl-3-[4-(trifluoromethyl)phenyl]-1H-pyrazole-4-carbaldehyde was synthesized from 1-methyl-3-[4-(trifluoromethyl)phenyl]-1H-pyrazol-5-ol (5.3 g, 21.45 mmol) according to General Method 3 to provide the title compound as an off-white solid (5.46 g, 82% yield) LC-MS: $t_R$=1.18 min, [M+H]$^+$=271. $^1$H NMR (500 MHz, DMSO-d$_6$) δ ppm: 9.74 (s, 1H), 8.14-7.94 (m, 2H), 7.84-7.69 (m, 2H), 3.64 (s, 3H).

4.3 1,4-Dimethyl-3-[4-(trifluoromethyl)phenyl]-1H-pyrazol-5-ol 1,4-Dimethyl-3-[4-(trifluoromethyl)phenyl]-1H-pyrazol-5-ol was synthesized from 5-hydroxy-1-methyl-3-[4-(trifluoromethyl)phenyl]-1H-pyrazole-4-carbaldehyde (5.3 g, 17.06 mmol) according to General Method 5 to provide the title compound as an orange solid (>99.9% yield). LC-MS: $t_R$=1.15 min, [M+H]$^+$=257. $^1$H NMR (500 MHz, DMSO-d$_6$) δ ppm: 7.91-7.68 (m, 4H), 3.17 (s, 3H), 2.05 (s, 3H).

4.4 4-Bromo-3-(4-trifluorophenyl)-1,4-dimethyl-4,5-dihydro-1H-pyrazol-5-one 4-Bromo-3-(4-trifluorophenyl)-1,4-dimethyl-4,5-dihydro-1H-pyrazol-5-one was synthesized from 1,4-dimethyl-3-[4-(trifluoromethyl)phenyl]-1H-pyrazol-5-ol (2.0 g, 6.79 mmol) according to General Method 6 to provide the title compound as a brown oil (2.8 g, 86% yield) and used directly in the next step.

4.5 4-{[(tert-Butoxy)carbonyl]({[(tert-butoxy)carbonyl]oxy})amino}-1,4-dimethyl-3-[4-(trifluoromethyl)phenyl]-4,5-dihydro-1H-pyrazol-5-one 4-{[(tert-Butoxy)carbonyl]({[(tert-butoxy)carbonyl]oxy})amino}-1,4-dimethyl-3-[4-(trifluoromethyl)phenyl]-4,5-dihydro-1H-pyrazol-5-one was synthesized from 4-bromo-3-(4-trifluorophenyl)-1,4-dimethyl-4,5-dihydro-1H-pyrazol-5-one (2.8 g, 5.84 mmol) according to General Method 8 and was chromatographed by silica gel column chromatography eluting with 10-30% ethyl acetate:heptanes to provide the title compound as an off-white solid (1.6 g, 38% yield) LC-MS: $t_R$=1.54 min, [M+Na]$^+$=510. $^1$H NMR (500 MHz, DMSO-d$_6$) δ ppm: 8.40-8.23 (m, 1H), 8.02-7.78 (m, 3H), 3.35 (s, 3H), 1.61-1.47 (m, 12H), 1.23 (s, 9H).

4.6 4-(Hydroxyamino)-1,4-dimethyl-3-[4-(trifluoromethyl)phenyl]-4,5-dihydro-1H-pyrazol-5-one 4-(Hydroxyamino)-1,4-dimethyl-3-[4-(trifluoromethyl)phenyl]-4,5-dihydro-1H-pyrazol-5-one was synthesized from 4-bromo-1,4-dimethyl-3-[4-(trifluoromethyl)phenyl]-4,5-dihydro-1H-pyrazol-5-one (1.6 g, 2.62 mmol) according to General Method 9 and was chromatographed by silica gel column chromatography eluting with 30-70% ethyl acetate:heptanes to obtain a yellow solid which was washed with DCM:heptanes (1:9 vol:vol) to provide the title compound as an off-white solid (0.44 g, 56% yield) LC-MS: $t_R$=1.21 min, [M+H]$^+$=288. $^1$H NMR (500 MHz, DMSO-d$_6$) δ ppm: 8.38-8.14 (m, 2H), 7.96-7.73 (m, 2H), 7.69 (s, 1H), 6.58 (s, 1H), 3.33 (s, 3H), 1.24 (s, 3H).

Example 5

Compound 5 [5-(4-fluorophenyl)-4-(hydroxyamino)-2,4-dimethyl-2,4-dihydro-3H-pyrazol-3-one]

5.1 3-(4-Fluorophenyl)-1-methyl-1H-pyrazol-5-ol 3-(4-Fluorophenyl)-1-methyl-1H-pyrazol-5-ol was synthesized from methyl 3-(4-fluorophenyl)-3-oxopropanoate (2.1 g, 10.7 mmol) according to General Method 2 to provide the title compound as an off-white solid (2.14 g, 91% yield). LC-MS: $t_R$=1.49 min, [M+H]$^+$=192. $^1$H NMR (500 MHz, DMSO-d$_6$) δ ppm: 7.71 (dd, J=8.6, 5.7 Hz, 2H), 7.16 (t, J=8.9 Hz, 2H), 5.76 (s, 1H), 3.54 (s, 3H).

5.2 3-(4-Fluorophenyl)-5-hydroxy-1-methyl-1H-pyrazole-4-carbaldehyde 3-(4-Fluorophenyl)-5-hydroxy-1-methyl-1H-pyrazole-4-carbaldehyde was synthesized from 3-(4-fluorophenyl)-1-methyl-1H-pyrazol-5-ol (2.1 g, 10.82 mmol) according to General Method 3 to provide the title compound as an orange solid (2.01 g, 44% yield) LC-MS: $t_R$=1.47 min, [M+H]$^+$=220.

5.3 3-(4-Fluorophenyl)-1,4-dimethyl-1H-pyrazol-5-ol 3-(4-Fluorophenyl)-1,4-dimethyl-1H-pyrazol-5-ol was synthesized from 3-(4-fluorophenyl)-5-hydroxy-1-methyl-1H-pyrazole-4-carbaldehyde (2.01 g, 9.13 mmol) according to General Method 5 to provide the title compound as a yellow solid (1.91 g, 93% yield). LC-MS: $t_R$=1.43 min, [M+H]$^+$=206. $^1$H NMR (500 MHz, CDCl$_3$) δ ppm: 7.68-7.50 (m, 2H), 7.20 (t, J=8.8 Hz, 2H), 3.52 (s, 3H), 1.98 (s, 3H).

5.4 4-Bromo-3-(4-fluorophenyl)-1,4-dimethyl-4,5-dihydro-1H-pyrazol-5-one

4-Bromo-3-(4-fluorophenyl)-1,4-dimethyl-4,5-dihydro-1H-pyrazol-5-one was synthesized from 3-(4-fluorophenyl)-1,4-dimethyl-1H-pyrazol-5-ol (1.5 g, 6.67 mmol) according to General Method 6 to provide the title compound as a brown oil (1.63 g, 73% yield). LC-MS: $t_R$=1.99 min, [M+H]$^+$=284.

5.5 4-{[(tert-Butoxy)carbonyl]({[(tert-butoxy)carbonyl]oxy})amino}-3-(4-fluorophenyl)-1,4-dimethyl-4,5-dihydro-1H-pyrazol-5-one 4-{[(tert-Butoxy)carbonyl]({[(tert-butoxy)carbonyl]oxy})amino}-3-(4-fluorophenyl)-1,4-dimethyl-4,5-dihydro-1H-pyrazol-5-one was synthesized from 4-bromo-3-(4-fluorophenyl)-1,4-dimethyl-4,5-dihydro-1H-pyrazol-5-one (1.63 g, 5.72 mmol) according to General Method 8 to provide the title compound as a yellow solid (1.3 g, 37% yield) LC-MS: $t_R$=2.41 min, [M+Na]$^+$=460.

5.6 3-(4-Fluorophenyl)-4-(hydroxyamino)-1,4-dimethyl-4,5-dihydro-1H-pyrazol-5-one 3-(4-Fluorophenyl)-4-(hydroxyamino)-1,4-dimethyl-4,5-dihydro-1H-pyrazol-5-one was synthesized from 4-{[(tert-butoxy)carbonyl]({[(tert-butoxy)carbonyl]oxy})amino}-3-(4-fluorophenyl)-1,4-dimethyl-4,5-dihydro-1H-pyrazol-5-one (1.3 g, 2.97 mmol)) according to General Method 9 to provide the title compound as an off-white solid (0.28 g, 41% yield). LC-MS: $t_R$=1.53 min, [M+H]$^+$=237. $^1$H NMR (500 MHz, DMSO-d$_6$) δ ppm: 8.17-8.04 (m, 2H), 7.65 (d, J=2.5 Hz, 1H), 7.30 (t, J=8.9 Hz, 2H), 6.50 (d, J=2.5 Hz, 1H), 3.28 (s, 3H), 1.19 (s, 3H).

Example 6

Compound 6 [4-(hydroxyamino)-2,5-dimethyl-4-phenyl-2,4-dihydro-3H-pyrazol-3-one]

6.1 Methyl 3-oxo-2-phenylbutanoate

Methyl 3-oxo-2-phenylbutanoate was synthesized from methyl 2-phenylacetate according to General Method 13 and was chromatographed by silica gel column chromatography (12% ethyl acetate in heptanes) to provide the title compound as a pale yellow oil (22 g, 50% yield). LC-MS: $t_R$=1.13/1.16 min, [M+H]$^+$=193.

6.2 5-(2-Methoxyphenyl)-2-methyl-2,3-dihydro-1H-pyrazol-3-one 5-(2-Methoxyphenyl)-2-methyl-2,3-dihydro-1H-pyrazol-3-one was synthesized from methyl 3-oxo-2-phenylbutanoate according to General Method 2. Once the starting material had been consumed, the reaction mixture was allowed to cool to a temperature of about 25° C. The solvent was removed under reduced pressure to provide an oil which was triturated with 1:3 DCM:heptanes (250 mL). The DCM was removed under reduced pressure to provide a white solid which was isolated by filtration and washed with ethyl acetate to provide the title compound as a white solid (14.02 g, 60% yield). LC-MS: $t_R$=0.93 min, [M+H]$^+$=189. $^1$H NMR (250 MHz, DMSO-d$_6$) δ ppm: 7.48 (dd, J=8.2, 1.1 Hz, 2H), 7.38-7.30 (m, 2H), 7.19-7.11 (m, 1H), 3.39 (s, 3H), 2.19 (s, 3H).

6.3 4-Bromo-1,3-dimethyl-4-phenyl-4,5-dihydro-1H-pyrazol-5-one

4-Bromo-1,3-dimethyl-4-phenyl-4,5-dihydro-1H-pyrazol-5-one was synthesized from 5-(2-methoxyphenyl)-2-methyl-2,3-dihydro-1H-pyrazol-3-one according to General Method 6 (19.6 g, >99.9 yield). LC-MS: $t_R$=1.25 min, [M+H]$^+$=267/269. $^1$H NMR (250 MHz, CDCl$_3$) δ ppm: 7.50-7.31 (m, 5H), 3.38 (s, 3H), 2.16 (s, 3H).

6.4 4-{[(tert-Butoxy)carbonyl]({[(tert-butoxy)carbonyl]oxy})amino}-1,3-dimethyl-4-phenyl-4,5-dihydro-1H-pyrazol-5-one 4-{[(tert-Butoxy)carbonyl]({[(tert-butoxy)carbonyl]oxy})amino}-1,3-dimethyl-4-phenyl-4,5-dihydro-1H-pyrazol-5-one was synthesized from 4-bromo-1,3-dimethyl-4-phenyl-4,5-dihydro-1H-pyrazol-5-one according to General Method 8 to provide the title compound as a yellow oil (33.2 g, 79% yield). LC-MS: $t_R$=1.53 min, [M+Na]$^+$=442.

6.5 4-(Hydroxyamino)-1,3-dimethyl-4-phenyl-4,5-dihydro-1H-pyrazol-5-one 4-(Hydroxyamino)-1,3-dimethyl-4-phenyl-4,5-dihydro-1H-pyrazol-5-one was synthesized from 4-{[(tert-butoxy)carbonyl]({[(tert-butoxy)carbonyl]oxy})amino}-1,3-dimethyl-4-phenyl-4,5-dihydro-1H-pyrazol-5-one according to General Method 9 and was chromatographed by silica gel column chromatography eluting in 0-90% ethyl acetate:heptanes to provide the title compound as a white solid (5.97 g, 47% yield). LC-MS: $t_R$=1.44 min, [M+H]$^+$=220. $^1$H NMR (250 MHz, DMSO-d$_6$) δ ppm: 7.84 (d, J=2.4 Hz, 1H), 7.43-7.29 (m, 3H), 7.27-7.14 (m, 2H), 6.89 (d, J=2.4 Hz, 1H), 3.19 (s, 3H), 1.93 (s, 3H).

Example 7

Compound 7 [5-(3,5-dimethylphenyl)-4-(hydroxyamino)-2,4-dimethyl-2,4-dihydro-3H-pyrazol-3-one]

7.1 Methyl 3-(3,5-dimethylphenyl)-3-oxopropanoate

Methyl 3-(3,5-dimethylphenyl)-3-oxopropanoate was synthesized from 1-(3,5-dimethylphenyl)ethan-1-one and dimethyl carbonate according to General Method 1 and was used directly in the synthesis of the corresponding pyrazolone (13.0 g, 53% yield). $^1$H NMR (400 MHz, CDCl$_3$) δ ppm: 7.54 (s, 2H), 7.23 (d, J=0.6 Hz, 1H), 3.98 (s, 2H), 3.75 (s, 3H), 2.37 (s, 6H).

7.2 3-(3,5-Dimethylphenyl)-1-methyl-1H-pyrazol-5-ol

To a solution of methyl 3-(3,5-dimethylphenyl)-3-oxopropanoate (0.5 g, 2.424 mmol) in ethanol (15 mL) was sequentially added methyldiazanediium sulfate (0.52 g, 3.637 mmol) as a solution in ethanol (15 mL) and triethylamine (0.68 mL, 4.489 mmol) and the resulting reaction was heated to 80° C. for 18 hours. After which time, the reaction mixture was concentrated under reduced pressure and the resulting solid was extracted into ethyl acetate (60 mL) and washed with water (10 mL) and brine (10 mL), before being dried over sodium sulfate, filtered and concentrated under reduced pressure. The desired compound was isolated by chromatography using silica gel column chromatography eluting with 15-20% ethyl acetate:hexane to provide the title compound as a white solid (0.07 g, 14% yield). $^1$H NMR (400 MHz, DMSO) δ ppm: 10.95 (s, 1H), 7.29 (s, 2H), 6.86 (s, 1H), 5.72 (s, 1H), 3.53 (s, 3H), 2.27 (s, 6H).

7.3 3-(3,5-Dimethylphenyl)-5-hydroxy-1-methyl-1H-pyrazole-4-carbaldehyde 3-(3,5-Dimethylphenyl)-5-hydroxy-1-methyl-1H-pyrazole-4-carbaldehyde was synthesized from 3-(3,5-dimethylphenyl)-1-methyl-1H-pyrazol-5-ol according to General Method 3. The method deviated from General Method 3 during the workup because the orange yellow precipitate formed by addition of water was dissolved into ethyl acetate (100 mL), the aqueous was extracted with ethyl acetate (2×100 mL), dried over sodium sulfate, filtered, and concentrated under reduced pressure. The title compound was isolated as a yellow solid by triturating with pentane (3.3 g, 69% yield). $^1$H NMR (400 MHz, DMSO) δ ppm: 9.69 (s, 1H), 7.36 (s, 2H), 7.02 (s, 1H), 3.58 (s, 3H), 2.30 (s, 6H).

7.4 3-(3,5-Dimethylphenyl)-1,4-dimethyl-1H-pyrazol-5-ol 3-(3,5-Dimethylphenyl)-1,4-dimethyl-1H-pyrazol-5-ol was synthesized from 3-(3,5-dimethylphenyl)-5-hydroxy-1- methyl-1H-pyrazole-4-carbaldehyde according to General Method 5. The method deviated from General Method 5 during the workup because water (50 mL) was added to the solid formed, the suspension was basified by the addition of sodium bicarbonate, and the pyrazolone was extracted into ethyl acetate (3×80 mL). The combined organic layers were dried over sodium sulfate, filtered and concentrated under reduced pressure. The resulting brown oil was chromatographed by column chromatography eluting with 8-10% ethyl acetate:hexanes to provide the title compound as an off white solid (2.3 g, 74% yield). $^1$H NMR (400 MHz, DMSO) δ ppm: 9.98 (s, 1H), 7.19 (s, 2H), 6.91 (s, 1H), 3.54 (s, 3H), 2.29 (s, 6H), 1.98 (s, 3H).

7.5 4-Bromo-3-(3,5-dimethylphenyl)-1,4-dimethyl-4,5-dihydro-1H-pyrazol-5-one 4-Bromo-3-(3,5-dimethylphenyl)-1,4-dimethyl-4,5-dihydro-1H-pyrazol-5-one was synthesized from 3-(3,5-dimethylphenyl)-1,4-dimethyl-1H-pyrazol-5-ol according to General Method 6 and was used directly in the next step without further analysis (2.2 g, 94% yield).

7.6 4-{[(tert-Butoxy)carbonyl]({[(tert-butoxy)carbonyl]oxy})amino}-3-(3,5-dimethylphenyl)-1,4-dimethyl-4,5-dihydro-1H-pyrazol-5-one 4-{[(tert-Butoxy)carbonyl]({[(tert-butoxy)carbonyl]oxy})amino}-3-(3,5-dimethylphenyl)-1,4-dimethyl-4,5-dihydro-1H-pyrazol-5-one was synthesized from the corresponding bromide according to General Method 8 and was chromatographed by silica gel column chromatography eluting with 7-10% ethyl acetate:hexanes (2 g, 60% yield) to provide the title compound as an off white solid. $^1$H NMR (400 MHz, DMSO) δ ppm: 7.78 (s, 1H), 7.11 (s, 1H), 7.04 (s, 1H), 3.30 (s, 3H), 2.30 (s, 6H), 1.52 (d, J=10.2 Hz, 9H), 1.25 (s, 3H), 1.24 (s, 9H).

7.7 3-(3,5-Dimethylphenyl)-4-(hydroxyamino)-1,4-dimethyl-4,5-dihydro-1H-pyrazol-5-one 3-(3,5-Dimethylphenyl)-4-(hydroxyamino)-1,4-dimethyl-4,5-dihydro-1H-pyrazol-5-one was synthesized from 4-{[(tert-butoxy)carbonyl]({[(tert-butoxy)carbonyl]oxy})amino}-3-(3,5-dimethylphenyl)-1,4-dimethyl-4,5-dihydro-1H-pyrazol-5-one according to General Method 9 and was triturated with DCM:pentane (1:100 vol:vol) to provide the title compound as an off white solid (0.47 g, 43% yield). $^1$H NMR (400 MHz, DMSO) δ ppm: 7.68 (s, 2H), 7.62 (d, J=2.1 Hz, 1H), 7.09 (s, 1H), 6.44 (d, J=2.2 Hz, 1H), 5.77 (s, 1H), 3.28 (s, 3H), 2.31 (s, 6H), 1.19 (s, 3H).

Example 8

Compound 8 [5-(2-chlorophenyl)-4-(hydroxyamino)-2-iso-propyl-4-methyl-2,4-dihydro-3H-pyrazol-3-one]

8.1 3-(2-Chlorophenyl)-1-(propan-2-yl)-1H-pyrazol-5-ol 3-(2-Chlorophenyl)-1-(propan-2-yl)-1H-pyrazol-5-ol was synthesized from methyl 3-(2-chlorophenyl)-3-oxopropanoate (1 g, 4.7 mmol) according to General Method 2 to provide the title compound as an off-white solid (1.14 g, 99% yield). LC-MS: $t_R$=1.76 min, [M+H]$^+$=237. $^1$H NMR (250 MHz, CDCl$_3$) δ ppm: 10.98 (s, 1H), 7.91-7.70 (m, 1H), 7.52-7.43 (m, 1H), 7.33 (qd, J=7.3, 1.9 Hz, 2H), 5.87 (s, 1H), 4.61-4.32 (m, 1H), 1.37 (d, J=6.7 Hz, 6H).

8.2 3-(2-Chlorophenyl)-5-hydroxy-1-(propan-2-yl)-1H-pyrazole-4-carbaldehyde 3-(2-Chlorophenyl)-5-hydroxy-1-(propan-2-yl)-1H-pyrazole-4-carbaldehyde was synthesized from 3-(2-chlorophenyl)-1-(propan-2-yl)-1H-pyrazol-5-ol (1.13 g, 4.77 mmol) according to General Method 3, after quenching with water and left standing for 48 hours the reaction mixture was extracted with diethyl ether (2×30 mL) and the solvent was removed under reduced pressure to provide the title compound as a brown oil (1.2 g, 79% yield). LC-MS: $t_R$=1.82 min, [M+H]$^+$=264. $^1$H NMR (250 MHz, DMSO-d$_6$) δ ppm: 9.53 (s, 1H), 7.60-7.30 (m, 4H), 4.68-4.44 (m, 1H), 1.36 (d, J=6.7 Hz, 6H).

8.3 3-(2-Chlorophenyl)-4-methyl-1-(propan-2-yl)-1H-pyrazol-5-ol 3-(2-Chlorophenyl)-4-methyl-1-(propan-2-yl)-1H-pyrazol-5-ol was synthesized from 3-(2-chlorophenyl)-5-hydroxy-1-(propan-2-yl)-1H-pyrazole-4-carbaldehyde (1.2 g, 4.13 mmol) according to General Method 5 to provide the title compound as a yellow sticky solid (1.1 g, 97% yield). LC-MS: $t_R$=1.61 min, [M+H]$^+$=250. $^1$H NMR (500 MHz, DMSO-d$_6$) δ ppm: 7.49 (d, J=7.0 Hz, 1H), 7.35 (dd, J=10.6, 3.8 Hz, 3H), 4.54-4.39 (m, 1H), 1.75 (s, 3H), 1.33 (d, J=6.6 Hz, 6H).

8.4 4-Bromo-3-(2-chlorophenyl)-4-methyl-1-(propan-2-yl)-4,5-dihydro-1H-pyrazol-5-one 4-Bromo-3-(2-chlorophenyl)-4-methyl-1-(propan-2-yl)-4,5-dihydro-1H-pyrazol-5-one was synthesized from 3-(2-chlorophenyl)-4-methyl-1-(propan-2-yl)-1H-pyrazol-5-ol (1.1 g, 4.39 mmol) according to General Method 6 (1.4 g, 75% yield). LC-MS: $t_R$=2.25 min, [M+H]$^+$=330.

8.5 4-{[(tert-Butoxy)carbonyl]({[(tert-butoxy)carbonyl]oxy})amino}-3-(2-chlorophenyl)-4-methyl-1-(propan-2-yl)-4,5-dihydro-1H-pyrazol-5-one 4-{[(tert-Butoxy)carbonyl]({[(tert-butoxy)carbonyl]oxy})amino}-3-(2-chlorophenyl)-4-methyl-1-(propan-2-yl)-4,5-dihydro-1H-pyrazol-5-one was synthesized from 4-bromo-3-(2-chlorophenyl)-4-methyl-1-(propan-2-yl)-4,5-dihydro-1H-pyrazol-5-one (1.4 g, 4.25 mmol) according to General Method 8 to provide the title compound as a yellow oil (1.4 g, 62% yield). LC-MS: $t_R$=2.57 min, [M+Na]$^+$=504.

8.6 3-(2-Chlorophenyl)-4-(hydroxyamino)-4-methyl-1-(propan-2-yl)-4,5-dihydro-1H-pyrazol-5-one 3-(2-Chlorophenyl)-4-(hydroxyamino)-4-methyl-1-(propan-2-yl)-4,5-dihydro-1H-pyrazol-5-one was synthesized from 4-{[(tert-butoxy)carbonyl]({[(tert-butoxy)carbonyl]oxy})amino}-3-(2-chlorophenyl)-4-methyl-1-(propan-2-yl)-4,5-dihydro-1H-pyrazol-5-one according to General Method 9 to provide the title compound as an off-white solid (0.35 g, 48% yield). LC-MS: $t_R$=1.79 min, [M+Na]$^+$=281. $^1$H NMR (500 MHz, DMSO-d$_6$) δ ppm: 7.94 (dd, J=7.3, 2.2 Hz, 1H), 7.76 (s, 1H), 7.58 (dd, J=7.7, 1.5 Hz, 1H), 7.52-7.37 (m, 2H), 4.38 (p, J=6.7 Hz, 1H), 1.25 (dd, J=27.7, 6.7 Hz, 6H), 1.00 (s, 3H).

Example 9

Compound 9 [5-(3,5-dichlorophenyl)-4-(hydroxyamino)-2,4-dimethyl-2,4-dihydro-3H-pyrazol-3-one]

9.1 Methyl 3-(3,5-dichlorophenyl)-3-oxopropanoate

Methyl 3-(3,5-dichlorophenyl)-3-oxopropanoate was synthesized from 1-(3,5-dichlorophenyl)ethan-1-one and dimethyl carbonate according to General Method 1 and was chromatographed by silica gel column chromatography eluting with ethyl acetate:hexanes (1:9 vol:vol) to provide the title compound as an off white solid (6.5 g, 62% yield). LC-MS: $t_R$=1.14 min, [M+H]$^+$=248.

9.2 3-(3,5-Dichlorophenyl)-1-methyl-1H-pyrazol-5-ol

To a solution of 3-(3,5-dichlorophenyl)-3-oxopropanoate (7.0 g, 28.33 mmol) in ethanol (50 mL) was sequentially added methyldiazanediium sulfate (6.04 g, 42.5 mmol) as a solution in ethanol (15 mL) and triethylamine (7.91 mL, 56.66 mmol) and the resulting reaction was heated to 70° C. for 8 hours. After which time, the reaction mixture was concentrated under reduced pressure and the resulting solid was extracted into ethyl acetate (75 mL) and washed with water (50 mL) and brine (10 mL), before being dried over sodium sulfate, filtered and concentrated under reduced pressure to provide the title compound (5.0 g, 73% yield). $^1$H NMR (400 MHz, CDCl$_3$) δ ppm: 7.53 (d, J=1.9 Hz, 2H), 7.39 (t, J=1.9 Hz, 1H), 3.71 (s, 1H), 3.55 (d, J=4.2 Hz, 1H), 3.42 (s, 3H).

9.3 3-(3,5-Dichlorophenyl)-5-hydroxy-1-methyl-1H-pyrazole-4-carbaldehyde 3-(3,5-Dichlorophenyl)-5-hydroxy-1-methyl-1H-pyrazole-4-carbaldehyde was synthesized from 3-(3,5-dichlorophenyl)-1-methyl-1H-pyrazol-5-ol according to General Method 3. The method deviated from General Method 3 during the workup because the orange yellow precipitate formed by addition of water was dissolved into ethyl acetate (250 mL), the aqueous was extracted with ethyl acetate (2×250 mL), the combined organic layers were washed with water (2×50 mL), dried over sodium sulfate, filtered, and concentrated under reduced pressure and used directly in the next step (3.0 g, 54% yield). $^1$H NMR (400 MHz, CDCl$_3$) δ ppm: 9.80 (s, 1H), 7.58 (t, J=3.5 Hz, 2H), 7.42 (dd, J=6.3, 4.4 Hz, 1H), 7.30 (d, J=1.9 Hz, 1H), 3.72 (s, 3H).

9.4 3-(3,5-Dichlorophenyl)-1,4-dimethyl-1H-pyrazol-5-ol 3-(3,5-Dichlorophenyl)-1,4-dimethyl-1H-pyrazol-5-ol was synthesized from 3-(3,5-dichlorophenyl)-5-hydroxy-1-methyl-1H-pyrazole-4-carbaldehyde according to General Method 5. The method deviated from General Method 5 during the workup because water (10 mL) was added to the solid formed, the suspension was basified by the addition of sodium bicarbonate, and the pyrazolone was extracted into ethyl acetate (3×10 mL). The combined organic layers were dried over sodium sulfate, filtered and concentrated under reduced pressure (1.3 g, 46% yield). $^1$H NMR (400 MHz, DMSO) δ ppm: 7.58 (d, J=1.9 Hz, 2H), 7.52 (s, 1H), 3.59 (s, 3H), 2.05 (s, 3H).

9.5 4-Bromo-3-(3,5-dichlorophenyl)-1,4-dimethyl-4,5-dihydro-1H-pyrazol-5-one 4-Bromo-3-(3,5-dichlorophenyl)-1,4-dimethyl-4,5-dihydro-1H-pyrazol-5-one was synthesized from 3-(3,5-dichlorophenyl)-1,4-dimethyl-1H-pyrazol-5-ol according to General Method 6 and was used directly in the next step without further analysis (0.87 g, 99% yield).

9.6 4-{[(tert-Butoxy)carbonyl]({[(tert-butoxy)carbonyl]oxy})amino}-3-(3,5-dichlorophenyl)-1,4-dimethyl-4,5-dihydro-1H-pyrazol-5-one 4-{[(tert-Butoxy)carbonyl]({[(tert-butoxy)carbonyl]oxy})amino}-3-(3,5-dichlorophenyl)-1,4-dimethyl-4,5-dihydro-1H-pyrazol-5-one was synthesized from 4-bromo-3-(3,5-dichlorophenyl)-1,4-dimethyl-4,5-dihydro-1H-pyrazol-5-one and was chromatographed by silica gel column chromatography eluting with ethyl acetate:hexanes (1:1 vol:vol) to provide the title compound as a yellow oil which was used directly in the next step (0.5 g, 39% yield).

9.7 3-(3,5-Dichlorophenyl)-4-(hydroxyamino)-1,4-dimethyl-4,5-dihydro-1H-pyrazol-5-one 3-(3,5-Dichlorophenyl)-4-(hydroxyamino)-1,4-dimethyl-4,5-dihydro-1H-pyrazol-5-one was synthesized from 4-{[(tert-butoxy)carbonyl]({[(tert-butoxy)carbonyl]oxy})amino}-3-(3,5-dichlorophenyl)-1,4-dimethyl-4,5-dihydro-1H-pyrazol-5-one according to General Method 9 and was chromatographed by reverse phase HPLC to provide the title compound as a white solid (0.12 g, 40% yield). $^1$H NMR (400 MHz, DMSO) δ ppm: 7.99 (d, J=1.9 Hz, 2H), 7.75 (d, J=2.6 Hz, 1H), 7.71 (t, J=1.9 Hz, 1H), 6.65 (d, J=2.6 Hz, 1H), 3.30 (s, 3H), 1.18 (s, 3H).

Example 10

Compound 10 [5-(tert-butyl)-4-(hydroxyamino)-4-(1-(methoxyimino)ethyl)-2-methyl-2,4-dihydro-3H-pyrazol-3-one]

10.1 3-tert-Butyl-1-methyl-1H-pyrazol-5-ol 3-tert-Butyl-1-methyl-1H-pyrazol-5-ol was synthesized from methyl 4,4-dimethyl-3-oxopentanoate (8.9 g, 56.26 mmol) according to General Method 2 to provide the title compound as an off-white solid (8.6 g, 99% yield). LC-MS: $t_R$=1.2 min, [M+H]$^+$=155.

10.2 1-(3-tert-Butyl-5-hydroxy-1-methyl-1H-pyrazol-4-yl) ethan-1-one 1-(3-tert-Butyl-5-hydroxy-1-methyl-1H-pyrazol-4-yl) ethan-1-one was synthesized from 3-tert-butyl-1-methyl-1H-pyrazol-5-ol (4.3 g, 0.03 mol) according to General Method 11 and was chromatographed by silica gel chromatography eluting in 0-40% ethyl acetate:heptanes to provide the title compound as an orange solid (2.46 g, 38% yield). LC-MS: $t_R$=1.32 min, [M+H]$^+$=197.

10.3 3-tert-Butyl-4-[1-(methoxyimino)ethyl]-1-methyl-1H-pyrazol-5-ol 3-tert-Butyl-4-[1-(methoxyimino)ethyl]-1-methyl-1H-pyrazol-5-ol was synthesized from 1-(3-tert-butyl-5-hydroxy-1-methyl-1H-pyrazol-4-yl)ethan-1-one (2.46 g, 12.54 mmol) according to General Method 12 to provide the title compound as brown oil (2.1 g, 74% yield). LC-MS: $t_R$=1.45 min, [M+H]$^+$=226. $^1$H NMR (500 MHz, DMSO-d$_6$) δ ppm: 3.80 (s, 3H), 1.99 (s, 3H), 1.96 (s, 3H), 1.23 (s, 9H).

10.4 4-Bromo-3-tert-butyl-4-[1-(methoxyimino) ethyl]-1-methyl-4,5-dihydro-1H-pyrazol-5-one 4-Bromo-3-tert-butyl-4-[1-(methoxyimino)ethyl]-1-methyl-4,5-dihydro-1H-pyrazol-5-one was synthesized from 3-tert-butyl-4-[1-(methoxyimino)ethyl]-1-methyl-1H-pyrazol-5-ol (1.4 g, 6.21 mmol) according to General method 6 (2.1 g, 81% yield). LC-MS: $t_R$=2.13 min, [M+H]$^+$=305.

10.5 4-{[(tert-Butoxy)carbonyl]({[(tert-butoxy)carbonyl]oxy})amino}-3-tert-butyl-4-[1-(methoxyimino)ethyl]-1-methyl-4,5-dihydro-1H-pyrazol-5-one 4-{[(tert-Butoxy)carbonyl]({[(tert-butoxy)carbonyl]oxy})amino}-3-tert-butyl-4-[1-(methoxyimino)ethyl]-1-methyl-4,5-dihydro-1H-pyrazol-5-one was synthesized from 4-bromo-3-tert-butyl-4-[1-(methoxyimino)ethyl]-1-methyl-4,5-dihydro-1H-pyrazol-5-one (2.1 g, 5.04 mmol) according to General Method 8 to provide the title compound as an orange oil (0.9 g, 35% yield). LC-MS: $t_R$=2.5 min, [M+Na]$^+$=479.

10.6 3-tert-Butyl-4-(hydroxyamino)-4-[1-(methoxyimino)ethyl]-1-methyl-4,5-dihydro-1H-pyrazol-5-one 3-tert-Butyl-4-(hydroxyamino)-4-[1-(methoxyimino)ethyl]-1-methyl-4,5-dihydro-1H-pyrazol-5-one was synthesized from 4-{[(tert-butoxy)carbonyl]({[(tert-butoxy)carbonyl]oxy})amino}-3-tert-butyl-4-[1-(methoxyimino)ethyl]-1-methyl-4,5-dihydro-1H-pyrazol-5-one according to General Method 9 to provide the title compound as a yellow oil (0.104 g, 20% yield). LC-MS: $t_R$=1.74 min, [M+H]$^+$=257. $^1$H NMR (500 MHz, DMSO-d$_6$) δ ppm: 7.59 (s, 1H), 3.81 (s, 3H), 3.19 (s, 3H), 3.18 (s, 1H), 1.59 (s, 3H), 1.23 (s, 9H).

Example 11

Compound 11 [4-(hydroxyamino)-2,4-dimethyl-5-(4-(methylsulfinyl)phenyl)-2,4-dihydro-3H-pyrazol-3-one]

11.1 Methyl 3-[4-(methylsulfanyl)phenyl]-3-oxopropanoate

Methyl 3-[4-(methylsulfanyl)phenyl]-3-oxopropanoate was synthesized 1-[4-(methylsulfanyl)phenyl]ethan-1-one (35 g, 210.54 mmol) according to General Method 1. The product (brown oily) solidified for about 16 hours at a temperature of about 25° C. The solid was dissolved in a minimum quantity of ethyl acetate (70 mL) while gentle heat was applied with aid of a heat gun, after complete dissolution, heptane (100 mL) was added and mixture sonicated for 30 minutes. The solid was filtered and dried under air to provide the title compound as a beige solid (40.7 g, 69% yield). LC-MS: $t_R$=1.25 min, [M+H]$^+$=224. $^1$H NMR (500 MHz, DMSO-d$_6$) δ ppm: 7.89-7.85 (m, 2H), 7.40-7.36 (m, 2H), 4.16 (s, 2H), 3.64 (s, 3H), 2.54 (s, 3H).

11.2 1-Methyl-3-[4-(methylsulfanyl)phenyl]-1H-pyrazol-5-ol

1-Methyl-3-[4-(methylsulfanyl)phenyl]-1H-pyrazol-5-ol was synthesized from methyl 3-[4-(methylsulfanyl)phenyl]-3-oxopropanoate (40.7 g, 181.47 mmol) according to General Method 2 to provide the title compound as an off-white solid (37 g, 89% yield). LC-MS: $t_R$=1.1 min, [M+H]$^+$=220. $^1$H NMR (250 MHz, DMSO-d$_6$) δ ppm: 10.99 (s, 1H), 7.63 (d, J=8.4 Hz, 2H), 7.23 (d, J=8.4 Hz, 2H), 5.75 (s, 1H), 3.55 (s, 3H), 2.48 (s, 3H).

11.3 5-Hydroxy-1-methyl-3-[4-(methylsulfanyl)phenyl]-1H-pyrazole-4-carbaldehyde 5-Hydroxy-1-methyl-3-[4-(methylsulfanyl)phenyl]-1H-pyrazole-4-carbaldehyde was synthesized from 1-methyl-3-[4-(methylsulfanyl)phenyl]-1H-pyrazol-5-ol (36.4 g, 160.28 mmol) according to General Method 4 to provide the title compound as a yellow solid (42 g, 98% yield). LC-MS: $t_R$=1.09 min, [M+H]$^+$=248. $^1$H NMR (500 MHz, DMSO-d$_6$) δ ppm: 9.71 (s, 1H), 7.83-7.70 (m, 2H), 7.35-7.24 (m, 2H), 3.60 (s, 3H), 2.51-2.50 (m, 3H).

11.4 1,4-Dimethyl-3-[4-(methylsulfanyl)phenyl]-1H-pyrazol-5-ol 1,4-Dimethyl-3-[4-(methylsulfanyl)phenyl]-1H-pyrazol-5-ol was synthesized from 5-hydroxy-1-methyl-3-[4-(methylsulfanyl)phenyl]-1H-pyrazole-4-carbaldehyde (43 g, 159.32 mmol) according to General Method 5 to provide the title compound as an off-white solid (45 g, 90% yield (containing about 25% acetic acid)). LC-MS: $t_R$=1.07 min, [M+H]$^+$=234. $^1$H NMR (500 MHz, DMSO-d$_6$) δ ppm: 11.07 (s, 1H), 7.53 (d, J=8.4 Hz, 2H), 7.28 (d, J=8.3 Hz, 2H), 3.51 (s, 3H), 2.48 (s, 3H), 1.98 (s, 3H).

11.5 4-Bromo-3-(4-methanesulfinylphenyl)-1,4-dimethyl-4,5-dihydro-1H-pyrazol-5-one 4-Bromo-3-(4-methanesulfinylphenyl)-1,4-dimethyl-4,5-dihydro-1H-pyrazol-5-one was synthesized from 1,4-dimethyl-3-[4-(methylsulfanyl)phenyl]-1H-pyrazol-5-ol (12.35 g, 42.17 mmol) according to General Method 6 (13.9 g, 68% yield). LC-MS: $t_R$=1.04 min, [M+H]$^-$=328.

11.6 4-{[(tert-Butoxy)carbonyl]({[(tert-butoxy)carbonyl]oxy})amino}-3-(4-methanesulfinylphenyl)-1,4-dimethyl-4,5-dihydro-1H-pyrazol-5-one 4-{[(tert-Butoxy)carbonyl]({[(tert-butoxy)carbonyl]oxy})amino}-3-(4-methanesulfinylphenyl)-1,4-dimethyl-4,5-dihydro-1H-pyrazol-5-one was synthesized from 4-bromo-3-(4-methanesulfinylphenyl)-1,4-dimethyl-4,5-dihydro-1H-pyrazol-5-one (14 g, 28.92 mmol) according to General Method 8 to provide the title compound as a yellow oil (10.5 g, 67% yield). LC-MS: $t_R$=1.28 min, [M+Na]$^+$=504.

11.7 4-(Hydroxyamino)-3-(4-methanesulfinylphenyl)-1,4-dimethyl-4,5-dihydro-1H-pyrazol-5-one 4-(Hydroxyamino)-3-(4-methanesulfinylphenyl)-1,4-dimethyl-4,5-dihydro-1H-pyrazol-5-one was synthesized from 4-{[(tert-butoxy)carbonyl]({[(tert-butoxy)carbonyl]oxy})amino}-3-(4-methanesulfinyl phenyl)-1,4-dimethyl-4,5-dihydro-1H-pyrazol-5-one (1.37 g, 2.85 mmol) according to General Method 9 with the product being chromatographed by column chromatography eluting with 50-100% ethyl acetate in heptanes (0.62 g, 78% yield). LC-MS: $t_R$=1.29 min, [M+H]$^+$=281.95. $^1$H NMR (500 MHz, DMSO-d$_6$) δ ppm: 8.22 (d, J=8.5 Hz, 2H), 7.76 (d, J=8.4 Hz, 2H), 7.67 (t, J=2.5 Hz, 1H), 6.55 (s, 1H), 2.78 (s, 3H), 1.23 (s, 3H).

Example 12

Compound 12 [5-(2-chloro-4-fluorophenyl)-4-(hydroxyamino)-2,4-dimethyl-2,4-dihydro-3H-pyrazol-3-one]

12.1 Ethyl 3-(2-chloro-4-fluorophenyl)-3-oxopropanoate

Ethyl 3-(2-chloro-4-fluorophenyl)-3-oxopropanoate was synthesized from 1-(2-chloro-4-fluorophenyl)ethanone and diethyl carbonate according to General Method 1 and was chromatographed by silica gel column chromatography eluting with heptanes:ethyl acetate gradients to provide the title compound as an orange oil (3.1 g, 40% yield). LC-MS: $t_R$=1.98 min, [M+H]$^+$=244.9.

12.2 3-(2-Chloro-4-fluorophenyl)-1-methyl-1H-pyrazol-5-ol 3-(2-Chloro-4-fluorophenyl)-1-methyl-1H-pyrazol-5-ol was synthesized from ethyl 3-(2-chloro-4-fluorophenyl)-3-oxopropanoate according to General Method 2 and the product was chromatographed by silica gel column chromatography eluting with heptanes:ethyl acetate (1:1 vol:vol) to provide the title compound as a white solid (1.37 g, 46% yield). LC-MS: $t_R$=1.09 min, [M+H]$^+$=226.9. $^1$H NMR (500 MHz, DMSO-d$_6$) δ ppm: 11.09 (s, 1H), 7.78 (dd, J=8.8, 6.5 Hz, 1H), 7.46 (dd, J=8.9, 2.6 Hz, 1H), 7.24 (td, J=8.5, 2.7 Hz, 1H), 5.85 (s, 1H), 3.58 (s, 3H).

12.3 3-(2-Chloro-4-fluorophenyl)-5-hydroxy-1-methyl-1H-pyrazole-4-carbaldehyde 3-(2-Chloro-4-fluorophenyl)-5-hydroxy-1-methyl-1H-pyrazole-4-carbaldehyde was synthesized from 3-(2-chloro-4-fluorophenyl)-1-methyl-1H-pyrazol-5-ol according to General Method 3 and was chromatographed by silica gel column chromatography eluting with heptanes:ethyl acetate gradients (0.51 g, 33% yield) LC-MS $t_R$=1.04 min, [M+H]$^+$=254.9.

12.4 3-(2-Chloro-4-fluorophenyl)-1,4-dimethyl-1H-pyrazol-5-ol 3-(2-Chloro-4-fluorophenyl)-1,4-dimethyl-1H-pyrazol-5-ol was synthesized from 3-(2-chloro-4-fluorophenyl)-5-hydroxy-1-methyl-1H-pyrazole-4-carbaldehyde according to General Method 5 (0.65 g, >99.9 yield). LC-MS $t_R$=1.06 min, [M+H]$^+$=240.9. $^1$H NMR (500 MHz, DMSO-d$_6$) δ ppm: 7.47 (d, J=7.2 Hz, 1H), 7.40-7.32 (m, 1H), 7.28-7.18 (m, 1H), 3.50 (s, 3H), 1.70 (s, 3H).

12.5 4-Bromo-3-(2-chloro-4-fluorophenyl)-1,4-dimethyl-4,5-dihydro-1H-pyrazol-5-one 4-Bromo-3-(2-chloro-4-fluorophenyl)-1,4-dimethyl-4,5-dihydro-1H-pyrazol-5-one was synthesized from 3-(2-chloro-4-fluorophenyl)-1,4-dimethyl-1H-pyrazol-5-ol according to General Method 6 and was used directly in the next step without further analysis (0.61 g, 70% yield).

12.6 4-{[(tert-Butoxy)carbonyl]({[(tert-butoxy)carbonyl]oxy})amino}-3-(2-chloro-4-fluorophenyl)-1,4-dimethyl-4,5-dihydro-1H-pyrazol-5-one 4-{[(tert-Butoxy)carbonyl]({[(tert-butoxy)carbonyl]oxy})amino}-3-(2-chloro-4-fluorophenyl)-1,4-dimethyl-4,5-dihydro-1H-pyrazol-5-one was synthesized from the corresponding bromide according to General Method 8 and was chromatographed by silica gel column chromatography eluting with heptanes:ethyl acetate (1:1 vol:vol) to provide the title compound as off white foam (0.26 g, 32% yield). LC-MS $t_R$=1.61 min, [M+Na]$^+$=494.10.

12.7 3-(2-Chloro-4-fluorophenyl)-4-(hydroxyamino)-1,4-dimethyl-4,5-dihydro-1H-pyrazol-5-one 3-(2-Chloro-4-fluorophenyl)-4-(hydroxyamino)-1,4-dimethyl-4,5-dihydro-1H-pyrazol-5-one was synthesized from 4-{[(tert-butoxy)carbonyl]({[(tert-butoxy)carbonyl]oxy})amino}-3-(2-chloro-4-fluoro phenyl)-1,4-dimethyl-4,5-dihydro-1H-pyrazol-5-one according to General Method 9 and was chromatographed by silica gel column chromatography eluting with heptanes:ethyl acetate gradients to provide the title compound as an off white solid (0.11 g, 80% yield). LC-MS $t_R$=1.63 min, [M+H]=271.95. $^1$H NMR (500 MHz, DMSO-d$_6$) δ ppm: 8.00 (dd, J=8.8, 6.4 Hz, 1H), 7.84 (d, J=2.1 Hz, 1H), 7.59 (dd, J=9.0, 2.6 Hz, 1H), 7.37 (td, J=8.5, 2.6 Hz, 1H), 6.49 (d, J=2.1 Hz, 1H), 3.28 (s, 3H), 1.03 (s, 3H).

Example 13

Compound 13 [4-(hydroxyamino)-4-(1-(methoxyimino)ethyl)-5-methyl-2,4-dihydro-3H-pyrazol-3-one]

Under an argon atmosphere at a temperature of about 25° C., to a mixture of 4-(1-(methoxyimino)ethyl)-3-methyl-1H-pyrazol-5(4H)-one (0.20 mmol), Angeli's salt (49 mg, 0.40 mmol), and powdered diethylenetriaminepentaacetic acid (39 mg, 0.10 mmol) was added via syringe a degassed mixture of ethanol:water (1:1 vol:vol, 1 mL). The resulting reaction mixture was allowed to stir for 1.5 hours at that temperature, diluted with ethanol (>5 mL), and concentrated to dryness under reduced pressure with a minimum of heating (<30° C.) to provide a residue. The residue was taken up in a minimum of ethanol, eluted through a short silica plug, and concentrated under reduced pressure to provide a product that was loaded, with methanol, onto an analytical TLC plate (250 m thickness) and developed in ethyl acetate. Using a metal spatula, the product band (Rf>0.5) was scraped off the plate into a flask. The product was eluted with methanol (10 mL), filtered through cotton, and concentrated under reduced pressure to provide the title compound as an off-white to white solid (35% yield). HR FAB-MS: found [M+H]$^+$=201.09920; calc. (for C$_7$H$_{13}$N$_4$O$_3$) [M+H]$^+$=201.09817. $^1$H NMR (400 MHz, DMSO-d$_6$) δ ppm: 10.96 (s, 1H), 7.76, (d, J=2.7 Hz, 1H), 6.60 (d, J=2.7 Hz, 1H), 3.76 (s, 3H), 1.98 (s, 3H), 1.79 (s, 3H). $^{13}$C NMR (100 MHz, DMSO-d$_6$) δ ppm: 173.93, 159.50, 151.82, 74.23, 61.60, 14.85, 10.57.

Example 14

Compound 14 [4-(hydroxyamino)-2,4-dimethyl-5-(4-(methylsulfonyl)phenyl)-2,4-dihydro-3H-pyrazol-3-one]

14.1 Methyl 3-[4-(methylsulfanyl)phenyl]-3-oxopropanoate

Methyl 3-[4-(methylsulfanyl)phenyl]-3-oxopropanoate was synthesized from 1-[4-(methylsulfanyl)phenyl]ethan-1-one (35 g, 210.54 mmol, available from Sigma-Aldrich) according to General Method 1. The brown oily product solidified after about 16 hours at a temperature of about 25° C. The solid was dissolved in a minimum quantity of ethyl acetate (70 mL) while gentle heat was applied with a heat gun. After dissolution, heptane (100 mL) was added and the mixture was sonicated for 30 minutes. The solid was filtered and dried under air to provide the title compound as a beige solid (40.7 g, 69% yield). LC-MS: $t_R$=1.25 min, $[M+H]^+$=224. $^1$H NMR (500 MHz, CDCl$_3$) δ 7.85 (d, J=8.6 Hz, 2H), 7.31-7.26 (m, 2H), 3.96 (s, 2H), 3.75 (s, 3H), 2.52 (d, J=7.0 Hz, 3H).

14.2 1-Methyl-3-[4-(methylsulfanyl)phenyl]-1H-pyrazol-5-ol

1-Methyl-3-[4-(methylsulfanyl)phenyl]-1H-pyrazol-5-ol was synthesized from methyl 3-[4-(methylsulfanyl)phenyl]-3-oxopropanoate (40.7 g, 181.47 mmol) according to General Method 2 to provide the title compound as an off-white solid (37 g, 89% yield). LC-MS: $t_R$=1.1 min, $[M+H]^+$=220. $^1$H NMR (250 MHz, DMSO-d$_6$) δ ppm: 10.99 (s, 1H), 7.63 (d, J=8.4 Hz, 2H), 7.23 (d, J=8.4 Hz, 2H), 5.75 (s, 1H), 3.55 (s, 3H), 2.48 (s, 3H).

14.3 5-Hydroxy-1-methyl-3-[4-(methylsulfanyl)phenyl]-1H-pyrazole-4-carbaldehyde 5-Hydroxy-1-methyl-3-[4-(methylsulfanyl)phenyl]-1H-pyrazole-4-carbaldehyde was synthesized from 1-methyl-3-[4-(methylsulfanyl)phenyl]-1H-pyrazol-5-ol (36.4 g, 160.28 mmol) according to General Method 4 to provide the title compound as a yellow solid (42 g, 98% yield). LC-MS: $t_R$=1.09 min, $[M+H]^+$=248. $^1$H NMR (500 MHz, DMSO-d$_6$) δ ppm: 9.71 (s, 1H), 7.83-7.70 (m, 2H), 7.35-7.24 (m, 2H), 3.60 (s, 3H), 2.51-2.50 (m, 3H).

14.4 1,4-Dimethyl-3-[4-(methylsulfanyl)phenyl]-1H-pyrazol-5-ol 1,4-Dimethyl-3-[4-(methylsulfanyl)phenyl]-1H-pyrazol-5-ol was synthesized from 5-hydroxy-1-methyl-3-[4-(methylsulfanyl)phenyl]-1H-pyrazole-4-carbaldehyde (43 g, 159.32 mmol) according to General Method 5 to provide the title compound as an off-white solid (45 g, 90% yield (containing 25% acetic acid)). LC-MS: $t_R$=1.07 min, $[M+H]^+$=234. $^1$H NMR (500 MHz, DMSO-d$_6$) δ ppm: 11.07 (s, 1H), 7.53 (d, J=8.4 Hz, 2H), 7.28 (d, J=8.3 Hz, 2H), 3.51 (s, 3H), 2.48 (s, 3H), 1.98 (s, 3H).

14.5 4-Bromo-3-(4-methanesulfinylphenyl)-1,4-dimethyl-4,5-dihydro-1H-pyrazol-5-one 4-Bromo-3-(4-methanesulfinylphenyl)-1,4-dimethyl-4,5-dihydro-1H-pyrazol-5-one was synthesized from 1,4-dimethyl-3-[4-(methylsulfanyl)phenyl]-1H-pyrazol-5-ol (12.35 g, 42.17 mmol) according to General Method 6 (13.93 g, 68% yield). LC-MS: $t_R$=1.04 min, $[M+H]^-$=328.

14.6 4-{[(tert-Butoxy)carbonyl]({[(tert-butoxy)carbonyl]oxy})amino}-3-(4-methanesulfinylphenyl)-1,4-dimethyl-4,5-dihydro-1H-pyrazol-5-one 4-{[(tert-Butoxy)carbonyl]({[(tert-butoxy)carbonyl]oxy})amino}-3-(4-methanesulfinylphenyl)-1,4-dimethyl-4,5-dihydro-1H-pyrazol-5-one was synthesized from 4-bromo-3-(4-methanesulfinylphenyl)-1,4-dimethyl-4,5-dihydro-1H-pyrazol-5-one (14 g, 28.92 mmol) according to General Method 8 to provide the title compound as a yellow oil (10.5 g, 67% yield). LC-MS: $t_R$=1.28 min, $[M+Na]^+$=504.

14.7 4-{[(tert-Butoxy)carbonyl]({[(tert-butoxy)carbonyl]oxy})amino}-3-(4-methanesulfonylphenyl)-1,4-dimethyl-4,5-dihydro-1H-pyrazol-5-one 4-{[(tert-Butoxy)carbonyl]({[(tert-butoxy)carbonyl]oxy})amino}-3-(4-methanesulfonylphenyl)-1,4-dimethyl-4,5-dihydro-1H-pyrazol-5-one was synthesized from 4-{[(tert-butoxy)carbonyl]({[(tert-butoxy)carbonyl]oxy})amino}-3-(4-methanesulfinylphenyl)-1,4-dimethyl-4,5-dihydro-1H-pyrazol-5-one (10 g, 18.48 mmol) according to General Method 10 to provide the title compound as a yellow sticky solid (12.6 g, 93% yield) LC-MS: $t_R$=1.39 min, $[M+Na]^+$=522.

14.8 4-(Hydroxyamino)-3-(4-methanesulfonylphenyl)-1,4-dimethyl-4,5-dihydro-1H-pyrazol-5-one 4-(Hydroxyamino)-3-(4-methanesulfonylphenyl)-1,4-dimethyl-4,5-dihydro-1H-pyrazol-5-one was synthesized from 4-{[(tert-butoxy)carbonyl]({[(tert-butoxy)carbonyl]oxy})amino}-3-(4-methanesulfonyl phenyl)-1,4-dimethyl-4,5-dihydro-1H-pyrazol-5-one (12.6 g, 17.47 mmol) according to General Method 9 and the product was chromatographed by silica gel column chromatography eluting with a 25-100% ethyl acetate:heptanes gradient. The isolated product was crystallized from ethyl acetate:heptanes (1:2 vol:vol) to obtain the desired product as an off-white solid (3.4 g, 64% yield). LC-MS: $t_R$=1.01 min, $[M+H]^+$=298. $^1$H NMR (500 MHz, DMSO-d$_6$) δ ppm: 8.34-8.23 (m, 2H), 8.04-7.95 (m, 2H), 7.69 (d, J=2.6 Hz, 1H), 6.60 (d, J=2.6 Hz, 1H), 3.33 (s, 3H), 3.25 (s, 3H), 1.24 (s, 3H).

Example 15

Compound 15 [4-(hydroxyamino)-2,4-dimethyl-5-phenyl-2,4-dihydro-3H-pyrazol-3-one]

15.1 2-Methyl-5-phenyl-2,3-dihydro-1H-pyrazol-3-one

2-Methyl-5-phenyl-2,3-dihydro-1H-pyrazol-3-one was synthesized from ethyl 3-oxo-3-phenylpropanoate according to General Method 2. Once the reaction was complete, the solution was left to stand at a temperature of about 25° C. for 16 hours, by which time partial precipitation occurred. The solvent was reduced under reduced pressure until 10 mL of solvent remained. The resulting solid was isolated by filtration and washed with ice-cold methanol to provide the title compound as a white solid (3.73 g, 82% yield). LC-MS: $t_R$=0.88 min, $[M+H]^+$=175. $^1$H NMR (250 MHz, DMSO-d$_6$)

δ ppm: 7.68 (dd, J=8.3, 1.3 Hz, 2H), 7.34 (t, J=7.4 Hz, 2H), 7.24 (t, J=7.2 Hz, 1H), 5.77 (s, 1H), 3.55 (s, 3H).

15.2 2-Methyl-3-oxo-5-phenyl-2,3-dihydro-1H-pyrazole-4-carbaldehyde

2-Methyl-3-oxo-5-phenyl-2,3-dihydro-1H-pyrazole-4-carbaldehyde was synthesized from 2-methyl-5-phenyl-2,3-dihydro-1H-pyrazol-3-one according to General Method 3 (3.82 g, 88% yield). LC-MS: $t_R$=0.93 min, [M+H]$^+$=203. $^1$H NMR (250 MHz, DMSO-$d_6$) δ ppm: 9.71 (s, 1H), 7.84-7.71 (m, 2H), 7.50-7.36 (m, 3H), 3.61 (s, 3H).

15.3 1,4-Dimethyl-3-phenyl-1H-pyrazol-5-ol 1,4-Dimethyl-3-phenyl-1H-pyrazol-5-ol was synthesized from 2-methyl-3-oxo-5-phenyl-2,3-dihydro-1H-pyrazole-4-carbaldehyde according to General Method 5 (4.07 g, 96% yield (containing 11.5% acetic acid)). LC-MS: $t_R$=0.94 min, [M+H]$^+$=189. $^1$H NMR (250 MHz, DMSO-$d_6$) δ ppm: 7.57 (d, J=7.2 Hz, 2H), 7.34 (t, J=7.6 Hz, 2H), 7.23 (d, J=6.8 Hz, 1H), 3.47 (s, 3H), 1.96 (s, 3H).

15.4 4-Bromo-1,4-dimethyl-3-phenyl-4,5-dihydro-1H-pyrazol-5-one

4-Bromo-1,4-dimethyl-3-phenyl-4,5-dihydro-1H-pyrazol-5-one was synthesized from 1,4-dimethyl-3-phenyl-1H-pyrazol-5-ol according to General Method 6 (4.24 g, 97% yield). LC-MS: $t_R$=1.32 min, [M+H]$^+$=267/269. $^1$H NMR (250 MHz, DMSO-$d_6$) δ ppm: 7.97-7.89 (m, 2H), 7.51 (q, J=3.7 Hz, 3H), 3.37 (s, 3H), 1.99 (s, 3H).

15.5 4-{[(tert-Butoxy)carbonyl]({[(tert-butoxy)carbonyl]oxy})amino}-1,4-dimethyl-3-phenyl-4,5-dihydro-1H-pyrazol-5-one 4-{[(tert-Butoxy)carbonyl]({[(tert-butoxy)carbonyl]oxy})amino}-1,4-dimethyl-3-phenyl-4,5-dihydro-1H-pyrazol-5-one was synthesized from 4-bromo-1,4-dimethyl-3-phenyl-4,5-dihydro-1H-pyrazol-5-one according to General Method 8 (7.4 g, 71% yield). LC-MS: $t_R$=1.57 min, [M+Na]$^+$=442.

15.6 4-(Hydroxyamino)-1,4-dimethyl-3-phenyl-4,5-dihydro-1H-pyrazol-5-one 4-(Hydroxyamino)-1,4-dimethyl-3-phenyl-4,5-dihydro-1H-pyrazol-5-one was synthesized from 4-{[(tert-butoxy)carbonyl]({[(tert-butoxy)carbonyl]oxy})amino}-1,4-dimethyl-3-phenyl-4,5-dihydro-1H-pyrazol-5-one according to General Method 9. Purification by silica gel chromatography, eluting in 0-60% ethyl acetate:heptanes, followed by trituration with DCM:heptanes (20 mL, 1:3 vol:vol) provided the title compound as an off-white solid (0.84 g, 32% yield). LC-MS: $t_R$=1.47 min, [M+H]$^+$=220. $^1$H NMR (500 MHz, DMSO-$d_6$) δ ppm: 8.08-8.01 (m, 2H), 7.63 (d, J=2.5 Hz, 1H), 7.45 (dd, J=5.3, 1.9 Hz, 3H), 6.45 (d, J=2.5 Hz, 1H), 3.29 (s, 3H), 1.20 (s, 3H).

Example 16

Compound 16 [4-(hydroxyamino)-5-iso-propyl-4-(1-(methoxyimino)ethyl)-2-phenyl-2,4-dihydro-3H-pyrazol-3-one]

16.1 1-Phenyl-3-(propan-2-yl)-1H-pyrazol-5-ol

To a solution of phenyl hydrazine (3.42 g, 31.61 mmol) in ethanol (50 mL) was added ethyl 4-methyl-3-oxopentanoate (5 g, 31.61 mmol). The resulting solution was heated at 70° C. for 1 hour. The reaction mixture was concentrated under reduced pressure to provide the title compound as a yellow oil (6 g, 82% yield). LC-MS: $t_R$=1.25 min, [M+H]$^+$=203. $^1$H NMR (500 MHz, DMSO-$d_6$) δ ppm: 11.41 (s, 1H), 7.71 (d, J=7.7 Hz, 2H), 7.47-7.33 (m, 2H), 7.20 (t, J=7.4 Hz, 1H), 5.39 (s, 1H), 3.35 (s, 3H), 2.78 (septet, J=7.0 Hz, 1H), 1.18 (2×d, J=6.8 Hz, 6H).

16.2 1-[5-Hydroxy-1-methyl-3-(propan-2-yl)-1H-pyrazol-4-yl]ethan-1-one

1-Phenyl-3-(propan-2-yl)-1H-pyrazol-5-ol (6 g, 0.03 mol) was taken up in 1,1,1-trimethoxyethane (13.21 mL, 0.1 mol) and the resulting solution was heated to 65° C. for 7 hours. The solution was concentrated under reduced pressure, and chromatographed by silica gel chromatography eluting with 50-80% ethyl acetate:heptanes to provide the title compound as a yellow/orange solid (5.4 g, 68% yield). LC-MS: $t_R$=1.39/1.43 min, [M+H]$^+$=245. $^1$H NMR (250 MHz, DMSO-$d_6$) δ ppm: 7.92 (dd, J=8.7, 1.1 Hz, 2H), 7.44-7.33 (m, 2H), 7.17-7.07 (m, 1H), 4.09 (s, 3H), 3.14 (septet, J=13.6, 6.8 Hz, 1H), 2.80 (s, 3H), 1.20 (d, J=6.8 Hz, 6H).

16.3 4-[1-(Methoxyimino)ethyl]-1-phenyl-3-(propan-2-yl)-1H-pyrazol-5-ol

4-[1-(Methoxyimino)ethyl]-1-phenyl-3-(propan-2-yl)-1H-pyrazol-5-ol was synthesized from 1-[5-hydroxy-1-methyl-3-(propan-2-yl)-1H-pyrazol-4-yl]ethan-1-one according to General Method 12 (3.75 g, 91% yield). LC-MS: $t_R$=1.48 min, [M+H]$^+$=274. $^1$H NMR (500 MHz, DMSO-$d_6$) δ ppm: 7.68 (d, J=7.8 Hz, 2H), 7.46 (t, J=7.9 Hz, 2H), 7.26 (t, J=7.4 Hz, 1H), 3.83 (s, 3H), 3.56-3.16 (m, 1H), 2.13 (s, 3H), 1.23 (d, J=6.9 Hz, 6H).

16.4 4-Bromo-4-[1-(methoxyimino)ethyl]-1-phenyl-3-(propan-2-yl)-4,5-dihydro-1H-pyrazol-5-one 4-Bromo-4-[1-(methoxyimino)ethyl]-1-phenyl-3-(propan-2-yl)-4,5-dihydro-1H-pyrazol-5-one was synthesized from 4-[1-(methoxyimino)ethyl]-1-phenyl-3-(propan-2-yl)-1H-pyrazol-5-ol according to General Method 6 and was used directly in the synthesis of 4-{[(tert-butoxy)carbonyl]({[(tert-butoxy)carbonyl]oxy})amino}-4-[1-(methoxyimino)ethyl]-1-phenyl-3-(propan-2-yl)-4,5-dihydro-1H-pyrazol-5-one assuming 100% yield. (The reaction also provided 4-bromo-1-(4-bromophenyl)-4-[1-(methoxyimino)ethyl]-3-(propan-2-yl)-4,5-dihydro-1H-pyrazol-5-one which was used in the synthesis of Example 17.) LC-MS: $t_R$=1.80 min, [M+H]$^+$=352/354. $^1$H NMR (500 MHz, DMSO-$d_6$) δ ppm: 7.87-7.19 (m, 5H), 3.88 (d, J=1.9 Hz, 3H), 2.92-2.75 (m, 1H), 2.08 (s, 3H), 1.42-1.30 (m, 6H).

16.5 4-{[(tert-Butoxy)carbonyl]({[(tert-butoxy)carbonyl]oxy})amino}-4-[1-(methoxyimino)ethyl]-1-phenyl-3-(propan-2-yl)-4,5-dihydro-1H-pyrazol-5-one 4-{[(tert-Butoxy)carbonyl]({[(tert-butoxy)carbonyl]oxy})amino}-4-[1-(methoxyimino)ethyl]-1-phenyl-3-(propan-2-yl)-4,5-dihydro-1H-pyrazol-5-one was synthesized from 4-bromo-4-[1-(methoxyimino)ethyl]-1-phenyl-3-(propan-2-yl)-4,5-dihydro-1H-pyrazol-5-one according to General Method 8 and was used directly in the synthesis of 4-(hydroxyamino)-4-[1-(methoxyimino)ethyl]-1-phenyl-3-

(propan-2-yl)-4,5-dihydro-1H-pyrazol-5-one (5.6 g, 73% yield, also containing 1-(4-bromophenyl)-4-{([(tert-butoxy)carbonyl]({[(tert-butoxy)carbanoyl]oxy})amino}-4-[1-(methoxyimino)ethyl]-3-(propan-2-yl)-4,5-dihydro-1H-pyrazol-5-one which was used in the synthesis of Example 17). LC-MS: $t_R$=2.79 min, [M+Na]$^+$=527.

16.6 4-(Hydroxyamino)-4-[1-(methoxyimino)ethyl]-1-phenyl-3-(propan-2-yl)-4,5-dihydro-1H-pyrazol-5-one 4-(Hydroxyamino)-4-[1-(methoxyimino)ethyl]-1-phenyl-3-(propan-2-yl)-4,5-dihydro-1H-pyrazol-5-one was synthesized from 4-{[(tert-butoxy)carbonyl]({[(tert-butoxy)carbonyl]oxy})amino}-4-[1-(methoxyimino)ethyl]-1-phenyl-3-(propan-2-yl)-4,5-dihydro-1H-pyrazol-5-one according to General Method 9 and chromatographed by silica gel chromatography eluting in 0-100% ethyl acetate:heptanes. Chromatography by acidic preparative HPLC on a small scale (160 mg) provided the title compound as a pale yellow oil (0.05 g, 2.1% yield). LC-MS: $t_R$=2.03 min, [M+H]$^+$=305. $^1$H NMR (500 MHz, DMSO-d$_6$) δ ppm: 7.89 (d, J=2.2 Hz, 1H), 7.86-7.78 (m, 2H), 7.50-7.37 (m, 2H), 7.20 (t, J=7.4 Hz, 1H), 6.84 (d, J=2.2 Hz, 1H), 3.79 (s, 3H), 2.88 (septet, J=6.9 Hz, 1H), 1.82 (s, 3H), 1.26 (2×d, J=6.9 Hz, 6H).

Example 17

Compound 17 [2-(4-bromophenyl)-4-(hydroxyamino)-5-iso-propyl-4-(1-(methoxyimino)ethyl)-2,4-dihydro-3H-pyrazol-3-one]

1-(4-Bromophenyl)-4-(hydroxyamino)-4-[1-(methoxyimino)ethyl]-3-(propan-2-yl)-4,5-dihydro-1H-pyrazol-5-one was isolated from the acidic preparative HPLC chromatography of 4-(hydroxyamino)-4-[1-(methoxyimino)ethyl]-1-phenyl-3-(propan-2-yl)-4,5-dihydro-1H-pyrazol-5-one to provide the title compound as a white solid (0.02 g, 1% yield). LC-MS: $t_R$=2.23 min, [M+H]$^+$=383/385. $^1$H NMR (500 MHz, DMSO-d$_6$) δ ppm: 7.92 (d, J=2.1 Hz, 1H), 7.86-7.75 (m, 2H), 7.70-7.58 (m, 2H), 6.90 (d, J=2.2 Hz, 1H), 3.78 (s, 3H), 2.88 (septet, J=6.8 Hz, 1H), 1.83 (s, 3H), 1.26 (2×d, J=6.9 Hz, 6H).

Example 18

Compound 18 [5-(tert-butyl)-4-(hydroxyamino)-4-(1-(methoxyimino)ethyl)-2-phenyl-2,4-dihydro-3H-pyrazol-3-one]

18.1 3-tert-Butyl-1-phenyl-4,5-dihydro-1H-pyrazol-5-one 3-tert-Butyl-1-phenyl-4,5-dihydro-1H-pyrazol-5-one was synthesized from corresponding beta-keto ester and phenyl hydrazine according to General Method 2 (6.7 g, 96% yield). LC-MS: $t_R$=1.98 min, [M+H]$^+$=217.00. $^1$H NMR (500 MHz, DMSO-d$_6$) δ ppm: 7.71 (d, J=7.7 Hz, 2H), 7.41 (t, J=7.9 Hz, 2H), 7.20 (t, J=7.3 Hz, 1H), 5.42 (s, 1H), 1.23 (s, 9H).

18.2 1-(3-tert-Butyl-5-hydroxy-1-phenyl-1H-pyrazol-4-yl)ethan-1-one 1-(3-tert-Butyl-5-hydroxy-1-phenyl-1H-pyrazol-4-yl)ethan-1-one was synthesized from 3-tert-butyl-1-phenyl-4,5-dihydro-1H-pyrazol-5-one according to General Method 11 (3.47 g, 60% yield). LC-MS: $t_R$=1.56 min, [M+H]$^+$=273.10. $^1$H NMR (500 MHz, DMSO-d$_6$) δ ppm: 7.92 (d, J=7.7 Hz, 2H), 7.39 (t, J=7.9 Hz, 2H), 7.13 (t, J=7.4 Hz, 1H), 2.86 (s, 3H), 1.30 (s, 9H).

18.3 3-tert-Butyl-4-[1-(methoxyimino)ethyl]-1-phenyl-1H-pyrazol-5-ol 3-tert-Butyl-4-[1-(methoxyimino)ethyl]-1-phenyl-1H-pyrazol-5-ol was synthesized from 1-(3-tert-butyl-5-hydroxy-1-phenyl-1H-pyrazol-4-yl)ethan-1-one according to General Method 12 (3.26 g, 84% yield). LC-MS: $t_R$=1.30 min, [M+H]$^+$=288.05. $^1$H NMR (500 MHz, DMSO-d$_6$) δ ppm: 7.69 (d, J=7.0 Hz, 2H), 7.46 (t, J=7.8 Hz, 2H), 7.27 (t, J=7.4 Hz, 1H), 3.86 (s, 3H), 2.04 (s, 3H), 1.30 (s, 9H).

18.4 4-Bromo-3-tert-butyl-4-[1-(methoxyimino)ethyl]-1-phenyl-4,5-dihydro-1H-pyrazol-5-one 4-Bromo-3-tert-butyl-4-[1-(methoxyimino)ethyl]-1-phenyl-4,5-dihydro-1H-pyrazol-5-one was synthesized from 3-tert-butyl-4-[1-(methoxyimino)ethyl]-1-phenyl-1H-pyrazol-5-ol according to General Method 6 which was directly used in the displacement reaction according to General Method 7 (4.2 g, >99.9 yield).

18.5 4-{[(tert-Butoxy)carbonyl]({[(tert-butoxy)carbonyl]oxy})amino}-3-tert-butyl-4-[1-(methoxyimino)ethyl]-1-phenyl-4,5-dihydro-1H-pyrazol-5-one 4-{[(tert-Butoxy)carbonyl]({[(tert-butoxy)carbonyl]oxy})amino}-3-tert-butyl-4-[1-(methoxyimino)ethyl]-1-phenyl-4,5-dihydro-1H-pyrazol-5-one was synthesized from the corresponding bromide according to General Method 8 which was used directly in the deprotection reaction according to General Method 9 (5.55 g, 35% yield). LC-MS: $t_R$=1.96, [M+H]$^+$=541.20.

18.6 3-tert-Butyl-4-(hydroxyamino)-4-[1-(methoxyimino)ethyl]-1-phenyl-4,5-dihydro-1H-pyrazol-5-one 3-tert-Butyl-4-(hydroxyamino)-4-[1-(methoxyimino)ethyl]-1-phenyl-4,5-dihydro-1H-pyrazol-5-one was synthesized from 4-{[(tert-butoxy)carbonyl]({[(tert-butoxy)carbonyl]oxy})amino}-3-tert-butyl-4-[1-(methoxyimino)ethyl]-1-phenyl-4,5-dihydro-1H-pyrazol-5-one according to General Method 9 with the product being chromatographed by column chromatography eluting with 0-40% ethyl acetate in heptanes (0.07 g, 6% yield). LC-MS: $t_R$=2.11 min, [M+H]$^+$=319.10. $^1$H NMR (500 MHz, DMSO-d$_6$) δ ppm: 7.85-7.79 (m, 3H), 7.48-7.42 (m, 2H), 7.25-7.19 (m, 1H), 6.60 (d, J=1.8 Hz, 1H), 3.81 (s, 3H), 1.69 (s, 3H), 1.31 (s, 9H).

Example 19

Compound 19 [5-(3-fluoro-4-methoxyphenyl)-4-(hydroxyamino)-2,4-dimethyl-2,4-dihydro-3H-pyrazol-3-one]

19.1 Methyl 3-(3-fluoro-4-methoxyphenyl)-3-oxopropanoate

Methyl 3-(3-fluoro-4-methoxyphenyl)-3-oxopropanoate was synthesized from 1-(3-fluoro-4-methoxyphenyl)ethanone (7 g, 41.63 mmol) according to General Method 1 to provide the title compound as a yellow solid (6.8 g, 69% yield). LC-MS: $t_R$=1.71 min, [M+H]$^+$=227. $^1$H NMR (500 MHz, CDCl$_3$) δ ppm: 7.82-7.63 (m, 2H), 7.00 (q, J=8.0 Hz, 1H), 3.97 (s, 3H), 3.94 (s, 2H), 3.75 (s, 3H).

19.2 3-(3-Fluoro-4-methoxyphenyl)-1-methyl-1H-pyrazol-5-ol 3-(3-Fluoro-4-methoxyphenyl)-1-methyl-1H-pyrazol-5-ol was synthesized from methyl 3-(3-fluoro-4-methoxyphenyl)-3-oxopropanoate (6.8 g, 26.15 mmol) according to General Method 2 to provide the title compound as a grey solid (3.5 g, 51% yield). LC-MS: $t_R$=1.53 min, [M+H]$^+$=223. $^1$H NMR (500 MHz, DMSO-d$_6$) δ ppm: 11.02 (s, 1H), 7.56-7.34 (m, 2H), 7.12 (t, J=8.8 Hz, 1H), 5.75 (s, 1H), 3.83 (s, 3H), 3.53 (s, 3H).

19.3 3-(3-Fluoro-4-methoxyphenyl)-5-hydroxy-1-methyl-1H-pyrazole-4-carbaldehyde 3-(3-Fluoro-4-methoxyphenyl)-5-hydroxy-1-methyl-1H-pyrazole-4-carbaldehyde was synthesized from 3-(3-fluoro-4-methoxyphenyl)-1-methyl-1H-pyrazol-5-ol (3.52 g, 15.84 mmol) according to General Method 4 to provide the title compound as yellow solid (3.6 g, 70% yield). LC-MS: $t_R$=1.46 min, [M+H]$^+$=250.

19.4 3-(3-Fluoro-4-methoxyphenyl)-1,4-dimethyl-1H-pyrazol-5-ol 3-(3-Fluoro-4-methoxyphenyl)-1,4-dimethyl-1H-pyrazol-5-ol was synthesized from 3-(3-fluoro-4-methoxyphenyl)-5-hydroxy-1-methyl-1H-pyrazole-4-carbaldehyde (3.62 g, 11.14 mmol) according to General Method 5 to provide the title compound as a brown solid (>99.9% yield). LC-MS: $t_R$=1.57 min, [M+H]$^+$=236.

19.5 4-Bromo-3-(3-fluoro-4-methoxyphenyl)-1,4-dimethyl-4,5-dihydro-1H-pyrazol-5-one 4-Bromo-3-(3-fluoro-4-methoxyphenyl)-1,4-dimethyl-4,5-dihydro-1H-pyrazol-5-one was synthesized from 3-(3-fluoro-4-methoxyphenyl)-1,4-dimethyl-1H-pyrazol-5-ol (2 g, 6.52 mmol) according to General Method 6 (2 g, 58% yield). LC-MS: $t_R$=1.98 min, [M+H]$^+$=316.

19.6 4-{[(tert-Butoxy)carbonyl]({[(tert-butoxy)carbonyl]oxy})amino}-3-(3-fluoro-4-methoxyphenyl)-1,4-dimethyl-4,5-dihydro-1H-pyrazol-5-one 4-{[(tert-Butoxy)carbonyl]({[(tert-butoxy)carbonyl]oxy})amino}-3-(3-fluoro-4-methoxyphenyl)-1,4-dimethyl-4,5-dihydro-1H-pyrazol-5-one synthesized from 4-bromo-3-(3-fluoro-4-methoxyphenyl)-1,4-dimethyl-4,5-dihydro-1H-pyrazol-5-one (2 g, 3.81 mmol) according to General Method 8 to provide the title compound as a yellow solid (0.42 g, 23% yield) LC-MS: $t_R$=2.19 min, [M+Na]$^+$=490.

19.7 3-(3-Fluoro-4-methoxyphenyl)-4-(hydroxyamino)-1,4-dimethyl-4,5-dihydro-1H-pyrazol-5-one 3-(3-Fluoro-4-methoxyphenyl)-4-(hydroxyamino)-1,4-dimethyl-4,5-dihydro-1H-pyrazol-5-one was synthesized from 4-{[(tert-butoxy)carbonyl]({[(tert-butoxy)carbonyl]oxy})amino}-3-(3-fluoro-4-methoxyphenyl)-1,4-dimethyl-4,5-dihydro-1H-pyrazol-5-one (0.41 g, 0.85 mmol) according to General Method 9 to provide the title compound as an off-white solid (0.122 g, 53% yield). LC-MS: $t_R$=1.65 min, [M+H]$^+$=267. $^1$H NMR (500 MHz, DMSO-d$_6$) δ ppm: 7.90-7.76 (m, 2H), 7.65 (d, J=2.5 Hz, 1H), 7.25 (t, J=9.0 Hz, 1H), 6.51 (d, J=2.5 Hz, 1H), 3.88 (s, 3H), 3.27 (s, 3H), 1.17 (s, 3H).

Example 20

Compound 20 [5-cyclopropyl-4-(hydroxyamino)-4-(1-(methoxyimino)ethyl)-2-methyl-2,4-dihydro-3H-pyrazol-3-one]

20.1 3-Cyclopropyl-1-methyl-4,5-dihydro-1H-pyrazol-5-one

3-Cyclopropyl-1-methyl-4,5-dihydro-1H-pyrazol-5-one was synthesized from methyl 3-cyclopropyl-3-oxopropanoate according to General Method 2. The solvent was removed under reduced pressure to provide a yellow solid, which was washed with 200 mL of heptanes and filtered to provide the title compound as a pale yellow solid (9.36 g, 96% yield). LC-MS: $t_R$=0.40 min, [M+H]$^+$=139. $^1$H NMR (500 MHz, CDCl$_3$) δ ppm: 3.25 (s, 3H), 3.03 (s, 2H), 1.76 (ddd, J=13.4, 8.4, 5.0 Hz, 1H), 1.01-0.87 (m, 2H), 0.87-0.71 (m, 2H).

20.2 1-(3-Cyclopropyl-5-hydroxy-1-methyl-1H-pyrazol-4-yl)ethan-1-one

3-Cyclopropyl-1-methyl-4,5-dihydro-1H-pyrazol-5-one (6.2 g, 0.04 mol) was taken up in 1,1,1-trimethoxyethane (20 mL, 0.16 mol) and the resulting solution was heated to 65° C. for 160 minutes. The solution was concentrated under reduced pressure and chromatographed by silica gel chromatography eluting in 0-10% DCM:methanol to provide the title compound as an orange oil (1.8 g, 14% yield). LC-MS: $t_R$=0.83 min, [M+H]$^+$=181.

20.3 3-Cyclopropyl-4-[1-(methoxyimino)ethyl]-1-methyl-1H-pyrazol-5-ol

3-Cyclopropyl-4-[1-(methoxyimino)ethyl]-1-methyl-1H-pyrazol-5-ol was synthesized from 1-(3-cyclopropyl-5-hydroxy-1-methyl-1H-pyrazol-4-yl)ethan-1-one according to General Method 12 (1.8 g, >99.9% yield). LC-MS: $t_R$=1.46 min, [M+H]$^+$=210. $^1$H NMR (500 MHz, CDCl$_3$) δ ppm: 3.88 (s, 3H), 3.56 (s, 3H), 2.36 (s, 3H), 1.84 (tt, J=8.2, 5.3 Hz, 1H), 0.90-0.81 (m, 4H).

20.4 4-Bromo-3-cyclopropyl-4-[1-(methoxyimino)ethyl]-1-methyl-4,5-dihydro-1H-pyrazol-5-one 4-Bromo-3-cyclopropyl-4-[1-(methoxyimino)ethyl]-1-methyl-4,5-dihydro-1H-pyrazol-5-one was synthesized from 3-cyclopropyl-4-[1-(methoxyimino)ethyl]-1-methyl-1H-pyrazol-5-ol according to General Method 6 and was used directly in the next step assuming 100% yield. LC-MS: $t_R$=1.37 min, [M+H]$^+$=288/290.

20.5 4-{[(tert-Butoxy)carbonyl]({[(tert-butoxy)carbonyl]oxy})amino}-3-cyclopropyl-4-[1-(methoxyimino)ethyl]-1-methyl-4,5-dihydro-1H-pyrazol-5-one 4-{[(tert-Butoxy)carbonyl]({[(tert-butoxy)carbonyl]oxy})amino}-3-cyclopropyl-4-[1-(methoxyimino)ethyl]-1- methyl-4,5-dihydro-1H-pyrazol-5-one was synthesized from 4-bromo-3-cyclopropyl-4-[1-(methoxyimino)ethyl]-1-methyl-4,5-dihydro-1H-pyrazol-5-one according to General Method 8 and was chromatographed by silica gel chromatography eluting in 0-40% ethyl acetate:heptanes to provide the title compound as a yellow oil (2.57 g, 55% yield). LC-MS: $t_R$=1.49 min, [M+Na]$^+$=463.

20.6 3-Cyclopropyl-4-(hydroxyamino)-4-[1-(methoxyimino)ethyl]-1-methyl-4,5-dihydro-1H-pyrazol-5-one 3-Cyclopropyl-4-(hydroxyamino)-4-[1-(methoxyimino) ethyl]-1-methyl-4,5-dihydro-1H-pyrazol-5-one was synthesized from 4-{[(tert-butoxy)carbonyl]({[(tert-butoxy)carbonyl]oxy})amino}-3-cyclopropyl-4-[1-(methoxyimino) ethyl]-1-methyl-4,5-dihydro-1H-pyrazol-5-one according to General Method 9 and chromatographed by silica gel chromatography eluting in 0-70% ethyl acetate:heptanes to provide the title compound as a yellow oil (0.81 g, 71% yield). LC-MS: $t_R$=1.42 min, [M+H]$^+$=241. $^1$H NMR (250 MHz, DMSO-d$_6$) δ ppm: 7.76 (s, 1H), 3.77 (s, 3H), 3.10 (s, 3H), 1.78 (s, 3H), 1.77-1.69 (m, 1H), 0.95-0.78 (m, 4H).

Example 21

Compound 21 [4-(hydroxyamino)-2,4-dimethyl-5-(2-(methylsulfinyl)phenyl)-2,4-dihydro-3H-pyrazol-3-one]

21.1 1-[2-Methylsulfanyl)phenyl]ethan-1-one

1-[2-Methylsulfanyl)phenyl]ethan-1-one was synthesized from 1-(2-chlorophenyl)ethanone according to General Method 14 and chromatographed by silica gel chromatography eluting in 0-40% ethyl acetate:heptanes to provide the title compound as an off-white solid (6.12 g, 53% yield). LC-MS: $t_R$=1.17 min, [M+H]$^+$=167. $^1$H NMR (250 MHz, CDCl$_3$) δ ppm: 7.84 (dd, J=7.8, 1.4 Hz, 1H), 7.49-7.33 (m, 1H), 7.33 (d, J=7.8 Hz, 1H), 7.24-7.15 (m, 1H), 2.62 (s, 3H), 2.44 (s, 3H).

21.2 Methyl 3-[2-(methylsulfanyl)phenyl]-3-oxopropanoate

Methyl 3-[2-(methylsulfanyl)phenyl]-3-oxopropanoate was synthesized from 1-[2-methylsulfanyl)phenyl]ethan-1-one according to General Method 1 and chromatographed by silica gel chromatography eluting in 0-40% ethyl acetate: heptanes to provide the title compound as a yellow oil (4.85 g, 48% yield). LC-MS: $t_R$=1.77 min, [M+H]$^+$=225. $^1$H NMR (500 MHz, CDCl$_3$) δ ppm: 7.80 (d, J=9.1 Hz, 1H), 7.54-7.44 (m, 1H), 7.35 (d, J=8.1 Hz, 1H), 7.21 (t, J=7.5 Hz, 1H), 4.02 (s, 2H), 3.75 (s, 3H), 2.45 (s, 3H).

21.3 1-Methyl-3-[2-(methylsulfanyl)phenyl]-4,5-dihydro-1H-pyrazol-5-one

1-Methyl-3-[2-(methylsulfanyl)phenyl]-4,5-dihydro-1H-pyrazol-5-one was synthesized from methyl 3-[2-(methylsulfanyl)phenyl]-3-oxopropanoate according to General Method 2. Purification by silica gel chromatography eluting in 0-10% methanol:DCM, followed by recrystallization from cold diethyl ether provided the title compound as a white solid (0.925 g, 19% yield). LC-MS: $t_R$=1.11 min, [M+H]$^+$=221. $^1$H NMR (500 MHz, DMSO-d$_6$) δ ppm: 9.65 (s, 1H), 7.45 (m, 1H), 7.34 (d, J=8.0 Hz, 1H), 7.22 (d, J=4.1 Hz, 2H), 5.48 (s, 1H), 2.41 (s, 3H).

21.4 5-Hydroxy-1-methyl-3-[2-(methylsulfanyl) phenyl]-1H-pyrazole-4-carbaldehyde 5-Hydroxy-1-methyl-3-[2-(methylsulfanyl)phenyl]-1H-pyrazole-4-carbaldehyde was synthesized from 1-methyl-3-[2-(methylsulfanyl)phenyl]-4,5-dihydro-1H-pyrazol-5-one according to General Method 4 (2 g, 115% yield). LC-MS: $t_R$=1.00 min, [M+H]$^+$=249.

21.5 1,4-Dimethyl-3-[2-(methylsulfanyl)phenyl]-4,5-dihydro-1H-pyrazol-5-one 1,4-Dimethyl-3-[2-(methylsulfanyl)phenyl]-4,5-dihydro-1H-pyrazol-5-one was synthesized from 5-hydroxy-1-methyl-3-[2-(methylsulfanyl)phenyl]-1H-pyrazole-4-carbaldehyde according to General Method 5 and used directly in the next step (2.8 g, >99.9% yield). LC-MS: $t_R$=1.06 min, [M+H]$^+$=235.

21.6 4-Bromo-1,4-dimethyl-3-[2-(methylsulfanyl) phenyl]-4,5-dihydro-1H-pyrazol-5-one 4-Bromo-1,4-dimethyl-3-[2-(methylsulfanyl)phenyl]-4,5-dihydro-1H-pyrazol-5-one was synthesized from 1,4-dimethyl-3-[2-(methylsulfanyl)phenyl]-4,5-dihydro-1H-pyrazol-5-one according to General Method 6 and used directly in the next step assuming 100% yield. LC-MS: $t_R$=1.06 min, [M+H]$^+$=329/331.

21.7 4-{[(tert-butoxy)carbonyl]({[(tert-butoxy)carbonyl]oxy})amino}-1,4-dimethyl-3-[2-(methylsulfanyl)phenyl]-4,5-dihydro-1H-pyrazol-5-one 4-{[(tert-butoxy)carbonyl]({[(tert-butoxy)carbonyl]oxy}) amino}-1,4-dimethyl-3-[2-(methylsulfanyl)phenyl]-4,5-dihydro-1H-pyrazol-5-one was synthesized from 4-bromo-1,4-dimethyl-3-[2-(methylsulfanyl)phenyl]-4,5-dihydro-1H-pyrazol-5-one according to General Method 8 to provide the title compound as a yellow oil (0.8 g, 14% yield). LC-MS: $t_R$=1.04 min, [M-Boc+Na]$^+$=404.

21.8 4-(Hydroxyamino)-3-(2-methanesulfinylphenyl)-1,4-dimethyl-4,5-dihydro-1H-pyrazol-5-one 4-(Hydroxyamino)-3-(2-methanesulfinylphenyl)-1,4-dimethyl-4,5-dihydro-1H-pyrazol-5-one was synthesized from 4-{[(tert-butoxy)carbonyl]({[(tert-butoxy)carbonyl] oxy})amino}-1,4-dimethyl-3-[2-(methylsulfanyl)phenyl]-4,5-dihydro-1H-pyrazol-5-one according to General Method 9 and chromatographed by silica gel chromatography eluting in 0-10% methanol:DCM, followed by acidic preparative HPLC to provide the title compound as a mixture of diastereoisomers (0.02 g, 3% yield). LC-MS: $t_R$=1.27/1.33 min, [M+H]$^+$=282. $^1$H NMR (250 MHz, DMSO-d$_6$) δ ppm: 8.44 (d, J=6.7 Hz, 1H), 8.24-8.13 (m, 2H), 7.82 (d, J=2.6 Hz, 1H), 7.80-7.65 (m, 3H), 7.63 (d, J=2.0 Hz, 0.5H), 6.64 (d, J=2.4 Hz, 1H), 6.50 (d, J=2.4 Hz, 0.5H), 2.83 (s, 3H), 2.77 (s, 2H), 1.37 (s, 1.5H), 1.13 (s, 3H) (CH$_3$ masked by water peak).

Example 22

Compound 22 [4-(hydroxyamino)-2,4-dimethyl-5-(3-(trifluoromethyl)phenyl)-2,4-dihydro-3H-pyrazol-3-one]

22.1 1-Methyl-3-[3-(trifluoromethyl)phenyl]-1H-pyrazol-5-ol

1-Methyl-3-[3-(trifluoromethyl)phenyl]-1H-pyrazol-5-ol was synthesized from ethyl 3-oxo-3-[3-(trifluoromethyl)

phenyl]propanoate and methyl hydrazine according to General Method 2 and was triturated with DCM (2.69 g, 96% yield). LC-MS: $t_R$=1.21 min, [M+H]$^+$=243. $^1$H NMR (500 MHz, DMSO-d$_6$) δ ppm: 11.24 (s, 1H), 8.05-7.93 (m, 2H), 7.60 (dd, J=4.7, 1.8 Hz, 2H), 5.94 (s, 1H), 3.59 (s, 3H).

22.2 5-Hydroxy-1-methyl-3-[3-(trifluoromethyl)phenyl]-1H-pyrazole-4-carbaldehyde 5-Hydroxy-1-methyl-3-[3-(trifluoromethyl)phenyl]-1H-pyrazole-4-carbaldehyde was synthesized from 1-methyl-3-[3-(trifluoromethyl)phenyl]-1H-pyrazol-5-ol according to General Method 4 (2.9 g, 91.8% yield). LC-MS: $t_R$=1.22 min, [M+H]$^+$=271. $^1$H NMR (500 MHz, DMSO-d$_6$) δ ppm: 9.79 (s, 1H), 8.25 (s, 1H), 8.18 (d, J=7.8 Hz, 1H), 7.91-7.77 (m, 1H), 7.75 (d, J=7.9 Hz, 1H), 7.67 (q, J=7.8, 7.1 Hz, 1H), 3.65 (s, 3H).

22.3 1,4-Dimethyl-3-[3-(trifluoromethyl)phenyl]-1H-pyrazol-5-ol 1,4-Dimethyl-3-[3-(trifluoromethyl)phenyl]-1H-pyrazol-5-ol was prepared from 5-hydroxy-1-methyl-3-[3-(trifluoromethyl)phenyl]-1H-pyrazole-4-carbaldehyde according to General Method 5 (3.53 g, 91% yield). LC-MS: $t_R$=1.27 min, [M+H]$^+$=257. $^1$H NMR (500 MHz, DMSO-d$_6$) δ ppm: 7.91-7.76 (m, 1H), 7.59 (d, J=7.5 Hz, 2H), 7.36-6.97 (m, 1H), 3.52 (s, 3H), 2.01 (s, 3H).

22.4 4-Bromo-1,4-dimethyl-3-[3-(trifluoromethyl)phenyl]-4,5-dihydro-1H-pyrazol-5-one 4-Bromo-1,4-dimethyl-3-[3-(trifluoromethyl)phenyl]-4,5-dihydro-1H-pyrazol-5-one was prepared from 1,4-dimethyl-3-[3-(trifluoromethyl)phenyl]-1H-pyrazol-5-ol according to General Method 6 and was used directly in the next step without further analysis (3.1 g, 94.8% yield).

22.5 4-{[(tert-Butoxy)carbonyl]({[(tert-butoxy)carbonyl]oxy})amino}-1,4-dimethyl-3-[3-(trifluoromethyl)phenyl]-4,5-dihydro-1H-pyrazol-5-one 4-{[(tert-Butoxy)carbonyl]({[(tert-butoxy)carbonyl]oxy})amino}-1,4-dimethyl-3-[3-(trifluoromethyl)phenyl]-4,5-dihydro-1H-pyrazol-5-one was synthesized from 4-bromo-1,4-dimethyl-3-[3-(trifluoromethyl)phenyl]-4,5-dihydro-1H-pyrazol-5-one according to General Method 8 and was chromatographed by silica gel column chromatography eluting with heptanes:ethyl acetate (1:1 vol:vol) to provide the title compound as a clear, colorless oil (2.5 g, 47% yield). LC-MS: $t_R$=1.73 min, [M+Na]$^+$=510.0.

22.6 4-(Hydroxyamino)-1,4-dimethyl-3-[3-(trifluoromethyl)phenyl]-4,5-dihydro-1H-pyrazol-5-one 4-(Hydroxyamino)-1,4-dimethyl-3-[3-(trifluoromethyl)phenyl]-4,5-dihydro-1H-pyrazol-5-one was synthesized from 4-{[(tert-butoxy)carbonyl]({[(tert-butoxy)carbonyl]oxy})amino}-1,4-dimethyl-3-[3-(trifluoromethyl)phenyl]-4,5-dihydro-1H-pyrazol-5-one according to General Method 9 and was chromatographed by silica gel column chromatography eluting with heptanes:ethyl acetate (1:1 vol:vol) to provide the title compound as a white solid (0.56 g, 42.9% yield). LC-MS: $t_R$=3.92 min, [M+H]$^+$=288. $^1$H NMR (500 MHz, DMSO-d$_6$) δ ppm: 8.35 (s, 1H), 8.32 (d, J=7.9 Hz, 1H), 7.82 (d, J=7.8 Hz, 1H), 7.75-7.70 (m, 2H), 6.61 (d, J=2.6 Hz, 1H), 3.33 (s, 3H), 1.23 (s, 3H).

Example 23

Compound 23 [5-(tert-butyl)-4-(hydroxyamino)-4-methyl-2-phenyl-2,4-dihydro-3H-pyrazol-3-one]

23.1 3-tert-Butyl-1-phenyl-4,5-dihydro-1H-pyrazol-5-one 3-tert-Butyl-1-phenyl-4,5-dihydro-1H-pyrazol-5-one was synthesized from the corresponding beta-keto ester and phenyl hydrazine according to General Method 2 (6.7 g, 96% yield). LC-MS: $t_R$=1.98 min, [M+H]$^+$=217.00. $^1$H NMR (500 MHz, DMSO-d$_6$) δ ppm: 7.71 (d, J=7.7 Hz, 2H), 7.41 (t, J=7.9 Hz, 2H), 7.20 (t, J=7.3 Hz, 1H), 5.42 (s, 1H), 1.23 (s, 9H).

23.2 3-tert-Butyl-5-hydroxy-1-phenyl-1H-pyrazole-4-carbaldehyde 3-tert-Butyl-5-hydroxy-1-phenyl-1H-pyrazole-4-carbaldehyde was synthesized from 3-tert-butyl-1-phenyl-4,5-dihydro-1H-pyrazol-5-one according to General Method 4. The method deviated from General Method 4 during the work up because no precipitation was observed. The pyrazolone was extracted from the aqueous layer with ethyl acetate (3×15 mL) and the combined organic extracts were washed with brine (15 mL), dried over sodium sulfate and concentrated under reduced pressure to provide the desired product (2.12 g, 89% yield). LC-MS: $t_R$=1.46 min, [M+H]$^+$=245.05. $^1$H NMR (500 MHz, DMSO-d$_6$) δ ppm: 9.43 (s, 1H), 7.76 (d, J=8.3 Hz, 2H), 7.47 (t, J=7.9 Hz, 2H), 7.29 (t, J=7.4 Hz, 1H), 1.34 (s, 9H).

23.3 3-tert-Butyl-4-methyl-1-phenyl-4,5-dihydro-1H-pyrazol-5-one 3-tert-Butyl-4-methyl-1-phenyl-4,5-dihydro-1H-pyrazol-5-one was synthesized from 3-tert-butyl-5-hydroxy-1-phenyl-1H-pyrazole-4-carbaldehyde according to General Method 5 (2.02 g, 86% yield). LC-MS: $t_R$=1.16 min, [M+H]$^+$=231.00. $^1$H NMR (500 MHz, DMSO-d$_6$) δ ppm: 7.73 (d, J=7.3 Hz, 2H), 7.40 (t, J=7.5 Hz, 2H), 7.17 (q, J=7.2, 6.7 Hz, 1H), 1.95 (s, 3H), 1.29 (s, 9H).

23.4 4-Bromo-3-tert-butyl-4-methyl-1-phenyl-4,5-dihydro-1H-pyrazol-5-one

4-Bromo-3-tert-butyl-4-methyl-1-phenyl-4,5-dihydro-1H-pyrazol-5-one was synthesized from 3-tert-butyl-4-methyl-1-phenyl-4,5-dihydro-1H-pyrazol-5-one according to General Method 6 which was directly used in the displacement reaction according to General Method 8 (2.7 g, >99.9 yield).

23.5 4-{[(tert-Butoxy)carbonyl]({[(tert-butoxy)carbonyl]oxy})amino}-3-tert-butyl-4-methyl-1-phenyl-4,5-dihydro-1H-pyrazol-5-one 4-{[(tert-Butoxy)carbonyl]({[(tert-butoxy)carbonyl]oxy})amino}-3-tert-butyl-4-methyl-1-phenyl-4,5-dihydro-1H-pyrazol-5-one was synthesized from the corresponding bromide according to General Method 8 (3.56 g, 35% yield). LC-MS: $t_R$=1.86 min, [M+H]$^+$=484.15.

23.6 3-tert-Butyl-4-(hydroxyamino)-4-methyl-1-phenyl-4,5-dihydro-1H-pyrazol-5-one 3-tert-Butyl-4-(hydroxyamino)-4-methyl-1-phenyl-4,5-dihydro-1H-pyrazol-5-one was synthesized from 4-{[(tert-butoxy)carbonyl]({[(tert-butoxy)carbonyl]oxy})amino}-3-tert-butyl-4-methyl-1-phenyl-4,5-dihydro-1H-pyrazol-5-one according to General Method 9 with the product being chromatographed by silica gel column chromatography eluting with 0-60% ethyl acetate in heptanes (0.03 g, 4% yield). LC-MS: $t_R$=1.35 min, [M+H]$^+$=262.00. $^1$H NMR (500 MHz, DMSO-d$_6$) δ ppm: 7.86 (d, J=7.7 Hz, 2H), 7.50 (d, J=2.0 Hz, 1H), 7.43 (t, J=8.0 Hz, 2H), 7.18 (t, J=7.4 Hz, 1H), 6.31 (d, J=1.9 Hz, 1H), 1.36 (s, 9H), 1.29 (s, 3H).

Example 24

Compound 24 [4-(hydroxyamino)-5-methyl-2,4-diphenyl-2,4-dihydro-3H-pyrazol-3-one]

24.1 Methyl 3-oxo-2-phenylbutanoate

Methyl 3-oxo-2-phenylbutanoate was synthesized from methyl 2-phenylacetate according to General Method 13 and was chromatographed by silica gel column chromatography (12% ethyl acetate in heptanes) to provide the title compound as a pale yellow oil (22 g, 50% yield). LC-MS: $t_R$=1.13/1.16 min, [M+H]$^+$=193.

24.2 3-Methyl-1,4-diphenyl-1H-pyrazol-5-ol

To a solution of methyl 3-oxo-2-phenylbutanoate (3 g, 15.61 mmol) in ethanol (25 mL) in a pressure tube, was added phenyl hydrazine (1.54 mL, 15.61 mmol). The reaction was stirred at 70° C. for 4 hours, cooled to a temperature of about 25° C. and left to stand for 72 hours. The precipitated white solid was removed by filtration and the filtrate chromatographed by silica gel chromatography eluting in 0-100% ethyl acetate:heptanes to provide the title compound as an orange solid (0.91 g, 23% yield). LC-MS: $t_R$=1.17 min, [M+H]$^+$=250. $^1$H NMR (500 MHz, DMSO-d$_6$) δ ppm: 7.76 (d, J=8.0 Hz, 2H), 7.54 (d, J=7.2 Hz, 2H), 7.51-7.44 (m, 2H), 7.39 (t, J=7.7 Hz, 2H), 7.24 (q, J=7.0 Hz, 2H), 2.31 (s, 3H).

24.3 4-Bromo-3-methyl-1,4-diphenyl-4,5-dihydro-1H-pyrazol-5-one

4-Bromo-3-methyl-1,4-diphenyl-4,5-dihydro-1H-pyrazol-5-one was synthesized from 3-methyl-1,4-diphenyl-1H-pyrazol-5-ol according to General Method 6 and was used directly in the synthesis of 4-{[(tert-butoxy)carbonyl]({[(tert-butoxy)carbonyl]oxy})amino}-3-methyl-1,4-diphenyl-4,5-dihydro-1H-pyrazol-5-one assuming 100% yield. (The reaction also provided 4-bromo-1-(4-bromophenyl)-3-methyl-4-phenyl-4,5-dihydro-1H-pyrazol-5-one which was used in the synthesis of Example 47.) LC-MS: $t_R$=1.61 min, [M+H]$^+$=329/331.

24.4 4-{[(tert-Butoxy)carbonyl]({[(tert-butoxy)carbonyl]oxy})amino}-3-methyl-1,4-diphenyl-4,5-dihydro-1H-pyrazol-5-one 4-{[(tert-Butoxy)carbonyl]({[(tert-butoxy)carbonyl]oxy})amino}-3-methyl-1,4-diphenyl-4,5-dihydro-1H-pyrazol-5-one was synthesized from 4-bromo-3-methyl-1,4-diphenyl-4,5-dihydro-1H-pyrazol-5-one according to General Method 8 and chromatographed by silica gel chromatography eluting in 0-15% ethyl acetate:heptanes to provide the title compound as a pale yellow solid (0.92 g, 39% yield, also containing 1-(4-bromophenyl)-4-{[(tert-butoxy)carbonyl]({[(tert-butoxy)carbonyl]oxy})amino}-3-methyl-4-phenyl-4,5-dihydro-1H-pyrazol-5-one which was used in the synthesis of Example 47). LC-MS: $t_R$=1.77 min, [M+Na]$^+$=504. $^1$H NMR (500 MHz, CDCl$_3$) δ ppm: 7.97-7.76 (m, 2H), 7.51 (d, J=17.2 Hz, 3H), 7.39-7.33 (m, 4H), 7.22-7.07 (m, 1H), 2.33 (s, 3H), 1.40 (s, 2×9H).

24.5 4-(Hydroxyamino)-3-methyl-1,4-diphenyl-4,5-dihydro-1H-pyrazol-5-one 4-(Hydroxyamino)-3-methyl-1,4-diphenyl-4,5-dihydro-1H-pyrazol-5-one was synthesized from 4-{[(tert-butoxy)carbonyl]({[(tert-butoxy)carbonyl]oxy})amino}-3-methyl-1,4-diphenyl-4,5-dihydro-1H-pyrazol-5-one according to General Method 9 and chromatographed by silica gel chromatography eluting in 0-20% ethyl acetate:heptanes. The resulting solid (also containing 1-(4-bromophenyl)-4-(hydroxyamino)-3-methyl-4-phenyl-4,5-dihydro-1H-pyrazol-5-one) was chromatographed by acidic preparative HPLC to provide the title compound as a white solid (0.13 g, 24% yield). LC-MS: $t_R$=1.29 min, [M+H]$^+$=282. $^1$H NMR (500 MHz, DMSO-d$_6$) δ ppm: 8.03 (d, J=2.6 Hz, 1H), 7.87 (d, J=7.7 Hz, 2H), 7.49-7.35 (m, 5H), 7.31-7.26 (m, 2H), 7.24-7.15 (m, 2H), 2.08 (s, 3H).

Example 25

Compound 25 [4-(hydroxyamino)-4-methyl-2,5-diphenyl-2,4-dihydro-3H-pyrazol-3-one]

25.1 5-Oxo-1,3-diphenyl-4,5-dihydro-1H-pyrazole-4-carbaldehyde

5-Oxo-1,3-diphenyl-4,5-dihydro-1H-pyrazole-4-carbaldehyde was synthesized from 1,3-diphenyl-4,5-dihydro-1H-pyrazol-5-one according to General Method 4 and used directly in the next step (2.4 g, >99.9% yield). LC-MS: $t_R$=1.33 min, [M+H]$^+$=265.

25.2 4-Methyl-1,3-diphenyl-4,5-dihydro-1H-pyrazol-5-one

4-Methyl-1,3-diphenyl-4,5-dihydro-1H-pyrazol-5-one was synthesized from 5-oxo-1,3-diphenyl-4,5-dihydro-1H-pyrazole-4-carbaldehyde according to General Method 5 and used directly in the next step (2.5 g, 85% yield). LC-MS: $t_R$=1.20 min, [M+H]$^+$=251.

25.3 4-Bromo-4-methyl-1,3-diphenyl-4,5-dihydro-1H-pyrazol-5-one

4-Bromo-4-methyl-1,3-diphenyl-4,5-dihydro-1H-pyrazol-5-one was synthesized from 4-methyl-1,3-diphenyl-4,5-dihydro-1H-pyrazol-5-one according to General Method 6 and used directly in the next step assuming 100% yield. (The reaction also provided 4-bromo-1-(4-bromophenyl)-4-methyl-3-phenyl-4,5-dihydro-1H-pyrazol-5-one which was used in the synthesis of Example 50).

25.4 4-{[(tert-Butoxy)carbonyl]({[(tert-butoxy)carbonyl]oxy})amino}-4-methyl-1,3-diphenyl-4,5-dihydro-1H-pyrazol-5-one 4-{[(tert-Butoxy)carbonyl]({[(tert-butoxy)carbonyl]oxy})amino}-4-methyl-1,3-diphenyl-4,5-di hydro-1H-pyrazol-5-one was synthesized from 4-bromo-4-methyl-1,3-diphenyl-4,5-dihydro-1H-pyrazol-5-one according to General Method 8 and chromatographed by silica gel chromatography eluting in 50% ethyl acetate:heptanes to provide the title compound as a sticky brown solid (3 g, 32% yield, also containing 1-(4-bromophenyl)-4-{[(tert-butoxy)carbonyl]({[(tert-butoxy)carbonyl]oxy})amino}-4-methyl-3-phenyl-4,5-dihydro-1H-pyrazol-5-one which was used in the synthesis of Example 50). LC-MS: $t_R$=1.82 min, [M+Na]$^+$=504.

25.5 4-(Hydroxyamino)-4-methyl-1,3-diphenyl-4,5-dihydro-1H-pyrazol-5-one 4-(Hydroxyamino)-4-methyl-1,3-diphenyl-4,5-dihydro-1H-pyrazol-5-one was synthesized from 4-{[(tert-butoxy)carbonyl]({[(tert-butoxy)carbonyl]oxy})amino}-4-methyl-1,3-diphenyl-4,5-dihydro-1H-pyrazol-5-one according to General Method 9 and chromatographed by silica gel chromatography eluting in 0-70% ethyl acetate:heptanes. Chromatography using acidic preparative HPLC provided the title compound as a white solid (0.1 g, 12% yield). LC-MS: $t_R$=1.36 min, [M+H]$^+$=282. $^1$H NMR (250 MHz, DMSO-d$_6$) δ ppm: 8.27-8.11 (m, 2H), 8.04-7.90 (m, 2H), 7.81 (d, J=2.5 Hz, 1H), 7.65-7.33 (m, 5H), 7.24 (t, J=7.4 Hz, 1H), 6.72 (d, J=2.4 Hz, 1H), 1.35 (s, 3H).

Example 26

Compound 26 [5-(2-fluorophenyl)-4-(hydroxyamino)-2-iso-propyl-4-methyl-2,4-dihydro-3H-pyrazol-3-one]

26.1 3-(2-Fluorophenyl)-1-(propan-2-yl)-1H-pyrazol-5-ol

Methyl 3-(2-fluorophenyl)-3-oxopropanoate (3 g, 15.29 mmol) was dissolved in ethanol (30 mL). N,N-diethylethanamine (3.22 mL, 22.94 mmol) and propan-2-ylhydrazine hydrochloride (1:1) (1.69 g, 15.29 mmol) were added and the reaction was heated at 70° C. for 3 hours. The mixture was concentrated under reduced pressure and the yellow solid obtained was dissolved in DCM (30 mL), washed with 1M HCl (20 mL), dried over magnesium sulfate, filtered and solvent removed under reduced pressure to provide an orange oil. The solvents were removed under reduced pressure and the resulting orange oil left to stand at a temperature of about 25° C. for 72 hours. The resulting brown solid was triturated with heptanes (50 mL), followed by diethyl ether (20 mL) to provide the title compound as a beige solid (2.0 g, 50% yield). LC-MS: $t_R$=1.22 min, [M+H]$^+$=221. $^1$H NMR (250 MHz, DMSO-d$_6$) δ ppm: 11.00 (s, 1H), 7.91 (td, J=7.7, 1.7 Hz, 1H), 7.36-7.12 (m, 3H), 5.74 (d, J=4.5 Hz, 1H), 4.49 (septet, J=6.6 Hz, 1H), 1.37 (d, J=6.7 Hz, 6H).

26.2 3-(2-Fluorophenyl)-5-hydroxy-1-(propan-2-yl)-1H-pyrazole-4-carbaldehyde 3-(2-Fluorophenyl)-1-(propan-2-yl)-4,5-dihydro-1H-pyrazol-5-one (2 g, 9.08 mmol) was dissolved in dimethylformamide-dimethylacetal ("DMF-DMA", 4.6 mL) and stirred at a temperature of about 25° C. for 3.5 hours. The DMF-DMA was removed under reduced pressure to provide the intermediate as a pale brown solid. The solid was taken up in 5N HCl (17 mL) and stirred at a temperature of about 25° C. for 16 hours to provide a brown gum. Ethyl acetate (50 mL) was added to the reaction mixture to dissolve the brown gum and to extract the aqueous layer. Further portions of ethyl acetate (3×50 mL) were used to fully dissolve the product and to re-extract the aqueous layer. The combined ethyl acetate layers were dried over magnesium sulfate, filtered and concentrated under reduced pressure to provide the title compound as a brown oil (1.51 g, 51.6% yield). LC-MS: $t_R$=1.23 min, [M+H]$^+$=249. $^1$H NMR (500 MHz, CDCl$_3$) δ ppm: 9.64 (d, J=3.3 Hz, 1H), 7.70 (td, J=7.5, 1.8 Hz, 1H), 7.44-7.38 (m, 1H), 7.24 (dd, J=7.5, 1.0 Hz, 1H), 7.20-7.15 (m, 1H), 4.61 (septet, J=6.7 Hz, 1H), 1.52 (d, J=6.7 Hz, 6H).

26.3 3-(2-Fluorophenyl)-4-methyl-1-(propan-2-yl)-1H-pyrazol-5-ol 3-(2-Fluorophenyl)-4-methyl-1-(propan-2-yl)-1H-pyrazol-5-ol was synthesized from 3-(2-fluorophenyl)-5-hydroxy-1-(propan-2-yl)-1H-pyrazole-4-carbaldehyde according to General Method 5 and recrystallized from ethyl acetate:heptanes mixtures to provide the title compound as a brown solid (0.79 g, 54% yield). LC-MS: $t_R$=1.09 min, [M+H]$^+$=235. $^1$H NMR (500 MHz, CDCl$_3$) δ ppm: 7.94-7.83 (m, 1H), 7.45-7.36 (m, 1H), 7.22 (t, J=7.6 Hz, 1H), 7.12 (dd, J=11.2, 8.4 Hz, 1H), 4.52 (septet, J=6.7 Hz, 1H), 1.38-1.35 (m, 6H).

26.4 4-Bromo-3-(2-fluorophenyl)-4-methyl-1-(propan-2-yl)-4,5-dihydro-1H-pyrazol-5-one 4-Bromo-3-(2-fluorophenyl)-4-methyl-1-(propan-2-yl)-4,5-dihydro-1H-pyrazol-5-one was synthesized from 3-(2-fluorophenyl)-4-methyl-1-(propan-2-yl)-1H-pyrazol-5-ol according to General Method 6 and used directly in the next step. LC-MS: $t_R$=1.48 min, [M+H]$^+$=313/315.

26.5 4-{[(tert-Butoxy)carbonyl]({[(tert-butoxy)carbonyl]oxy})amino}-3-(2-fluorophenyl)-4-methyl-1-(propan-2-yl)-4,5-dihydro-1H-pyrazol-5-one 4-{[(tert-Butoxy)carbonyl]({[(tert-butoxy)carbonyl]oxy})amino}-3-(2-fluorophenyl)-4-methyl-1-(propan-2-yl)-4,5-dihydro-1H-pyrazol-5-one was synthesized from 4-bromo-3-(2-fluorophenyl)-4-methyl-1-(propan-2-yl)-4,5-dihydro-1H-pyrazol-5-one according to General Method 8 and chromatographed by silica gel column chromatography eluting in 0-30% ethyl acetate:heptanes to provide the title compound as an orange oil (0.56 g, 33% yield). LC-MS: $t_R$=1.70 min, [M+Na]$^+$=488.

26.6 3-(2-Fluorophenyl)-4-(hydroxyamino)-4-methyl-1-(propan-2-yl)-4,5-dihydro-1H-pyrazol-5-one 3-(2-Fluorophenyl)-4-(hydroxyamino)-4-methyl-1-(propan-2-yl)-4,5-dihydro-1H-pyrazol-5-one was synthesized from 4-{[(tert-butoxy)carbonyl]({[(tert-butoxy)carbonyl]oxy})amino}-3-(2-fluorophenyl)-4-methyl-1-(propan-2-yl)-4,5-dihydro-1H-pyrazol-5-one according to General Method 9 and chromatographed by silica gel chromatography eluting in 0-60% ethyl acetate:heptanes to provide the title compound as an off-white solid (0.2 g, 87% yield). LC-MS: $t_R$=1.18 min, [M+H]$^+$=266. $^1$H NMR (250 MHz, DMSO-d$_6$) δ ppm: 8.22-8.05 (m, 1H), 7.64 (d, J=2.5 Hz, 1H), 7.57-7.41 (m, 1H), 7.40-7.21 (m, 2H), 6.39 (d, J=2.4 Hz, 1H), 4.37 (septet, J=6.7 Hz, 1H), 1.26 (2×d, J=6.7 Hz, 6H), 1.12 (s, 3H).

Example 27

Compound 27 [4-(4-fluorophenyl)-4-(hydroxyamino)-2,5-dimethyl-2,4-dihydro-3H-pyrazol-3-one]

27.1 Methyl 2-(4-fluorophenyl)-3-oxobutanoate

Methyl 2-(4-fluorophenyl)-3-oxobutanoate was synthesized from methyl 2-(4-fluorophenyl)acetate according to General Method 13 (2.64 g, 57% yield). LC-MS: $t_R$=1.22 min, [M+H]$^+$=210.90.

27.2 4-(4-Fluorophenyl)-2,5-dimethyl-2,3-dihydro-1H-pyrazol-3-one 4-(4-fluorophenyl)-2,5-dimethyl-2,3-dihydro-1H-pyrazol-3-one was synthesized from Methyl 2-(4-fluorophenyl)-3-oxobutanoate according to General Method 2 (2.5 g, 82% yield). LC-MS: $t_R$=0.99 min, [M+H]$^+$=206.90.

27.3 4-Bromo-4-(4-fluorophenyl)-1,3-dimethyl-4,5-dihydro-1H-pyrazol-5-one

4-Bromo-4-(4-fluorophenyl)-1,3-dimethyl-4,5-dihydro-1H-pyrazol-5-one was synthesized from 4-(4-fluorophenyl)-2,5-dimethyl-2,3-dihydro-1H-pyrazol-3-one according to General Method 6 which was directly used in the displacement reaction according to General Method 8 (1.2 g, >99.9 yield).

27.4 4-{[(tert-Butoxy)carbonyl]({[(tert-butoxy)carbonyl]oxy})amino}-4-(4-fluorophenyl)-1,3-dimethyl-4,5-dihydro-1H-pyrazol-5-one 4-{[(tert-Butoxy)carbonyl]({[(tert-butoxy)carbonyl]oxy})amino}-4-(4-fluorophenyl)-1,3-dimethyl-4,5-dihydro-1H-pyrazol-5-one was synthesized from the corresponding bromide according to General Method 8 with the product being chromatographed by silica gel column chromatography eluting with 0-55% ethyl acetate in heptanes (0.94 g, 52% yield). LC-MS: $t_R$=1.55, [M+H]$^+$=460.10.

27.5 4-(4-Fluorophenyl)-4-(hydroxyamino)-1,3-dimethyl-4,5-dihydro-1H-pyrazol-5-one 4-(4-Fluorophenyl)-4-(hydroxyamino)-1,3-dimethyl-4,5-dihydro-1H-pyrazol-5-one was synthesized from 4-{[(tert-butoxy)carbonyl]({[(tert-butoxy)carbonyl]oxy})amino}-4-(4-fluorophenyl)-1,3-dimethyl-4,5-dihydro-1H-pyrazol-5-one according to General Method 9 (0.15 g, 30% yield). LC-MS: $t_R$=3.45, [M+H]$^+$=238.10. $^1$H NMR (500 MHz, DMSO-$d_6$) δ ppm: 7.87 (s, 1H), 7.28-7.18 (m, 4H), 6.92 (s, 1H), 3.19 (s, 3H), 1.93 (s, 3H).

Example 28

Compound 28 [5-(tert-butyl)-4-(hydroxyamino)-2-iso-propyl-4-(1-(methoxyimino)ethyl)-2,4-dihydro-3H-pyrazol-3-one]

28.1 3-tert-Butyl-1-(propan-2-yl)-4,5-dihydro-1H-pyrazol-5-one

Methyl 4,4-dimethyl-3-oxopentanoate (3 g, 17.42 mmol) was dissolved in ethanol (30 mL). N,N-diethylethanamine (4.86 mL, 34.84 mmol) and propan-2-ylhydrazine hydrochloride (1:1) (2.89 g, 26.13 mmol) were added and the resulting reaction mixture was heated at 70° C. for 3 hours. The mixture was concentrated under reduced pressure. The yellow solid obtained was dissolved in DCM (30 mL), washed with 1M HCl (20 mL), dried over magnesium sulfate, and filtered. The solvent removed under reduced pressure to provide the title compound as an off white solid (2.23 g, 63% yield). LC-MS: $t_R$=1.40 min, [M+H]$^+$=183.05. $^1$H NMR (500 MHz, DMSO-$d_6$) δ ppm: 5.49 (s, 1H), 4.58 (m, 1H), 1.39 (d, J=6.8 Hz, 6H), 1.25 (s, 9H).

28.2 4-Acetyl-3-tert-butyl-1-(propan-2-yl)-4,5-dihydro-1H-pyrazol-5-one

4-Acetyl-3-tert-butyl-1-(propan-2-yl)-4,5-dihydro-1H-pyrazol-5-one was synthesized from 3-tert-butyl-1-(propan-2-yl)-4,5-dihydro-1H-pyrazol-5-one according to General Method 11 (2.23 g, 21% yield). LCMS: $t_R$=1.20, [M+H]$^+$=225.00.

28.3 3-tert-Butyl-4-[1-(methoxyimino)ethyl]-1-(propan-2-yl)-4,5-dihydro-1H-pyrazol-5-one 3-tert-Butyl-4-[1-(methoxyimino)ethyl]-1-(propan-2-yl)-4,5-dihydro-1H-pyrazol-5-one was synthesized from 4-acetyl-3-tert-butyl-1-(propan-2-yl)-4,5-dihydro-1H-pyrazol-5-one according to General Method 12 with the product being chromatographed by silica gel column chromatography eluting with 0-60% ethyl acetate in heptanes (0.79 g, 34% yield). LC-MS $t_R$=1.12 min, [M+H]$^+$=254.05.

28.4 4-Bromo-3-tert-butyl-4-[1-(methoxyimino)ethyl]-1-(propan-2-yl)-4,5-dihydro-1H-pyrazol-5-one 4-Bromo-3-tert-butyl-4-[1-(methoxyimino)ethyl]-1-(propan-2-yl)-4,5-dihydro-1H-pyrazol-5-one was synthesized from the corresponding oxime according to General Method 6 which was directly used in the displacement reaction according to General Method 8 (1.03 g, >99.9 yield).

28.5 4-{[(tert-Butoxy)carbonyl]({[(tert-butoxy)carbonyl]oxy})amino}-3-tert-butyl-4-[1-(methoxyimino)ethyl]-1-(propan-2-yl)-4,5-dihydro-1H-pyrazol-5-one 4-{[(tert-Butoxy)carbonyl]({[(tert-butoxy)carbonyl]oxy})amino}-3-tert-butyl-4-[1-(methoxyimino)ethyl]-1-(propan-2-yl)-4,5-dihydro-1H-pyrazol-5-one was synthesized from the corresponding bromide according to General Method 8 with the product being chromatographed by silica gel column chromatography eluting with 0-50% ethyl acetate in heptanes (0.45 g, 20% yield). LC-MS: $t_R$=1.90 min, [M+H]$^+$=507.20.

28.6 3-tert-Butyl-4-(hydroxyamino)-4-[1-(methoxyimino)ethyl]-1-(propan-2-yl)-4,5-dihydro-1H-pyrazol-5-one 3-tert-Butyl-4-(hydroxyamino)-4-[1-(methoxyimino)ethyl]-1-(propan-2-yl)-4,5-dihydro-1H-pyrazol-5-one was synthesized from {[(tert-butoxy)carbonyl]({[(tert-butoxy)carbonyl]oxy})amino}-3-tert-butyl-4-[1-(methoxyimino)ethyl]-1-(propan-2-yl)-4,5-dihydro-1H-pyrazol-5-on according to General Method 9 with the product being chromatographed by acidic preparative HPLC chromatography (0.02 g, 10% yield). LC-MS: $t_R$=1.32 min, [M+H]$^+$ =285.00. ¹H NMR (500 MHz, DMSO-d₆) δ ppm: 7.49 (d, J=1.9 Hz, 1H), 6.16 (d, J=1.8 Hz, 1H), 4.25 (m, 1H), 3.80 (s, 3H), 1.54 (s, 3H), 1.23-1.18 (m, 15H).

Example 29

Compound 29 [5-(2-fluorophenyl)-4-(hydroxyamino)-4-methyl-2-phenyl-2,4-dihydro-3H-pyrazol-3-one]

29.1 3-(2-Fluorophenyl)-1-phenyl-1H-pyrazol-5-ol 3-(2-Fluorophenyl)-1-phenyl-1H-pyrazol-5-ol was synthesized from methyl 3-(2-fluorophenyl)-3-oxopropanoate (3 g, 15.29 mmol) according to General Method 2 to provide the title compound as a brown solid (4.3 g, 97% yield). LC-MS: $t_R$=2.06 min, [M+H]⁺=255. ¹H NMR (500 MHz, DMSO-d₆) δ ppm: 11.89 (s, 1H), 8.09-7.96 (m, 1H), 7.90-7.76 (m, 2H), 7.50 (t, J=7.9 Hz, 2H), 7.39 (q, J=6.1, 5.5 Hz, 1H), 7.29 (dt, J=23.9, 7.2 Hz, 3H), 5.97 (d, J=4.2 Hz, 1H).

29.2 3-(2-Fluorophenyl)-5-hydroxy-1-phenyl-1H-pyrazole-4-carbaldehyde 3-(2-Fluorophenyl)-5-hydroxy-1-phenyl-1H-pyrazole-4-carbaldehyde was synthesized from 3-(2-fluorophenyl)-1-phenyl-1H-pyrazol-5-ol (2.3 g, 9.05 mmol) according to General Method 4 to provide the title compound as a yellow solid (2.3 g, 82% yield). LC-MS: $t_R$=1.91 min, [M+H]⁺=282. ¹H NMR (500 MHz, Acetonitrile-d3) δ ppm: 9.61 (d, J=3.0 Hz, 1H), 7.85 (dt, J=8.8, 1.7 Hz, 2H), 7.76 (td, J=7.5, 1.8 Hz, 1H), 7.59-7.50 (m, 3H), 7.41 (t, J=7.5 Hz, 1H), 7.37-7.26 (m, 2H).

29.3 3-(2-Fluorophenyl)-4-methyl-1-phenyl-1H-pyrazol-5-ol 3-(2-Fluorophenyl)-4-methyl-1-phenyl-1H-pyrazol-5-ol was synthesized from 3-(2-fluorophenyl)-5-hydroxy-1-phenyl-1H-pyrazole-4-carbaldehyde (2.3 g, 7.5 mmol) according to General Method 5 to provide the title compound as a brown solid (>99.9% yield). LC-MS: $t_R$=1.27 min, [M+H]⁺=268.

29.4 4-Bromo-3-(2-fluorophenyl)-4-methyl-1-phenyl-4,5-dihydro-1H-pyrazol-5-one

4-Bromo-3-(2-fluorophenyl)-4-methyl-1-phenyl-4,5-dihydro-1H-pyrazol-5-one was synthesized from 3-(2-fluorophenyl)-4-methyl-1-phenyl-1H-pyrazol-5-ol (2.4 g, 8.95 mmol) according to General Method 6 and was used directly in the next step without further analysis (3 g, 64% yield).

29.5 4-{[(tert-Butoxy)carbonyl]({[(tert-butoxy)carbonyl]oxy})amino}-3-(2-fluorophenyl)-4-methyl-1-phenyl-4,5-dihydro-1H-pyrazol-5-one 4-{[(tert-Butoxy)carbonyl]({[(tert-butoxy)carbonyl]oxy})amino}-3-(2-fluorophenyl)-4-methyl-1-phenyl-4,5-dihydro-1H-pyrazol-5-one was synthesized from 4-bromo-3-(2-fluorophenyl)-4-methyl-1-phenyl-4,5-dihydro-1H-pyrazol-5-one (3 g, 5.18 mmol) according to General Method 8 to provide the title compound as a yellow oil (2.22 g, 67% yield). LC-MS: $t_R$=1.79 min, [M+Na]⁺=522.

29.6 3-(2-Fluorophenyl)-4-(hydroxyamino)-4-methyl-1-phenyl-4,5-dihydro-1H-pyrazol-5-one 3-(2-Fluorophenyl)-4-(hydroxyamino)-4-methyl-1-phenyl-4,5-dihydro-1H-pyrazol-5-one was synthesized from 4-{[(tert-butoxy)carbonyl]({[(tert-butoxy)carbonyl]oxy})amino}-3-(2-fluorophenyl)-4-methyl-1-phenyl-4,5-dihydro-1H-pyrazol-5-one (2.22 g, 3.96 mmol) according to General Method 9 to provide the title compound as an off-white solid (0.9 g, 72% yield). LC-MS: $t_R$=1.34 min, [M+H]⁺=300. ¹H NMR (500 MHz, DMSO-d₆) δ ppm: 8.26 (td, J=7.9, 1.6 Hz, 1H), 7.96-7.83 (m, 3H), 7.61-7.53 (m, 1H), 7.48 (t, J=8.0 Hz, 2H), 7.43-7.32 (m, 2H), 7.24 (t, J=7.4 Hz, 1H), 6.69 (s, 1H), 1.29 (s, 3H).

Example 30

Compound 30 [4-(Hydroxyamino)-1-isopropyl-3-methyl-4-phenyl-1H-pyrazol-5(4H)-one]

30.1 3-Methyl-4-phenyl-1-(propan-2-yl)-1H-pyrazol-5-ol

Methyl 3-oxo-2-phenylbutanoate (2.07 g, 10.77 mmol) was dissolved in ethanol (20 mL) in a pressure tube. Propan-2-yl hydrazine hydrochloride (1:1) (1.19 g, 10.77 mmol) and triethylamine (2.27 mL, 16.15 mmol) were added and the reaction was heated at 70° C. for 2.5 hours, before leaving to stand at a temperature of about 25° C. for 16 hours. The reaction mixture was concentrated under reduced pressure to provide an off-white solid which was triturated with heptanes (40 mL) to provide 3.1 g of off-white solid. Recrystallization from DCM provided the title product as a white solid (1.78 g, 37% yield, containing 52% w/w triethylamine hydrochloride). LC-MS: $t_R$=1.01 min, [M+H]⁺=217. ¹H NMR (250 MHz, DMSO-d₆) δ ppm: 9.94 (s, 1H), 7.33 (t, J=7.6 Hz, 4H), 7.15 (t, J=7.2 Hz, 1H), 4.48 (septet, J=6.8 Hz, 1H), 2.22 (s, 3H), 1.29 (d, J=6.0 Hz, 6H).

30.2 4-Bromo-3-methyl-4-phenyl-1-(propan-2-yl)-4,5-dihydro-1H-pyrazol-5-one

4-Bromo-3-methyl-4-phenyl-1-(propan-2-yl)-4,5-dihydro-1H-pyrazol-5-one was synthesized from 3-methyl-4-phenyl-1-(propan-2-yl)-1H-pyrazol-5-ol according to General Method 6 and was used directly in the next step assuming 100% yield. LC-MS: $t_R$=1.41 min, [M+H]⁺=295/297.

30.3 4-{[(tert-Butoxy)carbonyl]({[(tert-butoxy)carbonyl]oxy})amino}-3-methyl-4-phenyl-1-(propan-2-yl)-4,5-dihydro-1H-pyrazol-5-one 4-{[(tert-Butoxy)carbonyl]({[(tert-butoxy)carbonyl]oxy})amino}-3-methyl-4-phenyl-1-(propan-2-yl)-4,5-dihydro-1H-pyrazol-5-one was synthesized from 4-bromo-3-methyl-4-phenyl-1-(propan-2-yl)-4,5-dihydro-1H-pyrazol-5-one according to General Method 8. 4-Bromo-3-methyl-4-phenyl-1-(propan-2-yl)-4,5-dihydro-1H-pyrazol-5-one was added as a solution in DMF via a pad of cotton wool to remove a solid impurity. The reaction was worked-up as detailed in General Method 8 to provide the title compound as a yellow oil (1.47 g, 93% yield). LC-MS: $t_R$=1.63 min, [M+Na]⁺=470.

30.4 4-(Hydroxyamino)-3-methyl-4-phenyl-1-(propan-2-yl)-4,5-dihydro-1H-pyrazol-5-one 4-(Hydroxyamino)-3-methyl-4-phenyl-1-(propan-2-yl)-4,5-dihydro-1H-pyrazol-5-one was synthesized from 4-{[(tert-butoxy)carbonyl]({[(tert-butoxy)carbonyl]oxy})amino}-3-methyl-4-phenyl-1-(propan-2-yl)-4,5-dihydro- 1H-pyrazol-5-one according to General Method 9 and chromatographed by silica gel chromatography eluting in 0-70% ethyl acetate:heptanes to provide a yellow solid which was washed with heptanes (10 mL) to provide the title compound as a pale yellow solid (0.153 g, 21% yield). LC-MS: $t_R$=1.08 min, [M+H]$^+$=248. $^1$H NMR (250 MHz, DMSO-d$_6$) δ ppm: 7.79 (d, J=2.6 Hz, 1H), 7.46-7.27 (m, 3H), 7.18 (dd, J=7.7, 1.9 Hz, 2H), 6.86 (d, J=2.7 Hz, 1H), 4.28 (septet, J=6.7 Hz, 1H), 1.93 (s, 3H), 1.24 (2×d, J=6.7 Hz, 6H).

Example 31

Compound 31 [4-ethyl-5-(2-fluorophenyl)-4-(hydroxyamino)-2-methyl-2,4-dihydro-3H-pyrazol-3-one]

31.1 2-Ethyl-1-(2-fluorophenyl)pentane-1,3-dione

To a solution of methyl 3-(2-fluorophenyl)-3-oxopropanoate (4 g, 20.39 mmol) in DMF (20 mL) was added iodoethane (1.8 mL, 22.43 mmol) and potassium carbonate (2.11 g, 15.29 mmol). The reaction was stirred at a temperature of about 25° C. for 18 hours and then quenched with water (80 mL). The product was then extracted with ethyl acetate (3×20 mL) and the combined organic extracts were washed with brine (10 mL), dried over sodium sulfate and concentrated under reduced pressure. The product was chromatographed by silica gel column chromatography eluting with 0-40% ethyl acetate in heptanes (4.21 g, 71% yield). LC-MS: $t_R$=1.30 min, [M+H]$^+$=224.90. $^1$H NMR (500 MHz, DMSO-d$_6$) δ ppm: 7.90-7.82 (m, 1H), 7.74-7.66 (m, 1H), 7.36 (t, J=8.7 Hz, 2H), 4.29 (t, J=6.9 Hz, 1H), 3.61 (s, 3H), 1.87 (dt, J=9.7, 7.2 Hz, 2H), 0.91 (t, J=7.4 Hz, 3H).

31.2 4-Ethyl-3-(2-fluorophenyl)-1-methyl-1H-pyrazol-5-ol

4-Ethyl-3-(2-fluorophenyl)-1-methyl-1H-pyrazol-5-ol was synthesized from 2-ethyl-1-(2-fluorophenyl)pentane-1,3-dione according to General Method 2 (1.88 g, 46% yield). LC-MS: $t_R$=1.01, [M+H]$^+$=220.95. $^1$H NMR (500 MHz, DMSO-d$_6$) δ ppm: 10.07 (s, 1H), 7.39 (s, 2H), 7.22 (d, J=6.7 Hz, 2H), 3.57 (s, 3H), 2.28 (d, J=7.0 Hz, 2H), 0.89 (t, J=7.0 Hz, 3H).

31.3 4-Bromo-4-ethyl-3-(2-fluorophenyl)-1-methyl-4,5-dihydro-1H-pyrazol-5-one

4-Bromo-4-ethyl-3-(2-fluorophenyl)-1-methyl-4,5-dihydro-1H-pyrazol-5-one was synthesized from 4-ethyl-3-(2-fluorophenyl)-1-methyl-1H-pyrazol-5-ol according to General Method 6 (0.54 g, >99.9 yield). LC-MS: $t_R$=1.33, [H+M]$^+$=298.90.

31.4 4-Ethyl-3-(2-fluorophenyl)-4-(hydroxyamino)-1-methyl-4,5-dihydro-1H-pyrazol-5-one To a solution of 4-bromo-4-ethyl-3-(2-fluorophenyl)-1-methyl-4,5-dihydro-1H-pyrazol-5-one (0.55 g, 1.84 mmol) in THF (12 mL) and water (2 mL) was added hydroxylamine (242.92 µl, 3.68 mmol). The reaction was left to stir at a temperature of about 25° C. for 2 hours and then the solvent was removed under reduced pressure. The product was then chromatographed by silica gel column chromatography eluting in 20-55% ethyl acetate in heptanes (0.02 g, 4% yield). LC-MS: $t_R$=1.04, [M+H]$^+$=251.95. $^1$H NMR (500 MHz, DMSO-d$_6$) δ ppm: 8.20 (td, J=7.8, 1.7 Hz, 1H), 7.70 (d, J=2.4 Hz, 1H), 7.49 (ddd, J=13.8, 5.2, 2.5 Hz, 1H), 7.35-7.25 (m, 2H), 6.46 (d, J=2.4 Hz, 1H), 3.29 (s, 3H), 1.60-1.48 (m, 2H), 0.56 (t, J=7.5 Hz, 3H).

Example 32

Compound 32 [4-(hydroxyamino)-2-iso-propyl-4-methyl-5-(4-(methylsulfonyl)phenyl)-2,4-dihydro-3H-pyrazol-3-one]

32.1 3-[4-(Methylsulfanyl)phenyl]-1-(propan-2-yl)-1H-pyrazol-5-ol

To a solution of methyl 3-[4-(methylsulfanyl)phenyl]-3-oxopropanoate (5 g, 22.29 mmol) in ethanol (50 mL) was added propan-2-ylhydrazine hydrochloride (1:1) (3.7 g, 33.44 mmol) and N,N-diethylethanamine (6.27 mL, 44.59 mmol) while stirring and the reaction was heated to reflux for 4 hours and then allowed to cool to a temperature of about 25° C. After 16 hours the reaction was concentrated under reduced pressure and the reaction mixture was dissolved in ethyl acetate (100 mL) and washed with 1M HCl (3×50 mL). The organic phase was washed with brine (100 mL) and the solvent removed under reduced pressure to obtain a brown oil. Upon crystallization from heptanes:ethyl acetate (5:1 vol:vol) a pale brown precipitate formed was filtered and washed with heptanes and dried under reduced pressure to provide the title compound as an off-white solid (3.99 g, 59% yield). LC-MS: $t_R$=1.23 min, [M+H]$^+$=249. $^1$H NMR (500 MHz, DMSO-d$_6$) δ ppm: 7.66 (dd, J=8.0, 2.6 Hz, 2H), 7.25 (d, J=8.1 Hz, 2H), 5.81-5.79 (m, 1H), 4.53-4.48 (m, J=5.7 Hz, 1H), 2.48 (s, 3H), 1.38 (d, J=5.5 Hz, 6H).

32.2 5-Hydroxy-3-[4-(methylsulfanyl)phenyl]-1-(propan-2-yl)-1H-pyrazole-4-carbaldehyde 5-Hydroxy-3-[4-(methylsulfanyl)phenyl]-1-(propan-2-yl)-1H-pyrazole-4-carbaldehyde was synthesized from 1-methyl-3-[4-(methylsulfanyl)phenyl]-1H-pyrazol-5-ol (3.9 g, 12.88 mmol) according to General Method 4 to provide the title compound as a brown oil (4.3 g, 73% yield). LC-MS: $t_R$=1.31 min, [M+H]$^+$=277.

32.3 4-Methyl-3-[4-(methylsulfanyl)phenyl]-1-(propan-2-yl)-1H-pyrazol-5-ol

4-Methyl-3-[4-(methylsulfanyl)phenyl]-1-(propan-2-yl)-1H-pyrazol-5-ol was synthesized from 5-hydroxy-3-[4-(methylsulfanyl)phenyl]-1-(propan-2-yl)-1H-pyrazole-4-carbaldehyde (4.3 g, 9.49 mmol) according to General Method 5 and the product was chromatographed by silica gel column chromatography eluting with a 25-100% ethyl acetate:heptanes gradient to provide the title compound as an off-white solid (1.2 g, 43% yield). LC-MS: $t_R$=1.13 min, [M+H]$^+$=262. $^1$H NMR (500 MHz, DMSO-d$_6$) δ ppm: 9.97 (s, 1H), 7.55 (d, J=8.3 Hz, 2H), 7.27 (d, J=8.3 Hz, 2H), 4.58-4.41 (m, 1H), 2.49 (s, 3H), 2.02 (s, 3H), 1.34 (d, J=6.6 Hz, 6H).

32.4 4-Bromo-3-(4-methanesulfinylphenyl)-4-methyl-1-(propan-2-yl)-4,5-dihydro-1H-pyrazol-5-one 4-Bromo-3-(4-methanesulfinylphenyl)-4-methyl-1-(propan-2-yl)-4,5-dihydro-1H-pyrazol-5-one was synthesized from 4-methyl-3-[4-(methylsulfanyl)phenyl]-1-(propan-2- yl)-1H-pyrazol-5-ol (1.12 g, 3.84 mmol) according to General Method 6 (1.3 g, 83% yield). LC-MS: $t_R$=1.18 min, [M+H]$^+$=358.

32.5 4-{[(tert-Butoxy)carbonyl](({[(tert-butoxy)carbonyl]oxy})amino}-3-(4-methanesulfinylphenyl)-4-methyl-1-(propan-2-yl)-4,5-dihydro-1H-pyrazol-5-one 4-{[(tert-Butoxy)carbonyl]({[(tert-butoxy)carbonyl]oxy})amino}-3-(4-methanesulfinylphenyl)-4-methyl-1-(propan-2-yl)-4,5-dihydro-1H-pyrazol-5-one was synthesized from 4-bromo-3-(4-methanesulfinylphenyl)-4-methyl-1-(propan-2-yl)-4,5-dihydro-1H-pyrazol-5-one according to General Method 8 to provide the title compound as a yellow solid (1.07 g, 59% yield). LC-MS: $t_R$=1.39 min, [M+Na]$^+$=532.

32.6 4-{[(tert-Butoxy)carbonyl](({[(tert-butoxy)carbonyl]oxy})amino}-3-(4-methanesulfonylphenyl)-4-methyl-1-(propan-2-yl)-4,5-dihydro-1H-pyrazol-5-one 4-{[(tert-Butoxy)carbonyl]({[(tert-butoxy)carbonyl]oxy})amino}-3-(4-methanesulfonylphenyl)-4-methyl-1-(propan-2-yl)-4,5-dihydro-1H-pyrazol-5-one was synthesized from 4-{[(tert-butoxy)carbonyl]({[(tert-butoxy)carbonyl]oxy})amino}-3-(4-methanesulfinylphenyl)-4-methyl-1-(propan-2-yl)-4,5-dihydro-1H-pyrazol-5-one according to General Method 10 to provide the title compound as a yellow oil (1.24 g, 93% yield). LC-MS: $t_R$=1.45 min, [M+Na]$^+$=548.

32.7 4-(Hydroxyamino)-3-(4-methanesulfonylphenyl)-4-methyl-1-(propan-2-yl)-4,5-dihydro-1H-pyrazol-5-one 4-(Hydroxyamino)-3-(4-methanesulfonylphenyl)-4-methyl-1-(propan-2-yl)-4,5-dihydro-1H-pyrazol-5-one was synthesized from 4-{[(tert-butoxy)carbonyl]({[(tert-butoxy)carbonyl]oxy})amino}-3-(4-methanesulfonylphenyl)-4-methyl-1-(propan-2-yl)-4,5-dihydro-1H-pyrazol-5-one according to General Method 9 to provide the title compound as an off-white solid (0.45 g, 72% yield). LC-MS: $t_R$=1.08 min, [M+H]$^+$=326. $^1$H NMR (500 MHz, DMSO-d$_6$) δ ppm: 8.33-8.27 (m, 2H), 8.09-7.94 (m, 2H), 7.64 (s, 1H), 6.57 (s, 1H), 4.40 (septet, J=6.7 Hz, 1H), 3.25 (s, 3H), 1.33 (d, J=6.7 Hz, 3H), 1.27 (d, J=6.7 Hz, 3H), 1.23 (s, 3H).

Example 33

Compound 33 [4-(hydroxyamino)-4,5-dimethyl-2-(4-(methylsulfonyl)phenyl)-2,4-dihydro-3H-pyrazol-3-one]

33.1 1-(4-Methanesulfonylphenyl)-3,4-dimethyl-1H-pyrazol-5-ol

To an solution of ethyl 2-methyl-3-oxobutanoate (1 g, 6.94 mmol) in ethanol (10 mL) was added (4-methanesulfonylphenyl)hydrazine hydrochloride (1.7 g, 7.63 mmol) and N,N-diethylethanamine (1.17 mL, 8.32 mmol) while stirring and the reaction mixture was heated to reflux for 6 hours then allowed to cool to a temperature of about 25° C. After 16 hours a precipitate formed (off-white) and was isolated and washed with heptanes and dried under reduced pressure. The product was heated in ethanol while stirring at 50° C. and the product was filtered and the solvent removed under reduced pressure to provide the title compound as an off-white solid (1.9 g, 73% yield (about 20% N,N-diethylethanamine HCl salt present)). LC-MS: $t_R$=0.9 min, [M+H]$^+$=267. $^1$H NMR (250 MHz, DMSO-d$_6$) δ ppm: 8.08-7.88 (m, 4H), 3.21 (d, J=2.5 Hz, 3H), 2.12 (s, 3H), 1.77 (s, 3H).

33.2 4-Bromo-1-(4-methanesulfonylphenyl)-3,4-dimethyl-4,5-dihydro-1H-pyrazol-5-one 4-Bromo-1-(4-methanesulfonylphenyl)-3,4-dimethyl-4,5-dihydro-1H-pyrazol-5-one was synthesized from 1-(4-methanesulfonylphenyl)-3,4-dimethyl-1H-pyrazol-5-ol (0.58 g, 1.83 mmol) according to General Method 6 (0.8 g, 83% yield). LC-MS: $t_R$=1.21 min, [M+H]$^+$=346.

33.3 4-{[(tert-Butoxy)carbonyl]({[(tert-butoxy)carbonyl]oxy})amino}-1-(4-methanesulfonylphenyl)-3,4-dimethyl-4,5-dihydro-1H-pyrazol-5-one 4-{[(tert-Butoxy)carbonyl]({[(tert-butoxy)carbonyl]oxy})amino}-1-(4-methanesulfonylphenyl)-3,4-dimethyl-4,5-dihydro-1H-pyrazol-5-one was synthesized from 4-bromo-1-(4-methanesulfonylphenyl)-3,4-dimethyl-4,5-dihydro-1H-pyrazol-5-one according to General Method 8 to provide the title compound as an off-white solid (0.51 g, 66% yield). LC-MS: $t_R$=1.44 min, [M+Na]$^+$=520.

33.4 4-(Hydroxyamino)-1-(4-methanesulfonylphenyl)-3,4-dimethyl-4,5-dihydro-1H-pyrazol-5-one 4-(Hydroxyamino)-1-(4-methanesulfonylphenyl)-3,4-dimethyl-4,5-dihydro-1H-pyrazol-5-one was synthesized from 4-{[(tert-butoxy)carbonyl]({[(tert-butoxy)carbonyl]oxy})amino}-1-(4-methanesulfonyl phenyl)-3,4-dimethyl-4,5-dihydro-1H-pyrazol-5-one (0.51 g, 1.0 mmol) according to General Method 9 to provide the title compound as a yellow solid (0.24 g, 78% yield). LC-MS: $t_R$=0.93 min, [M+H]$^+$=298. $^1$H NMR (500 MHz, DMSO-d$_6$) δ ppm: 8.11 (d, J=8.9 Hz, 2H), 8.04-7.93 (m, 2H), 7.77 (d, J=2.8 Hz, 1H), 6.60 (d, J=2.7 Hz, 1H), 3.19 (s, 3H), 2.15 (s, 3H), 1.18 (s, 3H).

Example 34

Compound 34 [4-(hydroxyamino)-2,4-dimethyl-5-(4-((trifluoromethyl)sulfonyl)phenyl)-2,4-dihydro-3H-pyrazol-3-one]

34.1 Methyl 3-oxo-3-{4-[(trifluoromethyl)sulfanyl]phenyl}propanoate

Methyl 3-oxo-3-{4-[(trifluoromethyl)sulfanyl]phenyl}propanoate was synthesized from 1-{4-[(trifluoromethyl)sulfanyl]phenyl}ethan-1-one according to General Method 1 with the product being chromatographed by silica gel column chromatography eluting with 5-15% ethyl acetate in heptanes (2.49 g, 63% yield). LC-MS: $t_R$=1.36 min, [M+H]$^+$=278.85. $^1$H NMR (500 MHz, DMSO-d$_6$) δ ppm: 8.09-8.05 (m, 2H), 7.88 (d, J=8.3 Hz, 2H), 4.28 (s, 2H), 3.66 (s, 3H).

34.2 1-Methyl-3-{4-[(trifluoromethyl)sulfanyl]phenyl}-4,5-dihydro-1H-pyrazol-5-one 1-Methyl-3-{4-[(trifluoromethyl)sulfanyl]phenyl}-4,5-dihydro-1H-pyrazol-5-one was synthesized from methyl 3-oxo-3-{4-[(trifluoromethyl)sulfanyl]phenyl}propanoate and methyl hydrazine according to General Method 2 (2.18 g, 89% yield). LC-MS: $t_R$=1.26 min, [M+H]$^+$=274.85. $^1$H NMR (500 MHz, DMSO-d$_6$) δ ppm: 7.85-7.82 (m, 2H), 7.70-7.65 (m, 2H), 5.87 (s, 1H), 3.58 (s, 3H).

34.3 1-Methyl-5-oxo-3-{4-[(trifluoromethyl)sulfanyl]phenyl}-4,5-dihydro-1H-pyrazole-4-carbaldehyde 1-Methyl-5-oxo-3-{4-[(trifluoromethyl)sulfanyl]phenyl}-4,5-dihydro-1H-pyrazole-4-carbaldehyde was synthesized from 1-methyl-3-{4-[(trifluoromethyl)sulfanyl]phenyl}-4,5-dihydro-1H-pyrazol-5-one according to General Method 4 (2.18 g, 82% yield). LC-MS: $t_R$=1.27 min, [M+H]$^+$=302.95. $^1$H NMR (500 MHz, DMSO-d$_6$) δ ppm: 9.77 (s, 1H), 8.01-7.96 (m, 2H), 7.75 (d, J=8.3 Hz, 2H), 3.63 (s, 3H).

34.4 1,4-Dimethyl-3-{4-[(trifluoromethyl)sulfanyl]phenyl}-4,5-dihydro-1H-pyrazol-5-one 1,4-Dimethyl-3-{4-[(trifluoromethyl)sulfanyl]phenyl}-4,5-dihydro-1H-pyrazol-5-one was synthesized from 1-methyl-5-oxo-3-{4-[(trifluoromethyl)sulfanyl]phenyl}-4,5-dihydro-1H-pyrazole-4-carbaldehyde according to General Method 5 (2.36 g, 96% yield). LC-MS: $t_R$=1.22 min, [M+H]$^+$=288.90. $^1$H NMR (500 MHz, DMSO-d$_6$) δ ppm: 7.76 (d, J=8.4 Hz, 2H), 7.70 (d, J=8.3 Hz, 2H), 3.55 (s, 3H), 2.03 (s, 3H).

34.5 4-Bromo-1,4-dimethyl-3-{4-[(trifluoromethyl)sulfanyl]phenyl}-4,5-dihydro-1H-pyrazol-5-one 4-Bromo-1,4-dimethyl-3-{4-[(trifluoromethyl)sulfanyl]phenyl}-4,5-dihydro-1H-pyrazol-5-one was synthesized from 1,4-dimethyl-3-{4-[(trifluoromethyl)sulfanyl]phenyl}-4,5-dihydro-1H-pyrazol-5-one according to General Method 6 (3.0 g, >99.9 yield). LC-MS: $t_R$=1.51 min, [M+H]$^+$=368.85.

34.6 4-{[(tert-Butoxy)carbonyl]({[(tert-butoxy)carbonyl]oxy})amino}-1,4-dimethyl-3-{4-[(trifluoromethyl) sulfanyl]phenyl}-4,5-dihydro-1H-pyrazol-5-one 4-{[(tert-Butoxy)carbonyl]({[(tert-butoxy)carbonyl]oxy})amino}-1,4-dimethyl-3-{4-[(trifluoromethyl) sulfanyl]phenyl}-4,5-dihydro-1H-pyrazol-5-one was synthesized from the corresponding bromide according to General Method 8 with the product being chromatographed by silica gel column chromatography eluting with 0-50% ethyl acetate in heptanes (1.6 g, 36% yield). LC-MS: $t_R$=1.67 min, [M+H]$^+$=542.10.

34.7 4-{[(tert-Butoxy)carbonyl]({[(tert-butoxy)carbonyl]oxy})amino}-1,4-dimethyl-3-(4-trifluoromethane sulfonylphenyl)-4,5-dihydro-1H-pyrazol-5-one To a solution of 4-{[(tert-butoxy)carbonyl]({[(tert-butoxy)carbonyl]oxy})amino}-1,4-dimethyl-3-{4-[(trifluoromethyl)sulfanyl]phenyl}-4,5-dihydro-1H-pyrazol-5-one (1.4 g, 2.69 mmol) in DCM (35 mL) was added meta chloroperoxybenzoic acid (70%, 2.66 g, 10.78 mmol). The reaction was stirred at a temperature of about 25° C. for 48 hours and the solution was washed with sodium bicarbonate solution (3×10 mL) and 1N sodium hydroxide solution (10 mL) before being dried over magnesium sulfate, filtered and concentrated under reduced pressure. The solid obtained was then chromatographed by silica gel column chromatography eluting with 0-40% ethyl acetate in heptanes (0.9 g, 59% yield). LC-MS: $t_R$=1.61 min, [M+H]$^+$=574.15.

34.8 4-(Hydroxyamino)-1,4-dimethyl-3-(4-trifluoromethanesulfonylphenyl)-4,5-dihydro-1H-pyrazol-5-one 4-(Hydroxyamino)-1,4-dimethyl-3-(4-trifluoromethanesulfonylphenyl)-4,5-dihydro-1H-pyrazol-5-one was synthesized from 4-{[(tert-butoxy)carbonyl]({[(tert-butoxy)carbonyl]oxy})amino}-1,4-dimethyl-3-(4-trifluoromethanesulfonylphenyl)-4,5-dihydro-1H-pyrazol-5-one according to General Method 9 with the product being chromatographed by silica gel column chromatography eluting with 30-70% ethyl acetate in heptanes (0.2 g, 34% yield). LC-MS: $t_R$=1.23 min, [M+H]$^+$=352.00. $^1$H NMR (500 MHz, DMSO-d$_6$) δ ppm: 8.49-8.41 (m, 2H), 8.23 (d, J=8.6 Hz, 2H), 7.72 (s, 1H), 6.69 (s, 1H), 3.36 (s, 3H), 1.28 (s, 3H).

Example 35

Compound 35 [4-(hydroxyamino)-2,4-dimethyl-5-(4-((trifluoromethyl)sulfinyl)phenyl)-2,4-dihydro-3H-pyrazol-3-one]

35.1 4-{[(tert-Butoxy)carbonyl]({[(tert-butoxy)carbonyl]oxy})amino}-1,4-dimethyl-3-(4-trifluoromethane sulfinylphenyl)-4,5-dihydro-1H-pyrazol-5-one To a solution of 4-{[(tert-butoxy)carbonyl]({[(tert-butoxy)carbonyl]oxy})amino}-1,4-dimethyl-3-{4-[(trifluoromethyl)sulfanyl]phenyl}-4,5-dihydro-1H-pyrazol-5-one (1.4 g, 2.69 mmol) in DCM (35 mL) was added meta-chloroperoxybenzoic acid (70%, 1.33 g, 5.4 mmol). The resulting reaction mixture was stirred at a temperature of about 25° C. for 24 hours. Thereafter, the mixture was washed with sodium bicarbonate solution (10 mL×3) and 1N aqueous sodium hydroxide solution (10 mL) before being dried over magnesium sulfate, filtered, and concentrated under reduced pressure. The solid obtained was chromatographed by silica gel column chromatography eluting with 0-40% ethyl acetate in heptanes (0.1 g, 7% yield). LC-MS: $t_R$=1.51 min, [M+H]$^+$=558.05.

35.2 4-(Hydroxyamino)-1,4-dimethyl-3-(4-trifluoromethanesulfinylphenyl)-4,5-dihydro-1H-pyrazol-5-one 4-(Hydroxyamino)-1,4-dimethyl-3-(4-trifluoromethanesulfinylphenyl)-4,5-dihydro-1H-pyrazol-5-one was synthesized from 4-{[(tert-butoxy)carbonyl]({[(tert-butoxy)carbonyl]oxy})amino}-1,4-dimethyl-3-(4-trifluoromethanesulfinylphenyl)-4,5-dihydro-1H-pyrazol-5-one according to General Method 9 with the product being chromatographed by acidic preparative HPLC chromatography (0.02 g, 34% yield). LC-MS: $t_R$=1.11 min, [M+H]$^+$=336.00. $^1$H NMR (500 MHz, DMSO-d$_6$) δ ppm: 8.37-8.31 (m, 2H), 7.97 (d, J=8.4 Hz, 2H), 7.70 (dd, J=5.5, 2.6 Hz, 1H), 6.61 (t, J=2.2 Hz, 1H), 3.33 (s, 3H), 1.25 (d, J=3.0 Hz, 3H).

Example 36

Compound 36 [4-(hydroxyamino)-2,4-dimethyl-5-(4-(methylthio)phenyl)-2,4-dihydro-3H-pyrazol-3-one]

36.1 4-Bromo-1,4-dimethyl-3-[4-(methylsulfanyl)phenyl]-4,5-dihydro-1H-pyrazol-5-one 4-Bromo-1,4-dimethyl-3-[4-(methylsulfanyl)phenyl]-4,5-dihydro-1H-pyrazol-5-one was synthesized from 1,4-dimethyl-3-[4-(methylsulfanyl)phenyl]-1H-pyrazol-5-ol according to General Method 6 (32 g, 95% yield). LC-MS: $t_R$=1.36 min, [M+H]$^+$=314.00.

36.2 4-{[(tert-Butoxy)carbonyl]({[(tert-butoxy)carbonyl]oxy})amino}-1,4-dimethyl-3-[4-(methylsulfanyl)phenyl]-4,5-dihydro-1H-pyrazol-5-one 4-{[(tert-Butoxy)carbonyl]({[(tert-butoxy)carbonyl]oxy})amino}-1,4-dimethyl-3-[4-(methylsulfanyl)phenyl]-4,5-dihydro-1H-pyrazol-5-one was synthesized from 4-bromo-1,4-dimethyl-3-[4-(methylsulfanyl)phenyl]-4,5-dihydro-1H-pyrazol-5-one according to General Method 8 and was chromatographed by silica gel column chromatography eluting with heptanes:ethyl acetate gradients (17.5 g, 39% yield). LC-MS: $t_R$=1.36 min, [M+Na]$^+$=488.15.

36.3 4-(Hydroxyamino)-1,4-dimethyl-3-[4-(methylsulfanyl)phenyl]-4,5-dihydro-1H-pyrazol-5-one 4-(Hydroxyamino)-1,4-dimethyl-3-[4-(methylsulfanyl)phenyl]-4,5-dihydro-1H-pyrazol-5-one was synthesized from 4-{[(tert-butoxy)carbonyl]({[(tert-butoxy)carbonyl]oxy})amino}-1,4-dimethyl-3-[4-(methylsulfanyl)phenyl]-4,5-dihydro-1H-pyrazol-5-one according to General Method 9 and was chromatographed by silica gel column chromatography eluting with heptanes:ethyl acetate (0.3 g, 21% yield). LC-MS: $t_R$=3.39 min, [M+H]$^+$=266.05. $^1$H NMR (500 MHz, DMSO-d$_6$) δ ppm: 7.98 (d, J=8.6 Hz, 2H), 7.61 (s, 1H), 7.32 (d, J=8.6 Hz, 2H), 6.43 (s, 1H), 3.28 (s, 3H), 2.51 (s, 3H), 1.19 (s, 3H).

Example 37

Compound 37 [4-(hydroxyamino)-2,5-dimethyl-4-(4-(methylsulfonyl)phenyl)-2,4-dihydro-3H-pyrazol-3-one]

37.1 Methyl 2-[4-(methylsulfanyl)phenyl]-3-oxobutanoate

Methyl 2-[4-(methylsulfanyl)phenyl]-3-oxobutanoate was synthesized from methyl 2-[4-(methylsulfanyl)phenyl]acetate according to General Method 13 and was chromatographed by silica gel chromatography eluting in 0-100% ethyl acetate:heptanes to provide the title compound as a yellow solid (5.6 g, 75% yield). LC-MS: $t_R$=1.25/1.27 min, [M+H]$^+$=239.

37.2 1,3-Dimethyl-4-[4-(methylsulfanyl)phenyl]-1H-pyrazol-5-ol 1,3-Dimethyl-4-[4-(methylsulfanyl)phenyl]-1H-pyrazol-5-ol was synthesized from methyl 2-[4-(methylsulfanyl)phenyl]-3-oxobutanoate according to General Method 2 and the resulting precipitate was filtered and washed with ethanol (10 mL) to provide the title compound as a white solid (4.42 g, 96% yield). LC-MS: $t_R$=1.03 min, [M+H]$^+$=235. $^1$H NMR (250 MHz, DMSO-d$_6$) δ ppm: 7.44 (d, J=8.1 Hz, 2H), 7.31-7.18 (m, 2H), 2.46 (s, 3H), 2.18 (s, 3H) (CH$_3$ masked by solvent peak).

37.3 4-Bromo-4-(4-methanesulfinylphenyl)-1,3-dimethyl-4,5-dihydro-1H-pyrazol-5-one 4-Bromo-4-(4-methanesulfinylphenyl)-1,3-dimethyl-4,5-dihydro-1H-pyrazol-5-one was synthesized from 1,3-dimethyl-4-[4-(methylsulfanyl)phenyl]-1H-pyrazol-5-ol according to General Method 6 and used directly in the next step assuming 100% yield. LC-MS: $t_R$=1.03 min, [M+H]$^+$=329/331.

37.4 4-{[(tert-Butoxy)carbonyl]({[(tert-butoxy)carbonyl]oxy})amino}-4-(4-methanesulfinylphenyl)-1,3-dimethyl-4,5-dihydro-1H-pyrazol-5-one 4-{[(tert-Butoxy)carbonyl]({[(tert-butoxy)carbonyl]oxy})amino}-4-(4-methanesulfinylphenyl)-1,3-dimethyl-4,5-dihydro-1H-pyrazol-5-one was synthesized from 4-bromo-4-(4-methanesulfinylphenyl)-1,3-dimethyl-4,5-dihydro-1H-pyrazol-5-one according to General Method 8 and chromatographed by silica gel chromatography eluting in 0-100% ethyl acetate:heptanes to provide the title compound as a colorless oil (8.3 g, 82% yield). LC-MS: $t_R$=1.27 min, [M+Na]$^+$=504. $^1$H NMR (250 MHz, CDCl$_3$) δ ppm: 7.65 (s, 4H), 3.25 (s, 3H), 2.70 (s, 3H), 2.21 (d, J=1.1 Hz, 3H), 1.42 (s, 18H).

37.5 4-{[(tert-Butoxy)carbonyl]({[(tert-butoxy)carbonyl]oxy})amino}-4-(4-methanesulfonylphenyl)-1,3-dimethyl-4,5-dihydro-1H-pyrazol-5-one 4-{[(tert-Butoxy)carbonyl]({[(tert-butoxy)carbonyl]oxy})amino}-4-(4-methanesulfonylphenyl)-1,3-dimethyl-4,5-dihydro-1H-pyrazol-5-one was synthesized from 4-{[(tert-butoxy)carbonyl]({[(tert-butoxy)carbonyl]oxy})amino}-4-(4-methanesulfinylphenyl)-1,3-dimethyl-4,5-dihydro-1H-pyrazol-5-one according to General Method 10 to provide the title compound as a white solid (5.2 g, 59% yield). LC-MS: $t_R$=1.33 min, [M+Na]$^+$=520. $^1$H NMR (250 MHz, CDCl$_3$) δ ppm: 7.94 (d, J=8.6 Hz, 2H), 7.70 (d, J=8.5 Hz, 2H), 3.27 (s, 3H), 3.03 (s, 3H), 2.22 (s, 3H), 1.43 (s, 18H).

37.6 4-(Hydroxyamino)-4-(4-methanesulfonylphenyl)-1,3-dimethyl-4,5-dihydro-1H-pyrazol-5-one 4-(Hydroxyamino)-4-(4-methanesulfonylphenyl)-1,3-dimethyl-4,5-dihydro-1H-pyrazol-5-one was synthesized from 4-{[(tert-butoxy)carbonyl]({[(tert-butoxy)carbonyl]oxy})amino}-4-(4-methanesulfonylphenyl)-1,3-dimethyl-4,5-dihydro-1H-pyrazol-5-one according to General Method 9, and was recrystallized from ethyl acetate:heptanes and then further washed with heptanes (10 mL) to provide the title compound as a white solid (1.96 g, 76% yield). LC-MS: $t_R$=0.83 min, [M+H]$^+$=298. $^1$H NMR (500 MHz, DMSO-d$_6$) δ ppm: 7.96 (d, J=2.5 Hz, 1H), 7.94 (d, J=8.5 Hz, 2H), 7.48 (d, J=8.5 Hz, 2H), 7.11 (d, J=2.5 Hz, 1H), 3.21 (2×s, 6H), 1.95 (s, 3H).

Example 38

Compound 38 [5-(3-fluoro-4-(methylsulfinyl)phenyl)-4-(hydroxyamino)-2,4-dimethyl-2,4-dihydro-3H-pyrazol-3-one]

38.1 1-[3-Fluoro-4-(methylsulfanyl)phenyl]ethan-1-one

1-[3-Fluoro-4-(methylsulfanyl)phenyl]ethan-1-one was synthesized from 1-(3,4-difluorophenyl)ethan-1-one according to General Method 14 (11.8 g, 97% yield). LC-MS: $t_R$=1.24 min, [M+H]$^+$=184.95. $^1$H NMR (500 MHz, DMSO-$d_6$) δ ppm: 7.80 (d, J=8.2 Hz, 1H), 7.69 (d, J=11.2 Hz, 1H), 7.46 (t, J=8.0 Hz, 1H), 2.56 (s, 6H).

38.2 Methyl 3-[3-fluoro-4-(methylsulfanyl)phenyl]-3-oxopropanoate

Methyl 3-[3-fluoro-4-(methylsulfanyl)phenyl]-3-oxopropanoate was synthesized from 1-[3-fluoro-4-(methylsulfanyl)phenyl]ethan-1-one according to General Method 1 with the product being chromatographed by silica gel column chromatography eluting with 5-35% ethyl acetate in heptanes (7.19 g, 46% yield). LC-MS: $t_R$=1.24 min, [M+H]$^+$=242.95. $^1$H NMR (500 MHz, DMSO-$d_6$) δ ppm: 7.80 (dd, J=8.3, 1.7 Hz, 1H), 7.71 (dd, J=11.2, 1.7 Hz, 1H), 7.48 (t, J=8.0 Hz, 1H), 4.20 (s, 2H), 3.65 (s, 3H), 2.57 (s, 3H).

38.3 3-[3-Fluoro-4-(methylsulfanyl)phenyl]-1-methyl-4,5-dihydro-1H-pyrazol-5-one 3-[3-Fluoro-4-(methylsulfanyl)phenyl]-1-methyl-4,5-dihydro-1H-pyrazol-5-one was synthesized from methyl 3-[3-fluoro-4-(methylsulfanyl)phenyl]-3-oxopropanoate according to General Method 2 (5.22 g, 74% yield). LC-MS: $t_R$=1.13 min, [M+H]$^+$=238.95. $^1$H NMR (500 MHz, DMSO-$d_6$) δ ppm: 7.54 (dd, J=8.2, 1.6 Hz, 1H), 7.48 (dd, J=11.7, 1.6 Hz, 1H), 7.33 (t, J=8.1 Hz, 1H), 5.84 (s, 1H), 3.56 (s, 3H), 2.49 (s, 3H).

38.4 3-[3-Fluoro-4-(methylsulfanyl)phenyl]-5-hydroxy-1-methyl-1H-pyrazole-4-carbaldehyde 3-[3-Fluoro-4-(methylsulfanyl)phenyl]-5-hydroxy-1-methyl-1H-pyrazole-4-carbaldehyde was synthesized from 3-[3-fluoro-4-(methylsulfanyl)phenyl]-1-methyl-4,5-dihydro-1H-pyrazol-5-one according to General Method 4 (4.96 g, 77% yield). LC-MS: $t_R$=1.17 min, [M+H]$^+$=266.95. $^1$H NMR (500 MHz, DMSO-$d_6$) δ ppm: 9.73 (s, 1H), 7.76 (d, J=1.6 Hz, 1H), 7.74 (dd, J=J=5.0, 1.5 Hz, 1H), 7.38 (t, J=8.3 Hz, 1H), 3.61 (s, 3H), 2.51 (s, 3H).

38.5 3-[3-Fluoro-4-(methylsulfanyl)phenyl]-1,4-dimethyl-1H-pyrazol-5-ol

3-[3-Fluoro-4-(methylsulfanyl)phenyl]-1,4-dimethyl-1H-pyrazol-5-ol was synthesized from 3-[3-fluoro-4-(methylsulfanyl)phenyl]-5-hydroxy-1-methyl-1H-pyrazole-4-carbaldehyde according to General Method 5 (6.49 g, 88% yield). LC-MS: $t_R$=1.09 min, [M+H]$^+$=253.00. $^1$H NMR (250 MHz, DMSO-$d_6$) δ ppm: 7.47-7.30 (m, 3H), 3.53 (s, 3H), 2.49 (s, 3H), 2.00 (s, 3H).

38.6 4-Bromo-3-[3-fluoro-4-(methylsulfanyl)phenyl]-1,4-dimethyl-4,5-dihydro-1H-pyrazol-5-one 4-Bromo-3-[3-fluoro-4-(methylsulfanyl)phenyl]-1,4-dimethyl-4,5-dihydro-1H-pyrazol-5-one was synthesized from 3-[3-fluoro-4-(methylsulfanyl)phenyl]-1,4-dimethyl-1H-pyrazol-5-ol according to General Method 6 (6.3 g, 84% yield). LC-MS: $t_R$=1.12 min, [M+H]$^+$=348.80.

38.7 4-{[(tert-Butoxy)carbonyl]({[(tert-butoxy)carbonyl]oxy})amino}-3-(3-fluoro-4-methanesulfinylphenyl)-1,4-dimethyl-4,5-dihydro-1H-pyrazol-5-one 4-{[(tert-Butoxy)carbonyl]({[(tert-butoxy)carbonyl]oxy})amino}-3-(3-fluoro-4-methanesulfinylphenyl)-1,4-dimethyl-4,5-dihydro-1H-pyrazol-5-one was synthesized from 4-bromo-3-[3-fluoro-4-(methylsulfanyl)phenyl]-1,4-dimethyl-4,5-dihydro-1H-pyrazol-5-one according to General Method 8 (7.74 g, 81% yield). LC-MS: $t_R$=1.33 min, [M+H]$^+$=522.00.

38.8 3-(3-Fluoro-4-methanesulfinylphenyl)-4-(hydroxyamino)-1,4-dimethyl-4,5-dihydro-1H-pyrazol-5-one 3-(3-Fluoro-4-methanesulfinylphenyl)-4-(hydroxyamino)-1,4-dimethyl-4,5-dihydro-1H-pyrazol-5-one was synthesized from 4-{[(tert-butoxy)carbonyl]({[(tert-butoxy)carbonyl]oxy})amino}-3-(3-fluoro-4-methanesulfinylphenyl)-1,4-dimethyl-4,5-dihydro-1H-pyrazol-5-one according to General Method 9 and the product was triturated using 30% ethyl acetate in heptanes (0.2 g, 52% yield). LC-MS: $t_R$=1.65 min, [M+H]$^+$=300.00. $^1$H NMR (500 MHz, DMSO-$d_6$) δ ppm: 8.11 (dd, J=8.2, 1.7 Hz, 1H), 7.94 (dd, J=11.1, 3.2 Hz, 1H), 7.84 (t, J=7.7 Hz, 1H), 7.74-7.70 (m, 1H), 6.62 (s, 1H), 3.32 (s, 3H), 2.86 (m, 3H), 1.23 (m, 3H).

Example 39

Compound 39 [4-(hydroxyamino)-2,4-dimethyl-5-(3-methyl-4-(methylsulfinyl)phenyl)-2,4-dihydro-3H-pyrazol-3-one]

39.1 1-[3-Methyl-4-(methylsulfanyl)phenyl]ethan-1-one

1-[3-Methyl-4-(methylsulfanyl)phenyl]ethan-1-one was synthesized from 1-(4-fluoro-3-methylphenyl)ethan-1-one according to General Method 14 (10.01 g, 74% yield). LC-MS: $t_R$=1.29 min, [M+H]$^+$=180.95. $^1$H NMR (500 MHz, CDCl$_3$) δ ppm: 7.71 (d, J=8.3 Hz, 1H), 7.65 (s, 1H), 7.09 (d, J=8.3 Hz, 1H), 2.50 (d, J=1.1 Hz, 3H), 2.47-2.42 (m, 3H), 2.29 (s, 3H).

39.2 Ethyl 3-[3-methyl-4-(methylsulfanyl)phenyl]-3-oxopropanoate

Ethyl 3-[3-methyl-4-(methylsulfanyl)phenyl]-3-oxopropanoate was synthesized from 1-[3-methyl-4-(methylsulfanyl)phenyl]ethan-1-one according to General Method 1. The product was chromatographed by silica gel column chromatography eluting with 0-50% ethyl acetate in heptanes (7.2 g, 41% yield). LC-MS: $t_R$=1.34 min, [M+H]$^+$=274.95. $^1$H NMR (500 MHz, CDCl$_3$) δ ppm: 7.78-7.72 (m, 1H), 7.71-7.67 (m, 1H), 7.17-7.14 (m, 1H), 4.23-4.17 (m, 2H), 3.94 (s, 2H), 2.53-2.48 (m, 3H), 2.35-2.31 (m, 3H), 1.29-1.21 (m, 3H).

39.3 1-Methyl-3-[3-methyl-4-(methylsulfanyl)phenyl]-1H-pyrazol-5-ol

1-Methyl-3-[3-methyl-4-(methylsulfanyl)phenyl]-1H-pyrazol-5-ol was synthesized from ethyl 3-[3-methyl-4-

(methylsulfanyl)phenyl]-3-oxopropanoate according to General Method 2. The product was chromatographed by silica gel column chromatography eluting with 0-100% ethyl acetate in heptanes (3.3 g, 85% yield). LC-MS: $t_R$=1.14 min, [M+H]$^+$=235.00. $^1$H NMR (500 MHz, CDCl$_3$) δ ppm: 7.51-7.40 (m, 2H), 7.18-7.08 (m, 1H), 3.57 (s, 2H), 3.40 (s, 3H), 2.50 (s, 3H), 2.35 (s, 3H).

39.4 1-Methyl-3-[3-methyl-4-(methylsulfanyl)phenyl]-5-oxo-4,5-dihydro-1H-pyrazole-4-carbaldehyde 1-Methyl-3-[3-methyl-4-(methylsulfanyl)phenyl]-5-oxo-4,5-dihydro-1H-pyrazole-4-carbaldehyde was synthesized from 1-methyl-3-[3-methyl-4-(methylsulfanyl)phenyl]-1H-pyrazol-5-ol according to General Method 4 (4.02 g, 92% yield). LC-MS: $t_R$=1.19 min, [M+H]$^+$=263.00. $^1$H NMR (500 MHz, CDCl$_3$) δ ppm: 9.77 (s, 1H), 7.52-7.41 (m, 2H), 7.24-7.18 (m, 1H), 3.70 (s, 3H), 2.51 (s, 3H), 2.38 (s, 3H).

39.5 1,4-Dimethyl-3-[3-methyl-4-(methylsulfanyl)phenyl]-1H-pyrazol-5-ol 1,4-Dimethyl-3-[3-methyl-4-(methylsulfanyl)phenyl]-1H-pyrazol-5-ol was synthesized from 1-methyl-3-[3-methyl-4-(methylsulfanyl)phenyl]-5-oxo-4,5-dihydro-1H-pyrazole-4-carbaldehyde by General Method 5 (4.5 g, 82% yield). LC-MS: $t_R$=1.11 min, [M+H]$^+$=249.00. $^1$H NMR (500 MHz, DMSO-d$_6$) δ ppm: 7.37 (s, 1H), 7.28-7.07 (m, 2H), 3.45 (s, 3H), 2.43 (s, 3H), 2.23 (s, 3H), 1.92 (s, 3H).

39.6 4-Bromo-1,4-dimethyl-3-[3-methyl-4-(methylsulfanyl)phenyl]-4,5-dihydro-1H-pyrazol-5-one 4-Bromo-1,4-dimethyl-3-[3-methyl-4-(methylsulfanyl)phenyl]-4,5-dihydro-1H-pyrazol-5-one was synthesized from 1,4-dimethyl-3-[3-methyl-4-(methylsulfanyl)phenyl]-1H-pyrazol-5-ol according to General Method 6 (4.14 g, 99% yield). LC-MS: $t_R$=1.09 min, [M+H]$^+$=344.85.

39.7 4-{[(tert-Butoxy)carbonyl]({[(tert-butoxy)carbonyl]oxy})amino}-3-(4-methanesulfinyl-3-methylphenyl)-1,4-dimethyl-4,5-dihydro-1H-pyrazol-5-one 4-{[(tert-Butoxy)carbonyl]({[(tert-butoxy)carbonyl]oxy})amino}-3-(4-methanesulfinyl-3-methylphenyl)-1,4-dimethyl-4,5-dihydro-1H-pyrazol-5-one was synthesized from 4-bromo-1,4-dimethyl-3-[3-methyl-4-(methylsulfanyl)phenyl]-4,5-dihydro-1H-pyrazol-5-one according to General Method 8 (5.2 g, 75% yield). LC-MS: $t_R$=1.32 min, [M+H]$^+$=340.05.

39.8 4-(Hydroxyamino)-3-(4-methanesulfinyl-3-methylphenyl)-1,4-dimethyl-4,5-dihydro-1H-pyrazol-5-one 4-(Hydroxyamino)-3-(4-methanesulfinyl-3-methylphenyl)-1,4-dimethyl-4,5-dihydro-1H-pyrazol-5-one was synthesized from 4-{[(tert-butoxy)carbonyl]({[(tert-butoxy)carbonyl]oxy})amino}-3-(4-methanesulfinyl-3-methylphenyl)-1,4-dimethyl-4,5-dihydro-1H-pyrazol-5-one according to General Method 9. The product was chromatographed using reverse phase low pH preparative HPLC (0.01 g, 2% yield). LC-MS: $t_R$=0.93 min, [M+H]$^+$=296.05. $^1$H NMR (500 MHz, DMSO-d$_6$) δ ppm: 8.18-8.09 (m, 1H), 7.97-7.91 (m, 1H), 7.87 (d, J=8.3 Hz, 1H), 7.82-7.52 (m, 1H), 5.74 (s, 1H), 3.31 (s, 3H), 2.71 (s, 3H), 2.38 (s, 3H), 1.29-1.15 (m, 3H).

Example 40

Compound 40 [5-(3-Fluoro-4-(methylsulfonyl)phenyl)-4-(hydroxyamino)-2,4-dimethyl-2,4-dihydro-3H-pyrazol-3-one]

40.1 4-{[(tert-Butoxy)carbonyl]({[(tert-butoxy)carbonyl]oxy})amino}-3-(3-fluoro-4-methanesulfonylphenyl)-1,4-dimethyl-4,5-dihydro-1H-pyrazol-5-one 4-{[(tert-Butoxy)carbonyl]({[(tert-butoxy)carbonyl]oxy})amino}-3-(3-fluoro-4-methanesulfonylphenyl)-1,4-dimethyl-4,5-dihydro-1H-pyrazol-5-one was synthesized from 4-{[(tert-butoxy)carbonyl]({[(tert-butoxy)carbonyl]oxy})amino}-3-(3-fluoro-4-methanesulfinylphenyl)-1,4-dimethyl-4,5-dihydro-1H-pyrazol-5-one according to General Method 10 (6.72 g, 97% yield). LC-MS: $t_R$=1.38 min, [M+H]$^+$=538.15.

40.2 3-(3-Fluoro-4-methanesulfonylphenyl)-4-(hydroxyamino)-1,4-dimethyl-4,5-dihydro-1H-pyrazol-5-one 3-(3-Fluoro-4-methanesulfonylphenyl)-4-(hydroxyamino)-1,4-dimethyl-4,5-dihydro-1H-pyrazol-5-one was synthesized from 4-{[(tert-butoxy)carbonyl]({[(tert-butoxy)carbonyl]oxy})amino}-3-(3-fluoro-4-methanesulfonylphenyl)-1,4-dimethyl-4,5-dihydro-1H-pyrazol-5-one according to General Method 9 with the product being chromatographed by silica gel column chromatography eluting with 35-100% ethyl acetate in heptanes (1.11 g, 36% yield). LC-MS: $t_R$=1.92 min, [M+H]$^+$=316.10. $^1$H NMR (500 MHz, DMSO-d$_6$) δ ppm: 8.09-8.04 (m, 2H), 7.95 (t, J=7.9 Hz, 1H), 7.74 (s, 1H), 6.67 (s, 1H), 3.36 (s, 3H), 1.24 (s, 3H).

Example 41

Compound 41 [4-(Hydroxyamino)-2,4-dimethyl-5-(3-methyl-4-(methylsulfonyl)phenyl)-2,4-dihydro-3H-pyrazol-3-one]

41.1 4-{[(tert-Butoxy)carbonyl]({[(tert-butoxy)carbonyl]oxy})amino}-3-(4-methanesulfonyl-3-methylphenyl)-1,4-dimethyl-4,5-dihydro-1H-pyrazol-5-one was synthesized from 4-{[(tert-butoxy)carbonyl]({[(tert-butoxy)carbonyl]oxy})amino}-3-(4-methanesulfinyl-3-methylphenyl)-1,4-dimethyl-4,5-dihydro-1H-pyrazol-5-one according to General Method 10 (2.96 g, 67% yield). LC-MS: $t_R$=1.37 min, [M+Na]$^+$=534.

41.2 4-(Hydroxyamino)-3-(4-methanesulfonyl-3-methylphenyl)-1,4-dimethyl-4,5-dihydro-1H-pyrazol-5-one 4-(Hydroxyamino)-3-(4-methanesulfonyl-3-methylphenyl)-1,4-dimethyl-4,5-dihydro-1H-pyrazol-5-one was synthesized from 4-{[(tert-butoxy)carbonyl]({[(tert-butoxy)carbonyl]oxy})amino}-3-(4-methanesulfonyl-3-methylphenyl)-1,4-dimethyl-4,5-dihydro-1H-pyrazol-5-one according to General Method 9. The product was triturated using DCM in ethyl acetate (1:1 vol:vol) (0.2 g, 14% yield). LC-MS: $t_R$=1.96 min, [M+H]$^+$=312. $^1$H NMR (500 MHz, DMSO-d$_6$) δ ppm: 8.13-8.04 (m, 2H), 8.01-7.90 (m, 1H), 7.70 (s, 1H), 6.58 (s, 1H), 3.33 (s, 3H), 3.25 (s, 3H), 2.69 (s, 3H), 1.24 (s, 3H).

Example 42

Compound 42 [4-(hydroxyamino)-4-(1-(methoxyimino)ethyl)-2-methyl-5-(4-(methylsulfonyl)phenyl)-2,4-dihydro-3H-pyrazol-3-one]

42.1 1-{5-Hydroxy-1-methyl-3-[4-(methylsulfanyl)phenyl]-1H-pyrazol-4-yl}ethan-1-one 1-{5-Hydroxy-1-methyl-3-[4-(methylsulfanyl)phenyl]-1H-pyrazol-4-yl}ethan-1-one was synthesized from 1-methyl-3-[4-(methylsulfanyl)phenyl]-1H-pyrazol-5-ol according to General Method 11. The reaction mixture was concentrated under reduced pressure and the resulting residue was dissolved in DCM and concentrated under reduced pressure to provide the title compound as a red amorphous solid (11.78 g, 84% yield). LC-MS: $t_R$=1.20 min, [M+H]$^+$=263.00. $^1$H NMR (500 MHz, CDCl$_3$) δ ppm: 7.42 (d, J=8.5 Hz, 2H), 7.23 (d, J=8.5 Hz, 2H), 3.83 (s, 3H), 2.79 (s, 3H), 2.04 (s, 3H).

42.2 4-[1-(Methoxyimino)ethyl]-1-methyl-3-[4-(methylsulfanyl)phenyl]-1H-pyrazol-5-ol 4-[1-(Methoxyimino)ethyl]-1-methyl-3-[4-(methylsulfanyl)phenyl]-1H-pyrazol-5-ol was synthesized from 1-{5-hydroxy-1-methyl-3-[4-(methylsulfanyl)phenyl]-1H-pyrazol-4-yl}ethan-1-one according to General Method 12. The reaction mixture was concentrated under reduced pressure, dissolved in water (30 mL) and extracted with DCM (3×100 mL). The combined organic extracts were dried over sodium sulfate and concentrated under reduced pressure. The resulting product was recrystallized from DCM:methanol (9:1 vol:vol) and chromatographed by silica gel chromatography eluting in 10-60% ethyl acetate in heptanes to provide the title compound as a beige powder (7.85 g, 70% yield). LC-MS: $t_R$=1.26 min, [M+H]$^+$=292.05. $^1$H NMR (500 MHz, CDCl$_3$) δ ppm: 7.37-7.34 (m, 2H), 7.26 (s, 2H), 3.90 (s, 3H), 3.70 (s, 3H), 2.50 (s, 3H), 1.86 (s, 3H).

42.3 4-Bromo-3-(4-methanesulfinylphenyl)-4-[1-(methoxyimino)ethyl]-1-methyl-4,5-dihydro-1H-pyrazol-5-one 4-Bromo-3-(4-methanesulfinylphenyl)-4-[1-(methoxyimino)ethyl]-1-methyl-4,5-dihydro-1H-pyrazol-5-one was synthesized from 4-[1-(methoxyimino)ethyl]-1-methyl-3-[4-(methylsulfanyl)phenyl]-1H-pyrazol-5-ol according to General Method 6 to provide the title compound as a light brown viscous oil (7.81 g, 95% yield). LC-MS: $t_R$=1.16 min, [M+H]$^+$=385.95/387.95. $^1$H NMR (500 MHz, CDCl$_3$) δ ppm: 7.99 (d, J=8.5 Hz, 2H), 7.65 (d, J=8.5 Hz, 2H), 3.70 (d, J=3.4 Hz, 3H), 3.46 (s, 3H), 2.76-2.74 (m, 3H), 2.18-2.16 (m, 3H).

42.4 4-{[(tert-Butoxy)carbonyl]({[(tert-butoxy)carbonyl]oxy})amino}-3-(4-methanesulfinylphenyl)-4-[1-(methoxyimino)ethyl]-1-methyl-4,5-dihydro-1H-pyrazol-5-one 4-{[(tert-Butoxy)carbonyl]({[(tert-butoxy)carbonyl]oxy})amino}-3-(4-methanesulfinylphenyl)-4-[1-(methoxyimino)ethyl]-1-methyl-4,5-dihydro-1H-pyrazol-5-one was synthesized from 4-bromo-3-(4-methanesulfinylphenyl)-4-[1-(methoxyimino)ethyl]-1-methyl-4,5-dihydro-1H-pyrazol-5-one according to General Method 8 to provide the title compound after the specified aqueous work-up as a yellow viscous oil (12.1 g, 98% yield). LC-MS: $t_R$=1.33 min, [M+Na]$^+$=461.10. $^1$H NMR (500 MHz, CDCl$_3$) δ ppm: 8.03-7.98 (m, 2H), 7.70-7.66 (m, 2H), 3.44 (s, 3H), 2.77 (s, 3H), 1.55 (s, 9H), 1.54 (s, 3H), 1.51 (s, 3H), 1.36-1.25 (m, 9H).

42.5 4-{[(tert-Butoxy)carbonyl]({[(tert-butoxy)carbonyl]oxy})amino}-3-(4-methanesulfonylphenyl)-4-[1-(methoxyimino)ethyl]-1-methyl-4,5-dihydro-1H-pyrazol-5-one 4-{[(tert-Butoxy)carbonyl]({[(tert-butoxy)carbonyl]oxy})amino}-3-(4-methanesulfonylphenyl)-4-[1-(methoxyimino)ethyl]-1-methyl-4,5-dihydro-1H-pyrazol-5-one was synthesized from 4-{[(tert-butoxy)carbonyl]({[(tert-butoxy)carbonyl]oxy})amino}-3-(4-methanesulfinylphenyl)-4-[1-(methoxyimino)ethyl]-1-methyl-4,5-dihydro-1H-pyrazol-5-one according to General Method 10. The product was chromatographed by silica gel column chromatography eluting with 0-25% ethyl acetate in heptanes to provide the title compound as a beige powder (7.26 g, 68% yield). LC-MS: $t_R$=1.40 min, [M+Na]$^+$=577.20. $^1$H NMR (500 MHz, CDCl$_3$) δ ppm: 8.30-7.98 (m, 2H), 7.98-7.92 (m, 2H), 3.73 (s, 3H), 3.43 (s, 3H), 3.08 (s, 3H), 2.04 (s, 3H), 1.54 (s, 9H), 1.39-1.20 (m, 9H).

42.6 4-(Hydroxyamino)-3-(4-methanesulfonylphenyl)-4-[1-(methoxyimino)ethyl]-1-methyl-4,5-dihydro-1H-pyrazol-5-one 4-(Hydroxyamino)-3-(4-methanesulfonylphenyl)-4-[1-(methoxyimino)ethyl]-1-methyl-4,5-dihydro-1H-pyrazol-5-one was synthesized from 4-{[(tert-butoxy)carbonyl]({[(tert-butoxy)carbonyl]oxy})amino}-3-(4-methanesulfonylphenyl)-4-[1-(methoxyimino)ethyl]-1-methyl-4,5-dihydro-1H-pyrazol-5-one according to General Method 9. The reaction mixture was concentrated under reduced pressure to provide a light yellow viscous oil which was triturated with diethyl ether to provide the title compound as a cream powder (2.37 g, 51% yield). LC-MS: $t_R$=1.08 min, [M+H]$^+$=355.05. $^1$H NMR (500 MHz, CDCl$_3$) δ ppm: 8.17 (d, J=8.5 Hz, 2H), 7.97 (d, J=8.5 Hz, 2H), 3.93 (s, 3H), 3.50 (s, 3H), 3.07 (s, 3H), 1.63 (s, 3H).

Example 43

Compound 43 [4-(hydroxyamino)-4-(4-methoxyphenyl)-1,3-dimethyl-1H-pyrazol-5(4H)-one]

43.1 Ethyl 2-(4-methoxyphenyl)-3-oxobutanoate

Ethyl 2-(4-methoxyphenyl)-3-oxobutanoate was synthesized from ethyl 2-(4-methoxyphenyl)acetate according to General Method 13 and was chromatographed by column chromatography eluting with 0-100% ethyl acetate in heptanes (5.4 g, 63% yield). LC-MS: $t_R$=1.89 min, [M+H]$^+$=237. $^1$H NMR (500 MHz, CDCl$_3$) δ ppm: 7.30-7.14 (m, 2H), 6.95-6.79 (m, 2H), 4.61 (s, 1H), 4.29-4.13 (m, 2H), 3.80 (s, 3H), 2.16 (s, 3H), 1.36-1.17 (m, 3H).

43.2 3-(4-Methoxyphenyl)-1-methyl-1H-pyrazol-5-ol 3-(4-Methoxyphenyl)-1-methyl-1H-pyrazol-5-ol was synthesized from ethyl 2-(4-methoxyphenyl)-3-oxobutanoate according to General Method 2 (3.6 g, 92% yield). LC-MS: $t_R$=0.97 min, [M+H]$^+$=219. $^1$H NMR (500 MHz, DMSO-d$_6$) δ ppm: 7.36 (s, 2H), 7.00-6.82 (m, 2H), 3.72 (s, 3H), 2.13 (s, 3H).

43.3 4-Bromo-4-(4-methoxyphenyl)-1,3-dimethyl-4, 5-dihydro-1H-pyrazol-5-one

4-Bromo-4-(4-methoxyphenyl)-1,3-dimethyl-4,5-dihydro-1H-pyrazol-5-one was synthesized from 3-(4-methoxyphenyl)-1-methyl-1H-pyrazol-5-ol according to General Method 6 (4.65 g, 99% yield). LC-MS: $t_R$=1.13 min, [M+H]$^+$=298. (The reaction also provided 4-bromo-4-(3-bromo-4-methoxyphenyl)-1,3-dimethyl-4,5-dihydro-1H-pyrazol-5-one which was used in the synthesis of Example 68.)

43.4 4-{[(tert-Butoxy)carbonyl]({[(tert-butoxy)carbonyl]oxy})amino}-4-(4-methoxyphenyl)-1,3-dimethyl-4,5-dihydro-1H-pyrazol-5-one 4-{[(tert-Butoxy)carbonyl]({[(tert-butoxy)carbonyl]oxy})amino}-4-(4-methoxyphenyl)-1,3-di methyl-4,5-dihydro-1H-pyrazol-5-one was synthesized from 4-bromo-4-(4-methoxyphenyl)-1,3-dimethyl-4,5-dihydro-1H-pyrazol-5-one according to General Method 8. The product was chromatographed by silica gel column chromatography eluting with 0-40% ethyl acetate in heptanes (3 g, 43% yield). LC-MS: $t_R$=1.18 min, [M+H]$^+$=263. (The reaction also provided 4-(3-bromo-4-methoxyphenyl)-4-{[(tert-butoxy)carbonyl]({[(tert-butoxy)carbonyl]oxy})amino}-1,3-dimethyl-4,5-dihydro-1H-pyrazol-5-one which was used in the synthesis of Example 68.)

43.5 4-(Hydroxyamino)-4-(4-methoxyphenyl)-1,3-dimethyl-4,5-dihydro-1H-pyrazol-5-one 4-(Hydroxyamino)-4-(4-methoxyphenyl)-1,3-dimethyl-4,5-dihydro-1H-pyrazol-5-one was synthesized from 4-{[(tert-butoxy)carbonyl]({[(tert-butoxy)carbonyl]oxy})amino}-4-(4-methoxyphenyl)-1,3-dimethyl-4,5-dihydro-1H-pyrazol-5-one according to General Method 9. The product was chromatographed by low pH preparative HPLC (0.02 g, 3% yield). LC-MS: $t_R$=0.98 min, [M+H]$^+$=272. $^1$H NMR (500 MHz, DMSO-d$_6$) δ ppm: 7.81 (s, 1H), 7.21-7.06 (m, 2H), 6.98-6.87 (m, 2H), 6.76 (s, 1H), 3.73 (s, 3H), 3.18 (s, 3H), 1.93 (s, 3H).

Example 44

Compound 44 [1-(4-bromophenyl)-3-(2-chlorophenyl)-4-(hydroxyamino)-4-methyl-1H-pyrazol-5(4H)-one]

44.1 3-(2-Chlorophenyl)-1-phenyl-1H-pyrazol-5-ol 3-(2-Chlorophenyl)-1-phenyl-1H-pyrazol-5-ol was synthesized from methyl 3-(2-chlorophenyl)-3-oxopropanoate (1 g, 4.7 mmol) according to General Method 2 to provide the title compound as a yellow solid (1.03 g, 81% yield). LC-MS: $t_R$=2.07 min, [M+H]$^+$=271. $^1$H NMR (500 MHz, DMSO-d$_6$) δ ppm: 11.84 (s, 1H), 7.86 (dd, J=7.4, 2.1 Hz, 1H), 7.82 (d, J=7.6 Hz, 2H), 7.54 (dd, J=7.5, 1.5 Hz, 1H), 7.50 (t, J=7.9 Hz, 2H), 7.40 (td, J=7.6, 1.7 Hz, 2H), 7.31 (t, J=7.4 Hz, 1H), 6.07 (s, 1H).

44.2 3-(2-Chlorophenyl)-5-hydroxy-1-phenyl-1H-pyrazole-4-carbaldehyde 3-(2-Chlorophenyl)-5-hydroxy-1-phenyl-1H-pyrazole-4-carbaldehyde was synthesized from 3-(2-chlorophenyl)-1-phenyl-1H-pyrazol-5-ol (1.03 g, 3.8 mmol) according to General Method 3 and was chromatographed by silica gel column chromatography eluting with 25% ethyl acetate in heptanes. The title compound was isolated as a brown oil, 0.4 g (32% yield). LC-MS: $t_R$=1.9 min, [M+H]$^+$=298.

44.3 3-(2-Chlorophenyl)-4-methyl-1-phenyl-1H-pyrazol-5-ol 3-(2-Chlorophenyl)-4-methyl-1-phenyl-1H-pyrazol-5-ol was synthesized from 3-(2-chlorophenyl)-5-hydroxy-1-phenyl-1H-pyrazole-4-carbaldehyde (0.4 g, 1.34 mmol) according to General Method 5 to provide the title compound as a brown solid (>99.9% yield). LC-MS: $t_R$=1.89 min, [M+H]$^+$=284.

44.4 4-Bromo-1-(4-bromophenyl)-3-(2-chlorophenyl)-4-methyl-4,5-dihydro-1H-pyrazol-5-one 4-Bromo-1-(4-bromophenyl)-3-(2-chlorophenyl)-4-methyl-4,5-dihydro-1H-pyrazol-5-one was synthesized from 3-(2-chlorophenyl)-4-methyl-1-phenyl-4,5-dihydro-1H-pyrazol-5-one (0.47 g, 1.65 mmol) according to General Method 6 (0.6 g, 82% yield). LC-MS: $t_R$=2.68 min, [M+H]$^+$=442.

44.5 1-(4-Bromophenyl)-4-{[(tert-butoxy)carbonyl]({[(tert-butoxy)carbonyl]oxy})amino}-3-(2-chlorophenyl)-4-methyl-4,5-dihydro-1H-pyrazol-5-one 1-(4-Bromophenyl)-4-{[(tert-butoxy)carbonyl]({[(tert-butoxy)carbonyl]oxy})amino}-3-(2-chlorophenyl)-4-methyl-4,5-dihydro-1H-pyrazol-5-one was synthesized from 4-bromo-1-(4-bromophenyl)-3-(2-chlorophenyl)-4-methyl-4,5-dihydro-1H-pyrazol-5-one according to General Method 8 and chromatographed by silica gel chromatography eluting in 0-25% ethyl acetate:heptanes to provide the title compound as a yellow oil (0.515 g, 31% yield) LC-MS: $t_R$=2.86 min, [M+Na]$^+$=617.

44.6 1-(4-Bromophenyl)-3-(2-chlorophenyl)-4-(hydroxyamino)-4-methyl-4,5-dihydro-1H-pyrazol-5-one 1-(4-Bromophenyl)-3-(2-chlorophenyl)-4-(hydroxyamino)-4-methyl-4,5-dihydro-1H-pyrazol-5-one was synthesized from 1-(4-bromophenyl)-4-{[(tert-butoxy)carbonyl]({[(tert-butoxy)carbonyl]oxy})amino}-3-(2-chlorophenyl)-4-methyl-4,5-dihydro-1H-pyrazol-5-one according to General Method 9 and was isolated by acidic preparative HPLC chromatography to provide the title compound as an off-white solid (0.97 g, 35% yield). LC-MS: $t_R$=2.23 min, [M+H]$^+$=395. $^1$H NMR (500 MHz, DMSO-d$_6$) δ ppm: 8.07 (dd, J=7.4, 2.0 Hz, 1H), 8.01 (d, J=2.2 Hz, 1H), 7.92-7.81 (m, 2H), 7.71-7.62 (m, 3H), 7.58-7.46 (m, 2H), 6.79 (d, J=2.1 Hz, 1H), 1.19 (s, 3H).

Example 45

Compound 45 [5-(3,5-difluoro-4-(methylsulfonyl)phenyl)-4-(hydroxyamino)-2,4-dimethyl-2,4-dihydro-3H-pyrazol-3-one]

45.1 1-[3,5-Difluoro-4-(methylsulfanyl)phenyl]ethan-1-one

1-[3,5-Difluoro-4-(methylsulfanyl)phenyl]ethan-1-one was synthesized from 1-(3,4,5-trifluorophenyl)ethan-1-one

45.2 Methyl 3-[3,5-difluoro-4-(methylsulfanyl)phenyl]-3-oxopropanoate

Methyl 3-[3,5-difluoro-4-(methylsulfanyl)phenyl]-3-oxopropanoate was synthesized from 1-[3,5-difluoro-4-(methylsulfanyl)phenyl]ethan-1-one according to General Method 1 with the product being chromatographed by silica gel column chromatography eluting with 0-30% ethyl acetate in heptanes (5.28 g, 59% yield). LC-MS: $t_R$=1.30 min, $[M+H]^+$=260.95. $^1$H NMR (500 MHz, DMSO-$d_6$) δ ppm: 7.71 (s, 1H), 7.69 (s, 1H), 4.24 (s, 2H), 3.65 (s, 3H), 2.56 (s, 3H).

45.3 3-[3,5-Difluoro-4-(methylsulfanyl)phenyl]-1-methyl-4,5-dihydro-1H-pyrazol-5-one 3-[3,5-Difluoro-4-(methylsulfanyl)phenyl]-1-methyl-4,5-dihydro-1H-pyrazol-5-one was synthesized from methyl 3-[3,5-difluoro-4-(methylsulfanyl)phenyl]-3-oxopropanoate and methyl hydrazine according to General Method 2 (5.06 g, 86% yield). LC-MS: $t_R$=1.20 min, $[M+H]^+$=256.95.

45.4 3-[3,5-Difluoro-4-(methylsulfanyl)phenyl]-1-methyl-5-oxo-4,5-dihydro-1H-pyrazole-4-carbaldehyde 3-[3,5-Difluoro-4-(methylsulfanyl)phenyl]-1-methyl-5-oxo-4,5-dihydro-1H-pyrazole-4-carbaldehyde was synthesized from 3-[3,5-difluoro-4-(methylsulfanyl)phenyl]-1-methyl-4,5-dihydro-1H-pyrazol-5-one according to General Method 4 (1.5 g, 30% yield). LC-MS: $t_R$=1.20 min, $[M+H]^+$=284.95. $^1$H NMR (500 MHz, DMSO-$d_6$) δ ppm: 9.73 (s, 1H), 7.75 (d, J=8.9 Hz, 2H), 3.63 (s, 3H), 2.47 (s, 3H).

45.5 3-[3,5-Difluoro-4-(methylsulfanyl)phenyl]-1,4-dimethyl-4,5-dihydro-1H-pyrazol-5-one 3-[3,5-Difluoro-4-(methylsulfanyl)phenyl]-1,4-dimethyl-4,5-dihydro-1H-pyrazol-5-one was synthesized from 3-[3,5-difluoro-4-(methylsulfanyl)phenyl]-1-methyl-5-oxo-4,5-dihydro-1H-pyrazole-4-carbaldehyde according to General Method 5 (1.97 g, 97% yield). LC-MS: $t_R$=1.16 min, $[M+H]^+$=270.95.

45.6 4-Bromo-3-(3,5-difluoro-4-methanesulfinylphenyl)-1,4-dimethyl-4,5-dihydro-1H-pyrazol-5-one 4-Bromo-3-(3,5-difluoro-4-methanesulfinylphenyl)-1,4-dimethyl-4,5-dihydro-1H-pyrazol-5-one was synthesized from 3-[3,5-difluoro-4-(methylsulfanyl)phenyl]-1,4-dimethyl-4,5-dihydro-1H-pyrazol-5-one according to General Method 6 (2.21 g, 96% yield). LC-MS: $t_R$=1.06 min, $[M+H]^+$=366.95.

45.7 4-{[(tert-Butoxy)carbonyl]({[(tert-butoxy)carbonyl]oxy})amino}-3-(3,5-difluoro-4-methanesulfinylphenyl)-1,4-dimethyl-4,5-dihydro-1H-pyrazol-5-one 4-{[(tert-Butoxy)carbonyl]({[(tert-butoxy)carbonyl]oxy})amino}-3-(3,5-difluoro-4-methanesulfinylphenyl)-1,4-dimethyl-4,5-dihydro-1H-pyrazol-5-one was synthesized from the corresponding bromide according to General Method 8 with the product being chromatographed by silica gel column chromatography eluting with 0-55% ethyl acetate in heptanes (1.2 g, 37% yield). LC-MS: $t_R$=1.35 min, $[M+H]^+$=540.15.

45.8 4-{[(tert-Butoxy)carbonyl]({[(tert-butoxy)carbonyl]oxy})amino}-3-(3,5-difluoro-4-methanesulfonylphenyl)-1,4-dimethyl-4,5-dihydro-1H-pyrazol-5-one 4-{[(tert-Butoxy)carbonyl]({[(tert-butoxy)carbonyl]oxy})amino}-3-(3,5-difluoro-4-methanesulfonylphenyl)-1,4-dimethyl-4,5-dihydro-1H-pyrazol-5-one was synthesized from 4-{[(tert-butoxy)carbonyl]({[(tert-butoxy)carbonyl]oxy})amino}-3-(3,5-difluoro-4-methanesulfinylphenyl)-1,4-dimethyl-4,5-dihydro-1H-pyrazol-5-one according to General Method 10 (0.83 g, 60% yield). LC-MS: $t_R$=1.42 min, $[M+H]^+$=556.15.

45.9 3-(3,5-Difluoro-4-methanesulfonylphenyl)-4-(hydroxyamino)-1,4-dimethyl-4,5-dihydro-1H-pyrazol-5-one 3-(3,5-Difluoro-4-methanesulfonylphenyl)-4-(hydroxyamino)-1,4-dimethyl-4,5-dihydro-1H-pyrazol-5-one was synthesized from 4-{[(tert-butoxy)carbonyl]({[(tert-butoxy)carbonyl]oxy})amino}-3-(3,5-difluoro-4-methanesulfonylphenyl)-1,4-dimethyl-4,5-dihydro-1H-pyrazol-5-one according to General Method 9 with the product being triturated in 100% methanol (0.19 g, 37% yield). LC-MS: $t_R$=2.94 min, $[M+H]^+$=333.95. $^1$H NMR (500 MHz, DMSO-$d_6$) δ ppm: 7.84 (d, J=10.4 Hz, 2H), 7.77 (s, 1H), 6.72 (s, 1H), 3.46 (s, 3H), 1.23 (s, 3H).

Example 46

Compound 46 [4-(hydroxyamino)-4-(1-(methoxyimino)ethyl)-2-methyl-5-phenyl-2,4-dihydro-3H-pyrazol-3-one]

46.1 1-(5-Hydroxy-1-methyl-3-phenyl-1H-pyrazol-4-yl)ethan-1-one 1-(5-Hydroxy-1-methyl-3-phenyl-1H-pyrazol-4-yl)ethan-1-one was synthesized from 1-methyl-3-phenyl-1H-pyrazol-5-ol according to General Method 11 (3.95 g, 22% yield). LC-MS: $t_R$=1.11 min, $[M+H]^+$=217.00.

46.2 4-[1-(Methoxyimino)ethyl]-1-methyl-3-phenyl-1H-pyrazol-5-ol

4-[1-(Methoxyimino)ethyl]-1-methyl-3-phenyl-1H-pyrazol-5-ol was synthesized from 1-(5-hydroxy-1-methyl-3-phenyl-1H-pyrazol-4-yl)ethan-1-one according to General Method 12 (3.5 g, 88% yield). LC-MS: $t_R$=1.17 min, $[M+H]^+$=246.05.

46.3 4-Bromo-4-[1-(methoxyimino)ethyl]-1-methyl-3-phenyl-4,5-dihydro-1H-pyrazol-5-one 4-Bromo-4-[1-(methoxyimino)ethyl]-1-methyl-3-phenyl-4,5-dihydro-1H-pyrazol-5-one was synthesized from 4-[1-(methoxyimino)ethyl]-1-methyl-3-phenyl-1H-pyrazol-5-ol according to General Method 6 (5.8 g, 55% yield). LC-MS: $t_R$=1.41 min, $[M+H]^+$=325.85.

according to General Method 14 (7.3 g, 88% yield). LC-MS: $t_R$=1.29 min, $[M+H]^+$=230.90. $^1$H NMR (500 MHz, DMSO-$d_6$) δ ppm: 7.69-7.62 (m, 2H), 2.58 (d, J=1.4 Hz, 3H), 2.54 (s, 3H).

46.4 4-{[(tert-Butoxy)carbonyl]({[(tert-butoxy)carbonyl]oxy})amino}-4-[1-(methoxyimino)ethyl]-1-methyl-3-phenyl-4,5-dihydro-1H-pyrazol-5-one 4-{[(tert-Butoxy)carbonyl]({[(tert-butoxy)carbonyl]oxy})amino}-4-[1-(methoxyimino)ethyl]-1-methyl-3-phenyl-4,5-dihydro-1H-pyrazol-5-one was synthesized from 4-bromo-4-[1-(methoxyimino)ethyl]-1-methyl-3-phenyl-4,5-dihydro-1H-pyrazol-5-one according to General Method 8 and was chromatographed by silica gel column chromatography eluting with 0-40% ethyl acetate in heptanes (0.43 g, 8% yield). LC-MS: $t_R$=1.61 min, [M+H]$^+$=499.95.

46.5 4-(Hydroxyamino)-4-[1-(methoxyimino)ethyl]-1-methyl-3-phenyl-4,5-dihydro-1H-pyrazol-5-one 4-(Hydroxyamino)-4-[1-(methoxyimino)ethyl]-1-methyl-3-phenyl-4,5-dihydro-1H-pyrazol-5-one was synthesized from 4-{[(tert-butoxy)carbonyl]({[(tert-butoxy)carbonyl]oxy})amino}-4-[1-(methoxyimino)ethyl]-1-methyl-3-phenyl-4,5-dihydro-1H-pyrazol-5-one according to General Method 9 and was chromatographed by silica gel column chromatography eluting with 0-45% ethyl acetate in heptanes (0.08 g, 46% yield). LC-MS: $t_R$=1.13 min, [M+H]$^+$=276.95. $^1$H NMR (500 MHz, DMSO-d$_6$) δ ppm: 7.89 (m, 2H), 7.82 (d, J=2.5 Hz, 1H), 7.44 (q, J=3.6 Hz, 3H), 6.57 (d, J=2.5 Hz, 1H), 3.75 (s, 3H), 3.32 (s, 3H), 1.63 (s, 3H).

Example 47

Compound 47 [1-(4-bromophenyl)-4-(hydroxyamino)-3-methyl-4-phenyl-1H-pyrazol-5(4H)-one]

1-(4-Bromophenyl)-4-(hydroxyamino)-3-methyl-4-phenyl-4,5-dihydro-1H-pyrazol-5-one was isolated from the acidic preparative HPLC chromatography of 4-(hydroxyamino)-3-methyl-1,4-diphenyl-4,5-dihydro-1H-pyrazol-5-one to provide the title compound as a white solid (105 mg, 15% yield). LC-MS: $t_R$=1.43 min, [M+H]$^+$=360/362. $^1$H NMR (500 MHz, DMSO-d$_6$) δ ppm: 8.05 (d, J=2.5 Hz, 1H), 7.89-7.81 (m, 2H), 7.69-7.59 (m, 2H), 7.45-7.34 (m, 3H), 7.27 (dd, J=8.0, 1.5 Hz, 2H), 7.24 (d, J=2.5 Hz, 1H), 2.08 (s, 3H).

Example 48

Compound 48 [4-(hydroxyamino)-2,4-dimethyl-5-(3-(methylsulfonyl)phenyl)-2,4-dihydro-3H-pyrazol-3-one](See Methods Disclosed in U.S. Pat. No. 6,211,244 of Van Wagenen et al.)

48.1 1-[3-(Methylsulfanyl)phenyl]ethan-1-one

A solution of 1-(3-aminophenyl)ethanone (2 g, 14.8 mmol) in HCl (7.24 mL, 0.3 mol) and ice water (10 mL) was cooled to 0-5° C. before a solution of sodium nitrite (1.09 g, 15.54 mmol) in water (6 mL) was added over 2-3 minutes maintaining the temperature about 6° C. The reaction mixture was then slowly added to a solution of sodium methanethiolate (1.32 g, 18.5 mmol) in water (6 mL) maintaining a temperature of 0-10° C. over 10 minutes. The reaction mixture was allowed to warm to a temperature of about 25° C. for 1 hour after which time the reaction mixture was partitioned between water (20 mL) and tert-butyl dimethyl ether (40 mL) and the organic layer was washed with saturated sodium bicarbonate solution (30 mL) and brine (30 mL). The organic portion was dried over magnesium sulfate, filtered and the solvent was removed under reduced pressure to obtain the product as a brown oil, which was chromatographed by silica gel column chromatography eluting with heptanes:ethyl acetate (3:1 vol:vol) gradient to provide the titled compound as a yellow oil (1.8 g, 57% yield). LC-MS: $t_R$=1.24 min, [M+H]$^+$=167. $^1$H NMR (500 MHz, DMSO-d$_6$) δ ppm: 7.75 (s, 1H), 7.74-7.70 (m, 1H), 7.55-7.51 (m, 1H), 7.47 (d, J=7.7 Hz, 1H), 2.60-2.57 (m, 3H), 2.54-2.52 (m, 3H).

48.2 Methyl 3-[3-(methylsulfanyl)phenyl]-3-oxopropanoate

Methyl 3-[3-(methylsulfanyl)phenyl]-3-oxopropanoate was synthesized from 1-[3-(methylsulfanyl)phenyl]ethan-1-one according to General Method 1. The product was chromatographed by silica gel column chromatography eluting with heptanes:ethyl acetate (3:1 vol:vol) to provide the title compound as a yellow solid (1.9 g, 45% yield). LC-MS: $t_R$=1.21 min, [M+Na]$^+$=246.

48.3 1-Methyl-3-[3-(methylsulfanyl)phenyl]-1H-pyrazol-5-ol

1-Methyl-3-[3-(methylsulfanyl)phenyl]-1H-pyrazol-5-ol was synthesized from methyl 3-[3-(methylsulfanyl)phenyl]-3-oxopropanoate according to General Method 2 and the product was chromatographed by silica gel column chromatography eluting with heptanes:ethyl acetate (1:1 vol:vol) gradient to provide the title compound as an off-white solid (1.16 g, 55% yield). LC-MS: $t_R$=1.1 min, [M+H]$^+$=221. $^1$H NMR (500 MHz, DMSO-d$_6$) δ ppm: 11.09 (s, 1H), 7.56 (s, 1H), 7.46 (d, J=7.8 Hz, 1H), 7.29 (t, J=7.8 Hz, 1H), 7.14 (d, J=7.9 Hz, 1H), 5.80 (s, 1H), 3.56 (s, 3H).

48.4 5-Hydroxy-1-methyl-3-[3-(methylsulfanyl)phenyl]-1H-pyrazole-4-carbaldehyde 5-Hydroxy-1-methyl-3-[3-(methylsulfanyl)phenyl]-1H-pyrazole-4-carbaldehyde was synthesized from 1-methyl-3-[3-(methylsulfanyl)phenyl]-1H-pyrazol-5-ol (1.16 g, 5.26 mmol) according to General Method 4 to provide the title compound as a brown solid (1.1 g, 62% yield). LC-MS: $t_R$=1.09 min, [M+H]$^+$=248.

48.5 1,4-Dimethyl-3-[3-(methylsulfanyl)phenyl]-1H-pyrazol-5-ol 1,4-Dimethyl-3-[3-(methylsulfanyl)phenyl]-1H-pyrazol-5-ol was synthesized from 5-hydroxy-1-methyl-3-[3-(methylsulfanyl)phenyl]-1H-pyrazole-4-carbaldehyde (1.09 g, 2.77 mmol) according to General Method 5 to provide the title compound as an off-white solid (0.4 g, 21% yield). LC-MS: $t_R$=1.05 min, [M+H]$^+$=235.

48.6 4-Bromo-3-(3-methanesulfinylphenyl)-1,4-dimethyl-4,5-dihydro-1H-pyrazol-5-one 4-Bromo-3-(3-methanesulfinylphenyl)-1,4-dimethyl-4,5-dihydro-1H-pyrazol-5-one was synthesized from 1,4-dimethyl-3-[3-(methylsulfanyl)phenyl]-1H-pyrazol-5-ol (0.4 g, 0.8 mmol) according to General Method 6 (0.3 g, 53% yield). LC-MS: $t_R$=1.02 min, [M+H]$^+$=331.

48.7 4-{[(tert-Butoxy)carbonyl]({[(tert-butoxy)carbonyl]oxy})amino}-3-(3-methanesulfinylphenyl)-1,4-dimethyl-4,5-dihydro-1H-pyrazol-5-one 4-{[(tert-Butoxy)carbonyl]({[(tert-butoxy)carbonyl]oxy})amino}-3-(3-methanesulfinylphenyl)-1,4-dimethyl-4,5-dihydro-1H-pyrazol-5-one was synthesized from 4-bromo-3-(4-methanesulfinylphenyl)-1,4-dimethyl-4,5-dihydro-1H-pyrazol-5-one according to General Method 8 to provide the title compound as a yellow oil (0.32 g, 26% yield). LC-MS: $t_R$=1.29 min, [M+Na]$^+$=504.

48.8 4-{[(tert-Butoxy)carbonyl]({[(tert-butoxy)carbonyl]oxy})amino}-3-(3-methanesulfonylphenyl)-1,4-dimethyl-4,5-dihydro-1H-pyrazol-5-one 4-{[(tert-Butoxy)carbonyl]({[(tert-butoxy)carbonyl]oxy})amino}-3-(3-methanesulfonylphenyl)-1,4-dimethyl-4,5-dihydro-1H-pyrazol-5-one was synthesized from 4-{[(tert-butoxy)carbonyl]({[(tert-butoxy)carbonyl]oxy})amino}-3-(3-methanesulfinylphenyl)-1,4-dimethyl-4,5-dihydro-1H-pyrazol-5-one according to General Method 10 to provide the title compound as a yellow sticky solid (0.23 g, 68% yield) LC-MS: $t_R$=1.20 min, [M+Na]$^+$=521.

48.9 4-(Hydroxyamino)-3-(3-methanesulfonylphenyl)-1,4-dimethyl-4,5-dihydro-1H-pyrazol-5-one 4-(Hydroxyamino)-3-(3-methanesulfonylphenyl)-1,4-dimethyl-4,5-dihydro-1H-pyrazol-5-one was synthesized from 4-{[(tert-butoxy)carbonyl]({[(tert-butoxy)carbonyl]oxy})amino}-3-(4-methanesulfonyl phenyl)-1,4-dimethyl-4,5-dihydro-1H-pyrazol-5-one according to General Method 9 and the product was isolated by acidic reverse phase preparative HPLC to provide the title compound as a yellow oil (0.007 g, 19% yield). LC-MS: $t_R$=0.98 min, [M+H]$^+$=298.

Example 49

Compound 49 [4-(4-(hydroxyamino)-1,4-dimethyl-5-oxo-4,5-dihydro-1H-pyrazol-3-yl)-N,N-dimethylbenzenesulfonamide]

49.1 4-Acetyl-N,N-dimethylbenzene-1-sulfonamide

To a solution of 4-acetylbenzene-1-sulfonyl chloride (10 g, 45.73 mmol) in DCM (50 mL) at 0° C. was added a solution of dimethylamine (69 mL of 2M in THF, 0.12 mol). The reaction mixture was heated to a temperature of about 25° C. and stirred until complete consumption of the starting material was observed by LC-MS. The reaction mixture was quenched with saturated sodium hydrogen carbonate (50 mL) and the product extracted with DCM (2×75 mL). The combined organic layers were washed with 2 M HCl (30 mL) and brine (30 mL). The organic portion was dried over sodium sulfate, filtered and concentrated under reduced pressure (9.7 g, 93% yield). LC-MS: $t_R$=1.07 min, [M+H]$^+$=227.9. $^1$H NMR (250 MHz, DMSO-d$_6$) δ ppm: 8.29-8.08 (m, 2H), 7.94-7.81 (m, 2H), 2.65-2.61 (m, 9H).

49.2 Methyl 3-[4-((dimethylamino)dimethylidene-sulfanyl)phenyl]-3-oxopropanoate Methyl 3-[4-((dimethylamino)dimethylidene-sulfanyl)phenyl]-3-oxopropanoate was synthesized from 4-acetyl-N,N-dimethylbenzene-1-sulfonamide according to General Method 1. The product was chromatographed by silica gel column chromatography using a gradient of 0-60% ethyl acetate in heptanes providing the desired product (12.3 g, 71% yield). LC-MS: $t_R$=1.12 min, [M+H]$^+$=286. $^1$H NMR (500 MHz, DMSO-d$_6$) δ ppm: 8.24-8.08 (m, 2H), 7.93-7.81 (m, 2H), 4.30 (s, 1H), 3.79 (s, 1H), 3.66 (s, 3H), 2.66-2.63 (m, 6H).

49.3 4-(5-Hydroxy-1-methyl-1H-pyrazol-3-yl)-N,N-dimethylbenzene-1-sulfonamide To a solution of methyl 3-[4-(dimethylsulfamoyl)phenyl]-3-oxopropanoate (9.1 g, 31.89 mmol) in ethanol (40 mL) was sequentially added methyldiazanediium sulfate (5.06 g, 35.08 mmol) as a solution in ethanol (20 mL) and triethylamine (3.36 mL, 23.92 mmol) and the resulting reaction was heated to 70° C. until complete consumption of the starting material by LC-MS. The reaction mixture was concentrated under reduced pressure and dissolved in DCM (15 mL) and washed with 1M HCl (20 mL). On concentration of the organic portion a precipitate was formed which was filtered and dried under reduced pressure. The resulting filtrate was concentrated under reduced pressure and the residue was sonicated in DCM (x mL) resulting in further precipitation. This material was combined with the original filtrate (7.25 g, 71% yield). LC-MS: $t_R$=1.00 min, [M+H]$^+$=282. $^1$H NMR (250 MHz, DMSO-d$_6$) δ ppm: 8.00-7.90 (m, 2H), 7.79-7.64 (m, 2H), 5.95 (s, 1H), 3.60 (s, 3H), 2.61 (s, 6H).

49.4 4-(4-Formyl-1-methyl-5-oxo-4,5-dihydro-1H-pyrazol-3-yl)-N,N-dimethylbenzene-1-sulfonamide 4-(4-Formyl-1-methyl-5-oxo-4,5-dihydro-1H-pyrazol-3-yl)-N,N-dimethylbenzene-1-sulfonamide was synthesized from 4-(5-hydroxy-1-methyl-1H-pyrazol-3-yl)-N,N-dimethylbenzene-1-sulfonamide according to General Method 4 (4.40 g, 70% yield). LC-MS: $t_R$=1.03 min, [M+H]$^+$=310. $^1$H NMR (250 MHz, DMSO-d$_6$) δ ppm: 9.75 (s, 1H), 8.18-8.02 (m, 2H), 7.80-7.74 (m, 2H), 3.64 (s, 3H), 2.64 (s, 6H).

49.5 4-(5-Hydroxy-1,4-dimethyl-1H-pyrazol-3-yl)-N,N-dimethylbenzene-1-sulfonamide 4-(5-Hydroxy-1,4-dimethyl-1H-pyrazol-3-yl)-N,N-dimethylbenzene-1-sulfonamide was synthesized from 4-(4-formyl-1-methyl-5-oxo-4,5-dihydro-1H-pyrazol-3-yl)-N,N-dimethylbenzene-1-sulfonamide according to General Method 5 (3.56 g, 65% yield). LC-MS: $t_R$=0.98 min, [M+H]$^+$=296. $^1$H NMR (250 MHz, DMSO-d$_6$) δ ppm: 7.92-7.82 (m, 2H), 7.76-7.70 (m, 2H), 3.57 (s, 3H), 2.61 (s, 6H), 2.06 (s, 3H).

49.6 4-(4-Bromo-1,4-dimethyl-5-oxo-4,5-dihydro-1H-pyrazol-3-yl)-N,N-dimethylbenzene-1-sulfonamide 4-(4-bromo-1,4-dimethyl-5-oxo-4,5-dihydro-1H-pyrazol-3-yl)-N,N-dimethylbenzene-1-sulfonamide was synthesized from 4-(5-hydroxy-1,4-dimethyl-1H-pyrazol-3-yl)-N,N-dimethylbenzene-1-sulfonamide according to General Method 6 (4.31 g, 97% yield). LC-MS: $t_R$=1.43 min, [M+H]$^+$=375.

49.7 4-(4-{[(tert-Butoxy)carbonyl]({[(tert-butoxy)carbonyl]oxy})amino}-1,4-dimethyl-5-oxo-4,5-dihydro-1H-pyrazol-3-yl)-N,N-dimethylbenzene-1-sulfonamide 4-(4-{[(tert-Butoxy)carbonyl]({[(tert-butoxy)carbonyl]oxy})amino}-1,4-dimethyl-5-oxo-4,5-di hydro-1H-pyrazol- 3-yl)-N,N-dimethylbenzene-1-sulfonamide was synthesized from 4-(4-bromo-1,4-dimethyl-5-oxo-4,5-dihydro-1H-pyrazol-3-yl)-N,N-dimethylbenzene-1-sulfonamide according to General Method 8. The product was chromatographed using silica gel column chromatography eluting with 0-60% ethyl acetate in heptanes (1.45 g, 34% yield). LC-MS: $t_R$=1.44 min, [M+Na]$^+$=549.

49.8 4-[4-(Hydroxyamino)-1,4-dimethyl-5-oxo-4,5-dihydro-1H-pyrazol-3-yl]-N,N-dimethylbenzene-1-sulfonamide 4-[4-(Hydroxyamino)-1,4-dimethyl-5-oxo-4,5-dihydro-1H-pyrazol-3-yl]-N,N-dimethylbenzene-1-sulfonamide was synthesized from 4-(4-{[(tert-butoxy)carbonyl]({[(tert-butoxy)carbonyl]oxy})amino}-1,4-dimethyl-5-oxo-4,5-dihydro-1H-pyrazol-3-yl)-N,N-dimethylbenzene-1-sulfonamide according to General Method 9. The product was triturated in methanol:heptanes (1:4 vol:vol) (0.27 g, 32% yield). LC-MS: $t_R$=1.07 min, [M+H]$^+$=327. $^1$H NMR (500 MHz, DMSO-d$_6$) δ ppm: 8.33-8.21 (m, 2H), 7.90-7.77 (m, 2H), 7.69 (s, 1H), 6.59 (s, 1H), 3.33 (s, 3H), 2.65 (s, 6H), 1.25 (s, 3H).

Example 50

Compound 50 [1-(4-Bromophenyl)-4-(hydroxyamino)-4-methyl-3-phenyl-1H-pyrazol-5(4H)-one]

1-(4-Bromophenyl)-4-(hydroxyamino)-4-methyl-3-phenyl-4,5-dihydro-1H-pyrazol-5-one was isolated from the acidic preparative HPLC chromatography of 4-(hydroxyamino)-4-methyl-1,3-diphenyl-4,5-dihydro-1H-pyrazol-5-one to provide the title compound as a white solid 0.09 g, 7.6% yield). LC-MS: $t_R$=1.50 min, [M+H]$^+$=360/362. $^1$H NMR (250 MHz, DMSO-d$_6$) δ ppm: 8.20 (dd, J=6.7, 3.1 Hz, 2H), 8.02-7.90 (m, 2H), 7.83 (s, 1H), 7.75-7.62 (m, 2H), 7.59-7.40 (m, 3H), 6.77 (s, 1H), 1.36 (s, 3H).

Example 51

Compound 51 [4-(Hydroxyamino)-1,4-dimethyl-3-(o-tolyl)-1H-pyrazol-5(4H)-one]

51.1 Ethyl 3-(2-methylphenyl)-3-oxopropanoate

To a solution of 1-(2-methylphenyl)ethan-1-one (5 g, 37.26 mmol) in toluene (130 mL) was added diethyl carbonate (13.21 g, 111.79 mmol) and NaH (60%, 2.98 g, 74.53 mmol). The reaction mixture was refluxed for 16 hours. After cooling, the reaction mixture was poured into ice water (200 mL) and extracted in to ethyl acetate (3×200 mL). The combined organic layers were dried over magnesium sulfate, filtered and evaporated under reduced pressure to provide 9.5 g of a yellow oil. The oil was chromatographed by silica gel column chromatography (ethyl acetate in heptanes) to provide the title compound as an orange oil (6.23 g, 54% yield). LC-MS: $t_R$=1.99 min, [M+H]$^+$=207.

51.2 2-Methyl-5-(2-methylphenyl)-2,3-dihydro-1H-pyrazol-3-one

2-Methyl-5-(2-methylphenyl)-2,3-dihydro-1H-pyrazol-3-one was synthesized from ethyl 3-(2-methylphenyl)-3-oxopropanoate according to General Method 2. Once the starting material had been consumed, the reaction mixture was concentrated and the resulting yellow solid triturated with ethyl acetate:heptanes (1:3 vol:vol, 15 mL). The solid was filtered, washed with heptanes (30 mL) and dried under reduced pressure. The solid was washed with methanol and the filtrate collected. The filtrate was concentrated under reduced pressure and the resulting oily solid was washed with methanol and filtered immediately to provide the title compound as a beige solid (0.65 g, 14% yield). LC-MS: $t_R$=1.36 min, [M+H]$^+$=189. $^1$H NMR (500 MHz, DMSO-d$_6$) δ ppm: 7.49-7.40 (m, 1H), 7.22-7.13 (m, 3H), 5.59 (s, 1H), 3.56 (s, 3H), 2.41 (s, 3H).

51.3 2-Methyl-5-(2-methylphenyl)-3-oxo-2,3-dihydro-1H-pyrazole-4-carbaldehyde 2-Methyl-5-(2-methylphenyl)-3-oxo-2,3-dihydro-1H-pyrazole-4-carbaldehyde was synthesized from 2-methyl-5-(2-methylphenyl)-2,3-dihydro-1H-pyrazol-3-one according to General Method 3. The product did not precipitate after addition of deionized water and diethyl ether (20 mL) was added to the yellow solution and the layers were separated. The aqueous layer was re-extracted with further portions of diethyl ether (3×40 mL), the organic layers were combined, dried over magnesium sulfate, filtered and concentrated under reduced pressure to provide the title compound as a yellow solid (0.6 g, 73% yield). LC-MS: $t_R$=1.43 min, [M+H]$^+$=217. $^1$H NMR (500 MHz, DMSO-d$_6$) δ ppm: 9.47 (s, 1H), 7.38-7.13 (m, 4H), 3.58 (s, 3H), 2.19 (s, 3H).

51.4 1,4-Dimethyl-3-(2-methylphenyl)-1H-pyrazol-5-ol 1,4-Dimethyl-3-(2-methylphenyl)-1H-pyrazol-5-ol was synthesized from 2-methyl-5-(2-methylphenyl)-3-oxo-2,3-dihydro-1H-pyrazole-4-carbaldehyde according to General Method 5 (0.4 g, 68% yield). LC-MS: $t_R$=1.49 min, [M+Na]$^+$=203. $^1$H NMR (500 MHz, DMSO-d$_6$) δ ppm: 7.36-7.06 (m, 4H), 3.48 (s, 3H), 2.21 (s, 3H), 1.68 (s, 3H).

51.5 4-Bromo-1,4-dimethyl-3-(2-methylphenyl)-4,5-dihydro-1H-pyrazol-5-one

4-Bromo-1,4-dimethyl-3-(2-methylphenyl)-4,5-dihydro-1H-pyrazol-5-one was synthesized from 1,4-dimethyl-3-(2-methylphenyl)-1H-pyrazol-5-ol according to General Method 6 and was used directly in the next step assuming 100% yield. LC-MS: $t_R$=1.31 min, [M+H]$^+$=281/283.

51.6 4-{[(tert-Butoxy)carbonyl]({[(tert-butoxy)carbonyl]oxy})amino}-1,4-dimethyl-3-(2-methylphenyl)-4,5-dihydro-1H-pyrazol-5-one 4-{[(tert-Butoxy)carbonyl]({[(tert-butoxy)carbonyl]oxy})amino}-1,4-dimethyl-3-(2-methylphenyl)-4,5-dihydro-1H-pyrazol-5-one was synthesized from 4-bromo-1,4-dimethyl-3-(2-methylphenyl)-4,5-dihydro-1H-pyrazol-5-one according to General Method 8 and was chromatographed by silica gel column chromatography (0-55% ethyl acetate in heptanes) to provide the title compound as a yellow oil (0.34 g, 42% yield). LC-MS: $t_R$=2.43 min, [M+Na]$^+$=456.

51.7 4-(Hydroxyamino)-1,4-dimethyl-3-(2-methylphenyl)-4,5-dihydro-1H-pyrazol-5-one 4-(Hydroxyamino)-1,4-dimethyl-3-(2-methylphenyl)-4,5-dihydro-1H-pyrazol-5-one was synthesized from 4-

{[(tert-butoxy)carbonyl]({[(tert-butoxy)carbonyl]oxy})amino}-1,4-dimethyl-3-(2-methylphenyl)-4,5-dihydro-1H-pyrazol-5-one according to General Method 9. The residue was dissolved in DCM (20 mL) and washed with water (2×20 mL). The DCM layer was isolated, dried over magnesium sulfate, filtered and concentrated under reduced pressure to provide a yellow solid. The solid was chromatographed by silica gel column chromatography (60% ethyl acetate in heptanes) to provide the title compound as a yellow solid (0.061 g, 36% yield). LC-MS: $t_R$=1.57 min, [M+H]$^+$234. $^1$H NMR (500 MHz, DMSO-$d_6$) δ ppm: 8.06 (d, J=7.6 Hz, 1H), 7.71 (d, J=2.3 Hz, 1H), 7.36-7.21 (m, 3H), 6.37 (d, J=2.2 Hz, 1H), 3.28 (s, 3H), 2.46 (s, 3H), 1.07 (s, 3H).

Example 52

Compound 52 [4-(hydroxyamino)-4-(1-(methoxyimino)ethyl)-1-methyl-3-(4-(trifluoromethyl)phenyl)-1H-pyrazol-5(4H)-one]

52.1 1-{5-Hydroxy-1-methyl-3-[4-(trifluoromethyl)phenyl]-1H-pyrazol-4-yl}ethan-1-one 1-{5-Hydroxy-1-methyl-3-[4-(trifluoromethyl)phenyl]-1H-pyrazol-4-yl}ethan-1-one was synthesized from 1-methyl-3-[4-(trifluoromethyl)phenyl]-1H-pyrazol-5-ol (2.08 g, 8.58 mmol) according to General Method 11 to provide the title compound as dark brown solid (1.5 g, 37% yield). $^1$H NMR (500 MHz, CDCl$_3$) δ ppm: 7.75 (d, J=7.9 Hz, 2H), 7.65 (d, J=8.0 Hz, 2H), 3.74 (s, 3H), 2.14 (s, 3H).

52.2 4-[1-(Methoxyimino)ethyl]-1-methyl-3-phenyl-1H-pyrazol-5-ol

4-[1-(Methoxyimino)ethyl]-1-methyl-3-phenyl-1H-pyrazol-5-ol was synthesized from 1-{5-hydroxy-1-methyl-3-[4-(trifluoromethyl)phenyl]-1H-pyrazol-4-yl}ethan-1-one (0.6 g, 211 mmol) according to General Method 12 to provide the title compound as an off-white solid (0.56 g, 84% yield) LC-MS: $t_R$=2.14 min, [M+H]$^+$=314. $^1$H NMR (500 MHz, CDCl$_3$) δ ppm: 7.67 (d, J=7.8 Hz, 2H), 7.59 (d, J=7.9 Hz, 2H), 3.93 (s, 3H), 3.77 (s, 3H), 1.86 (s, 3H).

52.3 4-Bromo-4-[1-(methoxyimino)ethyl]-1-methyl-3-[4-(trifluoromethyl)phenyl]-4,5-dihydro-1H-pyrazol-5-one 4-Bromo-4-[1-(methoxyimino)ethyl]-1-methyl-3-[4-(trifluoromethyl)phenyl]-4,5-dihydro-1H-pyrazol-5-one was synthesized from 4-[1-(methoxyimino)ethyl]-1-methyl-3-phenyl-1H-pyrazol-5-ol (0.56 g, 1.78 mmol) according to General Method 6 to provide the title compound as a brown oil (0.77 g, 94% yield). LC-MS: $t_R$=2.46 min, [M+H]$^+$=393.

52.4 4-{[(tert-Butoxy)carbonyl]({[(tert-butoxy)carbonyl]oxy})amino}-4-[1-(methoxyimino)ethyl]-1-methyl-3-[4-(trifluoromethyl)phenyl]-4,5-dihydro-1H-pyrazol-5-one 4-{[(tert-Butoxy)carbonyl]({[(tert-butoxy)carbonyl]oxy})amino}-4-[1-(methoxyimino)ethyl]-1-methyl-3-[4-(trifluoromethyl)phenyl]-4,5-dihydro-1H-pyrazol-5-one was synthesized from 4-bromo-4-[1-(methoxyimino)ethyl]-1-methyl-3-[4-(trifluoromethyl)phenyl]-4,5-dihydro-1H-pyrazol-5-one (0.77 g, 1.68 mmol) according to General Method 8 and was chromatographed by silica gel column chromatography eluting with 10-30% ethyl acetate:heptanes to provide the title compound as an off-white solid (0.78 g, 85% yield) LC-MS: $t_R$=2.65 min, [M+Na]$^+$=567.

52.5 4-(Hydroxyamino)-4-[1-(methoxyimino)ethyl]-1-methyl-3-[4-(trifluoromethyl)phenyl]-4,5-dihydro-1H-pyrazol-5-one 4-(Hydroxyamino)-4-[1-(methoxyimino)ethyl]-1-methyl-3-[4-(trifluoromethyl)phenyl]-4,5-dihydro-1H-pyrazol-5-one was synthesized from 4-{[(tert-butoxy)carbonyl]({[(tert-butoxy)carbonyl]oxy})amino}-4-[1-(methoxyimino)ethyl]-1-methyl-3-[4-(trifluoromethyl)phenyl]-4,5-dihydro-1H-pyrazol-5-one (0.78 g, 1.43 mmol) according to General Method 9 and was chromatographed by silica gel column chromatography eluting with 20-60% ethyl acetate:heptanes to obtain a yellow solid which was washed with DCM:heptanes (1:9 vol:vol) to provide the title compound as an off-white (0.21 g, 43% yield). LC-MS: $t_R$=2.01 min, [M+H]$^+$=345. $^1$H NMR (500 MHz, DMSO-$d_6$) δ ppm: 8.09 (d, J=8.2 Hz, 2H), 7.88 (d, J=2.0 Hz, 1H), 7.82 (d, J=8.4 Hz, 2H), 6.80 (d, J=1.7 Hz, 1H), 3.71 (s, 3H), 3.35 (s, 3H), 1.72 (s, 3H).

Example 53

Compound 53 [4-(hydroxyamino)-3-(4-methoxyphenyl)-1,4-dimethyl-1H-pyrazol-5(4H)-one]

53.1 3-Methoxyphenyl)-1-methyl-4,5-dihydro-1H-pyrazol-5-one

3-Methoxyphenyl)-1-methyl-4,5-dihydro-1H-pyrazol-5-one was synthesized from ethyl 3-(4-methoxyphenyl)-3-oxopropanoate (3.05 g, 13.72 mmol) according to General Method 2 to provide the title compound as an off-white solid (2.01 g, 71% yield). LC-MS: $t_R$=1.49 min, [M+H]$^+$=204. $^1$H NMR (500 MHz, CDCl$_3$) δ ppm: 7.60 (d, J=8.9 Hz, 2H), 6.93 (d, J=8.9 Hz, 2H), 3.85 (s, 3H), 3.58 (s, 2H), 3.39 (s, 3H).

53.2 5-Hydroxy-3-(4-methoxyphenyl)-1-methyl-1H-pyrazole-4-carbaldehyde

5-Hydroxy-3-(4-methoxyphenyl)-1-methyl-1H-pyrazole-4-carbaldehyde was synthesized from 3-methoxyphenyl)-1-methyl-4,5-dihydro-1H-pyrazol-5-one (1.5 g, 7.19 mmol) according to General Method 3 to provide the title compound as a yellow solid (1.25 g, 71% yield). LC-MS: $t_R$=1.45 min, [M+H]$^+$=232. $^1$H NMR (500 MHz, DMSO-$d_6$) δ ppm: 9.68 (s, 1H), 7.86-7.71 (m, 2H), 7.03-6.90 (m, 2H), 3.80 (s, 3H), 3.58 (s, 3H).

53.3 3-(4-Methoxyphenyl)-1,4-dimethyl-1H-pyrazol-5-ol 3-(4-Methoxyphenyl)-1,4-dimethyl-1H-pyrazol-5-ol was synthesized from 5-hydroxy-3-(4-methoxyphenyl)-1-methyl-1H-pyrazole-4-carbaldehyde (1.25 g, 5.11 mmol) according to General Method 5 to provide the title compound as a yellow solid (>99.9% yield). LC-MS: $t_R$=1.45 min, [M+H]$^+$=218. $^1$H NMR (500 MHz, DMSO-$d_6$) δ ppm: 7.50 (d, J=8.7 Hz, 2H), 6.96 (d, J=8.5 Hz, 2H), 3.77 (s, 3H), 3.48 (s, 3H), 1.96 (s, 3H).

53.4 4-Bromo-3-(4-methoxyphenyl)-1,4-dimethyl-4,5-dihydro-1H-pyrazol-5-one

4-Bromo-3-(4-methoxyphenyl)-1,4-dimethyl-4,5-dihydro-1H-pyrazol-5-one was synthesized from 3-(4- methoxyphenyl)-1,4-dimethyl-1H-pyrazol-5-ol (1.5 g, 5.15 mmol) according to General Method 6 to provide the title compound as a brown oil (1.6 g, 60% yield). LC-MS: $t_R$=1.94 min, [M+H]$^+$=298.

53.5 4-{[(tert-Butoxy)carbonyl]({[(tert-butoxy)carbonyl]oxy})amino}-3-(4-methoxyphenyl)-1,4-dimethyl-4,5-dihydro-1H-pyrazol-5-one 4-{[(tert-Butoxy)carbonyl]({[(tert-butoxy)carbonyl]oxy})amino}-3-(4-methoxyphenyl)-1,4-dimethyl-4,5-dihydro-1H-pyrazol-5-one was synthesized from 4-bromo-3-(4-methoxyphenyl)-1,4-dimethyl-4,5-dihydro-1H-pyrazol-5-one (1.5 g, 3.03 mmol) according to General Method 8 to provide the title compound as a brown oil (0.95 g, 16% yield) LC-MS: $t_R$=2.36 min, [M+Na]$^+$472.

53.6 4-(Hydroxyamino)-3-(4-methoxyphenyl)-1,4-dimethyl-4,5-dihydro-1H-pyrazol-5-one 4-(Hydroxyamino)-3-(4-methoxyphenyl)-1,4-dimethyl-4,5-dihydro-1H-pyrazol-5-one was synthesized from 4-{[(tert-butoxy)carbonyl]({[(tert-butoxy)carbonyl]oxy})amino}-3-(4-methoxyphenyl)-1,4-dimethyl-4,5-dihydro-1H-pyrazol-5-one (0.95 g, 2.11 mmol) according to General Method 9 to provide the title compound as an off-white solid (0.05 g, 10% yield). LC-MS: $t_R$=1.51 min, [M+H]$^+$=250. $^1$H NMR (500 MHz, DMSO-d$_6$) δ ppm: 8.13-7.92 (m, 2H), 7.60 (d, J=2.5 Hz, 1H), 7.10-6.93 (m, 2H), 6.42 (d, J=2.5 Hz, 1H), 3.81 (s, 3H), 3.27 (s, 3H), 1.18 (s, 3H).

Example 54

Compound 54 [3-(3-chlorophenyl)-4-(hydroxyamino)-1,4-dimethyl-1H-pyrazol-5(4H)-one]

54.1 3-(3-Chlorophenyl)-1-methyl-1H-pyrazol-5-ol 3-(3-Chlorophenyl)-1-methyl-1H-pyrazol-5-ol was synthesized from 3-(3-chlorophenyl)-3-oxopropanoate (5 g, 22.06 mmol) according to General Method 2 to provide the title compound as an off-white solid (3.66 g, 79% yield) LC-MS: $t_R$=1.61 min, [M+H]$^+$=208. $^1$H NMR (500 MHz, DMSO-d$_6$) δ ppm: 11.15 (s, 1H), 7.72 (t, J=1.7 Hz, 1H), 7.66 (d, J=7.8 Hz, 1H), 7.38 (t, J=7.9 Hz, 1H), 7.34-7.19 (m, 1H), 5.87 (s, 1H), 3.57 (s, 3H).

54.2 3-(3-Chlorophenyl)-5-hydroxy-1-methyl-1H-pyrazole-4-carbaldehyde 3-(3-Chlorophenyl)-5-hydroxy-1-methyl-1H-pyrazole-4-carbaldehyde was synthesized from 3-(3-chlorophenyl)-1-methyl-1H-pyrazol-5-ol (3.6 g, 17.06 mmol) according to General Method 3 to provide the title compound as a yellow solid (4.35 g, 86% yield). LC-MS: $t_R$=1.65 min, [M+H]$^+$=236. $^1$H NMR (500 MHz, DMSO-d$_6$) δ ppm: 9.69 (s, 1H), 8.37 (s, 1H), 8.06-7.91 (m, 1H), 7.85 (m, 1H), 7.43 (dd, J=3.7, 1.6 Hz, 2H), 3.59 (s, 3H).

54.3 3-(3-Chlorophenyl)-1,4-dimethyl-1H-pyrazol-5-ol 3-(3-Chlorophenyl)-1,4-dimethyl-1H-pyrazol-5-ol was synthesized from 3-(3-chlorophenyl)-5-hydroxy-1-methyl-1H-pyrazole-4-carbaldehyde (4.35 g, 18.38 mmol) according to General Method 5 to provide the title compound as a yellow solid (>99.9% yield). LC-MS: $t_R$=1.66 min, [M+H]$^+$=222. $^1$H NMR (500 MHz, DMSO-d$_6$) δ ppm: 7.60 (t, J=1.7 Hz, 1H), 7.55 (d, J=7.8 Hz, 1H), 7.40 (t, J=7.9 Hz, 1H), 7.36-7.26 (m, 1H), 2.48 (s, 3H), 2.01 (s, 3H).

54.4 4-Bromo-3-(3-chlorophenyl)-1,4-dimethyl-4,5-dihydro-1H-pyrazol-5-one

4-Bromo-3-(3-Chlorophenyl)-1,4-dimethyl-4,5-dihydro-1H-pyrazol-5-one was synthesized from 3-(3-chlorophenyl)-1,4-dimethyl-1H-pyrazol-5-ol (4.0 g, 15.9 mmol) according to General Method 6 to provide the title compound as a brown oil (3.9 g, 82% yield). LC-MS: $t_R$=2.17 min, [M+H]$^+$=302.

54.5 4-{[(tert-Butoxy)carbonyl]({[(tert-butoxy)carbonyl]oxy})amino}-3-(3-chlorophenyl)-1,4-dimethyl-4,5-dihydro-1H-pyrazol-5-one 4-{[(tert-Butoxy)carbonyl]({[(tert-butoxy)carbonyl]oxy})amino}-3-(3-chlorophenyl)-1,4-dimethyl-4,5-dihydro-1H-pyrazol-5-one was synthesized from 4-bromo-3-(3-chlorophenyl)-1,4-dimethyl-4,5-dihydro-1H-pyrazol-5-one (3.9 g, 13.23 mmol) according to General Method 8 to provide the title compound as a yellow solid (3.5 g, 45% yield). LC-MS: $t_R$=2.60 min, [M+Na]$^+$=476.

54.6 3-(3-Chlorophenyl)-4-(hydroxyamino)-1,4-dimethyl-4,5-dihydro-1H-pyrazol-5-one 3-(3-Chlorophenyl)-4-(hydroxyamino)-1,4-dimethyl-4,5-dihydro-1H-pyrazol-5-one was synthesized from 4-{[(tert-butoxy)carbonyl]({[(tert-butoxy)carbonyl]oxy})amino}-3-(3-chlorophenyl)-1,4-dimethyl-4,5-dihydro-1H-pyrazol-5-one (3.5 g, 7.71 mmol) according to General Method 9 to provide the title compound as an off-white solid (0.9 g, 46% yield). LC-MS: $t_R$=1.7 min, [M+H]$^+$=253. $^1$H NMR (500 MHz, DMSO-d$_6$) δ ppm: 8.08 (d, J=1.8 Hz, 1H), 7.98 (dt, J=7.0, 1.7 Hz, 1H), 7.71 (d, J=2.3 Hz, 1H), 7.59-7.40 (m, 2H), 6.57 (d, J=2.4 Hz, 1H), 3.31 (s, 3H), 1.20 (s, 3H).

Example 55

Compound 55 [4-(hydroxyamino)-3-(2-methoxyphenyl)-1,4-dimethyl-1H-pyrazol-5(4H)-one]

55.1 Ethyl 3-(2-methoxyphenyl)-3-oxopropanoate

Ethyl 3-(2-methoxyphenyl)-3-oxopropanoate was synthesized from 1-(2-methoxyphenyl)ethan-1-one (7 g, 46.61 mmol) according to General Method 1 to provide the title compound as a yellow oil (8.6 g, 76% yield). LC-MS: $t_R$=1.83 min, [M+H]$^+$=222.

55.2 5-(2-Methoxyphenyl)-2-methyl-2,3-dihydro-1H-pyrazol-3-one 5-(2-Methoxyphenyl)-2-methyl-2,3-dihydro-1H-pyrazol-3-one was synthesized from ethyl 3-(2-methoxyphenyl)-3-oxopropanoate (5 g, 21.15 mmol) according to General Method 2 to provide the title compound as a yellow solid (4.77 g, 99% yield). LC-MS: $t_R$=1.34 min, [M+H]$^+$=204.95. $^1$H NMR (500 MHz, DMSO-d$_6$) δ ppm: 7.80 (dd, J=7.7, 1.5 Hz, 1H), 7.29-7.18 (m, 1H), 7.04 (d, J=8.1 Hz, 1H), 6.93 (t, J=7.5 Hz, 1H), 5.86 (s, 1H), 3.82 (s, 3H), 3.55 (s, 3H).

55.3 5-(2-Methoxyphenyl)-2-methyl-3-oxo-2,3-dihydro-1H-pyrazole-4-carbaldehyde 5-(2-Methoxyphenyl)-2-methyl-3-oxo-2,3-dihydro-1H-pyrazole-4-carbaldehyde was synthesized from 5-(2- methoxyphenyl)-2-methyl-2,3-dihydro-1H-pyrazol-3-one (4.77 g, 21.25 mmol) according to General Method 3 to provide the title compound as a yellow solid (3.49 g, 61% yield). LC-MS: $t_R$=1.32 min, [M+H]$^+$=232.95. $^1$H NMR (500 MHz, DMSO-d$_6$) δ ppm: 9.40 (s, 1H), 7.43-7.38 (m, 1H), 7.30 (dd, J=7.5, 1.7 Hz, 1H), 7.09 (d, J=8.2 Hz, 1H), 7.01-6.98 (m, 1H), 3.71 (s, 3H), 3.56 (s, 3H).

55.4
3-(2-Methoxyphenyl)-1,4-dimethyl-1H-pyrazol-5-ol 3-(2-Methoxyphenyl)-1,4-dimethyl-1H-pyrazol-5-ol was synthesized from 5-(2-methoxyphenyl)-2-methyl-3-oxo-2,3-dihydro-1H-pyrazole-4-carbaldehyde (3.49 g, 13.07 mmol) according to General Method 5 to provide the title compound as a yellow solid (>99.9% yield). LC-MS: $t_R$=1.37 min, [M+H]$^+$=218.95.

55.5 4-Bromo-3-(2-methoxyphenyl)-1,4-dimethyl-4,5-dihydro-1H-pyrazol-5-one

4-Bromo-3-(2-methoxyphenyl)-1,4-dimethyl-4,5-dihydro-1H-pyrazol-5-one was synthesized from 3-(2-methoxyphenyl)-1,4-dimethyl-1H-pyrazol-5-ol (3.98 g, 13.84 mmol) according to General Method 6 (4.3 g, 57% yield). LC-MS: $t_R$=1.88 min, [M+H]$^+$=298.

55.6 4-{[(tert-Butoxy)carbonyl]({[(tert-butoxy)carbonyl]oxy})amino}-3-(2-methoxyphenyl)-1,4-dimethyl-4,5-dihydro-1H-pyrazol-5-one 4-{[(tert-Butoxy)carbonyl]({[(tert-butoxy)carbonyl]oxy})amino}-3-(2-methoxyphenyl)-1,4-dimethyl-4,5-dihydro-1H-pyrazol-5-one was synthesized from 4-bromo-3-(2-methoxyphenyl)-1,4-dimethyl-4,5-dihydro-1H-pyrazol-5-one according to General Method 8 to provide the title compound as a yellow oil (1.97 g, 36% yield). LC-MS: $t_R$=2.22 min, [M+H]$^+$=450.

55.7 4-(Hydroxyamino)-3-(2-methoxyphenyl)-1,4-dimethyl-4,5-dihydro-1H-pyrazol-5-one 4-(Hydroxyamino)-3-(2-methoxyphenyl)-1,4-dimethyl-4,5-dihydro-1H-pyrazol-5-one was synthesized from 4-{[(tert-butoxy)carbonyl]({[(tert-butoxy)carbonyl]oxy})amino}-3-(2-methoxyphenyl)-1,4-dimethyl-4,5-dihydro-1H-pyrazol-5-one (1.97 g, 3.2 mmol) according to General Method 9 to provide the title compound as an off-white solid (0.48 g, 45% yield). LC-MS: $t_R$=1.37 min, [M+H]$^+$=250. $^1$H NMR (500 MHz, DMSO-d$_6$) δ ppm: 7.77 (d, J=7.7 Hz, 1H), 7.62 (d, J=2.2 Hz, 1H), 7.43 (t, J=7.1 Hz, 1H), 7.12 (d, J=8.4 Hz, 1H), 7.02 (t, J=7.5 Hz, 1H), 6.25 (d, J=2.2 Hz, 1H), 3.80 (s, 3H), 3.26 (s, 3H), 1.07 (s, 3H).

Example 56

Compound 56 [4-(Hydroxyamino)-1,4-dimethyl-3-(2-(trifluoromethoxy)phenyl)-1H-pyrazol-5(4H)-one]

56.1 Methyl 3-oxo-3-[2-(trifluoromethoxy)phenyl]propanoate

Methyl 3-oxo-3-[2-(trifluoromethoxy)phenyl]propanoate was synthesized from 1-[2-(trifluoromethoxy)phenyl]ethan-1-one and dimethyl carbonate according to General Method 1 and was chromatographed by column chromatography eluting with ethyl acetate:hexane (2:98 vol:vol) to provide the title compound as a yellow oil (6.2 g, 48% yield) which was used directly in the synthesis of the corresponding pyrazolone.

56.2 1-Methyl-3-[2-(trifluoromethoxy)phenyl]-1H-pyrazol-5-ol

To a stirred solution of methyldiazanediium sulfate (9.75 g, 0.069 mol) in ethanol (100 mL) was added triethylamine (9.2 mL, 0.092 mol) followed by a solution of methyl 3-oxo-3-[2-(trifluoromethoxy)phenyl]propanoate (12 g, 0.0458 mol) in ethanol 920 mL). The reaction mixture was stirred at 80° C. for 16 hours, whereupon TLC showed complete consumption of the starting material. The solvent was removed under reduced pressure and the reaction mixture was extracted into ethyl acetate (2×150 mL) and washed with water (150 mL). The organic layers were combined, washed with brine (50 mL), dried over sodium sulfate, filtered, and concentrated under reduced pressure to provide the product, which was chromatographed by column chromatography eluting with 2% acetone:DCM (7.7 g, 78% yield). $^1$H NMR (400 MHz, DMSO) δ ppm: 11.11 (s, 1H), 8.00-7.95 (m, 1H), 7.42-7.36 (m, 3H), 5.80 (s, 1H), 3.60 (s, 3H).

56.3 5-Hydroxy-1-methyl-3-[2-(trifluoromethoxy)phenyl]-1H-pyrazole-4-carbaldehyde 5-Hydroxy-1-methyl-3-[2-(trifluoromethoxy)phenyl]-1H-pyrazole-4-carbaldehyde was synthesized from 1-methyl-3-[2-(trifluoromethoxy)phenyl]-1H-pyrazol-5-ol according to General Method 3 and was used directly in the reduction according to General Method 5 (5.1 g, 60% yield). LC-MS: $t_R$=0.89 min, [M+H]$^+$=287.

56.4 1,4-Dimethyl-3-[2-(trifluoromethoxy)phenyl]-1H-pyrazol-5-ol 1,4-Dimethyl-3-[2-(trifluoromethoxy)phenyl]-1H-pyrazol-5-ol was synthesized from 5-hydroxy-1-methyl-3-[2-(trifluoromethoxy)phenyl]-1H-pyrazole-4-carbaldehyde according to General Method 5. The method deviated from General Method 5 during the workup because water was added to the solid formed, the suspension was basified by the addition of sodium bicarbonate, and the pyrazolone was extracted into ethyl acetate (2×20 mL). The combined organic layer was dried over sodium sulfate, filtered and concentrated under reduced pressure to provide the product which was chromatographed by silica gel column chromatography eluting with ethyl acetate:hexane (1:9 vol:vol) to provide the product as a yellow solid (1.1 g, 53% yield). $^1$H NMR (400 MHz, DMSO) δ ppm: 10.19 (s, 1H), 7.54-7.46 (m, 2H), 7.42 (t, J=6.7 Hz, 2H), 3.58 (s, 3H), 1.79 (s, 3H).

56.5 4-Bromo-1,4-dimethyl-3-[2-(trifluoromethoxy)phenyl]-4,5-dihydro-1H-pyrazol-5-one 4-Bromo-1,4-dimethyl-3-[2-(trifluoromethoxy)phenyl]-4,5-dihydro-1H-pyrazol-5-one was synthesized from 1,4-dimethyl-3-[2-(trifluoromethoxy)phenyl]-1H-pyrazol-5-ol according to General Method 6 and was used directly in the next step without further analysis (2.4 g, 99% yield).

56.6 4-{[(tert-Butoxy)carbonyl]({[(tert-butoxy)carbonyl]oxy})amino}-1,4-dimethyl-3-[2-(trifluoromethoxy)phenyl]-4,5-dihydro-1H-pyrazol-5-one 4-{[(tert-Butoxy)carbonyl]({[(tert-butoxy)carbonyl]oxy})amino}-1,4-dimethyl-3-[2-(trifluoro methoxy)phenyl]-4,5-dihydro-1H-pyrazol-5-one was synthesized from 4-bromo-1,4-dimethyl-3-[2-(trifluoromethoxy)phenyl]-4,5-dihydro-1H-pyrazol-5-one according to General Method 8 and was chromatographed by silica gel column chromatography eluting with 10% ethyl acetate:heptanes to provide the title compound as a foam (1.9 g, 56% yield). $^1$H NMR (400 MHz, CDCl$_3$) δ ppm: 7.50-7.42 (m, 2H), 7.42-7.33 (m, 2H), 3.43 (s, 3H), 1.57 (d, J=2.7 Hz, 3H), 1.55-1.48 (m, 18H).

56.7 4-(Hydroxyamino)-1,4-dimethyl-3-[2-(trifluoromethoxy)phenyl]-4,5-dihydro-1H-pyrazol-5-one 4-(Hydroxyamino)-1,4-dimethyl-3-[2-(trifluoromethoxy)phenyl]-4,5-dihydro-1H-pyrazol-5-one was synthesized from 4-{[(tert-butoxy)carbonyl]({[(tert-butoxy)carbonyl]oxy})amino}-1,4-dimethyl-3-[2-(trifluoromethoxy)phenyl]-4,5-dihydro-1H-pyrazol-5-one according to General Method 9 and was chromatographed by silica gel column chromatography eluting with ethyl acetate:hexane (3:2 vol:vol) to provide the title compound as a white solid (0.60 g, 52% yield). $^1$H NMR (400 MHz, DMSO-d$_6$) δ ppm: 8.30 (dd, J=7.8, 1.8 Hz, 1H), 7.78 (d, J=2.3 Hz, 1H), 7.62-7.56 (m, 1H), 7.55-7.46 (m, 2H), 6.54 (d, J=2.4 Hz, 1H), 3.28 (s, 3H), 1.07 (s, 3H).

Example 57

Compound 57 [3-(2,3-dichlorophenyl)-4-(hydroxyamino)-1,4-dimethyl-1H-pyrazol-5(4H)-one]

57.1 Ethyl 3-(2,3-dichlorophenyl)-3-oxopropanoate

To a stirred solution of di-iso-propylamine (8.7 g, 0.086 mol) in THF (100 mL) cooled to −78° C. was added n-BuLi (49.2 mL of a 1.6 M solution in hexanes, 0.079 mol). Stirring was continued for 30 minutes after which time, freshly distilled ethyl acetate (6.94 g, 0.079 mol) was added drop wise at −78° C. The resulting solution was stirred for 30 minutes whereupon 2,3 dichloro benzoyl chloride (15 g, 0.072 mol) was added as a solution in THF (150 mL). The reaction mixture was stirred at −65 to −70° C. for 30 minutes and then terminated by the addition of 1 N HCl solution (until acidic). The resulting bi-phasic mixture was allowed to warm to a temperature of about 25° C. before being diluted with ethyl acetate (250 mL) and the organic layer was collected. The aqueous layer was extracted with ethyl acetate (2×150 mL) and the organic layers were combined, washed with brine (30 mL), dried over sodium sulfate, filtered and concentrated under reduced pressure to provide the beta-keto ester which was used directly in the next step.

57.2 3-(2,3-Dichlorophenyl)-1-methyl-1H-pyrazol-5-ol

To a solution of methyldiazanediium sulfate (14.7 g, 0.103 mol) in ethanol (90 mL) and triethylamine (19.2 mL, 0.138 mol) was added ethyl 3-(2,3-dichlorophenyl)-3-oxopropanoate (18 g, 0.069 mol) as a solution in ethanol (90 mL) at a temperature of about 25° C. The reaction mixture was heated to 80° C. for 2 hours, after which time TLC showed complete consumption of the starting material. The solvent was removed under reduced pressure and the resulting slurry was added to water (150 mL) and extracted with ethyl acetate (2×150 mL). The organic layers were combined, washed with brine (50 mL), dried over sodium sulfate, filtered and concentrated under reduced pressure to provide the cyclised product, which was chromatographed by silica gel column chromatography eluting with 20-25% ethyl acetate:hexane (5.6 g, 33.4% yield) $^1$H NMR (400 MHz, DMSO) δ ppm: 11.13 (s, 1H), 7.68 (dd, J=7.8, 1.6 Hz, 1H), 7.58 (dd, J=8.0, 1.6 Hz, 1H), 7.36 (t, J=7.9 Hz, 1H), 5.87 (s, 1H), 3.59 (s, 3H).

57.3 3-(2,3-Dichlorophenyl)-5-hydroxy-1-methyl-1H-pyrazole-4-carbaldehyde 3-(2,3-Dichlorophenyl)-5-hydroxy-1-methyl-1H-pyrazole-4-carbaldehyde was synthesized from 3-(2,3-dichlorophenyl)-1-methyl-1H-pyrazol-5-ol according to General Method 3. The method deviated from General Method 3 during the workup because the aqueous layer was extracted with ethyl acetate (3×250 mL), the organic layers were combined and washed with water (2×50 mL), dried over sodium sulfate, filtered, and concentrated under reduced pressure to provide the desired compound, which was triturated with pentane (2×100 mL) to provide a yellow solid (4.4 g, 78.9% yield). $^1$H NMR (400 MHz, DMSO) δ ppm: 9.56 (s, 1H), 7.69 (dd, J=7.8, 1.8 Hz, 1H), 7.40 (t, J=7.7 Hz, 1H), 7.35 (dd, J=7.6, 1.8 Hz, 1H), 3.61 (s, 3H).

57.4 3-(2,3-Dichlorophenyl)-1,4-dimethyl-1H-pyrazol-5-ol 3-(2,3-Dichlorophenyl)-1,4-dimethyl-1H-pyrazol-5-ol was synthesized from the corresponding aldehyde according to General Method 5. The method deviated from General Method 5 during the workup because water (50 mL) was added to the solid formed, the suspension was basified by the addition of sodium bicarbonate, and the pyrazolone was extracted into ethyl acetate (3×100 mL). The combined organic layer was dried over sodium sulfate, filtered and concentrated under reduced pressure to provide the product which was chromatographed by silica gel column chromatography eluting with 8-10% ethyl acetate:hexane to provide the product as a off white solid (3.3 g, 74% yield). $^1$H NMR (400 MHz, DMSO) δ ppm: 10.53 (s, 1H), 7.63 (d, J=7.5 Hz, 1H), 7.36 (t, J=7.8 Hz, 1H), 7.30 (d, J=6.6 Hz, 1H), 3.54 (s, 3H), 1.72 (s, 3H).

57.5 4-Bromo-3-(2,3-dichlorophenyl)-1,4-dimethyl-4,5-dihydro-1H-pyrazol-5-one 4-Bromo-3-(2,3-dichlorophenyl)-1,4-dimethyl-4,5-dihydro-1H-pyrazol-5-one was synthesized from 3-(2,3-dichlorophenyl)-1,4-dimethyl-1H-pyrazol-5-ol according to General Method 6 and was used directly in the next step without further analysis (0.1 g, 98% yield).

57.6 4-{[(tert-Butoxy)carbonyl]({[(tert-butoxy)carbonyl]oxy})amino}-3-(2,3-dichlorophenyl)-1,4-dimethyl-4,5-dihydro-1H-pyrazol-5-one 4-{[(tert-Butoxy)carbonyl]({[(tert-butoxy)carbonyl]oxy})amino}-3-(2,3-dichlorophenyl)-1,4-dimethyl-4,5-dihydro-1H-pyrazol-5-one was synthesized from 4-bromo-3-(2,3-dichlorophenyl)-1,4-dimethyl-4,5-dihydro-1H-pyrazol-5-one according to General Method 8 and chromatographed by silica gel column chromatography eluting with 7-10% ethyl acetate:heptanes, (0.12 g, 82% yield). $^1$H NMR (400 MHz, DMSO) δ ppm: 7.85-7.76 (m, 1H), 7.61-7.42 (m, 1H), 7.27-7.08 (m, 1H), 3.31 (s, 3H), 1.49-1.37 (m, 18H), 1.36 (s, 3H).

57.7 3-(2,3-Dichlorophenyl)-4-(hydroxyamino)-1,4-dimethyl-4,5-dihydro-1H-pyrazol-5-one 3-(2,3-Dichlorophenyl)-4-(hydroxyamino)-1,4-dimethyl-4,5-dihydro-1H-pyrazol-5-one was synthesized from 4-{[(tert-butoxy)carbonyl]({[(tert-butoxy)carbonyl]oxy})amino}-3-(2,3-dichlorophenyl)-1,4-dimethyl-4,5-dihydro-1H-pyrazol-5-one according to General Method 9 and was triturated from DCM:pentane (1:100 vol:vol) to provide the desired compound as a white solid (0.7 g, 53% yield). $^1$H NMR (400 MHz, DMSO) δ ppm: 7.90-7.81 (m, 2H), 7.76 (dd, J=8.1, 1.5 Hz, 1H), 7.48 (t, J=7.9 Hz, 1H), 6.49 (d, J=2.1 Hz, 1H), 3.28 (s, 3H), 1.04 (s, 3H).

Example 58

Compound 58 [3-(2,4-Dichlorophenyl)-4-(hydroxyamino)-1,4-dimethyl-1H-pyrazol-5(4H)-one]

58.1 Methyl 3-(2,4-dichlorophenyl)-3-oxopropanoate

Methyl 3-(2,4-dichlorophenyl)-3-oxopropanoate was synthesized from the corresponding acetophenone and dimethyl carbonate according to General Method 1 and was triturated using DCM:pentane (1:4 vol:vol) to provide the desired ester as a yellow solid (15 g, >99.9 yield). $^1$H NMR (400 MHz, DMSO) δ ppm: 7.85 (d, J=8.4 Hz, 1H), 7.78 (d, J=2.0 Hz, 1H), 7.63-7.57 (m, 1H), 4.19 (s, 2H), 3.65 (s, 3H).

58.2 3-(2,4-Dichlorophenyl)-1-methyl-1H-pyrazol-5-ol

To the suspension of methyl hydrazine sulfate (8.4 g, 59.5 mmol) in ethanol (80 mL) was added triethylamine (8.0 g, 79.33 mmol) dropwise. The reaction was stirred for 10 minutes before methyl 3-(2,4-dichlorophenyl)-3-oxopropanoate (10 g, 39.66 mmol) was added and the reaction mixture was heated at 70° C. for 2 hours. The reaction was cooled to a temperature of about 25° C. and concentrated under reduced pressure. The product was chromatographed by silica gel column chromatography eluting with 25% ethyl acetate:hexane to provide the title compound as an off white solid (7 g, 72% yield). $^1$H NMR (400 MHz, DMSO) δ ppm: 11.15 (s, 1H), 7.79 (d, J=8.5 Hz, 1H), 7.63 (d, J=2.2 Hz, 1H), 7.43 (dd, J=8.5, 2.2 Hz, 1H), 5.91 (s, 1H), 3.57 (d, J=20.0 Hz, 3H).

58.3 3-(2,4-Dichlorophenyl)-5-hydroxy-1-methyl-1H-pyrazole-4-carbaldehyde 3-(2,4-Dichlorophenyl)-5-hydroxy-1-methyl-1H-pyrazole-4-carbaldehyde was synthesized from 3-(2,4-dichlorophenyl)-1-methyl-1H-pyrazol-5-ol according to General Method 3. The method deviates from General Method 3 in the work up. The reaction was extracted in to ethyl acetate (200 mL) and washed with water (2×50 mL). The organic layer was washed with brine and dried over sodium sulfate, filtered and concentrated under reduced pressure to provide the title compound as a yellow solid (6.0 g, 75% yield).

58.4 3-(2,4-Dichlorophenyl)-1,4-dimethyl-1H-pyrazol-5-ol 3-(2,4-Dichlorophenyl)-1,4-dimethyl-1H-pyrazol-5-ol was synthesized from 3-(2,4-dichlorophenyl)-5-hydroxy-1-methyl-1H-pyrazole-4-carbaldehyde according to General Method 5. The method deviated from General Method 5 during the workup because water (50 mL) was added to the solid formed, the suspension was basified by the addition of sodium bicarbonate, and the pyrazolone was extracted into ethyl acetate (3×100 mL). The combined organic layer was dried over sodium sulfate, filtered and concentrated under reduced pressure to provide desired product as a yellow solid (4.5 g, 68% yield). $^1$H NMR (400 MHz, DMSO) δ ppm: 10.28 (s, 1H), 7.66 (d, J=2.0 Hz, 1H), 7.49-7.38 (m, 1H), 7.34 (d, J=8.3 Hz, 1H), 3.55 (s, 3H), 1.74 (s, 3H).

58.5 4-Bromo-3-(2,4-dichlorophenyl)-1,4-dimethyl-4,5-dihydro-1H-pyrazol-5-one 4-Bromo-3-(2,4-dichlorophenyl)-1,4-dimethyl-4,5-dihydro-1H-pyrazol-5-one was synthesized from 3-(2,4-dichlorophenyl)-1,4-dimethyl-1H-pyrazol-5-ol according to General Method 6 and was used directly in the next step without further analysis (4.0 g, 98% yield).

58.6 4-{[(tert-Butoxy)carbonyl]({[(tert-butoxy)carbonyl]oxy})amino}-3-(2,4-dichlorophenyl)-1,4-dimethyl-4,5-dihydro-1H-pyrazol-5-one 4-{[(tert-Butoxy)carbonyl]({[(tert-butoxy)carbonyl]oxy})amino}-3-(2,4-dichlorophenyl)-1,4-dimethyl-4,5-dihydro-1H-pyrazol-5-one was synthesized from 4-bromo-3-(2,4-dichlorophenyl)-1,4-dimethyl-4,5-dihydro-1H-pyrazol-5-one according to General Method 8 and was chromatographed by silica gel column chromatography eluting with 10% ethyl acetate in hexane. The title compound was isolated as a yellow oil (2.5 g 43% yield) and was taken on to the synthesis of 3-(2,4-dichlorophenyl)-4-(hydroxyamino)-1,4-dimethyl-4,5-dihydro-1H-pyrazol-5-one without any additional analysis.

58.7 3-(2,4-Dichlorophenyl)-4-(hydroxyamino)-1,4-dimethyl-4,5-dihydro-1H-pyrazol-5-one 3-(2,4-Dichlorophenyl)-4-(hydroxyamino)-1,4-dimethyl-4,5-dihydro-1H-pyrazol-5-one was synthesized from 4-{[(tert-butoxy)carbonyl]({[(tert-butoxy)carbonyl]oxy})amino}-3-(2,4-dichlorophenyl)-1,4-dimethyl-4,5-dihydro-1H-pyrazol-5-one according to General Method 9 and was chromatographed by silica gel column chromatography eluting with ethyl acetate:hexane (3:2 vol:vol) to provide the title compound as an off white solid (0.38 g, 53% yield). $^1$H NMR (400 MHz, DMSO) δ ppm: 8.01 (d, J=8.5 Hz, 1H), 7.89 (s, 1H), 7.80 (d, J=2.1 Hz, 1H), 7.60 (dd, J=8.4, 2.1 Hz, 1H), 6.55 (s, 1H), 3.31 (s, 3H), 1.06 (s, 3H).

Example 59

Compound 59 [4-(hydroxyamino)-1,4-dimethyl-3-(4-(trifluoromethoxy)phenyl)-1H-pyrazol-5(4H)-one]

59.1 Methyl 3-oxo-3-[4-(trifluoromethoxy)phenyl]propanoate

Methyl 3-oxo-3-[4-(trifluoromethoxy)phenyl]propanoate was synthesized from the corresponding acetophenone and dimethyl carbonate according to General Method 1 and was chromatographed by silica gel column chromatography eluting with 2% ethyl acetate in hexane to provide the title compound as a yellow oil (6.3 g, 33% yield). ¹H NMR (400 MHz, DMSO) δ ppm: 8.11-8.06 (m, 2H), 7.57-7.50 (m, 2H), 4.25 (s, 2H), 3.64 (s, 3H).

59.2 1-Methyl-3-[4-(trifluoromethoxy)phenyl]-1H-pyrazol-5-ol

To a solution of methyl 3-oxo-3-[4-(trifluoromethoxy) phenyl]propanoate (6.1 g, 23.27 mmol) in ethanol (60 mL) was sequentially added methyldiazanediium sulfate (4.96 g, 34.9 mmol) and triethylamine (6.49 mL, 46.53 mmol) and the resulting reaction was heated to 80° C. for 18 hours. After which time, the reaction mixture was concentrated under reduced pressure and the desired compound was isolated by chromatography using silica gel column chromatography eluting with 3% acetone in DCM to provide the title compound as a white solid (4.9 g, 81% yield). ¹H NMR (400 MHz, DMSO) δ ppm: 11.09 (s, 1H), 7.83-7.75 (m, 2H), 7.32 (d, J=8.1 Hz, 2H), 5.82 (s, 1H), 3.56 (s, 3H).

59.3 5-Hydroxy-1-methyl-3-[4-(trifluoromethoxy)phenyl]-1H-pyrazole-4-carbaldehyde 5-Hydroxy-1-methyl-3-[4-(trifluoromethoxy)phenyl]-1H-pyrazole-4-carbaldehyde was synthesized from 1-methyl-3-[4-(trifluoromethoxy)phenyl]-1H-pyrazol-5-ol according to General Method 3. The method deviated from General Method 3 during the workup because the orange yellow precipitate formed by addition of water was dissolved into ethyl acetate, the aqueous was extracted with ethyl acetate (3×20 mL), dried over sodium sulfate, filtered, and concentrated under reduced pressure. The title compound was isolated as a yellow solid by triturating with DCM:pentane (1:1 vol:vol) (3.3 g, 74% yield). ¹H NMR (400 MHz, DMSO) δ ppm: 9.71 (s, 1H), 7.95 (d, J=8.7 Hz, 2H), 7.39 (d, J=8.0 Hz, 2H), 3.60 (s, 3H).

59.4 1,4-Dimethyl-3-[4-(trifluoromethoxy)phenyl]-1H-pyrazol-5-ol 1,4-Dimethyl-3-[4-(trifluoromethoxy)phenyl]-1H-pyrazol-5-ol was synthesized from 5-hydroxy-1-methyl-3-[4-(trifluoromethoxy)phenyl]-1H-pyrazole-4-carbaldehyde according to General Method 5. The method deviated from General Method 5 during the workup because water (30 mL) was added to the solid formed, the suspension was basified by the addition of sodium bicarbonate, and the pyrazolone was extracted into ethyl acetate (3×100 mL). The combined organic layers were washed with water (30 mL), dried over sodium sulfate, filtered and concentrated under reduced pressure. The resulting solid was triturated with n-pentane to provide the title compound as a white solid (1.7 g, 64% yield). ¹H NMR (400 MHz, DMSO) δ ppm: 10.23 (s, 1H), 7.74-7.67 (m, 2H), 7.37 (d, J=8.0 Hz, 2H), 3.57 (s, 3H), 2.01 (d, J=15.4 Hz, 3H).

59.5 4-Bromo-1,4-dimethyl-3-[4-(trifluoromethoxy)phenyl]-4,5-dihydro-1H-pyrazol-5-one 4-Bromo-1,4-dimethyl-3-[4-(trifluoromethoxy)phenyl]-4,5-dihydro-1H-pyrazol-5-one was synthesized from 1,4-dimethyl-3-[4-(trifluoromethoxy)phenyl]-1H-pyrazol-5-ol according to General Method 6 and was used directly in the next step without further analysis (0.7 g, 98% yield).

59.6 4-{[(tert-Butoxy)carbonyl]({[(tert-butoxy)carbonyl]oxy})amino}-1,4-dimethyl-3-[4-(trifluoromethoxy)phenyl]-4,5-dihydro-1H-pyrazol-5-one 4-{[(tert-Butoxy)carbonyl]({[(tert-butoxy)carbonyl]oxy})amino}-1,4-dimethyl-3-[4-(trifluoromethoxy)phenyl]-4,5-dihydro-1H-pyrazol-5-one was synthesized from the corresponding bromide according to General Method 8 and was chromatographed by silica gel column chromatography eluting with 7-10% ethyl acetate:hexanes to provide an off white solid (0.7 g, 70% yield). ¹H NMR (400 MHz, DMSO) δ ppm: 8.25 (d, J=8.7 Hz, 2H), 7.49 (d, J=8.3 Hz, 2H), 3.33 (s, 3H), 1.53 (s, 9H), 1.24 (s, 3H), 1.23 (s, 9H).

59.7 4-(Hydroxyamino)-1,4-dimethyl-3-[4-(trifluoromethoxy)phenyl]-4,5-dihydro-1H-pyrazol-5-one 4-(Hydroxyamino)-1,4-dimethyl-3-[4-(trifluoromethoxy)phenyl]-4,5-dihydro-1H-pyrazol-5-one was synthesized from 4-{[(tert-butoxy)carbonyl]({[(tert-butoxy)carbonyl]oxy})amino}-1,4-dimethyl-3-[4-(trifluoromethoxy)phenyl]-4,5-dihydro-1H-pyrazol-5-one according to General Method 9 and was chromatographed by reverse phase HPLC to provide the title compound as a white solid (0.03 g, 7% yield). ¹H NMR (400 MHz, DMSO) δ ppm: 8.17 (d, J=9.0 Hz, 2H), 7.66 (d, J=2.6 Hz, 1H), 7.47 (s, 2H), 6.55 (d, J=2.6 Hz, 1H), 3.30 (s, 3H), 1.21 (s, 3H).

Example 60

Compound 60 [4-(hydroxyamino)-1,4-dimethyl-3-(2-(trifluoromethyl)phenyl)-1H-pyrazol-5(4H)-one]

60.1 2-Methyl-5-[2-(trifluoromethyl)phenyl]-2,3-dihydro-1H-pyrazol-3-one

2-Methyl-5-[2-(trifluoromethyl)phenyl]-2,3-dihydro-1H-pyrazol-3-one was synthesized from methyl 3-oxo-3-[2-(trifluoromethyl)phenyl]propanoate according to General Method 2. Once the starting material had been consumed, the reaction mixture was allowed to cool to a temperature of about 25° C. and the resulting solid was triturated with ethyl acetate:heptanes (1:3 vol:vol), followed by ethyl acetate to provide a white solid by filtration. The filtrate was reduced under reduced pressure and triturated with ethyl acetate to provide additional white solid and the process was repeated once more. The solids were combined to provide the title compound as a white solid (0.94 g, 19% yield). LC-MS: $t_R$=1.58 min, [M+H]⁺=243. ¹H NMR (500 MHz, DMSO-$d_6$) δ ppm: 7.75 (d, J=7.9 Hz, 1H), 7.66-7.63 (m, 2H), 7.52 (dt, J=9.0, 4.6 Hz, 1H), 5.56 (s, 1H), 3.56 (s, 3H).

60.2 2-Methyl-3-oxo-5-[2-(trifluoromethyl)phenyl]-2,3-dihydro-1H-pyrazole-4-carbaldehyde 2-Methyl-3-oxo-5-[2-(trifluoromethyl)phenyl]-2,3-dihydro-1H-pyrazole-4-carbaldehyde was synthesized from 2-methyl-5-[2-(trifluoromethyl)phenyl]-2,3-dihydro-1H-pyrazol-3-one according to General Method 3. Once complete, the reaction mixture was cooled and diluted with water (10 mL). It was allowed to stand at a temperature of about 25° C. for 41 hours. The product was extracted into diethyl ether (3×30 mL), dried over magnesium sulfate, filtered and concentrated under reduced pressure to provide an oil. The oil was chromatographed by silica gel column chromatography (ethyl acetate in heptanes) to provide the title compound as a brown solid (0.23 g, 17% yield). LC-MS: $t_R$=1.53 min, [M+H]⁺=271. ¹H NMR (500 MHz, DMSO-d₆) δ ppm: 9.45 (s, 1H), 7.79 (d, J=7.7 Hz, 1H), 7.73-7.58 (m, 2H), 7.43 (d, J=7.4 Hz, 1H), 3.56 (s, 3H).

60.3 1,4-Dimethyl-3-[2-(trifluoromethyl)phenyl]-1H-pyrazol-5-ol 1,4-Dimethyl-3-[2-(trifluoromethyl)phenyl]-1H-pyrazol-5-ol was synthesized from 2-methyl-3-oxo-5-[2-(trifluoromethyl)phenyl]-2,3-dihydro-1H-pyrazole-4-carbaldehyde according to General Method 5 (0.27 g, 88% yield, containing 30% w/w acetic acid). LC-MS: $t_R$=1.54 min, [M+H]⁺ =257. ¹H NMR (500 MHz, DMSO-d₆) δ ppm: 7.77 (d, J=7.7 Hz, 1H), 7.66 (t, J=7.4 Hz, 1H), 7.57 (d, J=7.6 Hz, 1H), 7.35 (d, J=7.2 Hz, 1H), 3.50 (s, 3H), 1.65 (s, 3H).

60.4 4-Bromo-1,4-dimethyl-3-[2-(trifluoromethyl)phenyl]-4,5-dihydro-1H-pyrazol-5-one 4-Bromo-1,4-dimethyl-3-[2-(trifluoromethyl)phenyl]-4,5-dihydro-1H-pyrazol-5-one was synthesized from 1,4-dimethyl-3-[2-(trifluoromethyl)phenyl]-1H-pyrazol-5-ol according to General Method 6 and was used directly in the next step assuming 100% yield. LC-MS: $t_R$=1.39 min, [M+H]⁺=335/337.

60.5 4-{[(tert-Butoxy)carbonyl]({[(tert-butoxy)carbonyl]oxy})amino}-1,4-dimethyl-3-[2-(trifluoromethyl)phenyl]-4,5-dihydro-1H-pyrazol-5-one 4-{[(tert-butoxy)carbonyl]({[(tert-butoxy)carbonyl]oxy})amino}-1,4-dimethyl-3-[2-(trifluoromethyl)phenyl]-4,5-dihydro-1H-pyrazol-5-one was synthesized from 4-bromo-1,4-dimethyl-3-[2-(trifluoromethyl)phenyl]-4,5-dihydro-1H-pyrazol-5-one according to General Method 8 and was chromatographed by silica gel chromatography (ethyl acetate in heptanes) to provide the title product as a pale yellow oil (0.12 g, 24% yield). LC-MS: $t_R$=2.40 min, [M+Na]⁺=510.

60.6 4-(Hydroxyamino)-1,4-dimethyl-3-[2-(trifluoromethyl)phenyl]-4,5-dihydro-1H-pyrazol-5-one 4-(Hydroxyamino)-1,4-dimethyl-3-[2-(trifluoromethyl)phenyl]-4,5-dihydro-1H-pyrazol-5-one was synthesized from 4-{[(tert-butoxy)carbonyl]({[(tert-butoxy)carbonyl]oxy})amino}-1,4-dimethyl-3-[2-(trifluoromethyl)phenyl]-4,5-dihydro-1H-pyrazol-5-one according to General Method 9. The residue was re-dissolved in DCM (20 mL) and washed with deionized water (3×20 mL) and brine (20 mL). The DCM layer was isolated, dried over magnesium sulfate, filtered and concentrated under reduced pressure to provide the title product as a pale orange solid (0.05 g, 63% yield). LC-MS: $t_R$=1.67 min, [M+H]⁺=288. ¹H NMR (500 MHz, CDCl₃) δ ppm: 7.91 (d, J=7.7 Hz, 1H), 7.84 (d, J=7.9 Hz, 1H), 7.66 (t, J=7.5 Hz, 1H), 7.59 (t, J=7.7 Hz, 1H), 5.68 (s, 1H), 4.95 (s, 1H), 3.44 (s, 3H), 1.17 (s, 3H).

Example 61

Compound 61 [4-(hydroxyamino)-4-methyl-1-phenyl-3-(trifluoromethyl)-1H-pyrazol-5(4H)-one]

61.1 5-Hydroxy-1-phenyl-3-(trifluoromethyl)-1H-pyrazole-4-carbaldehyde

5-Hydroxy-1-phenyl-3-(trifluoromethyl)-1H-pyrazole-4-carbaldehyde was synthesized from 2-phenyl-5-(trifluoromethyl)-2,4-dihydro-3H-pyrazol-3-one (1 g, 4.38 mmol) according to General Method 4 to provide the title compound as a yellow solid (1.07 g, 87% yield). LC-MS: $t_R$=1.63 min, [M+H]⁺=256. ¹H NMR (250 MHz, DMSO-d₆) δ ppm: 9.59 (s, 1H), 7.82 (d, J=7.9 Hz, 2H), 7.49 (d, J=7.7 Hz, 2H), 7.31 (t, J=7.4 Hz, 1H).

61.2 4-Methyl-1-phenyl-3-(trifluoromethyl)-1H-pyrazol-5-ol

4-Methyl-1-phenyl-3-(trifluoromethyl)-1H-pyrazol-5-ol was synthesized from 5-hydroxy-1-phenyl-3-(trifluoromethyl)-1H-pyrazole-4-carbaldehyde (1.05 g, 3.77 mmol) according to General Method 5 to provide the title compound as a brown solid (>99.9% yield). LC-MS: $t_R$=1.96 min, [M+H]⁺=242. ¹H NMR (500 MHz, DMSO-d₆) δ ppm: 7.71 (d, J=7.8 Hz, 2H), 7.48 (t, J=7.7 Hz, 2H), 7.34 (t, J=7.2 Hz, 1H), 1.99 (d, J=4.3 Hz, 3H).

61.3 4-Bromo-4-methyl-1-phenyl-3-(trifluoromethyl)-4,5-dihydro-1H-pyrazol-5-one 4-Bromo-4-methyl-1-phenyl-3-(trifluoromethyl)-4,5-dihydro-1H-pyrazol-5-one was synthesized from 4-methyl-1-phenyl-3-(trifluoromethyl)-1H-pyrazol-5-ol (1.1 g, 4.09 mmol) according to General Method 6 and was used directly in the next step without further analysis (1.35 g, 77% yield).

61.4 4-{[(tert-Butoxy)carbonyl]({[(tert-butoxy)carbonyl]oxy})amino}-4-methyl-1-phenyl-3-(trifluoromethyl)-4,5-dihydro-1H-pyrazol-5-one 4-{[(tert-Butoxy)carbonyl]({[(tert-butoxy)carbonyl]oxy})amino}-4-methyl-1-phenyl-3-(trifluoromethyl)-4,5-dihydro-1H-pyrazol-5-one was synthesized from 4-bromo-4-methyl-1-phenyl-3-(trifluoromethyl)-4,5-dihydro-1H-pyrazol-5-one (1.35 g, 4.2 mmol) according to General Method 8 to provide the title compound as a yellow oil (1.29 g, 55% yield). LC-MS: $t_R$=2.48 min, [M+Na]⁺=496.

61.5 4-(Hydroxyamino)-4-methyl-1-phenyl-3-(trifluoromethyl)-4,5-dihydro-1H-pyrazol-5-one 4-(Hydroxyamino)-4-methyl-1-phenyl-3-(trifluoromethyl)-4,5-dihydro-1H-pyrazol-5-one was synthesized from 4-{[(tert-butoxy)carbonyl]({[(tert-butoxy)carbonyl]oxy})amino}-4-methyl-1-phenyl-3-(trifluoromethyl)-4,5-dihydro-1H-pyrazol-5-one (1.29 g, 2.05 mmol) according to General Method 9 to provide the title compound as an off-white solid (0.41 g, 73% yield). LC-MS: $t_R$=1.81 min, [M+H]⁺=273. ¹H NMR (500 MHz, DMSO-d₆) δ ppm: 7.98 (s, 1H), 7.80-7.69 (m, 2H), 7.50 (t, J=8.0 Hz, 2H), 7.30 (t, J=7.4 Hz, 1H), 6.85 (s, 1H), 1.38 (s, 3H).

Example 62

Compound 62 [3-(2-ethoxy-4-fluorophenyl)-4-(hydroxyamino)-1,4-dimethyl-1H-pyrazol-5(4H)-one]

62.1 Ethyl 3-(2-ethoxy-4-fluorophenyl)-3-oxopropanoate

Ethyl 3-(2-ethoxy-4-fluorophenyl)-3-oxopropanoate was synthesized from 1-(2,4-difluorophenyl)ethan-1-one according to General Method 1, and was chromatographed by column chromatography eluting with 0-30% ethyl acetate in heptanes (7.5 g, 56% yield). LC-MS: $t_R$=1.36 min,

[M+H]$^+$=254.95. $^1$H NMR (250 MHz, CDCl$_3$) δ ppm: 7.92 (m, J=8.8, 7.0 Hz, 1H), 6.74-6.59 (m, 2H), 4.13 (m, J=16.6, 7.1 Hz, 4H), 3.97 (s, 2H), 1.48 (t, J=7.0 Hz, 3H), 1.23 (t, J=7.1 Hz, 3H).

62.2 3-(2-Ethoxy-4-fluorophenyl)-1-methyl-1H-pyrazol-5-ol 3-(2-Ethoxy-4-fluorophenyl)-1-methyl-1H-pyrazol-5-ol was synthesized from ethyl 3-(2-ethoxy-4-fluorophenyl)-3-oxopropanoate and methyl hydrazine according to General Method 2 (6.9 g, 83% yield). LC-MS: t$_R$=1.63 min, [M+H]$^+$=236.95. $^1$H NMR (500 MHz, CDCl$_3$) δ ppm: 7.93 (dd, J=8.7, 6.9 Hz, 1H), 6.72 (td, J=8.3, 2.4 Hz, 1H), 6.65 (dd, J=10.8, 2.4 Hz, 1H), 4.07 (q, J=7.0 Hz, 2H), 3.80 (s, 2H), 3.41 (s, 3H), 1.49 (t, J=7.0 Hz, 3H).

62.3 3-(2-Ethoxy-4-fluorophenyl)-1-methyl-5-oxo-4,5-dihydro-1H-pyrazole-4-carbaldehyde 3-(2-Ethoxy-4-fluorophenyl)-1-methyl-5-oxo-4,5-dihydro-1H-pyrazole-4-carbaldehyde was synthesized from 3-(2-ethoxy-4-fluorophenyl)-1-methyl-4,5-dihydro-1H-pyrazol-5-one according to General Method 3. The method deviated from General Method 3 during the work up because no precipitation was observed. The pyrazolone was extracted from the aqueous layer using diethyl ether (3×30 mL) and the combined organic extracts were washed with brine (30 mL), dried over magnesium sulfate and concentrated under reduced pressure to provide the desired product (4.52 g, 50% yield). LC-MS: t$_R$=1.08 min, [M+H]$^+$=264.95. $^1$H NMR (500 MHz, CDCl$_3$) δ ppm: 9.61 (s, 1H), 7.53 (dd, J=8.4, 6.8 Hz, 1H), 6.74-6.69 (m, 2H), 4.05 (q, J=7.0 Hz, 2H), 3.70 (s, 3H), 1.37 (t, J=7.0 Hz, 3H).

62.4 3-(2-Ethoxy-4-fluorophenyl)-1,4-dimethyl-4,5-dihydro-1H-pyrazol-5-one 3-(2-Ethoxy-4-fluorophenyl)-1,4-dimethyl-4,5-dihydro-1H-pyrazol-5-one was synthesized from the corresponding aldehyde according to General Method 5 (4.5 g, 91% yield). LC-MS: t$_R$=1.02 min, [M+H]$^+$=250.90. $^1$H NMR (500 MHz, CDCl$_3$) δ ppm: 7.72 (dd, J=8.6, 6.8 Hz, 1H), 6.71 (td, J=8.3, 2.4 Hz, 1H), 6.64 (dd, J=10.8, 2.3 Hz, 1H), 4.11-4.02 (m, 2H), 3.39 (s, 3H), 1.45 (t, J=7.0 Hz, 3H), 1.31 (d, J=7.9 Hz, 3H).

62.5 4-Bromo-3-(2-ethoxy-4-fluorophenyl)-1,4-dimethyl-4,5-dihydro-1H-pyrazol-5-one 4-Bromo-3-(2-ethoxy-4-fluorophenyl)-1,4-dimethyl-4,5-dihydro-1H-pyrazol-5-one was synthesized from 3-(2-ethoxy-4-fluorophenyl)-1,4-dimethyl-4,5-dihydro-1H-pyrazol-5-one according to General Method 6 which was directly used in the displacement reaction according to General Method 8 (2.9 g, >99.9 yield).

62.6 4-{[(tert-Butoxy)carbonyl]({[(tert-butoxy)carbonyl]oxy})amino}-3-(2-ethoxy-4-fluorophenyl)-1,4-dimethyl-4,5-dihydro-1H-pyrazol-5-one 4-{[(tert-Butoxy)carbonyl]({[(tert-butoxy)carbonyl]oxy})amino}-3-(2-ethoxy-4-fluorophenyl)-1,4-dimethyl-4,5-dihydro-1H-pyrazol-5-one was synthesized from the corresponding bromide according to General Method 8 with the product being chromatographed by silica gel column chromatography eluting with 0-50% ethyl acetate in heptanes (0.94 g, 24% yield). LC-MS t$_R$=1.58 min, [M+H]$^+$=504.20.

62.7 3-(2-Ethoxy-4-fluorophenyl)-4-(hydroxyamino)-1,4-dimethyl-4,5-dihydro-1H-pyrazol-5-one 3-(2-Ethoxy-4-fluorophenyl)-4-(hydroxyamino)-1,4-dimethyl-4,5-dihydro-1H-pyrazol-5-one was synthesized from 4-{[(tert-butoxy)carbonyl]({[(tert-butoxy)carbonyl]oxy})amino}-3-(2-ethoxy-4-fluorophenyl)-1,4-dimethyl-4,5-dihydro-1H-pyrazol-5-one according to General Method 9 with the product being chromatographed by silica gel column chromatography eluting with 20-100% ethyl acetate in heptanes (0.19 g, 33% yield). LC-MS t$_R$=1.11 min, [M+H]=282.00. $^1$H NMR (250 MHz, DMSO-d$_6$) δ ppm: 7.73 (dd, J=8.6, 7.2 Hz, 1H), 7.62 (s, 1H), 7.00 (dd, J=11.6, 2.4 Hz, 1H), 6.84 (td, J=8.4, 2.5 Hz, 1H), 4.15-4.03 (m, 2H), 3.24 (s, 3H), 1.30 (t, J=7.0 Hz, 3H), 1.08 (s, 3H).

Example 63

Compound 63 [4-(hydroxyamino)-3-isopropyl-4-(1-(methoxyimino)ethyl)-1-methyl-1H-pyrazol-5(4H)-one]

63.1 1-Methyl-3-(propan-2-yl)-1H-pyrazol-5-ol

To ethyl 4-methyl-3-oxopentanoate (10 g, 63.21 mmol) cooled to 0° C. by an ice bath was added methyl hydrazine (3.33 mL, 63.21 mmol) dropwise over 3 minutes with stirring. On complete addition, the reaction was subjected to sonication for 5 minutes whereupon a solid precipitated from solution. The reaction was diluted in ethanol (25 mL) and concentrated under reduced pressure to provide the pyrazolone as an off-white solid, which was triturated with heptane (50 mL) and concentrated under reduced pressure to provide the title compound as an off-white solid (8.1 g, 91% yield). LC-MS: t$_R$=0.93 min, [M+H]$^+$=141. $^1$H NMR (500 MHz, DMSO-d$_6$) δ ppm: 10.60 (s, 1H), 5.14 (s, 1H), 3.41 (s, 3H), 2.65 (septet, J=6.9 Hz, 1H), 1.10 (d, J=6.8 Hz, 6H).

63.2 1-[5-Hydroxy-1-methyl-3-(propan-2-yl)-1H-pyrazol-4-yl]ethan-1-one

1-Methyl-3-(propan-2-yl)-1H-pyrazol-5-ol (4 g, 0.29 mol) was taken up in 1,1,1-trimethoxyethane (13 mL, 0.1 mol) and the resulting solution was heated to 65° C. for 7 hours. The solution was concentrated under reduced pressure, and chromatographed by silica gel chromatography eluting with 100-90% DCM:MeOH to provide the title compound as a yellow solid (2 g, 35% yield). LC-MS: t$_R$=0.79 min, [M+H]$^+$=183. $^1$H NMR (500 MHz, CDCl$_3$) δ ppm: 3.58 (s, 3H), 3.17 (septet, J=6.8 Hz, 1H), 2.43 (s, 3H), 1.31 (d, J=6.9 Hz, 6H).

63.3 4-[1-(Methoxyimino)ethyl]-1-methyl-3-(propan-2-yl)-1H-pyrazol-5-ol from the corresponding acetate 4-[1-(Methoxyimino)ethyl]-1-methyl-3-(propan-2-yl)-1H-pyrazol-5-ol was synthesized from the corresponding acetate, 1-[5-hydroxy-1-methyl-3-(propan-2-yl)-1H-pyrazol-4-yl]ethan-1-one, according to General Method 12 (2.16 g, 93% yield). LC-MS: t$_R$=1.00 min, [M+H]$^+$=212. $^1$H NMR (250 MHz, CDCl₃) δ ppm: 3.88 (s, 3H), 3.61 (s, 3H), 3.11 (septet, J=6.8 Hz, 1H), 2.24 (s, 3H), 1.28 (d, J=6.8 Hz, 6H).

63.4 4-Bromo-4-[1-(methoxyimino)ethyl]-1-methyl-3-(propan-2-yl)-4,5-dihydro-1H-pyrazol-5-one 4-Bromo-4-[1-(methoxyimino)ethyl]-1-methyl-3-(propan-2-yl)-4,5-dihydro-1H-pyrazol-5-one was synthesized from 4-[1-(methoxyimino)ethyl]-1-methyl-3-(propan-2-yl)-1H-pyrazol-5-ol according to General Method 6 (3.1 g, 84% yield). LC-MS: $t_R$=1.45 min, [M+H]⁺=290/292. ¹H NMR (250 MHz, DMSO-d₆) δ ppm: 3.85 (s, 3H), 3.23 (s, 3H), 2.73 (septet, J=6.8 Hz, 1H), 2.00 (s, 3H), 1.31 (d, J=6.9 Hz, 3H), 1.26 (d, J=6.8 Hz, 3H).

63.5 4-{[(tert-Butoxy)carbonyl]({[(tert-butoxy)carbonyl]oxy})amino}-4-[1-(methoxyimino)ethyl]-1-methyl-3-(propan-2-yl)-4,5-dihydro-1H-pyrazol-5-one 4-{[(tert-Butoxy)carbonyl]({[(tert-butoxy)carbonyl]oxy})amino}-4-[1-(methoxyimino)ethyl]-1-methyl-3-(propan-2-yl)-4,5-dihydro-1H-pyrazol-5-one was synthesized from 4-bromo-4-[1-(methoxyimino)ethyl]-1-methyl-3-(propan-2-yl)-4,5-dihydro-1H-pyrazol-5-one according to General Method 8 (4.97 g, >99.9 yield). LC-MS: $t_R$=1.67 min, [M+Na]⁺=465.

63.6 4-(Hydroxyamino)-4-[1-(methoxyimino)ethyl]-1-methyl-3-(propan-2-yl)-4,5-dihydro-1H-pyrazol-5-one 4-(Hydroxyamino)-4-[1-(methoxyimino)ethyl]-1-methyl-3-(propan-2-yl)-4,5-dihydro-1H-pyrazol-5-one was synthesized from 4-{[(tert-butoxy)carbonyl]({[(tert-butoxy)carbonyl]oxy})amino}-4-[-1-(methoxyimino)ethyl]-1-methyl-3-(propan-2-yl)-4,5-dihydro-1H-pyrazol-5-one according to General Method 9 and chromatographed by silica gel chromatography, eluting in 0-35% ethyl acetate:heptanes to provide the title compound as a yellow oil (1.57 g, 72% yield). LC-MS: $t_R$=1.47 min, [M+H]⁺=243. ¹H NMR (500 MHz, DMSO-d₆) δ ppm: 7.71 (s, 1H), 3.77 (s, 3H), 3.15 (s, 3H), 2.76 (septet, J=6.8 Hz, 1H), 1.72 (s, 3H), 1.18 (d, J=6.8 Hz, 3H), 1.14 (d, J=6.9 Hz, 3H).

Example 64

Compound 64 [3-(4-fluorophenyl)-4-(hydroxyamino)-4-(1-(methoxyimino)ethyl)-1-methyl-1H-pyrazol-5(4H)-one]

64.1 3-(4-Fluorophenyl)-1-methyl-4,5-dihydro-1H-pyrazol-5-one 3-(4-Fluorophenyl)-1-methyl-4,5-dihydro-1H-pyrazol-5-one was synthesized from the corresponding beta-keto ester and methyl hydrazine according to General Method 2 (4.85 g, 99% yield). LC-MS: $t_R$=0.98, [M+H]⁺=192.90. ¹H NMR (500 MHz, DMSO-d₆) δ ppm: 11.01 (s, 1H), 7.71 (dd, J=8.7, 5.7 Hz, 2H), 7.16 (t, J=8.8 Hz, 2H), 5.77 (s, 1H), 3.55 (s, 3H).

64.2 4-Acetyl-3-(4-fluorophenyl)-1-methyl-4,5-dihydro-1H-pyrazol-5-one

4-Acetyl-3-(4-fluorophenyl)-1-methyl-4,5-dihydro-1H-pyrazol-5-one was synthesized from 3-(4-fluorophenyl)-1-methyl-4,5-dihydro-1H-pyrazol-5-one according to General Method 11 with the product being chromatographed by column chromatography eluting with 50-100% ethyl acetate in heptanes (1.23 g, 35% yield). LC-MS: $t_R$=1.10, [M+H]⁺=234.90. ¹H NMR (500 MHz, DMSO-d₆) δ ppm: 7.61-7.56 (m, 2H), 7.23 (t, J=8.9 Hz, 2H), 3.60 (d, J=4.0 Hz, 3H), 2.19 (s, 3H).

64.3 3-(4-Fluorophenyl)-4-[1-(methoxyimino)ethyl]-1-methyl-4,5-dihydro-1H-pyrazol-5-one 3-(4-Fluorophenyl)-4-[1-(methoxyimino)ethyl]-1-methyl-4,5-dihydro-1H-pyrazol-5-one was synthesized from 4-acetyl-3-(4-fluorophenyl)-1-methyl-4,5-dihydro-1H-pyrazol-5-one according to General Method 12 (1.09 g, 64% yield). LC-MS: $t_R$=1.20, [M+H]⁺=263.95.

64.4 4-Bromo-3-(4-fluorophenyl)-4-[1-(methoxyimino)ethyl]-1-methyl-4,5-dihydro-1H-pyrazol-5-one 4-Bromo-3-(4-fluorophenyl)-4-[1-(methoxyimino)ethyl]-1-methyl-4,5-dihydro-1H-pyrazol-5-one was synthesized from the corresponding oxime according to General Method 6 (1.40 g, >99.9 yield) which was used directly in the displacement reaction according to General Method 8.

64.5 4-{[(tert-Butoxy)carbonyl]({[(tert-butoxy)carbonyl]oxy})amino}-3-(4-fluorophenyl)-4-[1-(methoxyimino)ethyl]-1-methyl-4,5-dihydro-1H-pyrazol-5-one 4-{[(tert-Butoxy)carbonyl]({[(tert-butoxy)carbonyl]oxy})amino}-3-(4-fluorophenyl)-4-[1-(methoxyimino)ethyl]-1-methyl-4,5-dihydro-1H-pyrazol-5-one was synthesized from the corresponding bromide according to General Method 8 with the product being chromatographed by column chromatography using 0-50% ethyl acetate in heptanes (0.65 g, 30% yield). LC-MS: $t_R$=1.59, [M+H]⁺=517.15.

64.6 3-(4-Fluorophenyl)-4-(hydroxyamino)-4-[1-(methoxyimino)ethyl]-1-methyl-4,5-dihydro-1H-pyrazol-5-one 3-(4-Fluorophenyl)-4-(hydroxyamino)-4-[1-(methoxyimino)ethyl]-1-methyl-4,5-dihydro-1H-pyrazol-5-one was synthesized from 4-{[(tert-butoxy)carbonyl]({[(tert-butoxy)carbonyl]oxy})amino}-3-(4-fluorophenyl)-4-[1-(methoxyimino)ethyl]-1-methyl-4,5-dihydro-1H-pyrazol-5-one according to General Method 9 with the product being chromatographed by silica gel column chromatography eluting with 0-50% ethyl acetate in heptanes (0.14 g, 39% yield). LC-MS: $t_R$=1.17 g, [M+H]⁺=294.95. ¹H NMR (500 MHz, DMSO-d₆) δ ppm: 8.00-7.91 (m, 2H), 7.79 (s, 1H), 7.31-7.23 (m, 2H), 3.74 (s, 3H), 3.32 (s, 3H), 1.66 (s, 3H).

Example 65

Compound 65 [4-(hydroxyamino)-1,3-dimethyl-4-(4-(methylsulfinyl)phenyl)-1H-pyrazol-5(4H)-one]

4-(Hydroxyamino)-4-(4-methanesulfinylphenyl)-1,3-dimethyl-4,5-dihydro-1H-pyrazol-5-one was synthesized from 4-{[(tert-butoxy)carbonyl]({[(tert-butoxy)carbonyl]oxy})amino}-4-(4-methanesulfinylphenyl)-1,3-dimethyl-4,5-dihydro-1H-pyrazol-5-one according to General Method 9 and was chromatographed by acidic preparative HPLC to provide the title compound as a white solid (0.146 g, 26% yield). LC-MS: $t_R$=0.65 min, [M+H]$^+$=282. $^1$H NMR (250 MHz, DMSO-d$_6$) δ ppm: 7.91 (s, 1H), 7.69 (d, J=8.4 Hz, 2H), 7.41 (d, J=8.5 Hz, 2H), 7.03 (s, 1H), 3.20 (s, 3H), 2.73 (s, 3H), 1.95 (s, 3H).

Example 66

Compound 66 [4-(4-chlorophenyl)-4-(hydroxyamino)-1,3-dimethyl-1H-pyrazol-5(4H)-one]

66.1 Methyl 2-(4-chlorophenyl)-3-oxobutanoate

Methyl 2-(4-chlorophenyl)-3-oxobutanoate was synthesized from methyl 2-(4-chlorophenyl)acetate according to General Method 13 with the product being chromatographed by silica gel column chromatography eluting with 0-25% ethyl acetate in heptanes (5.51 g, 86% yield). LC-MS: $t_R$=1.27 min, [H+M]+=227.00. $^1$H NMR (500 MHz, DMSO-d$_6$) δ ppm: 7.45 (d, J=8.4 Hz, 2H), 7.34 (d, J=8.4 Hz, 2H), 5.22 (s, 1H), 3.67 (s, 3H), 2.16 (s, 3H).

66.2 4-(4-Chlorophenyl)-1,3-dimethyl-4,5-dihydro-1H-pyrazol-5-one 4-(4-Chlorophenyl)-1,3-dimethyl-4,5-dihydro-1H-pyrazol-5-one was synthesized from methyl 2-(4-chlorophenyl)-3-oxobutanoate and methyl hydrazine according to General Method 2 (5.03 g, 80% yield). LC-MS: $t_R$=1.06 min, [H+M]+=222.95. $^1$H NMR (500 MHz, DMSO-d$_6$) δ ppm: 7.54 (d, J=7.8 Hz, 2H), 7.39 (d, J=8.7 Hz, 2H), 3.39 (s, 3H), 2.21 (s, 3H).

66.3 4-Bromo-4-(4-chlorophenyl)-1,3-dimethyl-4,5-dihydro-1H-pyrazol-5-one

4-Bromo-4-(4-chlorophenyl)-1,3-dimethyl-4,5-dihydro-1H-pyrazol-5-one was synthesized from 4-(4-chlorophenyl)-1,3-dimethyl-4,5-dihydro-1H-pyrazol-5-one according to General Method 6 (6.5 g, 55% yield). LC-MS: $t_R$=1.33 min, [M+H]$^+$=302.80.

66.4 4-{[(tert-Butoxy)carbonyl]({[(tert-butoxy)carbonyl]oxy})amino}-4-(4-chlorophenyl)-1,3-dimethyl-4,5-dihydro-1H-pyrazol-5-one 4-{[(tert-Butoxy)carbonyl]({[(tert-butoxy)carbonyl]oxy})amino}-4-(4-chlorophenyl)-1,3-dimethyl-4,5-dihydro-1H-pyrazol-5-one was synthesized from 4-bromo-4-(4-chlorophenyl)-1,3-dimethyl-4,5-dihydro-1H-pyrazol-5-one according to General Method 8 with the product being chromatographed by silica gel column chromatography eluting with 0-50% ethyl acetate in heptanes (6.45 g, 96% yield). LC-MS: $t_R$=1.55 min, [M+H]$^+$=476.15.

66.5 4-(4-Chlorophenyl)-4-(hydroxyamino)-1,3-dimethyl-4,5-dihydro-1H-pyrazol-5-one 4-(4-Chlorophenyl)-4-(hydroxyamino)-1,3-dimethyl-4,5-dihydro-1H-pyrazol-5-one was synthesized from 4-{[(tert-butoxy)carbonyl]({[(tert-butoxy)carbonyl]oxy})amino}-4-(4-chlorophenyl)-1,3-dimethyl-4,5-dihydro-1H-pyrazol-5-one according to General Method 9 with the product being triturated with 100% methanol (0.3 g, 11% yield). LC-MS: $t_R$=1.04 min, [M+H]$^+$=254.00. $^1$H NMR (500 MHz, DMSO-d$_6$) δ ppm: 7.89 (s, 1H), 7.45 (d, J=8.6 Hz, 2H), 7.24-7.20 (m, 2H), 6.96 (s, 1H), 3.19 (s, 3H), 1.93 (s, 3H).

Example 67

Compound 67 [4-(Hydroxyamino)-1,4-dimethyl-3-(4-((trifluoromethyl)thio)phenyl)-1H-pyrazol-5(4H)-one]

4-(Hydroxyamino)-1,4-dimethyl-3-{4-[(trifluoromethyl)sulfanyl]phenyl}-4,5-dihydro-1H-pyrazol-5-one was synthesized from 4-{[(tert-butoxy)carbonyl]({[(tert-butoxy)carbonyl]oxy})amino}-1,4-dimethyl-3-{4-[(trifluoromethyl)sulfanyl]phenyl}-4,5-dihydro-1H-pyrazol-5-one according to General Method 9 with the product being chromatographed by silica gel column chromatography eluting with 0-50% ethyl acetate in heptanes (0.65 g, 56% yield). LC-MS: $t_R$=1.29 min, [M+H]$^+$=320.00. $^1$H NMR (500 MHz, DMSO-d$_6$) δ ppm: 8.21-8.13 (m, 2H), 7.80 (d, J=8.4 Hz, 2H), 7.68 (d, J=2.5 Hz, 1H), 6.56 (d, J=2.6 Hz, 1H), 3.31 (s, 3H), 1.23 (s, 3H).

Example 68

Compound 68 [4-(3-bromo-4-methoxyphenyl)-4-(hydroxyamino)-1,3-dimethyl-1H-pyrazol-5(4H)-one]

4-(3-Bromo-4-methoxyphenyl)-4-(hydroxyamino)-1,3-dimethyl-4,5-dihydro-1H-pyrazol-5-one was isolated after chromatography by reverse phase preparative HPLC of 4-(hydroxyamino)-4-(4-methoxyphenyl)-1,3-dimethyl-4,5-dihydro-1H-pyrazol-5-one (0.02 g, 1% yield). LC-MS: $t_R$=0.08 min, [M+H]$^+$=351.8. $^1$H NMR (500 MHz, DMSO-d$_6$) δ ppm: 7.89-7.83 (m, 1H), 7.46-7.39 (m, 1H), 7.15-7.08 (m, 2H), 6.94-6.88 (m, 1H), 3.83 (s, 3H), 3.18 (s, 3H), 1.94 (s, 3H).

Example 69

Compound 69 [3-(3,5-bis(Trifluoromethyl)phenyl)-4-(hydroxyamino)-1,4-dimethyl-1H-pyrazol-5(4H)-one]

69.1 Methyl 3-[3,5-bis(trifluoromethyl)phenyl]-3-oxopropanoate

Methyl 3-[3,5-bis(trifluoromethyl)phenyl]-3-oxopropanoate was synthesized from 1-[3,5-bis(trifluoromethyl)phenyl]ethan-1-one according to General Method 1 with the product being chromatographed by column chromatography eluting with 0-30% ethyl acetate in heptanes (5.69 g, 68% yield). LC-MS: $t_R$=1.39 min, [M+H]$^+$=314.80. $^1$H NMR (500 MHz, DMSO-d$_6$) δ ppm: 8.53 (s, 2H), 8.44 (s, 1H), 4.44 (s, 2H), 3.66 (s, 3H).

69.2 3-[3,5-bis(Trifluoromethyl)phenyl]-1-methyl-4,5-dihydro-1H-pyrazol-5-one

3-[3,5-bis(Trifluoromethyl)phenyl]-1-methyl-4,5-dihydro-1H-pyrazol-5-one was synthesized from methyl 3-[3,5-bis(trifluoromethyl)phenyl]-3-oxopropanoate according to General Method 2 (5.58 g, 95% yield). LC-MS: $t_R$=1.36 min, [M+H]$^+$=310.90. $^1$H NMR (500 MHz, DMSO-d$_6$) δ ppm: 8.31 (s, 2H), 7.94 (s, 1H), 6.15 (s, 1H), 3.61 (s, 3H).

69.3 3-[3,5-bis(Trifluoromethyl)phenyl]-1-methyl-5-oxo-4,5-dihydro-1H-pyrazole-4-carbaldehyde 3-[3,5-bis(Trifluoromethyl)phenyl]-1-methyl-5-oxo-4,5-dihydro-1H-pyrazole-4-carbaldehyde was synthesized from 3-[3,5-bis(trifluoromethyl)phenyl]-1-methyl-4,5-dihydro-1H-pyrazol-5-one according to General Method 4 (6.42 g, 97% yield). LC-MS: $t_R$=1.32 min, [M+H]$^+$=338.90. $^1$H NMR (500 MHz, DMSO-$d_6$) δ ppm: 9.78 (s, 1H), 8.63 (s, 2H), 8.10 (s, 1H), 3.67 (s, 3H).

69.4 3-[3,5-bis(Trifluoromethyl)phenyl]-1,4-dimethyl-4,5-dihydro-1H-pyrazol-5-one 3-[3,5-bis(Trifluoromethyl)phenyl]-1,4-dimethyl-4,5-dihydro-1H-pyrazol-5-one was synthesized from 3-[3,5-bis(trifluoromethyl)phenyl]-1-methyl-5-oxo-4,5-dihydro-1H-pyrazole-4-carbaldehyde according to General Method 5 (5.57 g, 72% yield). LC-MS: $t_R$=1.37 min, [M+H]$^+$=324.95. $^1$H NMR (500 MHz, DMSO-$d_6$) δ ppm: 8.14 (s, 2H), 7.93 (s, 1H), 3.56 (s, 3H), 2.53 (s, 1H), 2.04 (s, 3H).

69.5 3-[3,5-bis(trifluoromethyl)phenyl]-4-bromo-1,4-dimethyl-4,5-dihydro-1H-pyrazol-5-one 3-[3,5-bis(Trifluoromethyl)phenyl]-4-bromo-1,4-dimethyl-4,5-dihydro-1H-pyrazol-5-one was synthesized from 3-[3,5-bis(trifluoromethyl)phenyl]-1,4-dimethyl-4,5-dihydro-1H-pyrazol-5-one according to General Method 6 (6 g, 79% yield). LC-MS: $t_R$=1.54 min, [M+H]$^+$=404.85.

69.6 3-[3,5-bis(Trifluoromethyl)phenyl]-4-{[(tert-butoxy)carbonyl]({[(tert-butoxy)carbonyl]oxy})amino}-1,4-dimethyl-4,5-dihydro-1H-pyrazol-5-one 3-[3,5-bis(Trifluoromethyl)phenyl]-4-{[(tert-butoxy)carbonyl]({[(tert-butoxy)carbonyl]oxy})amino}-1,4-dimethyl-4,5-dihydro-1H-pyrazol-5-one was synthesized from 3-[3,5-bis(trifluoromethyl)phenyl]-4-bromo-1,4-dimethyl-4,5-dihydro-1H-pyrazol-5-one according to General Method 8 with the product being chromatographed by column chromatography eluting with 0-50% ethyl acetate in heptanes (4.15 g, 68% yield). LC-MS: $t_R$=1.69 min, [M+H]$^+$=578.20.

69.7 3-[3,5-bis(Trifluoromethyl)phenyl]-4-(hydroxyamino)-1,4-dimethyl-4,5-dihydro-1H-pyrazol-5-one 3-[3,5-bis(Trifluoromethyl)phenyl]-4-(hydroxyamino)-1,4-dimethyl-4,5-dihydro-1H-pyrazol-5-one was synthesized from 3-[3,5-bis(trifluoromethyl)phenyl]-4-{[(tert-butoxy)carbonyl]({[(tert-butoxy)carbonyl]oxy})amino}-1,4-dimethyl-4,5-dihydro-1H-pyrazol-5-one according to General Method 9 with the product being chromatographed by column chromatography eluting with 0-60% ethyl acetate in heptanes (1.2 g, 48% yield). LC-MS: $t_R$=1.40 min, [M+H]$^+$=356.00. $^1$H NMR (500 MHz, DMSO-$d_6$) δ ppm: 8.58 (s, 2H), 8.21 (br s, 1H), 7.81 (s, 1H), 6.75 (s, 1H), 3.35 (s, 3H), 1.23 (s, 3H).

Example 70

Compound 70 [3-(3-Chloro-4-methanesulfonylphenyl)-4-(hydroxyamino)-1,4-dimethyl-4,5-dihydro-1H-pyrazol-5-one]

70.1 1-[3-Chloro-4-(methylsulfanyl)phenyl]ethan-1-one

1-[3-Chloro-4-(methylsulfanyl)phenyl]ethan-1-one was synthesized from 1-(3-chloro-4-fluorophenyl)ethan-1-one according to General Method 14 (7.94 g, 58%). LC-MS $t_R$=1.32 min, [M+H]$^+$=200.85.

70.2 Ethyl 3-[3-chloro-4-(methylsulfanyl)phenyl]-3-oxopropanoate

Ethyl 3-[3-chloro-4-(methylsulfanyl)phenyl]-3-oxopropanoate was synthesized from 1-[3-chloro-4-(methylsulfanyl)phenyl]ethan-1-one according to General Method 1 with the product being purified using silica gel chromatography eluting with 0-35% ethyl acetate in heptanes (3.78 g, 28%). LC-MS $t_R$=1.36 min, [M+H]$^+$=272.90.

70.3 3-[3-Chloro-4-(methylsulfanyl)phenyl]-1-methyl-4,5-dihydro-1H-pyrazol-5-one To a solution of ethyl 3-[3-chloro-4-(methylsulfanyl)phenyl]-3-oxopropanoate (3.78 g, 13.86 mmol) in ethanol (10 mL) was added methylhydrazine sulfate (3 g, 20.79 mmol) as a solution in ethanol (10 mL) and N,N-diethylethanamine (3.87 mL, 27.72 mmol) and the resulting reaction mixture was heated to 80 OC until complete consumption of starting material was observed as monitored by LC-MS. The reaction mixture was concentrated under reduced pressure with the resulting solid being dissolved in ethyl acetate (20 mL) and washed with water (3×10 mL). The organic layer was dried over magnesium sulfate, filtered and concentrated under reduced pressure to yield the title compound as a brown solid (3 g, 68%). LC-MS $t_R$=1.17 min, [M+H]$^+$=254.90.

70.4 3-[3-Chloro-4-(methylsulfanyl)phenyl]-5-hydroxy-1-methyl-1H-pyrazole-4-carbaldehyde 3-[3-Chloro-4-(methylsulfanyl)phenyl]-5-hydroxy-1-methyl-1H-pyrazole-4-carbaldehyde was synthesized from 3-[3-chloro-4-(methylsulfanyl)phenyl]-1-methyl-4,5-dihydro-1H-pyrazol-5-one according to General Method 4 (3.38 g, 66%). LC-MS $t_R$=1.19 min, [M+H]$^+$=282.85; $^1$H NMR (500 MHz, DMSO-d6) δ 9.74 (s, 1H), 7.98 (d, J=1.8 Hz, 1H), 7.88 (dd, J=8.3, 1.8 Hz, 1H), 7.34 (d, J=8.4 Hz, 1H), 3.61 (s, 3H), 2.53 (s, 3H).

70.5 3-[3-Chloro-4-(methylsulfanyl)phenyl]-1,4-dimethyl-1H-pyrazol-5-ol

3-[3-Chloro-4-(methylsulfanyl)phenyl]-1,4-dimethyl-1H-pyrazol-5-ol was synthesized from 3-[3-chloro-4-(methylsulfanyl)phenyl]-5-hydroxy-1-methyl-1H-pyrazole-4-carbaldehyde according to General Method 5 (3.55 g, 54%). LC-MS $t_R$=1.14 min, [M+H]$^+$=268.90; $^1$H NMR (500 MHz, DMSO-d6) δ 7.61 (d, J=1.6 Hz, 1H), 7.57 (d, J=8.3 Hz, 1H), 7.31 (d, J=8.3 Hz, 1H), 3.53 (s, 3H), 2.51 (s, 3H), 2.00 (s, 3H).

70.6 4-Bromo-3-(3-chloro-4-methanesulfinylphenyl)-1,4-dimethyl-4,5-dihydro-1H-pyrazol-5-one 4-Bromo-3-(3-chloro-4-methanesulfinylphenyl)-1,4-dimethyl-4,5-dihydro-1H-pyrazol-5-one was synthesized from 3-[3-chloro-4-(methylsulfanyl)phenyl]-1,4-dimethyl-1H-pyrazol-5-ol according to General Method 6 and was used directly in the displacement reaction according to General Method 8 (2.26 g, 100%).

70.7 4-{[(tert-Butoxy)carbonyl]({[(tert-butoxy)carbonyl]oxy})amino}-3-(3-chloro-4-methanesulfinylphenyl)-1,4-dimethyl-4,5-dihydro-1H-pyrazol-5-one 4-{[(tert-Butoxy)carbonyl]({[(tert-butoxy)carbonyl]oxy})amino}-3-(3-chloro-4-methanesulfinylphenyl)-1,4-dimethyl-4,5-dihydro-1H-pyrazol-5-one was synthesized from 4-bromo-3-(3-chloro-4-methanesulfinylphenyl)-1,4-dimethyl-4,5-dihydro-1H-pyrazol-5-one according to General Method 8 with the product being purified using silica gel chromatography eluting in 20-100% ethyl acetate in heptanes (0.46 g, 8%). LC-MS $t_R$=1.39 min, $[M+H]^+$=538.10.

70.8 tert-Butyl N-[3-(3-chloro-4-methanesulfonylphenyl)-1,4-dimethyl-5-oxo-4,5-dihydro-1H-pyrazol-4-yl]-N-hydroxycarbamate tert-Butyl N-[3-(3-chloro-4-methanesulfonylphenyl)-1,4-dimethyl-5-oxo-4,5-dihydro-1H-pyrazol-4-yl]-N-hydroxycarbamate was synthesized from 4-{[(tert-butoxy)carbonyl]({[(tert-butoxy)carbonyl]oxy})amino}-3-(3-chloro-4-methanesulfinylphenyl)-1,4-dimethyl-4,5-dihydro-1H-pyrazol-5-one according to General Method 10 (0.29 g, 75%). LC-MS $t_R$=1.21 min, $[M+H]^+$=454.00.

70.9 3-(3-Chloro-4-methanesulfonylphenyl)-4-(hydroxyamino)-1,4-dimethyl-4,5-dihydro-1H-pyrazol-5-one 3-(3-Chloro-4-methanesulfonylphenyl)-4-(hydroxyamino)-1,4-dimethyl-4,5-dihydro-1H-pyrazol-5-one was synthesized from tert-butyl N-[3-(3-chloro-4-methanesulfonylphenyl)-1,4-dimethyl-5-oxo-4,5-dihydro-1H-pyrazol-4-yl]-N-hydroxycarbamate according to General Method 9 with the product being purified using acidic preparative HPLC (5 mg, 7%). LC-MS $t_R$=1.08 min, $[M+H]^+$=331.95; $^1$H NMR (500 MHz, DMSO-d6) δ 8.30 (d, J=1.5 Hz, 1H), 8.19 (dd, J=8.4, 1.6 Hz, 1H), 8.12 (d, J=8.4 Hz, 1H), 7.75 (d, J=2.6 Hz, 1H), 6.68 (d, J=2.6 Hz, 1H), 3.40 (s, 3H), 3.34 (s, 3H), 1.23 (s, 3H).

Example 71

Compound 71 [Methyl 4-[4-(hydroxyamino)-1,4-dimethyl-5-oxo-4,5-dihydro-1H-pyrazol-3-yl]benzoate]

71.1 Methyl 4-(3-methoxy-3-oxopropanoyl)benzoate

Methyl 4-(3-methoxy-3-oxopropanoyl)benzoate was synthesized from methyl 4-acetylbenzoate according to General Method 1 with the product being purified using silica gel chromatography eluting with 0-35% ethyl acetate in heptanes (10.45 g, 57%). LC-MS $t_R$=1.16 min, $[M+H]^+$=236.90; $^1$H NMR (500 MHz, DMSO-d6) δ 8.08 (m, 4H), 4.28 (s, 2H), 3.89 (s, 3H), 3.65 (s, 3H).

71.2 Methyl 4-(1-methyl-5-oxo-4,5-dihydro-1H-pyrazol-3-yl)benzoate

To a solution of methyl 4-(3-methoxy-3-oxopropanoyl) benzoate (10.44 g, 35.36 mmol) in ethanol (50 mL) was added methylhydrazine sulfate (5.61 g, 38.89 mmol) and N,N-diethylethanamine (5.43 mL, 38.89 mmol) and the resulting reaction mixture was heated to 80 OC until complete consumption of starting material was observed as monitored by LC-MS. The reaction mixture was concentrated under reduced pressure with the resulting solid was dissolved in ethyl acetate (60 mL) and washed with 1M HCl (3×30 mL), water (30 mL) and brine (30 mL). The organic layer was dried over magnesium sulfate, filtered and concentrated under reduced pressure to give the title compound as a brown solid (7.82 g, 69%). LC-MS $t_R$=1.04 min, $[M+H]^+$=232.90.

71.3 Methyl 4-(4-formyl-1-methyl-5-oxo-4,5-dihydro-1H-pyrazol-3-yl)benzoate Methyl 4-(4-formyl-1-methyl-5-oxo-4,5-dihydro-1H-pyrazol-3-yl)benzoate was synthesized from methyl 4-(1-methyl-5-oxo-4,5-dihydro-1H-pyrazol-3-yl)benzoate according to General Method 4 (5.88 g, 84%). LC-MS $t_R$=1.09 min, $[M+H]^+$=260.95; $^1$H NMR (250 MHz, DMSO-d6) δ 9.77 (s, 1H), 7.98 (s, 4H), 3.87 (s, 3H), 3.64 (s, 3H).

71.4 Methyl 4-(1,4-dimethyl-5-oxo-4,5-dihydro-1H-pyrazol-3-yl)benzoate

Methyl 4-(1,4-dimethyl-5-oxo-4,5-dihydro-1H-pyrazol-3-yl)benzoate was synthesized from methyl 4-(4-formyl-1-methyl-5-oxo-4,5-dihydro-1H-pyrazol-3-yl)benzoate according to General Method 5 (7.7 g, 97%). LC-MS $t_R$=1.01 min, $[M+H]^+$=246.95; $^1$H NMR (500 MHz, DMSO-d6) δ 7.95 (d, J=8.3 Hz, 2H), 7.75 (d, J=8.4 Hz, 2H), 3.85 (s, 3H), 3.55 (s, 3H), 2.04 (s, 3H).

71.5 Methyl 4-(4-bromo-1,4-dimethyl-5-oxo-4,5-dihydro-1H-pyrazol-3-yl)benzoate Methyl 4-(4-bromo-1,4-dimethyl-5-oxo-4,5-dihydro-1H-pyrazol-3-yl)benzoate was synthesized from methyl 4-(1,4-dimethyl-5-oxo-4,5-dihydro-1H-pyrazol-3-yl)benzoate according to General Method 6 which was directly used in the displacement reaction according to General Method 8 (3.96 g, 100%).

71.6 Methyl 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoate Methyl 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoate was synthesized from methyl 4-(4-bromo-1,4-dimethyl-5-oxo-4,5-dihydro-1H-pyrazol-3-yl) benzoate according to General Method 8 with the product being purified using silica gel chromatography eluting with 10-60% ethyl acetate in heptanes (1.36 g, 23%). LC-MS $t_R$=1.63 min, $[M+H]^+$=500.10.

71.7 Methyl 4-[4-(hydroxyamino)-1,4-dimethyl-5-oxo-4,5-dihydro-1H-pyrazol-3-yl]benzoate Methyl 4-[4-(hydroxyamino)-1,4-dimethyl-5-oxo-4,5-dihydro-1H-pyrazol-3-yl]benzoate was synthesized from methyl 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoate according to General Method 9 with the product being purified by washing the resulting solid in 20% ethyl acetate:heptanes (82 mg, 71%). LC-MS $t_R$=3.21 min, $[M+H]^+$=277.95; $^1$H NMR (250 MHz, DMSO-d6) δ 8.18 (d, J=8.6 Hz, 2H), 8.02 (d, J=8.5 Hz, 2H), 7.67 (s, 1H), 3.88 (s, 3H), 3.32 (s, 3H), 1.23 (s, 3H).

Example 72

Compound 72 [2,2,2-Trifluoro-N-({4-[4-(hydroxyamino)-1,4-dimethyl-5-oxo-4,5-dihydro-1H-pyrazol-3-yl]phenyl}(methyl)oxo-$\lambda^6$-sulfanylidene)acetamide]

72.1 N-{[4-(4-{[(tert-Butoxy)carbonyl]({[(tert-butoxy)carbonyl]oxy})amino}-1,4-dimethyl-5-oxo-4,5-dihydro-1H-pyrazol-3-yl)phenyl](methyl)oxo-sulfanylidene}-2,2,2-trifluoroacetamide To a solution of 4-{[(tert-butoxy)carbonyl]({[(tert-butoxy)carbonyl]oxy})amino}-3-(4-methanesulfinylphenyl)-1,4-dimethyl-4,5-dihydro-1H-pyrazol-5-one (1.40 g, 2.59 mmol) in DCM (10 mL) was added magnesium oxide (0.41 g, 10.23 mmol), tetrakis(acetato-kappaO)dirhodium(Rh—Rh) (28 mg, 0.06 mmol) and 2,2,2 trifluoroacetamide (0.58 g, 5.12 mmol). Stirring was continued for 5 minutes at room temperature before bis(acetyloxy)(phenyl)-lambda~3~-iodane (1.24 g, 3.84 mmol) was added and stirring continued for 3 hours at room temperature. The resulting precipitate formed was filtered and the remaining filtrate concentrated under reduced pressure yielding the title product (1.16 g, 73%). LC-MS $t_R$=1.51 min, [M+Na]$^+$=615.

72.2 2,2,2-Trifluoro-N-({4-[4-(hydroxyamino)-1,4-dimethyl-5-oxo-4,5-dihydro-1H-pyrazol-3-yl]phenyl}(methyl)oxo-sulfanylidene)acetamide 2,2,2-Trifluoro-N-({4-[4-(hydroxyamino)-1,4-dimethyl-5-oxo-4,5-dihydro-1H-pyrazol-3-yl]phenyl}(methyl)oxo-sulfanylidene)acetamide was synthesized from N-{[4-(4-{[(tert-butoxy)carbonyl]({[(tert-butoxy)carbonyl]oxy}) amino}-1,4-dimethyl-5-oxo-4,5-dihydro-1H-pyrazol-3-yl) phenyl](methyl)oxo-sulfanylidene}-2,2,2-trifluoroacetamide according to General Method 9. The product was purified using acidic preparative HPLC to yield the title compound (0.03 g, 2%). LC-MS $t_R$=1.14 min, [M+H]$^+$=393; $^1$H NMR (500 MHz, DMSO-d6) δ 8.41-8.16 (m, 2H), 8.14-7.95 (m, 2H), 7.79-7.71 (m, 1H), 6.74-6.54 (m, 1H), 4.07-3.76 (m, 3H), 3.35-3.32 (m, 3H), 1.51-1.18 (m, 3H).

Example 73

Compound 73 [4-(3,4-Dimethoxyphenyl)-4-(hydroxyamino)-1,3-dimethyl-4,5-dihydro-1H-pyrazol-5-one]

73.1 Ethyl 2-(3,4-dimethoxyphenyl)-3-oxobutanoate

Ethyl 2-(3,4-dimethoxyphenyl)-3-oxobutanoate was synthesized from methyl 2-(3,4-dimethoxyphenyl)acetate according to General Method 13 and was purified using silica gel chromatography eluting with 0-100% ethyl acetate in heptanes (4.91 g, 52%). LC-MS $t_R$=1.09 min, [M+H]$^+$=253; $^1$H NMR (500 MHz, DMSO-d6) δ 6.98-6.93 (m, 1H), 6.92-6.89 (m, 1H), 6.86-6.80 (m, 1H), 5.03 (s, 1H), 3.75-3.73 (m, 6H), 3.66-3.64 (m, 3H), 2.14-2.09 (m, 3H).

73.2 4-(3,4-Dimethoxyphenyl)-2,5-dimethyl-2,3-dihydro-1H-pyrazol-3-one 4-(3,4-Dimethoxyphenyl)-2,5-dimethyl-2,3-dihydro-1H-pyrazol-3-one was synthesized from ethyl 2-(3,4-dimethoxyphenyl)-3-oxobutanoate according to General Method 2 and was purified using silica gel chromatography eluting with 0-100% ethyl acetate in heptanes followed by 0-40% methanol in ethyl acetate (0.41 g, 11%). LC-MS $t_R$=0.91 min, [M+H]$^+$=249; $^1$H NMR (250 MHz, DMSO-d6) δ 7.09 (s, 1H), 6.94 (s, 2H), 3.74 (s, 6H), 3.40 (s, 3H), 3.17 (s, 1H), 2.18 (s, 3H).

73.3 4-Bromo-4-(3,4-dimethoxyphenyl)-1,3-dimethyl-4,5-dihydro-1H-pyrazol-5-one 4-Bromo-4-(3,4-dimethoxyphenyl)-1,3-dimethyl-4,5-dihydro-1H-pyrazol-5-one was synthesized from 4-(3,4-dimethoxyphenyl)-2,5-dimethyl-2,3-dihydro-1H-pyrazol-3-one according to General Method 6 (0.53 g, 99%). LC-MS $t_R$=1.24 min, [M+H]$^+$=328.

73.4 4-{[(tert-Butoxy)carbonyl]({[(tert-butoxy)carbonyl]oxy})amino}-4-(3,4-dimethoxyphenyl)-1,3-dimethyl-4,5-dihydro-1H-pyrazol-5-one 4-{[(tert-Butoxy)carbonyl]({[(tert-butoxy)carbonyl]oxy})amino}-4-(3,4-dimethoxyphenyl)-1,3-dimethyl-4,5-dihydro-1H-pyrazol-5-one was synthesized from 4-bromo-4-(3,4-dimethoxyphenyl)-1,3-dimethyl-4,5-dihydro-1H-pyrazol-5-one according to General Method 8. The product was purified using silica gel chromatography eluting with 0-100% ethyl acetate in heptanes (0.28 g, 30%). LC-MS $t_R$=1.39 min, [M+Na]$^+$=502.

73.5 4-(3,4-Dimethoxyphenyl)-4-(hydroxyamino)-1,3-dimethyl-4,5-dihydro-1H-pyrazol-5-one 4-(3,4-Dimethoxyphenyl)-4-(hydroxyamino)-1,3-dimethyl-4,5-dihydro-1H-pyrazol-5-one was synthesized from 4-{[(tert-butoxy)carbonyl]({[(tert-butoxy)carbonyl]oxy}) amino}-4-(3,4-dimethoxyphenyl)-1,3-dimethyl4,5-dihydro-1H-pyrazol-5-one according to General Method 9. The product was purified using acidic preparative HPLC (0.05 g, 36%). LC-MS $t_R$=0.88 min, [M+Na]$^+$=302; 1H NMR (500 MHz, DMSO-d6) δ 7.87-7.76 (m, 1H), 6.95-6.90 (m, 1H), 6.88-6.84 (m, 1H), 6.83-6.78 (m, 1H), 6.68-6.61 (m, 1H), 3.73 (s, 6H), 3.18 (s, 3H), 1.95 (s, 3H).

Example 74

Compound 74 [4-[4-(Hydroxyamino)-1,4-dimethyl-5-oxo-4,5-dihydro-1H-pyrazol-3-yl]benzoic acid]

74.1 Methyl 4-(3-methoxy-3-oxopropanoyl)benzoate

Methyl 4-(3-methoxy-3-oxopropanoyl)benzoate was synthesized from methyl 4-acetylbenzoate according to General Method 1 with the product being purified using silica gel chromatography eluting with 0-35% ethyl acetate in heptanes (10.45 g, 57%). LC-MS $t_R$=1.16 min, [M+H]$^+$=236.90; $^1$H NMR (500 MHz, DMSO-d6) δ 8.08 (m, 4H), 4.28 (s, 2H), 3.89 (s, 3H), 3.65 (s, 3H).

74.2 Methyl 4-(1-methyl-5-oxo-4,5-dihydro-1H-pyrazol-3-yl)benzoate

To a solution of methyl 4-(3-methoxy-3-oxopropanoyl)benzoate (10.44 g, 35.36 mmol) in ethanol (50 mL) was added methylhydrazine sulfate (5.61 g, 38.89 mmol) and N,N-diethylethanamine (5.43 mL, 38.89 mmol) and the resulting reaction mixture was heated to 80 ºC until complete consumption of starting material was observed as monitored by LC-MS. The reaction mixture was concentrated under reduced pressure and the resulting solid was dissolved in ethyl acetate (60 mL) and washed with 1M HCl (3×30 mL), water (30 mL) and brine (30 mL). The organic layer was then dried over magnesium sulfate, filtered and concentrated under reduced pressure to give the title compound as a brown solid (7.82 g, 69%). LC-MS $t_R$=1.04 min, [M+H]$^+$=232.90.

74.3 Methyl 4-(4-formyl-1-methyl-5-oxo-4,5-dihydro-1H-pyrazol-3-yl)benzoate

Methyl 4-(4-formyl-1-methyl-5-oxo-4,5-dihydro-1H-pyrazol-3-yl)benzoate was synthesized from methyl 4-(1-methyl-5-oxo-4,5-dihydro-1H-pyrazol-3-yl)benzoate according to General Method 4 (5.88 g, 84%). LC-MS $t_R$=1.09 min, [M+H]$^+$=260.95; $^1$H NMR (250 MHz, DMSO-d6) δ 9.77 (s, 1H), 7.98 (s, 4H), 3.87 (s, 3H), 3.64 (s, 3H).

74.4 Methyl 4-(1,4-dimethyl-5-oxo-4,5-dihydro-1H-pyrazol-3-yl)benzoate

Methyl 4-(1,4-dimethyl-5-oxo-4,5-dihydro-1H-pyrazol-3-yl)benzoate was synthesized from methyl 4-(4-formyl-1-methyl-5-oxo-4,5-dihydro-1H-pyrazol-3-yl)benzoate according to General Method 5 (7.7 g, 97%). LC-MS $t_R$=1.01 min, [M+H]$^+$=246.95; $^1$H NMR (500 MHz, DMSO-d6) δ 7.95 (d, J=8.3 Hz, 2H), 7.75 (d, J=8.4 Hz, 2H), 3.85 (s, 3H), 3.55 (s, 3H), 2.04 (s, 3H).

74.5 Methyl 4-(4-bromo-1,4-dimethyl-5-oxo-4,5-dihydro-1H-pyrazol-3-yl)benzoate Methyl 4-(4-bromo-1,4-dimethyl-5-oxo-4,5-dihydro-1H-pyrazol-3-yl)benzoate was synthesized from methyl 4-(1,4-dimethyl-5-oxo-4,5-dihydro-1H-pyrazol-3-yl)benzoate according to General Method 6 and was used directly in the displacement reaction according to General Method 8 (3.96 g, 100%).

74.6 Methyl 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoate Methyl 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoate was synthesized from methyl 4-(4-bromo-1,4-dimethyl-5-oxo-4,5-dihydro-1H-pyrazol-3-yl)benzoate according to General Method 8 and was purified using silica gel chromatography eluting with 10-60% ethyl acetate in heptanes (1.36 g, 23%). LC-MS $t_R$=1.63 min, [M+H]$^+$=500.10.

74.7 4-(4-{[(tert-Butoxy)carbonyl](hydroxy)amino}-1,4-dimethyl-5-oxo-4,5-dihydro-1H-pyrazol-3-yl)benzoic acid To a solution of lithium hydroxide (30.1 mg, 1.26 mmol) in water (6 mL) was added a solution of methyl 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoate (200 mg, 0.42 mmol) in THF (6 mL) and the reaction mixture was left to stir at room temperature until complete consumption of starting material was observed as monitored by LC-MS. The reaction mixture was concentrated under reduced pressure to remove the excess THF and the resulting solution was diluted with ethyl acetate (30 mL), washed with HCl (2×5 mL) and brine (20 mL), dried over magnesium sulfate, filtered and concentrated under reduced pressure to give the title compound as a white solid (134 mg, 84%). LC-MS $t_R$=1.05 min, [M+H]$^+$=386.00; $^1$H NMR (500 MHz, DMSO-d6) δ 10.29 (s, 1H), 8.00 (d, J=8.6 Hz, 2H), 7.95 (d, J=8.6 Hz, 2H), 3.32 (s, 3H), 1.54 (s, 3H), 1.17 (s, 9H).

74.8 4-[4-(Hydroxyamino)-1,4-dimethyl-5-oxo-4,5-dihydro-1H-pyrazol-3-yl]benzoic acid 4-[4-(Hydroxyamino)-1,4-dimethyl-5-oxo-4,5-dihydro-1H-pyrazol-3-yl]benzoic acid was synthesized from 4-(4-{[(tert-butoxy)carbonyl](hydroxy)amino}-1,4-dimethyl-5-oxo-4,5-dihydro-1H-pyrazol-3-yl)benzoic acid according to General Method 9 with the product being purified using acidic preparative chromatography (32 mg, 33%). LC-MS $t_R$=2.68 min, [M+H]$^+$=263.95; $^1$H NMR (500 MHz, DMSO-d6) δ 13.09 (br s, 1H), 8.15 (d, J=8.5 Hz, 2H), 8.00 (d, J=8.5 Hz, 2H), 7.66 (s, 1H), 6.53 (s, 1H), 3.32 (s, 3H), 1.23 (s, 3H).

Example 75

Compound 75 [4-(Hydroxyamino)-3-{4-[imino(methyl)oxo-λ$^6$-sulfanyl]phenyl}-1,4-dimethyl-4,5-dihydro-1H-pyrazol-5-one]

75.1 N-{[4-(4-{[(tert-Butoxy)carbonyl]({[(tert-butoxy)carbonyl]oxy})amino}-1,4-dimethyl-5-oxo-4,5-dihydro-1H-pyrazol-3-yl)phenyl](methyl)oxo-sulfanylidene}-2,2,2-trifluoroacetamide To a solution of 4-{[(tert-butoxy)carbonyl]({[(tert-butoxy)carbonyl]oxy})amino}-3-(4-methanesulfinylphenyl)-1,4-dimethyl-4,5-dihydro-1H-pyrazol-5-one (1.40 g, 2.59 mmol) in DCM (10 mL) was added magnesium oxide (0.41 g, 10.23 mmol), tetrakis(acetato-kappaO)dirhodium(Rh—Rh) (28 mg, 0.06 mmol) and 2,2,2 trifluoroacetamide (0.58 g, 5.12 mmol) and the resulting reaction mixture was stirred at room temperature for 5 minutes before bis(acetyloxy)(phenyl)-lambda~3~-iodane (1.24 g, 3.84 mmol) was added and stirring was continued for 3 hours at room temperature. The precipitate formed was filtered and the remaining filtrate concentrated under reduced pressure forming the title product (1.16 g, 73%) which was used directly without need for additional purification. LC-MS $t_R$=1.51 min, [M+Na]$^+$=615.

75.2 4-{[(tert-Butoxy)carbonyl](({[(tert-butoxy)carbonyl]oxy})amino}-3-{4-[imino(methyl)oxo-sulfanyl]phenyl}-1,4-dimethyl-4,5-dihydro-1H-pyrazol-5-one To a solution of N-{[4-(4-{[(tert-butoxy)carbonyl]({[(tert-butoxy)carbonyl]oxy})amino}-1,4-dimethyl-5-oxo-4,5-dihydro-1H-pyrazol-3-yl)phenyl](methyl)oxo-sulfanylidene}-2,2,2-trifluoroacetamide (1.16 g, 1.86 mmol) in methanol (20 mL) was added dipotassium carbonate (1.29 g, 9.30 mmol) and the reaction mixture was stirred at room temperature until complete consumption of the starting material was observed as monitored by LC-MS. The reaction mixture was concentrated under reduced pressure and partitioned between water (40 mL) and ethyl acetate (30 mL). The organics were separated and washed with brine (30 mL), dried over sodium sulfate, filtered and concentrated under reduced pressure (0.82 g, 89%). LC-MS $t_R$=1.31 min, [M+H]$^+$=497.

75.3 4-(Hydroxyamino)-3-{4-[imino(methyl)oxo-sulfanyl]phenyl}-1,4-dimethyl-4,5-dihydro-1H-pyrazol-5-one 4-(Hydroxyamino)-3-{4-[imino(methyl)oxo-sulfanyl]phenyl}-1,4-dimethyl-4,5-dihydro-1H-pyrazol-5-one was synthesized from 4-{[(tert-butoxy)carbonyl]({[(tert-butoxy)carbonyl]oxy})amino}-3-{4-[imino(methyl)oxo-sulfanyl]phenyl}-1,4-dimethyl-4,5-dihydro-1H-pyrazol-5-one according to General Method 9. The product was purified using acidic preparative HPLC (0.066 g, 14%). LC-MS $t_R$=2.77 min, [M+H]$^+$=297; $^1$H NMR (500 MHz, DMSO-d6) δ 8.30-8.17 (m, 2H), 8.05-7.95 (m, 2H), 7.70 (s, 1H), 6.57 (s, 1H), 3.33 (s, 3H), 3.11 (s, 3H), 1.24 (s, 3H).

Example 76

Compound 76 [4-(Hydroxyamino)-4-(4-methoxy-3-methylphenyl)-1,3-dimethyl-4,5-dihydro-1H-pyrazol-5-one]

76.1 Methyl 2-(4-methoxy-3-methylphenyl)-3-oxobutanoate

Methyl 2-(4-methoxy-3-methylphenyl)-3-oxobutanoate was synthesized from methyl 2-(4-methoxy-3-methylphenyl)acetate according to General Method 13 and was purified using silica gel chromatography eluting with 0-100% ethyl acetate in heptanes (4.61 g, 70%). LC-MS $t_R$=1.43 min, [M+H]$^+$=237; $^1$H NMR (250 MHz, DMSO-d6) δ 7.16-6.99 (m, 2H), 6.95-6.88 (m, 1H), 4.99 (s, 1H), 3.77 (s, 3H), 3.64 (s, 3H), 2.23-1.74 (m, 6H).

76.2 4-(4-Methoxy-3-methylphenyl)-1,3,4-trimethyl-4,5-dihydro-1H-pyrazol-5-one 4-(4-Methoxy-3-methylphenyl)-1,3,4-trimethyl-4,5-dihydro-1H-pyrazol-5-one was synthesized by adding methyl 2-(4-methoxy-3-methylphenyl)-3-oxobutanoate to a stirred solution of methyl hydrazine sulfate (2.8 g, 0.02 mol) and triethylamine (2 mL, 0.014 mol) in ethanol 15 mL. The reaction mixture was stirred at 70° C. for 2 hours, whereupon TLC showed complete consumption of the starting material. The solvent was removed under reduced pressure and was extracted into DCM (4×15 mL) and washed with 1 N HCl (30 mL). The organic layers were combined, washed with brine (20 mL), dried over sodium sulfate, filtered and concentrated under reduced pressure (4.41 g, 70%). LC-MS $t_R$=1.00 min, [M+H]$^+$=233.

76.3 4-Bromo-4-(4-methoxy-3-methylphenyl)-1,3-dimethyl-4,5-dihydro-1H-pyrazol-5-one 4-Bromo-4-(4-methoxy-3-methylphenyl)-1,3-dimethyl-4,5-dihydro-1H-pyrazol-5-one was synthesized from 4-(4-methoxy-3-methylphenyl)-1,3,4-trimethyl-4,5-dihydro-1H-pyrazol-5-one according to General Method 6 (3.84 g, 100%). LC-MS $t_R$=1.06 min, [M+H]$^+$=312.

76.4 4-{[(tert-Butoxy)carbonyl]({[(tert-butoxy)carbonyl]oxy})amino}-4-(4-methoxy-3-methylphenyl)-1,3-dimethyl-4,5-dihydro-1H-pyrazol-5-one 4-{[(tert-Butoxy)carbonyl]({[(tert-butoxy)carbonyl]oxy})amino}-4-(4-methoxy-3-methylphenyl)-1,3-dimethyl-4,5-dihydro-1H-pyrazol-5-one was synthesized from 4-bromo-4-(4-methoxy-3-methylphenyl)-1,3-dimethyl-4,5-dihydro-1H-pyrazol-5-one according to General Method 8. The product was purified using silica gel chromatography eluting with 0-75% ethyl acetate in heptanes (1.63 g, 26%). LC-MS $t_R$=1.50 min, [M+Na]$^+$=486; $^1$H NMR (500 MHz, DMSO-d6) δ 7.26-7.11 (m, 1H), 7.09-6.99 (m, 1H), 6.98-6.82 (m, 1H), 3.77 (s, 3H), 3.27-3.01 (m, 3H), 2.18-1.94 (m, 6H), 1.45-1.24 (m, 18H).

76.5 4-(Hydroxyamino)-4-(4-methoxy-3-methylphenyl)-1,3-dimethyl-4,5-dihydro-1H-pyrazol-5-one 4-(Hydroxyamino)-4-(4-methoxy-3-methylphenyl)-1,3-dimethyl-4,5-dihydro-1H-pyrazol-5-one was synthesized from 4-{[(tert-butoxy)carbonyl]({[(tert-butoxy)carbonyl]oxy})amino}-4-(4-methoxy-3-methylphenyl)-1,3-dimethyl-4,5-dihydro-1H-pyrazol-5-one according to General Method 9. Purification was carried out triturating from methanol:heptanes (1:10, v:v) (0.37 g, 45%). LC-MS $t_R$=1.02 min, [M+Na]$^+$=286; $^1$H NMR (500 MHz, DMSO-d6) δ 7.79 (s, 1H), 7.08-6.84 (m, 3H), 6.70 (s, 1H), 3.76 (s, 3H), 3.18 (s, 3H), 2.11 (s, 3H), 1.92 (s, 3H).

Example 77

Compound 77 [4-(Hydroxyamino)-3-(4-methanesulfonyl-3-methoxyphenyl)-1,4-dimethyl-4,5-dihydro-1H-pyrazol-5-one]

77.1 1-[3-Methoxy-4-(methylsulfanyl)phenyl]ethan-1-one

1-[3-Methoxy-4-(methylsulfanyl)phenyl]ethan-1-one was synthesized from 1-(4-fluoro-3methoxyphenyl)ethan-1-one according to General Method 14 (10.5 g, 87%). LC-MS $t_R$=1.21 min, [M+H]$^+$=197; $^1$H NMR (250 MHz, DMSO-d6) δ 7.62 (m, 1H), 7.39 (m, 1H), 7.25 (m, 1H), 3.89 (s, 3H), 2.56 (s, 3H), 2.45 (s, 3H).

77.2 Methyl 3-[3-methoxy-4-(methylsulfanyl)phenyl]-3-oxopropanoate

Methyl 3-[3-methoxy-4-(methylsulfanyl)phenyl]-3-oxopropanoate was synthesized from 1-[3-methoxy-4-(methylsulfanyl)phenyl]ethan-1-one according to General Method 1. The product was purified using silica gel chromatography eluting with 0-65% ethyl acetate in heptanes (9.7 g, 54%). LC-MS $t_R$=1.23 min, [M+H]$^+$=255; $^1$H NMR (500 MHz, DMSO-d6) δ 7.61 (m, 1H), 7.40 (m, 1H), 7.27 (m, 1H), 4.19 (s, 2H), 3.89 (s, 3H), 3.65 (s, 3H), 2.45 (m, 3H).

77.3 3-[3-Methoxy-4-(methylsulfanyl)phenyl]-1-methyl-1H-pyrazol-5-ol

To a suspension of methyl hydrazine sulfate (4.8 g, 33.9 mmol) in ethanol (40 mL) was added triethylamine (4.73 mL, 33.9 mmol) dropwise. Methyl 3-[3-methoxy-4-(methylsulfanyl)phenyl]-3-oxopropanoate (9.7 g, 28.23 mmol) was added and the reaction mixture heated at 80° C. for 6 hours. The reaction mixture was cooled to room temperature and concentrated under reduced pressure. The product was purified using silica gel chromatography eluting with 0-30% methanol in ethyl acetate (3.18 g, 30%). LC-MS $t_R$=1.12 min, [M+H]$^+$=251; $^1$H NMR (250 MHz, DMSO-d6) δ 7.29 (m, 2H), 7.12 (m, 1H), 5.85 (s, 1H), 3.86 (s, 3H), 3.57 (s, 3H), 2.39 (m, 4H).

77.4 5-Hydroxy-3-[3-methoxy-4-(methylsulfanyl) phenyl]-1-methyl-1H-pyrazole-4-carbaldehyde 5-Hydroxy-3-[3-methoxy-4-(methylsulfanyl)phenyl]-1-methyl-1H-pyrazole-4-carbaldehyde was synthesized from 3-[3-methoxy-4-(methylsulfanyl)phenyl]-1-methyl-1H-pyrazol-5-ol according to General Method 4 (2.71 g, 85%). LC-MS $t_R$=1.06 min, [M+H]$^+$=279; $^1$H NMR (250 MHz, DMSO-d6) δ 9.74 (s, 1H), 7.49 (m, 2H), 7.17 (m, 1H), 3.85 (s, 3H), 3.61 (s, 3H), 2.41 (s, 3H).

77.5 3-[3-Methoxy-4-(methylsulfanyl)phenyl]-1,4-dimethyl-1H-pyrazol-5-ol

3-[3-Methoxy-4-(methylsulfanyl)phenyl]-1,4-dimethyl-1H-pyrazol-5-ol was synthesized from 5-hydroxy-3-[3-methoxy-4-(methylsulfanyl)phenyl]-1-methyl-1H-pyrazole-4-carbaldehyde according to General Method 5 (1.86 g, 91%). LC-MS $t_R$=1.04 min, [M+H]$^+$=265; $^1$H NMR (250 MHz, DMSO-d6) δ 7.15 (s, 3H), 3.84 (s, 3H), 3.51 (s, 3H), 2.39 (s, 3H), 1.99 (s, 3H).

77.6 4-Bromo-3-(4-methanesulfinyl-3-methoxyphenyl)-1,4-dimethyl-4,5-dihydro-1H-pyrazol-5-one 4-Bromo-3-(4-methanesulfinyl-3-methoxyphenyl)-1,4-dimethyl-4,5-dihydro-1H-pyrazol-5-one was synthesized from 3-[3-methoxy-4-(methylsulfanyl)phenyl]-1,4-dimethyl-1H-pyrazol-5-ol according to General Method 6 (2.02 g, 99%). LC-MS $t_R$=1.06 min, [M+H]$^+$=359.

77.7 4-{[(tert-Butoxy)carbonyl]({[(tert-butoxy)carbonyl]oxy})amino}-3-(4-methanesulfinyl-3-methoxyphenyl)-1,4-dimethyl-4,5-dihydro-1H-pyrazol-5-one 4-{[(tert-Butoxy)carbonyl]({[(tert-butoxy)carbonyl]oxy})amino}-3-(4-methanesulfinyl-3-methoxyphenyl)-1,4-dimethyl-4,5-dihydro-1H-pyrazol-5-one was synthesized from 4-bromo-3-(4-methanesulfinyl-3-methoxyphenyl)-1,4-dimethyl-4,5-dihydro-1H-pyrazol-5-one according to General Method 8 (2.65 g, 57%). LC-MS $t_R$=1.33 min, [M+H]$^+$=512.

77.8 4-{[(tert-Butoxy)carbonyl]({[(tert-butoxy)carbonyl]oxy})amino}-3-(4-methanesulfonyl-3-methoxyphenyl)-1,4-dimethyl-4,5-dihydro-1H-pyrazol-5-one 4-{[(tert-Butoxy)carbonyl]({[(tert-butoxy)carbonyl]oxy})amino}-3-(4-methanesulfonyl-3-methoxyphenyl)-1,4-dimethyl-4,5-dihydro-1H-pyrazol-5-one was synthesized from 4-{[(tert-butoxy)carbonyl]({[(tert-butoxy)carbonyl]oxy})amino}-3-(4-methanesulfinyl-3-methoxyphenyl)-1,4-dimethyl-4,5-dihydro-1H-pyrazol-5-one according to General Method 10. The product was purified using silica gel chromatography eluting with 30-100% ethyl acetate in heptanes (0.73 g, 36%). LC-MS $t_R$=1.37 min, [M+Na]$^+$=550; $^1$H NMR (500 MHz, DMSO-d6) δ 8.05-7.83 (m, 2H), 7.73-7.46 (m, 1H), 4.04-4.02 (m, 3H), 3.36-3.35 (m, 3H), 3.29-3.21 (m, 3H), 1.59-1.46 (m, 9H), 1.42-1.34 (m, 3H), 1.28-1.20 (m, 9H).

77.9 4-(Hydroxyamino)-3-(4-methanesulfonyl-3-methoxyphenyl)-1,4-dimethyl-4,5-dihydro-1H-pyrazol-5-one 4-(Hydroxyamino)-3-(4-methanesulfonyl-3-methoxyphenyl)-1,4-dimethyl-4,5-dihydro-1H-pyrazol-5-one was synthesized from 4-{[(tert-butoxy)carbonyl]({[(tert-butoxy)carbonyl]oxy})amino}-3-(4-methanesulfonyl-3-methoxyphenyl)-1,4-dimethyl-4,5-dihydro-1H-pyrazol-5-one according to General Method 9. The product was purified using acidic preparative HPLC (0.10 g, 24%). LC-MS $t_R$=0.91 min, [M+H]$^+$=328; $^1$H NMR (500 MHz, DMSO-d6) δ 7.93-7.89 (m, 1H), 7.89-7.84 (m, 1H), 7.82-7.77 (m, 1H), 7.77-7.72 (m, 1H), 6.62-6.57 (m, 1H), 4.01 (s, 3H), 3.33 (s, 3H), 3.26 (s, 3H), 1.23 (s, 3H).

Example 78

Compound 78 [4-(Hydroxyamino)-1,4-dimethyl-3-[4-(propane-2-sulfonyl)phenyl]-4,5-dihydro-1H-pyrazol-5-one]

78.1 1-[4-(Propan-2-ylsulfanyl)phenyl]ethan-1-one

To a solution of 1-(4-chlorophenyl)ethan-1-one (7 g, 45.28 mmol) in DMF (60 mL) was added sodium propane-2-thiolate (4.89 g, 49.81 mmol) over 20 minutes using ice water cooling. The reaction mixture was left to stir for a further 17 hours before addition of deionized water (100 mL). The product was extracted into diethyl ether (3×150 mL), dried over magnesium sulfate, filtered and concentrated under reduced pressure to afford the title compound as an orange oil (8.57 g, 94%). LC-MS $t_R$=1.37 min, [M+H]$^+$=195; $^1$H NMR (500 MHz, Chloroform-d) δ 7.89-7.81 (m, 2H), 7.40-7.31 (m, 2H), 3.55 (hept, J=6.7 Hz, 1H), 2.56 (s, 3H), 1.36 (d, J=6.7 Hz, 6H).

78.2 Methyl 3-oxo-3-[4-(propan-2-ylsulfanyl)phenyl]propanoate

Methyl 3-oxo-3-[4-(propan-2-ylsulfanyl)phenyl]propanoate was synthesized from 1-[4-(propan-2-ylsulfanyl)phenyl]ethan-1-one according to General Method 1 and was purified using silica gel chromatography eluting in 0-75% ethyl acetate in heptanes to afford the title compound as a brown oil (9.88 g, 87%). LC-MS $t_R$=1.36 min, [M+H]$^+$=252.95; $^1$H NMR (500 MHz, Chloroform-d) δ 7.90-7.76 (m, 2H), 7.41-7.32 (m, 2H), 3.96 (s, 2H), 3.75 (s, 3H), 3.57 (hept, J=6.7 Hz, 1H), 1.37 (d, J=6.7 Hz, 6H).

78.3 1-Methyl-3-[4-(propan-2-ylsulfanyl)phenyl]-4,5-dihydro-1H-pyrazol-5-one 1-Methyl-3-[4-(propan-2-ylsulfanyl)phenyl]-4,5-dihydro-1H-pyrazol-5-one was synthesized from methyl 3-oxo-3-[4-(propan-2-ylsulfanyl)phenyl]propanoate according to General Method 2 to afford the title compound as a beige solid (7.02 g, 71%). LC-MS $t_R$=1.21 min, [M+H]$^+$=248.95; $^1$H NMR (500 MHz, DMSO-d6) δ 11.04 (s, 1H), 7.67-7.55 (m, 2H), 7.39-7.28 (m, 2H), 5.78 (s, 1H), 3.55 (s, 3H), 3.45 (tt, J=10.9, 5.5 Hz, 1H), 1.23 (d, J=6.7 Hz, 6H).

78.4 5-Hydroxy-1-methyl-3-[4-(propan-2-ylsulfanyl)phenyl]-1H-pyrazole-4-carbaldehyde 5-Hydroxy-1-methyl-3-[4-(propan-2-ylsulfanyl)phenyl]-1H-pyrazole-4-carbaldehyde was synthesized from 1-methyl-3-[4-(propan-2-ylsulfanyl)phenyl]-4,5-dihydro-1H-pyrazol-5-one according to General Method 3. 17 hours after the addition of deionized water, diethyl ether (40 mL) was added and the suspension stirred at room temperature for 10 minutes. The resulting fine yellow solid was collected by filtration. The diethyl ether layer was isolated and the aqueous layer re-extracted twice with diethyl ether (2×40 mL). The organic layers were combined and washed with water (3×40 mL). The solid was added to the organic solution along with 30 mL of ethyl acetate. The organic layer was dried over magnesium sulfate, filtered and concentrated under reduced pressure to afford the title compound as an orange solid (7.14 g, 85%). %). LC-MS $t_R$=1.23 min, [M+H]$^+$=276.95; $^1$H NMR (500 MHz, DMSO-d6) δ 9.71 (s, 1H), 7.83-7.73 (m, 2H), 7.41-7.36 (m, 2H), 3.60 (s, 3H), 3.57 (hept, J=2.2 Hz, 1H), 1.27 (d, J=6.6 Hz, 6H).

78.5 1,4-Dimethyl-3-[4-(propan-2-ylsulfanyl)phenyl]-1H-pyrazol-5-ol 1,4-Dimethyl-3-[4-(propan-2-ylsulfanyl)phenyl]-1H-pyrazol-5-ol was synthesized from 5-hydroxy-1-methyl-3-[4-(propan-2-ylsulfanyl)phenyl]-1H-pyrazole-4-carbaldehyde according to General Method 5 to afford the title compound as a yellow solid (7.73 g, 99%). LC-MS $t_R$=1.18 min, [M+H]$^+$=262.95; $^1$H NMR (250 MHz, DMSO-d6) δ 7.55 (d, J=8.4 Hz, 2H), 7.37 (d, J=8.4 Hz, 2H), 3.51 (s, 3H), 3.48-3.44 (m, 1H), 1.99 (s, 3H), 1.25 (d, J=6.6 Hz, 6H).

78.6 4-Bromo-1,4-dimethyl-3-[3-(propane-2-sulfinyl)phenyl]-4,5-dihydro-1H-pyrazol-5-one 4-Bromo-1,4-dimethyl-3-[3-(propane-2-sulfinyl)phenyl]-4,5-dihydro-1H-pyrazol-5-one was synthesized from 1,4-dimethyl-3-[4-(propan-2-ylsulfanyl)phenyl]-1H-pyrazol-5-ol according to General Method 6 and used directly in the synthesis of 4-{[(tert-butoxy)carbonyl]({[(tert-butoxy)carbonyl]oxy})amino}-1,4-dimethyl-3-[4-(propane-2-sulfinyl)phenyl]-4,5-dihydro-1H-pyrazol-5-one. LC-MS $t_R$=1.37 min, [M+H]$^+$=357/359.

78.7 4-{[(tert-Butoxy)carbonyl]({[(tert-butoxy)carbonyl]oxy})amino}-1,4-dimethyl-3-[4-(propane-2-sulfinyl)phenyl]-4,5-dihydro-1H-pyrazol-5-one 4-{[(tert-Butoxy)carbonyl]({[(tert-butoxy)carbonyl]oxy})amino}-1,4-dimethyl-3-[4-(propane-2-sulfinyl)phenyl]-4,5-dihydro-1H-pyrazol-5-one was synthesized from 4-bromo-1,4-dimethyl-3-[3-(propane-2-sulfinyl)phenyl]-4,5-dihydro-1H-pyrazol-5-one according to General Method 8 to afford the title compound as a sticky yellow solid (12.3 g, 80%). LC-MS $t_R$=1.37 min, [M+H]$^+$=510.

78.8 4-{[(tert-Butoxy)carbonyl]({[(tert-butoxy)carbonyl]oxy})amino}-1,4-dimethyl-3-[4-(propane-2-sulfonyl)phenyl]-4,5-dihydro-1H-pyrazol-5-one 4-{[(tert-Butoxy)carbonyl]({[(tert-butoxy)carbonyl]oxy})amino}-1,4-dimethyl-3-[4-(propane-2-sulfonyl)phenyl]-4,5-dihydro-1H-pyrazol-5-one was synthesized from 4-{[(tert-butoxy)carbonyl]({[(tert-butoxy)carbonyl]oxy})amino}-1,4-dimethyl-3-[4-(propane-2-sulfinyl)phenyl]-4,5-dihydro-1H-pyrazol-5-one according to General Method 10 and purified using silica gel chromatography eluting with 10-80% ethyl acetate:heptanes to yield the title compound as a yellow solid (5.93 g, 42%). LC-MS $t_R$=1.45 min, [M+H]$^+$=548.

78.9 4-(Hydroxyamino)-3-(4-methanesulfonyl-3,5-dimethylphenyl)-1,4-dimethyl-4,5-dihydro-1H-pyrazol-5-one 4-(Hydroxyamino)-3-(4-methanesulfonyl-3,5-dimethylphenyl)-1,4-dimethyl-4,5-dihydro-1H-pyrazol-5-one was synthesized from 4-{[(tert-butoxy)carbonyl]({[(tert-butoxy)carbonyl]oxy})amino}-1,4-dimethyl-3-[4-(propane-2-sulfonyl)phenyl]-4,5-dihydro-1H-pyrazol-5-one according to General Method 9. To the crude orange oil was added heptanes (50 mL) and the solvent was removed under reduced pressure where upon an orange solid formed. Ethyl acetate (5 mL) and heptanes (10 mL) were added to yield an orange solid which was stirred at 30 OC for 1 hour in ethyl acetate:heptanes (20 mL; 1:1 v:v). The resulting light orange solid was collected by filtration and dried under reduced pressure to afford the title compound as an orange solid (2.21 g, 60%). LC-MS $t_R$=3.08 min, [M+H]$^+$=326; $^1$H NMR (500 MHz, DMSO-d6) δ 8.33-8.24 (m, 2H), 7.98-7.87 (m, 2H), 7.68 (s, 1H), 6.60 (s, 1H), 3.46 (hept, J=6.8 Hz, 1H), 3.33 (s, 3H), 1.25 (s, 3H), 1.21-1.17 (m, 6H).

Example 79

Compound 79 [4-(Hydroxyamino)-3-(4-methanesulfonyl-3,5-dimethylphenyl)-1,4-dimethyl-4,5-dihydro-1H-pyrazol-5-one]

79.1 1-[3,5-Dimethyl-4-(methylsulfanyl)phenyl]ethan-1-one

1-[3,5-Dimethyl-4-(methylsulfanyl)phenyl]ethan-1-one was synthesized from 1-(4-fluoro-3,5-dimethylphenyl)ethan-1-one according to General Method 14 (5.30 g, 82%). LC-MS $t_R$=1.40 min, [M+H]$^+$=195; $^1$H NMR (500 MHz, DMSO-d6) δ 7.65 (s, 2H), 2.64-2.52 (m, 9H), 2.25 (s, 3H).

79.2 3-[3,5-Dimethyl-4-(methylsulfanyl)phenyl]-3-oxopropanoate

3-[3,5-Dimethyl-4-(methylsulfanyl)phenyl]-3-oxopropanoate was synthesized from 1-[3,5-dimethyl-4-(methylsulfanyl)phenyl]ethan-1-one according to General Method 1 (6.35 g, 87%). LC-MS $t_R$=1.39 min, [M+H]$^+$=253; $^1$H NMR (500 MHz, DMSO-d6) δ 7.70 (s, 2H), 4.16 (s, 2H), 3.64 (s, 3H), 2.54 (s, 6H), 2.26 (s, 3H).

79.3 3-[3,5-Dimethyl-4-(methylsulfanyl)phenyl]-1-methyl-4,5-dihydro-1H-pyrazol-5-one 3-[3,5-Dimethyl-4-(methylsulfanyl)phenyl]-1-methyl-4,5-dihydro-1H-pyrazol-5-one was synthesized from 3-[3,5-dimethyl-4-(methylsulfanyl)phenyl]-3-oxopropanoate according to General Method 2. The reaction mixture was concentrated under reduced pressure. 1 N HCl (50 mL) was added and the resulting solid was filtered and washed with water (25 mL) (9.20 g, 96%). LC-MS $t_R$=1.20 min, [M−H]$^-$=246.95; $^1$H NMR (500 MHz, DMSO-d6) δ 7.48 (s, 2H), 5.86 (s, 1H), 3.57 (s, 3H), 2.51 (s, 6H), 2.21 (s, 3H).

79.4 3-[3,5-Dimethyl-4-(methylsulfanyl)phenyl]-5-hydroxy-1-methyl-1H-pyrazole-4-carbaldehyde 3-[3,5-Dimethyl-4-(methylsulfanyl)phenyl]-5-hydroxy-1-methyl-1H-pyrazole-4-carbaldehyde was synthesized from 3-[3,5-dimethyl-4-(methylsulfanyl)phenyl]-1-methyl-4,5-dihydro-1H-pyrazol-5-one according to General Method 4 (6.10 g, 70%). LC-MS $t_R$=1.27 min, [M+H]$^+$=277; $^1$H NMR (500 MHz, DMSO-d6) δ 9.71 (s, 1H), 7.61-7.46 (m, 2H), 3.60-3.59 (m, 3H), 2.53 (s, 6H), 2.41 (s, 1H), 2.24 (s, 3H).

79.5 3-[3,5-Dimethyl-4-(methylsulfanyl)phenyl]-1,4-dimethyl-1H-pyrazol-5-ol

3-[3,5-Dimethyl-4-(methylsulfanyl)phenyl]-1,4-dimethyl-1H-pyrazol-5-ol was synthesized from 3-[3,5-dimethyl-4-(methylsulfanyl)phenyl]-5-hydroxy-1-methyl-1H-pyrazole-4-carbaldehyde according to General Method 5. The product was purified using silica gel chromatography eluting with 0-30% methanol in ethyl acetate (1.25 g, 32%). LC-MS $t_R$=1.18 min, [M+H]$^+$=263; $^1$H NMR (500 MHz, DMSO-d6) δ 7.36 (s, 2H), 3.62-3.44 (m, 3H), 2.54-2.51 (m, 6H), 2.23-2.20 (m, 3H), 2.08-1.95 (m, 3H), 1.91 (s, 1H).

79.6 4-Bromo-3-(4-methanesulfinyl-3,5-dimethylphenyl)-1,4-dimethyl-4,5-dihydro-1H-pyrazol-5-one 4-Bromo-3-(4-methanesulfinyl-3,5-dimethylphenyl)-1,4-dimethyl-4,5-dihydro-1H-pyrazol-5-one was synthesized from 3-[3,5-dimethyl-4-(methylsulfanyl)phenyl]-1,4-dimethyl-1H-pyrazol-5-ol according to General Method 6 (4.14 g, 99%). LC-MS $t_R$=1.11 min, [M+H]$^+$=358.

79.7 4-{[(tert-Butoxy)carbonyl]({[(tert-butoxy)carbonyl]oxy})amino}-3-(4-methanesulfinyl-3,5-dimethylphenyl)-1,4-dimethyl-4,5-dihydro-1H-pyrazol-5-one 4-{[(tert-Butoxy)carbonyl]({[(tert-butoxy)carbonyl]oxy})amino}-3-(4-methanesulfinyl-3,5-dimethylphenyl)-1,4-dimethyl-4,5-dihydro-1H-pyrazol-5-one was synthesized from 4-bromo-3-(4-methanesulfinyl-3,5-dimethylphenyl)-1,4-dimethyl-4,5-dihydro-1H-pyrazol-5-one according to General Method 8. The product was purified using silica gel chromatography eluting with 0-100% ethyl acetate in heptanes (0.27 g, 21%). LC-MS $t_R$=1.35 min, [M+H]$^+$=510; $^1$H NMR (500 MHz, DMSO-d6) δ 8.02-7.82 (m, 2H), 2.92 (s, 3H), 2.64 (s, 3H), 2.57 (s, 6H), 2.37 (s, 3H), 1.61-1.51 (m, 9H), 1.35-1.19 (m, 9H).

79.8 tert-Butyl N-hydroxy-N-[3-(4-methanesulfonyl-3,5-dimethylphenyl)-1,4-dimethyl-5-oxo-4,5-dihydro-1H-pyrazol-4-yl]carbamate tert-Butyl N-hydroxy-N-[3-(4-methanesulfonyl-3,5-dimethylphenyl)-1,4-dimethyl-5-oxo-4,5-dihydro-1H-pyrazol-4-yl]carbamate was synthesized from 4-{[(tert-butoxy)carbonyl]({[(tert-butoxy)carbonyl]oxy})amino}-3-(4-methanesulfinyl-3,5-dimethylphenyl)-1,4-dimethyl-4,5-dihydro-1H-pyrazol-5-one according to General Method 10 (0.29 g, 76%). LC-MS $t_R$=1.16 min, [M+Na]$^+$=448; $^1$H NMR (500 MHz, DMSO-d6) δ 7.72-7.61 (m, 2H), 5.76 (s, 1H), 3.35 (s, 2H), 3.26-3.22 (m, 4H), 2.68-2.66 (m, 6H), 1.55 (s, 3H), 1.27-1.21 (m, 9H).

79.9 4-(Hydroxyamino)-3-(4-methanesulfonyl-3,5-dimethylphenyl)-1,4-dimethyl-4,5-dihydro-1H-pyrazol-5-one 4-(Hydroxyamino)-3-(4-methanesulfonyl-3,5-dimethylphenyl)-1,4-dimethyl-4,5-dihydro-1H-pyrazol-5-one was synthesized from tert-butyl N-hydroxy-N-[3-(4-methanesulfonyl-3,5-dimethylphenyl)-1,4-dimethyl-5-oxo-4,5-dihydro-1H-pyrazol-4-yl]carbamate according to General Method 9. The product was purified using acidic preparative HPLC yielding the target compound (0.06 g, 49%). LC-MS $t_R$=1.01 min, [M+H]$^+$=326; $^1$H NMR (500 MHz, DMSO-d6) δ 7.87 (s, 2H), 7.72-7.66 (m, 1H), 6.61-6.51 (m, 1H), 3.23 (s, 3H), 2.68 (s, 6H), 1.22 (s, 3H).

Example 80

Compound 80 [4-(Hydroxyamino)-1,4-dimethyl-3-[4-(morpholine-4-sulfonyl)phenyl]-4,5-dihydro-1H-pyrazol-5-one]

80.1 1-[4-(Morpholine-4-sulfonyl)phenyl]ethan-1-one

To a solution of 4-acetylbenzene-1-sulfonyl chloride (7.5 g, 34.30 mmol) in DCM (35 mL) at 0° C. was added morpholine (3.3 mL, 38.26 mmol) and pyridine (2.8 mL, 34.69 mmol). The reaction mixture was stirred at room temperature until complete conversion of the starting material was observed by LC-MS. The reaction mixture was quenched with saturated sodium hydrogen carbonate (25 mL) and the product extracted into DCM (2×30 mL). The combined organic layers were washed with 2 M HCl (25 mL) and brine (25 mL) and dried over magnesium sulfate, filtered and concentrated under reduced pressure (7.68 g, 79%). LC-MS $t_R$=1.04 min, [M+H]$^+$=270; $^1$H NMR (500 MHz, DMSO-d6) δ 8.28-8.14 (m, 2H), 7.92-7.83 (m, 2H), 3.67-3.59 (m, 4H), 2.97-2.83 (m, 4H), 2.50 (s, 3H).

80.2 Methyl 3-[4-(morpholine-4-sulfonyl)phenyl]-3-oxopropanoate

Methyl 3-[4-(morpholine-4-sulfonyl)phenyl]-3-oxopropanoate was synthesized from 1-[4-(morpholine-4-sulfonyl)phenyl]ethan-1-one according to General Method 1. The product was purified using silica gel chromatography eluting with 0-70% ethyl acetate in heptanes (4.98 g, 51%). LC-MS $t_R$=1.08 min, [M+H]$^+$=328; $^1$H NMR (500 MHz, DMSO-d6) δ 8.30-8.06 (m, 2H), 7.93-7.78 (m, 2H), 4.31 (s, 2H), 3.82-3.65 (m, 3H), 3.65-3.60 (m, 4H), 2.94-2.90 (m, 4H).

80.3 1-Methyl-3-[4-(morpholine-4-sulfonyl)phenyl]-1H-pyrazol-5-ol

1-Methyl-3-[4-(morpholine-4-sulfonyl)phenyl]-1H-pyrazol-5-ol was synthesized from methyl 3-[4-(morpholine-4-sulfonyl)phenyl]-3-oxopropanoate according to General Method 2 (3.31 g, 78%). LC-MS $t_R$=0.99 min, [M+H]$^+$=324; $^1$H NMR (500 MHz, DMSO-d6) δ 8.06-7.89 (m, 2H), 7.76-7.59 (m, 2H), 5.94 (s, 1H), 3.66-3.61 (m, 4H), 3.60 (s, 3H), 2.96-2.78 (m, 4H).

80.4 5-Hydroxy-1-methyl-3-[4-(morpholine-4-sulfonyl)phenyl]-1H-pyrazole-4-carbaldehyde 5-Hydroxy-1-methyl-3-[4-(morpholine-4-sulfonyl)phenyl]-1H-pyrazole-4-carbaldehyde was synthesized from 1-methyl-3-[4-(morpholine-4-sulfonyl)phenyl]-1H-pyrazol-5-ol according to General Method 3. The product was extracted into DCM (3×40 mL), washed with brine (30 mL), dried over sodium sulfate, filtered and concentrated under reduced pressure (2.09 g, 64%). LC-MS $t_R$=0.97 min, [M+H]$^+$=352; $^1$H NMR (250 MHz, DMSO-d6) δ 9.75 (s, 1H), 8.23-8.03 (m, 2H), 7.80-7.70 (m, 2H), 5.76 (s, 1H), 3.64-3.63 (m, 3H), 2.90 (m, 6H), 2.07 (s, 2H).

80.5 1,4-Dimethyl-3-[4-(morpholine-4-sulfonyl)phenyl]-1H-pyrazol-5-ol 1,4-Dimethyl-3-[4-(morpholine-4-sulfonyl)phenyl]-1H-pyrazol-5-ol was synthesized from 5-hydroxy-1-methyl-3-

[4-(morpholine-4-sulfonyl)phenyl]-1H-pyrazole-4-carbaldehyde according to General Method 5 (0.93 g, 97%). LC-MS $t_R$=0.97 min, [M+H]$^+$=338; $^1$H NMR (250 MHz, DMSO-d6) δ 7.97-7.56 (m, 4H), 3.74-3.57 (m, 4H), 3.42 (s, 3H), 2.93-2.77 (m, 4H), 1.82 (s, 3H).

80.6 4-Bromo-1,4-dimethyl-3-[4(morpholine-4-sulfonyl)phenyl]-4,5-dihydro-1H-pyrazol-5-one 4-Bromo-1,4-dimethyl-3-[4(morpholine-4-sulfonyl)phenyl]-4,5-dihydro-1H-pyrazol-5-one was synthesized from 1,4-dimethyl-3-[4-(morpholine-4-sulfonyl)phenyl]-1H-pyrazol-5-ol according to General Method 6 (1.74 g, 93%). LC-MS $t_R$=1.23 min, [M+H]$^+$=417.

80.7 4-{[(tert-Butoxy)carbonyl]({[(tert-butoxy)carbonyl]oxy})amino}-1,4-dimethyl-3-[4-(morpholine-4-sulfonyl)phenyl]-4,5-dihydro-1H-pyrazol-5-one 4-{[(tert-Butoxy)carbonyl]({[(tert-butoxy)carbonyl]oxy})amino}-1,4-dimethyl-3-[4-(morpholine-4-sulfonyl)phenyl]-4,5-dihydro-1H-pyrazol-5-one was synthesized from 4-bromo-1,4-dimethyl-3-[4(morpholine-4-sulfonyl)phenyl]-4,5-dihydro-1H-pyrazol-5-one according to General Method 8 (0.70 g, 18%). LC-MS $t_R$=1.44 min, [M+Na]$^+$=591.

80.8 4-(Hydroxyamino)-1,4-dimethyl-3-[4-(morpholine-4-sulfonyl)phenyl]-4,5-dihydro-1H-pyrazol-5-one 4-(Hydroxyamino)-1,4-dimethyl-3-[4-(morpholine-4-sulfonyl)phenyl]-4,5-dihydro-1H-pyrazol-5-one was synthesized from 4-{[(tert-butoxy)carbonyl]({[(tert-butoxy)carbonyl]oxy})amino}-1,4-dimethyl-3-[4-(morpholine-4-sulfonyl)phenyl]-4,5-dihydro-1H-pyrazol-5-one according to General Method 9. The product was purified using acidic preparative HPLC to yield the target compound (0.09 g, 60%). LC-MS $t_R$=3.08 min, [M+H]$^+$=369; $^1$H NMR (500 MHz, DMSO-d6) δ 8.35-8.23 (m, 2H), 7.91-7.78 (m, 2H), 7.72-7.62 (m, 1H), 6.67-6.54 (m, 1H), 3.72-3.54 (m, 4H), 2.97-2.82 (m, 4H), 1.26 (s, 3H).

Example 81

Compound 81 [4-(Hydroxyamino)-1,4-dimethyl-3-[4-(morpholine-4-carbonyl)phenyl]-4,5-dihydro-1H-pyrazol-5-one]

81.1 Methyl 4-(3-methoxy-3-oxopropanoyl)benzoate

Methyl 4-(3-methoxy-3-oxopropanoyl)benzoate was synthesized from methyl 4-acetylbenzoate according to General Method 1 with the product being purified using silica gel chromatography eluting with 0-35% ethyl acetate in heptanes (10.45 g, 57%). LC-MS $t_R$=1.16 min, [M+H]$^+$=236.90; $^1$H NMR (500 MHz, DMSO-d6) δ 8.08 (m, 4H), 4.28 (s, 2H), 3.89 (s, 3H), 3.65 (s, 3H).

81.2 Methyl 4-(1-methyl-5-oxo-4,5-dihydro-1H-pyrazol-3-yl)benzoate

To a solution of methyl 4-(3-methoxy-3-oxopropanoyl)benzoate (10.44 g, 35.36 mmol) in ethanol (50 mL) was added methylhydrazine sulfate (5.61 g, 38.89 mmol) and N,N-diethylethanamine (5.43 mL, 38.89 mmol) and the resulting reaction mixture was heated to 80 ºC until complete consumption of starting material was observed as monitored by LC-MS. The reaction mixture was concentrated under reduced pressure and the resulting solid was dissolved in ethyl acetate (60 mL), washed with 1M HCl (3×30 mL), water (30 mL) and brine (30 mL). The organic layer was dried over magnesium sulfate, filtered and concentrated under reduced pressure to give the title compound as a brown solid (7.82 g, 69%). LC-MS $t_R$=1.04 min, [M+H]$^+$=232.90.

81.3 Methyl 4-(4-formyl-1-methyl-5-oxo-4,5-dihydro-1H-pyrazol-3-yl)benzoate Methyl 4-(4-formyl-1-methyl-5-oxo-4,5-dihydro-1H-pyrazol-3-yl)benzoate was synthesized from methyl 4-(1-methyl-5-oxo-4,5-dihydro-1H-pyrazol-3-yl)benzoate according to General Method 4 (5.88 g, 84%). LC-MS $t_R$=1.09 min, [M+H]$^+$=260.95; $^1$H NMR (250 MHz, DMSO-d6) δ 9.77 (s, 1H), 7.98 (s, 4H), 3.87 (s, 3H), 3.64 (s, 3H).

81.4 Methyl 4-(1,4-dimethyl-5-oxo-4,5-dihydro-1H-pyrazol-3-yl)benzoate

Methyl 4-(1,4-dimethyl-5-oxo-4,5-dihydro-1H-pyrazol-3-yl)benzoate was synthesized from methyl 4-(4-formyl-1-methyl-5-oxo-4,5-dihydro-1H-pyrazol-3-yl)benzoate according to General Method 5 (7.7 g, 97%). LC-MS $t_R$=1.01 min, [M+H]$^+$=246.95; $^1$H NMR (500 MHz, DMSO-d6) δ 7.95 (d, J=8.3 Hz, 2H), 7.75 (d, J=8.4 Hz, 2H), 3.85 (s, 3H), 3.55 (s, 3H), 2.04 (s, 3H).

81.5 Methyl 4-(4-bromo-1,4-dimethyl-5-oxo-4,5-dihydro-1H-pyrazol-3-yl)benzoate Methyl 4-(4-bromo-1,4-dimethyl-5-oxo-4,5-dihydro-1H-pyrazol-3-yl)benzoate was synthesized from methyl 4-(1,4-dimethyl-5-oxo-4,5-dihydro-1H-pyrazol-3-yl)benzoate according to General Method 6 and was used directly in the displacement reaction according to General Method 8 (5.56 g, 100%).

81.6 Methyl 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoate Methyl 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoate was synthesized from methyl 4-(4-bromo-1,4-dimethyl-5-oxo-4,5-dihydro-1H-pyrazol-3-yl)benzoate according to General Method 8 and the product was purified using silica gel chromatography eluting with 10-60% ethyl acetate in heptanes (2.4 g, 27%). LC-MS $t_R$=1.48 min, [M+H]$^+$=499.95.

81.7 4-(4-{[(tert-Butoxy)carbonyl](hydroxy)amino}-1,4-dimethyl-5-oxo-4,5-dihydro-1H-pyrazol-3-yl)benzoic acid To a solution of lithium hydroxide (361.1 mg, 15.08 mmol) in water (60 mL) was added a solution of methyl 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoate (2.4 g, 5.03 mmol) in THF (60 mL) and the reaction mixture was stirred at room temperature until consumption of the starting material was observed as monitored by LC-MS. The reaction mixture was concentrated under reduced pressure to remove the excess THF and the solution diluted with ethyl acetate (200 mL). HCl (20 mL) was added and the organic layer was extracted and washed with brine (20 mL), dried over magnesium sulfate and concentrated under reduced pressure. The crude material was purified using silica gel chromatography (using 40-100% ethyl acetate in heptanes) to give the title compound as an off-white solid (0.5 g, 25%). LC-MS $t_R$=1.06 min, [M+H]$^+$=386.15.

81.8 tert-Butyl N-{1,4-dimethyl-3-[4-(morpholine-4-carbonyl)phenyl]-5-oxo-4,5-dihydro-1H-pyrazol-4-yl}-N-hydroxycarbamate tert-Butyl N-{1,4-dimethyl-3-[4-(morpholine-4-carbonyl)phenyl]-5-oxo-4,5-dihydro-1H-pyrazol-4-yl}-N-hydroxycarbamate was synthesized from 4-(4-{[(tert-butoxy)carbonyl](hydroxy)amino}-1,4-dimethyl-5-oxo-4,5-dihydro-1H-pyrazol-3-yl)benzoic acid and morpholine according to General Method 15 (252 mg, 99%). LC-MS $t_R$=1.04 min, [M+H]$^+$=455.15.

81.9 4-(Hydroxyamino)-1,4-dimethyl-3-[4-(morpholine-4-carbonyl)phenyl]-4,5-dihydro-1H-pyrazol-5-one 4-(Hydroxyamino)-1,4-dimethyl-3-[4-(morpholine-4-carbonyl)phenyl]-4,5-dihydro-1H-pyrazol-5-one was synthesized from tert-butyl N-{1,4-dimethyl-3-[4-(morpholine-4-carbonyl)phenyl]-5-oxo-4,5-dihydro-1H-pyrazol-4-yl}-N-hydroxycarbamate according to General Method 9 and the product was purified using acidic preparative chromatography (60 mg, 31%). LC-MS $t_R$=0.93 min, [M+H]$^+$=332.95; $^1$H NMR (500 MHz, DMSO-d6) δ 8.14-8.08 (m, 2H), 7.64 (d, J=2.4 Hz, 1H), 7.53-7.44 (m, 2H), 6.51 (d, J=2.5 Hz, 1H), 3.59 (s, 4H), 3.34 (s, 4H), 3.30 (s, 4H), 1.22 (s, 3H).

Example 82

Compound 82 [4-(Hydroxyamino)-3-[4-methanesulfonyl-3-(morpholin-4-yl)phenyl]-1,4-dimethyl-4,5-dihydro-1H-pyrazol-5-one]

82.1 tert-Butyl N-hydroxy-N-{3-[4-methanesulfonyl-3-(morpholin-4-yl)phenyl]-1,4-dimethyl-5-oxo-4,5-dihydro-1H-pyrazol-4-yl}carbamate tert-Butyl N-hydroxy-N-{3-[4-methanesulfonyl-3-(morpholin-4-yl)phenyl]-1,4-dimethyl-5-oxo-4,5-dihydro-1H-pyrazol-4-yl}carbamate was synthesized from 4-{[(tert-butoxy)carbonyl]({[(tert-butoxy)carbonyl]oxy})amino}-3-(3-fluoro-4-methanesulfonylphenyl)-1,4-dimethyl-4,5-dihydro-1H-pyrazol-5-one according to General Method 16 to afford the title compound as a yellow oil (116 mg, 112%). LC-MS $t_R$=1.14 min, [M+H]$^+$=483.

82.2 4-(Hydroxyamino)-3-[4-methanesulfonyl-3-(morpholin-4-yl)phenyl]-1,4-dimethyl-4,5-dihydro-1H-pyrazol-5-one 4-(Hydroxyamino)-3-[4-methanesulfonyl-3-(morpholin-4-yl)phenyl]-1,4-dimethyl-4,5-dihydro-1H-pyrazol-5-one was synthesized from tert-butyl N-hydroxy-N-{3-[4-methanesulfonyl-3-(morpholin-4-yl)phenyl]-1,4-dimethyl-5-oxo-4,5-dihydro-1H-pyrazol-4-yl}carbamate according to General Method 9 and was purified using acidic preparative HPLC to afford the title compound as a white solid (50 mg, 29%). LC-MS $t_R$=1.02 min, [M+H]$^+$=383; $^1$H NMR (500 MHz, DMSO-d6) δ 8.19 (d, J=1.5 Hz, 1H), 8.06 (dd, J=8.4, 1.5 Hz, 1H), 7.99 (d, J=8.3 Hz, 1H), 7.72 (d, J=2.6 Hz, 1H), 6.63 (d, J=2.5 Hz, 1H), 3.78 (t, J=4.3 Hz, 4H), 3.44 (s, 3H), 3.03 (h, J=7.0 Hz, 4H), 1.23 (s, 3H).

Example 83

Compound 83 [4-(Hydroxyamino)-3-{4-methanesulfonyl-3-[(2-methoxyethyl)(methyl)amino]phenyl}-1,4-dimethyl-4,5-dihydro-1H-pyrazol-5-one]

83.1 tert-Butyl N-hydroxy-N-(3-{4-methanesulfonyl-3-[(2-methoxyethyl)(methyl)amino]phenyl}-1,4-dimethyl-5-oxo-4,5-dihydro-1H-pyrazol-4-yl)carbamate tert-Butyl N-hydroxy-N-(3-{4-methanesulfonyl-3-[(2-methoxyethyl)(methyl)amino]phenyl}-1,4-dimethyl-5-oxo-4,5-dihydro-1H-pyrazol-4-yl)carbamate was synthesized from 4-{[(tert-butoxy)carbonyl]({[(tert-butoxy)carbonyl]oxy})amino}-3-(3-fluoro-4-methanesulfonylphenyl)-1,4-dimethyl-4,5-dihydro-1H-pyrazol-5-one according to General Method 16 and was purified using silica gel chromatography, eluting in 12-100% ethyl acetate:heptanes to afford the title compound as a pale yellow oil (200 mg, 57%). LC-MS $t_R$=1.18 min, [M+H]$^+$=485; $^1$H NMR (250 MHz, DMSO-d6) δ 10.42 (s, 1H), 8.04-7.90 (m, 2H), 7.84 (d, J=8.4 Hz, 1H), 3.48 (s, 2H), 3.41 (s, 3H), 3.26-3.10 (m, 5H), 2.74 (d, J=4.5 Hz, 3H), 1.53 (s, 3H), 1.19 (d, J=4.7 Hz, 9H).

83.2 4-(Hydroxyamino)-3-{4-methanesulfonyl-3-[(2-methoxyethyl)(methyl)amino]phenyl}-1,4-dimethyl-4,5-dihydro-1H-pyrazol-5-one 4-(Hydroxyamino)-3-{4-methanesulfonyl-3-[(2-methoxyethyl)(methyl)amino]phenyl}-1,4-dimethyl-4,5-dihydro-1H-pyrazol-5-one was synthesized from tert-butyl N-hydroxy-N-(3-{4-methanesulfonyl-3-[(2-methoxyethyl)(methyl)amino]phenyl}-1,4-dimethyl-5-oxo-4,5-dihydro-1H-pyrazol-4-yl)carbamate according to General Method 9 and was purified using acidic preparative HPLC to afford the title compound as a white solid (63 mg, 40%). LC-MS $t_R$=1.08 min, [M+H]$^+$=385; $^1$H NMR (250 MHz, DMSO-d6) δ 8.15 (s, 1H), 8.07-7.93 (m, 2H), 7.69 (d, J=2.4 Hz, 1H), 6.60 (d, J=2.3 Hz, 1H), 3.52 (t, J=5.4 Hz, 2H), 3.41 (s, 3H), 3.22 (s, 3H), 3.20-3.13 (m, 2H), 2.75 (s, 3H), 1.22 (s, 3H).

Example 84

Compound 84 [4-[4-(Hydroxyamino)-1,4-dimethyl-5-oxo-4,5-dihydro-1H-pyrazol-3-yl]-N,N-dimethylbenzamide]

84.1 Methyl 4-(3-methoxy-3-oxopropanoyl)benzoate

Methyl 4-(3-methoxy-3-oxopropanoyl)benzoate was synthesized from methyl 4-acetylbenzoate according to General Method 1 and the product was purified using silica gel chromatography eluting with 0-35% ethyl acetate in heptanes (10.45 g, 57%). LC-MS $t_R$=1.16 min, [M+H]$^+$=236.90; $^1$H NMR (500 MHz, DMSO-d6) δ 8.08 (m, 4H), 4.28 (s, 2H), 3.89 (s, 3H), 3.65 (s, 3H).

84.2 Methyl 4-(1-methyl-5-oxo-4,5-dihydro-1H-pyrazol-3-yl)benzoate

To a solution of methyl 4-(3-methoxy-3-oxopropanoyl)benzoate (10.44 g, 35.36 mmol) in ethanol (50 mL) was added methylhydrazine sulfate (5.61 g, 38.89 mmol) and N,N-diethylethanamine (5.43 mL, 38.89 mmol) and the resulting reaction mixture was heated to 80 OC until complete consumption of the starting material was observed as monitored by LC-MS. The reaction mixture was concentrated under reduced pressure with the resulting solid was dissolved in ethyl acetate (60 mL) and washed with 1M HCl (3×30 mL), water (30 mL) and brine (30 mL). The organic layer was dried over magnesium sulfate, filtered and concentrated under reduced pressure to give the title compound as a brown solid (7.82 g, 69%). LC-MS $t_R$=1.04 min, $[M+H]^+$=232.90.

84.3 Methyl 4-(4-formyl-1-methyl-5-oxo-4,5-dihydro-1H-pyrazol-3-yl)benzoate

Methyl 4-(4-formyl-1-methyl-5-oxo-4,5-dihydro-1H-pyrazol-3-yl)benzoate was synthesized from methyl 4-(1-methyl-5-oxo-4,5-dihydro-1H-pyrazol-3-yl)benzoate according to General Method 4 (5.88 g, 84%). LC-MS $t_R$=1.09 min, $[M+H]^+$=260.95; $^1$H NMR (250 MHz, DMSO-d6) δ 9.77 (s, 1H), 7.98 (s, 4H), 3.87 (s, 3H), 3.64 (s, 3H).

84.4 Methyl 4-(1,4-dimethyl-5-oxo-4,5-dihydro-1H-pyrazol-3-yl)benzoate

Methyl 4-(1,4-dimethyl-5-oxo-4,5-dihydro-1H-pyrazol-3-yl)benzoate was synthesized from methyl 4-(4-formyl-1-methyl-5-oxo-4,5-dihydro-1H-pyrazol-3-yl)benzoate according to General Method 5 (7.7 g, 97%). LC-MS $t_R$=1.01 min, $[M+H]^+$=246.95; $^1$H NMR (500 MHz, DMSO-d6) δ 7.95 (d, J=8.3 Hz, 2H), 7.75 (d, J=8.4 Hz, 2H), 3.85 (s, 3H), 3.55 (s, 3H), 2.04 (s, 3H).

84.5 Methyl 4-(4-bromo-1,4-dimethyl-5-oxo-4,5-dihydro-1H-pyrazol-3-yl)benzoate Methyl 4-(4-bromo-1,4-dimethyl-5-oxo-4,5-dihydro-1H-pyrazol-3-yl)benzoate was synthesized from methyl 4-(1,4-dimethyl-5-oxo-4,5-dihydro-1H-pyrazol-3-yl)benzoate according to General Method 6 and was used directly in the displacement reaction according to General Method 8 (5.56 g, 100%).

84.6 Methyl 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoate Methyl 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoate was synthesized from methyl 4-(4-bromo-1,4-dimethyl-5-oxo-4,5-dihydro-1H-pyrazol-3-yl)benzoate according to General Method 8 and the product was purified using silica gel chromatography eluting with 10-60% ethyl acetate in heptanes (2.4 g, 27%). LC-MS $t_R$=1.48 min, $[M+H]^+$=499.95.

84.7 4-(4-{[(tert-Butoxy)carbonyl]({[(tert-butoxy)carbonyl]oxy})amino}-1,4-dimethyl-5-oxo-4,5-dihydro-1H-pyrazol-3-yl)benzoic acid To a solution of lithium hydroxide (361.1 mg, 15.08 mmol) in water (60 mL) was added a solution of methyl 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoate (2.4 g, 5.03 mmol) in THF (60 mL) and the reaction mixture was stirred at room temperature until full consumption of the starting material was observed as monitored by LC-MS. The reaction mixture was concentrated under reduced pressure to remove the excess THF and the solution was diluted with ethyl acetate (200 mL). HCl (20 mL) was added and the organic layer was extracted and washed with brine (20 mL), dried over magnesium sulfate and concentrated under reduced pressure. The crude material was purified using silica gel chromatography (using 40-100% ethyl acetate in heptanes) to give the title compound as an off-white solid (1.17 g, 45%). LC-MS $t_R$=1.32 min, $[M+H]^+$=486.15.

84.8 4-(4-{[(tert-Butoxy)carbonyl]({[(tert-butoxy)carbonyl]oxy})amino}-1,4-dimethyl-5-oxo-4,5-dihydro-1H-pyrazol-3-yl)-N,N-dimethylbenzamide 4-(4-{[(tert-Butoxy)carbonyl]({[(tert-butoxy)carbonyl]oxy})amino}-1,4-dimethyl-5-oxo-4,5-dihydro-1H-pyrazol-3-yl)-N,N-dimethylbenzamide was synthesized from 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoic acid and dimethylamine according to General Method 15 (131 mg, 66%). LC-MS $t_R$=1.35 min, $[M+H]^+$=513.05.

84.9 4-[4-(Hydroxyamino)-1,4-dimethyl-5-oxo-4,5-dihydro-1H-pyrazol-3-yl]-N,N-dimethylbenzamide 4-[4-(Hydroxyamino)-1,4-dimethyl-5-oxo-4,5-dihydro-1H-pyrazol-3-yl]-N,N-dimethylbenzamide was synthesized from 4-(4-{[(tert-butoxy)carbonyl]({[(tert-butoxy)carbonyl]oxy})amino}-1,4-dimethyl-5-oxo-4,5-dihydro-1H-pyrazol-3-yl)-N,N-dimethylbenzamide according to General Method 9 and the product was purified using acidic preparative chromatography (21 mg, 34%). LC-MS $t_R$=0.93 min, $[M+H]^+$=291.00; $^1$H NMR (500 MHz, DMSO-d6) δ 8.12-8.05 (m, 2H), 7.65 (d, J=2.6 Hz, 1H), 7.50-7.44 (m, 2H), 6.50 (d, J=2.6 Hz, 1H), 3.30 (s, 3H), 2.96 (d, J=31.2 Hz, 6H), 1.23 (s, 3H).

Example 85

Compound 85 [3-[4-(4,4-Difluoropiperidine-1-carbonyl)phenyl]-4-(hydroxyamino)-1,4-dimethyl-4,5-dihydro-1H-pyrazol-5-one]

85.1 Methyl 4-(3-methoxy-3-oxopropanoyl)benzoate

Methyl 4-(3-methoxy-3-oxopropanoyl)benzoate was synthesized from methyl 4-acetylbenzoate according to General Method 1 and the product was purified using silica gel chromatography eluting with 0-35% ethyl acetate in heptanes (10.45 g, 57%). LC-MS $t_R$=1.16 min, $[M+H]^+$=236.90; $^1$H NMR (500 MHz, DMSO-d6) δ 8.08 (m, 4H), 4.28 (s, 2H), 3.89 (s, 3H), 3.65 (s, 3H).

85.2 Methyl 4-(1-methyl-5-oxo-4,5-dihydro-1H-pyrazol-3-yl)benzoate

To a solution of methyl 4-(3-methoxy-3-oxopropanoyl)benzoate (10.44 g, 35.36 mmol) in ethanol (50 mL) was added methylhydrazine sulfate (5.61 g, 38.89 mmol) and N,N-diethylethanamine (5.43 mL, 38.89 mmol) and the resulting reaction mixture was heated to 80 OC until complete consumption of starting material was observed as monitored by LC-MS. The reaction mixture was concentrated under reduced pressure and the resulting solid was dissolved in ethyl acetate (60 mL) and washed with 1M HCl (3×30 mL), water (30 mL) and brine (30 mL). The organic layer was dried with magnesium sulfate, filtered and concentrated under reduced pressure to give the title compound as a brown solid (7.82 g, 69%). LC-MS $t_R$=1.04 min, $[M+H]^+$=232.90.

85.3 Methyl 4-(4-formyl-1-methyl-5-oxo-4,5-dihydro-1H-pyrazol-3-yl)benzoate

Methyl 4-(4-formyl-1-methyl-5-oxo-4,5-dihydro-1H-pyrazol-3-yl)benzoate was synthesized from methyl 4-(1-methyl-5-oxo-4,5-dihydro-1H-pyrazol-3-yl)benzoate according to General Method 4 (5.88 g, 84%). LC-MS $t_R$=1.09 min, $[M+H]^+$=260.95; $^1$H NMR (250 MHz, DMSO-d6) δ 9.77 (s, 1H), 7.98 (s, 4H), 3.87 (s, 3H), 3.64 (s, 3H).

85.4 Methyl 4-(1,4-dimethyl-5-oxo-4,5-dihydro-1H-pyrazol-3-yl)benzoate

Methyl 4-(1,4-dimethyl-5-oxo-4,5-dihydro-1H-pyrazol-3-yl)benzoate was synthesized from methyl 4-(4-formyl-1-methyl-5-oxo-4,5-dihydro-1H-pyrazol-3-yl)benzoate according to General Method 5 (7.7 g, 97%). LC-MS $t_R$=1.01 min, $[M+H]^+$=246.95; $^1$H NMR (500 MHz, DMSO-d6) δ 7.95 (d, J=8.3 Hz, 2H), 7.75 (d, J=8.4 Hz, 2H), 3.85 (s, 3H), 3.55 (s, 3H), 2.04 (s, 3H).

85.5 Methyl 4-(4-bromo-1,4-dimethyl-5-oxo-4,5-dihydro-1H-pyrazol-3-yl)benzoate Methyl 4-(4-bromo-1,4-dimethyl-5-oxo-4,5-dihydro-1H-pyrazol-3-yl)benzoate was synthesized from methyl 4-(1,4-dimethyl-5-oxo-4,5-dihydro-1H-pyrazol-3-yl)benzoate according to General Method 6 and was directly used in the displacement reaction according to General Method 8 (5.56 g, 100%).

85.6 Methyl 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoate Methyl 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoate was synthesized from methyl 4-(4-bromo-1,4-dimethyl-5-oxo-4,5-dihydro-1H-pyrazol-3-yl)benzoate according to General Method 8 and the product was purified using silica gel chromatography eluting with 10-60% ethyl acetate in heptanes (2.4 g, 27%). LC-MS $t_R$=1.48 min, $[M+H]^+$=499.95.

85.7 4-(4-{[(tert-Butoxy)carbonyl]({[(tert-butoxy)carbonyl]oxy})amino}-1,4-dimethyl-5-oxo-4,5-dihydro-1H-pyrazol-3-yl)benzoic acid To a solution of lithium hydroxide (361.1 mg, 15.08 mmol) in water (60 mL) was added a solution of methyl 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoate (2.4 g, 5.03 mmol) in THF (60 mL) and the reaction mixture was stirred at room temperature until consumption of the starting material was observed as monitored by LC-MS. The reaction mixture was concentrated under reduced pressure to remove the excess THF and the solution was diluted with ethyl acetate (200 mL). HCl (20 mL) was added and the organic layer was extracted and washed with brine (20 mL), dried over magnesium sulfate, filtered and concentrated under reduced pressure. The crude material was purified using silica gel chromatography eluting with ethyl acetate in heptanes (40-100%) to give the title compound as an off-white solid (1.17 g, 45%). LC-MS $t_R$=1.32 min, $[M+H]^+$=486.15.

85.8 4-{[(tert-Butoxy)carbonyl]({[(tert-butoxy)carbonyl]oxy})amino}-3-[4-(4,4-difluoropiperidine-1-carbonyl)phenyl]-1,4-dimethyl-4,5-dihydro-1H-pyrazol-5-one 4-{[(tert-Butoxy)carbonyl]({[(tert-butoxy)carbonyl]oxy})amino}-3-[4-(4,4-difluoropiperidine-1-carbonyl)phenyl]-1,4-dimethyl-4,5-dihydro-1H-pyrazol-5-one was synthesized from 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoic acid and 4,4-difluoropiperidine hydrochloride according to General Method 15 (0.26 g, 85%). LC-MS $t_R$=1.43 min, $[M+H]^+$=589.30.

85.9 3-[4-(4,4-Difluoropiperidine-1-carbonyl)phenyl]-4-(hydroxyamino)-1,4-dimethyl-4,5-dihydro-1H-pyrazol-5-one 3-[4-(4,4-Difluoropiperidine-1-carbonyl)phenyl]-4-(hydroxyamino)-1,4-dimethyl-4,5-dihydro-1H-pyrazol-5-one was synthesized from 4-{[(tert-butoxy)carbonyl]({[(tert-butoxy)carbonyl]oxy})amino}-3-[4-(4,4-difluoropiperidine-1-carbonyl)phenyl]-1,4-dimethyl-4,5-dihydro-1H-pyrazol-5-one according to General Method 9 and the product was purified by washing the crude with 40% ethyl acetate in heptanes (32 mg, 19%). LC-MS $t_R$=3.35 min, $[M+H]^+$=366.95; $^1$H NMR (500 MHz, DMSO-d6) δ 8.11 (d, J=8.3 Hz, 2H), 7.65 (d, J=2.5 Hz, 1H), 7.53 (d, J=8.3 Hz, 2H), 6.52 (d, J=2.5 Hz, 1H), 3.72 (s, 2H), 3.43 (s, 2H), 3.31 (s, 3H), 2.05 (s, 4H), 1.23 (s, 3H).

Example 86

Compound 86 [3-[4-(Ethanesulfonyl)phenyl]-4-(hydroxyamino)-1,4-dimethyl-4,5-dihydro-1H-pyrazol-5-one]

86.1 1-[4-(Ethylsulfanyl)phenyl]ethan-1-one

1-[4-(Ethylsulfanyl)phenyl]ethan-1-one was synthesized from 1-(4-chlorophenyl)ethan-1-one according to General Method 14 to afford the title compound as a brown oil (8.27 g, 78%). LC-MS $t_R$=1.29 min, $[M+H]^+$=181; $^1$H NMR (500 MHz, Chloroform-d) δ 7.88-7.82 (m, 2H), 7.33-7.26 (m, 2H), 3.02 (q, J=7.4 Hz, 2H), 2.56 (s, 3H), 1.37 (t, J=7.4 Hz, 3H).

86.2 Methyl 3-[4-(ethylsulfanyl)phenyl]-3-oxopropanoate

Methyl 3-[4-(ethylsulfanyl)phenyl]-3-oxopropanoate was synthesized from 1-[4-(ethylsulfanyl)phenyl]ethan-1-one (8.27 g, 35.3 mmol) according to General Method 1 to afford the title compound as brown powder (7.86 g, 90%). LC-MS $t_R$=1.29 min, $[M+H]^+$=239; $^1$H NMR (500 MHz, Chloroform-d) δ 7.86-7.81 (m, 2H), 7.33-7.27 (m, 2H), 3.96 (s, 2H), 3.74 (s, 3H), 3.02 (q, J=7.4 Hz, 2H), 1.38 (t, J=7.4 Hz, 3H).

86.3 3-[4-(Ethylsulfanyl)phenyl]-1-methyl-1H-pyrazol-5-ol

3-[4-(Ethylsulfanyl)phenyl]-1-methyl-1H-pyrazol-5-ol was synthesized from methyl 3-[4-(ethylsulfanyl)phenyl]-3-oxopropanoate (5.0 g, 19.5 mmol) according to General Method 2 to afford the title compound as an off-white powder (2.76 g, 60%). LC-MS $t_R$=1.13 min, [M+H]$^+$=235; $^1$H NMR (500 MHz, Chloroform-d) δ 7.58-7.51 (m, 2H), 7.32-7.27 (m, 2H), 3.56 (s, 2H), 3.39 (s, 3H), 2.98 (q, J=7.4 Hz, 2H), 1.34 (t, J=7.4 Hz, 3H).

86.4 3-[4-(Ethylsulfanyl)phenyl]-5-hydroxy-1-methyl-1H-pyrazole-4-carbaldehyde 3-[4-(Ethylsulfanyl)phenyl]-5-hydroxy-1-methyl-1H-pyrazole-4-carbaldehyde was synthesized from 3-[4-(ethylsulfanyl)phenyl]-1-methyl-1H-pyrazol-5-ol (2.76 g, 11.8 mmol) according to General Method 3 to afford the title compound as an orange powder (2.93 g, 95%). LC-MS $t_R$=1.17 min, [M+H]$^+$=261; $^1$H NMR (500 MHz, Chloroform-d) δ 9.77 (s, 1H), 7.63-7.57 (m, 2H), 7.40-7.36 (m, 2H), 3.71 (s, 3H), 3.00 (q, J=7.4 Hz, 2H), 1.35 (t, J=7.4 Hz, 3H).

86.5 3-[4-(Ethylsulfanyl)phenyl]-1,4-dimethyl-1H-pyrazol-5-ol

3-[4-(Ethylsulfanyl)phenyl]-1,4-dimethyl-1H-pyrazol-5-ol was synthesized from 3-[4-(ethylsulfanyl)phenyl]-5-hydroxy-1-methyl-1H-pyrazole-4-carbaldehyde (2.96 g, 11.3 mmol) according to General Method 5 to afford the title compound as a cream powder (2.65 g, 95%). LC-MS $t_R$=1.12 min, [M+H]$^+$=249; $^1$H NMR (500 MHz, DMSO-d6) δ 7.54 (d, J=8.1 Hz, 2H), 7.32 (d, J=8.0 Hz, 2H), 3.60 (t, J=6.5 Hz, 3H), 2.98 (q, J=7.2 Hz, 2H), 1.78-1.74 (m, 3H), 1.24 (t, J=7.3 Hz, 3H).

86.6 4-Bromo-3-[4-(ethanesulfinyl)phenyl]-1,4-dimethyl-4,5-dihydro-1H-pyrazol-5-one 4-Bromo-3-[4-(ethanesulfinyl)phenyl]-1,4-dimethyl-4,5-dihydro-1H-pyrazol-5-one was synthesized from 3-[4-(ethylsulfanyl)phenyl]-5-hydroxy-1-methyl-1H-pyrazole-4-carbaldehyde (2.29 g, 9.2 mmol) according to General Method 6 to afford the title compound as a brown oil (2.95 g, 93%). LC-MS $t_R$=1.10 min, [M+H]$^+$=343/345; $^1$H NMR (500 MHz, Chloroform-d) δ 8.12 (d, J=8.3 Hz, 2H), 7.69 (d, J=8.2 Hz, 2H), 3.48 (s, 3H), 3.00-2.92 (m, 1H), 2.84-2.76 (m, 1H), 2.02 (d, J=4.6 Hz, 3H), 1.24 (t, J=7.4 Hz, 3H).

86.7 4-{[(tert-Butoxy)carbonyl]({[(tert-butoxy)carbonyl]oxy})amino}-3-[4-(ethylsulfanyl)phenyl]-1,4-dimethyl-4,5-dihydro-1H-pyrazol-5-one 4-{[(tert-Butoxy)carbonyl]({[(tert-butoxy)carbonyl]oxy})amino}-3-[4-(ethylsulfanyl)phenyl]-1,4-dimethyl-4,5-dihydro-1H-pyrazol-5-one was synthesized from 4-bromo-3-[4-(ethanesulfinyl)phenyl]-1,4-dimethyl-4,5-dihydro-1H-pyrazol-5-one (3.0 g, 7.4 mmol) according to General Method 8 and was purified using silica gel chromatography eluting with 25-100% ethyl acetate in heptanes to afford the title compound as a brown oil (1.69 g, 36%). LC-MS $t_R$=1.34 min, [M+Na]$^+$=518.

86.8 4-{[(tert-Butoxy)carbonyl]({[(tert-butoxy)carbonyl]oxy})amino}-3-[4-(ethanesulfonyl)phenyl]-1,4-dimethyl-4,5-dihydro-1H-pyrazol-5-one 4-{[(tert-Butoxy)carbonyl]({[(tert-butoxy)carbonyl]oxy})amino}-3-[4-(ethanesulfonyl)phenyl]-1,4-dimethyl-4,5-dihydro-1H-pyrazol-5-one was synthesized from 4-{[(tert-butoxy)carbonyl]({[(tert-butoxy)carbonyl]oxy})amino}-3-[4-(ethylsulfanyl)phenyl]-1,4-dimethyl-4,5-dihydro-1H-pyrazol-5-one (1.69 g, 2.4 mmol) according to General Method 10 and was purified using silica gel chromatography eluting with 25-100% ethyl acetate in heptanes to afford the title compound as a yellow oil (1.39 g, 90%). LC-MS $t_R$=1.43 min, [M+Na]$^+$=534.

86.9 3-[4-(Ethanesulfonyl)phenyl]-4-(hydroxyamino)-1,4-dimethyl-4,5-dihydro-1H-pyrazol-5-one 3-[4-(Ethanesulfonyl)phenyl]-4-(hydroxyamino)-1,4-dimethyl-4,5-dihydro-1H-pyrazol-5-one was synthesized from 4-{[(tert-butoxy)carbonyl]({[(tert-butoxy)carbonyl]oxy})amino}-3-[4-(ethanesulfonyl)phenyl]-1,4-dimethyl-4,5-dihydro-1H-pyrazol-5-one (1.3 g, 1.9 mmol) according to General Method 9 and was purified using silica gel chromatography eluting with 0-100% ethyl acetate in heptanes to afford the title compound as a white solid (423 mg, 71%). LC-MS $t_R$=0.99 min, [M+H]$^+$=312; $^1$H NMR (500 MHz, DMSO-d6) δ 8.39-8.20 (m, 2H), 8.01-7.90 (m, 2H), 7.72-7.63 (m, 1H), 6.67-6.53 (m, 1H), 3.37-3.32 (m, 5H), 1.25 (s, 3H), 1.13 (t, J=7.4 Hz, 3H).

Example 87

Compound 87 [3-[3-(Dimethylamino)-4-methanesulfonylphenyl]-4-(hydroxyamino)-1,4-dimethyl-4,5-dihydro-1H-pyrazol-5-one]

87.1 tert-Butyl N-{3-[3-(dimethylamino)-4-methanesulfonylphenyl]-1,4-dimethyl-5-oxo-4,5-dihydro-1H-pyrazol-4-yl}-N-hydroxycarbamate To a solution of 4-{[(tert-butoxy)carbonyl]({[(tert-butoxy)carbonyl]oxy})amino}-3-(3-fluoro-4-methanesulfonylphenyl)-1,4-dimethyl-4,5-dihydro-1H-pyrazol-5-one (300 mg, 0.58 mmol) in MeCN (2 mL) was added 2M N-methylmethanamine in THF (1.45 mL) and the reaction mixture was stirred at 80° C. for 20 hours. Additional 2M N-methylmethanamine in THF (1.45 mL) was added and heating was continued at 80° C. for an additional 20 hours. Additional 2M N-methylmethanamine in THF (1 mL) was added and the reaction mixture was returned to 80° C. for 1 hour. The reaction mixture was cooled to room temperature and ethyl acetate (10 mL) was added. The aqueous layer was isolated and re-extracted with further ethyl acetate (3×10 mL). The combined organic layers were washed with water (2×10 mL), dried over magnesium sulfate, filtered and concentrated under reduced pressure. Purification using silica gel chromatography, eluting in 10-100% ethyl acetate: heptanes afforded the title compound as a pale yellow oil (184 mg, 66%). LC-MS $t_R$=1.20 min, [M+H]$^+$=441; $^1$H NMR (500 MHz, Chloroform-d) δ 8.10 (d, J=8.4 Hz, 1H), 8.04 (d, J=12.7 Hz, 1H), 7.99 (d, J=1.6 Hz, 1H), 7.83 (dd, J=8.4, 1.6 Hz, 1H), 3.46 (s, 3H), 3.32 (s, 3H), 2.83 (s, 6H), 1.72 (s, 3H), 1.29 (s, 9H).

87.2 3-[3-(Dimethylamino)-4-methanesulfonylphenyl]-4-(hydroxyamino)-1,4-dimethyl-4,5-dihydro-1H-pyrazol-5-one 3-[3-(Dimethylamino)-4-methanesulfonylphenyl]-4-(hydroxyamino)-1,4-dimethyl-4,5-dihydro-1H-pyrazol-5-one was synthesized from tert-butyl N-{3-[3-(dimethylamino)-4-methanesulfonylphenyl]-1,4-dimethyl-5-oxo-4,5-dihydro-1H-pyrazol-4-yl}-N-hydroxycarbamate according to General Method 9 and was purified using acidic preparative HPLC to afford the title compound as a white solid (37 mg, 26%). LC-MS $t_R$=3.24 min, [M+H]$^+$=341; $^1$H NMR (500 MHz, DMSO-d6) δ 8.18 (d, J=1.4 Hz, 1H), 8.02 (dd, J=8.4, 1.5 Hz, 1H), 7.96 (d, J=8.3 Hz, 1H), 7.69 (s, 1H), 6.60 (s, 1H), 3.36 (s, 3H), 2.75 (s, 6H), 1.23 (s, 3H).

Example 88

Compound 88 [4-(Hydroxyamino)-3-[4-methanesulfonyl-3-(4-methylpiperazin-1-yl)phenyl]-1,4-dimethyl-4,5-dihydro-1H-pyrazol-5-one]

88.1 tert-Butyl N-hydroxy-N-{3-[4-methanesulfonyl-3-(4-methylpiperazin-1-yl)phenyl]-1,4-dimethyl-5-oxo-4,5-dihydro-1H-pyrazol-4-yl}carbamate To a solution of 4-{[(tert-butoxy)carbonyl]({[(tert-butoxy)carbonyl]oxy})amino}-3-(3-fluoro-4-methanesulfonylphenyl)-1,4-dimethyl-4,5-dihydro-1H-pyrazol-5-one (300 mg, 0.58 mmol) in MeCN (2 mL) was added 1-methylpiperazine (64.55 µl, 0.58 mmol) and the reaction mixture was stirred at 80° C. for 23 hours. The reaction mixture was cooled to room temperature and an additional 4 equivalents of 1-methylpiperazine (258 µl) was added. Heating to 80° C. was continued for an additional 18 hours before the reaction mixture was cooled to room temperature and the acetonitrile was removed under reduced pressure. Purification was performed using silica gel chromatography eluting in 12% methanol:DCM to afford the title compound as a pale yellow oil (237 mg, 80%). LC-MS $t_R$=0.96 min, [M+H]$^+$=496.

88.2 4-(Hydroxyamino)-3-[4-methanesulfonyl-3-(4-methylpiperazin-1-yl)phenyl]-1,4-dimethyl-4,5-dihydro-1H-pyrazol-5-one To a solution of tert-butyl N-hydroxy-N-{3-[4-methanesulfonyl-3-(4-methylpiperazin-1-yl)phenyl]-1,4-dimethyl-5-oxo-4,5-dihydro-1H-pyrazol-4-yl}carbamate (237 mg, 0.48 mmol) in DCM (2 mL) was added 4M HCl in 1,4-dioxane (1.2 mL) and the reaction mixture was stirred at room temperature for 3 hours. The solvent was removed under reduced pressure to give a sticky yellow oil. Purification was performed using acidic preparative HPLC to afford the title compound as a white formate salt (26 mg, 12%). LC-MS $t_R$=2.21 min, [M+H]$^+$=396; $^1$H NMR (500 MHz, Deuterium Oxide) δ 8.48 (s, 1H), 8.20 (s, 1H), 8.15 (s, 2H), 3.74-3.65 (m, 2H), 3.56-3.51 (m, 2H), 3.51 (s, 3H), 3.48 (s, 3H), 3.48-3.41 (m, 2H), 3.34 (q, J=11.5 Hz, 2H), 3.04 (s, 3H), 1.44 (s, 3H).

Example 89

Compound 89 [3-[4-(Benzenesulfonyl)phenyl]-4-(hydroxyamino)-1,4-dimethyl-4,5-dihydro-1H-pyrazol-5-one]

89.1 Methyl 3-[4-(benzenesulfonyl)phenyl]-3-oxopropanoate

Methyl 3-[4-(benzenesulfonyl)phenyl]-3-oxopropanoate was synthesized from 1-[4-(benzenesulfonyl)phenyl]ethan-1-one according to General Method 1 (7.4 g, 85%). LC-MS $t_R$=1.22 min, [M+H]$^+$=319.

89.2 3-[4-(Benzenesulfonyl)phenyl]-1-methyl-1H-pyrazol-5-ol

To a solution of methyl 3-[4-(benzenesulfonyl)phenyl]-3-oxopropanoate (7.4 g, 23.25 mmol) in methanol (20 mL) was added methylhydrazine sulfate (3.35 g, 23.25 mmol) and triethylamine (3.27 mL, 23.25 mmol) and the reaction mixture was stirred at 80 OC until complete consumption of the starting material was observed as monitored by LCMS. The reaction mixture was acidified with 2M HCl (30 mL) and extracted into ethyl acetate (3×50 mL). The combined organic extracts were washed with brine (50 mL), dried over magnesium sulfate, filtered and concentrated under reduced pressure to yield the title compound as a brown oil (6.75 g, 77%). LC-MS $t_R$=1.11 min, [M+H]$^+$=314.95.

89.3 3-[4-(Benzenesulfonyl)phenyl]-5-hydroxy-1-methyl-1H-pyrazole-4-carbaldehyde 3-[4-(Benzenesulfonyl)phenyl]-5-hydroxy-1-methyl-1H-pyrazole-4-carbaldehyde was synthesized from 3-[4-(benzenesulfonyl)phenyl]-1-methyl-1H-pyrazol-5-ol according to General Method 3 (7.02 g, 84%). LC-MS $t_R$=1.09 min, [M+H]$^+$=343.00.

89.4 3-[4-(Benzenesulfonyl)phenyl]-1,4-dimethyl-4,5-dihydro-1H-pyrazol-5-ol 3-[4-(Benzenesulfonyl)phenyl]-1,4-dimethyl-4,5-dihydro-1H-pyrazol-5-ol was synthesized from 3-[4-(benzenesulfonyl)phenyl]-5-hydroxy-1-methyl-1H-pyrazole-4-carbaldehyde according to General Method 5 (4.3 g, 59%). LC-MS $t_R$=1.08 min, [M+H]$^+$=331.00.

89.5 3-[4-(Benzenesulfonyl)phenyl]-4-bromo-1,4-dimethyl-4,5-dihydro-1H-pyrazol-5-one 3-[4-(Benzenesulfonyl)phenyl]-4-bromo-1,4-dimethyl-4,5-dihydro-1H-pyrazol-5-one was synthesized from 3-[4-(benzenesulfonyl)phenyl]-1,4-dimethyl-4,5-dihydro-1H-pyrazol-5-ol according to General Method 6 and was directly used in the displacement reaction according to General Method 8 (5.33 g, 100%).

89.6 3-[4-(Benzenesulfonyl)phenyl]-4-{[(tert-butoxy)carbonyl]({[(tert-butoxy)carbonyl]oxy})amino}-1,4-dimethyl-4,5-dihydro-1H-pyrazol-5-one 3-[4-(Benzenesulfonyl)phenyl]-4-{[(tert-butoxy)carbonyl]({[(tert-butoxy)carbonyl]oxy})amino}-1,4-dimethyl-4,5-dihydro-1H-pyrazol-5-one was synthesized from 3-[4-(benzenesulfonyl)phenyl]-4-bromo-1,4-dimethyl-4,5-dihydro-1H-pyrazol-5-one according got General Method 8 and the product was purified using silica gel chromatography eluting with 20-75% ethyl acetate in heptanes (1.4 g, 14%). LC-MS $t_R$=1.57 min, [M+H]$^+$=581.95.

89.7 3-[4-(Benzenesulfonyl)phenyl]-4-(hydroxyamino)-1,4-dimethyl-4,5-dihydro-1H-pyrazol-5-one 3-[4-(Benzenesulfonyl)phenyl]-4-(hydroxyamino)-1,4-dimethyl-4,5-dihydro-1H-pyrazol-5-one was synthesized from 3-[4-(benzenesulfonyl)phenyl]-4-{[(tert-butoxy)carbonyl]({[(tert-butoxy)carbonyl]oxy})amino}-1,4-dimethyl-4,5-dihydro-1H-pyrazol-5-one according to General Method 9 and the product was purified using silica gel chromatography eluting with 20-65% ethyl acetate in heptanes (0.51 g, 57%). LC-MS $t_R$=1.19 min, [M+H]$^+$=359.90; $^1$H NMR (500 MHz, DMSO-d6) δ 8.24 (d, J=8.7 Hz, 2H); 8.03 (d, J=8.6 Hz, 2H), 8.01-7.96 (m, 2H), 7.71 (t, J=7.4 Hz, 1H), 7.64 (t, J=7.6 Hz, 2H), 7.62 (d, J=2.7 Hz, 1H), 6.56 (d, J=2.7 Hz, 1H), 3.31 (s, 3H), 1.21 (s, 3H).

Example 90

Compound 90 [4-[4-(Hydroxyamino)-1,4-dimethyl-5-oxo-4,5-dihydro-1H-pyrazol-3-yl]-N-(2-methoxyethyl)-N-methylbenzene-1-sulfonamide]

90.1 4-Acetyl-N-(2-methoxyethyl)-N-methylbenzene-1-sulfonamide

To a solution of 4-acetylbenzene-1-sulfonyl chloride (7.5 g, 34.30 mmol) in DCM (25 mL) at 0° C. was added (2-methoxyethyl)(methyl)amine (3.41 g, 38.26 mmol) and pyridine (2.8 mL, 34.69 mmol). The reaction mixture was allowed to warm to room temperature and stirring was continued until complete conversion of the starting material observed by LC-MS. The reaction mixture was quenched with saturated sodium hydrogen carbonate solution (25 mL) and the product was extracted into DCM (30 mL), washed with 2 M HCl (25 mL) and brine (25 mL) and dried over sodium sulfate, filtered and concentrated under reduced pressure (7.58 g, 77%). LC-MS $t_R$=1.09 min, [M+H]$^+$=272; $^1$H NMR (500 MHz, DMSO-d6) δ 8.24-8.07 (m, 2H), 8.01-7.80 (m, 2H), 3.49-3.43 (m, 2H), 3.24-3.14 (m, 5H), 2.75 (s, 3H), 2.64 (s, 3H).

90.2 Methyl 3-{4-[(2-methoxyethyl)(methyl)sulfamoyl]phenyl}-3-oxopropanoate

Methyl 3-{4-[(2-methoxyethyl)(methyl)sulfamoyl]phenyl}-3-oxopropanoate was synthesized from 4-acetyl-N-(2-methoxyethyl)-N-methylbenzene-1-sulfonamide according to General Method 1. The product was purified using silica gel chromatography eluting with 0-55% ethyl acetate in heptanes (4.11 g, 42%). LC-MS $t_R$=1.13 min, [M+H]$^+$=330; $^1$H NMR (500 MHz, DMSO-d6) δ 8.19-8.04 (m, 2H), 7.97-7.83 (m, 2H), 4.30 (s, 2H), 3.83-3.63 (m, 3H), 3.44 (m, 2H), 3.23-3.17 (m, 5H), 2.78-2.74 (m, 3H).

90.3 4-(5-Hydroxy-1-methyl-1H-pyrazol-3-yl)-N-(2-methoxyethyl)-N-methylbenzene-1-sulfonamide 4-(5-Hydroxy-1-methyl-1H-pyrazol-3-yl)-N-(2-methoxyethyl)-N-methylbenzene-1-sulfonamide was synthesized from methyl 3-{4-[(2-methoxyethyl)(methyl)sulfamoyl]phenyl}-3-oxopropanoate according to General Method 2. The product was concentrated under reduced pressure (3.91 g, 59%). LC-MS $t_R$=1.06 min, [M+H]$^+$=326; $^1$H NMR (250 MHz, DMSO-d6) δ 7.97-7.84 (m, 2H), 7.76-7.64 (m, 2H), 5.85 (s, 1H), 3.72-3.63 (m, 2H), 3.57 (s, 3H), 3.22-3.20 (m, 3H), 3.13 (m, 2H), 2.72-2.68 (m, 3H).

90.4 4-(4-Formyl-5-hydroxy-1-methyl-1H-pyrazol-3-yl)-N-(2-methoxyethyl)-N-methylbenzene-1-sulfonamide 4-(4-Formyl-5-hydroxy-1-methyl-1H-pyrazol-3-yl)-N-(2-methoxyethyl)-N-methylbenzene-1-sulfonamide was synthesized from 4-(5-hydroxy-1-methyl-1H-pyrazol-3-yl)-N-(2-methoxyethyl)-N-methylbenzene-1-sulfonamide according to General Method 3. The product was extracted into DCM (2×15 mL), washed with brine (30 mL vol), dried over sodium sulfate, filtered and concentrated under reduced pressure (3.90 g, 67%). LC-MS $t_R$=1.02 min, [M+H]$^+$=354; $^1$H NMR (250 MHz, DMSO-d6) δ 9.75 (s, 1H), 8.10-8.05 (m, 2H), 7.80-7.75 (m, 2H), 3.80-3.76 (m, 3H), 3.46-3.45 (m, 3H), 3.26-3.23 (m, 2H), 3.18-3.16 (m, 3H), 2.76-2.74 (m, 3H).

90.5 4-(5-Hydroxy-1,4-dimethyl-1H-pyrazol-3-yl)-N-(2-methoxyethyl)-N-methylbenzene-1-sulfonamide 4-(5-Hydroxy-1,4-dimethyl-1H-pyrazol-3-yl)-N-(2-methoxyethyl)-N-methylbenzene-1-sulfonamide was synthesized from 4-(4-formyl-5-hydroxy-1-methyl-1H-pyrazol-3-yl)-N-(2-methoxyethyl)-N-methylbenzene-1-sulfonamide according to General Method 5. The product was purified using silica gel chromatography eluting with 0-30% methanol in ethyl acetate (1.10 g, 29%). LC-MS $t_R$=0.98 min, [M+H]$^+$=340; $^1$H NMR (500 MHz, DMSO-d$_6$) δ 7.86-7.82 (m, 1H), 7.80-7.73 (m, 1H), 7.71-7.62 (m, 1H), 7.57-7.49 (m, 1H), 4.07-3.99 (m, 1H), 3.47-3.43 (m, 3H), 3.25-3.22 (m, 2H), 3.17 (m, 6H), 2.74-2.71 (m, 3H), 2.12-2.04 (m, 1H), 1.91 (m, 1H).

90.6 4-(4-Bromo1,4-dimethyl-5-oxo-4,5-dihydro-1H-pyrazol-3-yl)-N-(2-methoxyethyl)-N-methylbenzene-1-sulfonamide 4-(4-bromo 1,4-dimethyl-5-oxo-4,5-dihydro-1H-pyrazol-3-yl)-N-(2-methoxyethyl)-N-methylbenzene-1-sulfonamide was synthesized from 4-(5-hydroxy-1,4-dimethyl-1H-pyrazol-3-yl)-N-(2-methoxyethyl)-N-methylbenzene-1-sulfonamide according to General Method 6 (1.05 g, 77%). LC-MS $t_R$=1.27 min, [M+H]$^+$=418.

90.7 4-(4-{[(tert-Butoxy)carbonyl]({[(tert-butoxy)carbonyl]oxy})amino}-1,4-dimethyl-5-oxo-4,5-dihydro-1H-pyrazol-3-yl)-N-(2-methoxyethyl)-N-methylbenzene-1-sulfonamide 4-(4-{[(tert-Butoxy)carbonyl]({[(tert-butoxy)carbonyl]oxy})amino}-1,4-dimethyl-5-oxo-4,5-dihydro-1H-pyrazol-3-yl)-N-(2-methoxyethyl)-N-methylbenzene-1-sulfonamide was synthesized from 4-(4-bromo 1,4-dimethyl-5-oxo-4,5-dihydro-1H-pyrazol-3-yl)-N-(2-methoxyethyl)-N-methylbenzene-1-sulfonamide according to General Method 8 (1.04 g, 36%). LC-MS $t_R$=1.49 min, [M+Na]$^+$=593.

90.8 4-[4-(Hydroxyamino)-1,4-dimethyl-5-oxo-4,5-dihydro-1H-pyrazol-3-yl]-N-(2-methoxyethyl)-N-methylbenzene-1-sulfonamide 4-[4-(Hydroxyamino)-1,4-dimethyl-5-oxo-4,5-dihydro-1H-pyrazol-3-yl]-N-(2-methoxyethyl)-N-methylbenzene-1- sulfonamide was synthesized from 4-(4-{[(tert-butoxy)carbonyl]({[(tert-butoxy)carbonyl]oxy})amino}-1,4-dimethyl-5-oxo-4,5-dihydro-1H-pyrazol-3-yl)-N-(2-methoxyethyl)-N-methylbenzene-1-sulfonamide according to General Method 9. The product was purified using acidic preparative HPLC to yield the target compound (0.045 g, 24%). LC-MS $t_R$=3.33 min, [M+H]$^+$=371; $^1$H NMR (500 MHz, DMSO-d6) δ 8.30-8.18 (m, 2H), 7.89-7.80 (m, 2H), 7.70-7.64 (m, 1H), 6.62-6.55 (m, 1H), 3.52-3.42 (m, 2H), 3.31-3.27 (m, 3H), 3.24-3.20 (m, 3H), 3.19-3.15 (m, 2H), 2.79-2.70 (m, 3H), 1.24 (s, 3H).

Example 91

Compound 91 [3-(4-tert-Butylphenyl)-4-(hydroxyamino)-1,4-dimethyl-4,5-dihydro-1H-pyrazol-5-one]

91.1 Methyl 3-(4-tert-butylphenyl)-3-oxopropanoate

Methyl 3-(4-tert-butylphenyl)-3-oxopropanoate was synthesized from 1-(4-tert-butylphenyl)ethan-1-one according to General Method 1 (6.38 g, 89%). LC-MS $t_R$=1.41 min, [M+H]$^+$=235; $^1$H NMR (500 MHz, DMSO-d6) δ 7.96-7.83 (m, 2H), 7.59-7.51 (m, 2H), 4.23-4.08 (m, 2H), 3.67-3.61 (m, 3H), 1.31-1.29 (m, 9H).

91.2 3-(4-tert-Butylphenyl)-1-methyl-1H-pyrazol-5-ol 3-(4-tert-Butylphenyl)-1-methyl-1H-pyrazol-5-ol was synthesized from methyl 3-(4-tert-butylphenyl)-3-oxopropanoate according to General Method 2. The product was purified using silica gel chromatography eluting with 20-100% ethyl acetate in heptanes (4.51 g, 77%). LC-MS $t_R$=1.25 min, [M+H]$^+$=231; $^1$H NMR (250 MHz, DMSO-d6) δ 7.67-7.54 (m, 2H), 7.47-7.30 (m, 2H), 5.72 (s, 1H), 3.54 (s, 3H), 1.28 (s, 9H).

91.3 3-(4-tert-Butylphenyl)-5-hydroxy-1-methyl-1H-pyrazole-4-carbaldehyde 3-(4-tert-Butylphenyl)-5-hydroxy-1-methyl-1H-pyrazole-4-carbaldehyde was synthesized from 3-(4-tert-butylphenyl)-1-methyl-1H-pyrazol-5-ol according to General Method 3. The product was extracted into DCM (3×25 mL), washed with brine (30 mL), dried over magnesium sulfate filtered and concentrated under reduced pressure (5.02 g, 89%). LC-MS $t_R$=1.28 min, [M+H]$^+$=259; $^1$H NMR (500 MHz, DMSO-d6) δ 9.71 (s, 1H), 7.78-7.61 (m, 2H), 7.52-7.40 (m, 2H), 5.75 (s, 1H), 3.59 (s, 3H), 1.30 (s, 9H).

91.4 3-(4-tert-Butylphenyl)-1,4-dimethyl-1H-pyrazol-5-ol 3-(4-tert-Butylphenyl)-1,4-dimethyl-1H-pyrazol-5-ol was synthesized from 3-(4-tert-butylphenyl)-5-hydroxy-1-methyl-1H-pyrazole-4-carbaldehyde according to General Method 5 (8.30 g, 89%). LC-MS $t_R$=1.22 min, [M+H]$^+$=245; $^1$H NMR (500 MHz, DMSO-d6) δ 7.55-7.45 (m, 2H), 7.43-7.35 (m, 2H), 3.50 (s, 3H), 3.17 (s, 1H), 1.96 (s, 3H), 1.29 (s, 9H).

91.5 4-Bromo-3-(4-tert-butylphenyl)-1,4-dimethyl-4,5-dihydro-1H-pyrazol-5-one

4-Bromo-3-(4-tert-butylphenyl)-1,4-dimethyl-4,5-dihydro-1H-pyrazol-5-one was synthesized from 3-(4-tert-butylphenyl)-1,4-dimethyl-1H-pyrazol-5-ol according to General Method 6 (5.42 g, 97%). LC-MS $t_R$=1.59 min, [M+H]$^+$=324.

91.6 4-{[(tert-Butoxy)carbonyl]({[(tert-butoxy)carbonyl]oxy})amino}-3-(4-tert-butylphenyl)-1,4-dimethyl-4,5-dihydro-1H-pyrazol-5-one 4-{[(tert-Butoxy)carbonyl]({[(tert-butoxy)carbonyl]oxy})amino}-3-(4-tert-butylphenyl)-1,4-dimethyl-4,5-dihydro-1H-pyrazol-5-one was synthesized from 4-bromo-3-(4-tert-butylphenyl)-1,4-dimethyl-4,5-dihydro-1H-pyrazol-5-one according to General Method 8. The product was purified using silica gel chromatography eluting with 0-100% ethyl acetate in heptanes (2.4 g, 32%). LC-MS $t_R$=1.80 min, [M+Na]$^+$=498; $^1$H NMR (500 MHz, DMSO-d6) δ 8.16-8.02 (m, 1H), 7.73-7.32 (m, 3H), 3.30 (s, 3H), 1.57-1.48 (m, 9H), 1.33-1.19 (m, 21H).

91.7 3-(4-tert-Butylphenyl)-4-(hydroxyamino)-1,4-dimethyl-4,5-dihydro-1H-pyrazol-5-one 3-(4-tert-Butylphenyl)-4-(hydroxyamino)-1,4-dimethyl-4,5-dihydro-1H-pyrazol-5-one was synthesized from 4-{[(tert-butoxy)carbonyl]({[(tert-butoxy)carbonyl]oxy})amino}-3-(4-tert-butylphenyl)-1,4-dimethyl-4,5-dihydro-1H-pyrazol-5-one according to General Method 9. The product was purified by triturating in ethyl acetate:heptanes (1:4, v:v) to yield the target compound (1.05 g, 80%). LC-MS $t_R$=1.30 min, [M+H]$^+$=276; $^1$H NMR (250 MHz, DMSO-d6) δ 8.06-7.90 (m, 2H), 7.54-7.34 (m, 3H), 6.17 (s, 1H), 3.29 (s, 3H), 1.32 (s, 9H), 1.23 (s, 3H).

Example 92

Compound 92 [4-[4-(Hydroxyamino)-1,4-dimethyl-5-oxo-4,5-dihydro-1H-pyrazol-3-yl]benzamide]

92.1 Methyl 4-(3-methoxy-3-oxopropanoyl)benzoate

Methyl 4-(3-methoxy-3-oxopropanoyl)benzoate was synthesized from methyl 4-acetylbenzoate according to General Method 1 and the product was purified using silica gel chromatography eluting with 0-35% ethyl acetate in heptanes (10.45 g, 57%). LC-MS $t_R$=1.16 min, [M+H]$^+$=236.90; $^1$H NMR (500 MHz, DMSO-d6) δ 8.08 (m, 4H), 4.28 (s, 2H), 3.89 (s, 3H), 3.65 (s, 3H).

92.2 Methyl 4-(1-methyl-5-oxo-4,5-dihydro-1H-pyrazol-3-yl)benzoate

To a solution of methyl 4-(3-methoxy-3-oxopropanoyl) benzoate (10.44 g, 35.36 mmol) in ethanol (50 mL) was added methylhydrazine sulfate (5.61 g, 38.89 mmol) and N,N-diethylethanamine (5.43 mL, 38.89 mmol) and the resulting reaction mixture was heated to 80 OC until complete consumption of starting material was observed as monitored by LC-MS. The reaction mixture was concentrated under reduced pressure and the resulting solid was dissolved in ethyl acetate (60 mL) and washed with 1M HCl (3×30 mL), water (30 mL) and brine (30 mL). The organic layer was dried over magnesium sulfate, filtered and concentrated under reduced pressure to give the title compound as a brown solid (7.82 g, 69%). LC-MS $t_R$=1.04 min, [M+H]$^+$=232.90.

92.3 Methyl 4-(4-formyl-1-methyl-5-oxo-4,5-dihydro-1H-pyrazol-3-yl)benzoate

Methyl 4-(4-formyl-1-methyl-5-oxo-4,5-dihydro-1H-pyrazol-3-yl)benzoate was synthesized from methyl 4-(1-methyl-5-oxo-4,5-dihydro-1H-pyrazol-3-yl)benzoate according to General Method 4 (5.88 g, 84%). LC-MS $t_R$=1.09 min, [M+H]$^+$=260.95; $^1$H NMR (250 MHz, DMSO-d6) δ 9.77 (s, 1H), 7.98 (s, 4H), 3.87 (s, 3H), 3.64 (s, 3H).

92.4 Methyl 4-(1,4-dimethyl-5-oxo-4,5-dihydro-1H-pyrazol-3-yl)benzoate

Methyl 4-(1,4-dimethyl-5-oxo-4,5-dihydro-1H-pyrazol-3-yl)benzoate was synthesized from methyl 4-(4-formyl-1-methyl-5-oxo-4,5-dihydro-1H-pyrazol-3-yl)benzoate according to General Method 5 (7.7 g, 97%). LC-MS $t_R$=1.01 min, [M+H]$^+$=246.95; $^1$H NMR (500 MHz, DMSO-d6) δ 7.95 (d, J=8.3 Hz, 2H), 7.75 (d, J=8.4 Hz, 2H), 3.85 (s, 3H), 3.55 (s, 3H), 2.04 (s, 3H).

92.5 Methyl 4-(4-bromo-1,4-dimethyl-5-oxo-4,5-dihydro-1H-pyrazol-3-yl)benzoate Methyl 4-(4-bromo-1,4-dimethyl-5-oxo-4,5-dihydro-1H-pyrazol-3-yl)benzoate was synthesized from methyl 4-(1,4-dimethyl-5-oxo-4,5-dihydro-1H-pyrazol-3-yl)benzoate according to General Method 6 and was used directly in the displacement reaction according to General Method 8 (5.56 g, 100%).

92.6 Methyl 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoate Methyl 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoate was synthesized from methyl 4-(4-bromo-1,4-dimethyl-5-oxo-4,5-dihydro-1H-pyrazol-3-yl)benzoate according to General Method 8 and the product was purified using silica gel chromatography eluting with 10-60% ethyl acetate in heptanes (2.4 g, 27%). LC-MS $t_R$=1.48 min, [M+H]$^+$=499.95.

92.7 4-(4-{[(tert-Butoxy)carbonyl]({[(tert-butoxy)carbonyl]oxy})amino}-1,4-dimethyl-5-oxo-4,5-dihydro-1H-pyrazol-3-yl)benzoic acid To a solution of lithium hydroxide (361.1 mg, 15.08 mmol) in water (60 mL) was added a solution of methyl 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoate (2.4 g, 5.03 mmol) in THF (60 mL) and the reaction mixture was stirred at room temperature until full consumption of the starting material was observed as monitored by LC-MS. The reaction mixture was concentrated to remove the excess THF and the solution was diluted with ethyl acetate (200 mL). HCl (20 mL) was added and the organic layer was extracted and washed with brine (20 mL), dried over magnesium sulfate and concentrated under reduced pressure. The crude material was purified using silica gel chromatography (using 40-100% ethyl acetate in heptanes) to give the title compound as an off-white solid (1.17 g, 45%). LC-MS $t_R$=1.32 min, [M+H]$^+$=486.15.

92.8 4-(4-{[(tert-Butoxy)carbonyl]({[(tert-butoxy)carbonyl]oxy})amino}-1,4-dimethyl-5-oxo-4,5-dihydro-1H-pyrazol-3-yl)benzamide To a stirred solution of 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoic acid (200 mg, 0.43 mmol) in DCM (10 mL) was added 1-chloro-N,N,2-trimethylprop-1-en-1-amine (0.11 mL, 0.86 mmol). After 30 minutes 0.5 M ammonia in dioxane (17.26 mL) was added and the reaction mixture was left to stir for 1 hour at room temperature. The dioxane was removed under reduced pressure and the crude was dissolved in ethyl acetate (10 mL), washed with water (3×10 mL), dried over magnesium sulfate, filtered and concentrated under reduced pressure to yield the title compound as a colourless oil (250 mg, 45%). LC-MS $t_R$=1.34 min, [M+H]$^+$=486.05.

92.9 4-[4-(Hydroxyamino)-1,4-dimethyl-5-oxo-4,5-dihydro-1H-pyrazol-3-yl]benzamide 4-[4-(Hydroxyamino)-1,4-dimethyl-5-oxo-4,5-dihydro-1H-pyrazol-3-yl]benzamide was synthesized from 4-(4-{[(tert-butoxy)carbonyl]({[(tert-butoxy)carbonyl]oxy})amino}-1,4-dimethyl-5-oxo-4,5-dihydro-1H-pyrazol-3-yl)benzamide according to General Method 9 and the product was purified using acidic preparative chromatography (15 mg, 26%). LC-MS $t_R$=2.78 min, [M+H]$^+$=264.00; $^1$H NMR (500 MHz, DMSO-d6) δ 8.15 (d, J=8.4 Hz, 2H), 8.00 (d, J=8.5 Hz, 2H), 7.66 (s, 1H), 6.53 (d, J=2.0 Hz, 1H), 1.23 (s, 3H).

Example 93

Compound 93 [4-(Hydroxyamino)-3-[4-methanesulfonyl-3-(piperazin-1-yl)phenyl]-1,4-dimethyl-4,5-dihydro-1H-pyrazol-5-one]

93.1 tert-Butyl 4-[5-(4-{[(tert-butoxy)carbonyl](hydroxy)amino}-1,4-dimethyl-5-oxo-4,5-dihydro-1H-pyrazol-3-yl)-2-methanesulfonylphenyl]piperazine-1-carboxylate tert-Butyl 4-[5-(4-{[(tert-butoxy)carbonyl](hydroxy)amino}-1,4-dimethyl-5-oxo-4,5-dihydro-1H-pyrazol-3-yl)-2-methanesulfonylphenyl]piperazine-1-carboxylate was synthesized from 4-{[(tert-butoxy)carbonyl]({[(tert-butoxy)carbonyl]oxy})amino}-3-(3-fluoro-4-methanesulfonylphenyl)-1,4-dimethyl-4,5-dihydro-1H-pyrazol-5-one according to General Method 16 and was purified using silica gel chromatography eluting with heptane:ethyl acetate gradients followed using acidic preparative HPLC (0.12 g, 27%). LC-MS $t_R$=1.38 min, [M+H]$^+$=582.3; $^1$H NMR (500 MHz, Chloroform-d) δ 8.12 (d, J=8.3 Hz, 1H), 7.93 (d, J=1.5 Hz, 1H), 7.88 (dd, J=8.4, 1.5 Hz, 1H), 3.46 (d, J=1.9 Hz, 4H), 3.34 (s, 4H), 1.71 (s, 3H), 1.63 (s, 9H), 1.48 (s, 3H), 1.29 (s, 9H).

93.2 4-(Hydroxyamino)-3-[4-methanesulfonyl-3-(piperazin-1-yl)phenyl]-1,4-dimethyl-4,5-dihydro-1H-pyrazol-5-one To a solution of tert-butyl 4-[5-(4-{[(tert-butoxy)carbonyl](hydroxy)amino}-1,4-dimethyl-5-oxo-4,5-dihydro-1H-pyrazol-3-yl)-2-methanesulfonylphenyl]piperazine-1-carboxylate (0.12 g, 0.16 mmol) in DCM (2 mL) was added 4 M HCl in dioxane (1.4 mL) and the reaction mixture was stirred at room temperature until complete consumption of the starting material was evident by LC-MS. The solvent was removed under reduced pressure and the product purified using acidic preparative HPLC to yield the formate salt (31 mg, 46%). LC-MS $t_R$=1.06 min, [M+H]$^+$=381.5; $^1$H NMR (500 MHz, DMSO-d6) 8.27 (s, 1H), 8.16 (d, J=1.3 Hz, 1H), 8.05 (dd, J=8.4, 1.4 Hz, 1H), 7.98 (d, J=8.3 Hz, 1H), 6.62 (s, 1H), 3.41 (s, 3H), 3.33 (s, 3H), 3.01 (s, 8H), 1.23 (s, 3H).

Example 94

Compound 94 [(2-({4-[4-(Hydroxyamino)-1,4-dimethyl-5-oxo-4,5-dihydro-1H-pyrazol-3-yl]phenyl}formamido)propanoic acid]

94.1 Methyl 4-(3-methoxy-3-oxopropanoyl)benzoate

Methyl 4-(3-methoxy-3-oxopropanoyl)benzoate was synthesized from methyl 4-acetylbenzoate according to General Method 1 and the product was purified using silica gel chromatography eluting with 0-35% ethyl acetate in heptanes (10.45 g, 57%). LC-MS $t_R$=1.16 min, [M+H]$^+$=236.90; $^1$H NMR (500 MHz, DMSO-d6) δ 8.08 (m, 4H), 4.28 (s, 2H), 3.89 (s, 3H), 3.65 (s, 3H).

94.2 Methyl 4-(1-methyl-5-oxo-4,5-dihydro-1H-pyrazol-3-yl)benzoate

To a solution of methyl 4-(3-methoxy-3-oxopropanoyl)benzoate (10.44 g, 35.36 mmol) in ethanol (50 mL) was added methylhydrazine sulfate (5.61 g, 38.89 mmol) and N,N-diethylethanamine (5.43 mL, 38.89 mmol) and the resulting reaction mixture was heated to 80 OC until complete consumption of starting material was observed as monitored by LC-MS. The reaction mixture was concentrated under reduced pressure and the resulting solid was dissolved in ethyl acetate (60 mL), washed with 1M HCl (3×30 mL), water (30 mL) and brine (30 mL). The organic layer was dried over magnesium sulfate, filtered and concentrated under reduced pressure to give the title compound as a brown solid (7.82 g, 69%). LC-MS $t_R$=1.04 min, [M+H]$^+$=232.90.

94.3 Methyl 4-(4-formyl-1-methyl-5-oxo-4,5-dihydro-1H-pyrazol-3-yl)benzoate

Methyl 4-(4-formyl-1-methyl-5-oxo-4,5-dihydro-1H-pyrazol-3-yl)benzoate was synthesized from methyl 4-(1-methyl-5-oxo-4,5-dihydro-1H-pyrazol-3-yl)benzoate according to General Method 4 (5.88 g, 84%). LC-MS $t_R$=1.09 min, [M+H]$^+$=260.95; $^1$H NMR (250 MHz, DMSO-d6) δ 9.77 (s, 1H), 7.98 (s, 4H), 3.87 (s, 3H), 3.64 (s, 3H).

94.4 Methyl 4-(1,4-dimethyl-5-oxo-4,5-dihydro-1H-pyrazol-3-yl)benzoate

Methyl 4-(1,4-dimethyl-5-oxo-4,5-dihydro-1H-pyrazol-3-yl)benzoate was synthesized from methyl 4-(4-formyl-1-methyl-5-oxo-4,5-dihydro-1H-pyrazol-3-yl)benzoate according to General Method 5 (7.7 g, 97%). LC-MS $t_R$=1.01 min, [M+H]$^+$=246.95; $^1$H NMR (500 MHz, DMSO-d6) δ 7.95 (d, J=8.3 Hz, 2H), 7.75 (d, J=8.4 Hz, 2H), 3.85 (s, 3H), 3.55 (s, 3H), 2.04 (s, 3H).

94.5 Methyl 4-(4-bromo-1,4-dimethyl-5-oxo-4,5-dihydro-1H-pyrazol-3-yl)benzoate

Methyl 4-(4-bromo-1,4-dimethyl-5-oxo-4,5-dihydro-1H-pyrazol-3-yl)benzoate was synthesized from methyl 4-(1,4-dimethyl-5-oxo-4,5-dihydro-1H-pyrazol-3-yl)benzoate according to General Method 6 and was used directly in the displacement reaction according to General Method 8 (5.56 g, 100%).

94.6 Methyl 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoate Methyl 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoate was synthesized from methyl 4-(4-bromo-1,4-dimethyl-5-oxo-4,5-dihydro-1H-pyrazol-3-yl)benzoate according to General Method 8 and the product was purified using silica gel chromatography eluting with 10-60% ethyl acetate in heptanes (2.4 g, 27%). LC-MS $t_R$=1.48 min, [M+H]$^+$=499.95.

94.7 4-(4-{[(tert-Butoxy)carbonyl](hydroxy)amino}-1,4-dimethyl-5-oxo-4,5-dihydro-1H-pyrazol-3-yl)benzoic acid To a solution of lithium hydroxide (361.1 mg, 15.08 mmol) in water (60 mL) was added a solution of methyl 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoate (2.4 g, 5.03 mmol) in THF (60 mL) and the reaction mixture was left to stir at room temperature until consumption of the starting material was observed by LC-MS. The reaction mixture was concentrated under reduced pressure and the resulting solution was diluted with ethyl acetate (200 mL). HCl (20 mL) was added and the organic layer was extracted and washed with brine (20 mL), dried over magnesium sulfate, filtered and concentrated under reduced pressure. The crude material was purified using silica gel chromatography (using 40-100% ethyl acetate:heptanes) to give the title compound as an off white solid (0.5 g, 25%). LC-MS $t_R$=1.06 min, [M+H]$^+$=386.15.

94.8 tert-Butyl 2-{[4-(4-{[(tert-butoxy)carbonyl](hydroxy)amino}-1,4-dimethyl-5-oxo-4,5-dihydro-1H-pyrazol-3-yl)phenyl]formamido}propanoate tert-Butyl 2-{[4-(4-{[(tert-butoxy)carbonyl](hydroxy)amino}-1,4-dimethyl-5-oxo-4,5-dihydro-1H-pyrazol-3-yl)phenyl]formamido}propanoate was synthesized from 4-(4-{[(tert-butoxy)carbonyl](hydroxy)amino}-1,4-dimethyl-5-oxo-4,5-dihydro-1H-pyrazol-3-yl)benzoic acid and tert-butyl 2-aminopropanoate hydrochloride according to General Method 15 (205 mg, 71%). LC-MS $t_R$=1.29 min, [M+H]$^+$=513.10.

94.9 2-({4-[4-(Hydroxyamino)-1,4-dimethyl-5-oxo-4,5-dihydro-1H-pyrazol-3 yl]phenyl}formamido)propanoic acid 2-({4-[4-(Hydroxyamino)-1,4-dimethyl-5-oxo-4,5-dihydro-1H-pyrazol-3 yl]phenyl}formamido) propanoic acid was synthesized from tert-butyl 2-{[4-(4-{[(tert-butoxy)carbonyl](hydroxy)amino}-1,4-dimethyl-5-oxo-4,5-dihydro-1H-pyrazol-3-yl)phenyl]formamido}propanoate according to General Method 9 and the product was purified using acidic preparative chromatography (21 mg, 21%). LC-MS $t_R$=0.91 min, [M+H]$^+$=334.95; $^1$H NMR (500 MHz, DMSO-d6) δ 8.72 (d, J=7.2 Hz, 1H), 8.12 (d, J=8.5 Hz, 2H), 7.95 (d, J=8.5 Hz, 2H), 7.67 (s, 1H), 6.53 (s, 1H), 4.43 (p, J=7.3 Hz, 1H), 3.31 (s, 3H), 1.40 (d, J=7.3 Hz, 3H), 1.22 (s, 3H).

Example 95

Compound 95 [2-({4-[4-(Hydroxyamino)-1,4-dimethyl-5-oxo-4,5-dihydro-1H-pyrazol-3-yl]phenyl}formamido)acetic acid]

95.1 Methyl 4-(3-methoxy-3-oxopropanoyl)benzoate

Methyl 4-(3-methoxy-3-oxopropanoyl)benzoate was synthesized from methyl 4-acetylbenzoate according to General Method 1 with the product being purified using silica gel chromatography eluting with 0-35% ethyl acetate in heptanes (10.45 g, 57%). LC-MS $t_R$=1.16 min, [M+H]$^+$=236.90; $^1$H NMR (500 MHz, DMSO-d6) δ 8.08 (m, 4H), 4.28 (s, 2H), 3.89 (s, 3H), 3.65 (s, 3H).

95.2 Methyl 4-(1-methyl-5-oxo-4,5-dihydro-1H-pyrazol-3-yl)benzoate

To a solution of methyl 4-(3-methoxy-3-oxopropanoyl)benzoate (10.44 g, 35.36 mmol) in ethanol (50 mL) was added methylhydrazine sulfate (5.61 g, 38.89 mmol) and N,N-diethylethanamine (5.43 mL, 38.89 mmol) and the resulting reaction mixture was heated to 80 OC until complete consumption of starting material was observed as monitored by LC-MS. The reaction mixture was concentrated under reduced pressure and the resulting solid was dissolved in ethyl acetate (60 mL), washed with 1M HCl (3×30 mL), water (30 mL) and brine (30 mL). The organic layer was dried over magnesium sulfate, filtered and concentrated under reduced pressure to give the title compound as a brown solid (7.82 g, 69%). LC-MS $t_R$=1.04 min, [M+H]$^+$=232.90.

95.3 Methyl 4-(4-formyl-1-methyl-5-oxo-4,5-dihydro-1H-pyrazol-3-yl)benzoate

Methyl 4-(4-formyl-1-methyl-5-oxo-4,5-dihydro-1H-pyrazol-3-yl)benzoate was synthesized from methyl 4-(1-methyl-5-oxo-4,5-dihydro-1H-pyrazol-3-yl)benzoate according to General Method 4 (5.88 g, 84%). LC-MS $t_R$=1.09 min, [M+H]$^+$=260.95; $^1$H NMR (250 MHz, DMSO-d6) δ 9.77 (s, 1H), 7.98 (s, 4H), 3.87 (s, 3H), 3.64 (s, 3H).

95.4 Methyl 4-(1,4-dimethyl-5-oxo-4,5-dihydro-1H-pyrazol-3-yl)benzoate

Methyl 4-(1,4-dimethyl-5-oxo-4,5-dihydro-1H-pyrazol-3-yl)benzoate was synthesized from methyl 4-(4-formyl-1-methyl-5-oxo-4,5-dihydro-1H-pyrazol-3-yl)benzoate according to General Method 5 (7.7 g, 97%). LC-MS $t_R$=1.01 min, [M+H]$^+$=246.95; $^1$H NMR (500 MHz, DMSO-d6) δ 7.95 (d, J=8.3 Hz, 2H), 7.75 (d, J=8.4 Hz, 2H), 3.85 (s, 3H), 3.55 (s, 3H), 2.04 (s, 3H).

95.5 Methyl 4-(4-bromo-1,4-dimethyl-5-oxo-4,5-dihydro-1H-pyrazol-3-yl)benzoate Methyl 4-(4-bromo-1,4-dimethyl-5-oxo-4,5-dihydro-1H-pyrazol-3-yl)benzoate was synthesized from methyl 4-(1,4-dimethyl-5-oxo-4,5-dihydro-1H-pyrazol-3-yl)benzoate according to General Method 6 and was used directly in the displacement reaction according to General Method 8 (5.56 g, 100%).

95.6 Methyl 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoate Methyl 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoate was synthesized from methyl 4-(4-bromo-1,4-dimethyl-5-oxo-4,5-dihydro-1H-pyrazol-3-yl)benzoate according to General Method 8 and the product was purified using silica gel chromatography eluting with 10-60% ethyl acetate in heptanes (2.4 g, 27%). LC-MS $t_R$=1.48 min, [M+H]$^+$=499.95.

95.7 4-(4-{[(tert-Butoxy)carbonyl](hydroxy)amino}-1,4-dimethyl-5-oxo-4,5-dihydro-1H-pyrazol-3-yl)benzoic acid To a solution of lithium hydroxide (361.1 mg, 15.08 mmol) in water (60 mL) was added a solution of methyl 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoate (2.4 g, 5.03 mmol) in THF (60 mL) and the reaction mixture was left to stir at room temperature until consumption of the starting material was observed as monitored by LC-MS. The reaction mixture was concentrated and the resulting solution was diluted with ethyl acetate (200 mL). HCl (20 mL) was added and the organic layer was washed with brine (20 mL), dried over magnesium sulfate, filtered and concentrated under reduced pressure. The crude material was purified using silica gel chromatography (using 40-100% ethyl acetate in heptanes) to give the title compound as an off-white solid (0.5 g, 25%). LC-MS $t_R$=1.06 min, [M+H]$^+$=386.15.

95.8 tert-Butyl 2-{[4-(4-{[(tert-butoxy)carbonyl](hydroxy)amino}-1,4-dimethyl-5-oxo-4,5-dihydro-1H-pyrazol-3-yl)phenyl]formamido}acetate tert-Butyl 2-{[4-(4-{[(tert-butoxy)carbonyl](hydroxy)amino}-1,4-dimethyl-5-oxo-4,5-dihydro-1H-pyrazol-3-yl)phenyl]formamido}acetate was synthesized from 4-(4-{[(tert-butoxy)carbonyl](hydroxy)amino}-1,4-dimethyl-5-oxo-4,5-dihydro-1H-pyrazol-3-yl)benzoic acid and tert-butyl 2-aminoacetate hydrochloride according to General Method 15 (191 mg, 28%). LC-MS $t_R$=1.28 min, [M+H]$^+$=499.10

95.9 2-({4-[4-(Hydroxyamino)-1,4-dimethyl-5-oxo-4,5-dihydro-1H-pyrazol-3-yl]phenyl}formamido)acetic acid 2-({4-[4-(Hydroxyamino)-1,4-dimethyl-5-oxo-4,5-dihydro-1H-pyrazol-3-yl]phenyl}formamido)acetic acid was synthesized from tert-butyl 2-{[4-(4-{[(tert-butoxy)carbonyl](hydroxy)amino}-1,4-dimethyl-5-oxo-4,5-dihydro-1H-pyrazol-3-yl)phenyl]formamido}acetate according to General Method 9 and the product was purified using acidic preparative chromatography (10 mg, 36%). LC-MS $t_R$=0.85 min, [M+H]$^+$=320.95; $^1$H NMR (500 MHz, DMSO-d6) δ 8.90 (t, J=5.9 Hz, 1H), 8.13 (d, J=8.6 Hz, 2H), 7.94 (d, J=8.6

Hz, 2H), 7.67 (d, J=1.4 Hz, 1H), 6.64-6.46 (m, 1H), 3.94 (d, J=5.9 Hz, 2H), 3.31 (s, 3H), 1.22 (s, 3H).

Example 96

Compound 96 [4-(3-Fluorophenyl)-4-(hydroxyamino)-1,3-dimethyl-4,5-dihydro-1H-pyrazol-5-one]

96.1 Methyl 2-(3-fluorophenyl)-3-oxobutanoate

Methyl 2-(3-fluorophenyl)-3-oxobutanoate was synthesized from methyl 2-(3-fluorophenyl)acetate according to General Method 13 (7.41 g, 77%). LC-MS $t_R$=1.21 min, [M+H]$^+$=209; $^1$H NMR (500 MHz, DMSO-d6) δ 7.47-7.38 (m, 1H), 7.29-7.23 (m, 1H), 7.17-7.05 (m, 2H), 5.24 (s, 1H), 3.68 (s, 3H), 2.21-2.14 (m, 3H).

96.2 4-(3-Fluorophenyl)-2,5-dimethyl-2,3-dihydro-1H-pyrazol-3-one 4-(3-Fluorophenyl)-2,5-dimethyl-2,3-dihydro-1H-pyrazol-3-one was synthesized from methyl 2-(3-fluorophenyl)-3-oxobutanoate according to General Method 2. The product was purified using silica gel chromatography eluting with 30-100% ethyl acetate in heptanes followed by 0-30% methanol in ethyl acetate (3.46 g, 62%). LC-MS $t_R$=0.97 min, [M+H]$^+$=207; $^1$H NMR (500 MHz, DMSO-d6) δ 7.55-7.36 (m, 3H), 7.20-6.97 (m, 1H), 2.60 (s, 3H), 2.33 (s, 3H).

96.3 4-Bromo-4-(3-fluorophenyl)-1,3-dimethyl-4,5-dihydro-1H-pyrazol-5-one

4-Bromo-4-(3-fluorophenyl)-1,3-dimethyl-4,5-dihydro-1H-pyrazol-5-one was synthesized from 4-(3-fluorophenyl)-2,5-dimethyl-2,3-dihydro-1H-pyrazol-3-one according to General Method 6 (3.30 g, 81%). LC-MS $t_R$=1.29 min, [M+H]$^+$=286.

96.4 4-{[(tert-Butoxy)carbonyl]({[(tert-butoxy)carbonyl]oxy})amino}-4-(3-fluorophenyl)-1,3-dimethyl-4,5-dihydro-1H-pyrazol-5-one 4-{[(tert-Butoxy)carbonyl]({[(tert-butoxy)carbonyl]oxy})amino}-4-(3-fluorophenyl)-1,3-dimethyl-4,5-dihydro-1H-pyrazol-5-one was synthesized from 4-bromo-4-(3-fluorophenyl)-1,3-dimethyl-4,5-dihydro-1H-pyrazol-5-one according to General Method 8 (4.87 g, 67%). LC-MS $t_R$=1.54 min, [M+Na]$^+$=460; $^1$H NMR (500 MHz, DMSO-d6) δ 7.55-7.39 (m, 1H), 7.37-7.19 (m, 2H), 7.16-7.09 (m, 1H), 3.25-3.05 (m, 3H), 2.12 (s, 3H), 1.48-1.39 (m, 11H), 1.37-1.36 (m, 7H).

96.5 4-(3-Fluorophenyl)-4-(hydroxyamino)-1,3-dimethyl-4,5-dihydro-1H-pyrazol-5-one 4-(3-Fluorophenyl)-4-(hydroxyamino)-1,3-dimethyl-4,5-dihydro-1H-pyrazol-5-one was synthesized from 4-{[(tert-butoxy)carbonyl]({[(tert-butoxy)carbonyl]oxy})amino}-4-(3-fluorophenyl)-1,3-dimethyl-4,5-dihydro-1H-pyrazol-5-one according to General Method 9 and the resulting product was purified using acidic preparative HPLC (0.07 g, 4%). LC-MS $t_R$=0.98 min, [M+H]$^+$=238; $^1$H NMR (500 MHz, DMSO-d6) δ 7.95-7.83 (m, 1H), 7.46-7.36 (m, 1H), 7.25-7.16 (m, 1H), 7.12-7.05 (m, 1H), 7.04-7.00 (m, 1H), 6.99-6.94 (m, 1H), 3.19 (s, 3H), 1.94 (s, 3H).

Example 97

Compound 97 [4-(Hydroxyamino)-3-[4-methanesulfonyl-3-(trifluoromethyl)phenyl]-1,4-dimethyl-4,5-dihydro-1H-pyrazol-5-one]

97.1 1-[4-(Methylsulfanyl)-3-(trifluoromethyl)phenyl]ethan-1-one

1-[4-(Methylsulfanyl)-3-(trifluoromethyl)phenyl]ethan-1-one was synthesized from 1-[4-fluoro-3-(trifluoromethyl)phenyl]ethan-1-one according to General Method 14 (12.25 g, 71%). LC-MS $t_R$=1.33 min, [M+H]$^+$=234.90.

97.2 Methyl 3-[4-(methylsulfanyl)-3-(trifluoromethyl)phenyl]-3-oxopropanoate

Methyl 3-[4-(methylsulfanyl)-3-(trifluoromethyl)phenyl]-3-oxopropanoate was synthesized from 1-[4-(methylsulfanyl)-3-(trifluoromethyl)phenyl]ethan-1-one according to General Method and the product was purified using silica gel chromatography eluting with 0-25% ethyl acetate in heptanes (8.5 g, 46%). LC-MS $t_R$=1.34 min, [M+H]$^+$=292.90

97.3 1-Methyl-3-[4-(methylsulfanyl)-3-(trifluoromethyl)phenyl]-1H-pyrazol-5-ol

1-Methyl-3-[4-(methylsulfanyl)-3-(trifluoromethyl)phenyl]-1H-pyrazol-5-ol was synthesized from methyl 3-[4-(methylsulfanyl)-3-(trifluoromethyl)phenyl]-3-oxopropanoate according to General Method 2 and the product was purified using silica gel chromatography eluting with 0-10% methanol in DCM (6.6 g, 70%). LC-MS $t_R$=1.22 min, [M+H]$^+$=288.95

97.4 5-Hydroxy-1-methyl-3-[4-(methylsulfanyl)-3-(trifluoromethyl)phenyl]-1H-pyrazole-4-carbaldehyde 5-Hydroxy-1-methyl-3-[4-(methylsulfanyl)-3-(trifluoromethyl)phenyl]-1H-pyrazole-4-carbaldehyde was synthesized from 1-methyl-3-[4-(methylsulfanyl)-3-(trifluoromethyl)phenyl]-1H-pyrazol-5-ol according to General Method 4 (7.48 g, 97%). LC-MS $t_R$=1.25 min, [M+H]$^+$=316.90; $^1$H NMR (500 MHz, DMSO-d6) δ 9.80 (s, 1H), 8.28 (d, J=1.5 Hz, 1H), 8.18-8.12 (m, 1H), 7.56 (d, J=8.5 Hz, 1H), 3.63 (s, 3H), 2.59 (s, 3H).

97.5 1,4-Dimethyl-3-[4-(methylsulfanyl)-3-(trifluoromethyl)phenyl]-1H-pyrazol-5-ol 1,4-Dimethyl-3-[4-(methylsulfanyl)-3-(trifluoromethyl)phenyl]-1H-pyrazol-5-ol was synthesized from 5-hydroxy-1-methyl-3-[4-(methylsulfanyl)-3-(trifluoromethyl)phenyl]-1H-pyrazole-4-carbaldehyde according to General Method 5 (10.12 g, 79%). LC-MS $t_R$=1.21 min, [M+H]$^+$=302.90.

97.6 4-Bromo-3-[4-methanesulfinyl-3-(trifluoromethyl)phenyl]-1,4-dimethyl-4,5-dihydro-1H-pyrazol-5-one 4-Bromo-3-[4-methanesulfinyl-3-(trifluoromethyl)phenyl]-1,4-dimethyl-4,5-dihydro-1H-pyrazol-5-one was synthesized from 1,4-dimethyl-3-[4-(methylsulfanyl)-3-(trifluoromethyl)phenyl]-1H-pyrazol-5-ol according to General Method 6 which was used directly in the displacement reaction according to General Method 8 (6.71 g, 100%).

97.7 4-{[(tert-Butoxy)carbonyl](({[(tert-butoxy)carbonyl]oxy})amino}-3-[4-methanesulfinyl-3-(trifluoromethyl)phenyl]-1,4-dimethyl-4,5-dihydro-1H-pyrazol-5-one 4-{[(tert-Butoxy)carbonyl]({[(tert-butoxy)carbonyl]oxy})amino}-3-[4-methanesulfinyl-3-(trifluoromethyl)phenyl]-1,4-dimethyl-4,5-dihydro-1H-pyrazol-5-one was synthesized from 4-bromo-3-[4-methanesulfinyl-3-(trifluoromethyl)phenyl]-1,4-dimethyl-4,5-dihydro-1H-pyrazol-5-one according to General Method 8 and the product was purified using silica gel chromatography eluting with 20-70% ethyl acetate in heptanes (1.36 g, 23%). LC-MS $t_R$=1.44 min, [M+H]$^+$=550.2.

97.8 4-{[(tert-Butoxy)carbonyl]({[(tert-butoxy)carbonyl]oxy})amino}-3-[4-methanesulfonyl-3-(trifluoromethyl)phenyl]-1,4-dimethyl-4,5-dihydro-1H-pyrazol-5-one To a solution of 4-{[(tert-butoxy)carbonyl]({[(tert-butoxy)carbonyl]oxy})amino}-3-[4-methanesulfinyl-3-(trifluoromethyl)phenyl]-1,4-dimethyl-4,5-dihydro-1H-pyrazol-5-one (1.75 g, 2.9 mmol) in DCM (10 mL) was added a solution of mCPBA (70%, 2.86 g, 11.59 mmol) in DCM (10 mL) and the mixture was stirred at room temperature until complete consumption of the starting material was observed as monitored by LC-MS. The mixture was washed with 1M NaOH (3×10 mL), dried over magnesium sulfate, filtered and concentrated under reduced pressure to yield the title compound as an orange oil (1.76 g, 89%). LC-MS $t_R$=1.51 min, [M+H]$^+$=587.95.

97.9 4-(Hydroxyamino)-3-[4-methanesulfonyl-3-(trifluoromethyl)phenyl]-1,4-dimethyl-4,5-dihydro-1H-pyrazol-5-one 4-(Hydroxyamino)-3-[4-methanesulfonyl-3-(trifluoromethyl)phenyl]-1,4-dimethyl-4,5-dihydro-1H-pyrazol-5-one was synthesized from 4-{[(tert-butoxy)carbonyl]({[(tert-butoxy)carbonyl]oxy})amino}-3-[4-methanesulfonyl-3-(trifluoromethyl)phenyl]-1,4-dimethyl-4,5-dihydro-1H-pyrazol-5-one according to General Method 9 and the product was purified using silica gel chromatography eluting with 35-90% ethyl acetate in heptanes (0.25 g, 22%). LC-MS $t_R$=3.44 min, [M+H]$^+$=365.95; $^1$H NMR (500 MHz, DMSO-d6) δ 8.60 (s, 1H), 8.52 (dd, J=8.4, 1.3 Hz, 1H), 8.34 (d, J=8.4 Hz, 1H), 7.77 (d, J=2.7 Hz, 1H), 6.73 (d, J=2.7 Hz, 1H), 3.36 (s, 3H), 3.35 (s, 3H), 1.26 (s, 3H).

Example 98

Compound 98 [4-(Hydroxyamino)-1,3-dimethyl-4-(3-methylphenyl)-4,5-dihydro-1H-pyrazol-5-one]

98.1 Methyl 2-(3-methylphenyl)-3-oxobutanoate

Methyl 2-(3-methylphenyl)-3-oxobutanoate was synthesized from methyl 2-(3-methylphenyl)acetate according to General Method 13 (6.92 g, 72%). LC-MS $t_R$=1.48 min, [M+H]$^+$=207; $^1$H NMR (500 MHz, DMSO-d6) δ 7.28-7.25 (m, 1H), 7.22-7.17 (m, 1H), 7.14-7.12 (m, 1H), 7.09-7.03 (m, 1H), 5.08 (s, 1H), 3.66 (s, 3H), 2.30 (s, 3H), 2.12 (s, 3H).

98.2 1,3,4-Trimethyl-4-(3-methylphenyl)-4,5-dihydro-1H-pyrazol-5-one 1,3,4-Trimethyl-4-(3-methylphenyl)-4,5-dihydro-1H-pyrazol-5-one was synthesized from methyl 2-(3-methylphenyl)-3-oxobutanoate according to General Method 2. The product was purified using triturating with methanol:DCM (1:5, v:v) (1.79 g, 39%). LC-MS $t_R$=1.01 min, [M+H]$^+$=203; $^1$H NMR (500 MHz, DMSO-d6) δ 7.35-7.16 (m, 3H), 7.01-6.91 (m, 1H), 3.39 (s, 3H), 2.30 (s, 3H), 2.17 (s, 3H).

98.3 4-Bromo-1,3-dimethyl-4-(3-methylphenyl)-4,5-dihydro-1H-pyrazol-5-one

4-Bromo-1,3-dimethyl-4-(3-methylphenyl)-4,5-dihydro-1H-pyrazol-5-one was synthesized from 1,3,4-trimethyl-4-(3-methylphenyl)-4,5-dihydro-1H-pyrazol-5-one according to General Method 6 (2.31 g, 88%). LC-MS $t_R$=1.32 min, [M+H]$^+$=282.

98.4 4-{[(tert-Butoxy)carbonyl]({[(tert-butoxy)carbonyl]oxy})amino}-1,3-dimethyl-4-(3-methylphenyl)-4,5-dihydro-1H-pyrazol-5-one 4-{[(tert-Butoxy)carbonyl]({[(tert-butoxy)carbonyl]oxy})amino}-1,3-dimethyl-4-(3-methylphenyl)-4,5-dihydro-1H-pyrazol-5-one was synthesized from 4-bromo-1,3-dimethyl-4-(3-methylphenyl)-4,5-dihydro-1H-pyrazol-5-one according to General Method 8 (3.31 g, 72%). LC-MS $t_R$=1.52 min, [M+Na]$^+$=456.

98.5 4-(Hydroxyamino)-1,3-dimethyl-4-(3-methylphenyl)-4,5-dihydro-1H-pyrazol-5-one 4-(Hydroxyamino)-1,3-dimethyl-4-(3-methylphenyl)-4,5-dihydro-1H-pyrazol-5-one was synthesized from 4-{[(tert-butoxy)carbonyl]({[(tert-butoxy)carbonyl]oxy})amino}-1,3-dimethyl-4-(3-methylphenyl)-4,5-dihydro-1H-pyrazol-5-one according to General Method 9. The product was purified using silica gel chromatography eluting with 0-100% ethyl acetate in heptanes followed by triturating in ethyl acetate:heptanes (1:5, v:v) (0.60 g, 49%). LC-MS $t_R$=1.04 min, [M+H]$^+$=234; $^1$H NMR (500 MHz, DMSO-d6) δ 7.86-7.75 (m, 1H), 7.30-7.20 (m, 1H), 7.20-7.12 (m, 1H), 7.06-6.94 (m, 2H), 6.92-6.76 (m, 1H), 3.19 (s, 3H), 2.28 (s, 3H), 1.92 (s, 3H).

Example 99

Compound 99 [4-(3-Chlorophenyl)-4-(hydroxyamino)-1,3-dimethyl-4,5-dihydro-1H-pyrazol-5-one]

99.1 2-(3-Chlorophenyl)-3-oxobutanoate 2-(3-Chlorophenyl)-3-oxobutanoate was synthesized from methyl 2-(3-chlorophenyl)acetate according to General Method 13 (6.45 g, 68%). LC-MS $t_R$=1.49 min, [M+H]$^+$=226; $^1$H NMR (500 MHz, DMSO-d6) δ 7.36-7.26 (m, 4H), 3.72 (s, 1H), 3.68 (s, 3H), 2.18 (s, 3H).

99.2 4-(3-Chlorophenyl)-2,5-dimethyl-2,3-dihydro-1H-pyrazol-3-one 4-(3-Chlorophenyl)-2,5-dimethyl-2,3-dihydro-1H-pyrazol-3-one was synthesized from methyl 2-(3-chlorophenyl)-

3-oxobutanoate according to General Method 2. The product was purified using silica gel chromatography eluting with 0-100% ethyl acetate in heptanes then 0-30% methanol in ethyl acetate (2.70 g, 52%). LC-MS $t_R$=1.05 min, [M+H]$^+$=223; $^1$H NMR (500 MHz, DMSO-d6) δ 7.68-7.59 (m, 1H), 7.48-7.39 (m, 1H), 7.37-7.27 (m, 1H), 7.18-7.05 (m, 1H), 3.37 (s, 3H), 1.74 (s, 3H).

99.3 4-Bromo-4-(3-chlorophenyl)-1,3-dimethyl-4,5-dihydro-1H-pyrazol-5-one

4-Bromo-4-(3-chlorophenyl)-1,3-dimethyl-4,5-dihydro-1H-pyrazol-5-one was synthesized from 4-(3-chlorophenyl)-2,5-dimethyl-2,3-dihydro-1H-pyrazol-3-one according to General Method 6 (2.99 g, 82%). LC-MS $t_R$=1.36 min, [M+H]$^+$=302.

99.4 4-{[(tert-Butoxy)carbonyl]({[(tert-butoxy)carbonyl]oxy})amino}-4-(3-chlorophenyl)-1,3-dimethyl-4,5-dihydro-1H-pyrazol-5-one 4-{[(tert-Butoxy)carbonyl]({[(tert-butoxy)carbonyl]oxy})amino}-4-(3-chlorophenyl)-1,3-dimethyl-4,5-dihydro-1H-pyrazol-5-one was synthesized from 4-bromo-4-(3-chlorophenyl)-1,3-dimethyl-4,5-dihydro-1H-pyrazol-5-one according to General Method 8. The product was purified using silica gel chromatography eluting with 0-100% ethyl acetate in heptanes (1.1 g, 28%). LC-MS $t_R$=1.60 min, [M+Na]$^+$=476; $^1$H NMR (500 MHz, DMSO-d6) δ 7.62-7.36 (m, 3H), 7.31-7.02 (m, 1H), 3.23-3.06 (m, 3H), 2.17-2.05 (m, 3H), 1.40-1.21 (m, 18H).

99.5 4-(3-Chlorophenyl)-4-(hydroxyamino)-1,3-dimethyl-4,5-dihydro-1H-pyrazol-5-one 4-(3-Chlorophenyl)-4-(hydroxyamino)-1,3-dimethyl-4,5-dihydro-1H-pyrazol-5-one was synthesized from 4-{[(tert-butoxy)carbonyl]({[(tert-butoxy)carbonyl]oxy})amino}-4-(3-chlorophenyl)-1,3-dimethyl-4,5-dihydro-1H-pyrazol-5-one according to General Method 9. The product was purified using silica gel chromatography eluting with 0-100% ethyl acetate in heptanes to yield the target compound (0.30 g, 70%). LC-MS $t_R$=1.07 min, [M+H]$^+$=254; $^1$H NMR (500 MHz, DMSO-d6) δ 7.90 (s, 1H), 7.46-7.36 (m, 2H), 7.32-7.27 (m, 1H), 7.15-6.93 (m, 2H), 3.20 (s, 3H), 1.94 (s, 3H).

Example 100

Compound 100 [4-(Hydroxyamino)-4-(3-methoxyphenyl)-1,3-dimethyl-4,5-dihydro-1H-pyrazol-5-one]

100.1 2-(3-Methoxyphenyl)-3-oxobutanoate 2-(3-Methoxyphenyl)-3-oxobutanoate was synthesized from ethyl 2-(3-methoxyphenyl)acetate according to General Method 13 and was purified using silica gel chromatography eluting with 0-100% ethyl acetate in heptanes (1.95 g, 32%). LC-MS $t_R$=1.27 min, [M+H]$^+$=237.0; $^1$H NMR (500 MHz, Chloroform-d) δ 7.21 (t, J=7.9 Hz, 1H), 6.80-6.69 (m, 3H), 4.08 (q, J=7.1 Hz, 2H), 3.80 (s, 3H), 1.76 (s, 3H), 1.57 (s, 1H), 1.14 (t, J=7.1 Hz, 3H).

100.2 4-(3-Methoxyphenyl)-2,5-dimethylpyrazol-3-ol 4-(3-Methoxyphenyl)-2,5-dimethylpyrazol-3-ol was synthesized from 2-(3-methoxyphenyl)-3-oxobutanoate according to General Method 2 and was used directly in bromination reaction (1.78 g, 93%). LC-MS $t_R$=0.95 min, [M+H]$^+$=219.4; $^1$H NMR (500 MHz, DMSO-d6) δ 7.24 (t, J=7.9 Hz, 1H), 7.09 (s, 1H), 7.04 (d, J=7.7 Hz, 1H), 6.75-6.70 (m, 1H), 3.75 (s, 3H), 3.39 (s, 3H), 2.19 (s, 3H).

100.3 4-Bromo-3-(3-methoxyphenyl)-1,4-dimethyl-4,5-dihydro-1H-pyrazol-5-one 4-Bromo-3-(3-methoxyphenyl)-1,4-dimethyl-4,5-dihydro-1H-pyrazol-5-one was synthesized from 4-(3-methoxyphenyl)-2,5-dimethylpyrazol-3-ol according to General Method 6 and was used directly in the displacement reaction according to General Method 8 (2.42 g, 28%). LC-MS $t_R$=1.28 min, [M+H]$^+$=297/299.

100.4 4-(Hydroxyamino)-3-(3-methoxyphenyl)-1,4-dimethyl-4,5-dihydro-1H-pyrazol-5-one 4-(Hydroxyamino)-3-(3-methoxyphenyl)-1,4-dimethyl-4,5-dihydro-1H-pyrazol-5-one was synthesized from 4-bromo-3-(3-methoxyphenyl)-1,4-dimethyl-4,5-dihydro-1H-pyrazol-5-one according to General Method 8 (12 mg, 0.6%); $^1$H NMR (250 MHz, DMF-d7) δ 7.30 (t, J=7.9 Hz, 1H), 6.96-6.81 (m, 3H), 6.72 (d, J=7.8 Hz, 1H), 3.75 (s, 3H), 3.19 (s, 3H), 1.79 (s, 3H).

Example 101

Compound 101 [4-[4-(Hydroxyamino)-1,4-dimethyl-5-oxo-4,5-dihydro-1H-pyrazol-3-yl]-N-methanesulfonylbenzamide]

101.1 4-(4-{[(tert-Butoxy)carbonyl]({[(tert-butoxy)carbonyl]oxy})amino}-1,4-dimethyl-5-oxo-4,5-dihydro-1H-pyrazol-3-yl)-N-methanesulfonylbenzamide To a solution of 4-(4-{[(tert-butoxy)carbonyl]({[(tert-butoxy)carbonyl]oxy})amino}-1,4-dimethyl-5-oxo-4,5-dihydro-1H-pyrazol-3-yl)benzoic acid (0.30 g, 0.65 mmol) in DCM (3 mL) was added EDCI (0.20 g, 1.30 mmol) and DMAP (0.16 g, 1.30 mmol) and the reaction mixture was stirred at room temperature until complete conversion of the starting material observed by LC-MS. The reaction mixture was concentrated under reduced pressure and used directly in the following reaction (0.38 g, 43%). LC-MS $t_R$=1.36 min, [M+Na]$^+$=563.

101.2 4-[4-(Hydroxyamino)-1,4-dimethyl-5-oxo-4,5-dihydro-1H-pyrazol-3-yl]-N-methanesulfonylbenzamide 4-[4-(Hydroxyamino)-1,4-dimethyl-5-oxo-4,5-dihydro-1H-pyrazol-3-yl]-N-methanesulfonylbenzamide was synthesized from 4-(4-{[(tert-butoxy)carbonyl]({[(tert-butoxy)carbonyl]oxy})amino}-1,4-dimethyl-5-oxo-4,5-dihydro-1H-pyrazol-3-yl)-N-methanesulfonylbenzamide according to General Method 9 and was purified by acidic preparative HPLC (32 mg, 34%). LC-MS $t_R$=0.89 min, [M+H]$^+$=341; $^1$H NMR (500 MHz, DMSO-d6) δ 12.22 (s, 1H), 8.24-8.11 (m, 2H), 8.06-7.94 (m, 2H), 7.70 (s, 1H), 6.57 (s, 1H), 3.38 (s, 3H), 3.33 (s, 3H), 1.23 (s, 3H).

Example 102

Compound 102 [4-(Hydroxyamino)-1,3-dimethyl-4-[1-(phenoxyimino)ethyl]-4,5-dihydro-1H-pyrazol-5-one]

102.1 1-(5-Hydroxy-1,3-dimethyl-1H-pyrazol-4-yl)ethan-1-one 1-(5-Hydroxy-1,3-dimethyl-1H-pyrazol-4-yl)ethan-1-one was synthesized from 1,3-dimethyl-1H-pyrazol-5-ol according to General Method 11 (3.02 g, 44%). LC-MS $t_R$=0.19 min, [M+H]$^+$=154.90.

102.2 1,3-Dimethyl-4-[1-(phenoxyimino)ethyl]-1H-pyrazol-5-ol 1,3-Dimethyl-4-[1-(phenoxyimino)ethyl]-1H-pyrazol-5-ol was synthesized from 1-(5-hydroxy-1,3-dimethyl-1H-pyrazol-4-yl)ethan-1-one and O-phenylhydroxylamine hydrochloride according to General Method 12 (368 mg, 46%). LC-MS $t_R$=1.13 min, [M+H]$^+$=245.95; $^1$H NMR (500 MHz, DMSO-d6) δ 7.36-7.28 (m, 2H), 7.16 (d, J=7.8 Hz, 2H), 6.98 (t, J=7.3 Hz, 1H), 3.34 (s, 3H), 2.36 (s, 3H), 2.29 (s, 3H).

102.3 4-Bromo-1,3-dimethyl-4-[1-(phenoxyimino)ethyl]-4,5-dihydro-1H-pyrazol-5-one 4-Bromo-1,3-dimethyl-4-[1-(phenoxyimino)ethyl]-4,5-dihydro-1H-pyrazol-5-one was synthesized from 1,3-dimethyl-4-[1-(phenoxyimino)ethyl]-1H-pyrazol-5-ol according to General Method 6 which was directly used in the displacement reaction according to General Method 8 (486 mg, 100%). LC-MS $t_R$=1.49 min, [M+H]$^+$=323.80.

102.4 4-{[(tert-Butoxy)carbonyl]({[(tert-butoxy)carbonyl]oxy})amino}-1,3-dimethyl-4-[1-(phenoxyimino)ethyl]-4,5-dihydro-1H-pyrazol-5-one 4-{[(tert-Butoxy)carbonyl]({[(tert-butoxy)carbonyl]oxy})amino}-1,3-dimethyl-4-[1-(phenoxyimino)ethyl]-4,5-dihydro-1H-pyrazol-5-one was synthesized from 4-bromo-1,3-dimethyl-4-[1-(phenoxyimino)ethyl]-4,5-dihydro-1H-pyrazol-5-one according to General Method 8 and was purified using silica gel chromatography eluting with 0-35% ethyl acetate in heptanes (412 mg, 31%). LC-MS $t_R$=1.69 min, [M+H]$^+$=499.05.

102.5 4-(Hydroxyamino)-1,3-dimethyl-4-[1-(phenoxyimino)ethyl]-4,5-dihydro-1H-pyrazol-5-one 4-(Hydroxyamino)-1,3-dimethyl-4-[1-(phenoxyimino)ethyl]-4,5-dihydro-1H-pyrazol-5-one was synthesized from 4-{[(tert-butoxy)carbonyl]({[(tert-butoxy)carbonyl]oxy})amino}-1,3-dimethyl-4-[1-(phenoxyimino)ethyl]-4,5-dihydro-1H-pyrazol-5-one according to General Method 9 and was purified using acidic preparative chromatography (HPLC) (101 mg, 42%). LC-MS $t_R$=1.16 min, [M+H]$^+$=276.95; $^1$H NMR (500 MHz, DMSO-d6) δ 7.91 (d, J=2.5 Hz, 1H), 7.33 (q, J=9.0 Hz, 2H), 7.10 (d, J=7.9 Hz, 2H), 7.04 (t, J=7.3 Hz, 1H), 6.93 (d, J=2.4 Hz, 1H), 3.16 (s, 3H), 2.12 (s, 3H), 2.07 (s, 3H).

Example 103

Compound 103 [4-(Hydroxyamino)-1,3-dimethyl-4-[1-(benzyloxyimino)ethyl]-4,5-dihydro-1H-pyrazol-5-one]

103.1 1-(5-Hydroxy-1,3-dimethyl-1H-pyrazol-4-yl)ethan-1-one 1-(5-Hydroxy-1,3-dimethyl-1H-pyrazol-4-yl)ethan-1-one was synthesized from 1,3-dimethyl-1H-pyrazol-5-ol according to General Method 11 (3.02 g, 44%). LC-MS $t_R$=0.19 min, [M+H]$^+$=154.90.

103.2 4-[1-[(Benzyloxy)imino]ethyl]-1,3-dimethyl-1H-pyrazol-5-ol

4-[1-[(Benzyloxy)imino]ethyl]-1,3-dimethyl-1H-pyrazol-5-ol was synthesized from 1-(5-hydroxy-1,3-dimethyl-1H-pyrazol-4-yl)ethan-1-one and O-benzylhydroxylamine according to General Method 12 (544 mg, 36%). LC-MS $t_R$=1.19 min, [M+H]$^+$=260.45.

103.3 4-[1-[(Benzyloxy)imino]ethyl]-4-bromo-1,3-dimethyl-4,5-dihydro-1H-pyrazol-5-one 4-[1-[(Benzyloxy)imino]ethyl]-4-bromo-1,3-dimethyl-4,5-dihydro-1H-pyrazol-5-one was synthesized according to General Method 6 and was used directly in the displacement reaction according to General Method 8. LC-MS $t_R$=1.51 min, [M+H]$^+$=339.85.

103.4 4-[1-[(Benzyloxy)imino]ethyl]-4-{[(tert-butoxy)carbonyl]({[(tert-butoxy)carbonyl]oxy})amino}-1,3-dimethyl-4,5-dihydro-1H-pyrazol-5-one 4-[1-[(Benzyloxy)imino]ethyl]-4-{[(tert-butoxy)carbonyl]({[(tert-butoxy)carbonyl]oxy})amino}-1,3-dimethyl-4,5-dihydro-1H-pyrazol-5-one was synthesized from 4-[1-[(benzyloxy)imino]ethyl]-4-bromo-1,3-dimethyl-4,5-dihydro-1H-pyrazol-5-one according to General Method 8 and was purified using silica gel chromatography eluting with 0-30% ethyl acetate in heptanes (100 mg, 11%). LC-MS $t_R$=1.69 min, [M+H]$^+$=513.10.

103.5 4-[1-[(Benzyloxy)imino]ethyl]-4-(hydroxyamino)-1,3-dimethyl-4,5-dihydro-1H-pyrazol-5-one 4-[1-[(Benzyloxy)imino]ethyl]-4-(hydroxyamino)-1,3-dimethyl-4,5-dihydro-1H-pyrazol-5-one was synthesized from 4-[1-[(benzyloxy)imino]ethyl]-4-{[(tert-butoxy)carbonyl]({[(tert-butoxy)carbonyl]oxy})amino}-1,3-dimethyl-4,5-dihydro-1H-pyrazol-5-one according to General Method 9 (39 mg, 63%). LC-MS $t_R$=1.17 min, [M+H]$^+$=290.95; $^1$H NMR (500 MHz, DMSO-d6) δ 7.78 (d, J=2.6 Hz, 1H), 7.39-7.27 (m, 5H), 6.68 (d, J=2.6 Hz, 1H), 5.09-4.95 (m, 2H), 3.12 (s, 3H), 1.95 (s, 3H), 1.85 (s, 3H).

Example 104

Compound 104 [3-(3,4-Dimethanesulfonylphenyl)-4-(hydroxyamino)-1,4-dimethyl-4,5-dihydro-1H-pyrazol-5-one]

104.1 tert-Butyl N-hydroxy-N-{3-[4-methanesulfonyl-3-(methylsulfanyl)phenyl]-1,4-dimethyl-5-oxo-4,5-dihydro-1H-pyrazol-4-yl}carbamate tert-Butyl N-hydroxy-N-{3-[4-methanesulfonyl-3-(methylsulfanyl)phenyl]-1,4-dimethyl-5-oxo-4,5-dihydro-1H- pyrazol-4-yl}carbamate was synthesized from 4-{[(tert-butoxy)carbonyl]({[(tert-butoxy)carbonyl]oxy})amino}-3-(3-fluoro-4-methanesulfonylphenyl)-1,4-dimethyl-4,5-dihydro-1H-pyrazol-5-one according to General Method 16 (0.43 g, 71%). LC-MS $t_R$=1.19 min, [M+H]$^+$=465.95.

104.2 4-{[(tert-Butoxy)carbonyl]({[(tert-butoxy)carbonyl]oxy})amino}-3-(3,4-dimethanesulfonylphenyl)-1,4-dimethyl-4,5-dihydro-1H-pyrazol-5-one 4-{[(tert-Butoxy)carbonyl]({[(tert-butoxy)carbonyl]oxy})amino}-3-(3,4-dimethanesulfonylphenyl)-1,4-dimethyl-4,5-dihydro-1H-pyrazol-5-one was synthesized from tert-butyl N-hydroxy-N-{3-[4-methanesulfonyl-3-(methylsulfanyl)phenyl]-1,4-dimethyl-5-oxo-4,5-dihydro-1H-pyrazol-4-yl}carbamate according to General Method 10 (0.23 g, 32%). LC-MS $t_R$=1.43 min, [M+H]$^+$=597.90.

104.3 3-(3,4-Dimethanesulfonylphenyl)-4-(hydroxyamino)-1,4-dimethyl-4,5-dihydro-1H-pyrazol-5-one 3-(3,4-Dimethanesulfonylphenyl)-4-(hydroxyamino)-1,4-dimethyl-4,5-dihydro-1H-pyrazol-5-one was synthesized from 4-{[(tert-butoxy)carbonyl]({[(tert-butoxy)carbonyl]oxy})amino}-3-(3,4-dimethanesulfonylphenyl)-1,4-dimethyl-4,5-dihydro-1H-pyrazol-5-one according to General Method 9 (27 mg, 18%). LC-MS $t_R$=1.01 min, [M+H]$^+$=375.90; $^1$H NMR (250 MHz, DMSO-d6) δ 8.89 (d, J=1.7 Hz, 1H), 8.58 (dd, J=8.3, 1.8 Hz, 1H), 8.32 (d, J=8.3 Hz, 1H), 7.72 (d, J=2.7 Hz, 1H), 6.72 (d, J=2.7 Hz, 1H), 3.50 (d, J=4.3 Hz, 6H), 3.36 (s, 3H), 1.28 (s, 3H).

Example 105

Compound 105 [4-(Hydroxyamino)-1,3-dimethyl-4-[1-[(2-methylpropoxy)imino]ethyl]-4,5-dihydro-1H-pyrazol-5-one]

105.1 1,3-Dimethyl-4-[1-[(2-methylpropoxy)imino]ethyl]-4,5-dihydro-1H-pyrazol-5-one 1,3-Dimethyl-4-[1-[(2-methylpropoxy)imino]ethyl]-4,5-dihydro-1H-pyrazol-5-one was synthesized from 1-(5-hydroxy-1,3-dimethyl-1H-pyrazol-4-yl)ethan-1-one and O-(2-methylpropyl)hydroxylamine hydrochloride according to General Method 12 (0.80 g, 55%). LC-MS $t_R$=1.19 min, [M+H]$^+$=226; $^1$H NMR (500 MHz, Chloroform-d) δ 3.74 (d, J=6.8 Hz, 2H), 3.50 (s, 3H), 2.24 (s, 3H), 2.16 (s, 3H), 1.95 (d, J=6.7 Hz, 1H), 0.89 (d, J=6.7 Hz, 6H).

105.2 4-Bromo-1,3-dimethyl-4-[1-[(2-methylpropoxy)imino]ethyl]-4,5-dihydro-1H-pyrazol-5-one 4-Bromo-1,3-dimethyl-4-[1-[(2-methylpropoxy)imino]ethyl]-4,5-dihydro-1H-pyrazol-5-one was synthesized from 1,3-dimethyl-4-[1-[(2-methylpropoxy)imino]ethyl]-4,5-dihydro-1H-pyrazol-5-one according to General Method 6 (0.82 g, 94%). LC-MS $t_R$=1.56 min, [M+H]$^+$=304.

105.3 4-{[(tert-Butoxy)carbonyl]({[(tert-butoxy)carbonyl]oxy})amino}-1,3-dimethyl-4-[1-[(2-methylpropoxy)imino]ethyl]-4,5-dihydro-1H-pyrazol-5-one 4-{[(tert-Butoxy)carbonyl]({[(tert-butoxy)carbonyl]oxy})amino}-1,3-dimethyl-4-[1-[(2-methylpropoxy)imino] ethyl]-4,5-dihydro-1H-pyrazol-5-one was synthesized from 4-bromo-1,3-dimethyl-4-[1-[(2-methylpropoxy)imino]ethyl]-4,5-dihydro-1H-pyrazol-5-one according to General Method 8 (0.90 g, 70%). LC-MS $t_R$=1.74 min, [M+H]$^+$=457; $^1$H NMR (500 MHz, DMSO-d6) δ 3.91-3.71 (m, 2H), 3.13 (s, 3H), 1.88-1.86 (m, 1H), 1.47-1.40 (m, 18H), 1.39-1.37 (m, 6H), 0.87-0.81 (m, 6H).

105.4 4-(Hydroxyamino)-1,3-dimethyl-4-[1-[(2-methylpropoxy)imino]ethyl]-4,5-dihydro-1H-pyrazol-5-one 4-(Hydroxyamino)-1,3-dimethyl-4-[1-[(2-methylpropoxy)imino]ethyl]-4,5-dihydro-1H-pyrazol-5-one was synthesized from 4-{[(tert-butoxy)carbonyl]({[(tert-butoxy)carbonyl]oxy})amino}-1,3-dimethyl-4-[1-[(2-methylpropoxy)imino]ethyl]-4,5-dihydro-1H-pyrazol-5-one according to General Method 9 and was purified using silica gel chromatography eluting with 0-100% ethyl acetate in heptanes (0.28 g, 57%). LC-MS $t_R$=1.17 min, [M+H]$^+$=257; $^1$H NMR (500 MHz, DMSO-d6) δ 7.77 (s, 1H), 6.67 (s, 1H), 3.84-3.65 (m, 2H), 3.12 (s, 3H), 2.01 (s, 3H), 1.92-1.79 (m, 4H), 0.90-0.77 (m, 6H).

Example 106

Compound 106 [4-[1-(Ethoxyimino)ethyl]-4-(hydroxyamino)-1,3-dimethyl-4,5-dihydro-1H-pyrazol-5-one]

106.1 1,3-Dimethyl-4-[1-[(2-methylpropoxy)imino]ethyl]-4,5-dihydro-1H-pyrazol-5-one 4-[1-(Ethoxyimino)ethyl]-1,3-dimethyl-4,5-dihydro-1H-pyrazol-5-one was synthesized using 1-(5-hydroxy-1,3-dimethyl-1H-pyrazol-4-yl)ethan-1-one and O-ethylhydroxylamine hydrochloride according to General Method 12 (0.65 g, 51%). LC-MS $t_R$=0.95 min, [M+H]$^+$=198; $^1$H NMR (500 MHz, Chloroform-d) δ 4.10 (q, J=7.0 Hz, 2H), 3.58 (s, 3H), 2.31 (s, 3H), 2.23 (s, 3H), 1.31 (t, J=7.0 Hz, 3H).

106.2 4-Bromo-4-[1-(ethoxyimino)ethyl]-1,3-dimethyl-4,5-dihydro-1H-pyrazol-5-one 4-Bromo-4-[1-(ethoxyimino)ethyl]-1,3-dimethyl-4,5-dihydro-1H-pyrazol-5-one was synthesized from 4-[1-(ethoxyimino)ethyl]-1,3-dimethyl-4,5-dihydro-1H-pyrazol-5-one according to General Method 6 (0.91 g, 88%). LC-MS $t_R$=1.57 min, [M+H]$^+$=276.

106.3 4-{[(tert-Butoxy)carbonyl]({[(tert-butoxy)carbonyl]oxy})amino}-4-[1-(ethoxyimino)ethyl]-1,3-dimethyl-4,5-dihydro-1H-pyrazol-5-one 4-{[(tert-Butoxy)carbonyl]({[(tert-butoxy)carbonyl]oxy})amino}-4-[1-(ethoxyimino)ethyl]-1,3-dimethyl-4,5-dihydro-1H-pyrazol-5-one was synthesized from 4-bromo-4-[1-(ethoxyimino)ethyl]-1,3-dimethyl-4,5-dihydro-1H-pyrazol-5-one according to General Method 8 (1.3 g, 61%). LC-MS $t_R$=1.59 min, [M+Na]$^+$=451; $^1$H NMR (500 MHz, DMSO-d6) δ 4.15-3.96 (m, 2H), 3.18-3.10 (m, 3H), 2.21-1.75 (m, 6H), 1.50-1.31 (m, 18H), 1.20-1.11 (m, 3H).

106.4 4-[1-(Ethoxyimino)ethyl]-4-(hydroxyamino)-1,3-dimethyl-4,5-dihydro-1H-pyrazol-5-one 4-[1-(Ethoxyimino)ethyl]-4-(hydroxyamino)-1,3-dimethyl-4,5-dihydro-1H-pyrazol-5-one was synthesized from 4-{[(tert-butoxy)carbonyl]({[(tert-butoxy)carbonyl]oxy})amino}-4-[1-(ethoxyimino)ethyl]-1,3-dimethyl-4,5-dihydro-1H-pyrazol-5-one according to General Method 9 and was purified using silica gel chromatography eluting with 0-100% ethyl acetate in heptanes (0.24 g, 63%). LC-MS $t_R$=0.97 min, [M+H]$^+$=229; $^1$H NMR (500 MHz, DMSO-d6) δ 7.77 (s, 1H), 6.67 (s, 1H), 4.12-3.91 (m, 2H), 3.12 (s, 3H), 2.02 (s, 3H), 1.81 (s, 3H), 1.22-1.09 (m, 3H).

Example 107

Compound 107 [4-(Hydroxyamino)-4-[1-(methoxyimino)ethyl]-3-(4-methoxyphenyl)-1-methyl-4,5-dihydro-1H-pyrazol-5-one]

107.1 Methyl 3-(4-methoxyphenyl)-3-oxopropanoate

Methyl 3-(4-methoxyphenyl)-3-oxopropanoate was synthesized from 1-(4-methoxyphenyl)ethan-1-one according to General Method 1 (10.18 g, 87%). LC-MS $t_R$=1.13 min, [M+H]$^+$=209.

107.2 3-(4-Methoxyphenyl)-1-methyl-4,5-dihydro-1H-pyrazol-5-one 3-(4-Methoxyphenyl)-1-methyl-4,5-dihydro-1H-pyrazol-5-one was synthesized from methyl 3-(4-methoxyphenyl)-3-oxopropanoate according to General Method 2 and the product was purified using silica gel chromatography eluting with 60-100% ethyl acetate in heptanes (9.5 g, 87%). LC-MS $t_R$=0.95 min, [M+H]$^+$=205.

107.3 4-Acetyl-3-(4-methoxyphenyl)-1-methyl-4,5-dihydro-1H-pyrazol-5-one

4-Acetyl-3-(4-methoxyphenyl)-1-methyl-4,5-dihydro-1H-pyrazol-5-one was synthesized from 3-(4-methoxyphenyl)-1-methyl-4,5-dihydro-1H-pyrazol-5-one according to General Method 11 (5.73 g, 33%). LC-MS $t_R$=1.09 min, [M+H]$^+$=247.

107.4 4-[1-(Methoxyimino)ethyl]-3-(4-methoxyphenyl)-1-methyl-1H-pyrazol-5-ol

4-[1-(Methoxyimino)ethyl]-3-(4-methoxyphenyl)-1-methyl-1H-pyrazol-5-ol was synthesized from 4-acetyl-3-(4-methoxyphenyl)-1-methyl-4,5-dihydro-1H-pyrazol-5-one according to General Method 12 and the product was purified by silica gel chromatography eluting with 30-80% ethyl acetate in heptanes (2.62 g, 41%). LC-MS $t_R$=1.17 min, [M+H]$^+$=276; $^1$H NMR (500 MHz, DMSO-d6) δ 7.42 (d, J=8.0 Hz, 2H), 6.94 (d, J=8.3 Hz, 2H), 3.80 (s, 3H), 3.76 (d, J=2.9 Hz, 3H), 3.56 (s, 3H), 1.88 (s, 3H).

107.5 4-Bromo-4-[1-(methoxyimino)ethyl]-3-(4-methoxyphenyl)-1-methyl-4,5-dihydro-1H-pyrazol-5-one 4-Bromo-4-[1-(methoxyimino)ethyl]-3-(4-methoxyphenyl)-1-methyl-4,5-dihydro-1H-pyrazol-5-one was synthesized from 4-[1-(methoxyimino)ethyl]-3-(4-methoxyphenyl)-1-methyl-1H-pyrazol-5-ol according to General Method 6 (5.53 g, 99%). LC-MS $t_R$=1.43 min, [M+H]$^+$=354.

107.6 4-{[(tert-Butoxy)carbonyl]({[(tert-butoxy)carbonyl]oxy})amino}-4-[1-(methoxyimino)ethyl]-3-(4-methoxyphenyl)-1-methyl-4,5-dihydro-1H-pyrazol-5-one 4-{[(tert-Butoxy)carbonyl]({[(tert-butoxy)carbonyl]oxy})amino}-4-[1-(methoxyimino)ethyl]-3-(4-methoxyphenyl)-1-methyl-4,5-dihydro-1H-pyrazol-5-one was synthesized from 4-bromo-4-[1-(methoxyimino)ethyl]-3-(4-methoxyphenyl)-1-methyl-4,5-dihydro-1H-pyrazol-5-one according to General Method 8 and was purified by silica gel chromatography eluting with 0-50% ethyl acetate in heptanes (5.31 g, 57%). LC-MS $t_R$=1.60 min, [M+Na]$^+$=529.

107.7 4-(Hydroxyamino)-4-[1-(methoxyimino)ethyl]-3-(4-methoxyphenyl)-1-methyl-4,5-dihydro-1H-pyrazol-5-one 4-(Hydroxyamino)-4-[1-(methoxyimino)ethyl]-3-(4-methoxyphenyl)-1-methyl-4,5-dihydro-1H-pyrazol-5-one was synthesized from 4-{[(tert-butoxy)carbonyl]({[(tert-butoxy)carbonyl]oxy})amino}-4-[1-(methoxyimino)ethyl]-3-(4-methoxyphenyl)-1-methyl-4,5-dihydro-1H-pyrazol-5-one according to General Method 9 and was purified by acidic preparative HPLC (0.23 g, 7%). LC-MS $t_R$=1.16 min, [M+H]$^+$=307; $^1$H NMR (500 MHz, DMSO-d6) δ 7.88-7.82 (m, 2H), 7.77 (d, J=2.5 Hz, 1H), 7.03-6.97 (m, 2H), 6.49 (d, J=2.6 Hz, 1H), 3.80 (s, 3H), 3.77 (s, 3H), 3.30 (s, 3H), 1.60 (s, 3H).

Example 108

Compound 108 [3-(4-Bromophenyl)-4-(hydroxyamino)-1,4-dimethyl-4,5-dihydro-1H-pyrazol-5-one]

108.1 Methyl 3-(4-bromophenyl)-3-oxopropanoate

Methyl 3-(4-bromophenyl)-3-oxopropanoate was synthesized from 1-(4-bromophenyl)ethan-1-one according to General Method 1 (15.18 g, 88%). LC-MS $t_R$=1.27 min, [M+H]$^+$=257.

108.2 3-(4-Bromophenyl)-1-methyl-4,5-dihydro-1H-pyrazol-5-one 3-(4-Bromophenyl)-1-methyl-4,5-dihydro-1H-pyrazol-5-one was synthesized from methyl 3-(4-bromophenyl)-3-oxopropanoate was synthesized according to General Method 2 (10.4 g, 70%). LC-MS $t_R$=1.14 min, [M+H]$^+$=253; $^1$H NMR (500 MHz, DMSO-d6) δ 7.66-7.61 (m, 2H), 7.57-7.46 (m, 2H), 5.80 (s, 1H), 3.61 (s, 1H), 3.55 (s, 3H).

108.3 3-(4-Bromophenyl)-1-methyl-5-oxo-4,5-dihydro-1H-pyrazole-4-carbaldehyde 3-(4-Bromophenyl)-1-methyl-5-oxo-4,5-dihydro-1H-pyrazole-4-carbaldehyde was synthesized from 3-(4-bromophenyl)-1-methyl-4,5-dihydro-1H-pyrazol-5-one according to General Method 4 (7.44 g, 82%). LC-MS $t_R$=1.14 min, [M+H]$^+$=281; $^1$H NMR (500 MHz, DMSO-d6) δ 9.71 (s, 1H), 7.86-7.70 (m, 2H), 7.63-7.54 (m, 2H), 3.61 (s, 3H).

108.4 3-(4-Bromophenyl)-1,4-dimethyl-4,5-dihydro-1H-pyrazol-5-one 3-(4-Bromophenyl)-1,4-dimethyl-4,5-dihydro-1H-pyrazol-5-one was synthesized from 3-(4-bromophenyl)-1-methyl-5-oxo-4,5-dihydro-1H-pyrazole-4-carbaldehyde according to General Method 5 (5.83 g, 61%). LC-MS $t_R$=1.11 min, [M+H]$^+$=267; $^1$H NMR (500 MHz, DMSO-d6) δ 7.63-7.42 (m, 4H), 3.49 (s, 3H), 1.94 (s, 3H).

108.5 4-Bromo-3-(4-bromophenyl)-1,4-dimethyl-4,5-dihydro-1H-pyrazol-5-one

4-Bromo-3-(4-bromophenyl)-1,4-dimethyl-4,5-dihydro-1H-pyrazol-5-one was synthesized from 3-(4-bromophenyl)-1,4-dimethyl-4,5-dihydro-1H-pyrazol-5-one according to General Method 6 (0.94 g, 64%). LC-MS $t_R$=1.46 min, [M+H]$^+$=347.

108.6 3-(4-Bromophenyl)-4-{[(tert-butoxy)carbonyl]({[(tert-butoxy)carbonyl]oxy})amino}-1,4-dimethyl-4,5-dihydro-1H-pyrazol-5-one 3-(4-Bromophenyl)-4-{[(tert-butoxy)carbonyl]({[(tert-butoxy)carbonyl]oxy})amino}-1,4-dimethyl-4,5-dihydro-1H-pyrazol-5-one was synthesized from 4-bromo-3-(4-bromophenyl)-1,4-dimethyl-4,5-dihydro-1H-pyrazol-5-one according to General Method 8 and was purified using silica gel chromatography eluting with 20-100% ethyl acetate in heptanes (0.42 g, 30%). LC-MS $t_R$=1.70 min, [M+Na]$^+$=499; $^1$H NMR (250 MHz, DMSO-d6) δ 8.10-7.95 (m, 1H), 7.83-7.34 (m, 3H), 3.31 (s, 3H), 1.67-1.41 (m, 9H), 1.36-1.12 (m, 12H).

108.7 3-(4-Bromophenyl)-4-(hydroxyamino)-1,4-dimethyl-4,5-dihydro-1H-pyrazol-5-one 3-(4-Bromophenyl)-4-(hydroxyamino)-1,4-dimethyl-4,5-dihydro-1H-pyrazol-5-one was synthesized from 3-(4-bromophenyl)-4-{[(tert-butoxy)carbonyl]({[(tert-butoxy)carbonyl]oxy})amino}-1,4-dimethyl-4,5-dihydro-1H-pyrazol-5-one according to General Method 9 and was purified using silica gel chromatography eluting with 20-100% ethyl acetate in heptanes (0.05 g, 29%). LC-MS $t_R$=1.14 min, [M+H]$^+$=300; $^1$H NMR (500 MHz, DMSO-d6) δ 8.06-7.90 (m, 2H), 7.70-7.60 (m, 3H), 6.50 (s, 1H), 3.29 (s, 3H), 1.19 (s, 3H).

Example 109

Compound 109 [4-(Hydroxyamino)-1-methyl-3,4-diphenyl-4,5-dihydro-1H-pyrazol-5-one]

109.1 Methyl 3-oxo-2,3-diphenylpropanoate

Methyl 3-oxo-2,3-diphenylpropanoate was synthesized from methyl 2-phenylacetate and benzoic anhydride according to General Method 13 and was purified by silica gel chromatography eluting in 0-100% ethyl acetate:heptanes to afford the title compound as a white solid (8.5 g, 97%). LC-MS $t_R$=1.35 min, [M+H]$^+$=255. $^1$H NMR (250 MHz, Chloroform-d) δ 8.04-7.84 (m, 2H), 7.58-7.48 (m, 1H), 7.47-7.26 (m, 7H), 5.64 (s, 1H), 3.76 (s, 3H).

109.2 1-Methyl-3,4-diphenyl-1H-pyrazol-5-ol

To a solution of methyl 3-oxo-2,3-diphenylpropanoate (8.00 g, 31.46 mmol) in ethanol (30 mL) was added methyl hydrazine (1.66 mL, 31.46 mmol) and the reaction mixture was heated to 70° C. for 4 hours before cooling to room temperature and leaving to stand for 72 hours. The resulting white solid was discarded and the filtrate was concentrated under reduced pressure and re-dissolved in ethanol (20 mL). Methyl hydrazine (1.5 mL) was added and the reaction mixture was re-heated to 70° C. for 4.5 hours. The reaction mixture was cooled to room temperature and the resulting white solid was discarded. The filtrate was concentrated under reduced pressure and purified using silica gel chromatography eluting in 20-100% ethyl acetate:heptanes, followed by 0-20% methanol:ethyl acetate (3.61 g, 46%). LC-MS $t_R$=1.14 min, [M+H]$^+$=251. $^1$H NMR (250 MHz, DMSO-d6) δ 7.88-7.12 (m, 10H), 3.62 (s, 3H).

109.3 4-Bromo-1-methyl-3,4-diphenyl-4,5-dihydro-1H-pyrazol-5-one

4-Bromo-1-methyl-3,4-diphenyl-4,5-dihydro-1H-pyrazol-5-one was synthesized from 1-methyl-3,4-diphenyl-1H-pyrazol-5-ol according to General Method 6 and used directly in the synthesis of 4-{[(tert-butoxy)carbonyl]({[(tert-butoxy)carbonyl]oxy})amino}-1-methyl-3,4-diphenyl-4,5-dihydro-1H-pyrazol-5-one. LC-MS $t_R$=1.28 min, [M+H]$^+$=329/330.

109.4 4-{[(tert-Butoxy)carbonyl]({[(tert-butoxy)carbonyl]oxy})amino}-1-methyl-3,4-diphenyl-4,5-dihydro-1H-pyrazol-5-one To a solution of tert-butyl [(tert-butoxycarbonyl)oxy]carbamate (1.49 g, 6.38 mmol) in dimethyl formamide (10 mL) was added sodium hydride (60%, 0.26 g, 6.38 mmol). The reaction mixture was stirred for 45 minutes before the addition of 4-bromo-1-methyl-3,4-diphenyl-4,5-dihydro-1H-pyrazol-5-one (2.1 g, 6.4 mmol) as a solution in DMF (10 mL). The reaction mixture was stirred at room temperature for 20 hours before addition of sodium [(tert-butoxy)carbonyl]({[(tert-butoxy)carbonyl]oxy})sodiumuide (prepared from a solution of tert-butyl [(tert-butoxycarbonyl)oxy]carbamate (1.49 g, 6.38 mmol) in dimethyl formamide (10 mL) and sodium hydride (60%, 0.26 g, 6.38 mmol) which was performed by stirring for 45 minutes at room temperature). The reaction mixture was stirred for 2 hours at room temperature before being quenched with saturated ammonium chloride solution (20 mL). The organics were extracted into diethyl ether (30 mL) and the aqueous layer was re-extracted with diethyl ether (2×20 mL). The ether layers were combined, washed with water (3×30 mL) and brine (30 mL), dried over sodium sulfate, filtered and concentrated under reduced pressure. Purification using silica gel chromatography, eluting in 0-50% ethyl acetate:heptanes afforded the title compound as an off-white solid (1.34 g, 31%). LC-MS $t_R$=1.44 min, [M+Na]$^+$=504.

109.5 4-(Hydroxyamino)-1-methyl-3,4-diphenyl-4,5-dihydro-1H-pyrazol-5-one 4-(Hydroxyamino)-1-methyl-3,4-diphenyl-4,5-dihydro-1H-pyrazol-5-one was synthesized from 4-{[(tert-butoxy)carbonyl]({[(tert-butoxy)carbonyl]oxy})amino}-1-methyl-3,4-diphenyl-4,5-dihydro-1H-pyrazol-5-one according to General Method 9 and purified using silica gel chromatography, eluting in 0-50% ethyl acetate:heptanes to afford the title compound as a white solid (170 mg, 30%). LC-MS $t_R$=3.64 min, [M+H]$^+$=282. $^1$H NMR (250 MHz, DMSO-d6)

δ 7.89 (d, J=2.2 Hz, 1H), 7.86-7.80 (m, 2H), 7.38-7.27 (m, 6H), 7.22 (dd, J=8.8, 2.3 Hz, 3H), 3.35 (s, 3H).

Example 110

Compound 110 [3-Ethoxy-4-(hydroxyamino)-4-[1-(methoxyimino)ethyl]-1-phenyl-4,5-dihydro-1H-pyrazol-5-one]

110.1 1-Phenylpyrazolidine-3,5-dione

To a solution of phenylhydrazine (0.7 mL, 7.09 mmol) in THF (10 mL) was added a solution of propanedioyl dichloride (0.69 mL, 7.09 mmol) in THF (10 mL) and the resulting solution was stirred for 1 hour at room temperature. The resulting suspension was concentrated under reduced pressure and added to saturated sodium bicarbonate solution until basic (20 mL). The basic aqueous was extracted into diethyl ether (2×20 mL) and this was discarded. The aqueous was re-acidified with 6N HCl and extracted into ethyl acetate (2×30 mL), before being dried over magnesium sulfate, filtered and concentrated under reduced pressure to yield the crude material as an orange solid which was purified using silica gel chromatography eluting with a 0-10% DCM:MeOH gradient to yield the title compound as a yellow solid (0.39 g, 31%). LC-MS $t_R$=0.66 min, [M+H]$^+$=176.9; 1H NMR (500 MHz, DMSO-d6) δ 7.63 (s, 2H), 7.41 (t, J=7.9 Hz, 2H), 7.17 (t, J=7.2 Hz, 1H), 3.58 (s, 2H)

110.2 3-Ethoxy-1-phenyl-1H-pyrazol-5-ol

To a solution of 1-phenylpyrazolidine-3,5-dione (1.6 g, 9.08 mmol) in ethanol (30 mL) was added a catalytic amount of concentrated sulfuric acid and the reaction mixture was heated to reflux for 12 hours through a soxlet condenser filled with 4 A molecular sieves. The resulting solution was concentrated under reduced pressure and purified using silica gel chromatography eluting with heptane:ethyl acetate (30%) to yield the title compound as a yellow solid (0.8 g, 43%). LC-MS $t_R$=1.10 min, [M+H]$^+$=205; $^1$H NMR (500 MHz, DMSO-d6) δ 7.80 (dd, J=8.7, 1.1 Hz, 2H), 7.44-7.36 (m, 2H), 7.18-7.10 (m, 1H), 4.31 (q, J=7.1 Hz, 2H), 3.81 (s, 2H), 1.35 (t, J=7.1 Hz, 3H).

110.3 1-(3-Ethoxy-5-hydroxy-1-phenyl-1H-pyrazol-4-yl)ethan-1-one 1-(3-Ethoxy-5-hydroxy-1-phenyl-1H-pyrazol-4-yl)ethan-1-one was synthesized from 3-ethoxy-1-phenyl-1H-pyrazol-5-ol according to General Method 11 and was used directly in the synthesis of the corresponding oxime (0.67 g, 70%). $^1$H NMR (500 MHz, DMSO-d6) δ 7.91-7.88 (m, 2H), 7.37 (dd, J=8.6, 7.4 Hz, 2H), 7.12-7.07 (m, 1H), 4.32 (q, J=7.0 Hz, 2H), 2.78 (s, 3H), 1.36 (t, J=7.1 Hz, 3H).

110.4 3-Ethoxy-4-[1-(methoxyimino)ethyl]-1-phenyl-1H-pyrazol-5-ol

3-Ethoxy-4-[1-(methoxyimino)ethyl]-1-phenyl-1H-pyrazol-5-ol was synthesized from 1-(3-ethoxy-5-hydroxy-1-phenyl-1H-pyrazol-4-yl)ethan-1-one according to General Method 12 and was purified using silica gel chromatography eluting with heptanes:ethyl acetate (100-80%) to yield the title compound as a yellow solid (0.58 g, 77%). LC-MS $t_R$=1.51 min, [M+H]$^+$=276.4; $^1$H NMR (500 MHz, Chloroform-d) δ 7.87 (dd, J=8.7, 1.1 Hz, 2H), 7.41-7.35 (m, 2H), 7.17-7.12 (m, 1H), 4.37 (q, J=7.1 Hz, 2H), 3.87 (s, 3H), 2.37 (s, 3H), 1.42 (t, J=7.1 Hz, 3H).

110.5 4-Bromo-3-ethoxy-4-[1-(methoxyimino) ethyl]-1-phenyl-4,5-dihydro-1H-pyrazol-5-one 4-Bromo-3-ethoxy-4-[1-(methoxyimino)ethyl]-1-phenyl-4,5-dihydro-1H-pyrazol-5-one was synthesized from 3-ethoxy-4-[1-(methoxyimino)ethyl]-1-phenyl-1H-pyrazol-5-ol according to General Method 6 and was used directly in the synthesis of 4-{[(tert-butoxy)carbonyl]({[(tert-butoxy) carbonyl]oxy})amino}-3-ethoxy-4-[1-(methoxyimino) ethyl]-1-phenyl-4,5-dihydro-1H-pyrazol-5-one assuming 100% yield (also containing 4-bromo-1-(4-bromophenyl)-3-ethoxy-4-[1-(methoxyimino)ethyl]-4,5-dihydro-1H-pyrazol-5-one). LC-MS $t_R$=1.41 min, [M+H]$^+$=355.85.

110.6 4-{[(tert-Butoxy)carbonyl]({[(tert-butoxy) carbonyl]oxy})amino}-3-ethoxy-4-[1-(methoxyimino)ethyl]-1-phenyl-4,5-dihydro-1H-pyrazol-5-one 4-{[(tert-Butoxy)carbonyl]({[(tert-butoxy)carbonyl] oxy})amino}-3-ethoxy-4-[1-(methoxyimino)ethyl]-1-phenyl-4,5-dihydro-1H-pyrazol-5-one was synthesized from 4-bromo-3-ethoxy-4-[1-(methoxyimino)ethyl]-1-phenyl-4,5-dihydro-1H-pyrazol-5-one according to General Method 8 and was purified using silica gel chromatography eluting with 20% ethyl acetate:heptanes to yield the title compound as a 1:1 mixture with the corresponding bromide (See Example 113) (0.35 g, isolated as a 1:1 mixture, 28%). LC-MS $t_R$=1.52 min, [M+Na]$^+$=529.05.

110.7 3-Ethoxy-4-(hydroxyamino)-4-[1-(methoxyimino)ethyl]-1-phenyl-4,5-dihydro-1H-pyrazol-5-one 3-Ethoxy-4-(hydroxyamino)-4-[1-(methoxyimino)ethyl]-1-phenyl-4,5-dihydro-1H-pyrazol-5-one was synthesized from 4-{[(tert-butoxy)carbonyl]({[(tert-butoxy)carbonyl] oxy})amino}-3-ethoxy-4-[1-(methoxyimino)ethyl]-1-phenyl-4,5-dihydro-1H-pyrazol-5-one according to General Method 9 and was purified using low pH HPLC (47 mg, 11%). LC-MS $t_R$=3.96 min, [M+H]$^+$=307; $^1$H NMR (500 MHz, DMSO-d6) δ 8.06 (d, J=2.2 Hz, 1H), 7.83 (d, J=8.0 Hz, 2H), 7.42 (t, J=7.9 Hz, 2H), 7.17 (t, J=7.4 Hz, 1H), 6.80 (d, J=2.1 Hz, 1H), 4.52-4.31 (m, 2H), 3.77 (s, 3H), 1.87 (s, 3H), 1.39 (t, J=7.0 Hz, 3H).

Example 111

Compound 111 [1-(4-Bromophenyl)-3-ethoxy-4-(hydroxyamino)-4-[1-(methoxyimino)ethyl]-4,5-dihydro-1H-pyrazol-5-one]

111.1 1-(4-Bromophenyl)-3-ethoxy-4-(hydroxyamino)-4-[1-(methoxyimino)ethyl]-4,5-dihydro-1H-pyrazol-5-one 1-(4-Bromophenyl)-3-ethoxy-4-(hydroxyamino)-4-[1-(methoxyimino)ethyl]-4,5-dihydro-1H-pyrazol-5-one was isolated from the acidic preparative HPLC purification of 3-ethoxy-4-(hydroxyamino)-4-[1-(methoxyimino)ethyl]-1-phenyl-4,5-dihydro-1H-pyrazol-5-one to yield the title compound as a white solid (0.04 g, 7%). LC-MS $t_R$=4.41 min, [M+H]$^+$=385/387. $^1$H NMR (500 MHz, DMSO-d6) δ 8.09

(s, 1H), 7.80 (d, J=8.7 Hz, 2H), 7.61 (d, J=8.7 Hz, 2H), 6.86 (s, 1H), 4.53-4.28 (m, 2H), 3.77 (s, 3H), 1.86 (s, 3H), 1.38 (t, J=6.9 Hz, 3H).

Example 112

Compound 112 [3-tert-Butyl-4-[1-(ethoxyimino) ethyl]-4-(hydroxyamino)-1-methyl-4,5-dihydro-1H-pyrazol-5-one]

112.1 3-tert-Butyl-1-methyl-1H-pyrazol-5-ol 3-tert-Butyl-1-methyl-1H-pyrazol-5-ol was synthesized from methyl 4,4-dimethyl-3-oxopentanoate according to General Method 2 (5.10 g, 84%). LC-MS $t_R$=0.73 min, $[M+H]^+$=155; $^1$H NMR (500 MHz, DMSO-d6) δ 5.15 (s, 1H), 3.61 (s, 3H), 1.14 (s, 9H).

112.2 1-(3-tert-Butyl-5-hydroxy-1-methyl-1H-pyrazol-4-yl)ethan-1-one 1-(3-tert-Butyl-5-hydroxy-1-methyl-1H-pyrazol-4-yl) ethan-1-one was synthesized from 3-tert-butyl-1-methyl-1H-pyrazol-5-ol according to General Method 11 and was purified using silica gel chromatography eluting with 20-100% ethyl acetate in heptanes (2.62 g, 38%). LC-MS $t_R$=0.82 min, $[M+H]^+$=197; $^1$H NMR (500 MHz, DMSO-d6) δ 4.05 (s, 1H), 2.35 (s, 3H), 1.27 (s, 9H), 1.21 (s, 3H).

112.3 4-[(1-[(tert-Butoxy)imino]ethyl]-3-tert-butyl-1-methyl-4,5-dihydro-1H-pyrazol-5-one To a solution of 1-(3-tert-butyl-5-hydroxy-1-methyl-1H-pyrazol-4-yl)ethan-1-one (650 mg, 5.96 mmol) in methanol (10 mL) was added O-ethylhydroxylamine hydrochloride (0.58 g, 2.98 mmol) and sodium bicarbonate (0.25 g, 2.98 mmol). The reaction mixture was stirred at 80° C. until complete conversion of the starting material was observed by LC-MS. The reaction mixture was concentrated under reduced pressure and taken up into DCM (40 mL), washed with 1 M HCl (20 mL), brine (30 mL), dried over sodium sulfate, filtered and concentrated under reduced pressure (0.53 g, 59%). LC-MS $t_R$=0.93 min, $[M+H]^+$=240; $^1$H NMR (500 MHz, DMSO-d6) δ 4.11-4.02 (m, 2H), 3.44-3.40 (m, 6H), 1.26-1.17 (m, 12H).

112.4 4-Bromo-3-tert-butyl-4-[1-(ethoxyimino) ethyl]-1-methyl-4,5-dihydro-1H-pyrazol-5-one 4-Bromo-3-tert-butyl-4-[1-(ethoxyimino)ethyl]-1-methyl-4,5-dihydro-1H-pyrazol-5-one was synthesized from 3-tert-butyl-4-[1-(ethoxyimino)ethyl]-1-methyl-4,5-dihydro-1H-pyrazol-5-one according to General Method 6 (0.67 g, 83%). LC-MS $t_R$=1.51 min, $[M+H]^+$=493.

112.5 4-{[(tert-Butoxy)carbonyl]({[(tert-butoxy) carbonyl]oxy})amino}-3-tert-butyl-4-[1-(ethoxyimino)ethyl]-1-methyl-4,5-dihydro-1H-pyrazol-5-one 4-{[(tert-Butoxy)carbonyl]({[(tert-butoxy)carbonyl] oxy})amino}-3-tert-butyl-4-[1-(ethoxyimino)ethyl]-1-methyl-4,5-dihydro-1H-pyrazol-5-one was synthesized from 4-bromo-3-tert-butyl-4-[1-(ethoxyimino)ethyl]-1-methyl-4,5-dihydro-1H-pyrazol-5-one according to General Method 8 and was purified using silica gel chromatography eluting with 0-40% ethyl acetate in heptanes (0.62 g, 75%). LC-MS $t_R$=1.51 min, $[M+Na]^+$=493.

112.6 3-tert-Butyl-4-[1-(ethoxyimino)ethyl]-4-(hydroxyamino)-1-methyl-4,5-dihydro-1H-pyrazol-5-one 3-tert-Butyl-4-[1-(ethoxyimino)ethyl]-4-(hydroxyamino)-1-methyl-4,5-dihydro-1H-pyrazol-5-one was synthesized from 4-{[(tert-butoxy)carbonyl]({[(tert-butoxy) carbonyl]oxy})amino}-3-tert-butyl-4-[1-(ethoxyimino) ethyl]-1-methyl-4,5-dihydro-1H-pyrazol-5-one according to General Method 9 and was purified using silica gel chromatography eluting with 0-70% ethyl acetate in heptanes (84 mg, 28%). LC-MS $t_R$=1.04 min, $[M+H]^+$=271; $^1$H NMR (500 MHz, DMSO-d6) δ 7.59-7.55 (m, 1H), 6.29-6.22 (m, 1H), 4.13-3.99 (m, 2H), 3.18 (s, 3H), 1.57 (s, 3H), 1.22 (s, 9H), 1.20-1.14 (m, 3H).

Example 113

Compound 113 [3-tert-Butyl-4-(hydroxyamino)-1-methyl-4-phenyl-4,5-dihydro-1H-pyrazol-5-one]

113.1 Methyl 4,4-dimethyl-3-oxo-2-phenylpentanoate

Methyl 4,4-dimethyl-3-oxo-2-phenylpentanoate was synthesized from methyl 2-phenylacetate and pivalic anhydride according to General Method 13 and purified using silica gel chromatography, eluting in 0-30% ethyl acetate:heptanes to afford the title compound as a colourless oil (7.3 g, 94%). LC-MS $t_R$=1.20 min, $[M+H]^+$=235. $^1$H NMR (500 MHz, Chloroform-d) δ 7.40-7.27 (m, 5H), 5.21 (s, 1H), 3.71 (s, 3H), 1.15 (s, 9H).

113.2 3-tert-Butyl-1-methyl-4-phenyl-1H-pyrazol-5-ol

To a solution of methyl 4,4-dimethyl-3-oxo-2-phenylpentanoate (7.3 g, 31.16 mmol) in ethanol (30 mL) was added methyl hydrazine (1.64 mL, 31.16 mmol) and the reaction mixture was heated to 80° C. for 24 hours. Upon cooling, the solvent was removed under reduced pressure and the residue was re-dissolved in ethanol (20 mL) and an additional equivalent of methyl hydrazine (1.6 mL) was added. The reaction mixture was stirred for 5 days at room temperature and the resulting white solid was removed by filtration to afford a white solid and yellow filtrate which showed a similar profile by LC-MS and were subsequently re-combined, concentrated under reduced pressure and purified using silica gel chromatography, eluting in 0-100% ethyl acetate:heptanes (2.73 g, 38%). LC-MS $t_R$=3.31 min, $[M+H]^+$=231. $^1$H NMR (500 MHz, DMSO-d6) δ 7.34 (t, J=7.3 Hz, 2H), 7.30-7.23 (m, 1H), 7.22-7.15 (m, 2H), 3.45 (s, 3H), 1.08 (s, 9H).

113.3 4-Bromo-3-tert-butyl-1-methyl-4-phenyl-4,5-dihydro-1H-pyrazol-5-one

To 3-tert-butyl-1-methyl-4-phenyl-1H-pyrazol-5-ol (2 g, 8.68 mmol) in DCM (10 mL):water (10 mL) was added saturated sodium bicarbonate solution (0.88 g, 10.42 mmol). The biphasic reaction mixture was vigorously stirred while bromine (0.45 mL, 8.68 mmol) was added. Stirring was continued for 90 minutes before the reaction mixture was transferred to a separating funnel and shaken until a clear, colourless aqueous layer resulted. The organic layer was removed; the aqueous was re-extracted with DCM (2×10 mL) and combined with the organic layer. The combined organics were washed with brine (10 mL), dried over magnesium sulfate, filtered and concentrated under reduced pressure to afford the title compound as a yellow oily solid which was used directly in the synthesis of 4-{[(tert-butoxy)carbonyl]({[(tert-butoxy)carbonyl]oxy})amino}-3-tert-butyl-1-methyl-4-phenyl-4,5-dihydro-1H-pyrazol-5-one (100% yield assumed). LC-MS $t_R$=1.27 min, [M+H]$^+$=309/311

113.4 4-{[(tert-Butoxy)carbonyl]({[(tert-butoxy)carbonyl]oxy})amino}-3-tert-butyl-1-methyl-4-phenyl-4,5-dihydro-1H-pyrazol-5-one To a solution of tert-butyl [(tert-butoxycarbonyl)oxy]carbamate (3.04 g, 13.03 mmol) in dimethyl formamide (10 mL) was added sodium hydride (60%, 0.52 g, 13.03 mmol). The reaction mixture was left for 60 minutes before addition of 4-bromo-3-tert-butyl-1-methyl-4-phenyl-4,5-dihydro-1H-pyrazol-5-one (2.69 g, 8.68 mmol) as a solution in DMF (10 mL). The reaction mixture was stirred at room temperature for 20 hours before addition of sodium [(tert-butoxy)carbonyl]({[(tert-butoxy)carbonyl]oxy})azanide (prepared from a solution of tert-butyl [(tert-butoxycarbonyl)oxy]carbamate (3.04 g, 13.03 mmol) in dimethyl formamide (8 mL) and sodium hydride (60%, 0.52 g, 13.03 mmol) which was pre-formed by stirring for 30 minutes at room temperature). The reaction mixture was stirred for 2 hours at room temperature, followed by heating at 40° C. for 2 hours. The reaction mixture was allowed to cool to room temperature and stirring was continued for 18 hours before quenching with saturated ammonium chloride solution (20 mL). The product was extracted in to diethyl ether (30 mL) and the aqueous layer was re-extracted into diethyl ether (2×20 mL), the ether layers were combined and washed with water (3×30 mL) and brine (30 mL), dried over magnesium sulfate, filtered and concentrated under reduced pressure. Purification was performed using silica gel chromatography, eluting in 0-30% ethyl acetate:heptanes) to afford the title compound as a white foam (970 mg, 18%). LC-MS $t_R$=1.46 min, [M+Na]$^+$=462. $^1$H NMR (500 MHz, DMSO-d6) δ 7.38-7.30 (m, 5H), 3.09 (s, 3H), 1.45 (s, 9H), 1.39 (s, 9H), 1.20 (s, 9H).

113.5 3-tert-Butyl-4-(hydroxyamino)-1-methyl-4-phenyl-4,5-dihydro-1H-pyrazol-5-one To a solution of 4-{[(tert-butoxy)carbonyl]({[(tert-butoxy)carbonyl]oxy})amino}-3-tert-butyl-1-methyl-4-phenyl-4,5-dihydro-1H-pyrazol-5-one (0.97 g, 2.1 mmol) in DCM (5 mL) was added TFA (1.61 mL, 21.02 mmol) and the reaction mixture was vigorously stirred for 4 hours. The solvent was removed under reduced pressure and the crude residue was purified using silica gel chromatography, eluting in 0-50% ethyl acetate:heptanes followed by trituration with diethyl ether. (352 mg, 83%). LC-MS $t_R$=3.63 min, [M+Na]$^+$=262. $^1$H NMR (500 MHz, DMSO-d6) δ 7.70 (s, 1H), 7.38-7.26 (m, 3H), 7.15-7.05 (m, 2H), 6.81 (s, 1H), 3.23 (s, 3H), 1.03 (s, 9H).

Example 114

Compound 114 [3-{4-[(4,4-Difluoropiperidin-1-yl)sulfonyl]phenyl}-4-(hydroxyamino)-1,4-dimethyl-4,5-dihydro-1H-pyrazol-5-one]

114.1 1-{4-[(4,4-difluoropiperidin-1-yl)sulfonyl]phenyl}ethan-1-one

To a solution of 4-acetylbenzene-1-sulfonyl chloride (6.75 g, 30.87 mmol) in DCM (25 mL) at 0° C. was added (2-methoxyethyl)(methyl)amine (5.00 g, 31.73 mmol) and pyridine (2.3 mL, 27.99 mmol). The reaction mixture was stirred at room temperature until complete conversion of the starting material was observed by LC-MS. The reaction mixture was quenched with saturated sodium hydrogen carbonate (25 mL) and the product extracted into DCM (2×30 mL). The combined organic layers were washed with 2 M HCl (25 mL) and brine (25 mL) and the organic portion was dried over sodium sulfate, filtered and concentrated under reduced pressure (7.95 g, 83%). LC-MS $t_R$=1.09 min, [M+H]$^+$=304; 1H NMR (500 MHz, DMSO-d6) δ 8.21-8.15 (m, 2H), 7.93-7.92 (m, 2H), 3.17-3.06 (m, 4H), 2.65 (s, 3H), 2.15-1.98 (m, 4H).

114.2 Methyl 3-{4-[(4,4-difluoropiperidin-1-yl)sulfonyl]phenyl}-3-oxopropanoate Methyl 3-{4-[(4,4-difluoropiperidin-1-yl)sulfonyl]phenyl}-3-oxopropanoate was synthesized from 1-{4-[(4,4-difluoropiperidin-1-yl)sulfonyl]phenyl}ethan-1-one according to General Method 1 and was purified using silica gel chromatography eluting with 0-60% ethyl acetate in heptanes (4.04 g, 39%). LC-MS $t_R$=1.11 min, [M+H]$^+$=362; $^1$H NMR (500 MHz, DMSO-d6) δ 8.24-8.11 (m, 2H), 7.96-7.93 (m, 2H), 4.31 (s, 2H), 3.66 (s, 3H), 3.17-3.10 (m, 4H), 2.12-2.01 (m, 4H).

114.3 3-{4-[(4,4-Difluoropiperidin-1-yl)sulfonyl]phenyl}-1-methyl-1H-pyrazol-5-ol 3-{4-[(4,4-Difluoropiperidin-1-yl)sulfonyl]phenyl}-1-methyl-1H-pyrazol-5-ol was synthesized from methyl 3-{4-[(4,4-difluoropiperidin-1-yl)sulfonyl]phenyl}-3-oxopropanoate according to General Method 2 and was purified using silica gel chromatography eluting with 0-100% ethyl acetate in heptanes (1.32 g, 33%). LC-MS $t_R$=1.01 min, [M+H]$^+$=358; $^1$H NMR (500 MHz, DMSO-d6) δ 7.98-7.93 (m, 2H), 7.76-7.73 (m, 2H), 5.94 (s, 1H), 3.60 (s, 3H), 3.12-3.07 (m, 4H), 2.17-1.95 (m, 4H).

114.4 3-{4-[(4,4-Difluoropiperidin-1-yl)sulfonyl]phenyl}-5-hydroxy-1-methyl-1H-pyrazole-4-carbaldehyde 3-{4-[(4,4-Difluoropiperidin-1-yl)sulfonyl]phenyl}-5-hydroxy-1-methyl-1H-pyrazole-4-carbaldehyde was synthesized from 3-{4-[(4,4-difluoropiperidin-1-yl)sulfonyl]phenyl}-1-methyl-1H-pyrazol-5-ol according to General Method 4 (1.22 g, 86%). LC-MS $t_R$=1.00 min, [M+H]$^+$=386; $^1$H NMR (500 MHz, DMSO-d6) δ 9.74 (s, 1H), 8.14-8.09 (m, 2H), 7.83-7.77 (m, 2H), 3.63 (s, 3H), 3.14-3.04 (m, 4H), 2.19-1.92 (m, 4H).

114.5 3-{4-[(4,4-Difluoropiperidin-1-yl)sulfonyl]phenyl}-1,4-dimethyl-4,5-dihydro-1H-pyrazol-5-one 3-{4-[(4,4-Difluoropiperidin-1-yl)sulfonyl]phenyl}-1,4-dimethyl-4,5-dihydro-1H-pyrazol-5-one was synthesized from 3-{4-[(4,4-difluoropiperidin-1-yl)sulfonyl]phenyl}-5-hydroxy-1-methyl-1H-pyrazole-4-carbaldehyde according to General Method 5 (1.03 g, 80%). LC-MS $t_R$=0.98 min, [M+H]$^+$=372; 1H NMR (500 MHz, DMSO-d6) δ 7.94-7.83 (m, 2H), 7.80-7.73 (m, 2H), 3.56 (s, 3H), 3.11-3.07 (m, 4H), 2.09-2.01 (m, 7H).

114.6 4-Bromo-3-{4-[(4,4-difluoropiperidin-1-yl) sulfonyl]phenyl}-1,4-dimethyl-4,5-dihydro-1H-pyrazol-5-one 4-Bromo-3-{4-[(4,4-difluoropiperidin-1-yl)sulfonyl]phenyl}-1,4-dimethyl-4,5-dihydro-1H-pyrazol-5-one was synthesized from 3-{4-[(4,4-difluoropiperidin-1-yl)sulfonyl]phenyl}-1,4-dimethyl-4,5-dihydro-1H-pyrazol-5-one according to General Method 6 (1.13 g, 76%). LC-MS $t_R$=1.21 min, [M+H]$^+$=451.

114.7 4-{[(tert-Butoxy)carbonyl]({[(tert-butoxy)carbonyl]oxy})amino}-3-{4-[(4,4-difluoropiperidin-1-yl)sulfonyl]phenyl}-1,4-dimethyl-4,5-dihydro-1H-pyrazol-5-one 4-{[(tert-Butoxy)carbonyl]({[(tert-butoxy)carbonyl]oxy})amino}-3-{4-[(4,4-difluoropiperidin-1-yl)sulfonyl]phenyl}-1,4-dimethyl-4,5-dihydro-1H-pyrazol-5-one was synthesized from 4-bromo-3-{4-[(4,4-difluoropiperidin-1-yl)sulfonyl]phenyl}-1,4-dimethyl-4,5-dihydro-1H-pyrazol-5-one according to General Method 8 and was purified using silica gel chromatography eluting with 0-60% ethyl acetate in heptanes (0.81 g, 51%). LC-MS $t_R$=1.36 min, [M+Na]$^+$=625; 1H NMR (500 MHz, DMSO-d6) δ 8.41-8.29 (m, 1H), 8.01-7.82 (m, 3H), 3.46-3.39 (m, 3H), 3.14-3.06 (m, 4H), 2.10-2.00 (m, 4H), 1.66-1.58 (m, 3H), 1.55-1.43 (m, 9H), 1.23-1.14 (m, 9H).

114.8 3-{4-[(4,4-Difluoropiperidin-1-yl)sulfonyl]phenyl}-4-(hydroxyamino)-1,4-dimethyl-4,5-dihydro-1H-pyrazol-5-one 3-{4-[(4,4-Difluoropiperidin-1-yl)sulfonyl]phenyl}-4-(hydroxyamino)-1,4-dimethyl-4,5-dihydro-1H-pyrazol-5-one was synthesized from 4-{[(tert-butoxy)carbonyl]({[(tert-butoxy)carbonyl]oxy})amino}-3-{4-[(4,4-difluoropiperidin-1-yl)sulfonyl]phenyl}-1,4-dimethyl-4,5-dihydro-1H-pyrazol-5-one according to General Method 9 and was purified using silica gel chromatography eluting with 0-80% ethyl acetate in heptanes (0.04 g, 10%). LC-MS $t_R$=3.63 min, [M+H]$^+$=403; 1H NMR (500 MHz, DMSO-d6) δ 8.33-8.24 (m, 2H), 7.89-7.82 (m, 2H), 7.69-7.65 (m, 1H), 6.61-6.58 (m, 1H), 3.12 (s, 4H), 2.13-2.02 (m, 4H), 1.25 (s, 3H).

Example 115

Compound 115 [4-[1-[(Benzyloxy)imino]ethyl]-3-tert-butyl-4-(hydroxyamino)-1-methyl-4,5-dihydro-1H-pyrazol-5-one]

115.1 4-[1-[(tert-Butoxy)imino]ethyl]-3-tert-butyl-1-methyl-4,5-dihydro-1H-pyrazol-5-one To a solution of 1-(3-tert-butyl-5-hydroxy-1-methyl-1H-pyrazol-4-yl)ethan-1-one (300 mg, 1.38 mmol) in methanol (10 mL) was added O-benzylhydroxylamine hydrochloride (0.34 g, 2.75 mmol) and sodium bicarbonate (0.12 g, 1.38 mmol). The reaction mixture was stirred at 80° C. until complete conversion of the starting material was observed by LC-MS. The reaction mixture was concentrated under reduced pressure and re-dissolved in DCM (40 mL). The product was washed with 1 M HCl (20 mL), brine (30 mL) and dried over sodium sulfate. The product was filtered and concentrated under reduced pressure (0.90 g, 82%). LC-MS $t_R$=1.06 min, [M+H]$^+$=302; 1H NMR (500 MHz, DMSO-d6) δ 7.44-7.22 (m, 5H), 5.07 (s, 2H), 2.02-1.95 (m, 3H), 1.11 (s, 9H).

115.2 4-[1-[(Benzyloxy)imino]ethyl]-4-bromo-3-tert-butyl-1-methyl-4,5-dihydro-1H-pyrazol-5-one 4-[1-[(Benzyloxy)imino]ethyl]-4-bromo-3-tert-butyl-1-methyl-4,5-dihydro-1H-pyrazol-5-one was synthesized from 4-[1-[(benzyloxy)imino]ethyl]-3-tert-butyl-1-methyl-4,5-dihydro-1H-pyrazol-5-one according to General Method 6 (0.15 g, 78%). LC-MS $t_R$=1.41 min, [M+H]$^+$=380.

115.3 4-[1-[(Benzyloxy)imino]ethyl]-4-{[(tert-butoxy)carbonyl]({[(tert-butoxy)carbonyl]oxy}) amino}-3-tert-butyl-1-methyl-4,5-dihydro-1H-pyrazol-5-one 4-[1-[(Benzyloxy)imino]ethyl]-4-{[(tert-butoxy)carbonyl]({[(tert-butoxy)carbonyl]oxy})amino}-3-tert-butyl-1-methyl-4,5-dihydro-1H-pyrazol-5-one was synthesized from 4-[1-[(benzyloxy)imino]ethyl]-4-bromo-3-tert-butyl-1-methyl-4,5-dihydro-1H-pyrazol-5-one according to General Method 8 (0.18 g, 22%). LC-MS $t_R$=1.58 min, [M+Na]$^+$=555.

115.4 4-[1-[(Benzyloxy)imino]ethyl]-3-tert-butyl-4-(hydroxyamino)-1-methyl-4,5-dihydro-1H-pyrazol-5-one 4-[1-[(Benzyloxy)imino]ethyl]-3-tert-butyl-4-(hydroxyamino)-1-methyl-4,5-dihydro-1H-pyrazol-5-one was synthesized from 4-[1-[(benzyloxy)imino]ethyl]-4-{[(tert-butoxy)carbonyl]({[(tert-butoxy)carbonyl]oxy})amino}-3-tert-butyl-1-methyl-4,5-dihydro-1H-pyrazol-5-one according to General Method 9. The product was purified using acidic preparative HPLC (6 mg, 27%). LC-MS $t_R$=1.17 min, [M+H]$^+$=333; 1H NMR (500 MHz, DMSO-d6) δ 7.59-7.58 (m, 1H), 7.41-7.38 (m, 1H), 7.36-7.34 (m, 1H), 7.33-7.33 (m, 2H), 6.29-6.12 (m, 1H), 5.25 (s, 1H), 5.08 (s, 2H), 3.17 (s, 3H), 1.61 (s, 3H), 1.14 (s, 9H).

Example 116

Compound 116 [4-(Hydroxyamino)-3-methoxy-4-[1-(methoxyimino)ethyl]-1-phenyl-4,5-dihydro-1H-pyrazol-5-one]

3-Methoxy-1-phenyl-4,5-dihydro-1H-pyrazol-5-one was isolated as an unexpected by-product in the formation of 1-(3-ethoxy-5-hydroxy-1-phenyl-1H-pyrazol-4-yl)ethan-1-one 116.1 1-(5-Hydroxy-3-methoxy-1-phenyl-1H-pyrazol-4-yl)ethan-1-one 1-(5-Hydroxy-3-methoxy-1-phenyl-1H-pyrazol-4-yl)ethan-1-one was synthesized from 3-methoxy-1-phenyl-4,5-dihydro-1H-pyrazol-5-one according to General Method 11 (0.49 g, 90%), LC-MS $t_R$=1.23 min, [M+H]$^+$=233.05; 1H NMR (500 MHz, DMSO-d6) δ 7.92-7.89 (m, 2H), 7.37 (dd, J=8.6, 7.4 Hz, 2H), 7.12-7.07 (m, 1H), 4.05 (s, 3H), 2.78 (s, 3H).

116.2 3-Methoxy-4-[1-(methoxyimino)ethyl]-1-phenyl-1H-pyrazol-5-ol

3-Methoxy-4-[1-(methoxyimino)ethyl]-1-phenyl-1H-pyrazol-5-ol was synthesized from 1-(5-hydroxy-3-methoxy-1-phenyl-1H-pyrazol-4-yl)ethan-1-one according to General Method 12 and was purified using silica gel chromatography eluting with heptanes:ethyl acetate (100-80%) to yield the title compound as a brown solid (0.56 g, 47%). LC-MS $t_R$=1.23 min, [M+H]$^+$=262.4; $^1$H NMR (500 MHz, DMSO-d6) δ 7.88 (d, J=7.7 Hz, 2H), 7.39 (t, J=7.9 Hz, 2H), 7.16-7.10 (m, 1H), 3.92 (s, 3H), 3.85 (s, 3H), 2.36 (s, 3H).

116.3 4-Bromo-3-methoxy-4-[1-(methoxyimino)ethyl]-1-phenyl-4,5-dihydro-1H-pyrazol-5-one 4-Bromo-3-methoxy-4-[1-(methoxyimino)ethyl]-1-phenyl-4,5-dihydro-1H-pyrazol-5-one was synthesized from 3-methoxy-4-[1-(methoxyimino)ethyl]-1-phenyl-1H-pyrazol-5-ol according to General Method 6 and was used directly in the synthesis of 4-{[(tert-butoxy)carbonyl]({[(tert-butoxy)carbonyl]oxy})amino}-3-methoxy-4-[1-(methoxyimino)ethyl]-1-phenyl-4,5-dihydro-1H-pyrazol-5-one (0.45 g, 98%). LC-MS $t_R$=1.31 min, [M+H]$^+$=341/343

116.4 4-{[(tert-Butoxy)carbonyl]({[(tert-butoxy)carbonyl]oxy})amino}-3-methoxy-4-[1-(methoxyimino)ethyl]-1-phenyl-4,5-dihydro-1H-pyrazol-5-one 4-{[(tert-Butoxy)carbonyl]({[(tert-butoxy)carbonyl]oxy})amino}-3-methoxy-4-[1-(methoxyimino)ethyl]-1-phenyl-4,5-dihydro-1H-pyrazol-5-one was synthesized from 4-bromo-3-methoxy-4-[1-(methoxyimino)ethyl]-1-phenyl-4,5-dihydro-1H-pyrazol-5-one according to General Method 8 and was purified using silica gel chromatography eluting with heptanes:ethyl acetate (100-80%) to yield the title compound as a colourless oil (0.4 g, 61%), LC-MS $t_R$=1.48 min, [M+Na]$^+$=515.

116.5 4-(Hydroxyamino)-3-methoxy-4-[1-(methoxyimino)ethyl]-1-phenyl-4,5-dihydro-1H-pyrazol-5-one 4-(Hydroxyamino)-3-methoxy-4-[1-(methoxyimino)ethyl]-1-phenyl-4,5-dihydro-1H-pyrazol-5-one was synthesized from 4-{[(tert-butoxy)carbonyl]({[(tert-butoxy)carbonyl]oxy})amino}-3-methoxy-4-[1-(methoxyimino)ethyl]-1-phenyl-4,5-dihydro-1H-pyrazol-5-one according to General Method 9 and was purified using low pH preparative HPLC (0.09 g, 41%). LC-MS $t_R$=3.75 min, [M+H]$^+$=293; $^1$H NMR (500 MHz, DMSO-d6) δ 8.09 (s, 1H), 7.84 (d, J=8.0 Hz, 2H), 7.43 (t, J=7.9 Hz, 2H), 7.18 (t, J=7.3 Hz, 1H), 6.85 (s, 1H), 3.99 (s, 3H), 3.78 (s, 3H), 1.87 (s, 3H).

Example 117

Compound 117 [4-[1-[(tert-Butoxy)imino]ethyl]-3-tert-butyl-4-(hydroxyamino)-1-methyl-4,5-dihydro-1H-pyrazol-5-one]

117.1 4-[1-[(tert-Butoxy)imino]ethyl]-3-tert-butyl-1-methyl-4,5-dihydro-1H-pyrazol-5-one To a solution of 1-(3-tert-butyl-5-hydroxy-1-methyl-1H-pyrazol-4-yl)ethan-1-one (500 mg, 2.29 mmol) in methanol (10 mL) was added O-tert-butylhydroxylamine hydrochloride (0.58 g, 4.59 mmol) and sodium bicarbonate (0.19 g, 2.29 mmol). The reaction mixture was stirred at 80° C. until complete conversion of the starting material was observed by LC-MS. The reaction mixture was concentrated under reduced pressure and taken up into DCM (30 mL), washed with 1 M HCl (20 mL), brine (30 mL) and dried over sodium sulfate. The product was filtered and concentrated under reduced pressure (0.64 g, 89%). LC-MS $t_R$=1.06 min, [M+H]$^+$=268; $^1$H NMR (500 MHz, DMSO-d6) δ 5.74 (s, 1H), 3.41 (s, 3H), 1.96 (s, 3H), 1.26 (s, 9H), 1.24 (s, 9H).

117.2 4-Bromo-4-[1-[(tert-butoxy)imino]ethyl]-3-tert-butyl-1-methyl-4,5-dihydro-1H-pyrazol-5-one 4-Bromo-4-[1-[(tert-butoxy)imino]ethyl]-3-tert-butyl-1-methyl-4,5-dihydro-1H-pyrazol-5-one was synthesized from 4-[1-[(tert-butoxy)imino]ethyl]-3-tert-butyl-1-methyl-4,5-dihydro-1H-pyrazol-5-one according to General Method 6 (0.72 g, 85%). LC-MS $t_R$=1.48 min, [M+H]$^+$=346.

117.3 4-{[(tert-Butoxy)carbonyl]({[(tert-butoxy)carbonyl]oxy})amino}-4-[1-[(tert-butoxy)imino]ethyl]-3-tert-butyl-1-methyl-4,5-dihydro-1H-pyrazol-5-one 4-{[(tert-Butoxy)carbonyl]({[(tert-butoxy)carbonyl]oxy})amino}-4-[1-[(tert-butoxy)imino]ethyl]-3-tert-butyl-1-methyl-4,5-dihydro-1H-pyrazol-5-one was synthesized from 4-bromo-4-[1-[(tert-butoxy)imino]ethyl]-3-tert-butyl-1-methyl-4,5-dihydro-1H-pyrazol-5-one according to General Method 8 and was purified using silica gel chromatography eluting with 0-50% ethyl acetate in heptanes (0.92 g, 49%). LC-MS $t_R$=1.61 min, [M+Na]$^+$=521; $^1$H NMR (500 MHz, DMSO-d6) δ 3.20-3.08 (m, 3H), 1.50-1.48 (m, 3H), 1.45 (s, 9H), 1.41 (s, 9H), 1.26-1.15 (m, 18H).

117.4 4-[1-[(tert-Butoxy)imino]ethyl]-3-tert-butyl-4-(hydroxyamino)-1-methyl-4,5-dihydro-1H-pyrazol-5-one 4-[1-[(tert-Butoxy)imino]ethyl]-3-tert-butyl-4-(hydroxyamino)-1-methyl-4,5-dihydro-1H-pyrazol-5-one was synthesized by 4-{[(tert-butoxy)carbonyl]({[(tert-butoxy)carbonyl]oxy})amino}-4-[1-[(tert-butoxy)imino]ethyl]-3-tert-butyl-1-methyl-4,5-dihydro-1H-pyrazol-5-one according to General Method 9 and was purified using acidic preparative HPLC (26 mg, 10%). LC-MS $t_R$=1.16 min, [M+H]$^+$=299; $^1$H NMR (500 MHz, DMSO-d6) δ 7.56 (s, 1H), 6.27 (s, 1H), 3.18 (s, 3H), 1.54 (s, 3H), 1.23-1.18 (m, 18H).

Example 118

Compound 118 [4-[1-[(4-Bromophenoxy)imino]ethyl]-3-tert-butyl-4-(hydroxyamino)-1-methyl-4,5-dihydro-1H-pyrazol-5-one]

118.1 4-[1-[(tert-butoxy)imino]ethyl]-3-tert-butyl-1-methyl-4,5-dihydro-1H-pyrazol-5-one To a solution of 1-(3-tert-butyl-5-hydroxy-1-methyl-1H-pyrazol-4-yl)ethan-1-one (500 mg, 2.29 mmol) in methanol (10 mL) was added O-phenylhydroxylamine hydrochloride (0.67 g, 4.59 mmol) and sodium bicarbonate (0.19 g, 2.29 mmol). The reaction mixture was stirred at 80° C. until complete conversion of the starting material was observed by LC-MS and the reaction mixture was concentrated under reduced pressure, taken up into DCM (40 mL), washed with 1 M HCl (25 mL), brine (30 mL) and dried over sodium sulfate. The product was filtered and concentrated under reduced pressure (0.90 g, 82%). LC-MS $t_R$=1.06 min, [M+H]$^+$=288; $^1$H NMR (500 MHz, DMSO-d6) δ 7.39-7.30 (m, 2H), 7.18-7.10 (m, 3H), 5.74 (s, 1H), 3.45 (s, 3H), 2.24 (s, 3H), 1.28 (s, 9H).

118.2 4-Bromo-4-[1-[(4-bromophenoxy)imino]ethyl]-3-tert-butyl-1-methyl-4,5-dihydro-1H-pyrazol-5-one 4-Bromo-4-[1-[(4-bromophenoxy)imino]ethyl]-3-tert-butyl-1-methyl-4,5-dihydro-1H-pyrazol-5-one was synthesized from 3-tert-butyl-1-methyl-4-[1-(phenoxyimino)ethyl]-1H-pyrazol-5-ol according to General Method 6 (0.93 g, 33%). LC-MS $t_R$=1.53 min, [M+H]$^+$=445.

118.3 4-[1-[(4-Bromophenoxy)imino]ethyl]-4-{[(tert-butoxy)carbonyl]({[(tert-butoxy)carbonyl]oxy})amino}-3-tert-butyl-1-methyl-4,5-dihydro-1H-pyrazol-5-one 4-[1-[(4-Bromophenoxy)imino]ethyl]-4-{[(tert-butoxy)carbonyl]({[(tert-butoxy)carbonyl]oxy})amino}-3-tert-butyl-1-methyl-4,5-dihydro-1H-pyrazol-5-one was synthesized from 4-bromo-4-[1-[(4-bromophenoxy)imino]ethyl]-3-tert-butyl-1-methyl-4,5-dihydro-1H-pyrazol-5-one according to General Method 8 and was purified by silica gel chromatography eluting with 0-50% ethyl acetate in heptanes (0.73 g, 42%). LC-MS $t_R$=1.66 min, [M+Na]$^+$=619.

118.4 4-[1-[(4-Bromophenoxy)imino]ethyl]-3-tert-butyl-4-(hydroxyamino)-1-methyl-4,5-dihydro-1H-pyrazol-5-one 4-[1-[(4-Bromophenoxy)imino]ethyl]-3-tert-butyl-4-(hydroxyamino)-1-methyl-4,5-dihydro-1H-pyrazol-5-one was synthesized from 4-[1-[(4-bromophenoxy)imino]ethyl]-4-{[(tert-butoxy)carbonyl]({[(tert-butoxy)carbonyl]oxy})amino}-3-tert-butyl-1-methyl-4,5-dihydro-1H-pyrazol-5-one according to General Method 8 and was purified by acidic preparative HPLC (39 mg, 30%). LC-MS $t_R$=1.26 min, [M+H]$^+$=398; $^1$H NMR (500 MHz, DMSO-d6) δ 7.71-7.64 (m, 1H), 7.54-7.49 (m, 2H), 7.22-7.13 (m, 2H), 6.74-6.69 (m, 1H), 3.22 (s, 3H), 1.82 (s, 3H), 1.25 (s, 9H).

Example 119

Compound 119 [3-tert-Butyl-4-(hydroxyamino)-1-methyl-4-[1-(phenoxyimino)ethyl]-4,5-dihydro-1H-pyrazol-5-one]

119.1 4-Bromo-3-tert-butyl-1-methyl-4-[1-(phenoxyimino)ethyl]-4,5-dihydro-1H-pyrazol-5-one 4-Bromo-3-tert-butyl-1-methyl-4-[1-(phenoxyimino)ethyl]-4,5-dihydro-1H-pyrazol-5-one was synthesized from 3-tert-butyl-1-methyl-4-[1-(phenoxyimino)ethyl]-1H-pyrazol-5-ol according to General Method 6 (0.93 g, 41%). LC-MS $t_R$=1.43 min, [M+H]$^+$=366.

119.2 4-{[(tert-Butoxy)carbonyl]({[(tert-butoxy)carbonyl]oxy})amino}-3-tert-butyl-1-methyl-4-[1-(phenoxyimino)ethyl]-4,5-dihydro-1H-pyrazol-5-one 4-{[(tert-Butoxy)carbonyl]({[(tert-butoxy)carbonyl]oxy})amino}-3-tert-butyl-1-methyl-4-[1-(phenoxyimino)ethyl]-4,5-dihydro-1H-pyrazol-5-one was synthesized from 4-bromo-3-tert-butyl-1-methyl-4-[1-(phenoxyimino)ethyl]-4,5-dihydro-1H-pyrazol-5-one according to General Method 8 and was purified by silica gel chromatography eluting with 0-50% ethyl acetate in heptanes (0.73 g, 89%). LC-MS $t_R$=1.58 min, [M+Na]$^+$=532.

119.3 3-tert-Butyl-4-(hydroxyamino)-1-methyl-4-[1-(phenoxyimino)ethyl]-4,5-dihydro-1H-pyrazol-5-one 3-tert-Butyl-4-(hydroxyamino)-1-methyl-4-[1-(phenoxyimino)ethyl]-4,5-dihydro-1H-pyrazol-5-one was synthesized from 4-{[(tert-butoxy)carbonyl]({[(tert-butoxy)carbonyl]oxy})amino}-3-tert-butyl-1-methyl-4-[1-(phenoxyimino)ethyl]-4,5-dihydro-1H-pyrazol-5-one according to General Method 9 and was purified by acidic preparative HPLC (5 mg, 5%). LC-MS $t_R$=1.17 min, [M+H]$^+$=319; $^1$H NMR (500 MHz, DMSO-d6) δ 7.70-7.63 (m, 1H), 7.39-7.30 (m, 2H), 7.24-7.16 (m, 2H), 7.09-7.01 (m, 1H), 6.72-6.64 (m, 1H), 3.23 (s, 3H), 1.84 (s, 3H), 1.26 (s, 9H).

Example 120

Compound 120 [4-(Hydroxyamino)-3-{4-[imino(oxo)propan-2-yl-λ$^6$-sulfanyl]phenyl}-1,4-dimethyl-4,5-dihydro-1H-pyrazol-5-one]

120.1 N-{[4-(4-{[(tert-Butoxy)carbonyl]({[(tert-butoxy)carbonyl]oxy})amino}-1,4-dimethyl-5-oxo-4,5-dihydro-1H-pyrazol-3-yl)phenyl](oxo)propan-2-yl-λλ-sulfanylidene}-2,2,2-trifluoroacetamide To a suspension of 4-{[(tert-butoxy)carbonyl]({[(tert-butoxy)carbonyl]oxy})amino}-1,4-dimethyl-3-[4-(propane-2-sulfinyl)phenyl]-4,5-dihydro-1H-pyrazol-5-one (3.43 g, 6.19 mmol), oxomagnesium (278.85 µl, 0.02 mol), tetrakis(acetato-kappaO)dirhodium(Rh—Rh) (0.07 g, 0.15 mmol) and 2,2,2-trifluoroacetamide (1.4 g, 12.38 mmol) in DCM (20 ml), was added bis(acetyloxy)(phenyl)-lambda~3~-iodane (2.99 g, 9.29 mmol) and the reaction mixture was stirred at room temperature for 4 hours. The precipitate was removed by filtration and discarded and the filtrate was concentrated under reduced pressure yielding a brown oil, which was purified by silica gel chromatography, eluting in 0-70% ethyl acetate:heptanes. The desired compound was isolated as a pale yellow solid (2.82 g, 62%). LC-MS $t_R$=1.39 min, [M+Na]$^+$=643.

120.2 tert-Butyl N-hydroxy-N-(3-{4-[imino(oxo)propan-2-yl-λλ-sulfanyl]phenyl}-1,4-dimethyl-5-oxo-4,5-dihydro-1H-pyrazol-4-yl)carbamate To a solution of N-{[4-(4-{[(tert-butoxy)carbonyl]({[(tert-butoxy)carbonyl]oxy})amino}-1,4-dimethyl-5-oxo-4,5-dihydro-1H-pyrazol-3-yl)phenyl](oxo)propan-2-yl-λλ-sulfanylidene}-2,2,2-trifluoroacetamide (2.82 g, 3.82 mmol) in MeOH (14 ml) was added dipotassium carbonate (2.64 g, 19.08 mmol) and the reaction mixture was stirred at room temperature for 15 minutes before the reaction mixture was concentrated under reduced pressure and diluted with water (30 ml). The product was extracted into ethyl acetate (3×60 mL), washed with brine (30 mL), dried over magnesium sulfate, filtered and concentrated under reduced pressure to afford the title compound as a white crystalline solid (2.27 g, quant.). LC-MS $t_R$=0.94 min, [M+Na]$^+$=425.

120.3 4-(Hydroxyamino)-3-{4-[imino(oxo)propan-2-yl-λλ-sulfanyl]phenyl}-1,4-dimethyl-4,5-dihydro-1H-pyrazol-5-one 4-(Hydroxyamino)-3-{4-[imino(oxo)propan-2-yl-λλ-sulfanyl]phenyl}-1,4-dimethyl-4,5-dihydro-1H-pyrazol-5-one was synthesized from N-{[4-(4-{[(tert-butoxy)carbonyl]({[(tert-butoxy)carbonyl]oxy})amino}-1,4-dimethyl-5-oxo-4,5-dihydro-1H-pyrazol-3-yl)phenyl](oxo)propan-2-yl-λλ-sulfanylidene}-2,2,2-trifluoroacetamide according to General Method 9 and was purified by silica gel chromatography eluting in 0-100% ethyl acetate:heptanes, followed by recrystallization from ethyl acetate:heptanes. Lyophilisation afforded the title compound as a pale orange solid (705 mg, 50%). LC-MS $t_R$=0.94 min, [M+Na]$^+$=425; $^1$H NMR (500 MHz, DMSO-d6) δ 8.24 (d, J=8.5 Hz, 2H), 7.93 (d, J=8.2 Hz, 2H), 7.69 (s, 1H), 6.54 (s, 1H), 3.32 (s, 3H), 1.24 (s, 3H), 1.16 (d, J=6.8 Hz, 6H).

Example 121

Compound 121 [4-[4-(Hydroxyamino)-4-[1-(methoxyimino)ethyl]-1-methyl-5-oxo-4,5-dihydro-1H-pyrazol-3-yl]-N,N-dimethylbenzene-1-sulfonamide]

121.1 4-(4-Acetyl-1-methyl-5-oxo-4,5-dihydro-1H-pyrazol-3-yl)-N,N-dimethylbenzene-1-sulfonamide 4-(4-Acetyl-1-methyl-5-oxo-4,5-dihydro-1H-pyrazol-3-yl)-N,N-dimethylbenzene-1-sulfonamide was synthesized from 4-(5-hydroxy-1-methyl-1H-pyrazol-3-yl)-N,N-dimethylbenzene-1-sulfonamide according to General Method 11 (0.78 g, 37%). LC-MS $t_R$=0.98 min, [M+H]$^+$=324.

121.2 4-{4-[1-(Methoxyimino)ethyl]-1-methyl-5-oxo-4,5-dihydro-1H-pyrazol-3-yl}-N,N-dimethylbenzene-1-sulfonamide 4-{4-[1-(Methoxyimino)ethyl]-1-methyl-5-oxo-4,5-dihydro-1H-pyrazol-3-yl}-N,N-dimethylbenzene-1-sulfonamide was synthesized from 4-(4-acetyl-1-methyl-5-oxo-4,5-dihydro-1H-pyrazol-3-yl)-N,N-dimethylbenzene-1-sulfonamide according to General Method 12 and was purified using silica gel chromatography eluting with 0-50% ethyl acetate in heptanes (0.10 g, 20%). LC-MS $t_R$=1.05 min, [M+H]$^+$=353; $^1$H NMR (500 MHz, DMSO-d6) δ 7.77-7.76 (m, 2H), 7.74-7.73 (m, 2H), 3.77 (s, 3H), 3.63 (s, 3H), 2.62 (s, 3H), 2.61 (s, 6H).

121.3 4-{4-Bromo-4-[1-(methoxyimino)ethyl]-1-methyl-5-oxo-4,5-dihydro-1H-pyrazol-3-yl}-N,N-dimethylbenzene-1-sulfonamide 4-{4-Bromo-4-[1-(methoxyimino)ethyl]-1-methyl-5-oxo-4,5-dihydro-1H-pyrazol-3-yl}-N,N-dimethylbenzene-1-sulfonamide was synthesized from 4-{4-[1-(methoxyimino)ethyl]-1-methyl-5-oxo-4,5-dihydro-1H-pyrazol-3-yl}-N,N-dimethylbenzene-1-sulfonamide according to General Method 6 (0.09 g, 71%). LC-MS $t_R$=1.22 min, [M+H]$^+$=431.

121.4 4-(4-{[(tert-Butoxy)carbonyl]({[(tert-butoxy)carbonyl]oxy})amino}-4-[1-(methoxyimino)ethyl]-1-methyl-5-oxo-4,5-dihydro-1H-pyrazol-3-yl)-N,N-dimethylbenzene-1-sulfonamide 4-(4-{[(tert-Butoxy)carbonyl]({[(tert-butoxy)carbonyl]oxy})amino}-4-[1-(methoxyimino)ethyl]-1-methyl-5-oxo-4,5-dihydro-1H-pyrazol-3-yl)-N,N-dimethylbenzene-1-sulfonamide was synthesized from 4-{4-bromo-4-[1-(methoxyimino)ethyl]-1-methyl-5-oxo-4,5-dihydro-1H-pyrazol-3-yl}-N,N-dimethylbenzene-1-sulfonamide according to General Method 8 and was purified using silica gel chromatography eluting with 10-80% ethyl acetate in heptanes (0.08 g, 47%). LC-MS $t_R$=1.35 min, [M+Na]$^+$=606; $^1$H NMR (500 MHz, DMSO-d6) δ 8.08-7.74 (m, 4H), 3.68 (s, 3H), 3.35 (s, 3H), 2.69-2.53 (m, 6H), 1.50-1.40 (m, 12H), 1.28-1.12 (m, 9H).

121.5 4-[4-(Hydroxyamino)-4-[1-(methoxyimino)ethyl]-1-methyl-5-oxo-4,5-dihydro-1H-pyrazol-3-yl]-N,N-dimethylbenzene-1-sulfonamide 4-[4-(Hydroxyamino)-4-[1-(methoxyimino)ethyl]-1-methyl-5-oxo-4,5-dihydro-1H-pyrazol-3-yl]-N,N-dimethylbenzene-1-sulfonamide was synthesized from 4-(4-{[(tert-butoxy)carbonyl]({[(tert-butoxy)carbonyl]oxy})amino}-4-[1-(methoxyimino)ethyl]-1-methyl-5-oxo-4,5-dihydro-1H-pyrazol-3-yl)-N,N-dimethylbenzene-1-sulfonamide according to General Method 9 and was purified using silica gel chromatography eluting with 10-60% ethyl acetate in heptanes (12 mg, 38%). LC-MS $t_R$=1.02 min, [M+H]$^+$=384; $^1$H NMR (500 MHz, DMSO-d6) δ 8.18-8.09 (m, 2H), 7.90 (s, 1H), 7.85-7.77 (m, 2H), 6.83 (s, 1H), 3.71 (s, 3H), 3.36 (s, 3H), 2.65 (s, 6H), 1.74 (s, 3H).

Example 122

Compound 122 [4-[3-tert-Butyl-4-(hydroxyamino)-1-methyl-5-oxo-4,5-dihydro-1H-pyrazol-4-yl]-N,N-dimethylbenzene-1-sulfonamide]

122.1 4-Bromo-3-tert-butyl-1-methyl-1H-pyrazol-5-ol

4-Bromo-3-tert-butyl-1-methyl-1H-pyrazol-5-ol was synthesized from 3-tert-butyl-1-methyl-1H-pyrazol-5-ol according to General Method 6 to afford the title compound as a yellow oil (0.439 g, 61%). LC-MS $t_R$=0.87 min, [M+H]$^+$=233/235. $^1$H NMR (250 MHz, Chloroform-d) δ 4.66 (s, 1H), 3.31 (s, 3H), 1.32 (s, 9H).

122.2 4-Bromo-3-tert-butyl-1-methyl-1H-pyrazol-5-yl benzoate

To a solution of benzoyl chloride (196.9 μl, 1.69 mmol) and triethylamine (236.24 μl, 1.69 mmol) in DCM (5 mL) was added a solution of 4-bromo-3-tert-butyl-1-methyl-4,5-dihydro-1H-pyrazol-5-one (0.44 g, 1.88 mmol) in DCM (5 mL) and the reaction mixture was stirred at ambient temperature for 1.5 hours. The reaction was quenched by the addition of 1M HCl (10 mL) and the organics were washed with saturated aqueous sodium bicarbonate solution (10 mL), dried over magnesium sulfate and concentrated under reduced pressure to afford the crude product as a yellow oil. Purification was performed by silica gel chromatography, eluting in 0-40% ethyl acetate/heptanes to afford the title compound as a yellow oil (379 mg, 57%). LC-MS $t_R$=1.42 min, [M+H]$^+$=337/339; $^1$H NMR (250 MHz, Chloroform-d) δ 8.30-8.07 (m, 2H), 7.77-7.65 (m, 1H), 7.56 (t, J=7.6 Hz, 2H), 3.68 (s, 3H), 1.41 (s, 9H).

122.3 4-(3-tert-Butyl-1-methyl-5-oxo-4,5-dihydro-1H-pyrazol-4-yl)-N,N-dimethylbenzene-1-sulfonamide A solution of 4-bromo-3-tert-butyl-1-methyl-1H-pyrazol-5-yl benzoate (345 mg, 1.023 mmol), N,N-dimethyl-4-(4,4,5,5-tetramethyl-1,3,2-dioxaborolan-2-yl)benzenesulfonamide (323 mg, 1.037 mmol) and sodium bicarbonate (326 mg, 3.078 mmol) in 1,4-dioxane (8 mL) and water (1 mL) was purged with nitrogen and treated with tetrakis(triphenylphosphine)palladium(0) (60.29 mg, 0.052 mmol). The reaction mixture was heated at 130° C. for 45 minutes (75 W) in a Biotage Initiator plus microwave. The crude reaction mixture was filtered over glass fibre filter paper to remove the catalyst residues and the aqueous layer was extracted separately with ethyl acetate (3×20 mL) and with 2:1 chloroform:IPA (3×30 mL). The combined organic layers were dried over magnesium sulfate, filtered and concentrated under reduced pressure. The resulting solid was washed with ethyl acetate to afford the title compound as an orange solid (64 mg, 12%). LC-MS $t_R$=0.96 min, [M+H]$^+$=338.

122.4 4-[3-tert-Butyl-4-(hydroxyamino)-1-methyl-5-oxo-4,5-dihydro-1H-pyrazol-4-yl]-N,N-dimethylbenzene-1-sulfonamide To a solution of 4-(3-tert-butyl-5-hydroxy-1-methyl-1H-pyrazol-4-yl)-N,N-dimethylbenzene-1-sulfonamide (64 mg, 0.19 mmol) in ethanol (2 mL) at room temperature was added N-hydroxy-2-methanesulfonylbenzene-1-sulfonamide (52.42 mg, 0.21 mmol) and the resulting cloudy suspension was stirred at room temperature for 5 minutes before the reaction mixture was cooled to −5° C. and an aqueous solution of potassium carbonate (34.08 mg, 0.25 mmol) and N,N-bis{2-[bis(carboxymethyl)amino]ethyl}glycine (22.38 mg, 0.06 mmol) in water (2 mL) was added dropwise over 5 minutes. Stirring was continued for 90 minutes, before further N-hydroxy-2-methanesulfonylbenzene-1-sulfonamide (52.42 mg, 0.21 mmol) was added and stirring continued for a further 90 minutes. An additional aqueous solution of potassium carbonate (34.08 mg, 0.25 mmol) and N,N-bis{2-[bis(carboxymethyl)amino]ethyl}glycine (22.38 mg, 0.06 mmol) in water (2 mL) was added dropwise over 5 minutes and stirring was continued for 2 hours at room temperature. The crude reaction mixture was diluted with ethyl acetate (10 mL) and water (5 mL) and the organic layer was isolated. The aqueous layer was re-extracted with ethyl acetate (2×10 mL) and the combined organic layers were washed with brine (10 mL), dried over magnesium sulfate, filtered and concentrated under reduced pressure to afford the crude product as an orange oil. Purification was performed by acidic preparative HPLC to afford the title compound as a white solid (21.9 mg 46% yield). LC-MS $t_R$=3.57 min, [M+H]$^+$=369; $^1$H NMR (500 MHz, DMSO-d6) δ 7.83 (s, 1H), 7.74 (d, J=8.5 Hz, 2H), 7.38 (d, J=8.4 Hz, 2H), 7.05 (s, 1H), 3.26 (s, 3H), 2.58 (s, 6H), 1.03 (s, 9H).

Example 123

Compound 123 [4-[4-(Hydroxyamino)-4-[1-(methoxyimino)ethyl]-1-methyl-5-oxo-4,5-dihydro-1H-pyrazol-3-yl]-N,N-dimethylbenzamide]

123.1 Methyl 4-(4-acetyl-1-methyl-5-oxo-4,5-dihydro-1H-pyrazol-3-yl)benzoate Methyl 4-(4-acetyl-1-methyl-5-oxo-4,5-dihydro-1H-pyrazol-3-yl)benzoate was synthesized from methyl 4-(5-hydroxy-1-methyl-1H-pyrazol-3-yl)benzoate according to General Method 11 (8.20 g, 51%). LC-MS $t_R$=1.01 min, [M+H]$^+$=275; $^1$H NMR (500 MHz, DMSO-d6) δ 8.01-7.93 (m, 2H), 7.73-7.64 (m, 2H), 3.88-3.86 (m, 3H), 3.84 (s, 3H), 3.62 (s, 3H), 3.26 (s, 1H).

123.2 Methyl 4-{4-[1-(methoxyimino)ethyl]-1-methyl-5-oxo-4,5-dihydro-1H-pyrazol-3-yl}benzoate Methyl 4-{4-[1-(methoxyimino)ethyl]-1-methyl-5-oxo-4,5-dihydro-1H-pyrazol-3-yl}benzoate was synthesized from methyl 4-(4-acetyl-1-methyl-5-oxo-4,5-dihydro-1H-pyrazol-3-yl)benzoate according to General Method 12 and was purified using silica gel chromatography eluting with 0-60% ethyl acetate in heptanes (3.50 g, 58%). LC-MS $t_R$=1.08 min, [M+H]$^+$=304; $^1$H NMR (500 MHz, DMSO-d6) δ 7.97-7.93 (m, 2H), 7.70-7.55 (m, 2H), 3.86-3.84 (m, 3H), 3.79 (s, 3H), 3.63-3.59 (m, 3H), 3.51 (s, 3H).

123.3 Methyl 4-{4-bromo-4-[1-(methoxyimino)ethyl]-1-methyl-5-oxo-4,5-dihydro-1H-pyrazol-3-yl}benzoate Methyl 4-{4-bromo-4-[1-(methoxyimino)ethyl]-1-methyl-5-oxo-4,5-dihydro-1H-pyrazol-3-yl}benzoate was synthesized from methyl 4-{4-[1-(methoxyimino)ethyl]-1-methyl-5-oxo-4,5-dihydro-1H-pyrazol-3-yl}benzoate according to General Method 6 (3.88 g, 78%). LC-MS $t_R$=1.28 min, [M+H]$^+$=382.

123.4 Methyl 4-(4-{[(tert-butoxy)carbonyl]({[(tert-butoxy)carbonyl]oxy})amino}-4-[1-(methoxyimino)ethyl]-1-methyl-5-oxo-4,5-dihydro-1H-pyrazol-3-yl)benzoate Methyl 4-(4-{[(tert-butoxy)carbonyl]({[(tert-butoxy)carbonyl]oxy})amino}-4-[1-(methoxyimino)ethyl]-1-methyl-5-oxo-4,5-dihydro-1H-pyrazol-3-yl)benzoate was synthesized from methyl 4-{4-bromo-4-[1-(methoxyimino)ethyl]-1-methyl-5-oxo-4,5-dihydro-1H-pyrazol-3-yl}benzoate according to General Method 8 and was purified using silica gel chromatography eluting with 0-60% ethyl acetate in heptanes (4.2 g, 87%). LC-MS $t_R$=1.42 min, [M+Na]$^+$=557; $^1$H NMR (500 MHz, DMSO-d6) δ 8.05-7.99 (m, 2H), 7.83 (s, 2H), 3.87 (s, 3H), 3.67 (s, 3H), 1.96 (s, 3H), 1.49 (s, 9H), 1.40-0.98 (m, 12H).

123.5 4-(4-{[(tert-Butoxy)carbonyl]({[(tert-butoxy)carbonyl]oxy})amino}-4-[1-(methoxyimino)ethyl]-1-methyl-5-oxo-4,5-dihydro-1H-pyrazol-3-yl)benzoic acid To a solution of methyl 4-(4-{[(tert-butoxy)carbonyl]({[(tert-butoxy)carbonyl]oxy})amino}-4-[1-(methoxyimino)ethyl]-1-methyl-5-oxo-4,5-dihydro-1H-pyrazol-3-yl)benzoate (4.20 g, 7.07 mmol) in THF (30 mL) was added a solution of lithium hydroxide (0.51 g, 21.21 mmol) in water (30 mL) and the reaction mixture was stirred at room temperature until complete consumption of the starting material was observed by LC-MS. The product was concentrated under reduced pressure to remove the organic solvent and the resulting solution was acidified with 6 M HCl (30 mL). The product was extracted into ethyl acetate (50 mL) and washed with brine (30 mL), dried over sodium sulfate, filtered and concentrated under reduced pressure (3.54 g, 87%). LC-MS $t_R$=1.25 min, [M+Na]$^+$=543; $^1$H NMR (500 MHz, DMSO-d6) δ 8.07-7.41 (m, 4H), 3.73-3.66 (m, 3H), 3.34 (s, 3H), 1.91 (s, 3H), 1.49 (s, 9H), 1.39-1.10 (m, 9H).

123.6 4-(4-{[(tert-Butoxy)carbonyl]({[(tert-butoxy)carbonyl]oxy})amino}-4-[1-(methoxyimino)ethyl]-1-methyl-5-oxo-4,5-dihydro-1H-pyrazol-3-yl)-N,N-dimethylbenzamide To a solution of 4-(4-{[(tert-butoxy)carbonyl]({[(tert-butoxy)carbonyl]oxy})amino}-4-[1-(methoxyimino)ethyl]-1-methyl-5-oxo-4,5-dihydro-1H-pyrazol-3-yl)benzoic acid (0.25 g, 0.46 mmol) in DCM (3 mL) was added EDCI (0.18 g, 0.91 mmol) and DMAP (0.11 g, 0.91 mmol). The reaction mixture was stirred at room temperature until complete consumption of the starting material was observed by LC-MS. The reaction mixture was concentrated under reduced pressure and purified by silica gel chromatography eluting with 20-80% ethyl acetate in heptanes (0.20 g, 73%). LC-MS $t_R$=1.27 min, [M+Na]$^+$=570.

123.7 4-[4-(Hydroxyamino)-4-[1-(methoxyimino)ethyl]-1-methyl-5-oxo-4,5-dihydro-1H-pyrazol-3-yl]-N,N-dimethylbenzamide To a solution of 4-(4-{[(tert-butoxy)carbonyl]({[(tert-butoxy)carbonyl]oxy})amino}-4-[1-(methoxyimino)ethyl]-1-methyl-5-oxo-4,5-dihydro-1H-pyrazol-3-yl)-N,N-dimethylbenzamide (0.22 g, 0.37 mmol) in DCM (5 mL) was added hydrogen chloride as a 4 M solution in dioxane (1 mL) and the reaction mixture was stirred at room temperature until complete consumption of starting material was observed by LC-MS. The reaction mixture was concentrated under reduced pressure and purified by acidic preparative HPLC (65 mg, 50%). LC-MS $t_R$=0.92 min, [M+H]$^+$=348; $^1$H NMR (500 MHz, DMSO-d6) δ 7.95-7.91 (m, 2H), 7.85 (s, 1H), 7.48-7.43 (m, 2H), 6.67-6.64 (m, 1H), 3.74 (s, 3H), 3.02-2.88 (m, 6H), 1.67 (s, 3H).

Example 124

Compound 124 [4-[3-tert-Butyl-4-(hydroxyamino)-1-methyl-5-oxo-4,5-dihydro-1H-pyrazol-4-yl]-N,N-dimethylbenzamide]

124.1 4-(3-tert-Butyl-5-hydroxy-1-methyl-1H-pyrazol-4-yl)-N,N-dimethylbenzamide A solution of 4-bromo-3-tert-butyl-1-methyl-1H-pyrazol-5-yl benzoate (316 mg, 0.94 mmol), [4-(dimethylcarbamoyl)phenyl]boronic acid (183.4 mg, 0.95 mmol) and sodium bicarbonate (299 mg, 2.82 mmol) in 1,4-dioxane (6 mL) and water (0.75 mL) was purged with nitrogen and treated with tetrakis(triphenylphosphine)palladium(0) (55.23 mg, 0.05 mmol). The reaction mixture was stirred at 130° C. for 15 minutes (75 W) in a Biotage Initiator plus microwave. The crude reaction mixture was filtered over glass fibre filter paper and the aqueous layer was extracted with ethyl acetate (3×20 mL) and 2:1 chloroform:IPA (3×30 mL). The ethyl acetate extracts were discarded and the IPA:chloroform extracts were dried over magnesium sulfate, filtered and concentrated under reduced pressure. The resulting solid was washed with ethyl acetate to afford the title compound as an orange solid (138 mg, 28%). LC-MS $t_R$=0.88 min, [M+H]$^+$=302; $^1$H NMR (500 MHz, DMSO-d$_6$) δ 7.37 (d, J=8.1 Hz, 2H), 7.26 (d, J=8.1 Hz, 2H), 3.47 (s, 3H), 2.98 (s, 6H), 1.11 (s, 9H).

124.2 4-[3-tert-Butyl-4-(hydroxyamino)-1-methyl-5-oxo-4,5-dihydro-1H-pyrazol-4-yl]-N,N-dimethylbenzamide To a solution of 4-(3-tert-butyl-5-hydroxy-1-methyl-1H-pyrazol-4-yl)-N,N-dimethylbenzamide (135 mg, 0.3 mmol) in ethanol (4 mL) at room temperature was added N-hydroxy-2-methanesulfonylbenzene-1-sulfonamide (81.72 mg, 0.33 mmol) and the resulting cloudy suspension was stirred at room temperature for 5 minutes before the reaction mixture was cooled to −5° C. and an aqueous solution of potassium carbonate (53.12 mg, 0.38 mmol) and N,N-bis{2-[bis(carboxymethyl)amino]ethyl}glycine (34.89 mg, 0.09 mmol) in water (4 mL) was added. The reaction mixture was allowed to warm to room temperature and stirring was continued for a further 60 minutes, after which time analysis by LC-MS showed residual starting material evident and the reaction mixture was re-cooled to −5° C. and re-treated with N-hydroxy-2-methanesulfonylbenzene-1-sulfonamide (81.72 mg, 0.33 mmol) and left to stir for 1 hour before addition of a further solution of potassium carbonate (24 mg, 1.8 mmol) in water (0.5 mL). The reaction mixture was stirred for 3 hours before additional N-hydroxy-2-methanesulfonylbenzene-1-sulfonamide (163.4 mg, 0.66 mmol) and potassium carbonate (40 mg, 0.3 mmol) was added and stirring was continued for 17 hours. The crude reaction mixture was diluted with ethyl acetate (10 mL) and water (5 mL) and the organic layer was isolated. The aqueous layer was re-extracted with ethyl acetate (2×10 mL) and the combined organic layers were washed with brine (10 mL), dried over magnesium sulfate, filtered and concentrated under reduced pressure to afford the crude product. Purification was performed by acidic preparative HPLC to afford the title compound as a white solid (12 mg, 12% yield) after lyophilisation. LC-MS $t_R$=3.16 min, [M+H]$^+$=333; $^1$H NMR (500 MHz, DMSO-d6) δ 7.74 (d, J=1.4 Hz, 1H), 7.37 (d, J=8.3 Hz, 2H), 7.15 (d, J=8.2 Hz, 2H), 6.90 (s, 1H), 3.24 (s, 3H), 2.96 (s, 3H), 2.85 (s, 3H), 1.04 (s, 9H).

Example 125

Compound 125 [4-[1-[(Benzyloxy)imino]ethyl]-3-ethoxy-4-(hydroxyamino)-1-methyl-4,5-dihydro-1H-pyrazol-5-one]

125.1 1-Methylpyrazolidine-3,5-dione

To a solution of propanedioyl dichloride (3.5 mL, 35.47 mmol) in THF (15 ml) at room temperature was added a solution of methyl hydrazine (1.5 mL, 35.47 mmol) in THF (15 mL) and stirring was continued for 2 hours. The reaction mixture was concentrated under reduced pressure forming an orange solid (3.66 g, 54%); $^1$H NMR (500 MHz, Methanol-d4) δ 3.55 (s, 1H), 2.80 (s, 3H).

125.2 3-Ethoxy-1-methyl-1H-pyrazol-5-ol

A solution of 1-methylpyrazolidine-3,5-dione (3.66 g, 16.04 mmol) in ethanol (40 ml) and sulphuric acid (45 ul, 0.80 mmol) was heated to reflux for 15 hours through a soxlet condenser filled with 4 A molecular sieves. Additional sulphuric acid (45 ul, 0.80 mmol) was added and the reaction mixture heated to reflux for an additional 6 hours. The resulting solution was concentrated under reduced pressure forming the product as a yellow oil (2.56 g, 56%); $^1$H NMR (500 MHz, DMSO-d6) δ 4.14-4.09 (m, 2H), 2.98 (s, 1H), 2.59 (s, 3H), 1.24-1.14 (m, 3H).

125.3 4-Acetyl-3-ethoxy-1-methyl-4,5-dihydro-1H-pyrazol-5-one

3-Ethoxy-1-methyl-1H-pyrazol-5-ol (1.98 g, 6.96 mmol) was taken up in 1,1,1-trimethoxyethane (20 mL, 0.16 mol) and the resulting solution was heated to 75° C. for 18 hours. The solution was concentrated under reduced pressure and the resulting product dissolved in water and held for 6 hours at 5° C. The product remained as an oil so was extracted from the aqueous with DCM (2×40 mL), washed with brine (30 mL), dried over sodium sulfate, filtered and concentrated under reduced pressure to form the crude product as a brown oil. The product was purified using an SCX cartridge and was released with methanol (1.86 g, 58%). LC-MS $t_R$=0.94 min, [M+H]$^+$=185; $^1$H NMR (500 MHz, DMSO-d6) δ 4.25-4.16 (m, 2H), 3.64 (s, 1H), 3.16 (s, 3H), 2.34-2.17 (m, 3H), 1.42-1.24 (m, 3H).

125.4 4-[1-[(Benzyloxy)imino]ethyl]-3-ethoxy-1-methyl-1H-pyrazol-5-ol

To a suspension of 4-acetyl-3-ethoxy-1-methyl-4,5-dihydro-1H-pyrazol-5-one (1 g, 1.63 mmol) in methanol (25 mL) was added O-benzylhydroxylamine HCl (0.26 g, 1.63 mmol) and sodium bicarbonate (0.14 g, 1.63 mmol). The reaction mixture was heated to reflux for 2 hours, allowed to cool to room temperature and concentrated under reduced pressure. The crude product was purified by silica gel chromatography eluting with 0-30% ethyl acetate:heptanes to yield the title compound as a yellow oil (335 mg, 46%). LC-MS $t_R$=1.29 min, [M+H]$^+$=290; $^1$H NMR (500 MHz, DMSO-d6) δ 7.28-7.26 (m, 5H), 5.74 (s, 2H), 4.12-4.10 (m, 2H), 3.36 (s, 3H), 2.14 (s, 3H), 1.27 (t, J=7.0 Hz, 3H).

125.5 4-[1-[(Benzyloxy)imino]ethyl]-3-ethoxy-4-(hydroxyamino)-1-methyl-4,5-dihydro-1H-pyrazol-5-one To a solution of 4-[1-[(benzyloxy)imino]ethyl]-3-ethoxy-1-methyl-1H-pyrazol-5-ol (285 mg, 0.64 mmol) in ethanol (3 mL) at room temperature was added N-hydroxy-2-methanesulfonylbenzene-1-sulfonamide (354 mg, 1.41 mmol) and the reaction mixture was stirred at room temperature for 5 minutes before the reaction mixture was cooled to −5° C. and an aqueous solution of potassium carbonate (460.14 mg, 3.33 mmol) and N,N-bis {2-[bis(carboxymethyl)amino]ethyl}glycine (75.55 mg, 0.19 mmol) in water (2 mL) was added dropwise over 5 minutes. Stirring was continued for 1 hour, before further N-hydroxy-2-methanesulfonylbenzene-1-sulfonamide (354 mg, 1.41 mmol) and potassium carbonate (230 mg, 1.67 mmol) was added and stirring continued for a further 2 hours. The crude reaction mixture was extracted into ethyl acetate (2×25 mL), combined and washed with brine (30 mL), dried over sodium sulfate, filtered and concentrated under reduced pressure to afford the crude product as a yellow oil. Purification was performed by acidic preparative HPLC to afford the title compound as an oil (62 mg 30% yield). LC-MS $t_R$=1.06 min, [M+H]$^+$=321; $^1$H NMR (500 MHz, DMSO-d6) δ 7.92-7.86 (m, 1H), 7.40-7.24 (m, 5H), 6.52-6.47 (m, 1H), 5.06-4.95 (m, 2H), 4.28-4.14 (m, 2H), 3.09 (s, 3H), 1.81 (s, 3H), 1.27 (t, J=7.1 Hz, 3H).

Example 126

Compound 126 [3-Ethoxy-4-(hydroxyamino)-4-[1-(methoxyimino)ethyl]-1-methyl-4,5-dihydro-1H-pyrazol-5-one]

126.1 3-Ethoxy-4-[1-(methoxyimino)ethyl]-1-methyl-1H-pyrazol-5-ol

To a suspension of 1-(3-ethoxy-5-hydroxy-1-methyl-1H-pyrazol-4-yl)ethan-1-one (854 mg, 1.39 mmol) in methanol (20 mL) was added O-methylhydroxylamine HCl (0.17 g, 2.09 mmol) and sodium hydrogen carbonate (0.12 g, 1.39 mmol) and the reaction mixture was heated to reflux for 2 hours. The reaction mixture was allowed to cool to room temperature, concentrated under reduced pressure and the product was purified by silica gel chromatography eluting with 0-100% ethyl acetate in heptane (110 mg, 22%). LC-MS $t_R$=0.98 min, [M+H]$^+$=214; $^1$H NMR (250 MHz, DMSO-d6) δ 4.23-4.10 (m, 2H), 3.82-3.76 (m, 3H), 3.38 (s, 3H), 2.14 (s, 3H), 1.30 (t, J=7.0 Hz, 3H).

126.2 3-Ethoxy-4-(hydroxyamino)-4-[1-(methoxyimino)ethyl]-1-methyl-4,5-dihydro-1H-pyrazol-5-one To a solution of 3-ethoxy-4-[1-(methoxyimino)ethyl]-1-methyl-1H-pyrazol-5-ol (110 mg, 0.31 mmol) in ethanol (3 mL) at room temperature was added N-hydroxy-2-methanesulfonylbenzene-1-sulfonamide (171 mg, 0.68 mmol) and the reaction mixture was stirred at room temperature for 5 minutes before the reaction mixture was cooled to −5° C. and an aqueous solution of potassium carbonate (112 mg, 0.81 mmol) and N,N-bis{2-[bis(carboxymethyl)amino]ethyl}glycine (37 mg, 0.09 mmol) in water (2 mL) was added dropwise over 5 minutes. Stirring was continued for 1 hour, before further N-hydroxy-2-methanesulfonylbenzene-1-sulfonamide (100 mg, 0.4 mmol) was added and stirring continued for 2 hours. The crude reaction mixture was extracted into ethyl acetate (3×30 mL), combined and washed with brine (40 mL), dried over sodium sulfate, filtered and concentrated under reduced pressure to afford the crude product as a yellow oil. Purification was performed by silica gel chromatography eluting with 0-75% ethyl acetate in heptanes and lyophilized to yield the title compound as an off white solid (21 mg, 27%). LC-MS $t_R$=0.85 min, [M+H]$^+$=245; $^1$H NMR (500 MHz, DMSO-d6) δ 7.91-7.89 (m, 1H), 6.49-6.47 (m, 1H), 4.29-4.18 (m, 2H), 3.76 (s, 3H), 3.10 (s, 3H), 1.78 (s, 3H), 1.31 (t, J=7.1 Hz, 3H).

Example 127

Compound 127 [3-Ethoxy-4-(hydroxyamino)-4-methyl-1-phenyl-4,5-dihydro-1H-pyrazol-5-one]

127.1 2-Methylpropanedioyl dichloride

To a solution of 2-methylpropanedioic acid (3.0 g, 25.40 mmol) in DCM (20 mL) cooled to 0° C. was sequentially added DMF (0.01 mL) and oxalyl chloride (6.5 mL, 76.21 mmol). The reaction mixture was allowed to warm to a temperature of about 25° C. and stirred until complete consumption of the starting material was observed by TLC. The reaction mixture was concentrated under reduced pressure forming the title product (3.15 g, 60% yield). 1H NMR (500 MHz, DMSO-d6) δ 4.54 (q, J=6.9 Hz, 1H), 1.18 (d, J=7.2 Hz, 3H).

127.2 4-Methyl-1-phenylpyrazolidine-3,5-dione

To a solution of 2-methylpropanedioyl dichloride (3.15 g, 15.24 mmol) in THF (20 mL) cooled to −40° C. was added a solution of phenyl hydrazine (1.5 mL, 15.24 mmol) in THF (20 mL) over 10 minutes. The reaction mixture was then allowed to warm to a temperature of about 25° C. and stirred until complete consumption of the starting material was observed by LC-MS. The reaction mixture was concentrated under reduced pressure and the product was purified by silica gel chromatography eluting with 0-80% ethyl acetate in heptanes (1.72 g, 39% yield). LC-MS $t_R$=0.78 min, $[M+H]^+$=191, $^1$H NMR (500 MHz, DMSO-d6) δ 7.51-7.16 (m, 5H), 3.65-3.64 (m, 1H), 1.28-1.20 (m, 3H).

127.3 3-Ethoxy-4-methyl-1-phenyl-4,5-dihydro-1H-pyrazol-5-one

To a solution of 4-methyl-1-phenylpyrazolidine-3,5-dione (1.72 g, 5.88 mmol) in ethanol (35 mL) was added sulfuric acid (16 μL) and the reaction mixture was heated to 80° C. until complete consumption of the starting material was observed by LC-MS. The reaction mixture was concentrated under reduced pressure and the product was purified by silica gel chromatography eluting with 0-20% ethyl acetate in heptanes (0.16 g, 9% yield). LC-MS $t_R$=1.18 min, $[M+H]^+$=219, $^1$H NMR (250 MHz, DMSO-d6) δ 7.86-7.77 (m, 1H), 7.69-7.61 (m, 1H), 7.47-7.29 (m, 2H), 7.16-7.10 (m, 1H), 4.20-4.00 (m, 2H), 3.67-3.41 (m, 1H), 1.33-1.23 (m, 3H), 1.22-1.14 (m, 3H).

127.4 3-Ethoxy-4-(hydroxyamino)-4-methyl-1-phenyl-4,5-dihydro-1H-pyrazol-5-one To a solution of 3-ethoxy-4-methyl-1-phenyl-4,5-dihydro-1H-pyrazol-5-one (0.16 g, 0.55 mmol) in ethanol (2 mL) cooled to 0° C. was added N-hydroxy-2-methanesulfonylbenzene-1-sulfonamide (0.30 g, 1.20 mmol) and the reaction mixture was stirred for 5 minutes before an aqueous solution of potassium carbonate (0.20 g, 1.42 mmol) and N,N-bis{2-[bis(carboxymethyl)amino]ethyl}glycine (0.06 g, 0.16 mmol) in water (2 mL) was added over 5 minutes. The reaction mixture was allowed to warm to a temperature of about 25° C. and stirred until complete consumption of the starting material was observed by LC-MS. The reaction mixture was diluted with water (10 mL) and extracted into ethyl acetate (2×20 mL). The organic layers were combined, washed with brine (20 mL), dried over sodium sulfate, filtered and concentrated under reduced pressure and the product was purified using acidic preparative HPLC (15 mg, 11% yield). LC-MS $t_R$=1.09 min, $[M+H]^+$=250, $^1$H NMR (500 MHz, DMSO-d6) δ 7.91-7.77 (m, 3H), 7.48-7.33 (m, 2H), 7.19-7.10 (m, 1H), 6.48-6.36 (m, 1H), 4.45-4.27 (m, 2H), 1.38 (t, J=7.1 Hz, 3H), 1.21 (s, 3H).

Example 128

Compound 128 [4-(Hydroxyamino)-4-[1-(methoxyimino)ethyl]-1-phenyl-3-(phenylsulfanyl)-4,5-dihydro-1H-pyrazol-5-one]

128.1 1-Phenyl-3-(phenylsulfanyl)-1H-pyrazol-5-ol

3-Ethoxy-1-phenyl-4,5-dihydro-1H-pyrazol-5-one (1.45 g, 4.97 mmol) was added to methanesulfonic acid (1.9 mL 19.88 mmol) and benzenethiol (0.77 mL, 7.45 mmol) and the reaction mixture was heated at 130° C. for 6 hours. The reaction mixture was cooled to about 25° C. and DCM (30 mL) was added. The organics were washed with brine (30 mL), dried over sodium sulfate, concentrated under reduced pressure and the product was purified using silica gel chromatography eluting with 0-80% ethyl acetate in heptanes (0.74 g, 46% yield). LC-MS $t_R$=1.20 min, $[M+H]^+$=269, $^1$H NMR (500 MHz, DMSO-d6) δ 7.76-7.67 (m, 2H), 7.51-7.44 (m, 2H), 7.43-7.12 (m, 6H), 5.57 (s, 1H).

128.2 1-[5-Hydroxy-1-phenyl-3-(phenylsulfanyl)-1H-pyrazol-4-yl]ethan-1-one

1-[5-Hydroxy-1-phenyl-3-(phenylsulfanyl)-1H-pyrazol-4-yl]ethan-1-one was synthesized from 1-phenyl-3-(phenylsulfanyl)-1H-pyrazol-5-ol according to General Method 11 (0.65 g, 32% yield). LC-MS $t_R$=1.35 min, $[M+H]^+$=311, $^1$H NMR (500 MHz, DMSO-d6) δ 7.71-7.59 (m, 2H), 7.54-7.49 (m, 2H), 7.46-7.17 (m, 6H), 3.20-3.10 (m, 3H).

128.3 4-[1-(Methoxyimino)ethyl]-1-phenyl-3-(phenylsulfanyl)-4,5-dihydro-1H-pyrazol-5-one 4-[1-(Methoxyimino)ethyl]-1-phenyl-3-(phenylsulfanyl)-4,5-dihydro-1H-pyrazol-5-one was synthesized from 1-[5-hydroxy-1-phenyl-3-(phenylsulfanyl)-1H-pyrazol-4-yl]ethan-1-one according to General Method 12 and the product was purified by silica gel chromatography eluting with 0-40% ethyl acetate in heptanes (0.14 g, 65% yield). LC-MS $t_R$=1.46 min, $[M+H]^+$=340, $^1$H NMR (500 MHz, DMSO-d6) δ 7.89-7.69 (m, 2H), 7.52-7.43 (m, 3H), 7.39-7.32 (m, 5H), 3.80 (s, 3H), 2.11 (s, 3H).

128.4 4-Bromo-4-[1-(methoxyimino)ethyl]-1-phenyl-3-(phenylsulfanyl)-4,5-dihydro-1H-pyrazol-5-one 4-Bromo-4-[1-(methoxyimino)ethyl]-1-phenyl-3-(phenylsulfanyl)-4,5-dihydro-1H-pyrazol-5-one was synthesised from 4-[1-(methoxyimino)ethyl]-1-phenyl-3-(phenylsulfanyl)-4,5-dihydro-1H-pyrazol-5-one according to General Method 6 (0.07 g, 41% yield). LC-MS $t_R$=1.52 min, $[M+H]^+$=418.

128.5 4-{[(tert-Butoxy)carbonyl]({[(tert-butoxy)carbonyl]oxy})amino}-4-[1-(methoxyimino)ethyl]-1-phenyl-3-(phenylsulfanyl)-4,5-dihydro-1H-pyrazol-5-one 4-{[(tert-Butoxy)carbonyl]({[(tert-butoxy)carbonyl]oxy})amino}-4-[1-(methoxyimino)ethyl]-1-phenyl-3-(phenylsulfanyl)-4,5-dihydro-1H-pyrazol-5-one was synthesized from 4-bromo-4-[1-(methoxyimino)ethyl]-1-phenyl-3-(phenylsulfanyl)-4,5-dihydro-1H-pyrazol-5-one according to General Method 8 and the product was purified by silica gel chromatography eluting with 0-20% ethyl acetate in heptanes (0.08 g, 91% yield). LC-MS $t_R$=1.58 min, $[M+Na]^+$=593.

128.6 4-(Hydroxyamino)-4-[1-(methoxyimino)ethyl]-1-phenyl-3-(phenylsulfanyl)-4,5-dihydro-1H-pyrazol-5-one 4-(Hydroxyamino)-4-[1-(methoxyimino)ethyl]-1-phenyl-3-(phenylsulfanyl)-4,5-dihydro-1H-pyrazol-5-one was synthesized from 4-{[(tert-butoxy)carbonyl]({[(tert-butoxy)carbonyl]oxy})amino}-4-[1-(methoxyimino)ethyl]-1-phenyl-3-(phenylsulfanyl)-4,5-dihydro-1H-pyrazol-5-one according to General Method 9 and the product was purified by acidic preparative HPLC (2 mg, 7% yield). LC-MS $t_R$=1.25 min, [M+H]$^+$=371, $^1$H NMR (500 MHz, DMSO-d6) δ 8.19-8.14 (m, 1H), 7.73-7.67 (m, 2H), 7.64-7.57 (m, 2H), 7.53-7.45 (m, 3H), 7.42-7.35 (m, 2H), 7.22-7.13 (m, 1H), 7.01-6.97 (m, 1H), 3.81 (s, 3H), 1.90 (s, 3H).

Example 129

Compound 129 [3-(Benzenesulfonyl)-4-(hydroxyamino)-4-[1-(methoxyimino)ethyl]-1-phenyl-4,5-dihydro-1H-pyrazol-5-one pyrazol-5-one]

129.1 3-(Benzenesulfonyl)-4-{[(tert-butoxy)carbonyl]({[(tert-butoxy)carbonyl]oxy})amino}-4-[1-(methoxyimino)ethyl]-1-phenyl-4,5-dihydro-1H-pyrazol-5-one 3-(Benzenesulfonyl)-4-{[(tert-butoxy)carbonyl]({[(tert-butoxy)carbonyl]oxy})amino}-4-[1-(methoxyimino)ethyl]-1-phenyl-4,5-dihydro-1H-pyrazol-5-one was synthesized from 4-{[(tert-butoxy)carbonyl]({[(tert-butoxy)carbonyl]oxy})amino}-4-[1-(methoxyimino)ethyl]-1-phenyl-3-(phenylsulfanyl)-4,5-dihydro-1H-pyrazol-5-one according to General Method 10 (399 mg, 35% yield). LC-MS $t_R$=1.46 min, [M+Na]$^+$=626.

129.2 3-(Benzenesulfonyl)-4-(hydroxyamino)-4-[1-(methoxyimino)ethyl]-1-phenyl-4,5-dihydro-1H-pyrazol-5-one pyrazol-5-one 3-(Benzenesulfonyl)-4-(hydroxyamino)-4-[1-(methoxyimino)ethyl]-1-phenyl-4,5-dihydro-1H-pyrazol-5-one pyrazol-5-one was synthesized from 3-(benzenesulfonyl)-4-{[(tert-butoxy)carbonyl]({[(tert-butoxy)carbonyl]oxy})amino}-4-[1-(methoxyimino)ethyl]-1-phenyl-4,5-dihydro-1H-pyrazol-5-one according to General Method 9 and the product was purified by acidic preparative HPLC (8 mg, 8% yield). LC-MS $t_R$=1.25 min, [M+H]$^+$=403, $^1$H NMR (500 MHz, DMSO-d6) δ 8.39-8.29 (m, 1H), 8.13-8.00 (m, 2H), 7.86-7.77 (m, 1H), 7.77-7.67 (m, 2H), 7.64-7.58 (m, 2H), 7.52-7.46 (m, 2H), 7.38-7.27 (m, 1H), 6.91-6.83 (m, 1H), 3.65 (s, 3H), 1.87 (s, 3H).

Example 130

Compound 130 [3-(Benzenesulfinyl)-4-(hydroxyamino)-4-[1-(methoxyimino)ethyl]-1-phenyl-4,5-dihydro-1H-pyrazol-5-one]

130.1 3-(Benzenesulfinyl)-4-{[(tert-butoxy)carbonyl]({[(tert-butoxy)carbonyl]oxy})amino}-4-[1-(methoxyimino)ethyl]-1-phenyl-4,5-dihydro-1H-pyrazol-5-one 3-(Benzenesulfinyl)-4-{[(tert-butoxy)carbonyl]({[(tert-butoxy)carbonyl]oxy})amino}-4-[1-(methoxyimino)ethyl]-1-phenyl-4,5-dihydro-1H-pyrazol-5-one was synthesized from 4-{[(tert-butoxy)carbonyl]({[(tert-butoxy)carbonyl]oxy})amino}-4-[1-(methoxyimino)ethyl]-1-phenyl-3-(phenylsulfanyl)-4,5-dihydro-1H-pyrazol-5-one according to General Method 10 (399 mg, 36% yield). LC-MS $t_R$=1.41 min, [M+Na]$^+$=609.

130.2 3-(Benzenesulfinyl)-4-(hydroxyamino)-4-[1-(methoxyimino)ethyl]-1-phenyl-4,5-dihydro-1H-pyrazol-5-one 3-(Benzenesulfinyl)-4-(hydroxyamino)-4-[1-(methoxyimino)ethyl]-1-phenyl-4,5-dihydro-1H-pyrazol-5-one was synthesised from 3-(benzenesulfinyl)-4-{[(tert-butoxy)carbonyl]({[(tert-butoxy)carbonyl]oxy})amino}-4-[1-(methoxyimino)ethyl]-1-phenyl-4,5-dihydro-1H-pyrazol-5-one according to General Method 9 and the product was purified by acidic preparative HPLC (26 mg, 25% yield). LC-MS $t_R$=1.13 min, [M+H]$^+$=387, $^1$H NMR (500 MHz, DMSO-d6) δ 8.30-8.25 (m, 1H), 7.90-7.81 (m, 2H), 7.69-7.56 (m, 5H), 7.50-7.41 (m, 2H), 7.29-7.24 (m, 1H), 6.94-6.88 (m, 1H), 3.75-3.72 (m, 3H), 1.83 (s, 3H).

Example 131

Compound 131 [3-tert-Butyl-4-(hydroxyamino)-4-[1-(methoxyimino)ethyl]-4,5-dihydro-1H-pyrazol-5-one]

131.1 3-tert-Butyl-1H-pyrazol-5-ol

To a solution of ethyl 4,4-dimethyl-3-oxopentanoate (10 g, 58.06 mmol) in ethanol (40 mL) was added a solution of hydrazine hydrate (2.91 mL) and the reaction mixture was heated to 70° C. until complete consumption of the starting material was observed by LC-MS. The reaction mixture was allowed to cool to about 25° C. and concentrated under reduced pressure (6.40 g, 72% yield). LC-MS $t_R$=0.66 min, [M+H]$^+$=141, $^1$H NMR (500 MHz, DMSO-d6) δ 5.22 (s, 1H), 1.20 (s, 9H).

131.2 1-(3-tert-Butyl-5-hydroxy-1H-pyrazol-4-yl)ethan-1-one 1-(3-tert-Butyl-5-hydroxy-1H-pyrazol-4-yl)ethan-1-one was synthesized from 3-tert-butyl-1H-pyrazol-5-ol according to General Method 11 and the product was purified by silica gel chromatography eluting with 20-100% ethyl acetate in heptanes (6.52 g, 68% yield). LC-MS $t_R$=0.82 min, [M+H]$^+$=183, $^1$H NMR (500 MHz, DMSO-d6) δ 4.03 (s, 3H), 1.30 (s, 9H).

131.3 3-tert-Butyl-4-[1-(methoxyimino)ethyl]-1H-pyrazol-5-ol 3-tert-Butyl-4-[1-(methoxyimino)ethyl]-1H-pyrazol-5-ol was synthesized from 1-(3-tert-butyl-5-hydroxy-1H-pyrazol-4-yl)ethan-1-one according to General Method 12 and the product was purified by silica gel chromatography eluting with 20-80% ethyl acetate in heptanes (444 mg, 92% yield). LC-MS $t_R$=0.82 min, [M+H]$^+$=212, $^1$H NMR (500 MHz, DMSO-d6) δ 3.80 (s, 3H), 1.97 (s, 3H), 1.27 (s, 9H).

131.4 tert-Butyl N-{3-tert-butyl-4-[1-(methoxyimino)ethyl]-5-oxo-4,5-dihydro-1H-pyrazol-4-yl}-N-hydroxycarbamate tert-Butyl N-{3-tert-butyl-4-[1-(methoxyimino)ethyl]-5-oxo-4,5-dihydro-1H-pyrazol-4-yl}-N-hydroxycarbamate was synthesized from 3-tert-butyl-4-[1-(methoxyimino)ethyl]-1H-pyrazol-5-ol according to General Method 17 and was purified by silica gel chromatography eluting with 10-70% ethyl acetate in heptanes (533 mg, 29% yield). LC-MS $t_R$=1.09 min, [M+Na]$^+$=365.

131.5 3-tert-Butyl-4-(hydroxyamino)-4-[1-(methoxyimino)ethyl]-4,5-dihydro-1H-pyrazol-5-one 3-tert-Butyl-4-(hydroxyamino)-4-[1-(methoxyimino) ethyl]-4,5-dihydro-1H-pyrazol-5-one was synthesized from tert-butyl N-{3-tert-butyl-4-[1-(methoxyimino)ethyl]-5-oxo-4,5-dihydro-1H-pyrazol-4-yl}-N-hydroxycarbamate according to General Method 9 and the product was purified by acidic preparative HPLC (13 mg, 11% yield). LC-MS $t_R$=0.92 min, [M+H]$^+$=243, $^1$H NMR (500 MHz, DMSO-d6) δ 7.62-7.52 (m, 1H), 6.20-6.11 (m, 1H), 3.80 (s, 3H), 1.58 (s, 3H), 1.21 (s, 9H).

Example 132

Compound 132 [4-(Hydroxyamino)-1,3-dimethyl-4-(5-phenyl-1,2,4-oxadiazol-3-yl)-4,5-dihydro-1H-pyrazol-5-one]

132.1 N'-hydroxy-5-methoxy-1,3-dimethyl-1H-pyrazole-4-carboximidamide

5-Methoxy-1,3-dimethyl-1H-pyrazole-4-carbonitrile (0.74 g, 4.92 mmol), hydroxylamine chloride (0.68 g, 9.84 mmol) and potassium carbonate (0.85 g, 6.15 mmol) were dissolved in ethanol (10 mL) and the reaction mixture was heated to 80 OC for 48 hours. The reaction mixture was allowed to cool to about 25° C. and filtered to remove the inorganic salts. The resulting filtrate was concentrated under reduced pressure to afford 0.652 g of a beige solid, which was dissolved in methanol and loaded on to a 10 g SCX cartridge. The cartridge was flushed with methanol (20 mL) and 2 M ammonia in methanol (20 mL). The latter was concentrated under reduced pressure to yield the title compound. (270 mg, 30% yield). LC-MS $t_R$=0.16 min, [M+H]$^+$=185.

132.2 [Amino(5-methoxy-1,3-dimethyl-1H-pyrazol-4-yl)methylidene]amino benzoate To a solution of benzoic acid (149.17 µl, 1.61 mmol) in dry DMF (4 mL) was added HATU (613.09 mg, 1.61 mmol) and DIPEA (280.85 µl, 1.61 mmol) and the reaction mixture was stirred at about 25° C. for 0.5 hours under a nitrogen atmosphere. N'-hydroxy-5-methoxy-1,3-dimethyl-1H-pyrazole-4-carboximidamide (270 mg, 1.47 mmol) was added and the reaction mixture was stirred for 17 hours. DMF was removed under reduced pressure and the residue was dissolved in DCM (20 mL), washed with 1M sodium bicarbonate (20 mL), water (20 mL) and brine (20 mL). The resulting organic layer was dried over sodium sulfate, filtered and concentrated on to silica. Purification was performed by silica gel chromatography eluting with 0-100% ethyl acetate in heptanes (308 mg, 71% yield). LC-MS $t_R$=0.98 min, [M+H]$^+$=289.

132.3 3-(5-Methoxy-1,3-dimethyl-1H-pyrazol-4-yl)-5-phenyl-1,2,4-oxadiazole

To a solution of [amino(5-methoxy-1,3-dimethyl-1H-pyrazol-4-yl)methylidene]amino benzoate (225 mg, 0.78 mmol) in 1,4-dioxane (3 mL) in a pressure vessel was added potassium carbonate (216 mg, 1.56 mmol) and the reaction mixture was heated to 120 OC for 60 minutes. The reaction mixture was cooled to about 25° C., filtered and washed with 1,4-dioxane and the resulting orange filtrate was concentrated under reduced pressure and purified by silica gel chromatography eluting with 0-80% ethyl acetate in heptanes (20 mg, 8% yield). LC-MS $t_R$=1.16 min, [M+H]$^+$=271.

132.4 1,3-Dimethyl-4-(5-phenyl-1,2,4-oxadiazol-3-yl)-1H-pyrazol-5-ol

To a solution of 3-(5-methoxy-1,3-dimethyl-1H-pyrazol-4-yl)-5-phenyl-1,2,4-oxadiazole (20 mg, 0.07 mmol) in anhydrous DCM (1.5 mL) cooled to 0° C. was added 1M BBr$_3$ in DCM (296 µl, 0.296 mmol) drop wise. The reaction mixture was allowed to warm to about 25° C. and was retreated with 1M BBr$_3$ in DCM (296 µl, 0.296 mmol) after 2 hours and again after 17 hours (100 µl, 0.1 mmol). The reaction mixture was stirred at about 25° C. for an additional 2 hours before ice-water (5 mL) and DCM (15 mL) were added to the reaction mixture and the layers were separated. The aqueous layer was re-extracted with DCM (3×10 mL) and the DCM layers combined. The combined organic layers were dried over magnesium sulfate, filtered and concentrated under reduced pressure (24 mg, 100% yield). LC-MS $t_R$=0.97 min, [M+H]$^+$=257.

132.5 tert-Butyl N-[1,3-dimethyl-5-oxo-4-(5-phenyl-1,2,4-oxadiazol-3-yl)-4,5-dihydro-1H-pyrazol-4-yl]-N-hydroxycarbamate tert-Butyl N-[1,3-dimethyl-5-oxo-4-(5-phenyl-1,2,4-oxadiazol-3-yl)-4,5-dihydro-1H-pyrazol-4-yl]-N-hydroxycarbamate was synthesized from 1,3-dimethyl-4-(5-phenyl-1,2,4-oxadiazol-3-yl)-1H-pyrazol-5-ol according to General Method 17 (40.4 mg, 89% yield). LC-MS $t_R$=1.13 min, [M+Na]$^+$=410.

132.6 4-(Hydroxyamino)-1,3-dimethyl-4-(5-phenyl-1,2,4-oxadiazol-3-yl)-4,5-dihydro-1H-pyrazol-5-one 4-(Hydroxyamino)-1,3-dimethyl-4-(5-phenyl-1,2,4-oxadiazol-3-yl)-4,5-dihydro-1H-pyrazol-5-one was synthesized from tert-butyl N-[1,3-dimethyl-5-oxo-4-(5-phenyl-1,2,4-oxadiazol-3-yl)-4,5-dihydro-1H-pyrazol-4-yl]-N-hydroxycarbamate according to General Method 8 and was purified using acidic preparative HPLC (4.9 mg, 21% yield). LC-MS $t_R$=0.97 min, [M+H]$^+$=288. $^1$H NMR (500 MHz, DMSO-d6) δ 8.17 (d, J=2.8 Hz, 1H), 8.11-8.04 (m, 2H), 7.77-7.69 (m, 1H), 7.64 (t, J=7.7 Hz, 2H), 7.03 (d, J=2.7 Hz, 1H), 3.23 (s, 3H), 2.06 (s, 3H).

Example 133

Compound 133 [4-(Hydroxyamino)-3-(4-methanesulfonylphenyl)-4-methyl-4,5-dihydro-1H-pyrazol-5-one]

133.1 3-[4-(Methylsulfanyl)phenyl]-1H-pyrazol-5-ol

To a solution of methyl 3-[4-(methylsulfanyl)phenyl]-3-oxopropanoate (10 g, 44.59 mmol) in ethanol (100 mL) was added hydrazine hydrate (2.68 mL, 53.51 mmol) and the reaction mixture was stirred at 70° C. for 4 hours. The reaction mixture was allowed to cool to about 25° C. and the resulting solid was isolated by filtration and washed with heptanes (20 mL). LC-MS $t_R$=0.94 min, [M+H]$^+$=207, $^1$H NMR (250 MHz, DMSO-d6) δ 7.70-7.51 (m, 2H), 7.37-7.17 (m, 2H), 5.86 (s, 1H), 2.49 (s, 3H).

133.2 5-Hydroxy-3-[4-(methylsulfanyl)phenyl]-1H-pyrazole-4-carbaldehyde

5-Hydroxy-3-[4-(methylsulfanyl)phenyl]-1H-pyrazole-4-carbaldehyde was synthesized from 3-[4-(methylsulfanyl)phenyl]-1H-pyrazol-5-ol according to General Method 3 and was used directly without additional purification (3.5 g, 80%). LC-MS $t_R$=0.93 min, [M+H]$^+$=235, $^1$H NMR (250 MHz, DMSO-d6) δ 9.75 (s, 1H), 7.86-7.72 (m, 2H), 7.42-7.28 (m, 2H), 2.53 (s, 3H).

133.3 4-Methyl-3-[4-(methylsulfanyl)phenyl]-1H-pyrazol-5-ol

4-Methyl-3-[4-(methylsulfanyl)phenyl]-1H-pyrazol-5-ol was synthesized from 5-hydroxy-3-[4-(methylsulfanyl)phenyl]-1H-pyrazole-4-carbaldehyde according to General Method 5 and was purified by trituration with methanol (3.8 g, 95%). LC-MS $t_R$=1.72 min, [M+H]$^+$=221, $^1$H NMR (500 MHz, DMSO-d6) δ 11.69 (s, 1H), 7.47 (d, J=8.1 Hz, 2H), 7.35 (d, J=7.0 Hz, 2H), 1.94 (s, 6H).

133.4 N-Hydroxy-N-{4-methyl-3-[4-(methylsulfanyl)phenyl]-5-oxo-4,5-dihydro-1H-pyrazol-4-yl}carbamate N-Hydroxy-N-{4-methyl-3-[4-(methylsulfanyl)phenyl]-5-oxo-4,5-dihydro-1H-pyrazol-4-yl}carbamate was synthesised from 4-methyl-3-[4-(methylsulfanyl)phenyl]-1H-pyrazol-5-ol according to General Method 17 and was purified by silica gel chromatography eluting with 0-100% ethyl acetate in heptanes (413 mg, 59%). LC-MS $t_R$=1.05 min, [M−H]$^-$=350, $^1$H NMR (500 MHz, Methanol-d$_4$) δ 7.85 (d, J=8.7 Hz, 2H), 7.30 (d, J=8.7 Hz, 2H), 2.51 (s, 3H), 1.64 (s, 3H), 1.28 (s, 9H).

133.5 tert-Butyl N-hydroxy-N-[3-(4-methanesulfonylphenyl)-4-methyl-5-oxo-4,5-dihydro-1H-pyrazol-4-yl]carbamate Potassium O-(hydroperoxysulfonyl)oxidanidolate (5.56 g, 9.06 mmol) in water (10 vol) was added dropwise to a solution of N-hydroxy-N-{4-methyl-3-[4-(methylsulfanyl)phenyl]-5-oxo-4,5-dihydro-1H-pyrazol-4-yl}carbamate (1.59 g, 4.53 mmol) (1 equiv) in 1,4-dioxane (10 vol) at 0 OC. The reaction mixture was stirred at about 25° C. for 1 hour after which time the reaction mixture was filtered. The filtrate was diluted with ethyl acetate (10 vol) and the aqueous layer was re-extracted into ethyl acetate (2×10 vol). The combined organic layers were washed with brine (10 vol), dried over sodium sulfate, filtered and concentrated under reduced pressure. The crude product was used directly without additional purification (1.7 g, 79%). LC-MS $t_R$=0.88 min, [M−H]$^-$=382, $^1$H NMR (500 MHz, Methanol-d4) δ 8.20-8.14 (m, 2H), 8.05-7.99 (m, 2H), 3.15 (s, 3H), 1.67 (s, 3H), 1.29 (s, 9H).

133.6 4-(Hydroxyamino)-3-(4-methanesulfonylphenyl)-4-methyl-4,5-dihydro-1H-pyrazol-5-one 4-(Hydroxyamino)-3-(4-methanesulfonylphenyl)-4-methyl-4,5-dihydro-1H-pyrazol-5-one was synthesized from tert-butyl N-hydroxy-N-[3-(4-methanesulfonylphenyl)-4-methyl-5-oxo-4,5-dihydro-1H-pyrazol-4-yl]carbamate according to General Method 9 (using 50 equiv of TFA) and was purified by silica gel chromatography eluting with 0-70% ethyl acetate in heptanes (836 mg, 76%). LC-MS $t_R$=0.77 min, [M−H]$^-$=282, $^1$H NMR (500 MHz, DMSO-d$_6$) δ 11.66 (s, 1H), 8.30-8.24 (m, 2H), 8.00 (d, J=8.6 Hz, 2H), 7.66 (d, J=2.6 Hz, 1H), 6.52 (d, J=2.6 Hz, 1H), 3.25 (s, 3H), 1.22 (s, 3H).

Example 134

Compound 134 [3-tert-Butyl-4-[1-(ethoxyimino)ethyl]-4-(hydroxyamino)-4,5-dihydro-1H-pyrazol-5-one]

134.1 3-tert-Butyl-4-[1-(ethoxyimino)ethyl]-1H-pyrazol-5-ol 3-tert-Butyl-4-[1-(ethoxyimino)ethyl]-1H-pyrazol-5-ol was synthesized from 1-(3-tert-butyl-5-hydroxy-1H-pyrazol-4-yl)ethan-1-one according to General Method 12 and the product was purified by silica gel chromatography eluting with 20-80% ethyl acetate in heptanes (0.38 g, 78% yield). LC-MS $t_R$=1.01 min, [M+H]$^+$=226, $^1$H NMR (500 MHz, DMSO-d6) δ 4.11-4.01 (m, 2H), 1.97 (s, 3H), 1.30-1.17 (m, 12H).

134.2 tert-Butyl N-{3-tert-butyl-4-[1-(ethoxyimino)ethyl]-5-oxo-4,5-dihydro-1H-pyrazol-4-yl}-N-hydroxycarbamate tert-Butyl N-{3-tert-butyl-4-[1-(ethoxyimino)ethyl]-5-oxo-4,5-dihydro-1H-pyrazol-4-yl}-N-hydroxycarbamate was synthesized from 3-tert-butyl-4-[1-(ethoxyimino)ethyl]-1H-pyrazol-5-ol according to General Method 17. Purification was carried out by silica gel chromatography eluting with 10-70% ethyl acetate in heptanes (0.53 g, 39% yield). LC-MS $t_R$=1.13 min, [M+Na]$^+$=379, $^1$H NMR (500 MHz, DMSO-d6) δ 8.51-8.40 (m, 1H), 4.10-3.90 (m, 2H), 2.15-1.81 (m, 3H), 1.41-1.35 (m, 12H), 1.24-1.13 (m, 9H).

134.2 3-tert-Butyl-4-(hydroxyamino)-4-[1-(ethoxyimino)ethyl]-4,5-dihydro-1H-pyrazol-5-one 3-tert-Butyl-4-(hydroxyamino)-4-[1-(ethoxyimino)ethyl]-4,5-dihydro-1H-pyrazol-5-one was synthesized from tert-butyl N-{3-tert-butyl-4-[1-(ethoxyimino)ethyl]-5-oxo-4,5-dihydro-1H-pyrazol-4-yl}-N-hydroxycarbamate according to General Method 9 and the product was purified by acidic preparative HPLC (7 mg, 6% yield). LC-MS $t_R$=2.43 min, [M+H]$^+$=257, $^1$H NMR (500 MHz, DMSO-d6) δ 11.19 (s, 1H), 7.53 (s, 1H), 6.16 (s, 1H), 4.05 (q, J=7.0 Hz, 2H), 1.57 (s, 3H), 1.20 (s, 9H), 1.17 (t, J=7.0 Hz, 3H).

134.3 3-tert-Butyl-4-[1-(ethoxyimino)ethyl]-4-(hydroxyamino)-4,5-dihydro-1H-pyrazol-5-one

Example 135

Compound 135 [4-[4-(Hydroxyamino)-4-methyl-5-oxo-4,5-dihydro-1H-pyrazol-3-yl]-N,N-dimethylbenzene-1-sulfonamide]

135.1 Methyl 3-[4-(dimethylsulfamoyl)phenyl]-2-methyl-3-oxopropanoate

To a solution of methyl 3-[4-(dimethylsulfamoyl)phenyl]-3-oxopropanoate (0.69 g, 2.42 mmol) in DMF (5 mL) was added potassium carbonate (0.33 g, 2.42 mmol) and methyl iodide (0.17 mL, 2.66 mmol). The resulting reaction mixture was stirred for 3 hours at about 25° C. before water (10 mL) was added and the resulting solution was extracted with dichloromethane (3×20 mL). The combined organic extracts were washed with brine (10 mL), dried over sodium sulfate and concentrated under reduced pressure to afford a colourless oil which solidified on standing (0.7 g, 75%). LC-MS $t_R$=1.06 min, [M+H]$^+$=300, $^1$H NMR (500 MHz, DMSO-d6) δ 8.21 (d, J=8.5 Hz, 2H), 7.94-7.90 (m, 2H), 4.81 (q, J=7.0 Hz, 1H), 3.62 (s, 3H), 2.66 (s, 6H), 1.36 (d, J=7.0 Hz, 3H).

135.2 4-(5-Hydroxy-4-methyl-1H-pyrazol-3-yl)-N,N-dimethylbenzene-1-sulfonamide To a solution of methyl 3-[4-(dimethylsulfamoyl)phenyl]-2-methyl-3-oxopropanoate (0.7 g, 2.34 mmol) in ethanol (10 mL) was added hydrazine hydrate (0.08 mL, 2.81 mmol) and the resulting suspension was heated to 70 OC for 4 hours. The reaction mixture was allowed to cool to about 25° C. and the solvent was removed under reduced pressure. The resulting solid was collected by filtration and washed with methanol (20 mL). The filtrate was concentrated under reduced pressure to yield a second crop of the title compound (0.53 g, 81% in total). LC-MS $t_R$=0.91 min, [M+H]$^+$=282, $^1$H NMR (250 MHz, DMSO-d6) δ 7.81 (s, 4H), 2.64 (s, 6H), 2.04 (s, 3H).

135.3 tert-Butyl N-{3-[4-(dimethylsulfamoyl)phenyl]-4-methyl-5-oxo-4,5-dihydro-1H-pyrazol-4-yl}-N-hydroxycarbamate tert-Butyl N-{3-[4-(dimethylsulfamoyl)phenyl]-4-methyl-5-oxo-4,5-dihydro-1H-pyrazol-4-yl}-N-hydroxycarbamate was synthesized from 4-(5-hydroxy-4-methyl-1H-pyrazol-3-yl)-N,N-dimethylbenzene-1-sulfonamide according to General Method 17 (0.4 g, 81%). LC-MS $t_R$=0.98 min, [M−H]$^−$=411, $^1$H NMR (250 MHz, DMSO-d6) δ 11.76 (s, 1H), 10.30 (s, 1H), 8.07 (d, J=8.7 Hz, 2H), 7.83 (d, J=8.6 Hz, 2H), 2.63 (s, 6H), 1.54 (s, 3H), 1.21 (s, 9H).

135.4 4-[4-(Hydroxyamino)-4-methyl-5-oxo-4,5-dihydro-1H-pyrazol-3-yl]-N,N-dimethylbenzene-1-sulfonamide 4-[4-(Hydroxyamino)-4-methyl-5-oxo-4,5-dihydro-1H-pyrazol-3-yl]-N,N-dimethylbenzene-1-sulfonamide was synthesized from tert-butyl N-{3-[4-(dimethylsulfamoyl)phenyl]-4-methyl-5-oxo-4,5-dihydro-1H-pyrazol-4-yl}-N-hydroxycarbamate according to General Method 9 and was purified by trituration with diethyl ether (0.22 g, 73%). LC-MS $t_R$=2.87 min, [M+H]$^+$=313, $^1$H NMR (250 MHz, DMSO-d6) δ 11.65 (s, 1H), 8.27 (d, J=8.7 Hz, 2H), 7.82 (d, J=8.7 Hz, 2H), 7.65 (s, 1H), 6.51 (s, 1H), 2.65 (s, 6H), 1.23 (s, 3H).

Example 136

Compound 136 [4-(Hydroxyamino)-3-(4-methanesulfonylphenyl)-4-methyl-1-phenyl-4,5-dihydro-1H-pyrazol-5-one]

136.1 3-[4-(Methylsulfanyl)phenyl]-1-phenyl-1H-pyrazol-5-ol

To a solution of methyl 3-[4-(methylsulfanyl)phenyl]-3-oxopropanoate (10 g, 44.59 mmol) in ethanol (100 mL) was added phenylhydrazine (5.26 mL, 53.51 mmol) and the reaction mixture was heated to 70 OC for 4 hours after which time the reaction mixture was allowed to cool to about 25° C. over 17 hours. The solvent was removed under reduced pressure and the crude product was purified via silica gel chromatography eluting with 0-60% ethyl acetate in heptanes to give the title compound as a brown solid (10.6 g, 76%). LC-MS $t_R$=1.24 min, [M+H]$^+$=283, $^1$H NMR (500 MHz, DMSO-d6) δ 11.81 (s, 1H), 7.81 (dd, J=8.6, 1.0 Hz, 2H), 7.79-7.74 (m, 2H), 7.53-7.44 (m, 2H), 7.30 (dd, J=7.8, 3.5 Hz, 3H), 5.99 (s, 1H).

136.2 5-Hydroxy-3-[4-(methylsulfanyl)phenyl]-1-phenyl-1H-pyrazole-4-carbaldehyde To a solution of 3-[4-(methylsulfanyl)phenyl]-1-phenyl-1H-pyrazol-5-ol (1 g, 3.54 mmol) in DMF (10 mL) was added phosphorus oxychloride (0.23 mL, 2.48 mmol) over two minutes. The reaction mixture was then heated to 65° C. for 2.5 hours after which time LC-MS showed formation of the desired intermediate. The reaction mixture was then diluted with 6N HCl (15 mL) and stirred vigorously for 17 hours. The resulting sticky solid was sonicated for 1.5 hours yielding a granular solid which was isolated by filtration and the brown solid was purified by silica gel chromatography eluting with 20-100% heptanes:ethyl acetate. The desired compound was isolated as a white solid (0.25 g, 18%). LC-MS $t_R$=1.22 min, [M+H]$^+$=311.

136.3 4-Methyl-3-[4-(methylsulfanyl)phenyl]-1-phenyl-1H-pyrazol-5-ol

4-Methyl-3-[4-(methylsulfanyl)phenyl]-1-phenyl-1H-pyrazol-5-ol was synthesized from 5-hydroxy-3-[4-(methylsulfanyl)phenyl]-1-phenyl-1H-pyrazole-4-carbaldehyde according to General Method 5 and was used directly to continue the synthesis. (0.23 g, 76%), LC-MS $t_R$=1.20 min, [M+H]$^+$=297.

136.4 tert-Butyl N-hydroxy-N-{4-methyl-3-[4-(methylsulfanyl)phenyl]-5-oxo-1-phenyl-4,5-dihydro-1H-pyrazol-4-yl}carbamate tert-Butyl N-hydroxy-N-{4-methyl-3-[4-(methylsulfanyl)phenyl]-5-oxo-1-phenyl-4,5-dihydro-1H-pyrazol-4-yl}carbamate was synthesized from 4-methyl-3-[4-(methylsulfanyl)phenyl]-1-phenyl-1H-pyrazol-5-ol according to General Method 17 and was purified by silica gel chromatography eluting with 0-40% ethyl acetate:heptanes (0.1 g, 15%). LC-MS $t_R$=1.34 min, [M+Na+H]$^+$=450, $^1$H NMR (250 MHz, DMSO-d6) δ 10.41 (s, 1H), 8.01-7.90 (m, 4H), 7.55-7.45 (m, 2H), 7.39 (d, J=8.7 Hz, 2H), 7.25 (t, J=7.4 Hz, 1H), 2.54 (s, 3H), 1.66 (s, 3H), 1.40 (s, 9H).

136.5 tert-Butyl N-hydroxy-N-[3-(4-methanesulfonylphenyl)-4-methyl-5-oxo-1-phenyl-4,5-dihydro-1H-pyrazol-4-yl]carbamate tert-Butyl N-hydroxy-N-[3-(4-methanesulfonylphenyl)-4-methyl-5-oxo-1-phenyl-4,5-dihydro-1H-pyrazol-4-yl]carbamate was synthesized from tert-butyl N-hydroxy-N-{4-methyl-3-[4-(methylsulfanyl)phenyl]-5-oxo-1-phenyl-4,5-dihydro-1H-pyrazol-4-yl}carbamate according to General Method 10 (0.1 g, 78%). LC-MS $t_R$=1.16 min, [M−BOC+H]$^+$=360, $^1$H NMR (250 MHz, DMSO-d6) δ 10.52 (s, 1H), 8.24 (d, J=8.7 Hz, 2H), 8.09 (d, J=8.7 Hz, 2H), 8.02-7.92 (m, 2H), 7.62-7.46 (m, 2H), 7.29 (t, J=7.4 Hz, 1H), 3.29 (s, 3H), 1.40 (s, 9H), 1.15 (s, 3H).

136.6 4-(Hydroxyamino)-3-(4-methanesulfonylphenyl)-4-methyl-1-phenyl-4,5-dihydro-1H-pyrazol-5-one 4-(Hydroxyamino)-3-(4-methanesulfonylphenyl)-4-methyl-1-phenyl-4,5-dihydro-1H-pyrazol-5-one was synthesized from tert-butyl N-hydroxy-N-[3-(4-methanesulfonylphenyl)-4-methyl-5-oxo-1-phenyl-4,5-dihydro-1H-pyrazol-4-yl]carbamate according to General Method 9 and was purified by acidic reverse phase HPLC (0.012 g, 15%). LC-MS $t_R$=3.76 min, [M+H]$^+$=360, $^1$H NMR (500 MHz, DMSO-d6) δ 8.43 (d, J=8.4 Hz, 2H), 8.07 (d, J=8.4 Hz, 2H), 7.97 (d, J=8.0 Hz, 2H), 7.89 (d, J=2.3 Hz, 1H), 7.51 (t, J=7.9 Hz, 2H), 7.28 (t, J=7.3 Hz, 1H), 6.86 (d, J=2.2 Hz, 1H), 3.29 (s, 3H), 1.40 (s, 3H).

Example 137

Compound 137 [4-(Hydroxyamino)-3-methyl-4-phenyl-4,5-dihydro-1H-pyrazol-5-one]

137.1 3-Methyl-4-phenyl-1H-pyrazol-5-ol

To a solution of methyl 3-oxo-2-phenylbutanoate (1 g, 5.2 mmol) in ethanol (20 mL) was added hydrazine hydrate (0.26 mL, 5.2 mmol) and the reaction mixture was heated to reflux for 4 hours. The reaction mixture was cooled to about 25° C., concentrated under reduced pressure and the crude product was suspended in 50 mL heptane:ethyl acetate (1:2, v:v), sonicated, filtered and dried under reduced pressure to give the title compound as a white solid (500 mg, 55%). LC-MS $t_R$=0.88 min, [M+H]$^+$=175, $^1$H NMR (500 MHz, DMSO-d6) δ 11.46 (br.s, 1H), 9.84 (br.s, 1H), 7.46 (d, J=7.1 Hz, 2H), 7.34 (t, J=7.8 Hz, 2H), 7.15 (t, J=7.4 Hz, 1H), 2.27 (s, 3H).

137.2 tert-Butyl N-hydroxy-N-{4-methyl-3-[4-(methylsulfanyl)phenyl]-5-oxo-4,5-dihydro-1H-pyrazol-4-yl}carbamate tert-Butyl N-hydroxy-N-{4-methyl-3-[4-(methylsulfanyl)phenyl]-5-oxo-4,5-dihydro-1H-pyrazol-4-yl}carbamate was synthesized from 3-methyl-4-phenyl-1H-pyrazol-5-ol according to General Method 17 and the product was purified by silica gel chromatography eluting with 0-100% ethyl acetate in heptanes (799 mg, 87% yield). LC-MS $t_R$=3.17 min, [M+Na]$^+$=328, $^1$H NMR (500 MHz, Methanol-d$_4$) δ 7.45-7.35 (m, 5H), 2.16 (s, 3H), 1.45 (s, 9H).

137.3 4-(Hydroxyamino)-3-methyl-4-phenyl-4,5-dihydro-1H-pyrazol-5-one 4-(Hydroxyamino)-3-methyl-4-phenyl-4,5-dihydro-1H-pyrazol-5-one was synthesized from tert-butyl N-hydroxy-N-{4-methyl-3-[4-(methylsulfanyl)phenyl]-5-oxo-4,5-dihydro-1H-pyrazol-4-yl}carbamate according to General Method 9 (using 50 equiv of TFA) and was purified by silica gel chromatography eluting with 0-100% ethyl acetate in heptanes (375 mg, 73%). LC-MS $t_R$=1.38 min, [M+H]$^+$=206, $^1$H NMR (500 MHz, Methanol-d4) δ 7.45-7.35 (m, 5H), 2.16 (s, 3H), 1.45 (s, 9H).

Example 138

Compound 138 [4-(Hydroxyamino)-3-(4-methanesulfonylphenyl)-4-methyl-1-(pyrazin-2-yl)-4,5-dihydro-1H-pyrazol-5-one]

138.1 Methyl 2-methyl-3-[4-(methylsulfanyl)phenyl]-3-oxopropanoate

To a solution of methyl 3-[4-(methylsulfanyl)phenyl]-3-oxopropanoate (3 g, 13.38 mmol) in DMF (5 mL) was added potassium carbonate (1.85 g, 13.38 mmol) and methyl iodide (916 µL, 14.71 mmol). The resulting reaction mixture was stirred overnight at about 25° C. Water was then added and the resulting solution was extracted with DCM (3×50 mL). The combined organic layers were washed with brine (25 mL), dried over sodium sulfate and concentrated under reduced pressure to afford a dark brown oil. The crude oil was purified by silica gel chromatography eluting with 10-50% ethyl acetate:heptanes to give the title compound as a yellow oil (2.0 g, 63%). LC-MS $t_R$=1.14 min, [M+H]$^+$=239, $^1$H NMR (250 MHz, DMSO-d6) δ 7.92 (d, J=8.7 Hz, 2H), 7.39 (d, J=8.7 Hz, 2H), 4.70 (q, J=7.0 Hz, 1H), 3.60 (s, 3H), 2.55 (s, 3H), 1.32 (d, J=7.0 Hz, 3H).

138.2 Methyl 3-(4-methanesulfonylphenyl)-2-methyl-3-oxopropanoate

To a solution of methyl 2-methyl-3-[4-(methylsulfanyl)phenyl]-3-oxopropanoate (2.0 g, 8.39 mmol) in 1,4-dioxane and water was added potassium O-(hydroperoxysulfonyl)oxidanidolate (2.55 g, 16.79 mmol) and the reaction mixture was stirred at about 25° C. overnight, after which time the solids were removed by filtration. Additional potassium O-(hydroperoxysulfonyl)oxidanidolate (2.55 g, 16.79 mmol) was added to the reaction mixture and the reaction mixture was stirred for an additional 24 hours at about 25° C. The reaction mixture was filtered and the solution was extracted into ethyl acetate (2×20 mL), dried over sodium sulfate and concentrated under reduced pressure to give the title compound as a yellow oil (2.0 g, 88%). LC-MS $t_R$=0.96 min, [M−H]$^-$=269, $^1$H NMR (250 MHz, DMSO-d6) 68.25-8.18 (m, 2H), 8.13-8.07 (m, 2H), 4.82 (q, J=6.9 Hz, 1H), 3.61 (s, 3H), 3.30 (s, 6H), 1.35 (dd, J=7.0, 2.2 Hz, 3H).

138.3 3-(4-Methanesulfonylphenyl)-4-methyl-1-(pyrazin-2-yl)-1H-pyrazol-5-ol A solution of methyl 3-(4-methanesulfonylphenyl)-2-methyl-3-oxopropanoate (1 g, 3.7 mmol) and 2-hydrazinylpyrazine (0.41 g, 3.7 mmol) in ethanol (15 mL) was heated in a pressure tube for 2 hours at 70° C., followed by 72 hours at about 25° C. and 24 hours at 70° C. The reaction mixture was cooled to about 25° C. and the solvent was removed under reduced pressure to afford a brown oil. The crude oil was purified by silica gel chromatography eluting in 0-30% methanol:ethyl acetate, followed by an SCX-2 cartridge eluting in methanol to give the title compound as a yellow solid (40 mg, 3%). LC-MS $t_R$=0.95 min, [M+H]$^+$=331, $^1$H NMR (500 MHz, Methanol-d4) δ 9.56 (s, 1H), 8.59-8.50 (m, 2H), 8.14 (d, J=8.5 Hz, 2H), 8.05 (d, J=8.5 Hz, 2H), 3.22 (s, 3H), 2.16 (s, 3H).

138.4 tert-Butyl N-hydroxy-N-[3-(4-methanesulfonylphenyl)-4-methyl-5-oxo-1-(pyrazin-2-yl)-4,5-dihydro-1H-pyrazol-4-yl]carbamate tert-Butyl N-hydroxy-N-[3-(4-methanesulfonylphenyl)-4-methyl-5-oxo-1-(pyrazin-2-yl)-4,5-dihydro-1H-pyrazol- 4-yl]carbamate was synthesized from 3-(4-methanesulfonylphenyl)-4-methyl-1-(pyrazin-2-yl)-1H-pyrazol-5-ol according to General Method 17 and purified by silica gel chromatography eluting in 0-80% ethyl acetate:heptanes to afford the title compound as a colourless oil (27 mg, 38%). LC-MS $t_R$=0.98 min, [M+H]$^+$=462.

138.5 4-(Hydroxyamino)-1,3-dimethyl-4-(5-phenyl-1,2,4-oxadiazol-3-yl)-4,5-dihydro-1H-pyrazol-5-one 4-(Hydroxyamino)-1,3-dimethyl-4-(5-phenyl-1,2,4-oxadiazol-3-yl)-4,5-dihydro-1H-pyrazol-5-one was synthesized from tert-butyl N-hydroxy-N-[3-(4-methanesulfonylphenyl)-4-methyl-5-oxo-1-(pyrazin-2-yl)-4,5-dihydro-1H-pyrazol-4-yl]carbamate according to General Method 9 and was purified using acidic preparative HPLC (14 mg, 66%). LC-MS $t_R$=2.86 min, [M+H]$^+$=362, $^1$H NMR (500 MHz, DMSO-d6) δ 9.24 (d, J=1.1 Hz, 1H), 8.66-8.60 (m, 1H), 8.58 (d, J=2.5 Hz, 1H), 8.43 (d, J=8.5 Hz, 2H), 8.08 (d, J=8.5 Hz, 2H), 7.96 (d, J=2.5 Hz, 1H), 6.98 (d, J=2.3 Hz, 1H), 3.29 (s, 3H), 1.43 (s, 3H).

Example 139

Compound 139 [[3-(4-Methanesulfonylphenyl)-1,4-dimethyl-5-oxo-4,5-dihydro-1H-pyrazol-4-yl]amino acetate]

139.1 3-(4-Methanesulfonylphenyl)-1,4-dimethyl-1H-pyrazol-5-ol

To a solution of 1,4-dimethyl-3-[4-(methylsulfanyl)phenyl]-1H-pyrazol-5-ol (16 g, 34.14 mmol) in dioxane:water (100 mL, 1:1 v:v) at room temperature was added potassium O-(hydroperoxysulfonyl)oxidanidolate (12.47 g, 81.94 mmol) in portions and stirring was continued for 18 hours. The reaction mixture was concentrated in vacuo and the aqueous was diluted into ethyl acetate (200 mL) and washed with water (100 mL) and brine (100 mL). The organic portion was dried over magnesium sulfate and the solvent was removed in vacuo to obtain the crude product as a yellow oil which was purified by silica gel chromatography eluting with dichloromethane:methanol (9:1, v:v) to yield the title compound as a white solid (1.1 g, 12% yield). LC-MS $t_R$=0.83 min, [M+Na]$^+$=266, $^1$H NMR (500 MHz, DMSO-d6) δ 7.96 (d, J=8.4 Hz, 2H), 7.90-7.84 (m, 2H), 3.63 (s, 3H), 3.24 (s, 3H), 2.09 (s, 3H).

139.2 tert-Butyl N-hydroxy-N-[3-(4-methanesulfonylphenyl)-1,4-dimethyl-5-oxo-4,5-dihydro-1H-pyrazol-4-yl]carbamate tert-Butyl N-hydroxy-N-[3-(4-methanesulfonylphenyl)-1,4-dimethyl-5-oxo-4,5-dihydro-1H-pyrazol-4-yl]carbamate was synthesised from 3-(4-methanesulfonylphenyl)-1,4-dimethyl-1H-pyrazol-5-ol according to General Method 17 and was purified by silica gel chromatography eluting with heptanes:ethyl acetate (0-90%) yielding the title compound as an orange solid (80 mg, 4% yield). $^1$H NMR (500 MHz, Methanol-d4) δ 8.32-8.26 (m, 2H), 8.09-8.01 (m, 2H), 3.42 (s, 3H), 3.18 (s, 3H), 1.63 (s, 3H), 1.37 (s, 9H).

139.3 [(tert-Butoxy)carbonyl][3-(4-methanesulfonylphenyl)-1,4-dimethyl-5-oxo-4,5-dihydro-1H-pyrazol-4-yl]amino acetate To a solution of tert-butyl N-hydroxy-N-[3-(4-methanesulfonylphenyl)-1,4-dimethyl-5-oxo-4,5-dihydro-1H-pyrazol-4-yl]carbamate (80 mg, 0.14 mmol) in DCM (1.5 mL) cooled to 0° C. was added triethylamine (21 μL, 0.15 mmol) and acetyl chloride (10 μL, 0.14 mmol), and the reaction mixture was allowed to warm to room temperature over 90 minutes. After 90 minutes, the reaction mixture was re-treated with acetyl chloride (20 μL, 0.27 mmol) and triethylamine (42 μL, 0.3 mmol) and stirring was continued for an additional 2 hours at room temperature. After 2 hours the reaction mixture was retreated with acetyl chloride (20 μL, 0.27 mmol) and triethylamine (42 μL, 0.3 mmol) and stirring continued for 18 hours at room temperature. The reaction mixture was diluted with DCM (20 mL) and the reaction was quenched by the addition of water (20 mL). The organic layer was separated and the aqueous layer re-extracted with DCM (2×20 mL). The organic layers were combined, washed with brine (20 mL), then dried over sodium sulfate, filtered and concentrated under reduced pressure to yield the crude product as an orange oil which was purified by silica gel chromatography eluting with 0-50% ethyl acetate:heptanes to yield the title compound as an orange oil (39 mg, 39% yield), LC-MS $t_R$=1.13 min, [M-BOC+H]$^+$=340.

139.4 [3-(4-Methanesulfonylphenyl)-1,4-dimethyl-5-oxo-4,5-dihydro-1H-pyrazol-4-yl]amino acetate To a solution of [(tert-butoxy)carbonyl][3-(4-methanesulfonylphenyl)-1,4-dimethyl-5-oxo-4,5-dihydro-1H-pyrazol-4-yl]amino acetate (66 mg, 0.07 mmol) in DCM (1 mL) was added trifluoroacetic acid (267.2 μl, 3.5 mmol). The reaction mixture was stirred at room temperature for 1 hour, after which time the reaction mixture was concentrated in vacuo and azeotroped with DCM (5 mL) followed by heptane (5 mL) to yield the crude compound as an orange oil which was purified by acidic, reverse phase HPLC to yield the title compound as a white solid (18 mg, 75% yield), LC-MS $t_R$=2.84 min, [M+H]$^+$=340, $^1$H NMR (500 MHz, DMSO-d6) δ 10.90 (s, 1H), 8.20 (s, 2H), 8.00 (d, J=8.5 Hz, 2H), 3.34 (s, 3H), 3.27 (s, 3H), 1.64 (s, 3H), 1.54 (s, 3H).

Example 140

Compound 140 [(1,4-Dimethyl-5-oxo-3-phenyl-4,5-dihydro-1H-pyrazol-4-yl)amino acetate]

140.1 N-(1,4-Dimethyl-5-oxo-3-phenyl-4,5-dihydro-1H-pyrazol-4-yl)-N-hydroxycarbamate N-(1,4-Dimethyl-5-oxo-3-phenyl-4,5-dihydro-1H-pyrazol-4-yl)-N-hydroxycarbamate was synthesised from 1,4-dimethyl-3-phenyl-1H-pyrazol-5-ol according to General Method 17 and was purified by silica gel chromatography eluting with 0-50% heptane:ethyl acetate to yield the title compound as yellow solid (0.18 g, 59% yield), LC-MS $t_R$=1.08 min, [M+Na]$^+$=342, $^1$H NMR (500 MHz, Methanol-d4) δ 7.97-7.90 (m, 2H), 7.48-7.39 (m, 3H), 3.38 (s, 3H), 1.65 (s, 3H), 1.25 (s, 9H).

140.2 [(tert-Butoxy)carbonyl](1,4-dimethyl-5-oxo-3-phenyl-4,5-dihydro-1H-pyrazol-4-yl)amino acetate To a solution of N-(1,4-Dimethyl-5-oxo-3-phenyl-4,5-dihydro-1H-pyrazol-4-yl)-N-hydroxycarbamate (182 mg, 0.48 mmol) in DCM (3.3 mL) cooled to 0° C. was added triethylamine (74 μL, 0.53 mmol) and acetyl chloride (35 μL, 0.48 mmol), and the reaction mixture was allowed to warm to room temperature overnight. The reaction mixture was then re-treated with acetyl chloride (18 μL, 0.24 mmol)

and triethylamine (37 µL, 0.27 mmol) and stirring was continued for an additional 90 minutes at room temperature. After 90 minutes, the reaction mixture was retreated with acetyl chloride (18 µL, 0.24 mmol) and triethylamine (37 µL, 0.27 mmol) and stirring continued for 45 minutes at room temperature. The reaction mixture was diluted with DCM (20 mL) and the reaction was quenched by the addition of water (20 mL). The organic layer was separated and the aqueous layer re-extracted with DCM (2×20 mL), the organic layers were combined, washed with brine (20 mL), dried over sodium sulfate, filtered and concentrated under reduced pressure to yield the crude product as an orange oil which was purified by silica gel chromatography eluting with 0-50% ethyl acetate:heptanes (156 mg, 72% yield). LC-MS $t_R$=1.18 min, [M-tBu+H]$^+$=306.

140.3 (1,4-Dimethyl-5-oxo-3-phenyl-4,5-dihydro-1H-pyrazol-4-yl)amino acetate To a solution of [(tert-butoxy)carbonyl](1,4-dimethyl-5-oxo-3-phenyl-4,5-dihydro-1H-pyrazol-4-yl)amino acetate (156 mg, 0.35 mmol) in DCM (6 mL) was added trifluoroacetic acid (1.34 ml, 17.5 mmol). The reaction mixture was stirred at room temperature for 2 hours, after which time the reaction mixture was concentrated in vacuo and azeotroped with DCM (5 mL) followed by heptane (5 mL) and was purified by silica gel chromatography eluting with 0-60% ethyl acetate:heptanes to yield the title compound as a white powder (65 mg, 71% yield), LC-MS $t_R$=3.62 min, [M+H]$^+$=262, $^1$H NMR (500 MHz, DMSO-d6) δ 8.54 (s, 1H), 8.06-7.99 (m, 2H), 7.49-7.42 (m, 3H), 3.33 (s, 3H), 1.85 (s, 3H), 1.39 (s, 3H).

Example 141

Compound 141 [4-[4-(Hydroxyamino)-4-methyl-5-oxo-4,5-dihydro-1H-pyrazol-3-yl]-N-methoxy-N-methylbenzene-1-sulfonamide]

141.1 4-Acetyl-N-methoxy-N-methylbenzene-1-sulfonamide

To a solution of 4-acetylbenzene-1-sulfonyl chloride (5 g, 0.02 mol) in DCM (40 mL) cooled to 0° C. was added pyridine (1.85 mL, 0.02 mol) and methoxy(methyl)amine (1.54 g, 0.03 mol). The reaction mixture was allowed to warm to room temperature and stirring was continued for 18 hours, after which time, the reaction was quenched by addition of saturated sodium bicarbonate solution (60 mL) and the organic layer was separated and washed with 2M HCl (50 mL) and brine (50 mL), then dried over sodium sulfate, filtered and concentrated under reduced pressure to yield the title compound as a yellow solid. (4.8 g, 86% yield), $^1$H NMR (250 MHz, DMSO-d6) δ 8.24-8.17 (m, 2H), 8.01-7.93 (m, 2H), 3.74 (s, 3H), 2.77 (s, 3H), 2.66 (s, 3H).

141.2 3-{4-[Methoxy(methyl)sulfamoyl]phenyl}-3-oxopropanoate

3-{4-[Methoxy(methyl)sulfamoyl]phenyl}-3-oxopropanoate was synthesised from 4-acetyl-N-methoxy-N-methylbenzene-1-sulfonamide according to General Method 1 and was purified by silica gel chromatography eluting with 0-60% heptane:ethyl acetate (1.0 g, 17% yield), $^1$H NMR (250 MHz, DMSO-d6) δ 8.21 (d, J=8.6 Hz, 2H), 7.98 (d, J=8.5 Hz, 2H), 4.31 (s, 2H), 3.74 (s, 3H), 3.66 (s, 3H), 2.77 (s, 3H).

141.3 3-{4-[Methoxy(methyl)sulfamoyl]phenyl}-2-methyl-3-oxopropanoate

To a solution of methyl 3-{4-[methoxy(methyl)sulfamoyl]phenyl}-3-oxopropanoate (1 g, 3.32 mmol) in DMF (5 mL) was added potassium carbonate (0.46 g, 3.32 mmol) and iodomethane (0.23 mL, 3.65 mmol)). The resulting reaction mixture was stirred for 3 hours at room temperature before water (25 mL) was added and the resulting solution was extracted with dichloromethane (3×50 mL). The combined organic extracts were washed with brine (25 mL), then dried over sodium sulfate and concentrated in vacuo to afford a yellow oil (1 g, 74%). LC-MS $t_R$=1.13 min, [M+H]$^+$=316, $^1$H NMR (250 MHz, DMSO-d6) δ 8.29-8.21 (m, 2H), 8.04-7.97 (m, 2H), 4.82 (q, J=7.0 Hz, 1H), 3.74 (2, 3H), 3.62 (s, 3H), 2.78 (s, 3H), 1.37 (d, J=7.0 Hz, 3H).

141.4 4-(5-Hydroxy-4-methyl-1H-pyrazol-3-yl)-N-methoxy-N-methylbenzene-1-sulfonamide To a solution of methyl 3-{4-[methoxy(methyl)sulfamoyl]phenyl}-2-methyl-3-oxopropanoate (1 g, 3.17 mmol) in ethanol (10 mL) was added hydrazine hydrate (0.17 mL, 3.81 mmol) and the resulting suspension was heated to 70 OC for 4 hours. The reaction mixture was allowed to cool to room temperature and the solvent was removed in vacuo. The resulting solid was collected by filtration and washed with heptane:ethyl acetate (1:1, v:v, 20 mL), (0.68 g, 72% yield). LC-MS $t_R$=0.98 min, [M+H]$^+$=298, $^1$H NMR (250 MHz, DMSO-d6) δ 7.92-7.81 (m, 4H), 3.73 (s, 3H), 2.77 (s, 3H), 2.05 (s, 3H).

141.5 tert-Butyl N-hydroxy-N-(3-{4-[methoxy(methyl)sulfamoyl]phenyl}-4-methyl-5-oxo-4,5-dihydro-1H-pyrazol-4-yl)carbamate tert-Butyl N-hydroxy-N-(3-{4-[methoxy(methyl)sulfamoyl]phenyl}-4-methyl-5-oxo-4,5-dihydro-1H-pyrazol-4-yl)carbamate was synthesised from 4-(5-Hydroxy-4-methyl-1H-pyrazol-3-yl)-N-methoxy-N-methylbenzene-1-sulfonamide according to General Method 17 and was purified by silica gel chromatography eluting with heptane:ethyl acetate (0.2 g, 89% yield). LC-MS $t_R$=1.05 min, [M–H]$^-$=427, $^1$H NMR (250 MHz, DMSO-d6) δ 11.82 (s, 1H), 10.31 (s, 1H), 8.09 (d, J=8.7 Hz, 2H), 7.90 (d, J=8.7 Hz, 2H), 3.73 (s, 3H), 2.75 (s, 3H), 1.55 (s, 3H), 1.20 (s, 9H).

141.6 4-[4-(Hydroxyamino)-4-methyl-5-oxo-4,5-dihydro-1H-pyrazol-3-yl]-N-methoxy-N-methylbenzene-1-sulfonamide 4-[4-(Hydroxyamino)-4-methyl-5-oxo-4,5-dihydro-1H-pyrazol-3-yl]-N-methoxy-N-methylbenzene-1-sulfonamide was synthesised from tert-Butyl N-hydroxy-N-(3-{4-[methoxy(methyl)sulfamoyl]phenyl}-4-methyl-5-oxo-4,5-dihydro-1H-pyrazol-4-yl)carbamate according to General Method 9 and was purified by trituration from diethyl ether, (0.13 g, 82% yield). LC-MS $t_R$=3.24 min, [M+H]$^+$=329, $^1$H NMR (250 MHz, DMSO-d6) δ 11.70 (s, 1H), 8.30 (d, J=8.7 Hz, 2H), 7.89 (d, J=8.6 Hz, 2H), 7.67 (s, 1H), 3.74 (s, 3H), 2.79 (s, 3H), 1.23 (s, 3H).

Example 142

Compound 142 [Ethyl-3-[4-(Hydroxyamino)-3-methyl-5-oxo-4,5-dihydro-1H-pyrazol-4yl]propanoate]

142.1 3-(5-Hydroxy-3-methyl-1H-pyrazol-4-yl)propanoate

A solution of 1,5-diethyl 2-acetylpentanedioate (1 g, 4.34 mmol) in ethanol (5 mL) was treated with hydrazine hydrate (0.24 mL, 5.21 mmol) and the resulting reaction mixture was heated to 70° C. for 4 hours. The solvent was then removed under vacuum and the crude was purified by silica gel chromatography eluting with 0-10% MeOH:DCM to yield the title compound as a white solid (0.8 g, 93% yield). LC-MS $t_R$=0.76 min, $[M+H]^+$=199, $^1$H NMR (250 MHz, DMSO-d6) δ 4.03 (q, J=7.1 Hz, 2H), 2.43 (q, J=4.7 Hz, 4H), 2.04 (s, 3H), 1.16 (t, J=7.1 Hz, 3H).

142.2 3-(4-{[(tert-Butoxy)carbonyl](hydroxy)amino}-3-methyl-5-oxo-4,5-dihydro-1H-pyrazol-4-yl)propanoate 3-(4-{[(tert-Butoxy)carbonyl](hydroxy)amino}-3-methyl-5-oxo-4,5-dihydro-1H-pyrazol-4-yl)propanoate was synthesised from 3-(5-hydroxy-3-methyl-1H-pyrazol-4-yl)propanoate according to General Method 17 and was purified by silica gel chromatography eluting with 40-80% ethyl acetate:heptane (94 mg, 57% yield). LC-MS $t_R$=0.92 min, $[M+Na]^+$=352, $^1$H NMR (250 MHz, DMSO-d6) δ 10.93 (s, 1H), 9.82 (s, 1H), 4.04 (q, J=7.1 Hz, 2H), 2.35-2.22 (m, 2H), 2.21-2.07 (m, 1H), 2.03-1.91 (m, 1H), 1.86 (s, 3H), 1.36 (s, 8H), 1.17 (t, J=7.1 Hz, 3H).

142.3 Ethyl-3-[4-(hydroxyamino)-3-methyl-5-oxo-4,5-dihydro-1H-pyrazol-4-yl]propanoate Ethyl-3-[4-(hydroxyamino)-3-methyl-5-oxo-4,5-dihydro-1H-pyrazol-4-yl]propanoate was synthesised from 3-(4-{[(tert-butoxy)carbonyl](hydroxy)amino}-3-methyl-5-oxo-4,5-dihydro-1H-pyrazol-4-yl)propanoate according to General Method 9 and was purified by silica gel chromatography eluting with 0-10% MeOH:DCM, (15 mg, 24% yield). LC-MS $t_R$=0.64 min, $[M+H]^+$=230, $^1$H NMR (250 MHz, DMSO-d6) δ 10.86 (s, 1H), 7.54 (d, J=2.7 Hz, 1H), 6.30 (d, J=2.5 Hz, 1H), 4.03 (q, J=7.1 Hz, 2H), 2.10 (td, J=7.7, 7.3, 4.7 Hz, 2H), 1.94 (s, 3H), 1.70 (t, J=8.1 Hz, 2H), 1.16 (t, J=7.1 Hz, 3H).

Example 143

Compound 143 [3a-(Hydroxyamino)-3-methyl-3aH,4H,5H,6H-pyrano[2,3-c]pyrazol-6-one]

143.1 3a-(Hydroxyamino)-3-methyl-3aH,4H,5H,6H-pyrano[2,3-c]pyrazol-6-one 3a-(Hydroxyamino)-3-methyl-3aH,4H,5H,6H-pyrano[2,3-c]pyrazol-6-one was isolated from ethyl-3-[4-(hydroxyamino)-3-methyl-5-oxo-4,5-dihydro-1H-pyrazol-4-yl]propanoate during purification by silica gel chromatography eluting with DCM:MeOH (33 mg, 66% yield). LC-MS $t_R$=0.87 min, $[M+H]^+$=184, $^1$H NMR (250 MHz, DMSO-d6) δ 11.18 (s, 1H), 9.93 (s, 1H), 2.48-2.40 (m, 2H), 2.21-2.00 (m, 2H), 1.98 (s, 3H).

Example 144

Compound 144 [3a-(Hydroxyamino)-3,3a,4,5,6,7-hexahydro-2H-indazol-3-one]

144.1 tert-Butyl N-hydroxy-N-(3-oxo-3,3a,4,5,6,7-hexahydro-2H-indazol-3a-yl)carbamate tert-Butyl N-hydroxy-N-(3-oxo-3,3a,4,5,6,7-hexahydro-2H-indazol-3a-yl)carbamate was synthesised from 4,5,6,7-tetrahydro-2H-indazol-3-ol according to General Method 17 and was purified by silica gel chromatography eluting with 0-10% DCM:MeOH (0.5 g, 34% yield), LC-MS $t_R$=1.05 min, $[M-H]^-$=427, $^1$H NMR (250 MHz, DMSO-d6) δ 11.82 (s, 1H), 10.31 (s, 1H), 8.09 (d, J=8.7 Hz, 2H), 7.90 (d, J=8.7 Hz, 2H), 3.73 (s, 3H), 2.75 (s, 3H), 1.55 (s, 3H), 1.20 (s, 9H).

144.2 3a-(Hydroxyamino)-3,3a,4,5,6,7-hexahydro-2H-indazol-3-one 3a-(Hydroxyamino)-3,3a,4,5,6,7-hexahydro-2H-indazol-3-one was synthesised from tert-butyl N-hydroxy-N-(3-oxo-3,3a,4,5,6,7-hexahydro-2H-indazol-3a-yl)carbamate according to General Method 9 and was purified by trituration from ethyl acetate (212 mg, 67% yield). LC-MS $t_R$=1.44 min, $[M+H]^+$=170, $^1$H NMR (250 MHz, DMSO-d6) δ 10.82 (s, 1H), 7.50 (s, 1H), 2.47-2.31 (m, 1H), 2.08-1.92 (m, 1H), 1.85-1.60 (m, 2H), 1.56-1.41 (m, 1H), 1.40-1.12 (m, 2H).

4.2 Example 145

Nitroxyl Production from Pyrazolone Derivative Compounds as Determined Via $N_2O$ Quantification in the Headspace Protocol Nitrous oxide ($N_2O$) is produced via the dimerization and dehydration of HNO, and is the most common marker for nitroxyl production (Fukuto et al., *Chem. Res. Toxicol.* 18:790-801 (2005)). Nitroxyl, however, can also be partially quenched by oxygen to provide a product that does not produce $N_2O$ (see Mincione et al., *J. Enzyme Inhibition* 13:267-284 (1998); and Scozzafava et al., *J. Med. Chem.* 43:3677-3687 (2000)). Using either nitrous oxide gas or Angeli's salt ("AS") as a standard, the relative amounts of $N_2O$ released from compounds of the disclosure is examined via gas chromatography ("GC") headspace analysis.

A procedure for determining the relative amounts of $N_2O$ released from compounds of the disclosure is as follows. GC is performed on an Agilent gas chromatograph equipped with a split injector (10:1 splitting), microelectron capture detector, and a HP-MOLSIV 30 m×0.32 mm×25 m molecular sieve capillary column. Helium is used as the carrier (4 mL/min) gas and nitrogen is used as the make-up (20 mL/min) gas. The injector oven and the detector oven are kept at 200° C. and 325° C., respectively. All nitrous oxide analyses are performed with the column oven held at a constant temperature of 200° C.

All gas injections are made using an automated headspace analyzer. Vial pressurization is 15 psi. The analyzer's sample oven, sampling valve, and transfer line are kept at 40° C., 45° C., and 50° C., respectively. The oven stabilization, vial pressurization, loop fill, loop equilibration, and sample injection times are 1.00 min., 0.20 min., 0.20 min., 0.05 min., and 1.00 min., respectively.

All determinations use a batch of nominal 20 mL headspace vials with volumes pre-measured for sample uniformity (actual vial volume varied by <2.0% relative standard deviation (n=6)). The average vial volume for the batch is determined from six randomly-selected vials by calculating the weight difference between the capped and sealed empty (i.e., air-filled) vial and the capped and sealed deionized water-filled vial using the known density of deionized water, then averaging. Blanks are prepared by sealing and capping 2 vials then purging each for 20 seconds with a gentle argon stream. Nitroxyl standards are prepared by sealing and capping four vials then purging each for 1 minute with a gentle stream, from a gas cylinder, of a 3000 ppm nitroxyl standard.

"Standards" are prepared by, in duplicate, accurately weighing 10±0.5 mg of a compound of formula (Ia), (Ib), (Ic), (Id), (Ie), (If), (Ig), (Ih) or (Ii) and adding it to each 4 mL vial. Using an auto pipette, 1 mL of argon-purged anhydrous DMF (Sigma-Aldrich) is added to each 4 mL vial to form a stock solution for each sample and the vials are capped and shaken and/or sonicated to insure complete dissolution upon visual observation. Using an auto pipette, 20 mL vials are charged with 5 mL of PBS (purged for at least 30 min. with argon prior to use), purged with argon for at least 20 sec., and sealed with a rubber septum. Using a 50 µL syringe, 50 µL of the stock solution is injected into each 20 mL vial containing the PBS.

Samples are prepared as follows. In duplicate, 18±1 mg of each sample is accurately weighed into each 4 mL vial. Using an auto pipette, 1 mL of argon-purged anhydrous DMF is added to each 4 mL vial to form a sample stock solution for each sample and the vials are capped and shaken and/or sonicated to insure complete sample dissolution upon visual observation. Using an auto pipette, 20 mL vials are charged with 5 mL of PBS (purged for at least 30 min. with argon prior to use), purged with argon for at least 20 sec., and sealed with a rubber septum. The vials are equilibrated for at least 10 min. at 37° C. in a dry block heater. Thereafter, using a 50 µL syringe, 50 µL of a sample stock solution is injected into each 20 mL vial containing the PBS. The vials are then held at 37° C. in the dry block heater for a time period such that the sum of the time spent in the dry block heater plus the time spent in the automated headspace analyzer oven before sample injection equals the desired incubation time.

Another procedure for determining the relative amounts of $N_2O$ released from compounds of the disclosure is as follows. GC is performed on a Varian CP-3800 instrument equipped with a 1041 manual injector, electron capture detector, and a 25 m 5 Å molecular sieve capillary column. Grade 5.0 nitrogen is used as both the carrier (8 mL/min) and the make-up (22 mL/min) gas. The injector oven and the detector oven are kept at 200° C. and 300° C., respectively. All nitrous oxide analyses are performed with the column oven held at a constant temperature of 150° C. All gas injections are made using a 100 µL gas-tight syringe with a sample-lock. Samples are prepared in 15 mL amber headspace vials with volumes pre-measured for sample uniformity (actual vial volume ranges from 15.19 to 15.20 mL). Vials are charged with 5 mL of PBS containing diethylenetriamine pentaacetic anhydride ("DTPAN"), purged with argon, and sealed with a rubber septum. The vials are equilibrated for at least 10 minutes at 37° C. in a dry block heater. A 10 mM stock solution of AS is prepared in 10 mM sodium hydroxide, and solutions of the nitroxyl donors are prepared in either acetonitrile or methanol and used immediately after preparation. From these stock solutions, 50 µL is introduced into individual thermally-equilibrated headspace vials using a 100 µL gas-tight syringe with a sample-lock to provide final substrate concentrations of 0.1 mM. Substrates are then incubated for 90 minutes or 360 minutes. The headspace (60 µL) is then sampled and injected five successive times into the GC apparatus using the gas-tight syringe with a sample lock. This procedure is repeated for 2 or more vials per donor.

4.3 Example 146

Nitroxyl Production from Pyrazolone Derivative Compounds as Determined Via $^1$H NMR Protocol Using TXPTS The $^1$H NMR procedure used was based on an HPLC protocol developed by S. Bruce King and coworkers (Reisz et al., *Org. Lett.* 11:2719-2721 (2009), Reisz et al., *J. Am. Chem. Soc.* 133:11675-11685 (2011) and Guthrie et al., *J. Org. Chem.* 80:1338-1348 (2015)). According to this procedure, the amount of HNO released from a pyrazolone derivative compound was determined by reacting the compound with the triarylphosphine TXPTS and monitoring the resulting aza-ylide formation. Scheme 1 shows the conversion of compound of formula (Ia) to its corresponding pyrazol-5-ol (III) and HNO (trapped as one molecule of aza-ylide and one molecule of phosphine oxide).

Scheme 1:

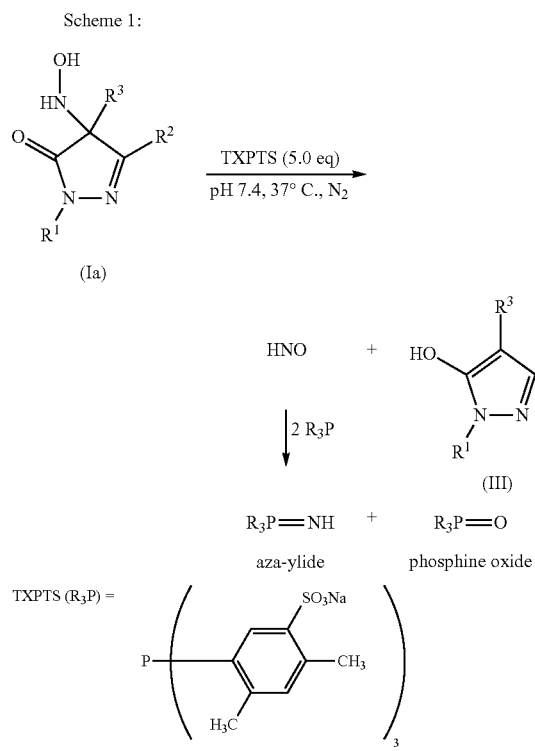

FT-NMR spectrometer using a 1 second presaturation pulse to suppress the water signal. To a nitrogen-purged NMR solution (1.00 mL) containing TXPTS (3.3 mg, 5 mM) was added a pyrazolone derivative compound (10 µL of 100 mM in methanol-$d_4$) to give 1 mM as the initial concentration of the pyrazolone derivative compound. The solution was briefly mixed, about 0.5 mL was transferred to a nitrogen-purged NMR tube and an initial $^1$H NMR spectrum (time=0) was obtained. Thereafter, the sample was internally incubated at 37° C. and $^1$H NMR spectra were collected at regular intervals for 8 hours.

The HNO donating pyrazolone derivative compound, by-product (e.g., (III) in Scheme 1), and TXPTS aza-ylide concentrations, determined from NMR spectra taken over 8 hours, were plotted as a function of time, and each data set was fitted to a single exponential function. The NMR half-lives for the disappearance of the HNO donating pyrazolone derivative compound and the appearance of by-product and TXPTS aza-ylide were determined from the respective plots. The HNO donating pyrazolone derivative compound was quantitatively converted to by-product and HNO; the TXPTS aza-ylide yield was found to be 71%. The NMR half-lives determined for six pyrazolone derivative compounds are provided in Table 2. A control compound, compound 7 disclosed in WO 2013/059194, was also evaluated.

TABLE 2

Pyrazolone Derivative Compound NMR Half-lives ($T_{1/2}$)

| Compound No. | Compound Name | NMR-$T_{1/2}$ (minutes) |
| --- | --- | --- |
| 1 | 5-(4-chlorophenyl)-4-(hydroxyamino)-2,4-dimethyl-2,4-dihydro-3H-pyrazol-3-one | 780 |
| 2 | 5-(2-chlorophenyl)-4-(hydroxyamino)-2,4-dimethyl-2,4-dihydro-3H-pyrazol-3-one | 50 |
| 3 | 5-(2-fluorophenyl)-4-(hydroxyamino)-2,4-dimethyl-2,4-dihydro-3H-pyrazol-3-one | 237 |
| 6 | 4-(hydroxyamino)-2,5-dimethyl-4-phenyl-2,4-dihydro-3H-pyrazol-3-one | 34 |
| 14 | 4-(hydroxyamino)-2,4-dimethyl-5-(4-(methylsulfonyl)phenyl)-2,4-dihydro-3H-pyrazol-3-one | 379 |
| 15 | 4-(hydroxyamino)-2,4-dimethyl-5-phenyl-2,4-dihydro-3H-pyrazol-3-one | 1005 |
| Control | Compound 7 disclosed in WO 2013/059194 | 11 |

The procedure for determining the amount of HNO released from certain compounds from Table 1 was as follows.

Tris(4,6-dimethyl-3-sulfanatophenyl)phosphine trisodium salt (TXPTS) was of reagent grade and used without further purification. Synthetic TXPTS aza-ylide was obtained through the amidation of TXPTS using hydroxylamine O-sulfonic acid in water (Armstrong et al., *Org. Lett.* 7:713-716 (2005)). All other materials were of reagent grade and used without further purification.

All $^1$H NMR spectra were obtained in an adjusted-to pH 7.4 solution containing 0.25 M phosphate buffer, 0.2 mM of the metal chelator diethylenetriaminepentaacetic acid ("DTPAC"), and 10% $D_2O$ on a Bruker Avance 250 MHz 4.4 Example 147

In Vitro Plasma Stability of Pyrazolone Derivative Compounds in Plasma

Certain compounds from Table 1 were tested for their stability in plasma. The assay system comprised plasma from rat, dog or human (at least 3 donors, male, pooled) at pH 7.4, and (ii) an anticoagulant (sodium heparin or sodium citrate). Each test compound (5 µM) was incubated in plasma at 37° C. on a THERMOMIXER® with shaking. Three samples (n=3) were taken at each of seven sampling time points: 0, 10, 30, 60, 90, 180 and 360 minutes. The samples were immediately combined with 3 volumes (i.e., 3 times the volume of plasma) of acetonitrile containing 1% formic acid and an internal standard to terminate the reaction. AB SCIEX API 3000 LC-MS/MS analysis of the test compounds was performed without a standard curve. Plasma half-lives ($T_{1/2}$) of the test compounds were determined from graphs of the percent remaining values using the peak area response ratio. The plasma half-lives determined are provided in Table 3.

TABLE 3

PYRAZOLONE DERIVATIVE COMPOUND PLASMA HALF-LIVES ($T_{1/2}$)

| Compound No. | Compound Name | $T_{1/2}$ (minutes) Dog | $T_{1/2}$ (minutes) Rat | $T_{1/2}$ (minutes) Human |
|---|---|---|---|---|
| 1 | 5-(4-chlorophenyl)-4-(hydroxyamino)-2,4-dimethyl-2,4-dihydro-3H-pyrazol-3-one | 148 | 80 | 84 |
| 2 | 5-(2-chlorophenyl)-4-(hydroxyamino)-2,4-dimethyl-2,4-dihydro-3H-pyrazol-3-one | 72 | 61 | 52 |
| 3 | 5-(2-fluorophenyl)-4-(hydroxyamino)-2,4-dimethyl-2,4-dihydro-3H-pyrazol-3-one | 28 | 37 | 32 |
| 4 | 4-(hydroxyamino)-2,4-dimethyl-5-(4-(trifluoromethyl)phenyl)-2,4-dihydro-3H-pyrazol-3-one | 69 | 38 | 31 |
| 5 | 5-(4-fluorophenyl)-4-(hydroxyamino)-2,4-dimethyl-2,4-dihydro-3H-pyrazol-3-one | 172 | 78 | 108 |
| 6 | 4-(hydroxyamino)-2,5-dimethyl-4-phenyl-2,4-dihydro-3H-pyrazol-3-one | 12 | N/A | 38 |
| 7 | 5-(3,5-dimethylphenyl)-4-(hydroxyamino)-2,4-dimethyl-2,4-dihydro-3H-pyrazol-3-one | 117 | 34 | 104 |
| 8 | 5-(2-chlorophenyl)-4-(hydroxyamino)-2-iso-propyl-4-methyl-2,4-dihydro-3H-pyrazol-3-one | 170 | N/A | N/A |
| 9 | 5-(3,5-dichlorophenyl)-4-(hydroxyamino)-2,4-dimethyl-2,4-dihydro-3H-pyrazol-3-one | 59 | 17 | 43 |
| 10 | 5-(tert-butyl)-4-(hydroxyamino)-4-(1-(methoxyimino)ethyl)-2-methyl-2,4-dihydro-3H-pyrazol-3-one | 40 | 21 | 12 |
| 11 | 4-(hydroxyamino)-2,4-dimethyl-5-(4-(methylsulfinyl)phenyl)-2,4-dihydro-3H-pyrazol-3-one | 39 | 88 | 65 |
| 12 | 5-(2-chloro-4-fluorophenyl)-4-(hydroxyamino)-2,4-dimethyl-2,4-dihydro-3H-pyrazol-3-one | 28 | 20 | 18 |
| 13 | 4-(Hydroxyamino)-4-(1-(methoxyimino)ethyl)-5-methyl-2,4-dihydro-3H-pyrazol-3-one | N/A | N/A | N/A |
| 14 | 4-(hydroxyamino)-2,4-dimethyl-5-(4-(methylsulfonyl)phenyl)-2,4-dihydro-3H-pyrazol-3-one | 66 | 40 | 49 |
| 15 | 4-(hydroxyamino)-2,4-dimethyl-5-phenyl-2,4-dihydro-3H-pyrazol-3-one | 100 | 67 | 80 |
| 16 | 4-(hydroxyamino)-5-iso-propyl-4-(1-(methoxyimino)ethyl)-2-phenyl-2,4-dihydro-3H-pyrazol-3-one | 8 | N/A | N/A |
| 17 | 2-(4-bromophenyl)-4-(hydroxyamino)-5-iso-propyl-4-(1-(methoxyimino)ethyl)-2,4-dihydro-3H-pyrazol-3-one | <1 | N/A | N/A |
| 18 | 5-(tert-butyl)-4-(hydroxyamino)-4-(1-(methoxyimino)ethyl)-2-phenyl-2,4-dihydro-3H-pyrazol-3-one | 13 | 17 | 26 |
| 19 | 5-(3-fluoro-4-methoxyphenyl)-4-(hydroxyamino)-2,4-dimethyl-2,4-dihydro-3H-pyrazol-3-one | 95 | 90 | 163 |
| 20 | 5-cyclopropyl-4-(hydroxyamino)-4-(1-(methoxyimino)ethyl)-2-methyl-2,4-dihydro-3H-pyrazol-3-one | 20 | N/A | N/A |
| 21 | 4-(hydroxyamino)-2,4-dimethyl-5-(2-(methylsulfinyl)phenyl)-2,4-dihydro-3H-pyrazol-3-one | 24 | 36 | 41 |
| 22 | 4-(hydroxyamino)-2,4-dimethyl-5-(3-(trifluoromethyl)phenyl)-2,4-dihydro-3H-pyrazol-3-one | 114 | 44 | 55 |
| 23 | 5-(tert-butyl)-4-(hydroxyamino)-4-methyl-2-phenyl-2,4-dihydro-3H-pyrazol-3-one | 120 | 136 | 104 |

TABLE 3-continued

PYRAZOLONE DERIVATIVE COMPOUND PLASMA HALF-LIVES ($T_{1/2}$)

| Compound No. | Compound Name | $T_{1/2}$ (minutes) Dog | $T_{1/2}$ (minutes) Rat | $T_{1/2}$ (minutes) Human |
|---|---|---|---|---|
| 24 | 4-(hydroxyamino)-5-methyl-2,4-diphenyl-2,4-dihydro-3H-pyrazol-3-one | 16 | 10 | 11 |
| 25 | 4-(Hydroxyamino)-4-methyl-2,5-diphenyl-2,4-dihydro-3H-pyrazol-3-one | N/A | N/A | N/A |
| 26 | 5-(2-fluorophenyl)-4-(hydroxyamino)-2-iso-propyl-4-methyl-2,4-dihydro-3H-pyrazol-3-one | 65 | 42 | 45 |
| 27 | 4-(4-fluorophenyl)-4-(hydroxyamino)-2,5-dimethyl-2,4-dihydro-3H-pyrazol-3-one | 23 | 19 | 21 |
| 28 | 5-(tert-butyl)-4-(hydroxyamino)-2-iso-propyl-4-(1-(methoxyimino)ethyl)-2,4-dihydro-3H-pyrazol-3-one | 87 | N/A | N/A |
| 29 | 5-(2-fluorophenyl)-4-(hydroxyamino)-4-methyl-2-phenyl-2,4-dihydro-3H-pyrazol-3-one | 58 | N/A | N/A |
| 30 | 4-(hydroxyamino)-1-isopropyl-3-methyl-4-phenyl-1H-pyrazol-5(4H)-one | 84 | 32 | 22 |
| 31 | 4-ethyl-5-(2-fluorophenyl)-4-(hydroxyamino)-2-methyl-2,4-dihydro-3H-pyrazol-3-one | 201 | 66 | 59 |
| 32 | 4-(hydroxyamino)-2-iso-propyl-4-methyl-5-(4-(methylsulfonyl)phenyl)-2,4-dihydro-3H-pyrazol-3-one | 148 | 64 | 100 |
| 33 | 4-(hydroxyamino)-4,5-dimethyl-2-(4-(methylsulfonyl)phenyl)-2,4-dihydro-3H-pyrazol-3-one | 100 | 175 | 130 |
| 34 | 4-(hydroxyamino)-2,4-dimethyl-5-(4-((trifluoromethyl)sulfonyl)phenyl)-2,4-dihydro-3H-pyrazol-3-one | 25 | 28 | 36 |
| 35 | 4-(hydroxyamino)-2,4-dimethyl-5-(4-((trifluoromethyl)sulfinyl)phenyl)-2,4-dihydro-3H-pyrazol-3-one | 44 | 79 | 76 |
| 36 | 4-(hydroxyamino)-2,4-dimethyl-5-(4-(methylthio)phenyl)-2,4-dihydro-3H-pyrazol-3-one | 133 | 300 | 152 |
| 37 | 4-(hydroxyamino)-2,5-dimethyl-4-(4-(methylsulfonyl)phenyl)-2,4-dihydro-3H-pyrazol-3-one | 3 | 5 | 8 |
| 38 | 5-(3-Fluoro-4-(methylsulfinyl)phenyl)-4-(hydroxyamino)-2,4-dimethyl-2,4-dihydro-3H-pyrazol-3-one | 33 | 54 | 46 |
| 39 | 4-(Hydroxyamino)-2,4-dimethyl-5-(3-methyl-4-(methylsulfinyl)phenyl)-2,4-dihydro-3H-pyrazol-3-one | 59 | 134 | 60 |
| 40 | 5-(3-fluoro-4-(methylsulfonyl)phenyl)-4-(hydroxyamino)-2,4-dimethyl-2,4-dihydro-3H-pyrazol-3-one | 48 | 39 | 39 |
| 41 | 4-(hydroxyamino)-2,4-dimethyl-5-(3-methyl-4-(methylsulfonyl)phenyl)-2,4-dihydro-3H-pyrazol-3-one | 38 | 64 | 54 |
| 42 | 4-(hydroxyamino)-4-(1-(methoxyimino)ethyl)-2-methyl-5-(4-(methylsulfonyl)phenyl)-2,4-dihydro-3H-pyrazol-3-one | 5 | 9 | 6 |
| 43 | 4-(hydroxyamino)-4-(4-methoxyphenyl)-1,3-dimethyl-1H-pyrazol-5(4H)-one | 23 | 25 | 35 |
| 44 | 1-(4-Bromophenyl)-3-(2-chlorophenyl)-4-(hydroxyamino)-4-methyl-1H-pyrazol-5(4H)-one | 26 | N/A | N/A |
| 45 | 5-(3,5-difluoro-4-(methylsulfonyl)phenyl)-4-(hydroxyamino)-2,4-dimethyl-2,4-dihydro-3H-pyrazol-3-one | 31 | 25 | 40 |
| 46 | 4-(hydroxyamino)-4-(1-(methoxyimino)ethyl)-2-methyl-5-phenyl-2,4-dihydro-3H-pyrazol-3-one | 12 | 9 | 11 |
| 47 | 1-(4-bromophenyl)-4-(hydroxyamino)-3-methyl-4-phenyl-1H-pyrazol-5(4H)-one | 11 | N/A | N/A |

TABLE 3-continued

PYRAZOLONE DERIVATIVE COMPOUND PLASMA HALF-LIVES ($T_{1/2}$)

| Compound No. | Compound Name | $T_{1/2}$ (minutes) Dog | $T_{1/2}$ (minutes) Rat | $T_{1/2}$ (minutes) Human |
|---|---|---|---|---|
| 48 | 4-(Hydroxyamino)-2,4-dimethyl-5-(3-(methylsulfonyl)phenyl)-2,4-dihydro-3H-pyrazol-3-one | 49 | 53 | 49 |
| 49 | 4-(4-(Hydroxyamino)-1,4-dimethyl-5-oxo-4,5-dihydro-1H-pyrazol-3-yl)-N,N-dimethylbenzenesulfonamide | 39 | 70 | 52 |
| 50 | 1-(4-bromophenyl)-4-(hydroxyamino)-4-methyl-3-phenyl-1H-pyrazol-5(4H)-one | 356 | N/A | N/A |
| 51 | 4-(Hydroxyamino)-1,4-dimethyl-3-(o-tolyl)-1H-pyrazol-5(4H)-one | N/A | N/A | N/A |
| 52 | 4-(Hydroxyamino)-4-(1-(methoxyimino)ethyl)-1-methyl-3-(4-(trifluoromethyl)phenyl)-1H-pyrazol-5(4H)-one | 8 | N/A | N/A |
| 53 | 4-(hydroxyamino)-3-(4-methoxyphenyl)-1,4-dimethyl-1H-pyrazol-5(4H)-one | 256 | 350 | 480 |
| 54 | 3-(3-Chlorophenyl)-4-(hydroxyamino)-1,4-dimethyl-1H-pyrazol-5(4H)-one | 159 | N/A | N/A |
| 55 | 4-(Hydroxyamino)-3-(2-methoxyphenyl)-1,4-dimethyl-1H-pyrazol-5(4H)-one | 116 | N/A | N/A |
| 56 | 4-(Hydroxyamino)-1,4-dimethyl-3-(2-(trifluoromethoxy)phenyl)-1H-pyrazol-5(4H)-one | 69 | N/A | N/A |
| 57 | 3-(2,3-Dichlorophenyl)-4-(hydroxyamino)-1,4-dimethyl-1H-pyrazol-5(4H)-one | 15 | N/A | N/A |
| 58 | 3-(2,4-Dichlorophenyl)-4-(hydroxyamino)-1,4-dimethyl-1H-pyrazol-5(4H)-one | 19 | N/A | N/A |
| 59 | 4-(hydroxyamino)-1,4-dimethyl-3-(4-(trifluoromethoxy)phenyl)-1H-pyrazol-5(4H)-one | 150 | 80 | 77 |
| 60 | 4-(Hydroxyamino)-1,4-dimethyl-3-(2-(trifluoromethyl)phenyl)-1H-pyrazol-5(4H)-one | 49 | N/A | N/A |
| 61 | 4-(Hydroxyamino)-4-methyl-1-phenyl-3-(trifluoromethyl)-1H-pyrazol-5(4H)-one | >360 | N/A | N/A |
| 62 | 3-(2-ethoxy-4-fluorophenyl)-4-(hydroxyamino)-1,4-dimethyl-1H-pyrazol-5(4H)-one | 44 | 114 | N/A |
| 63 | 4-(hydroxyamino)-3-isopropyl-4-(1-(methoxyimino)ethyl)-1-methyl-1H-pyrazol-5(4H)-one | >360 | N/A | N/A |
| 64 | 3-(4-fluorophenyl)-4-(hydroxyamino)-4-(1-(methoxyimino)ethyl)-1-methyl-1H-pyrazol-5(4H)-one | 16 | 6 | 8 |
| 65 | 4-(Hydroxyamino)-1,3-dimethyl-4-(4-(methylsulfinyl)phenyl)-1H-pyrazol-5(4H)-one | 8 | N/A | N/A |
| 66 | 4-(4-chlorophenyl)-4-(hydroxyamino)-1,3-dimethyl-1H-pyrazol-5(4H)-one | 7 | 7 | 10 |
| 67 | 4-(Hydroxyamino)-1,4-dimethyl-3-(4-((trifluoromethyl)thio)phenyl)-1H-pyrazol-5(4H)-one | 78 | 106 | 59 |
| 68 | 4-(3-Bromo-4-methoxyphenyl)-4-(hydroxyamino)-1,3-dimethyl-1H-pyrazol-5(4H)-one | N/A | N/A | N/A |
| 69 | 1-(2-Chlorophenyl)-4-(hydroxyamino)-3,4-dimethyl-4,5-dihydro-1H-pyrazol-5-one | 172 | 162 | 208 |
| 70 | 3-(3-Chloro-4-methanesulfonylphenyl)-4-(hydroxyamino)-1,4-dimethyl-4,5-dihydro-1H-pyrazol-5-one | 27 | 43 | 31 |
| 71 | Methyl 4-[4-(hydroxyamino)-1,4-dimethyl-5-oxo-4,5-dihydro-1H-pyrazol-3-yl]benzoate | 71 | 3 | 58 |
| 72 | 2,2,2-Trifluoro-N-({4-[4-(hydroxyamino)-1,4-dimethyl-5-oxo-4,5-dihydro-1H-pyrazol-3- | 12 | 9 | 13 |

TABLE 3-continued

PYRAZOLONE DERIVATIVE COMPOUND PLASMA HALF-LIVES ($T_{1/2}$)

| Compound No. | Compound Name | $T_{1/2}$ (minutes) Dog | $T_{1/2}$ (minutes) Rat | $T_{1/2}$ (minutes) Human |
|---|---|---|---|---|
| | yl]phenyl}(methyl)oxo-$\lambda^6$-sulfanylidene)acetamide | | | |
| 73 | 4-(3,4-Dimethoxyphenyl)-4-(hydroxyamino)-1,3-dimethyl-4,5-dihydro-1H-pyrazol-5-one | 13 | 18 | 14 |
| 74 | 4-[4-(Hydroxyamino)-1,4-dimethyl-5-oxo-4,5-dihydro-1H-pyrazol-3-yl]benzoic acid | 175 | 243 | 183 |
| 75 | 4-(Hydroxyamino)-3-{4-[imino(methyl)oxo-$\lambda^6$-sulfanyl]phenyl}-1,4-dimethyl-4,5-dihydro-1H-pyrazol-5-one | 47 | 113 | 49 |
| 76 | 4-(Hydroxyamino)-4-(4-methoxy-3-methylphenyl)-1,3-dimethyl-4,5-dihydro-1H-pyrazol-5-one | 21 | N/A | N/A |
| 77 | 4-(Hydroxyamino)-3-(4-methanesulfonyl-3-methoxyphenyl)-1,4-dimethyl-4,5-dihydro-1H-pyrazol-5-one | 37 | 62 | 40 |
| 78 | 4-(Hydroxyamino)-1,4-dimethyl-3-[4-(propane-2-sulfonyl)phenyl]-4,5-dihydro-1H-pyrazol-5-one | 42 | 75 | 43 |
| 79 | 4-(Hydroxyamino)-3-(4-methanesulfonyl-3,5-dimethylphenyl)-1,4-dimethyl-4,5-dihydro-1H-pyrazol-5-one | 49 | 85 | 49 |
| 80 | 4-(Hydroxyamino)-1,4-dimethyl-3-[4-(morpholine-4-sulfonyl)phenyl]-4,5-dihydro-1H-pyrazol-5-one | 49 | 80 | 46 |
| 81 | 4-(Hydroxyamino)-1,4-dimethyl-3-[4-(morpholine-4-carbonyl)phenyl]-4,5-dihydro-1H-pyrazol-5-one | 84 | 148 | 76 |
| 82 | 4-(Hydroxyamino)-3-[4-methanesulfonyl-3-(morpholin-4-yl)phenyl]-1,4-dimethyl-4,5-dihydro-1H-pyrazol-5-one | 56 | 69 | 46 |
| 83 | 4-(Hydroxyamino)-3-{4-methanesulfonyl-3-[(2-methoxyethyl)(methyl)amino]phenyl}-1,4-dimethyl-4,5-dihydro-1H-pyrazol-5-one | 66 | 89 | 51 |
| 84 | 4-[4-(Hydroxyamino)-1,4-dimethyl-5-oxo-4,5-dihydro-1H-pyrazol-3-yl]-N,N-dimethylbenzamide | 100 | 161 | 89 |
| 85 | 3-[4-(4,4-Difluoropiperidine-1-carbonyl)phenyl]-4-(hydroxyamino)-1,4-dimethyl-4,5-dihydro-1H-pyrazol-5-one | 86 | 125 | 105 |
| 86 | 3-[4-(Ethanesulfonyl)phenyl]-4-(hydroxyamino)-1,4-dimethyl-4,5-dihydro-1H-pyrazol-5-one | 39 | 61 | 47 |
| 87 | 3-[3-(Dimethylamino)-4-methanesulfonylphenyl]-4-(hydroxyamino)-1,4-dimethyl-4,5-dihydro-1H-pyrazol-5-one | 42 | 63 | 47 |
| 88 | 4-(Hydroxyamino)-3-[4-methanesulfonyl-3-(4-methylpiperazin-1-yl)phenyl]-1,4-dimethyl-4,5-dihydro-1H-pyrazol-5-one | 42 | 65 | 49 |
| 89 | 3-[4-(Benzenesulfonyl)phenyl]-4-(hydroxyamino)-1,4-dimethyl-4,5-dihydro-1H-pyrazol-5-one | 29 | 36 | 57 |
| 90 | 4[4-(Hydroxyamino)-1,4-dimethyl-5-oxo-4,5-dihydro-1H-pyrazol-3-yl]-N-(2-methoxyethyl)-N-methylbenzene-1-sulfonamide | 37 | 72 | 49 |
| 91 | 3-(4-tert-Butylphenyl)-4-(hydroxyamino)-1,4-dimethyl-4,5-dihydro-1H-pyrazol-5-one | 226 | N/A | N/A |
| 92 | 4-[4-(Hydroxyamino)-1,4-dimethyl-5-oxo-4,5-dihydro-1H-pyrazol-3-yl]benzamide | 166 | 270 | 169 |
| 93 | 4-(Hydroxyamino)-3-[4-methanesulfonyl-3-(piperazin-1- | 32 | 66 | 35 |

TABLE 3-continued

PYRAZOLONE DERIVATIVE COMPOUND PLASMA HALF-LIVES ($T_{1/2}$)

| Compound No. | Compound Name | $T_{1/2}$ (minutes) Dog | $T_{1/2}$ (minutes) Rat | $T_{1/2}$ (minutes) Human |
|---|---|---|---|---|
| 94 | yl)phenyl]-1,4-dimethyl-4,5-dihydro-1H-pyrazol-5-one (2S)-2-({4-[4-(Hydroxyamino)-1,4-dimethyl-5-oxo-4,5-dihydro-1H-pyrazol-3-yl]phenyl}formamido)propanoic acid | 114 | 191 | 103 |
| 95 | 2-({4-[4-(Hydroxyamino)-1,4-dimethyl-5-oxo-4,5-dihydro-1H-pyrazol-3-yl]phenyl}formamido)acetic acid | 120 | N/A | N/A |
| 96 | 4-(3-Fluorophenyl)-4-(hydroxyamino)-1,3-dimethyl-4,5-dihydro-1H-pyrazol-5-one | 6 | N/A | N/A |
| 97 | 4-(Hydroxyamino)-3-[4-methanesulfonyl-3-(trifluoromethyl)phenyl]-1,4-dimethyl-4,5-dihydro-1H-pyrazol-5-one | 32 | 23 | 25 |
| 98 | 4-(Hydroxyamino)-1,3-dimethyl-4-(3-methylphenyl)-4,5-dihydro-1H-pyrazol-5-one | 16 | 11 | 12 |
| 99 | 4-(3-Chlorophenyl)-4-(hydroxyamino)-1,3-dimethyl-4,5-dihydro-1H-pyrazol-5-one | 4 | N/A | N/A |
| 100 | 4-[4-(Hydroxyamino)-1,4-dimethyl-5-oxo-4,5-dihydro-1H-pyrazol-3-yl]-N-methanesulfonylbenzamide | 118 | 256 | 220 |
| 102 | 4-(Hydroxyamino)-1,3-dimethyl-4-[1-(phenoxyimino)ethyl]-4,5-dihydro-1H-pyrazol-5-one | <1 | N/A | N/A |
| 103 | 4-(Hydroxyamino)-1,3-dimethyl-4-[1-(benzyloxyimino)ethyl]-4,5-dihydro-1H-pyrazol-5-one | 3 | N/A | N/A |
| 104 | 3-(3,4-Dimethanesulfonylphenyl)-4-(hydroxyamino)-1,4-dimethyl-4,5-dihydro-1H-pyrazol-5-one | 33 | 59 | 28 |
| 105 | 4-(Hydroxyamino)-1,3-dimethyl-4-[1-[(2-methylpropoxy)imino]ethyl]-4,5-dihydro-1H-pyrazol-5-one | 4 | 4 | 6 |
| 106 | 4-[1-(Ethoxyimino)ethyl]-4-(hydroxyamino)-1,3-dimethyl-4,5-dihydro-1H-pyrazol-5-one | 8 | 7 | 6 |
| 107 | 4-(Hydroxyamino)-4-[1-(methoxyimino)ethyl]-3-(4-methoxyphenyl)-1-methyl-4,5-dihydro-1H-pyrazol-5-one | 10 | 49 | 18 |
| 108 | 3-(4-Bromophenyl)-4-(hydroxyamino)-1,4-dimethyl-4,5-dihydro-1H-pyrazol-5-one | 136 | 89 | 61 |
| 109 | 4-(Hydroxyamino)-1-methyl-3,4-diphenyl-4,5-dihydro-1H-pyrazol-5-one | 11 | 8 | 10 |
| 110 | 3-Ethoxy-4-(hydroxyamino)-4-[1-(methoxyimino)ethyl]-1-phenyl-4,5-dihydro-1H-pyrazol-5-one | 12 | 62 | 11 |
| 111 | 1-(4-Bromophenyl)-3-ethoxy-4-(hydroxyamino)-4-[1-(methoxyimino)ethyl]-4,5-dihydro-1H-pyrazol-5-one | 24 | 23 | 29 |
| 112 | 3-tert-Butyl-4-[1-(ethoxyimino)ethyl]-4-(hydroxyamino)-1-methyl-4,5-dihydro-1H-pyrazol-5-one | 21 | 19 | 10 |
| 113 | 3-tert-Butyl-4-(hydroxyamino)-1-methyl-4-phenyl-4,5-dihydro-1H-pyrazol-5-one | 75 | 53 | 30 |
| 114 | 3-{4-[(4,4-Difluoropiperidin-1-yl)sulfonyl]phenyl}-4-(hydroxyamino)-1,4-dimethyl-4,5-dihydro-1H-pyrazol-5-one | 42 | 49 | 25 |
| 115 | 4-[1-[(Benzyloxy)imino]ethyl]-3-tert-butyl-4-(hydroxyamino)-1-methyl-4,5-dihydro-1H-pyrazol-5-one | 27 | 32 | 14 |
| 116 | 4-(Hydroxyamino)-3-methoxy-4-[1-(methoxyimino)ethyl]-1-phenyl-4,5-dihydro-1H-pyrazol-5-one | 18 | 48 | 9 |

TABLE 3-continued

PYRAZOLONE DERIVATIVE COMPOUND PLASMA HALF-LIVES (T$_{1/2}$)

| Compound No. | Compound Name | T$_{1/2}$ (minutes) Dog | T$_{1/2}$ (minutes) Rat | T$_{1/2}$ (minutes) Human |
|---|---|---|---|---|
| 117 | 4-[1-[(tert-Butoxy)imino]ethyl]-3-tert-butyl-4-(hydroxyamino)-1-methyl-4,5-dihydro-1H-pyrazol-5-one | 34 | 36 | 16 |
| 118 | 4-[1-[(4-Bromophenoxy)imino]ethyl]-3-tert-butyl-4-(hydroxyamino)-1-methyl-4,5-dihydro-1H-pyrazol-5-one | 24 | 22 | 5 |
| 119 | 3-tert-Butyl-4-(hydroxyamino)-1-methyl-4[1-(phenoxyimino)ethyl]-4,5-dihydro-1H-pyrazol-5-one | 118 | 91 | 12 |
| 120 | 4-(Hydroxyamino)-3-{4-[imino(oxo)propan-2-yl-$\lambda^6$-sulfanyl]phenyl}-1,4-dimethyl-4,5-dihydro-1H-pyrazol-5-one | 31 | 56 | 32 |
| 121 | 4-[4-(Hydroxyamino)-4-[1-(methoxyimino)ethyl]-1-methyl-5-oxo-4,5-dihydro-1H-pyrazol-3-yl]-N,N-dimethylbenzene-1-sulfonamide | 4 | 8 | 2 |
| 122 | 4-[3-tert-Butyl-4-(hydroxyamino)-1-methyl-5-oxo-4,5-dihydro-1H-pyrazol-4-yl]-N,N-dimethylbenzene-1-sulfonamide | 35 | 34 | 31 |
| 123 | 4-[4-(Hydroxyamino)-4-[1-(methoxyimino)ethyl]-1-methyl-5-oxo-4,5-dihydro-1H-pyrazol-3-yl]-N,N-dimethylbenzamide | 6 | 11 | 6 |
| 124 | 4-[3-tert-Butyl-4-(hydroxyamino)-1-methyl-5-oxo-4,5-dihydro-1H-pyrazol-4-yl]-N,N-dimethylbenzamide | 45 | 44 | 31 |
| 125 | 4-[1-[(Benzyloxy)imino]ethyl]-3-ethoxy-4-(hydroxyamino)-1-methyl-4,5-dihydro-1H-pyrazol-5-one | 13 | 15 | 10 |
| 126 | 3-Ethoxy-4-(hydroxyamino)-4-[1-(methoxyimino)ethyl]-1-methyl-4,5-dihydro-1H-pyrazol-5-one | 30 | 18 | 18 |
| 127 | 3-Ethoxy-4-(hydroxyamino)-4-methyl-1-phenyl-4,5-dihydro-1H-pyrazol-5-one | >480 | >480 | >480 |
| 128 | 4-(Hydroxyamino)-4-[1(methoxyimino)ethyl]-1-phenyl-3-(phenylsulfanyl)-4,5-dihydro-1H-pyrazol-5-one | 3 | 7 | N/A |
| 129 | 3-(Benzenesulfonyl)-4-(hydroxyamino)-4[1-(methoxyimino)ethyl]-1-phenyl-4,5-dihydro-1H-pyrazol-5-one pyrazol-5-one | N/A | N/A | N/A |
| 130 | 3-(Benzenesulfinyl)-4-(hydroxyamino)4[1-(methoxyimino)ethyl]-1-phenyl-4,5-dihydro1H-pyrazol-5-one | <1 | <1 | <1 |
| 131 | 3-tert-Butyl-4-(hydroxyamino)-4-[1-(methoxyimino)ethyl]-4,5-dihydro-1H-pyrazol-5-one | 7 | 24 | 15 |
| 132 | 4-(Hydroxyamino)-1,3-dimethyl-4-(5-phenyl-1,2,4-oxadiazol-3-yl)-4,5-dihydro-1H-pyrazol-5-one | <1 | <1 | <1 |
| 133 | 4-(Hydroxyamino)-3-(4-methanesulfonylphenyl)-4-methyl-4,5-dihydro-1H-pyrazol-5-one | 126 | 116 | 110 |
| 134 | 3-tert-Butyl-4-[1-(ethoxyimino)ethyl]-4-(hydroxyamino)-4,5-dihydro-1H-pyrazol-5-one | 26 | 20 | 17 |
| 135 | 4-[4-(Hydroxyamino)-4-methyl-5-oxo-4,5-dihydro-1H-pyrazol-3-yl]-N,N-dimethylbenzene-1-sulfonamide | N/A | N/A | N/A |
| 136 | 4-(Hydroxyamino)-3-(4-methanesulfonylphenyl)-4-methyl-1-phenyl-4,5-dihydro-1H-pyrazol-5-one | N/A | N/A | N/A |
| 137 | 4-(Hydroxyamino)-3-methyl-4-phenyl-4,5-dihydro-1H-pyrazol-5-one | N/A | N/A | N/A |

TABLE 3-continued

PYRAZOLONE DERIVATIVE COMPOUND PLASMA HALF-LIVES ($T_{1/2}$)

| Compound No. | Compound Name | $T_{1/2}$ (minutes) Dog | $T_{1/2}$ (minutes) Rat | $T_{1/2}$ (minutes) Human |
|---|---|---|---|---|
| 138 | 4-(Hydroxyamino)-3-(4-methanesulfonylphenyl)-4-methyl-1-(pyrazin-2-yl)-4,5-dihydro-1H-pyrazol-5-one | N/A | N/A | N/A |

4.4 Example 148

Melting Point of Pyrazolone Derivative Compounds

The melting points of certain compounds from Table 1 were determined on a METTLER TOLEDO 50 instrument with a start temperature of 80° C. at a rate of 5° C./min. to an end temperature of 300° C. The results obtained are provided in Table 4. "Oil" denotes that because the compound was not a solid but an oil, no melting point could be determined. "Decomposed" denotes that at the temperature at which the compound melted the compound also appeared to decompose or appeared to begin to decompose.

TABLE 4

Pyrazolone Derivative Compound Melting Points

| Compound No. | Compound Name | Melting Point (° C.) |
|---|---|---|
| 1 | 5-(4-chlorophenyl)-4-(hydroxyamino)-2,4-dimethyl-2,4-dihydro-3H-pyrazol-3-one | 164 |
| 2 | 5-(2-chlorophenyl)-4-(hydroxyamino)-2,4-dimethyl-2,4-dihydro-3H-pyrazol-3-one | 125 |
| 3 | 5-(2-fluorophenyl)-4-(hydroxyamino)-2,4-dimethyl-2,4-dihydro-3H-pyrazol-3-one | 102 |
| 4 | 4-(hydroxyamino)-2,4-dimethyl-5-(4-(trifluoromethyl)phenyl)-2,4-dihydro-3H-pyrazol-3-one | 167 |
| 5 | 5-(4-fluorophenyl)-4-(hydroxyamino)-2,4-dimethyl-2,4-dihydro-3H-pyrazol-3-one | 189 |
| 6 | 4-(hydroxyamino)-2,5-dimethyl-4-phenyl-2,4-dihydro-3H-pyrazol-3-one | 153 |
| 7 | 5-(3,5-dimethylphenyl)-4-(hydroxyamino)-2,4-dimethyl-2,4-dihydro-3H-pyrazol-3-one | 151 |
| 8 | 5-(2-chlorophenyl)-4-(hydroxyamino)-2-iso-propyl-4-methyl-2,4-dihydro-3H-pyrazol-3-one | 114 |
| 9 | 5-(3,5-dichlorophenyl)-4-(hydroxyamino)-2,4-dimethyl-2,4-dihydro-3H-pyrazol-3-one | 152 |
| 10 | 5-(tert-butyl)-4-(hydroxyamino)-4-(1-(methoxyimino)ethyl)-2-methyl-2,4-dihydro-3H-pyrazol-3-one | oil |
| 11 | 4-(hydroxyamino)-2,4-dimethyl-5-(4-(methylsulfinyl)phenyl)-2,4-dihydro-3H-pyrazol-3-one | 163 |
| 12 | 5-(2-chloro-4-fluorophenyl)-4-(hydroxyamino)-2,4-dimethyl-2,4-dihydro-3H-pyrazol-3-one | 159 |
| 13 | 4-(Hydroxyamino)-4-(1-(methoxyimino)ethyl)-5-methyl-2,4-dihydro-3H-pyrazol-3-one | N/A |
| 14 | 4-(hydroxyamino)-2,4-dimethyl-5-(4-(methylsulfonyl)phenyl)-2,4-dihydro-3H-pyrazol-3-one | 172 |
| 15 | 4-(hydroxyamino)-2,4-dimethyl-5-phenyl-2,4-dihydro-3H-pyrazol-3-one | 146 |
| 16 | 4-(hydroxyamino)-5-iso-propyl-4-(1-(methoxyimino)ethyl)-2-phenyl-2,4-dihydro-3H-pyrazol-3-one | oil |
| 17 | 2-(4-bromophenyl)-4-(hydroxyamino)-5-iso-propyl-4-(1-(methoxyimino)ethyl)-2,4-dihydro-3H-pyrazol-3-one | 116 |
| 18 | 5-(tert-butyl)-4-(hydroxyamino)-4-(1-(methoxyimino)ethyl)-2-phenyl-2,4-dihydro-3H-pyrazol-3-one | 134 |
| 19 | 5-(3-fluoro-4-methoxyphenyl)-4-(hydroxyamino)-2,4-dimethyl-2,4-dihydro-3H-pyrazol-3-one | 171 |
| 20 | 5-cyclopropyl-4-(hydroxyamino)-4-(1-(methoxyimino)ethyl)-2-methyl-2,4-dihydro-3H-pyrazol-3-one | oil |
| 21 | 4-(Hydroxyamino)-2,4-dimethyl-5-(2-(methylsulfinyl)phenyl)-2,4-dihydro-3H-pyrazol-3-one | 151 |
| 22 | 4-(hydroxyamino)-2,4-dimethyl-5-(3-(trifluoromethyl)phenyl)-2,4-dihydro-3H-pyrazol-3-one | 141 |
| 23 | 5-(tert-Butyl)-4-(hydroxyamino)-4-methyl-2-phenyl-2,4-dihydro-3H-pyrazol-3-one | 96 |
| 24 | 4-(hydroxyamino)-5-methyl-2,4-diphenyl-2,4-dihydro-3H-pyrazol-3-one | 146 |
| 25 | 4-(hydroxyamino)-4-methyl-2,5-diphenyl-2,4-dihydro-3H-pyrazol-3-one | 150 |

TABLE 4-continued

Pyrazolone Derivative Compound Melting Points

| Compound No. | Compound Name | Melting Point (° C.) |
|---|---|---|
| 26 | 5-(2-fluorophenyl)-4-(hydroxyamino)-2-iso-propyl-4-methyl-2,4-dihydro-3H-pyrazol-3-one | 126 |
| 27 | 4-(4-fluorophenyl)-4-(hydroxyamino)-2,5-dimethyl-2,4-dihydro-3H-pyrazol-3-one | 140 |
| 28 | 5-(tert-butyl)-4-(hydroxyamino)-2-iso-propyl-4-(1-(methoxyimino)ethyl)-2,4-dihydro-3H-pyrazol-3-one | oil |
| 29 | 5-(2-fluorophenyl)-4-(hydroxyamino)-4-methyl-2-phenyl-2,4-dihydro-3H-pyrazol-3-one | 98 |
| 30 | 4-(hydroxyamino)-1-isopropyl-3-methyl-4-phenyl-1H-pyrazol-5(4H)-one | 130 |
| 31 | 4-ethyl-5-(2-fluorophenyl)-4-(hydroxyamino)-2-methyl-2,4-dihydro-3H-pyrazol-3-one | 127 |
| 32 | 4-(hydroxyamino)-2-iso-propyl-4-methyl-5-(4-(methylsulfonyl)phenyl)-2,4-dihydro-3H-pyrazol-3-one | 160 |
| 33 | 4-(hydroxyamino)-4,5-dimethyl-2-(4-(methylsulfonyl)phenyl)-2,4-dihydro-3H-pyrazol-3-one | 170 |
| 34 | 4-(hydroxyamino)-2,4-dimethyl-5-(4-((trifluoromethyl)sulfonyl)phenyl)-2,4-dihydro-3H-pyrazol-3-one | 153 |
| 35 | 4-(hydroxyamino)-2,4-dimethyl-5-(4-((trifluoromethyl)sulfinyl)phenyl)-2,4-dihydro-3H-pyrazol-3-one | <80 |
| 36 | 4-(hydroxyamino)-2,4-dimethyl-5-(4-(methylthio)phenyl)-2,4-dihydro-3H-pyrazol-3-one | 156 |
| 37 | 4-(hydroxyamino)-2,5-dimethyl-4-(4-(methylsulfonyl)phenyl)-2,4-dihydro-3H-pyrazol-3-one | 147 |
| 38 | 5-(3-fluoro-4-(methylsulfinyl)phenyl)-4-(hydroxyamino)-2,4-dimethyl-2,4-dihydro-3H-pyrazol-3-one | 157 |
| 39 | 4-(hydroxyamino)-2,4-dimethyl-5-(3-methyl-4-(methylsulfinyl)phenyl)-2,4-dihydro-3H-pyrazol-3-one | 162 |
| 40 | 5-(3-fluoro-4-(methylsulfonyl)phenyl)-4-(hydroxyamino)-2,4-dimethyl-2,4-dihydro-3H-pyrazol-3-one | 163 |
| 41 | 4-(hydroxyamino)-2,4-dimethyl-5-(3-methyl-4-(methylsulfonyl)phenyl)-2,4-dihydro-3H-pyrazol-3-one | 213 |
| 42 | 4-(hydroxyamino)-4-(1-(methoxyimino)ethyl)-2-methyl-5-(4-(methylsulfonyl)phenyl)-2,4-dihydro-3H-pyrazol-3-one | 147 |
| 43 | 4-(hydroxyamino)-4-(4-methoxyphenyl)-1,3-dimethyl-1H-pyrazol-5(4H)-one | 106 |
| 44 | 1-(4-bromophenyl)-3-(2-chlorophenyl)-4-(hydroxyamino)-4-methyl-1H-pyrazol-5(4H)-one | 129 |
| 45 | 5-(3,5-difluoro-4-(methylsulfonyl)phenyl)-4-(hydroxyamino)-2,4-dimethyl-2,4-dihydro-3H-pyrazol-3-one | 159 |
| 46 | 4-(Hydroxyamino)-4-(1-(methoxyimino)ethyl)-2-methyl-5-phenyl-2,4-dihydro-3H-pyrazol-3-one | 109 |
| 47 | 1-(4-bromophenyl)-4-(hydroxyamino)-3-methyl-4-phenyl-1H-pyrazol-5(4H)-one | 171 |
| 48 | 4-(Hydroxyamino)-2,4-dimethyl-5-(3-(methylsulfonyl)phenyl)-2,4-dihydro-3H-pyrazol-3-one | 150 |
| 49 | 4-(4-(hydroxyamino)-1,4-dimethyl-5-oxo-4,5-dihydro-1H-pyrazol-3-yl)-N,N-dimethylbenzenesulfonamide | 166 |
| 50 | 1-(4-bromophenyl)-4-(hydroxyamino)-4-methyl-3-phenyl-1H-pyrazol-5(4H)-one | 174 |
| 51 | 4-(hydroxyamino)-1,4-dimethyl-3-(o-tolyl)-1H-pyrazol-5(4H)-one | 120 |
| 52 | 4-(hydroxyamino)-4-(1-(methoxyimino)ethyl)-1-methyl-3-(4-(trifluoromethyl)phenyl)-1H-pyrazol-5(4H)-one | 104 |
| 53 | 4-(hydroxyamino)-3-(4-methoxyphenyl)-1,4-dimethyl-1H-pyrazol-5(4H)-one | 159 |
| 54 | 3-(3-chlorophenyl)-4-(hydroxyamino)-1,4-dimethyl-1H-pyrazol-5(4H)-one | 137 |
| 55 | 4-(hydroxyamino)-3-(2-methoxyphenyl)-1,4-dimethyl-1H-pyrazol-5(4H)-one | 97 |
| 56 | 4-(hydroxyamino)-1,4-dimethyl-3-(2-(trifluoromethoxy)phenyl)-1H-pyrazol-5(4H)-one | 118 |
| 57 | 3-(2,3-dichlorophenyl)-4-(hydroxyamino)-1,4-dimethyl-1H-pyrazol-5(4H)-one | 137 |
| 58 | 3-(2,4-dichlorophenyl)-4-(hydroxyamino)-1,4-dimethyl-1H-pyrazol-5(4H)-one | 165 (decomposed) |
| 59 | 4-(hydroxyamino)-1,4-dimethyl-3-(4-(trifluoromethoxy)phenyl)-1H-pyrazol-5(4H)-one | 140 |
| 60 | 4-(Hydroxyamino)-1,4-dimethyl-3-(2-(trifluoromethyl)phenyl)-1H-pyrazol-5(4H)-one | N/A |
| 61 | 4-(hydroxyamino)-4-methyl-1-phenyl-3-(trifluoromethyl)-1H-pyrazol-5(4H)-one | 107 |

TABLE 4-continued

Pyrazolone Derivative Compound Melting Points

| Compound No. | Compound Name | Melting Point (° C.) |
|---|---|---|
| 62 | 3-(2-ethoxy-4-fluorophenyl)-4-(hydroxyamino)-1,4-dimethyl-1H-pyrazol-5(4H)-one | 122 |
| 63 | 4-(hydroxyamino)-3-isopropyl-4-(1-(methoxyimino)ethyl)-1-methyl-1H-pyrazol-5(4H)-one | oil |
| 64 | 3-(4-fluorophenyl)-4-(hydroxyamino)-4-(1-(methoxyimino)ethyl)-1-methyl-1H-pyrazol-5(4H)-one | 109 |
| 65 | 4-(Hydroxyamino)-1,3-dimethyl-4-(4-(methylsulfinyl)phenyl)-1H-pyrazol-5(4H)-one | N/A |
| 66 | 4-(4-chlorophenyl)-4-(hydroxyamino)-1,3-dimethyl-1H-pyrazol-5(4H)-one | 141 |
| 67 | 4-(hydroxyamino)-1,4-dimethyl-3-(4-((trifluoromethyl)thio)phenyl)-1H-pyrazol-5(4H)-one | 126 |
| 68 | 4-(3-bromo-4-methoxyphenyl)-4-(hydroxyamino)-1,3-dimethyl-1H-pyrazol-5(4H)-one | 146 |
| 69 | 1-(2-Chlorophenyl)-4-(hydroxyamino)-3,4-dimethyl-4,5-dihydro-1H-pyrazol-5-one | 145 |
| 70 | 3-(3-Chloro-4-methanesulfonylphenyl)-4-(hydroxyamino)-1,4-dimethyl-4,5-dihydro-1H-pyrazol-5-one | 195 |
| 71 | Methyl 4-[4-(hydroxyamino)-1,4-dimethyl-5-oxo-4,5-dihydro-1H-pyrazol-3-yl]benzoate | 150 |
| 72 | 2,2,2-Trifluoro-N-({4-[4-(hydroxyamino)-1,4-dimethyl-5-oxo-4,5-dihydro-1H-pyrazol-3-yl]phenyl}(methyl)oxo-$\lambda^6$-sulfanylidene)acetamide | 87 |
| 73 | 4-(3,4-Dimethoxyphenyl)-4-(hydroxyamino)-1,3-dimethyl-4,5-dihydro-1H-pyrazol-5-one | 116 |
| 74 | 4-[4-(Hydroxyamino)-1,4-dimethyl-5-oxo-4,5-dihydro-1H-pyrazol-3-yl]benzoic acid | 195 |
| 75 | 4-(Hydroxyamino)-3-{4-[imino(methyl)oxo-$\lambda^6$-sulfanyl]phenyl}-1,4-dimethyl-4,5-dihydro-1H-pyrazol-5-one | 84 |
| 76 | 4-(Hydroxyamino)-4-(4-methoxy-3-methylphenyl)-1,3-dimethyl-4,5-dihydro-1H-pyrazol-5-one | 176 |
| 77 | 4-(Hydroxyamino)-3-(4-methanesulfonyl-3-methoxyphenyl)-1,4-dimethyl-4,5-dihydro-1H-pyrazol-5-one | 179 |
| 78 | 4-(Hydroxyamino)-1,4-dimethyl-3-[4-(propane-2-sulfonyl)phenyl]-4,5-dihydro-1H-pyrazol-5-one | 167 |
| 79 | 4-(Hydroxyamino)-3-(4-methanesulfonyl-3,5-dimethylphenyl)-1,4-dimethyl-4,5-dihydro-1H-pyrazol-5-one | 169 |
| 80 | 4-(Hydroxyamino)-1,4-dimethyl-3-[4-(morpholine-4-sulfonyl)phenyl]-4,5-dihydro-1H-pyrazol-5-one | 113 |
| 81 | 4-(Hydroxyamino)-1,4-dimethyl-3-[4-(morpholine-4-carbonyl)phenyl]-4,5-dihydro-1H-pyrazol-5-one | 172 |
| 82 | 4-(Hydroxyamino)-3-[4-methanesulfonyl-3-(morpholin-4-yl)phenyl]-1,4-dimethyl-4,5-dihydro-1H-pyrazol-5-one | 198 |
| 83 | 4-(Hydroxyamino)-3-{4-methanesulfonyl-3-[(2-methoxyethyl)(methyl)amino]phenyl}-1,4-dimethyl-4,5-dihydro-1H-pyrazol-5-one | 132 |
| 84 | 4-[4-(Hydroxyamino)-1,4-dimethyl-5-oxo-4,5-dihydro-1H-pyrazol-3-yl]-N,N-dimethylbenzamide | 172 |
| 85 | 3-[4-(4,4-(Difluoropiperidine-1-carbonyl)phenyl]-4-(hydroxyamino)-1,4-dimethyl-4,5-dihydro-1H-pyrazol-5-one | 172 |
| 86 | 3-[4-(Ethanesulfonyl)phenyl]-4-(hydroxyamino)-1,4-dimethyl-4,5-dihydro-1H-pyrazol-5-one | 168 |
| 87 | 3-[3-(Dimethylamino)-4-methanesulfonylphenyl]-4-(hydroxyamino)-1,4-dimethyl-4,5-dihydro-1H-pyrazol-5-one | 180 |
| 88 | 4-(Hydroxyamino)-3-[4-methanesulfonyl-3-(4-methylpiperazin-1-yl)phenyl]-1,4-dimethyl-4,5-dihydro-1H-pyrazol-5-one | 146 |
| 89 | 3-[4-(Benzenesulfonyl)phenyl]-4-(hydroxyamino)-1,4-dimethyl-4,5-dihydro-1H-pyrazol-5-one | 166 |
| 90 | 4-[4-(Hydroxyamino)-1,4-dimethyl-5-oxo-4,5-dihydro-1H-pyrazol-3-yl]-N-(2-methoxyethyl)-N-methylbenzene-1-sulfonamide | 117 |
| 91 | 3-(4-tert-Butylphenyl)-4-(hydroxyamino)-1,4-dimethyl-4,5-dihydro-1H-pyrazol-5-one | 108 |
| 92 | 4-[4-Hydroxyamino)-1,4-dimethyl-5-oxo-4,5-dihydro-1H-pyrazol-3-yl]benzamide | 190 |
| 93 | 4-(Hydroxyamino)-3-[4-methanesulfonyl-3-(piperazin-1-yl)phenyl]-1,4-dimethyl-4,5-dihydro-1H-pyrazol-5-one | 140 |
| 94 | (2S)-2-({4-[4-(Hydroxyamino)-1,4-dimethyl-5-oxo-4,5-dihydro-1H-pyrazol-3-yl]phenyl}formamido)propanoic acid | 133 |
| 95 | 2-({4-[4-(Hydroxyamino)-1,4-dimethyl-5-oxo-4,5-dihydro-1H-pyrazol-3-yl]phenyl}formamido)acetic acid | 138 |
| 96 | 4-(3-Fluorophenyl)-4-(hydroxyamino)-1,3-dimethyl-4,5-dihydro-1H-pyrazol-5-one | 131 |
| 97 | 4-(Hydroxyamino)-1,3-dimethyl-4-(3-methylphenyl)-4,5-dihydro-1H-pyrazol-5-one | 146 |

TABLE 4-continued

Pyrazolone Derivative Compound Melting Points

| Compound No. | Compound Name | Melting Point (° C.) |
|---|---|---|
| 99 | 4-(3-Chlorophenyl)-4-(hydroxyamino)-1,3-dimethyl-4,5-dihydro-1H-pyrazol-5-one | 109 |
| 100 | 4-(Hydroxyamino)-1,3-dimethyl-4-[1-[(2-methylpropoxy)imino]ethyl]-4,5-dihydro-1H-pyrazol-5-one | 48 |
| 106 | 4-[1-(Ethoxyimino)ethyl]-4-(hydroxyamino)-1,3-dimethyl-4,5-dihydro-1H-pyrazol-5-one | 107 |
| 107 | 3-(4-Bromophenyl)-4-(hydroxyamino)-1,4-dimethyl-4,5-dihydro-1H-pyrazol-5-one | 178 |
| 109 | 4-(Hydroxyamino)-1-methyl-3,4-diphenyl-4,5-dihydro-1H-pyrazol-5-one | 160 |
| 110 | 3-tert-Butyl-4-[1-(ethoxyimino)ethyl]-4-(hydroxyamino)-1-methyl-4,5-dihydro-1H-pyrazol-5-one | 69 |
| 113 | 3-tert-Butyl-4-(hydroxyamino)-1-methyl-4-phenyl-4,5-dihydro-1H-pyrazol-5-one | 180 |
| 114 | 3-{4-[(4,4-Difluoropiperidin-1-yl)sulfonyl]phenyl}-4-(hydroxyamino)-1,4-dimethyl-4,5-dihydro-1H-pyrazol-5-one | 173 |
| 115 | 4-[1-[(tert-Butoxy)imino]ethyl]-3-tert-butyl-4-(hydroxyamino)-1-methyl-4,5-dihydro-1H-pyrazol-5-one | 118 |
| 118 | 4-[1-[(4-Bromophenoxy)imino]ethyl]-3-tert-butyl-4-(hydroxyamino)-1-methyl-4,5-dihydro-1H-pyrazol-5-one | 61 |
| 119 | 3-tert-Butyl-4-(hydroxyamino)-1-methyl-4-[1-(phenoxyimino)ethyl]-4,5-dihydro-1H-pyrazol-5-one | 44 |
| 120 | 4-[3-tert-Butyl-4-(hydroxyamino)-1-methyl-5-oxo-4,5-dihydro-1H-pyrazol-4-yl]-N,N-dimethylbenzene-1-sulfonamide | 55 |
| 123 | 4-[4-(Hydroxyamino)-4-[1-(methoxyimino)ethyl]-1-methyl-5-oxo-4,5-dihydro-1H-pyrazol-3-yl]-N,N-dimethylbenzamide | 84 |
| 124 | 4-[3-tert-Butyl-4-(hydroxyamino)-1-methyl-5-oxo-4,5-dihydro-1H-pyrazol-4-yl]-N,N-dimethylbenzamide | N/A |
| 125 | 4-[1-[(Benzyloxy)imino]ethyl]-3-ethoxy-4-(hydroxyamino)-1-methyl-4,5-dihydro-1H-pyrazol-5-one | N/A |
| 126 | 3-Ethoxy-4-(hydroxyamino)-4-[1-(methoxyimino)ethyl]-1-methyl-4,5-dihydro-1H-pyrazol-5-one | 83 |
| 127 | 3-Ethoxy-4-(hydroxyamino)-4-methyl-1-phenyl-4,5-dihydro-1H-pyrazol-5-one | 107 |
| 128 | 4-(Hydroxyamino)-4-[1(methoxyimino)ethyl]-1-phenyl-3-(phenylsulfanyl)-4,5-dihydro-1H-pyrazol-5-one | 43 |
| 129 | 3-(Benzenesulfonyl)-4-(hydroxyamino)-4[1-(methoxyimino)ethyl]-1-phenyl-4,5-dihydro-1H-pyrazol-5-one pyrazol-5-one | 49 |
| 130 | 3-(Benzenesulfinyl)-4-(hydroxyamino)4[1-(methoxyimino)ethyl]-1-phenyl-4,5-dihydro1H-pyrazol-5-one | 45 |
| 131 | 3-tert-Butyl-4-(hydroxyamino)-4-[1-(methoxyimino)ethyl]-4,5-dihydro-1H-pyrazol-5-one | 96 |
| 132 | 4-(Hydroxyamino)-1,3-dimethyl-4-(5-phenyl-1,2,4-oxadiazol-3-yl)-4,5-dihydro-1H-pyrazol-5-one | 171 |
| 133 | 4-(Hydroxyamino)-3-(4-methanesulfonylphenyl)-4-methyl-4,5-dihydro-1H-pyrazol-5-one | 176 (decomposed) |
| 134 | 3-tert-Butyl-4-[1-(ethoxyimino)ethyl]-4-(hydroxyamino)-4,5-dihydro-1H-pyrazol-5-one | 119 |
| 135 | 4-[4-(Hydroxyamino)-4-methyl-5-oxo-4,5-dihydro-1H-pyrazol-3-yl]-N,N-dimethylbenzene-1-sulfonamide | 176 (decomposed) |
| 136 | 4-(Hydroxyamino)-3-(4-methanesulfonylphenyl)-4-methyl-1-phenyl-4,5-dihydro-1H-pyrazol-5-one | N/A |
| 137 | 4-(Hydroxyamino)-3-methyl-4-phenyl-4,5-dihydro-1H-pyrazol-5-one | 140 |
| 138 | 4-(Hydroxyamino)-3-(4-methanesulfonylphenyl)-4-methyl-1-(pyrazin-2-yl)-4,5-dihydro-1H-pyrazol-5-one | 198 |

4.5 Example 149

Solid-State Stability of Pyrazolone Derivative Compounds

Solid, powdered samples of certain compounds from Table 1 were sealed in double polyethylene bags and stored at 40° C., 75% relative humidity ("RH") for up to 3 months. A control compound, compound 7 disclosed in WO 2013/059194, was also tested. Initially and after 1 month, 2 months, and 3 months of storage, the samples were analyzed for purity, as determined by high performance liquid chromatography ("HPLC"). Additionally, certain compounds from Table 1 were admixed at a level of 50% by weight with one of the following excipients before stability testing: lactose, microcrystalline cellulose, or croscarmellose sodium. The resulting admixtures were also stored as described above then analyzed for purity of the pyrazolone derivative component, as determined by HPLC. The HPLC apparatus comprised a quaternary or binary pump, an auto sampler, a thermostated column compartment, and a UV/visible detector. The HPLC measurement conditions were as follows:

Column: Zorbax Eclipse XDB-C18, 2.1×50 mm, 3.5 μm (Agilent Technologies, Santa Clara, Calif.)

Injection Volume: 2 μL

Detection Wavelength: 220 nm
Mobile Phase A: 0.1% by volume formic acid ("FA") in water
Mobile Phase B: 0.1% by volume FA in acetonitrile
Diluent: About 0.2 mg sample/mL acetonitrile
Gradient:

| Time (min) | % A | % B |
|---|---|---|
| 0 | 99 | 1 |
| 15 | 70 | 30 |
| 20 | 99 | 1 |
| 23 | 99 | 1 |

Flow Rate: 0.8 mL/min
Column Temperature: 25° C.
The results obtained are provided in Table 5.

TABLE 5

Pyrazolone Derivative Compound Solid-State Stability at 40° C. and 75% RH

| | Time | | | |
|---|---|---|---|---|
| Compound No. | 0 Months | 1 Month | 2 Months | 3 Months |
| 1 | 100 | 99.2 | 99.8 | 99.8 |
| 2 | 91.2 | <10 | <10 | <10 |
| 6 | 99.8 | <10 | N/A | N/A |
| 14 | 99.3 | 97.0, 61.0 | 68.0 | N/A |
| 15 | 98.3 | <10 | N/A | N/A |
| Control | 99.5 | <10 | <10 | <10 |

4.6 Example 150

Separation of Pyrazolone Derivative Compound Enantiomers

The pyrazolone ring carbon atom of each pyrazolone derivative compound that is not bonded to oxo is optically active; thus, these compounds can exist as, inter alia, enantiomers. The enantiomers of a pyrazolone derivative compound can be separated by, e.g., chiral preparative supercritical fluid chromatography ("SFC") using the following procedure. A CHIRALPAK IA (250 mm×20 mm×5 μm) SFC semi-prep column (Daicel Corp., Osaka, Japan) eluting with 25% methanol (plus diethylamine):75% carbon dioxide can be used. The flow rate is 50 mL/min. UV detection at 215 nm is used.

In one embodiment, a pyrazolone derivative compound of the disclosure is present as a racemic mixture. In another embodiment, a pyrazolone derivative compound of the disclosure is present as a substantially pure enantiomer, for example, in about 90% or greater enantiomeric excess in one embodiment, in about 92% or greater enantiomeric excess in another embodiment, in about 94% or greater enantiomeric excess in another embodiment, in about 95% or greater enantiomeric excess in another embodiment, in about 96% or greater enantiomeric excess in another embodiment, in about 97% or greater enantiomeric excess in another embodiment, in about 98% or greater enantiomeric excess in another embodiment, in about 99% or greater enantiomeric excess in another embodiment, in about 99.5% or greater enantiomeric excess in another embodiment, and in about 99.8% or greater enantiomeric excess in another embodiment.

4.7 Example 151

Pharmacodynamic Activity of Pyrazolone Derivative Compounds in Dogs

The effect of certain compounds from Table 1 on blood pressure in freely moving telemetered normal beagle dogs (n=3) after single oral doses was evaluated. The animals were surgically implanted with a pressure transducer equipped telemetry transmitter. The transmitter assembly was secured internally and a fluid-filled catheter was placed into the abdominal aorta to allow for collection of cardiovascular data. To evaluate cardiovascular effects, 3 dogs were given single oral doses of a compound from Table 1 (100% PEG300 in gelatin capsules) at a concentration of 100 mg/mL and at doses of 30 mg/kg. Systemic blood pressure and heart rate were evaluated continuously for 2 hr before and for 24 hr after dosing (results not shown). To compare the pharmacodynamic activity for all tested compounds, the mean systolic blood pressure (SBP) decrease during the first 2 hr post-dose was determined relative to the baseline SBP (30-120 min pre-dose) (Table 6).

TABLE 6

Systolic Blood Pressure Decrease in Dogs Following Oral Administration

| Compound No. | Mean SBP decrease (mmHg) |
|---|---|
| 1 | 3 |
| 2 | 2 |
| 3 | 28 |
| 4 | 6 |
| 6 | 22 |
| 14 | 13 |
| 15 | 31 |
| 34 | 18 |
| 40 | 15 |
| 48 | 17 |
| 49 | 18 |
| 75 | 12 |
| 78 | 27 |
| 80 | 13 |
| 84 | 15 |
| 112 | 21 |
| 113 | 18 |

It will be apparent to those in the art that specific embodiments of the disclosed subject matter may be directed to one or more of the above- and below-indicated embodiments in any combination.

While the invention has been disclosed in some detail by way of illustration and example for purposes of clarity of understanding, it is apparent to those in the art that various changes may be made and equivalents may be substituted without departing from the true spirit and scope of the invention. Therefore, the description and examples should not be construed as limiting the scope of the invention.

All references, publications, patents, and patent applications disclosed herein are hereby incorporated by reference in their entirety.

What is claimed is:

1. A compound of formula (Ia)

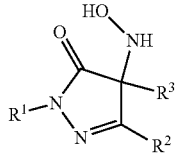

or a pharmaceutically acceptable salt thereof, wherein:
$R^1$ is $(C_1\text{-}C_6)$alkyl or unsubstituted phenyl;
$R^2$ is phenyl wherein said phenyl is unsubstituted or substituted with 1, 2, 3, 4, or 5 substituent(s) independently selected from halo, $(C_1\text{-}C_6)$alkyl, $(C_1\text{-}C_4)$haloalkyl, $(C_1\text{-}C_4)$perhaloalkyl, $(C_1\text{-}C_6)$alkoxy, $(C_1\text{-}C_4)$haloalkoxy, $(C_1\text{-}C_4)$perhaloalkoxy, $(C_1\text{-}C_6)$alkylsulfanyl, $(C_1\text{-}C_4)$haloalkylsulfanyl, $(C_1\text{-}C_4)$perhaloalkylsulfanyl, $(C_1\text{-}C_6)$alkylsulfinyl, $(C_1\text{-}C_6)$alkylsulfonyl, $(C_3\text{-}C_6)$cycloalkylsulfonyl, $(C_1\text{-}C_4)$haloalkylsulfinyl, $(C_1\text{-}C_4)$haloalkylsulfonyl, $(C_1\text{-}C_4)$perhaloalkylsulfinyl, $(C_1\text{-}C_4)$perhaloalkylsulfonyl, $-S(O)_2-NH_2$, $N-(C_1\text{-}C_6)$alkylaminosulfonyl, and $N,N$-di$(C_1\text{-}C_6)$alkylaminosulfonyl; and
$R^3$ is $(C_1\text{-}C_6)$alkyl or $-C(=NOR^9)R^{10}$ wherein $R^9$ and $R^{10}$ are independently selected from $(C_1\text{-}C_6)$alkyl.

2. The compound of claim 1, wherein $R^1$ is $(C_1\text{-}C_6)$alkyl unsubstituted or substituted with $C(=O)OH$.

3. The compound of claim 1, wherein $R^1$ is unsubstituted phenyl.

4. The compound of claim 1, wherein $R^2$ is phenyl substituted with 1, 2, or 3 substituent(s) independently selected from halo, $(C_1\text{-}C_6)$alkyl, $(C_1\text{-}C_4)$perhaloalkyl, $(C_1\text{-}C_6)$alkoxy, $(C_1\text{-}C_4)$haloalkoxy, $(C_1\text{-}C_4)$perhaloalkoxy, $(C_1\text{-}C_6)$alkylsulfanyl, $(C_1\text{-}C_6)$alkylsulfinyl, $(C_1\text{-}C_6)$alkylsulfonyl, $(C_1\text{-}C_4)$haloalkylsulfinyl, $(C_1\text{-}C_4)$haloalkylsulfonyl, $(C_1\text{-}C_4)$perhaloalkylsulfinyl, $(C_1\text{-}C_4)$perhaloalkylsulfonyl, $-S(O)_2-NH_2$, or $N,N$-di$(C_1\text{-}C_6)$alkylaminosulfonyl.

5. The compound of claim 1, wherein $R^2$ is unsubstituted phenyl.

6. The compound of claim 1, wherein $R^3$ is $(C_1\text{-}C_6)$alkyl.

7. The compound of claim 1, wherein $R^3$ is $-C(=NOR^9)R^{10}$.

8. The compound of claim 1, wherein, $R^3$ is $-C(=NOR^9)R^{10}$ wherein each of $R^9$ and $R^{10}$ is methyl.

9. A pharmaceutical composition comprising the compound of claim 1 and at least one pharmaceutically acceptable excipient.

10. The pharmaceutical composition of claim 9, wherein the pharmaceutical composition is suitable for oral administration.

11. The pharmaceutical composition of claim 9, wherein the pharmaceutical composition is formulated for administration in solid form.

12. The pharmaceutical composition of claim 9, wherein the at least one pharmaceutically acceptable excipient is selected from lactose, microcrystalline cellulose, croscarmellose, or any mixture thereof.

13. A method of treating a cardiovascular disease, comprising administering an effective amount of the compound of claim 1 or a pharmaceutical composition of claim 9 to a patient in need thereof.

14. The method of claim 13, wherein the cardiovascular disease is heart failure.

15. The method of claim 13, wherein the cardiovascular disease is acute decompensated heart failure.

16. The method of claim 13, wherein the compound or the pharmaceutical composition is administered orally.

17. A compound of formula (Ib)

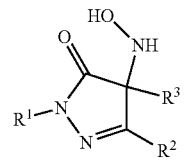

or a pharmaceutically acceptable salt thereof, wherein:
$R^1$ is $(C_1\text{-}C_6)$alkyl or unsubstituted phenyl;
$R^2$ is $(C_1\text{-}C_6)$alkyl, $(C_1\text{-}C_4)$haloalkyl, or $(C_1\text{-}C_4)$perhaloalkyl;
$R^3$ is (5- or 6-membered)heteroaryl or phenyl wherein said heteroaryl and phenyl are unsubstituted or substituted with 1, 2, 3, 4, or 5 substituent(s) independently selected from halo, $(C_1\text{-}C_6)$alkyl, $(C_1\text{-}C_6)$alkoxy, phenyl, $-C(=O)NR^4R^5$, $(C_1\text{-}C_6)$alkylsulfinyl, $(C_1\text{-}C_6)$alkylsulfonyl, and $N,N$-di$(C_1\text{-}C_6)$alkylaminosulfonyl; and
$R^4$ and $R^5$ are independently H or $(C_1\text{-}C_6)$alkyl.

18. The compound of claim 17, wherein $R^1$ is $(C_1\text{-}C_6)$alkyl.

19. The compound of claim 17, wherein $R^2$ is methyl.

20. The compound of claim 17, wherein $R^3$ is phenyl substituted with halo or $(C_1\text{-}C_6)$alkylsulfonyl.

21. The compound of claim 17, wherein:
$R^1$ is $(C_1\text{-}C_6)$alkyl or unsubstituted phenyl;
$R^2$ is $(C_1\text{-}C_6)$alkyl, $(C_1\text{-}C_4)$haloalkyl, or $(C_1\text{-}C_4)$perhaloalkyl; and
$R^3$ is phenyl wherein said phenyl is unsubstituted or substituted with 1, 2, 3, 4, or 5 substituent(s) independently selected from halo, $(C_1\text{-}C_6)$alkoxy, $(C_1\text{-}C_6)$alkylsulfinyl and $(C_1\text{-}C_6)$alkylsulfonyl.

22. The compound of claim 17, wherein $R^1$ is unsubstituted phenyl.

23. The compound of claim 17, wherein $R^3$ is unsubstituted phenyl.

24. A pharmaceutical composition comprising the compound of claim 17 and at least one pharmaceutically acceptable excipient.

25. A compound of formula (Ic)

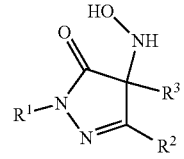

or a pharmaceutically acceptable salt thereof, wherein:
$R^1$ is $(C_1\text{-}C_6)$alkyl or phenyl, wherein said phenyl is unsubstituted or substituted with 1, 2, or 3 substituent(s) independently selected from halo;
$R^2$ is $(C_1\text{-}C_6)$alkoxy, phenylsulfanyl, phenylsulfonyl, phenylsulfinyl or $(C_3\text{-}C_6)$cycloalkyl; and
$R^3$ is $(C_1\text{-}C_6)$alkyl or $-C(=NOR^9)R^{10}$ wherein $R^9$ and $R^{10}$ are independently selected from $(C_1\text{-}C_6)$alkyl.

26. The compound of claim 25, wherein $R^1$ is $(C_1-C_6)$alkyl.

27. The compound of claim 25, wherein $R^1$ is unsubstituted phenyl.

28. The compound of claim 25, wherein $R^2$ is cyclopropyl.

29. The compound of claim 25, wherein $R^3$ is $-C(=NOR^9)R^{10}$ wherein each of $R^9$ and $R^{10}$ is methyl.

30. The compound of claim 25, wherein:
   $R^1$ is $(C_1-C_6)$alkyl or phenyl, wherein said phenyl is unsubstituted or substituted with 1, 2, or 3 substituent(s) independently selected from halo;
   $R^2$ is $(C_3-C_6)$cycloalkyl; and
   $R^3$ is $-C(=NOR^9)R^{10}$ wherein $R^9$ and $R^{10}$ are independently selected from $(C_1-C_6)$alkyl.

31. The compound of claim 25, wherein $R^1$ is phenyl substituted with 1, 2, or 3 substituent(s) independently selected from halo.

32. A pharmaceutical composition comprising the compound of claim 25 and at least one pharmaceutically acceptable excipient.

33. A compound selected from:
   5-(4-chlorophenyl)-4-(hydroxyamino)-2,4-dimethyl-2,4-dihydro-3H-pyrazol-3-one,
   5-(2-chlorophenyl)-4-(hydroxyamino)-2,4-dimethyl-2,4-dihydro-3H-pyrazol-3-one,
   5-(2-fluorophenyl)-4-(hydroxyamino)-2,4-dimethyl-2,4-dihydro-3H-pyrazol-3-one,
   4-(hydroxyamino)-2,4-dimethyl-5-(4-(trifluoromethyl)phenyl)-2,4-dihydro-3H-pyrazol-3-one,
   5-(4-fluorophenyl)-4-(hydroxyamino)-2,4-dimethyl-2,4-dihydro-3H-pyrazol-3-one,
   4-(hydroxyamino)-2,5-dimethyl-4-phenyl-2,4-dihydro-3H-pyrazol-3-one,
   5-(3,5-dimethylphenyl)-4-(hydroxyamino)-2,4-dimethyl-2,4-dihydro-3H-pyrazol-3-one,
   5-(2-chlorophenyl)-4-(hydroxyamino)-2-iso-propyl-4-methyl-2,4-dihydro-3H-pyrazol-3-one,
   5-(3,5-dichlorophenyl)-4-(hydroxyamino)-2,4-dimethyl-2,4-dihydro-3H-pyrazol-3-one,
   4-(hydroxyamino)-2,4-dimethyl-5-(4-(methylsulfinyl)phenyl)-2,4-dihydro-3H-pyrazol-3-one,
   5-(2-chloro-4-fluorophenyl)-4-(hydroxyamino)-2,4-dimethyl-2,4-dihydro-3H-pyrazol-3-one,
   4-(hydroxyamino)-2,4-dimethyl-5-(4-(methylsulfonyl)phenyl)-2,4-dihydro-3H-pyrazol-3-one,
   4-(hydroxyamino)-2,4-dimethyl-5-phenyl-2,4-dihydro-3H-pyrazol-3-one,
   2-(4-bromophenyl)-4-(hydroxyamino)-5-iso-propyl-4-(1-(methoxyimino)ethyl)-2,4-dihydro-3H-pyrazol-3-one,
   5-(3-fluoro-4-methoxyphenyl)-4-(hydroxyamino)-2,4-dimethyl-2,4-dihydro-3H-pyrazol-3-one,
   5-cyclopropyl-4-(hydroxyamino)-4-(1-(methoxyimino)ethyl)-2-methyl-2,4-dihydro-3H-pyrazol-3-one,
   4-(hydroxyamino)-2,4-dimethyl-5-(2-(methylsulfinyl)phenyl)-2,4-dihydro-3H-pyrazol-3-one,
   4-(hydroxyamino)-2,4-dimethyl-5-(3-(trifluoromethyl)phenyl)-2,4-dihydro-3H-pyrazol-3-one,
   5-(tert-butyl)-4-(hydroxyamino)-4-methyl-2-phenyl-2,4-dihydro-3H-pyrazol-3-one,
   4-(hydroxyamino)-5-methyl-2,4-diphenyl-2,4-dihydro-3H-pyrazol-3-one,
   4-(hydroxyamino)-4-methyl-2,5-diphenyl-2,4-dihydro-3H-pyrazol-3-one,
   5-(2-fluorophenyl)-4-(hydroxyamino)-2-iso-propyl-4-methyl-2,4-dihydro-3H-pyrazol-3-one,
   4-(4-fluorophenyl)-4-(hydroxyamino)-2,5-dimethyl-2,4-dihydro-3H-pyrazol-3-one,
   5-(tert-butyl)-4-(hydroxyamino)-2-iso-propyl-4-(1-(methoxyimino)ethyl)-2,4-dihydro-3H-pyrazol-3-one,
   5-(2-fluorophenyl)-4-(hydroxyamino)-4-methyl-2-phenyl-2,4-dihydro-3H-pyrazol-3-one,
   4-(hydroxyamino)-1-isopropyl-3-methyl-4-phenyl-1H-pyrazol-5(4H)-one,
   4-ethyl-5-(2-fluorophenyl)-4-(hydroxyamino)-2-methyl-2,4-dihydro-3H-pyrazol-3-one,
   4-(hydroxyamino)-2-iso-propyl-4-methyl-5-(4-(methylsulfonyl)phenyl)-2,4-dihydro-3H-pyrazol-3-one,
   4-(hydroxyamino)-2,4-dimethyl-5-(4-((trifluoromethyl)sulfonyl)phenyl)-2,4-dihydro-3H-pyrazol-3-one,
   4-(hydroxyamino)-2,4-dimethyl-5-(4-((trifluoromethyl)sulfinyl)phenyl)-2,4-dihydro-3H-pyrazol-3-one,
   4-(hydroxyamino)-2,4-dimethyl-5-(4-(methylthio)phenyl)-2,4-dihydro-3H-pyrazol-3-one,
   4-(hydroxyamino)-2,5-dimethyl-4-(4-(methylsulfonyl)phenyl)-2,4-dihydro-3H-pyrazol-3-one,
   5-(3-fluoro-4-(methylsulfinyl)phenyl)-4-(hydroxyamino)-2,4-dimethyl-2,4-dihydro-3H-pyrazol-3-one,
   4-(hydroxyamino)-2,4-dimethyl-5-(3-methyl-4-(methylsulfinyl)phenyl)-2,4-dihydro-3H-pyrazol-3-one,
   5-(3-fluoro-4-(methylsulfonyl)phenyl)-4-(hydroxyamino)-2,4-dimethyl-2,4-dihydro-3H-pyrazol-3-one,
   4-(hydroxyamino)-2,4-dimethyl-5-(3-methyl-4-(methylsulfonyl)phenyl)-2,4-dihydro-3H-pyrazol-3-one,
   4-(hydroxyamino)-4-(1-(methoxyimino)ethyl)-2-methyl-5-(4-(methylsulfonyl)-phenyl)-2,4-dihydro-3H-pyrazol-3-one,
   4-(hydroxyamino)-4-(4-methoxyphenyl)-1,3-dimethyl-1H-pyrazol-5(4H)-one,
   5-(3,5-difluoro-4-(methylsulfonyl)phenyl)-4-(hydroxyamino)-2,4-dimethyl-2,4-dihydro-3H-pyrazol-3-one,
   4-(hydroxyamino)-4-(1-(methoxyimino)ethyl)-2-methyl-5-phenyl-2,4-dihydro-3H-pyrazol-3-one,
   4-(hydroxyamino)-2,4-dimethyl-5-(3-(methylsulfonyl)phenyl)-2,4-dihydro-3H-pyrazol-3-one,
   4-(4-(hydroxyamino)-1,4-dimethyl-5-oxo-4,5-dihydro-1H-pyrazol-3-yl)-N,N-dimethylbenzenesulfonamide,
   4-(hydroxyamino)-1,4-dimethyl-3-(o-tolyl)-1H-pyrazol-5(4H)-one,
   4-(hydroxyamino)-4-(1-(methoxyimino)ethyl)-1-methyl-3-(4-(trifluoromethyl)phenyl)-1H-pyrazol-5(4H)-one,
   4-(hydroxyamino)-3-(4-methoxyphenyl)-1,4-dimethyl-1H-pyrazol-5(4H)-one,
   3-(3-chlorophenyl)-4-(hydroxyamino)-1,4-dimethyl-1H-pyrazol-5(4H)-one,
   4-(hydroxyamino)-3-(2-methoxyphenyl)-1,4-dimethyl-1H-pyrazol-5(4H)-one,
   4-(hydroxyamino)-1,4-dimethyl-3-(2-(trifluoromethoxy)phenyl)-1H-pyrazol-5(4H)-one,
   3-(2,3-dichlorophenyl)-4-(hydroxyamino)-1,4-dimethyl-1H-pyrazol-5(4H)-one,
   3-(2,4-dichlorophenyl)-4-(hydroxyamino)-1,4-dimethyl-1H-pyrazol-5(4H)-one,
   4-(hydroxyamino)-1,4-dimethyl-3-(4-(trifluoromethoxy)phenyl)-1H-pyrazol-5(4H)-one,
   4-(hydroxyamino)-1,4-dimethyl-3-(2-(trifluoromethyl)phenyl)-1H-pyrazol-5(4H)-one,
   4-(hydroxyamino)-4-methyl-1-phenyl-3-(trifluoromethyl)-1H-pyrazol-5(4H)-one, 3-(2-ethoxy-4-fluorophenyl)-4-(hydroxyamino)-1,4-dimethyl-1H-pyrazol-5(4H)-one,
3-(4-fluorophenyl)-4-(hydroxyamino)-4-(1-(methoxyimino)ethyl)-1-methyl-1H-pyrazol-5(4H)-one,
4-(hydroxyamino)-1,3-dimethyl-4-(4-(methylsulfinyl)phenyl)-1H-pyrazol-5(4H)-one,
4-(4-chlorophenyl)-4-(hydroxyamino)-1,3-dimethyl-1H-pyrazol-5(4H)-one,
4-(hydroxyamino)-1,4-dimethyl-3-(4-((trifluoromethyl)thio)phenyl)-1H-pyrazol-5(4H)-one,
4-(3-bromo-4-methoxyphenyl)-4-(hydroxyamino)-1,3-dimethyl-1H-pyrazol-5(4H)-one,
3-(3,5-bis(trifluoromethyl)phenyl)-4-(hydroxyamino)-1,4-dimethyl-1H-pyrazol-5(4H)-one,
3-(3-Chloro-4-methanesulfonylphenyl)-4-(hydroxyamino)-1,4-dimethyl-4,5-dihydro-1H-pyrazol-5-one,
methyl 4-[4-(hydroxyamino)-1,4 dimethyl-5-oxo-4,5-dihydro-1H-pyrazol-3-yl]benzoate,
2,2,2-trifluoro-N-({4-[4-(hydroxyamino)-1,4-dimethyl-5-oxo-4,5-dihydro-1H-pyrazol-3-yl]phenyl}(methyl)oxo-$\lambda^6$-sulfanylidene) acetamide,
4-(3,4-dimethoxyphenyl)-4-(hydroxyamino)-1,3-dimethyl-4,5-dihydro-1H-pyrazol-5-one,
4-[4-(hydroxyamino)-1,4-dimethyl-5-oxo-4,5-dihydro-1H-pyrazol-3-yl]benzoic acid,
4-(hydroxyamino)-3-{4-[imino(methyl)oxo-$\lambda^6$-sulfanyl]phenyl}-1,4-dimethyl-4,5-dihydro-1H-pyrazol-5-one,
4-(hydroxyamino)-4-(4-methoxy-3-methylphenyl)-1,3-dimethyl-4,5-dihydro-1H-pyrazol-5-one,
4-(hydroxyamino)-3-(4-methanesulfonyl-3-methoxyphenyl)-1,4-dimethyl-4,5-dihydro-1H-pyrazol-5-one,
4-(hydroxyamino)-1,4-dimethyl-3-[4-(propane-2-sulfonyl)phenyl]-4,5-dihydro-1H-pyrazol-5-one,
4-(hydroxyamino)-3-(4-methanesulfonyl-3,5-dimethylphenyl)-1,4-dimethyl-4,5-dihydro-1H-pyrazol-5-one,
4-(hydroxyamino)-1,4-dimethyl-3-[4-(morpholine-4-sulfonyl)phenyl]-4,5-dihydro-1H-pyrazol-5-one,
4-(hydroxyamino)-1,4-dimethyl-3-[4-(morpholine-4-carbonyl)phenyl]-4,5-dihydro-1H-pyrazol-5-one,
4-(hydroxyamino)-3-[4-methanesulfonyl-3-(morpholin-4-yl)phenyl]-1,4-dimethyl-4,5-dihydro-1H-pyrazol-5-one,
4-(hydroxyamino)-3-{4-methanesulfonyl-3-[(2-methoxyethyl)(methyl)amino]phenyl}-1,4-dimethyl-4,5-dihydro-1H-pyrazol-5-one,
4-[4-(hydroxyamino)-1,4-dimethyl-5-oxo-4,5-dihydro-1H-pyrazol-3-yl]-N,N-dimethylbenzamide,
3-[4-(4,4-difluoropiperidine-1-carbonyl)phenyl]-4-(hydroxyamino)-1,4-dimethyl-4,5-dihydro-1H-pyrazol-5-one,
3-[4-(ethanesulfonyl)phenyl]-4-(hydroxyamino)-1,4-dimethyl-4,5-dihydro-1H-pyrazol-5-one,
3-[3-(dimethylamino)-4-methanesulfonylphenyl]-4-(hydroxyamino)-1,4-dimethyl-4,5-dihydro-1H-pyrazol-5-one,
4-(hydroxyamino)-3-[4-methanesulfonyl-3-(4-methylpiperazin-1-yl)phenyl]-1,4-dimethyl-4,5-dihydro-1H-pyrazol-5-one,
3-[4-(benzenesulfonyl)phenyl]-4-(hydroxyamino)-1,4-dimethyl-4,5-dihydro-1H-pyrazol-5-one,
4-[4-(hydroxyamino)-1,4-dimethyl-5-oxo-4,5-dihydro-1H-pyrazol-3-yl]-N-(2-methoxyethyl)-N-methylbenzene-1-sulfonamide,
3-(4-tert-butylphenyl)-4-(hydroxyamino)-1,4-dimethyl-4,5-dihydro-1H-pyrazol-5-one,
4-[4-(hydroxyamino)-1,4-dimethyl-5-oxo-4,5-dihydro-1H-pyrazol-3-yl]benzamide,
4-(hydroxyamino)-3-[4-methanesulfonyl-3-(piperazin-1-yl)phenyl]-1,4-dimethyl-4,5-dihydro-1H-pyrazol-5-one,
2-({4-[4-(hydroxyamino)-1,4-dimethyl-5-oxo-4,5-dihydro-1H-pyrazol-3-yl]phenyl}formamido)propanoic acid,
2-({4-[4-(hydroxyamino)-1,4-dimethyl-5-oxo-4,5-dihydro-1H-pyrazol-3-yl]phenyl}formamido)acetic acid,
4-(3-fluorophenyl)-4-(hydroxyamino)-1,3-dimethyl-4,5-dihydro-1H-pyrazol-5-one,
4-(hydroxyamino)-3-[4-methanesulfonyl-3-(trifluoromethyl)phenyl]-1,4-dimethyl-4,5-dihydro-1H-pyrazol-5-one,
4-(hydroxyamino)-1,3-dimethyl-4-(3-methylphenyl)-4,5-dihydro-1H-pyrazol-5-one,
4-(3-chlorophenyl)-4-(hydroxyamino)-1,3-dimethyl-4,5-dihydro-1H-pyrazol-5-one,
4-(hydroxyamino)-4-(3-methoxyphenyl)-1,3-dimethyl-4,5-dihydro-1H-pyrazol-5-one,
4-[4-(hydroxyamino)-1,4-dimethyl-5-oxo-4,5-dihydro-1H-pyrazol-3-yl]-N-methanesulfonylbenzamide,
3-(3,4-dimethanesulfonylphenyl)-4-(hydroxyamino)-1,4-dimethyl-4,5-dihydro-1H-pyrazol-5-one,
4-(hydroxyamino)-4-[1-(methoxyimino)ethyl]-3-(4-methoxyphenyl)-1-methyl-4,5-dihydro-1H-pyrazol-5-one,
3-(4-bromophenyl)-4-(hydroxyamino)-1,4-dimethyl-4,5-dihydro-1H-pyrazol-5-one,
4-(hydroxyamino)-1-methyl-3,4-diphenyl-4,5-dihydro-1H-pyrazol-5-one,
3-ethoxy-4-(hydroxyamino)-4-[1-(methoxyimino)ethyl]-1-phenyl-4,5-dihydro-1H-pyrazol-5-one,
1-(4-bromophenyl)-3-ethoxy-4-(hydroxyamino)-4-[1-(methoxyimino)ethyl]-4,5-dihydro-1H-pyrazol-5-one,
3-tert-butyl-4-(hydroxyamino)-1-methyl-4-phenyl-4,5-dihydro-1H-pyrazol-5-one,
3-{4-[(4,4-difluoropiperidin-1-yl)sulfonyl]phenyl}-4-(hydroxyamino)-1,4-dimethyl-4,5-dihydro-1H-pyrazol-5-one,
4-(hydroxyamino)-3-methoxy-4-[1-(methoxyimino)ethyl]-1-phenyl-4,5-dihydro-1H-pyrazol-5-one,
4-(hydroxyamino)-3-{4-[imino(oxo)propan-2-yl-$\lambda^6$-sulfanyl]phenyl}-1,4-dimethyl-4,5-dihydro-1H-pyrazol-5-one,
4-[4-(hydroxyamino)-4-[1-(methoxyimino)ethyl]-1-methyl-5-oxo-4,5-dihydro-1H-pyrazol-3-yl]-N,N-dimethylbenzene-1-sulfonamide,
4-[3-tert-butyl-4-(hydroxyamino)-1-methyl-5-oxo-4,5-dihydro-1H-pyrazol-4-yl]-N,N-dimethylbenzene-1-sulfonamide,
4-[4-(hydroxyamino)-4-[1-(methoxyimino)ethyl]-1-methyl-5-oxo-4,5-dihydro-1H-pyrazol-3-yl]-N,N-dimethylbenzamide,
4-[3-tert-butyl-4-(hydroxyamino)-1-methyl-5-oxo-4,5-dihydro-1H-pyrazol-4-yl]-N,N-dimethylbenzamide,
4-[1-[(benzyloxy)imino]ethyl]-3-ethoxy-4-(hydroxyamino)-1-methyl-4,5-dihydro-1H-pyrazol-5-one,
3-ethoxy-4-(hydroxyamino)-4-[1-(methoxyimino)ethyl]-1-methyl-4,5-dihydro-1H-pyrazol-5-one,
3-ethoxy-4-(hydroxyamino)-4-methyl-1-phenyl-4,5-dihydro-1H-pyrazol-5-one,
4-(hydroxyamino)-4-[1 (methoxyimino)ethyl]-1-phenyl-3-(phenylsulfanyl)-4,5-dihydro-1H-pyrazol-5-one,
3-(benzenesulfonyl)-4-(hydroxyamino)-4-[1-(methoxyimino)ethyl]-1-phenyl-4,5-dihydro-1H-pyrazol-5-one, 3-(benzenesulfinyl)-4-(hydroxyamino)4-[1-(methoxy-imino)ethyl]-1-phenyl-4,5-dihydro 1H-pyrazol-5-one, 4-(hydroxyamino)-1,3-dimethyl-4-(5-phenyl-1,2,4-oxadiazol-3-yl)-4,5-dihydro-1H-pyrazol-5-one, 4-[4-(hydroxyamino)-4-methyl-5-oxo-4,5-dihydro-1H-pyrazol-3-yl]-N,N-dimethylbenzene-1-sulfonamide, 4-(hydroxyamino)-3-(4-methanesulfonylphenyl)-4-methyl-1-phenyl-4,5-dihydro-1H-pyrazol-5-one, 4-(hydroxyamino)-3-(4-methanesulfonylphenyl)-4-methyl-1-(pyrazin-2-yl)-4,5-dihydro-1H-pyrazol-5-one and 2-(4-(hydroxyamino)-4-methyl-3-(4-(methylsulfonyl)phenyl)-5-oxo-4,5-dihydro-1H-pyrazol-1-yl)acetic acid.

34. The compound of claim 33, which is 5-(4-chlorophenyl)-4-(hydroxyamino)-2,4-dimethyl-2,4-dihydro-3H-pyrazol-3-one.

35. The compound of claim 33, which is 4-(hydroxyamino)-2,4-dimethyl-5-(4-(methylsulfonyl)phenyl)-2,4-dihydro-3H-pyrazol-3-one.

36. The compound of claim 33, which is 5-(2-fluorophenyl)-4-(hydroxyamino)-2,4-dimethyl-2,4-dihydro-3H-pyrazol-3-one.

37. The compound of claim 33, which is 4-(hydroxyamino)-2,4-dimethyl-5-(4-(trifluoromethyl)phenyl)-2,4-dihydro-3H-pyrazol-3-one.

38. The compound of claim 33, which is 4-(hydroxyamino)-2-iso-propyl-4-methyl-5-(4-(methylsulfonyl)phenyl)-2,4-dihydro-3H-pyrazol-3-one.

39. The compound of claim 33, which is 5-(2-fluorophenyl)-4-(hydroxyamino)-2-iso-propyl-4-methyl-2,4-dihydro-3H-pyrazol-3-one.

40. A compound of formula (Ia)

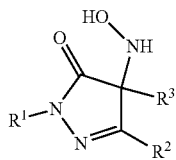

(Ia)

or a pharmaceutically acceptable salt thereof, wherein:

$R^1$ is $(C_1-C_6)$alkyl substituted with C(=O)OH or unsubstituted (5- or 6-membered)heteroaryl;

$R^2$ is phenyl wherein said phenyl is unsubstituted or substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O($C_1-C_6$)alkyl, —C(=O)NR$^4$R$^5$, —C(=O)—$(C_5-C_7)$heterocycloalkyl, $(C_5-C_7)$heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$—(C$_5$-C$_7$)heterocycloalkyl, —S(=O)(=NR$^8$)($C_1-C_6$)alkyl, —NR$^4$R$^5$, N—($C_1-C_6$)alkylaminosulfonyl, or N,N-di($C_1-C_6$)alkylaminosulfonyl, wherein said $(C_5-C_7)$heterocycloalkyl is unsubstituted or substituted with 1 or 2 substituent(s) independently selected from halo or $(C_1-C_6)$alkyl;

$R^4$ and $R^6$ are independently H or $(C_1-C_6)$alkyl;

$R^5$ is H, $(C_1-C_6)$alkyl or $(C_1-C_6)$alkylsulfonyl, wherein said alkyl is unsubstituted or substituted with C(=O)OH or wherein a methylene group of said alkyl is optionally replaced with an oxygen atom;

$R^7$ is H or $(C_1-C_6)$alkyl, wherein a methylene group of said alkyl is optionally replaced with an oxygen atom;

$R^8$ is H, —(C=O)($C_1-C_6$)alkyl or —(C=O)($C_1-C_4$)perhaloalkyl; and $R^3$ is $(C_1-C_6)$alkyl or —C(=NOR$^9$)R$^{10}$ wherein $R^9$ and $R^{10}$ are independently selected from $(C_1-C_6)$alkyl.

41. The compound of claim 40, wherein $R^2$ is phenyl substituted with 1, 2, or 3 substituent(s) independently selected from halo, $(C_1-C_6)$alkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O($C_1-C_6$)alkyl, —C(=O)NR$^4$R$^5$, —C(=O)—$(C_5-C_7)$heterocycloalkyl, $(C_5-C_7)$heterocycloalkyl, $(C_1-C_6)$alkylsulfanyl, $(C_1-C_6)$alkylsulfinyl, $(C_1-C_6)$alkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NR$^6$R$^7$, —S(O)$_2$-phenyl, —S(O)$_2$-($C_5-C_7$)heterocycloalkyl, —S(=O)(=NR$^8$)($C_1-C_6$)alkyl, —NR$^4$R$^5$, or N,N-di($C_1-C_6$)alkylaminosulfonyl, wherein said $(C_5-C_7)$heterocycloalkyl is unsubstituted or substituted with 1 or 2 substituent(s) independently selected from halo or $(C_1-C_6)$alkyl.

42. The compound of claim 40, wherein $R^1$ is $(C_1-C_6)$alkyl substituted with C(=O)OH.

43. The compound of claim 40, wherein $R^3$ is $(C_1-C_6)$alkyl.

44. The compound of claim 40, wherein $R^2$ is unsubstituted phenyl.

45. The compound of claim 40, wherein $R^3$ is —C(=NOR$^9$)R$^{10}$.

46. The compound of claim 40, wherein, $R^3$ is —C(=NOR$^9$)R$^{10}$ wherein each of $R^9$ and $R^{10}$ is methyl.

47. A pharmaceutical composition comprising the compound of claim 40 and at least one pharmaceutically acceptable excipient.

48. A method of treating a cardiovascular disease, comprising administering an effective amount of the compound of claim 40 or a pharmaceutical composition of claim 47 to a patient in need thereof.

* * * * *

UNITED STATES PATENT AND TRADEMARK OFFICE
CERTIFICATE OF CORRECTION

| | | |
|---|---|---|
| PATENT NO. | : 9,682,938 B2 | Page 1 of 1 |
| APPLICATION NO. | : 14/722141 | |
| DATED | : June 20, 2017 | |
| INVENTOR(S) | : Vincent Jacob Kalish et al. | |

It is certified that error appears in the above-identified patent and that said Letters Patent is hereby corrected as shown below:

In the Specification

Column 1, Line 4 immediately after the title please insert the following paragraph (government support statement):
--STATEMENT OF GOVERNMENTAL INTEREST
This invention was made with government support under grant number 1213438, awarded by the National Science Foundation. The government has certain rights in the invention.--

Signed and Sealed this
Sixth Day of February, 2018

Joseph Matal
*Performing the Functions and Duties of the*
*Under Secretary of Commerce for Intellectual Property and*
*Director of the United States Patent and Trademark Office*